US007787946B2

(12) United States Patent
Stahmann et al.

(10) Patent No.: US 7,787,946 B2
(45) Date of Patent: Aug. 31, 2010

(54) PATIENT MONITORING, DIAGNOSIS, AND/OR THERAPY SYSTEMS AND METHODS

(75) Inventors: Jeffrey E. Stahmann, Ramsey, MN (US); Kent Lee, Shoreview, MN (US); Jesse W. Hartley, Lino Lakes, MN (US); Quan Ni, Shoreview, MN (US); John D. Hatlestad, Maplewood, MN (US); Qingsheng Zhu, Wexford, PA (US); Krzysztof Z Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 410 days.

(21) Appl. No.: 10/943,721

(22) Filed: Sep. 17, 2004

(65) Prior Publication Data

US 2005/0115561 A1 Jun. 2, 2005

Related U.S. Application Data

(60) Provisional application No. 60/504,229, filed on Sep. 18, 2003.

(51) Int. Cl.
*A61N 1/362* (2006.01)

(52) U.S. Cl. .......................................................... 607/3

(58) Field of Classification Search ..................... 607/3, 607/20, 42; 600/529, 534, 536
See application file for complete search history.

(56) References Cited

U.S. PATENT DOCUMENTS 3,650,277 A 3/1972 Sjostrand et al.
4,091,818 A 5/1978 Brownlee et al.
4,312,355 A 1/1982 Funke
4,312,734 A 1/1982 Nichols
4,365,636 A 12/1982 Barker
4,390,405 A 6/1983 Hahn et al.
4,414,982 A 11/1983 Durkan (Continued)

FOREIGN PATENT DOCUMENTS

EP 0547734 6/1993

(Continued)

OTHER PUBLICATIONS

Bradley et al, *Cardiac Output Response To Continuous Positive Airway Pressure In Congestive Heart Failure*, 145 Am. Rev. Respir. Dis. 377-382 (1992). (Abstract only).

(Continued)

*Primary Examiner*—George R Evanisko
(74) *Attorney, Agent, or Firm*—Hollingsworth & Funk, LLC

(57) ABSTRACT

Systems and methods involve an implantable device configured to perform at least one cardiac-related function, a patient-external respiratory therapy device, and a communication channel configured to facilitate communication between the implantable device and the respiratory therapy device. The implantable and respiratory therapy devices operate cooperatively via the communication channel to provide one or more of patient monitoring, diagnosis, and therapy. The communication channel may be configured to facilitate communication between an external processing system and at least one of the implantable device and the respiratory therapy device. The processing system is communicatively coupled to at least one of the implantable and respiratory therapy devices via the communication channel to provide one or more of patient monitoring, diagnosis, and therapy.

19 Claims, 213 Drawing Sheets

U.S. PATENT DOCUMENTS 4,562,841 A 1/1986 Brockway et al.
4,648,407 A 3/1987 Sackner
4,702,253 A 10/1987 Nappholz et al.
4,721,110 A 1/1988 Lampadius
4,777,962 A 10/1988 Watson et al.
4,784,162 A 11/1988 Ricks et al.
4,791,931 A 12/1988 Slate
4,802,485 A 2/1989 Bowers et al.
4,807,629 A 2/1989 Baudino et al.
4,813,427 A 3/1989 Schlaefke et al.
4,827,935 A 5/1989 Geddes et al.
4,827,943 A 5/1989 Bornn et al.
4,830,008 A 5/1989 Meer
4,836,219 A 6/1989 Hobson et al.
4,856,524 A 8/1989 Baker, Jr.
4,860,766 A 8/1989 Sackner
4,875,477 A 10/1989 Waschke et al.
4,886,064 A 12/1989 Strandberg
4,928,688 A 5/1990 Mower
4,953,551 A 9/1990 Mehra et al.
4,958,632 A 9/1990 Duggan
4,961,423 A 10/1990 Canducci
4,972,842 A 11/1990 Korten et al.
4,982,738 A 1/1991 Griebel
5,003,975 A 4/1991 Hafelfinger et al.
5,010,888 A 4/1991 Jadvar et al.
5,024,222 A 6/1991 Thacker
5,036,849 A 8/1991 Hauck et al.
5,047,930 A 9/1991 Martens et al.
5,063,927 A 11/1991 Webb et al.
5,074,301 A 12/1991 Gill
5,101,831 A 4/1992 Koyama et al.
5,105,354 A 4/1992 Nishimura
5,111,815 A 5/1992 Mower
5,123,425 A 6/1992 Shannon, Jr. et al.
5,133,353 A 7/1992 Hauser
5,146,918 A 9/1992 Kallok et al.
5,156,157 A 10/1992 Valenta, Jr. et al.
5,158,089 A 10/1992 Swezey et al.
5,170,784 A 12/1992 Ramon et al.
5,174,287 A 12/1992 Kallok et al.
5,178,156 A 1/1993 Takishima et al.
5,179,945 A 1/1993 Van Hofwegen et al.
5,183,038 A 2/1993 Hoffman et al.
5,187,657 A 2/1993 Forbes
5,188,106 A 2/1993 Nappholz et al.
5,190,035 A 3/1993 Salo et al.
5,199,424 A 4/1993 Sullivan et al.
5,199,428 A 4/1993 Obel et al.
5,203,326 A 4/1993 Collins
5,203,348 A 4/1993 Dahl et al.
5,209,229 A 5/1993 Gilli
5,211,173 A 5/1993 Kallok et al.
5,215,082 A 6/1993 Kallok et al.
5,230,337 A 7/1993 Dahl et al.
5,233,983 A 8/1993 Markowitz
5,243,979 A 9/1993 Stein et al.
5,243,980 A 9/1993 Mehra
5,245,995 A 9/1993 Sullivan et al.
5,259,373 A 11/1993 Gruenke et al.
5,261,400 A 11/1993 Bardy
5,275,159 A 1/1994 Griebel
5,280,791 A 1/1994 Lavie
5,284,136 A 2/1994 Hauck et al.
5,292,338 A 3/1994 Bardy
5,299,118 A 3/1994 Martens et al.
5,300,106 A 4/1994 Dahl et al.
5,301,677 A 4/1994 Hsung
5,306,293 A 4/1994 Zacouto
5,313,953 A 5/1994 Yomtov et al.
5,314,459 A 5/1994 Swanson et al.
5,318,592 A 6/1994 Schaldach
5,318,593 A 6/1994 Duggan
5,318,594 A 6/1994 Limousin et al.
5,318,597 A 6/1994 Hauck et al.
5,330,505 A 7/1994 Cohen
5,330,507 A 7/1994 Schwartz
5,331,966 A 7/1994 Bennett et al.
5,334,221 A 8/1994 Bardy
5,334,222 A 8/1994 Salo et al.
5,335,657 A 8/1994 Terry, Jr. et al.
5,353,788 A 10/1994 Miles
5,356,425 A 10/1994 Bardy et al.
5,360,442 A 11/1994 Dahl et al.
5,366,496 A 11/1994 Dahl et al.
5,372,606 A 12/1994 Lang et al.
5,376,103 A 12/1994 Anderson et al.
5,376,106 A 12/1994 Stahmann et al.
5,376,476 A 12/1994 Eylon
5,377,671 A 1/1995 Biondi et al.
5,388,578 A 2/1995 Yomtov et al.
5,391,187 A 2/1995 Freeman
5,391,200 A 2/1995 KenKnight et al.
5,397,342 A 3/1995 Heil, Jr. et al.
5,398,682 A 3/1995 Lynn
5,404,877 A 4/1995 Nolan et al.
5,411,031 A 5/1995 Yomtov
5,411,525 A 5/1995 Swanson et al.
5,411,531 A 5/1995 Hill et al.
5,411,539 A 5/1995 Neisz
5,417,717 A 5/1995 Salo et al.
5,437,285 A 8/1995 Verrier et al.
5,439,482 A 8/1995 Adams et al.
5,441,518 A 8/1995 Adams et al.
5,466,245 A 11/1995 Heemels et al.
5,468,254 A 11/1995 Hahn et al.
5,476,485 A 12/1995 Weinberg et al.
5,483,969 A 1/1996 Testerman et al.
5,485,851 A 1/1996 Erickson
5,487,755 A 1/1996 Snell et al.
5,490,502 A 2/1996 Rapoport et al.
5,507,784 A 4/1996 Hill et al.
5,517,983 A 5/1996 Deigham et al.
5,520,176 A 5/1996 Cohen
5,520,191 A 5/1996 Karlsson et al.
5,522,382 A 6/1996 Sullivan et al.
5,522,854 A 6/1996 Ideker et al.
5,522,862 A 6/1996 Testerman et al.
5,527,345 A 6/1996 Infinger
5,531,779 A 7/1996 Dahl et al.
5,540,727 A 7/1996 Tockman et al.
5,540,732 A 7/1996 Testerman
5,540,734 A 7/1996 Zabara
5,545,186 A 8/1996 Olson et al.
5,545,202 A 8/1996 Dahl et al.
5,549,655 A 8/1996 Erickson
5,554,177 A 9/1996 Kieval
5,578,061 A 11/1996 Stroetmann et al.
5,590,648 A 1/1997 Mitchell et al.
5,591,216 A 1/1997 Testerman et al.
5,593,431 A 1/1997 Sheldon
5,601,607 A 2/1997 Adams
5,603,331 A 2/1997 Heemels et al.
5,603,732 A 2/1997 Dahl et al.
5,605,151 A 2/1997 Lynn
5,606,969 A 3/1997 Butler et al.
5,607,385 A 3/1997 Francischelli et al.
5,620,466 A 4/1997 Haefner et al.
5,622,178 A 4/1997 Gilham
5,626,151 A 5/1997 Linden
5,632,281 A 5/1997 Rayburn
5,634,938 A 6/1997 Swanson et al.
5,641,326 A 6/1997 Adams
5,645,570 A 7/1997 Corbucci

| | | | |
|---|---|---|---|
| 5,658,318 A | 8/1997 | Stroetmann et al. | |
| 5,662,688 A | 9/1997 | Haefner et al. | |
| 5,690,681 A | 11/1997 | Geddes et al. | |
| 5,693,000 A | 12/1997 | Crosby et al. | |
| 5,697,951 A | 12/1997 | Harpstead et al. | |
| 5,697,953 A | 12/1997 | Kroll et al. | |
| 5,700,282 A | 12/1997 | Zabara | |
| 5,701,894 A | 12/1997 | Cherry et al. | |
| 5,704,345 A | 1/1998 | Berthon-Jones | |
| 5,704,365 A | 1/1998 | Albrecht et al. | |
| 5,707,400 A | 1/1998 | Terry, Jr. et al. | |
| 5,713,355 A | 2/1998 | Richardson et al. | |
| 5,713,933 A | 2/1998 | Condie et al. | |
| 5,715,812 A | 2/1998 | Deigham et al. | |
| 5,716,377 A | 2/1998 | Rise et al. | |
| 5,720,771 A | 2/1998 | Snell | |
| 5,724,984 A | 3/1998 | Arnold et al. | |
| 5,738,102 A | 4/1998 | Lemelson | |
| 5,740,797 A | 4/1998 | Dickson | |
| 5,782,883 A | 7/1998 | Kroll et al. | |
| 5,792,188 A | 8/1998 | Starkweather et al. | |
| 5,794,615 A | 8/1998 | Estes | |
| 5,797,967 A | 8/1998 | KenKnight | |
| 5,800,470 A | 9/1998 | Stein et al. | |
| 5,802,188 A | 9/1998 | McDonough | |
| 5,814,079 A | 9/1998 | Kieval | |
| 5,814,087 A | 9/1998 | Renirie | |
| 5,826,579 A | 10/1998 | Remmers et al. | |
| 5,827,326 A | 10/1998 | Kroll et al. | |
| 5,836,987 A | 11/1998 | Baumann et al. | |
| 5,844,680 A | 12/1998 | Sperling | |
| 5,855,593 A | 1/1999 | Olson et al. | |
| 5,860,918 A | 1/1999 | Schradi et al. | |
| 5,861,011 A | 1/1999 | Stoop | |
| 5,869,970 A | 2/1999 | Palm et al. | |
| 5,876,353 A | 3/1999 | Riff | |
| 5,891,023 A | 4/1999 | Lynn | |
| 5,895,414 A | 4/1999 | Sanchez-Zambrano | |
| 5,902,250 A | 5/1999 | Verrier et al. | |
| 5,911,218 A | 6/1999 | DiMarco | |
| 5,916,239 A | 6/1999 | Geddes et al. | |
| 5,916,243 A | 6/1999 | KenKnight et al. | |
| 5,919,141 A | 7/1999 | Money et al. | |
| 5,944,680 A | 8/1999 | Christopherson et al. | |
| 5,957,861 A | 9/1999 | Combs et al. | |
| 5,957,956 A | 9/1999 | Kroll et al. | |
| 5,961,446 A | 10/1999 | Beller et al. | |
| 5,961,450 A | 10/1999 | Merchant et al. | |
| 5,964,778 A | 10/1999 | Fugoso et al. | |
| 5,964,788 A | 10/1999 | Greenhut | |
| 5,970,975 A | 10/1999 | Estes et al. | |
| 5,974,340 A | 10/1999 | Kadhiresan | |
| 5,974,349 A | 10/1999 | Levine | |
| 5,981,011 A | 11/1999 | Overcash et al. | |
| 5,997,526 A | 12/1999 | Giba et al. | |
| 6,006,134 A | 12/1999 | Hill et al. | |
| 6,015,388 A | 1/2000 | Sackner et al. | |
| 6,021,351 A | 2/2000 | Kadhiresan et al. | |
| 6,026,320 A | 2/2000 | Carlson et al. | |
| 6,044,297 A | 3/2000 | Sheldon et al. | |
| 6,044,298 A | 3/2000 | Salo et al. | |
| 6,045,513 A | 4/2000 | Stone et al. | |
| 6,047,203 A | 4/2000 | Sackner et al. | |
| 6,050,940 A | 4/2000 | Braun et al. | |
| 6,055,454 A | 4/2000 | Heemels | |
| 6,058,331 A | 5/2000 | King | |
| 6,059,725 A | 5/2000 | Steinschneider | |
| 6,064,910 A | 5/2000 | Andersson et al. | |
| 6,073,048 A | 6/2000 | Kieval et al. | |
| 6,076,015 A | 6/2000 | Hartley et al. | |
| 6,091,973 A | 7/2000 | Colla et al. | |
| 6,091,986 A | 7/2000 | Keimel | |
| 6,099,479 A | 8/2000 | Christopherson et al. | |
| 6,105,575 A | 8/2000 | Estes et al. | |
| 6,115,628 A | 9/2000 | Stadler et al. | |
| 6,120,441 A | 9/2000 | Griebel | |
| 6,126,611 A | 10/2000 | Bourgeois et al. | |
| 6,128,534 A | 10/2000 | Park et al. | |
| 6,132,384 A | 10/2000 | Christopherson et al. | |
| 6,134,470 A | 10/2000 | Hartlaub | |
| 6,141,581 A | 10/2000 | Olson et al. | |
| 6,141,590 A | 10/2000 | Renirie et al. | |
| 6,144,866 A | 11/2000 | Miesel et al. | |
| 6,148,230 A | 11/2000 | KenKnight | |
| 6,148,233 A | 11/2000 | Owen et al. | |
| 6,148,814 A | 11/2000 | Clemmer et al. | |
| 6,155,976 A | 12/2000 | Sackner et al. | |
| 6,161,042 A | 12/2000 | Hartley et al. | |
| 6,165,155 A | 12/2000 | Jacobsen et al. | |
| 6,168,568 B1 | 1/2001 | Gavriely | |
| 6,178,349 B1 | 1/2001 | Kieval | |
| 6,181,961 B1 | 1/2001 | Prass | |
| 6,181,966 B1 | 1/2001 | Nigam | |
| 6,190,326 B1 | 2/2001 | McKinnon et al. | |
| 6,200,265 B1 | 3/2001 | Walsh et al. | |
| 6,205,357 B1 | 3/2001 | Ideker et al. | |
| 6,208,894 B1 * | 3/2001 | Schulman et al. | 607/2 |
| 6,212,435 B1 | 4/2001 | Lattner et al. | |
| 6,221,011 B1 | 4/2001 | Bardy | |
| 6,227,072 B1 | 5/2001 | Ritchey et al. | |
| 6,236,873 B1 | 5/2001 | Holmström | |
| 6,240,314 B1 | 5/2001 | Plicchi et al. | |
| 6,240,316 B1 | 5/2001 | Richmond et al. | |
| 6,251,126 B1 | 6/2001 | Ottenhoff et al. | |
| 6,258,039 B1 | 7/2001 | Okamoto et al. | |
| 6,259,947 B1 | 7/2001 | Olson et al. | |
| 6,261,238 B1 | 7/2001 | Gavriely | |
| 6,263,244 B1 | 7/2001 | Mann et al. | |
| 6,264,606 B1 | 7/2001 | Ekwall et al. | |
| 6,269,269 B1 | 7/2001 | Ottenhoff et al. | |
| 6,270,457 B1 | 8/2001 | Bardy | |
| 6,272,377 B1 | 8/2001 | Sweeney et al. | |
| 6,275,727 B1 | 8/2001 | Hopper et al. | |
| 6,277,072 B1 | 8/2001 | Bardy | |
| 6,280,380 B1 | 8/2001 | Bardy | |
| 6,280,462 B1 | 8/2001 | Hauser et al. | |
| 6,285,907 B1 | 9/2001 | Kramer et al. | |
| 6,286,508 B1 | 9/2001 | Remmers et al. | |
| 6,287,264 B1 | 9/2001 | Hoffman | |
| 6,292,695 B1 | 9/2001 | Webster et al. | |
| 6,299,581 B1 | 10/2001 | Rapoport et al. | |
| 6,303,270 B1 | 10/2001 | Flaim et al. | |
| 6,306,088 B1 | 10/2001 | Krausman | |
| 6,310,085 B1 | 10/2001 | Willis | |
| 6,312,378 B1 | 11/2001 | Bardy | |
| 6,314,319 B1 | 11/2001 | Kroll et al. | |
| 6,317,627 B1 | 11/2001 | Ennen et al. | |
| 6,327,499 B1 | 12/2001 | Alt | |
| 6,331,536 B1 | 12/2001 | Radulovacki et al. | |
| 6,336,903 B1 | 1/2002 | Bardy | |
| 6,351,669 B1 | 2/2002 | Harley et al. | |
| 6,351,670 B1 | 2/2002 | Kroll | |
| 6,353,759 B1 | 3/2002 | Harley et al. | |
| 6,357,444 B1 | 3/2002 | Parker | |
| 6,358,203 B2 | 3/2002 | Bardy | |
| 6,360,127 B1 | 3/2002 | Ding et al. | |
| 6,361,494 B1 | 3/2002 | Lindenthaler | |
| 6,361,522 B1 | 3/2002 | Scheiner et al. | |
| 6,363,270 B1 | 3/2002 | Colla et al. | |
| 6,366,813 B1 | 4/2002 | DiLorenzo | |
| 6,368,284 B1 | 4/2002 | Bardy | |
| 6,368,287 B1 | 4/2002 | Hadas | |
| 6,371,922 B1 | 4/2002 | Baumann et al. | |
| 6,375,614 B1 | 4/2002 | Braun et al. | |
| 6,375,621 B1 | 4/2002 | Sullivan | |
| 6,375,623 B1 | 4/2002 | Gavriely | |

6,387,907 B1 5/2002 Hendricks et al.
6,397,845 B1 6/2002 Burton
6,398,727 B1 6/2002 Bui et al.
6,398,728 B1 6/2002 Bardy
6,398,739 B1 6/2002 Sullivan et al.
6,400,982 B2 6/2002 Sweeney et al.
6,409,675 B1 6/2002 Turcott
6,411,845 B1 6/2002 Mower et al.
6,411,848 B2 6/2002 Kramer et al.
6,411,850 B1 6/2002 Kay et al.
6,414,183 B1 7/2002 Sakamoto et al.
6,415,174 B1 7/2002 Bebehani et al.
6,415,183 B1 7/2002 Scheiner et al.
6,421,557 B1 7/2002 Meyer
6,424,865 B1 7/2002 Ding
6,431,171 B1 8/2002 Burton
6,438,407 B1 8/2002 Ousdigian et al.
6,438,410 B2 8/2002 Hsu et al.
6,440,066 B1 8/2002 Bardy
6,442,413 B1 8/2002 Silver
6,442,433 B1 8/2002 Linberg
6,449,503 B1 9/2002 Hsu
6,449,507 B1 9/2002 Hill et al.
6,450,957 B1 9/2002 Yoshimi
6,454,708 B1 9/2002 Ferguson et al.
6,454,719 B1 9/2002 Greenhut
6,459,929 B1 10/2002 Hopper et al.
6,463,326 B1 10/2002 Hartley et al.
6,467,333 B2 10/2002 Lewis et al.
6,468,219 B1 10/2002 Njemanze
6,473,644 B1 10/2002 Terry, Jr. et al.
6,480,733 B1 11/2002 Turcott
6,487,443 B2 11/2002 Olson et al.
6,487,450 B1 11/2002 Chen et al.
6,491,639 B1 12/2002 Turcott
6,491,675 B1 12/2002 Shimada et al.
6,493,585 B2 12/2002 Plicchi et al.
6,496,715 B1 12/2002 Lee et al.
6,505,067 B1 1/2003 Lee et al.
6,511,500 B1 1/2003 Rahme
6,512,940 B1 1/2003 Brabec et al.
6,514,218 B2 2/2003 Yamamoto
6,522,915 B1 2/2003 Ceballos et al.
6,522,926 B1 2/2003 Kieval et al.
6,527,729 B1 3/2003 Turcott
6,532,388 B1 3/2003 Hill et al.
6,542,774 B2 4/2003 Hill et al.
6,542,775 B2 4/2003 Ding et al.
6,547,743 B2 4/2003 Brydon
6,564,096 B2 5/2003 Mest
6,564,106 B2 5/2003 Guck et al.
6,572,543 B1 6/2003 Christopherson et al.
6,574,507 B1 6/2003 Bonnet
6,580,944 B1 6/2003 Katz et al.
6,584,351 B1 6/2003 Ekwall
6,589,188 B1 7/2003 Street et al.
6,595,928 B2 7/2003 Mansy et al.
6,597,951 B2 7/2003 Kramer et al.
6,600,949 B1 7/2003 Turcott
6,606,993 B1 8/2003 Wiesmann et al.
6,607,509 B2 8/2003 Bobroff et al.
6,611,713 B2 8/2003 Schauerte
6,615,083 B2 9/2003 Kupper
6,618,618 B2 9/2003 Kalgren et al.
6,622,041 B2 9/2003 Terry, Jr. et al.
6,622,046 B2 9/2003 Fraley et al.
6,628,986 B1 9/2003 Mouchawar et al.
6,628,987 B1 9/2003 Hill et al.
6,641,542 B2 11/2003 Cho et al.
6,658,292 B2 12/2003 Kroll et al.
6,662,032 B1 12/2003 Gavish et al.
6,694,186 B2 2/2004 Bardy
6,704,590 B2 3/2004 Haldeman
6,708,058 B2 3/2004 Kim et al.
6,723,055 B2 4/2004 Hoffman
6,731,984 B2 5/2004 Cho et al.
6,741,885 B1 5/2004 Park et al.
6,748,252 B2 6/2004 Lynn et al.
6,752,765 B1 6/2004 Jensen et al.
6,752,766 B2 6/2004 Kowallik et al.
6,760,615 B2 7/2004 Ferek-Petric
6,766,190 B2 7/2004 Ferek-Petric
6,773,404 B2 8/2004 Poezevera et al.
6,810,287 B2 10/2004 Zhu et al.
6,811,538 B2 11/2004 Westbrook et al.
6,830,548 B2 12/2004 Bonnet et al.
6,832,609 B2 12/2004 Wright et al.
6,857,428 B2 2/2005 Thomton
6,876,881 B2 4/2005 Baumann et al.
6,881,192 B1 4/2005 Park
6,890,306 B2 5/2005 Poezevera
6,892,095 B2 5/2005 Salo
6,904,320 B2 6/2005 Park et al.
6,910,481 B2 6/2005 Kimmel et al.
6,928,324 B2 8/2005 Park et al.
6,934,583 B2 8/2005 Weinberg et al.
6,964,641 B2 11/2005 Cho et al.
6,988,498 B2 1/2006 Berthon-Jones et al.
7,025,729 B2 4/2006 Chazal et al.
7,025,730 B2 * 4/2006 Cho et al. .................. 600/529
7,027,871 B2 4/2006 Burnes et al.
7,039,468 B2 5/2006 Freed et al.
7,062,308 B1 6/2006 Jackson
7,081,095 B2 7/2006 Lynn et al.
7,089,936 B2 8/2006 Madaus et al.
7,092,755 B2 8/2006 Florio
7,094,207 B1 8/2006 Koh
7,101,341 B2 9/2006 Tsukashima et al.
7,115,097 B2 10/2006 Johnson
7,127,290 B2 10/2006 Girouard
7,130,687 B2 10/2006 Cho et al.
7,136,704 B2 11/2006 Schulman
7,155,278 B2 12/2006 King et al.
7,179,229 B1 2/2007 Koh
7,184,817 B2 2/2007 Zhu et al.
7,189,204 B2 3/2007 Ni et al.
7,194,313 B2 3/2007 Libbus
7,204,805 B2 4/2007 Dean
7,207,945 B2 4/2007 Bardy
7,225,013 B2 5/2007 Geva et al.
7,225,021 B1 5/2007 Park et al.
7,225,809 B1 6/2007 Bowen et al.
7,231,250 B2 6/2007 Band et al.
7,252,640 B2 8/2007 Ni et al.
7,258,670 B2 8/2007 Bardy
7,269,459 B1 9/2007 Koh
7,302,295 B2 11/2007 Stahmann et al.
7,413,549 B1 8/2008 Koh
7,425,200 B2 9/2008 Brockway et al.
7,435,221 B1 10/2008 Bharmi et al.
7,486,991 B2 2/2009 Libbus et al.
7,509,166 B2 3/2009 Libbus
2001/0000346 A1 4/2001 Ruton et al.
2001/0005790 A1 6/2001 Ripart
2001/0018547 A1 8/2001 Mechlenburg et al.
2001/0031930 A1 10/2001 Roizen et al.
2002/0002327 A1 1/2002 Grant et al.
2002/0026222 A1 2/2002 Schauerte et al.
2002/0035376 A1 3/2002 Bardy et al.
2002/0035377 A1 3/2002 Bardy et al.
2002/0035378 A1 3/2002 Bardy et al.
2002/0035379 A1 3/2002 Bardy et al.
2002/0035380 A1 3/2002 Rissmann et al.
2002/0035381 A1 3/2002 Bardy et al.
2002/0042629 A1 4/2002 Bardy et al.
2002/0042630 A1 4/2002 Bardy et al.

2002/0042634 A1 4/2002 Bardy et al.
2002/0049475 A1 4/2002 Bardy et al.
2002/0049476 A1 4/2002 Bardy et al.
2002/0052636 A1 5/2002 Bardy et al.
2002/0058877 A1 5/2002 Baumann et al.
2002/0068958 A1 6/2002 Bardy et al.
2002/0072773 A1 6/2002 Bardy et al.
2002/0072776 A1 6/2002 Osorio et al.
2002/0082652 A1 6/2002 Wentkowski et al.
2002/0082658 A1 6/2002 Heinrich et al.
2002/0085741 A1 7/2002 Shimizu
2002/0091414 A1 7/2002 Bardy et al.
2002/0095184 A1 7/2002 Bardy et al.
2002/0103510 A1 8/2002 Bardy et al.
2002/0107544 A1 8/2002 Ostroff et al.
2002/0107545 A1 8/2002 Rissmann et al.
2002/0107546 A1 8/2002 Ostroff et al.
2002/0107547 A1 8/2002 Erlinger et al.
2002/0107548 A1 8/2002 Bardy et al.
2002/0107549 A1 8/2002 Bardy et al.
2002/0107553 A1 8/2002 Hill et al.
2002/0107559 A1 8/2002 Sanders et al.
2002/0120207 A1 8/2002 Hoffman
2002/0120299 A1 8/2002 Ostroff et al.
2002/0136328 A1 9/2002 Shimizu
2002/0143264 A1 10/2002 Ding et al.
2002/0143369 A1 10/2002 Hill et al.
2002/0147473 A1 10/2002 Chen et al.
2002/0161410 A1 10/2002 Kramer et al.
2002/0165586 A1 11/2002 Hill et al.
2002/0169485 A1 11/2002 Pless et al.
2002/0183237 A1 12/2002 Puskas
2002/0193685 A1 12/2002 Mate et al.
2002/0193697 A1 12/2002 Cho et al.
2002/0193839 A1 12/2002 Cho et al.
2002/0198570 A1 12/2002 Puskas
2003/0003052 A1 1/2003 Hampton
2003/0004546 A1 1/2003 Casey
2003/0004549 A1 1/2003 Hill et al.
2003/0004552 A1 1/2003 Plombon et al.
2003/0023175 A1 1/2003 Arzbaecher et al.
2003/0023184 A1 1/2003 Pitts-Crick et al.
2003/0023271 A1 1/2003 KenKnight et al.
2003/0023279 A1 1/2003 Spinelli et al.
2003/0036773 A1 2/2003 Whitehurst et al.
2003/0036778 A1 2/2003 Ostroff et al.
2003/0045904 A1 3/2003 Bardy et al.
2003/0045909 A1 3/2003 Gross et al.
2003/0045914 A1 3/2003 Cohen et al.
2003/0050538 A1 3/2003 Naghavi et al.
2003/0055461 A1 3/2003 Girouard et al.
2003/0060848 A1 3/2003 Kieval et al.
2003/0060857 A1 3/2003 Perrson et al.
2003/0060858 A1 3/2003 Kieval et al.
2003/0069609 A1 4/2003 Thompson
2003/0073919 A1 4/2003 Hampton et al.
2003/0074039 A1 4/2003 Puskas
2003/0078629 A1 4/2003 Chen
2003/0083241 A1 5/2003 Young
2003/0083587 A1 5/2003 Ferek-Petric
2003/0088027 A1 5/2003 Chin et al.
2003/0088278 A1 5/2003 Bardy et al.
2003/0088279 A1 5/2003 Rissmann et al.
2003/0088280 A1 5/2003 Ostroff
2003/0088281 A1 5/2003 Ostroff et al.
2003/0088282 A1 5/2003 Ostroff
2003/0088283 A1 5/2003 Ostroff
2003/0088286 A1 5/2003 Ostroff et al.
2003/0097153 A1 5/2003 Bardy et al.
2003/0100924 A1 5/2003 Foreman et al.
2003/0100925 A1 5/2003 Pape et al.
2003/0105493 A1 6/2003 Salo et al.
2003/0105497 A1 6/2003 Zhu et al.
2003/0114887 A1 6/2003 KenKnight
2003/0121519 A1 7/2003 Estes et al.
2003/0139780 A1 7/2003 Markowitz et al.
2003/0149450 A1 8/2003 Mayberg
2003/0149457 A1 8/2003 Tcheng et al.
2003/0153953 A1 8/2003 Park et al.
2003/0153954 A1 8/2003 Park et al.
2003/0153955 A1 8/2003 Park et al.
2003/0153956 A1 8/2003 Park et al.
2003/0163059 A1 8/2003 Poezevera et al.
2003/0163169 A1 8/2003 Hill et al.
2003/0171687 A1 9/2003 Irie et al.
2003/0176894 A1 9/2003 Stahmann et al.
2003/0178031 A1 9/2003 Du Pen et al.
2003/0181951 A1 9/2003 Cates
2003/0187336 A1 10/2003 Odagiri et al.
2003/0195571 A1 10/2003 Burnes et al.
2003/0195578 A1 10/2003 Perron et al.
2003/0199945 A1 10/2003 Ciulla
2003/0204146 A1 10/2003 Carlson
2003/0204213 A1 10/2003 Jensen et al.
2003/0204216 A1 10/2003 Ries et al.
2003/0209246 A1 11/2003 Schroeder et al.
2003/0212436 A1 11/2003 Brown
2003/0212440 A1 11/2003 Boveja
2003/0216789 A1 11/2003 Deem et al.
2003/0216792 A1 11/2003 Levin et al.
2003/0236558 A1 12/2003 Whitehurst
2004/0002742 A1 1/2004 Florio
2004/0010303 A1 1/2004 Bolea
2004/0019364 A1 1/2004 Kieval et al.
2004/0030362 A1 2/2004 Hill et al.
2004/0039605 A1 2/2004 Bardy
2004/0059240 A1 3/2004 Cho et al.
2004/0064177 A1 4/2004 Bardy et al.
2004/0073093 A1 4/2004 Hatlestad
2004/0088015 A1 5/2004 Casavant et al.
2004/0088027 A1 5/2004 Burnes et al.
2004/0102814 A1 5/2004 Sorensen et al.
2004/0111021 A1 6/2004 Olson
2004/0116981 A1 6/2004 Mazar
2004/0122487 A1 6/2004 Hatlestad et al.
2004/0122488 A1 6/2004 Mazar et al.
2004/0128161 A1 7/2004 Mazar et al.
2004/0133079 A1 7/2004 Mazar et al.
2004/0134496 A1 7/2004 Cho et al.
2004/0138719 A1 7/2004 Cho et al.
2004/0163648 A1 8/2004 Burton
2004/0172074 A1 9/2004 Yoshihito
2004/0176695 A1 9/2004 Poezevara
2004/0176809 A1 9/2004 Cho et al.
2004/0193231 A1 9/2004 David et al.
2004/0199210 A1 10/2004 Shelchuk
2004/0210154 A1 10/2004 Kline
2004/0210155 A1 10/2004 Takemura et al.
2004/0215240 A1 10/2004 Lovett et al.
2004/0215258 A1 10/2004 Lovett et al.
2004/0215289 A1 10/2004 Fukui
2004/0230229 A1 11/2004 Lovett et al.
2004/0230230 A1 11/2004 Lindstrom
2004/0230243 A1 11/2004 Haefner
2004/0243012 A1 12/2004 Ciaccio et al.
2004/0249416 A1 12/2004 Yun et al.
2004/0254616 A1 12/2004 Rossing et al.
2005/0004615 A1 1/2005 Sanders
2005/0039745 A1 2/2005 Stahmann et al.
2005/0042589 A1 2/2005 Hatlestad et al.
2005/0043644 A1 2/2005 Stahmann et al.
2005/0043652 A1 2/2005 Lovett et al.
2005/0043772 A1 2/2005 Stahmann et al.
2005/0061315 A1 3/2005 Lee et al.
2005/0061319 A1 3/2005 Hartley et al.
2005/0065447 A1 3/2005 Lee et al.

| | | | |
|---|---|---|---|
| 2005/0065567 | A1 | 3/2005 | Lee et al. |
| 2005/0065572 | A1 | 3/2005 | Hartley et al. |
| 2005/0065575 | A1 | 3/2005 | Dobak |
| 2005/0069322 | A1 | 3/2005 | Tegge et al. |
| 2005/0085864 | A1 | 4/2005 | Schulman et al. |
| 2005/0085865 | A1 | 4/2005 | Tehrani |
| 2005/0096705 | A1 | 5/2005 | Pastore et al. |
| 2005/0101841 | A9 | 5/2005 | Kaylor et al. |
| 2005/0107838 | A1 | 5/2005 | Lovett et al. |
| 2005/0113710 | A1 | 5/2005 | Stahmann et al. |
| 2005/0119711 | A1 | 6/2005 | Cho et al. |
| 2005/0131467 | A1 | 6/2005 | Boveja |
| 2005/0137645 | A1 | 6/2005 | Voipio et al. |
| 2005/0142070 | A1 | 6/2005 | Hartley et al. |
| 2005/0143779 | A1 | 6/2005 | Libbus et al. |
| 2005/0143787 | A1 | 6/2005 | Boveja et al. |
| 2005/0145246 | A1 | 7/2005 | Hartley et al. |
| 2005/0149126 | A1 | 7/2005 | Libbus et al. |
| 2005/0149127 | A1 | 7/2005 | Libbus et al. |
| 2005/0149128 | A1 | 7/2005 | Heil, Jr. et al. |
| 2005/0149129 | A1 | 7/2005 | Libbus et al. |
| 2005/0149131 | A1 | 7/2005 | Libbus et al. |
| 2005/0149132 | A1 | 7/2005 | Libbus et al. |
| 2005/0149133 | A1 | 7/2005 | Libbus et al. |
| 2005/0149143 | A1 | 7/2005 | Libbus et al. |
| 2005/0149155 | A1 | 7/2005 | Scheiner et al. |
| 2005/0149156 | A1 | 7/2005 | Libbus et al. |
| 2005/0159784 | A1 | 7/2005 | Arceta |
| 2005/0197675 | A1 | 9/2005 | David et al. |
| 2005/0240240 | A1 | 10/2005 | Park et al. |
| 2005/0288728 | A1 | 12/2005 | Libbus et al. |
| 2006/0047333 | A1 | 3/2006 | Tockman |
| 2006/0079945 | A1 | 4/2006 | Libbus |
| 2006/0106428 | A1 | 5/2006 | Libbus et al. |
| 2006/0106429 | A1 | 5/2006 | Libbus et al. |
| 2006/0116737 | A1 | 6/2006 | Libbus |
| 2006/0122675 | A1 | 6/2006 | Libbus et al. |
| 2006/0195041 | A1 | 8/2006 | Lynn et al. |
| 2006/0206153 | A1 | 9/2006 | Libbus et al. |
| 2006/0206154 | A1 | 9/2006 | Moffitt et al. |
| 2006/0217772 | A1 | 9/2006 | Libbus et al. |
| 2006/0224188 | A1 | 10/2006 | Libbus et al. |
| 2006/0293714 | A1 | 12/2006 | Salo et al. |
| 2007/0005114 | A1 | 1/2007 | Salo et al. |
| 2007/0055115 | A1 | 3/2007 | Kwok et al. |
| 2007/0093875 | A1 | 4/2007 | Chavan et al. |
| 2007/0112388 | A1 | 5/2007 | Salo |
| 2007/0142741 | A1 | 6/2007 | Berthon-Jones et al. |
| 2007/0142871 | A1 | 6/2007 | Libbus et al. |
| 2007/0149860 | A1 | 6/2007 | Lynn et al. |
| 2007/0150014 | A1 | 6/2007 | Kramer et al. |
| 2007/0161873 | A1 | 7/2007 | Ni et al. |
| 2007/0239057 | A1 | 10/2007 | Pu et al. |
| 2007/0282215 | A1 | 12/2007 | Ni et al. |
| 2008/0045813 | A1 | 2/2008 | Phuah et al. |
| 2009/0007918 | A1 | 1/2009 | Darkin et al. |

FOREIGN PATENT DOCUMENTS

| | | |
|---|---|---|
| EP | 0750920 | 1/1997 |
| EP | 0 940 155 A | 3/1999 |
| EP | 0940155 A | 8/1999 |
| EP | 1038498 | 9/2000 |
| EP | 1151718 | 11/2001 |
| EP | 1162125 | 12/2001 |
| EP | 1 172 125 A1 | 1/2002 |
| EP | 1234597 | 8/2002 |
| EP | 1304137 | 4/2003 |
| EP | 1486232 | 12/2004 |
| EP | 1541193 | 6/2005 |
| WO | WO8402080 | 7/1984 |
| WO | WO8605965 | 10/1986 |
| WO | WO9203983 | 3/1992 |
| WO | WO9217240 | 10/1992 |
| WO | WO92020402 | 11/1992 |
| WO | WO9301862 | 2/1993 |
| WO | WO9904841 | 2/1999 |
| WO | WO0001438 | 1/2000 |
| WO | WO0009206 | 2/2000 |
| WO | WO 00/17615 | 3/2000 |
| WO | WO0017615 | 3/2000 |
| WO | WO0124876 | 4/2001 |
| WO | WO0143804 | 6/2001 |
| WO | WO0176689 | 10/2001 |
| WO | WO0226318 | 4/2002 |
| WO | WO0234327 | 5/2002 |
| WO | WO02085448 | 10/2002 |
| WO | WO02087696 | 11/2002 |
| WO | WO03003905 | 1/2003 |
| WO | WO03011388 | 2/2003 |
| WO | WO03041559 | 5/2003 |
| WO | WO03075744 | 9/2003 |
| WO | WO03076008 | 9/2003 |
| WO | WO03082080 | 10/2003 |
| WO | WO03099373 | 12/2003 |
| WO | WO03099377 | 12/2003 |
| WO | WO2004012814 | 2/2004 |
| WO | WO2004062485 | 7/2004 |
| WO | WO2004084990 | 10/2004 |
| WO | WO2004084993 | 10/2004 |
| WO | WO2004103455 | 12/2004 |
| WO | WO2004105870 | 12/2004 |
| WO | WO2004110549 | 12/2004 |
| WO | WO2005018739 | 3/2005 |
| WO | WO2005028029 | 3/2005 |
| WO | WO2005042091 | 5/2005 |
| WO | WO2005053788 | 6/2005 |
| WO | WO2005063332 | 7/2005 |
| WO | WO2005065771 | 7/2005 |
| WO | WO2006031331 | 3/2006 |

OTHER PUBLICATIONS

Buda et al., *Effect Of Intrathoracic Pressure On Left Ventricular Performance*, 301 Engl. J. Med. 453-459 (1979). (Abstract only).

Calvin et al., *Positive End-Expiratory Pressure (PEEP) Does Not Depress Left Ventricular Function In Patients With Pulmonary Edema*, 124 Am. Rev. Respir. Dis. 121-128(1981). (Abstract only).

De Hoyos et al., *Haemodynamic Effects Of Continuous Positive Airway Pressure In Humans With Normal And Impaired Left Ventricular Function*, 88 Clin. Sci. (Lond). 173-8 (1995). (Abstract only).

Giardino et al., *Respiratory Sinus Arrhythmia is Associated with the Efficiency of Pulmonary Gas Exchange in Healthy Humans*, 284 Am. J. Physiol. H1585-1591 (2003). (Abstract only).

Hanson et al., *Cardiac Gated Ventilation*, 2433 SPIE 303-308 (1995).

Holger Steltner et al., *Diagnosis of Sleep Apnea by Automatic Analysis of Nasal Pressure and Forced Oscillation Impedance*. Am. Journal Respiratory Critical Care Medicine, vol. 165, pp. 940-944 (2002).

Kaye et al., *Acute Effects Of Continuous Positive Airway Pressure On Cardiac Sympathetic Tone In Congestive Heart Failure*, 103 Circulation 2336-24338 (2001).

Laude et al., Effects of Breathing Pattern on Blood Pressure and Heart Rate Oscillations in Humans, 20 Clin. Exp. Pharmol. Phisiol 619, 625 (1993). Abstract only.

Lenique et al., *Ventilatory And Hemodynamic Effects Of Continuous Positive Airway Pressure In Left Heart Failure*, 155 Am. J. Respir. Crit. Care Med. 500-505 (1997). (Abstract only).

Lugaresi et al., *Snoring*, 39 Electroencephalogr. Clin. Neurophysiol. 59-64 (1975). Abstract only.

Mansfield, D. et al., *Effects of Continuous Positive Airway Pressure on Lung Function in Patients with Chronic Obstructive Pulmonary Disease and Sleep Disordered Breathing*, Respirology 365-70 (1999). Abstract only.

Mehta et al., *Effects Of Continuous Positive Airway Pressure On Cardiac Volumes In Patients With Ischemic And Dilated Cardiomyopathy*, 161 Am. J. Respir. Crit. Care Med. 128-134 (2000).

Naughton et al., *Effects Of Continuous Positive Airway Pressure On Intrathoracic And Left Ventricular Transmural Pressure In Congestive Heart Failure*, 91 Circulation 1725-1731 (1995).
Pinsky et al., *Hemodynamic Effect Of Cardiac Cycle-Specific Increases In Intrathoracic Pressure*, 6 J. Appl. Physiol. 604-612 (1986). (Abstract only).
Potkin et al., *Effect of positive end-expiratory pressure on right and left ventricular function in patients with the adult respiratory distress syndrome*, 135 Am. Rev. Respir. Dis. 307-311 (1987). (Abstract only).
Reddel et al., *Analysis of Adherence to Peak Flow Monitoring When Recording of Data is Electronic*, BMJ 146-147 (2002).
Scharf, *Effects Of Continuous Positive Airway Pressure On Cardiac Output In Experimental Heart Failure*, 19 Sleep S240-2 (1996). (Abstract only).
Balaban et al., *Feasibility of Screening for Sleep Apnea Using Pacemaker Impedance Sensor*, NASPE (2001).
Bradley et al., *Pathophysiologic and Therapeutic Implications of Sleep Apnea in Congestive Heart Failure*, 3 J. Cardiac Failure 223-240 (1996). Abstract only.
Bradley et al., *Sleep Apnea and Heart Failure, Park I: Obstructive Sleep Apnea*, 107 Circulation 1671-1678 (2003).
Garrigue et al., *Night Atrial Overdrive with DDD Pacing Results in a Significant Reduction of Sleep Apnea Episodes and QOL Improvement in Heart Failure Patients*, NASPE (2001).
Garrigue et al., *Benefit of Atrial Pacing in Sleep Apnea Syndrome*, 346 N. Engl. J. Med. 404-412 (2002).
Hilton et al., *Evaluation of Frequency and Time-frequency Spectral Analysis of Heart Rate Variability as a Diagnostic Marker of the Sleep Apnea Syndrome*, 37 Med. Biol. Eng. Comput. 760-769 (1999).
Jais et al., *Night Atrial Overdrive with DDD Pacing: a New Therapy for Sleep Apnea Syndrome*, NASPE (2000).
Javaheri et al., *Sleep Apnea in 81 Ambulatory Male Patients with Stable Heart Failure: Types and Their Prevalences, Consequences, and Presentations*, 97 Circulation 2154-2159 (1998).
Olusola et al., *Nightcap: Laboratory and home-based evaluation of a portable sleep monitor*, 32 Psychophysiology, 32-98 (1995).
Verrier et al., *Sleep, dreams, and sudden death: the case for sleep as an autonomic stress test for the heart*, 31 Cardiovascular Research 181-211 (1996).
Verrier et al., *Sleep Related Cardiovascular Risk: New Home-Based Monitoring Technology for Improved Diagnosis and Therapy*, 2 A.N. E. 158-175 (1997).
Roche et al., *Screening of Obstructive Sleep Apnea Syndrome by Heart Rate Variability Analysis*, 100 Circulation 1411-1455 (1999).
Shahrokh, *A Mechanism of Central Sleep Apnea In Patients With Heart Failure*,341 N. Engl. J. Med. 949-954 (1999).
Weber et al. *Effects of CPAP and BIPAP on stroke volume in patients with obstructive sleep apnea syndrome*. Pneumolgie 1995 Mar;49(3):233-5. Translated Abstract only.
Vanninen et al., *Cardiac Sympathovagal Balance During Sleep Apnea Episodes*, 16 Clin. Physiol. 209-216 (1996).
Waldemark et al., *Detection of Apnea using Short Window FFT Technique and Artificial Neural Network*, 3390 SPIE International Society for Optical Engineering 122-133 (1998).
Young et al., *The Occurrence of Sleep-Disordered Breathing Among Middle Aged Adults*, N. Engl. J. Med. 1230-1235 (1993).
Aircraft Noise and Sleep Disturbance: Final Report', prepared by the Civil Aviation Authority London on behalf of the Department of Trade, Aug. 2, 1980 (CAA Report).
Andersen, Long-term follow-up of patients from a randomized trial of atrial versus ventricular pacing for sick-sinus syndrome, Lancet, 350(9086), Oct. 25, 1997, 1210-6. Abstract only.
Baratz et al., Effect Of Nasal Continuous Positive Airway Pressure On Cardiac Output And Oxygen Delivery In Patients With Congestive Heart Failure, 102 Chest, 1992, pp. 1397-1401.
Benchimol, Cardiac hemodynamics during stimulation of the right atrium, right ventricle, and left ventricle in normal and abnormal hearts, Circulation, 33(6), Jun. 1966, 933-44.
Bevan et al., Postganglionic sympathetic delay in vascular smooth muscle, Journal of Pharmacology & Experimental Therapeutics, 152(2), May 1966, 221-30.
Bevan et al., Sympathetic nerve-free vascular muscle, Journal of Pharmacology & Experimental Therapeutics, 157(1), Jul. 1967, 117-24.
Braunwald et al., Carotid sinus nerve stimulation in the treatment of angina pectoris and supraventricular trachycardia, California Medicine, 112(3), Mar. 1970, 41-50.
Chapleau, Contrasting effects of static and pulsatile pressure on carotid baroreceptor activity in dogs, Circulation, vol. 61, No. 5, Nov. 1987, pp. 648-658.
Chapleau, Pulsatile activation of baroreceptors causes central facilitation of baroreflex, American Journal Physiol Heart Circ Physiol, Jun. 1989, 256:H1735-1741.
Coleridge et al. "The distribution, connexions and histology of baroreceptors in the pulmonary artery, with some observations on the sensory innervation of the ductus arteriosus." Physiology, May 1961, pp. 591-602.
Cooper et al., Neural effects on sinus rate and atrioventricular conduction produced by electrical stimulation from a transvenous electrode catheter in the canine right pulmonary artery, Circulation Research, 46(1), Jan. 1980, 48-57.
Dark et al., Breathing Pattern Abnormalities and Arterial Oxygen Desaturation During Sleep in the Congestive Heart Failure Syndrome, Chest, Jun. 1987, 6:833-6.
De Landsheere et al., Effect of spinal cord stimulation on regional myocardial perfusion assessed by positron emission tomography, American Journal of Cardiology, 69(14), May 1, 1992, 1143-9, Abstract only.
Feliciano et al., Vagal nerve stimulation releases vasoactive intestinal peptide which significantly increases coronary artery blood flow, Cardiovascular Research, 40(1), Oct. 1998, 45-55.
Fromer et al., Ultrarapid subthreshold stimulation for termination of atrioventricular node reentrant tachycardia, Journal of the American College of Cardiology, 20(4), Oct. 1992, 879-83, Abstract only.
Gallois et al., Multi-Channel Analysis of the EEG Signals and Statistic Particularities for Epileptic Seizure Forecast, Second Joint EMBS/BMES Conference, pp. 208-215, Oct. 23-26, 2002.
Gradaus et al., Nonthoracotomy Implantable Cardioverter Defibrillator Placement in Children: Use of a Subcutaneous Array Leads and Abdominally Placed Implantable Cardioverter Defibrillators in Children, J. of Cardiovascular Electrophysiology, vol. 12, No. 3, pp. 356-360, Mar. 2001.
Grassi et al., Baroreflex and non-baroreflex modulation of vagal cardiac control after myocardial infarction, Am J Cardiol, 84(5), Sep. 1, 1999, 525-9, Abstract only.
Hartz et al., New Approach to Defibrillator Insertion, J. Thoracic Cardiovascular Surgery, vol. 97, pp. 920-922, 1989.
Henning, Effects of autonomic nerve stimulation, asynchrony, and load on dP/dtmax and on dP/dtmin, American Journal of Physiology, 260(4PT2), Apr. 1991, H1290-8.
Henning et al., Vagal nerve stimulation increases right ventricular contraction and relaxation and heart rate, Cardiovascular Research, 32(5), Nov. 1996, 846-53.
Hilton et al., Evaluation of Frequency and Time-frequency Spectral Analysis of Heart Rate Variability as a Diagnostic Marker of the Sleep Apnea Syndrome. Med Biol Eng Comput Nov. 1999, 37(6), 760-9. Abstract only.
Hoffman et al., Cheyne-Stokes Respiration in Patients Recovering from Acute Cardiogenic Pulmonary Edema, Chest 1990, 97:410-12.
Hood Jr. et al., Asynchronous contraction due to late systolic bulging at left ventricular pacing sites, American Journal Physiology, 217(1), Jul. 1969, 215-21.
Ishise, Time course of sympathovagal imbalance and left ventricular dysfunction in conscious dogs with heart failure, Journal of Applied Physiology 84(4), Apr. 1998, 1234-41.
Janes, "Anatomy of human extrinsic cardiac nerves and ganglia", Am J Cardiol., 57(4), Feb. 1, 1986, 299-309.
Javaheri et al., Sleep Apnea in 81 Ambulatory Male Patients with Stable Heart Failure, from the Sleep Disorders Laboratory, Department of Veterans Affairs Medical Center, and the Department of Medicine, University of Cincinnati College of Medicine, Cincinnati, OH, pp. 2154-2159.
Jessurun et al., Coronary blood flow dynamics during transcutaneous electrical nerve stimulation for stable angina pectoris associated with severe narrowing of one major coronary artery, American Journal of Cardiology, 82(8), erratum appears in Am J Cardiol, Feb. 1999, 15;83(4):642, Oct. 15, 1998, 921-6. Abstract only.
Kandel et al., Part VII: Arousal, Emotion, and Behavioral Homeostasis, In: Principles of neural science, New York:McGraw-Hill, Health Professions Division, 2000, 966-969, No copy available.
Karpawich et al., Altered cardiac histology following apical right ventricular pacing in patients with congenital atrioventricular block, Pacing Clin Electrophysiol, 22(9), Sep. 1999, 1372-7, Abstract only.
Kolettis et al., Submammary Implantation of a Cardioverter-Defibrillator with a Nonthoractomy Lead System, Am. Heart J., vol. 126, pp. 1222-1223, Nov. 1993.
Krahn et al. Recurrent syncope. Experience with an implantable loop record. Cardiol. Clin., vol. 15(2), May 1997, pp. 316-326 Abstract only.
Leclercq et al., Hemodynamic importance of preserving the normal sequence of ventricular activation in permanent cardiac pacing, Am Heart J., 129(6), Jun. 1995, 1133-41, Abstract only.
Leng et al., Lead Configuration for Defibrillator Implantation in a Patient with Congenital Heart Disease and a Mechanical Prosthetic Tricuspid Valve, PACE, vol. 24, No. 8, Aug. 2001, pp. 1291-1292.
Li, "Vagal nerve stimulation markedly improves long-term survival after chronic heart failure in rats", Circulation, 109(1), Epub Dec. 8, 2003, Jan. 6, 2004, pp. 120-124.
Mannheimer et al., Epidural spinal electrical stimulation in severe angina pectoris, British Heart Journal, 59(1), Jan. 1988, 56-61, Abstract only.
Mannheimer et al., Transcutaneous electrical nerve stimulation in severe angina pectoris, European Heart Journal, 3(4), Aug. 1982, 297-302, Abstract only.
Mannheimer et al., Transcutaneous electrical nerve stimulation (TENS) in angina pectoris, Pain, 26(3), Sep. 1986, 291-300, Abstract only.
Mazgalev et al., Autonomic modification of the atrioventricular node during atrial fibrillation: role in the slowing of ventricular rate, Circulation 99(21), Jun. 1, 1999, 2806-14.
Millar-Craig et al., Circadian variation of blood-pressure, Lancet, 1(8068), Apr. 15, 1978, 795-7, Abstract only.
Minisi et al., Regional left ventricular deafferentation increases baroreflex sensitivity following myocardial infarction, Cardiovasc Res., 58(1), Apr. 1, 2003, 136-41, Abstract only.
Murphy et al., Intractable angina pectoris: management with dorsal column stimulation, Medical Journal of Australia, 146(5), Mar. 2, 1987, 260, Abstract only.
Neil et al. "Effects of electrical stimulation of the aortic nerve on blood pressure and respiration in cats and rabbits under chloralose and nembutal anaesthesia." *Journal of Physiology*. Sep. 1949. vol. 109 (3-4), pp. 392-401.
Park et al., Use of an Implantable Cardioverter Defibrillator in an Eight-Month-Old Infant with Ventricular Fibrillation Arising from a Myocardial Fibroma, PACE, vol. 22, No. 1, pp. 138-139, Jan. 1999.
Peters et al. "Temporal and spatial summation caused by aortic nerve stimulation in rabbits. Effects of stimulation frequencies and amplitudes." Journal of the Autonomic Nervous System. 1989. vol. 27, pp. 193-205, Abstract only.
Peters et al., The principle of electrical carotid sinus nerve stimulation: a nerve pacemaker system for angina pectoris and hypertension therapy, Annals of Biomedical Engineering, 8(4-6), 1980, 445-58, Abstract only.
Philbin et al., Inappropriate shocks delivered by an ICD as a result of sensed potentials from a transcutaneous electronic nerve stimulation unit, Pacing & Clinical Electrophysiology, 21(10), Oct. 1998, 2010-1, Abstract only.
Pinsky et al., Hemodynamic Effects Of Cardiac Cycle-Specific Increases In Intrathoracic Pressure, 6 J. Appl. Physiol., 1986, 604-612.
Pinsky et al., Augmentation Of Cardiac Function By Elevation Of Intrathoracic Pressure, 54 J. Appl. Physiol., 1983, 950-955. Abstract only.
Prakash et al. Asymmetrical distribution of aortic nerve fibers in the pig, Anat Rec., 158(1), May 1967, 51-7, Abstract only.
Rasanen et al., Acute Myocardial Infarction Complicated By Left Ventricular Dysfunction And Respiratory Failure. The Effects Of Continuous Positive Airway Pressure, 87 Chest, 1985, 158-62.
Rees et al., Paroxysmal Nocturnal Dyspnoea and Periodic Respiration, The Lancet, Dec. 22-29, 1979, pp. 1315-1317, Abstract only.
Rosenqvist, The effect of ventricular activation sequence on cardiac performance during pacing, Pacing and Electro-physiology, 19(9), 1996, 1279-1286.
Sato et al. "Novel Therapeutic Strategy against Central Baroreflex Failure: A Bionic Baroreflex System." Circulation. Jul. 1999, vol. 100, pp. 299-304.
Satoh et al., "Role of Hypoxic Drive in Regulation of Postapneic Ventilation During Sleep in Patients with Obstructive Sleep Apnea", Am Rev Respir Dis, 1991 Mar. 143(3): 481-485, Abstract only.
Schauerte et al., Catheter stimulation of cardiac parasympathetic nerves in humans: a novel approach to the cardiac autonomic nervous system, Circulation, 104(20), Nov. 13, 2001, 2430-5.
Schauerte et al., Transvenous parasympathetic cardiac nerve stimulation: an approach for stable sinus rate control, Journal of Cardiovascular Electrophysiology, 10(11), Nov. 1999, 1517-24.
Schauerte, Transvenous Parasympathetic Nerve Stimulation in the Inferior Vena Cava and Atrioventricular Conduction, Journal of Cardiovascular Electrophysiology, 11(1), Jan. 2000, 64-69.
Schauerte et al., Ventricular rate control during atrial fibrillation by cardiac parasympathetic nerve stimulation: a transvenous approach, Journal of the American College of Cariology, 34(7), Dec. 1999, 2043-50.
Scherlag, Endovascular Neural Stimulation via a Novel Basket Electrode Catheter: Comparison of Electrode Configurations, Journal of Interventional Cardiac Electrophysiology, 4(1), Apr. 2000, 219-224, Abstract only.
Schuder et al., Experimental Ventricular Defibrillation with an Automatic and Completely Implanted System, Trans. Am. Soc. Artif. Int. Organs, vol. 16, pp. 207-212, 1970.
Schuder et al., Ventricular Defibrillation in the Dog Using Implanted and Partially Implanted Electrode Systems, Am. J. of Cardiology, vol. 33, pp. 243-247, Feb. 1974.
Schuder et al., Transthoracic Ventricular Defibrillation in the Dog with Truncated and Untruncated Exponential Stimuli, IEEE Trans. On Bio-Medical Engin., vol. BME-18, No. 6, pp. 410-415, Nov. 1971.
Smits et al., Defibrillation Threshold (DFT) Model of a Fully Subcutaneous ICD System, Europace Supplements, vol. 2, Jun. 2001 at col. 778, p. B83.
Steltner et al., Diagnosis of Sleep Apnea by Automatic Analysis of Nasal Pressure and Forced Oscillation Impedance. Am. Journal Respiratory Critical Care Medicine, vol. 165, pp. 940-944, 2002.
Stirbis et al., Optimizing the Shape of Implanted Artificial Pacemakers, Kaunas Medical Institute. Translated from Meditsinskaya Tekhnika, No. 6, pp. 25-27, 1986.
Takahashi, Vagal modulation of ventricular tachyarrhythmias induced by left ansae subclaviae stimulation in rabbits, Japanese Heart Journal, 39(4), Jul. 1998, 503-11, Abstract only.
Thrasher et al., Unloading arterial baroreceptors causes neurogenic hypertension, American Journal Physiol. Regulatory Integrative Comp. Physiol. 2002. vol. 282, R1044-R1053.
Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.
Tse et al., Long-term effect of right ventricular pacing on myocardial perfusion and function, J Am Coll Cardiol., 29(4), Mar. 15, 1997, 744-9.
Vanoli, Vagal stimulation and prevention of sudden death in conscious dogs with a healed myocardial infarction, Circulation Research, 68(5), May 1991, 1471-81, Abstract only.
Veerman et al., Circadian profile of systemic hemodynamics, Hypertension, 26(1), Jul. 1995, 55-9.
Verity et al., Plurivesicular nerve endings in the pulmonary artery, Nature, 211(48), Jul. 30, 1966, 537-8, Abstract only.
Wallick, Selective AV nodal vagal stimulation improves hemodynamics during acute atrial fibrillation in dogs, American Journal of Physiology-Heart & Circulatory Physiology, 281(4), Oct. 2001, H1490-7.

Waninger et al., Electrophysiological control of ventricular rate during atrial fibrillation, Pacing & Clinical Electrophysiology, 23(8), Aug. 2000, 1239-44, Abstract only.
Weber et al., Effects of CPAP and BIPAP on stroke volume in patients with obstructive sleep apnea syndrome. Pneumolgie 1995 Mar; 49(3):233-5. Translated Abstract only.
Wiggers et al., The muscular reactions of the mammalian ventricles to artificial surface stimuli, American Journal of Physiology, 1925, 346-378.
Young et al., The Occurrence of Sleep-disordered Breathing Among Middle-aged Adults, The New England Journal of Medicine, vol. 328, No. 17, pp. 1230-1235.
Zarzoso et al., Noninvasive Fetal Electrocardiogram Extraction: Blind Separation Versus Adaptive Noise Cancellation, IEEE Transactions on Biomedical Engineering, vol. 48, No. 1, pp. 12-18, Jan. 2001.
Zhang et al., Optimal ventricular rate slowing during atrial fibrillation by feedback AV nodal-selective vagal stimulation, American Journal of Physiology-Heart & Circulatory Physiology, 282(3), Mar. 2002, H1102-10.
Zhou et al., Prevention of high incidence of neurally mediated ventricular arrhythmias by afferent nerve stimulation in dogs, Circulation, 101(7), Feb. 22, 2000, 819-24.
Office Action dated Jun. 29, 2007 from co-pending U.S. Appl. No. 10/643,016 filed Aug. 18, 2003.
Office Action from patent Appl. No. 10/939,586 dated Mar. 14, 2008, 15 pages.
Office Action Response submitted Jul. 14, 2008 to office action dated Mar. 14, 2008 from patent Appl. No. 10/939,586, 8 pages.
Office Action from patent Appl. No. 10/939,586 dated Nov. 17, 2008, 28 pages.
Office Action Response submitted Feb. 16, 2009 to office action dated Nov. 17, 2008 from patent Appl. No. 10/939,586, 12 pages.
Office Action Response with RCE submitted Apr. 14, 2009 to office action dated Mar. 14, 2008 from patent Appl. No. 10/939,586, 12 pages.
Notice of Allowance dated Jun. 18, 2009 from patent Appl. No. 10/939,586, 10 pages.

* cited by examiner

Sleep Logbook 4100

| Sleep Period | Onset Date/Time | Offset Date/Time | AHI | USE |
|---|---|---|---|---|
| 9 | 19-NOV-2000 22:26 | 20-NOV-2000 02:55 | 0.5 | 80 |
| 8 | 18-NOV-2000 22:24 | 19-NOV-2000 04:05 | 1.1 | 77 |
| 7 | 18-NOV-2000 03:20 | 18-NOV-2000 08:05 | 2.9 | 69 |
| 6 | 17-NOV-2000 23:46 | 18-NOV-2000 01:19 | 3.0 | 68 |
| 5 | 16-NOV-2000 23:19 | 17-NOV-2000 05:11 | 1.9 | 72 |
| 4 | 15-NOV-2000 22:22 | 16-NOV-2000 08:01 | 2.1 | 71 |
| 3 | 14-NOV-2000 20:10 | 15-NOV-2000 03:45 | 1.8 | 73 |
| 2 | 13-NOV-2000 23:54 | 14-NOV-2000 04:17 | 2.7 | 68 |
| 1 | 12-NOV-2000 22:26 | 13-NOV-2000 06:05 | 1.5 | 74 |

Episodes: Select All, Select None, Save to Disk, Prev, Next, Detail, Print, Signals Episode Query Selection
Show All Episodes Modify Query DETECTION OF PULMONARY DISEASES/DISORDERS
Conditions and Sensors

6201

| | Right Ventricular Egram | Left Ventricular Egram | RA Egram | LA Egram | Accelerometer |
|---|---|---|---|---|---|
| CRM Sensors | x | x | x | x | x |
| CPAP Sensors | | | | | |
| External Non-CPAP/CRM | x | x | x | x | x |

6204

6210-1

| Physiological Changes | RV R-wave Temporal Location | RV R-wave Morphology | RV R-wave Amplitude | RV T-wave Temporal Location | RV T-wave Morphology | RV QT Segment Elevation | LV R-wave Temporal Location | LV R-wave Morphology | LV R-wave Amplitude | LV T-wave Temporal Location | LV T-wave Morphology | LV QT Segment Elevation | RA P-wave Temporal Location | RA P-wave Morphology | RA P-wave Amplitude | RA P-wave Temporal Location | RA P-wave Morphology | RA P-wave Amplitude | Activity | Heart Sounds | Respiration Sounds | Posture |
|---|---|---|---|---|---|---|---|---|---|---|---|---|---|---|---|---|---|---|---|---|---|---|
| **Dyspnea** | | | | | | | | | | | | | | | | | | | | | | |
| Non-specific Dyspnea | | | | | | | | | | | | | | | | | | | | | X | |
| Orthopnea | | | | | | | | | | | | | | | | | | | | | | |
| Exertional Dyspnea | | | | | | | | | | | | | | | | | | | X | | | |
| Paroxysmal Noctural Dyspnea | | | | | | | | | | | | | | | | | | | | | | X |
| | | | | | | | | | | | | | | | | | | | | | | |
| **Blood / Respiratory Gases** | | | | | | | | | | | | | | | | | | | | | | |
| Cyanosis | | | | | | | | | | | | | | | | | | | | | | |
| Hypoxemia | X | | | | | | X | | | | | | X | | | X | | | | | | |
| Hypercapnea | X | | | | | | X | | | | | | X | | | X | | | | | | |
| Low pCO2 | | | | | | | | | | | | | | | | | | | | | | |
| Arterial acidosis | | | | | | | | | | | | | | | | | | | | | | |
| High Alveolar-Arterial pO2 Diff | | | | | | | | | | | | | | | | | | | | | | |
| | | | | | | | | | | | | | | | | | | | | | | |
| **Respiratory Sounds** | | | | | | | | | | | | | | | | | | | | | | |
| Wheezing | | | | | | | | | | | | | | | | | | | | | X | |
| Crackles | | | | | | | | | | | | | | | | | | | | | X | |
| Rhonchi | | | | | | | | | | | | | | | | | | | | | X | |
| Fiction Rub | | | | | | | | | | | | | | | | | | | | | X | |
| Attenuated Breath Sounds | | | | | | | | | | | | | | | | | | | | | X | |
| Snoring | | | | | | | | | | | | | | | | | | | | | X | |

Fig. 62B-1

DETECTION OF PULMONARY DISEASES/DISORDERS
Conditions and Sensors

6201

| | Right Ventricular Egram | Left Ventricular Egram | RA Egram | LA Egram | Accelerometer |
|---|---|---|---|---|---|
| CRM Sensors | x | x | x | x | x |
| CPAP Sensors | | | | | |
| External Non-CPAP/CRM | x | x | x | x | x |

6204

6210-2

| Physiological Changes | RV R-wave Temporal Location | RV R-wave Morphology | RV R-wave Amplitude | RV T-wave Temporal Location | RV T-wave Morphology | RV QT Segment Elevation | LV R-wave Temporal Location | LV R-wave Morphology | LV R-wave Amplitude | LV T-wave Temporal Location | LV T-wave Morphology | LV QT Segment Elevation | RA P-wave Temporal Location | RA P-wave Morphology | RA P-wave Amplitude | RA P-wave Temporal Location | RA P-wave Morphology | RA P-wave Amplitude | Activity | Heart Sounds | Respiration Sounds | Posture |
|---|---|---|---|---|---|---|---|---|---|---|---|---|---|---|---|---|---|---|---|---|---|---|
| | | | | | | | | | | | | | | | | | | | | | | |
| **Pulmonary Function** | | | | | | | | | | | | | | | | | | | | | | |
| Low FEV, FVC, FEV/FVC | | | | | | | | | | | | | | | | | | | | | | |
| Low FEF | | | | | | | | | | | | | | | | | | | | | | |
| High FRC, TLC | | | | | | | | | | | | | | | | | | | | | | |
| High RV | | | | | | | | | | | | | | | | | | | | | | |
| High Lung Compliance | | | | | | | | | | | | | | | | | | | | | | |
| Slow Exhalation | | | | | | | | | | | | | | | | | | | | | | |
| Tachypnea | | | | | | | | | | | | | | | | | | | | | | |
| Shallow (Low Tidal Volume) Breathing | | | X | | | | | | X | | | | | | X | | | X | | | X | |
| High Minute Ventilation | | | | | | | | | | | | | | | | | | | | | | |
| Respiratory Failure | | | | | | | | | | | | | | | | | | | | | | |
| Reduced Diffusion Capacity | | | | | | | | | | | | | | | | | | | | | | |
| | | | | | | | | | | | | | | | | | | | | | | |

Fig. 62B-2

DETECTION OF PULMONARY DISEASES/DISORDERS
Conditions and Sensors

| | Transthoracic Impedance | Blood Pressure | Blood Gas |
|---|---|---|---|
| CRM Sensors | x | x | x |
| CPAP Sensors | | | |
| External Non-CPAP/CRM | x | x | x |

6201

6204

| Physiological Changes | Respiration Rate | Tidal Volume | Minute Ventilation | Inspiration Time | Exhalation Time | Heart Motion Morphology | DC Thoracic Impedance | Systolic Blood Pressure | Diastolic Blood Pressure | Pulse Pressure | Wedge Pressure | Contractility (dP/dt) | Blood pO2 | Blood pCO2 | Arterial / Venous pO2 |
|---|---|---|---|---|---|---|---|---|---|---|---|---|---|---|---|
| **Dyspnea** | | | | | | | | | | | | | | | |
| Non-specific Dyspnea | X | X | X | X | X | | | | | | | | X | X | X |
| Orthopnea | | | | | | | | | | | | | X | X | X |
| Exertional Dyspnea | X | X | X | | | | | | | | | | X | X | X |
| Paroxysmal Noctural Dyspnea | X | X | X | | | | | | | | | | X | X | X |
| | | | | | | | | | | | | | | | |
| **Blood / Respiratory Gases** | | | | | | | | | | | | | | | |
| Cyanosis | | | | | | | | | | | | | X | | X |
| Hypoxemia | X | X | | | | | | X | X | X | | | D | | X |
| Hypercapnea | X | X | | | | | | X | X | X | | | | X | |
| Low pCO2 | X | X | | | | | | | | | | | | | |
| Arterial acidosis | | | | | | | | | | | | | | | |
| High Alveolar-Arterial pO2 Dif | | | | | | | | | | | | | X | | X |
| | | | | | | | | | | | | | | | |
| **Respiratory Sounds** | | | | | | | | | | | | | | | |
| Wheezing | | | | X | X | | | | | | | | | | |
| Crackles | | | | X | X | | | | | | | | | | |
| Rhonchi | | | | X | X | | | | | | | | | | |
| Fiction Rub | | | | X | X | | | | | | | | | | |
| Attenuated Breath Sounds | | | | X | X | | | | | | | | | | |
| Snoring | | | | X | X | | | | | | | | | | |

DETECTION OF PULMONARY DISEASES/DISORDERS
Conditions and Sensors

6201

| | Transthoracic Impedance | Blood Pressure | Blood Gas |
|---|---|---|---|
| CRM Sensors | x | x | x |
| CPAP Sensors | | | |
| External Non-CPAP/CRM | x | x | x |

6204

6210-4

| Physiological Changes | Respiration Rate | Tidal Volume | Minute Ventilation | Inspiration Time | Exhalation Time | Heart Motion Morphology | DC Thoracic Impedance | Systolic Blood Pressure | Diastolic Blood Pressure | Pulse Pressure | Wedge Pressure | Contractility (dP/dt) | Blood pO2 | Blood pCO2 | Arterial / Venous pO2 |
|---|---|---|---|---|---|---|---|---|---|---|---|---|---|---|---|
| | | | | | | | | | | | | | | | |
| **Pulmonary Function** | | | | | | | | | | | | | | | |
| Low FEV, FVC, FEV/FVC | | | X | X | | | | | | | | | | | |
| Low FEF | | | X | X | | | | | | | | | | | |
| High FRC, TLC | | | X | X | | | | | | | | | | | |
| High RV | | | X | X | | | | | | | | | | | |
| High Lung Compliance | | | X | X | | | | | | | | | | | |
| Slow Exhalation | | | | X | | | | | | | | | | | |
| Tachypnea | X | | | | | | | | | | | | | | |
| Shallow (Low Tidal Volume) Breathing | X | X | X | | | | | | | | | | | | |
| High Minute Ventilation | X | X | X | | | | | | | | | | | | |
| Respiratory Failure | X | X | X | X | X | | | X | X | X | X | X | X | X | X |
| Reduced Diffusion Capacity | | | | | | | | | | | | | | | |
| | | | | | | | | | | | | | | | |

Fig. 62B-4

DETECTION OF PULMONARY DISEASES/DISORDERS
Conditions and Sensors

6201

| | Vent Gas | Vent Flow | Vent Pres | pH | Finger | Scale | Temp | Data Base | Direct Patient Query |
|---|---|---|---|---|---|---|---|---|---|
| CRM Sensors | | | | x | | | x | | |
| CPAP Sensors | x | x | x | | | | | | |
| External Non-CPAP/CRM | x | x | x | | x | x | x | x | x |

6204

6212-1

| Physiological Changes | Exhaled % O2 | Exhaled % CO2 | X | Expiratory Flow | Inspiratory Flow | X | Expiratory Pressure | Inspiratory Pressure | X | Blood pH | Relative Pulse Pressure | Blood pO2 | Weight | X | Core Temperature | X | Medications | History | X | Pain | Abnormal Breathing / Coughing | Duration of Symptoms | Falls | Other Symptoms |
|---|---|---|---|---|---|---|---|---|---|---|---|---|---|---|---|---|---|---|---|---|---|---|---|---|
| **Dyspnea** | | | | | | | | | | | | | | | | | | | | | | | | |
| Non-specific Dyspnea | X | X | | X | X | | | | | | | X | | | | | | | | | D | D | | |
| Orthopnea | X | X | | X | X | | | | | | | X | | | | | | | | | D | D | | |
| Exertional Dyspnea | X | X | | X | X | | | | | | | X | | | | | | | | | D | D | | |
| Paroxysmal Noctural Dyspnea | X | X | | X | X | | | | | | | X | | | | | | | | | D | D | | |
| | | | | | | | | | | | | | | | | | | | | | | | | |
| **Blood / Respiratory Gases** | | | | | | | | | | | | | | | | | | | | | | | | |
| Cyanosis | X | | | | | | | | | | | X | | | | | | | | | D | D | | |
| Hypoxemia | X | | | | | | | | | | | X | | | | | | | | | | | | |
| Hypercapnea | | X | | | | | | | | X | | | | | | | | | | | | | | |
| Low pCO2 | | X | | | | | | | | X | | | | | | | | | | | | | | |
| Arterial acidosis | | X | | | | | | | | X | | | | | | | | | | | | | | |
| High Alveolar-Arterial pO2 Diff | X | | | | | | | | | | | X | | | | | | | | | | | | |
| | | | | | | | | | | | | | | | | | | | | | | | | |
| **Respiratory Sounds** | | | | | | | | | | | | | | | | | | | | | | | | |
| Wheezing | | | | | | | | | | | | | | | | | | | | | X | X | | |
| Crackles | | | | | | | | | | | | | | | | | | | | | X | X | | |
| Rhonchi | | | | | | | | | | | | | | | | | | | | | | | | |
| Fiction Rub | | | | | | | | | | | | | | | | | | | | | | | | |
| Attenuated Breath Sounds | | | | | | | | | | | | | | | | | | | | | | | | |
| Snoring | | | | | | | | | | | | | | | | | | | | | D | D | | |

Fig. 62C-1

DETECTION OF PULMONARY DISEASES/DISORDERS
Conditions and Sensors

6201

| | Vent Gas | Vent Flow | Vent Pres | pH | Finger | Scale | Temp | Data Base | Direct Patient Query |
|---|---|---|---|---|---|---|---|---|---|
| CRM Sensors | | | | x | | | x | | |
| CPAP Sensors | x | x | x | | | | | | |
| External Non-CPAP/CRM | x | x | x | | x | x | x | x | x |

6204

6212-2

| Physiological Changes | Exhaled % O2 | Exhaled % CO2 | X | Expiratory Flow | Inspiratory Flow | X | Expiratory Pressure | Inspiratory Pressure | X | Blood pH | Relative Pulse Pressure | Blood pO2 | Weight | X | Core Temperature | X | Medications | History | X | Pain | Abnormal Breathing / Coughing | Duration of Symptoms | Falls | Other Symptoms |
|---|---|---|---|---|---|---|---|---|---|---|---|---|---|---|---|---|---|---|---|---|---|---|---|---|
| | | | | | | | | | | | | | | | | | | | | | | | | |
| **Pulmonary Function** | | | | | | | | | | | | | | | | | | | | | | | | |
| Low FEV, FVC, FEV/FVC | | | | X | X | | X | X | | | | | | | | | | | | | | | | |
| Low FEF | | | | X | X | | X | X | | | | | | | | | | | | | | | | |
| High FRC, TLC | | | | X | X | | X | X | | | | | | | | | | | | | | | | |
| High RV | | | | X | X | | X | X | | | | | | | | | | | | | | | | |
| High Lung Compliance | | | | X | X | | X | X | | | | | | | | | | | | | | | | |
| Slow Exhalation | | | | X | X | | X | X | | | | | | | | | | | | | | | | |
| Tachypnea | | | | | | | | | | | | | | | | | | | | | X | X | | |
| Shallow (Low Tidal Volume) Breathing | | | | | | | | | | | | | | | | | | | | | X | X | | |
| High Minute Ventilation | | | | | | | | | | | | | | | | | | | | | | | | |
| Respiratory Failure | X | X | | | | | | | | X | X | X | | | | | | | | | X | X | | |
| Reduced Diffusion Capacity | | | | | | | | | | | | | | | | | | | | | | | | |
| | | | | | | | | | | | | | | | | | | | | | | | | |

Fig. 62C-2

DETECTION OF PULMONARY DISEASES/DISORDERS
Conditions and Sensors

6201

| | Right Ventricular Egram | Left Ventricular Egram | RA Egram | LA Egram | Accelerometer |
|---|---|---|---|---|---|
| CRM Sensors | x | x | x | x | x |
| CPAP Sensors | | | | | |
| External Non-CPAP/CRM | x | x | x | x | x |

6204

6214-1

| Physiological Changes | RV R-wave Temporal Location | RV R-wave Morphology | RV R-wave Amplitude | RV T-wave Temporal Location | RV T-wave Morphology | RV QT Segment Elevation | LV R-wave Temporal Location | LV R-wave Morphology | LV R-wave Amplitude | LV T-wave Temporal Location | LV T-wave Morphology | LV QT Segment Elevation | RA P-wave Temporal Location | RA P-wave Morphology | RA P-wave Amplitude | RA P-wave Temporal Location | RA P-wave Morphology | RA P-wave Amplitude | Activity | Heart Sounds | Respiration Sounds | Posture |
|---|---|---|---|---|---|---|---|---|---|---|---|---|---|---|---|---|---|---|---|---|---|---|
| **Other Pulmonary** | | | | | | | | | | | | | | | | | | | | | | |
| Hemoptysis | | | | | | | | | | | | | | | | | | | | | | |
| Cough | | | | | | | | | | | | | | | | | | | | | X | |
| Pleuritic Chest Pain | | | | | X | X | | | | | X | X | | | | | | | | | X | |
| Local Inflammation | | | | | | | | | | | | | | | | | | | | | | |
| Excess Mucous Production | | | | | | | | | | | | | | | | | | | | | X | |
| Chest Pain | | | | | X | X | | | | | X | X | | | | | | | | | | |
| Respiratory Infection (slight. elev. WBC) | | | | | | | | | | | | | | | | | | | | | | |
| Pulmonary Mucus | | | | | | | | | | | | | | | | | | | | | | |
| Overinflat. Lungs->barrel-shaped chest | | | | | | | | | | | | | | | | | | | | | | |
| Alveolar wall breakdown | | | | | | | | | | | | | | | | | | | | | | |
| Mucosal Pulmonary Edema | | | | | | | | | | | | | | | | | | | | | | |
| Ventilation-perfusion mismatch | | | | | | | | | | | | | | | | | | | | | | |
| Subepithelial Fibrosis (chronically) | | | | | | | | | | | | | | | | | | | | | | |
| Respiratory Muscle Fatigue | | | | | | | | | | | | | | | | | | | | | | |
| High small airway resistance | | | | | | | | | | | | | | | | | | | | | X | |
| Hoarseness | | | | | | | | | | | | | | | | | | | | | | |
| | | | | | | | | | | | | | | | | | | | | | | |

Fig. 62D-1

DETECTION OF PULMONARY DISEASES/DISORDERS
Conditions and Sensors

6201

6204

6214-2

| | Right Ventricular Egram | | | | | | Left Ventricular Egram | | | | | | RA Egram | | | LA Egram | | | Accelerometer | | | |
|---|---|---|---|---|---|---|---|---|---|---|---|---|---|---|---|---|---|---|---|---|---|---|
| CRM Sensors | x | | | | | | x | | | | | | x | | | x | | | x | | | |
| CPAP Sensors | | | | | | | | | | | | | | | | | | | | | | |
| External Non-CPAP/CRM | x | | | | | | x | | | | | | x | | | x | | | x | | | |
| Physiological Changes | RV R-wave Temporal Location | RV R-wave Morphology | RV R-wave Amplitude | RV T-wave Temporal Location | RV T-wave Morphology | RV QT Segment Elevation | LV R-wave Temporal Location | LV R-wave Morphology | LV R-wave Amplitude | LV T-wave Temporal Location | LV T-wave Morphology | LV QT Segment Elevation | RA P-wave Temporal Location | RA P-wave Morphology | RA P-wave Amplitude | RA P-wave Temporal Location | RA P-wave Morphology | RA P-wave Amplitude | Activity | Heart Sounds | Respiration Sounds | Posture |
| **Cardiovascular** | | | | | | | | | | | | | | | | | | | | | | |
| Pulmonary Hypertension | | | | | | | | | | | | | | | | | | | | | | |
| High Pulmonary Vascular Resistance | | | | | | | | | | | | | | | | | | | | | | |
| Tachycardia | X | | | | | | X | | | | | | X | | | X | | | | | | |
| Circulatory Collapse | | | | | | | | | | | | | | | | | | | | | | |
| Pulsus Paradoxicus | | | | | | | | | | | | | | | | | | | | | | |
| Syncope | | | | | | | | | | | | | | | | | | | | | | |
| Hypertension | | | | | | | | | | | | | | | | | | | | | | |
| S3 Heart Sound | | | | | | | | | | | | | | | | | | | | X | | |
| Split S2 Heart Sound | | | | | | | | | | | | | | | | | | | | X | | |
| RV Hypertrophy | | | X | | | | | | | | | | | | | | | | | | | |
| Systolic Murmur | | | | | | | | | | | | | | | | | | | | X | | |
| | | | | | | | | | | | | | | | | | | | | | | |
| **General Systemic** | | | | | | | | | | | | | | | | | | | | | | |
| Fever | | | | | | | | | | | | | | | | | | | | | | |
| Weight Loss | | | | | | | | | | | | | | | | | | | | | | |
| Weight Gain | | | | | | | | | | | | | | | | | | | | | | |
| Night Sweats | | | | | | | | | | | | | | | | | | | | | | |
| Peripheral Edema | | | | | | | | | | | | | | | | | | | | | | |
| High Hemoglobin | | | | | | | | | | | | | | | | | | | | | | |
| Fatigue | | | | | | | | | | | | | | | | | | | X | | | |
| Joint Pain | | | | | | | | | | | | | | | | | | | X | | | |
| Hypersomnolence | | | | | | | | | | | | | | | | | | | X | | | |

Fig. 62D-2

DETECTION OF PULMONARY DISEASES/DISORDERS
Conditions and Sensors

6201

| | Transthoracic Impedance | Blood Pressure | Blood Gas |
|---|---|---|---|
| CRM Sensors | x | x | x |
| CPAP Sensors | | | |
| External Non-CPAP/CRM | x | x | x |

6204

6214-3

| Physiological Changes | Respiration Rate | Tidal Volume | Minute Ventilation | Inspiration Time | Exhalation Time | Heart Motion Morphology | DC Thoracic Impedance | Systolic Blood Pressure | Diastolic Blood Pressure | Pulse Pressure | Wedge Pressure | Contractility (dP/dt) | Blood pO2 | Blood pCO2 | Arterial / Venous pO2 |
|---|---|---|---|---|---|---|---|---|---|---|---|---|---|---|---|
| **Other Pulmonary** | | | | | | | | | | | | | | | |
| Hemoptysis | | | | | | | | | | | | | | | |
| Cough | | X | | | | | | | | | | | | | |
| Pleuritic Chest Pain | | X | X | X | X | | | | | | | | | | |
| Local Inflammation | | | | | | | | | | | | | | | |
| Excess Mucous Production | | | | X | X | | | | | | | | | | |
| Chest Pain | X | X | X | X | X | | | | | | | | | | |
| Respiratory Infection (slight. elev. WBC) | | | | | | | | | | | | | | | |
| Pulmonary Mucus | X | X | X | X | X | | | | | | | | | | |
| Overinflat. Lungs->barrel-shaped chest | X | X | X | X | X | | X | | | | | | | | |
| Alveolar wall breakdown | | | | | | | | | | | | | | | |
| Mucosal Pulmonary Edema | X | X | X | X | X | | X | | | | | | | | |
| Ventilation-perfusion mismatch | | | | | | | | | | | | | X | X | X |
| Subepithelial Fibrosis (chronically) | | | | | | | | | | | | | | | |
| Respiratory Muscle Fatigue | X | X | X | X | X | | | | | | | | | | |
| High small airway resistance | X | X | X | X | X | | | | | | | | | | |
| Hoarseness | | | | | | | | | | | | | | | |
| | | | | | | | | | | | | | | | |

Fig. 62D-3

DETECTION OF PULMONARY DISEASES/DISORDERS
Conditions and Sensors

6201

| | Transthoracic Impedance | Blood Pressure | Blood Gas |
|---|---|---|---|
| CRM Sensors | x | x | x |
| CPAP Sensors | | | |
| External Non-CPAP/CRM | x | x | x |

6204

6214-4

| Physiological Changes | Respiration Rate | Tidal Volume | Minute Ventilation | Inspiration Time | Exhalation Time | Heart Motion Morphology | DC Thoracic Impedance | Systolic Blood Pressure | Diastolic Blood Pressure | Pulse Pressure | Wedge Pressure | Contractility (dP/dt) | Blood pO2 | Blood pCO2 | Arterial / Venous pO2 |
|---|---|---|---|---|---|---|---|---|---|---|---|---|---|---|---|
| **Cardiovascular** | | | | | | | | | | | | | | | |
| Pulmonary Hypertension | | | | | | | | | | | | | | | |
| High Pulmonary Vascular Resistance | | | | | | | | | | | | | | | |
| Tachycardia | | | | | | X | | X | X | | | | | | |
| Circulatory Collapse | | | | | | | | X | X | X | X | X | X | X | X |
| Pulsus Paradoxicus | | | | | | | | X | X | X | X | X | | | |
| Syncope | | | | | | | | X | X | X | | | X | | X |
| Hypertension | | | | | | | | D | D | | | | | | |
| S3 Heart Sound | | | | | | | | | | | | | | | |
| Split S2 Heart Sound | | | | | | | | | | | | | | | |
| RV Hypertrophy | | | | | | | | | | | | | | | |
| Systolic Murmur | | | | | | | | | | | | | | | |
| | | | | | | | | | | | | | | | |
| **General Systemic** | | | | | | | | | | | | | | | |
| Fever | | | | | | | | X | | | | | | | |
| Weight Loss | | | | | | | | | | | | | | | |
| Weight Gain | | | | | | | | | | | | | | | |
| Night Sweats | | | | | | | | | | | | | | | |
| Peripheral Edema | | | | | | | | | | | | | | | |
| High Hemoglobin | | | | | | | | | | | | | | | |
| Fatigue | | | X | | | | | | | | | | | | |
| Joint Pain | | | X | | | | | | | | | | | | |
| Hypersomnolence | | | X | | | | | | | | | | | | |

Fig. 62D-4

DETECTION OF PULMONARY DISEASES/DISORDERS
Conditions and Sensors

6201

| | Vent Gas | Vent Flow | Vent Pres | pH | Finger | Scale | Temp | Data Base | Direct Patient Query |
|---|---|---|---|---|---|---|---|---|---|
| CRM Sensors | | | | x | | | x | | |
| CPAP Sensors | x | x | x | | | | | | |
| External Non-CPAP/CRM | x | x | x | | x | x | x | x | x |

6204

6216-1

| Physiological Changes | Exhaled % O2 | Exhaled % CO2 | X | Expiratory Flow | Inspiratory Flow | X | Expiratory Pressure | Inspiratory Pressure | X | Blood pH | Relative Pulse Pressure | Blood pO2 | Weight | X | Core Temperature | X | Medications | History | X | Pain | Abnormal Breathing / Coughing | Duration of Symptoms | Falls | Other Symptoms |
|---|---|---|---|---|---|---|---|---|---|---|---|---|---|---|---|---|---|---|---|---|---|---|---|---|
| **Other Pulmonary** | | | | | | | | | | | | | | | | | | | | | | | | |
| Hemoptysis | | | | | | | | | | | | | | | | | | | | | D | D | | |
| Cough | | | | | | | | | | | | | | | | | | | | | D | D | | |
| Pleuritic Chest Pain | | | | | | | | | | | | | | | | | | | | D | | D | | |
| Local Inflammation | | | | | | | | | | | | | | | X | | | | | | | | | |
| Excess Mucous Production | | | | | | | | | | | | | | | | | | | | | D | D | | |
| Chest Pain | | | | | | | | | | | | | | | | | | | | D | | D | | |
| Respiratory Infection (slight. elev. WBC) | | | | | | | | | | | | | | | | | | | | | | | | |
| Pulmonary Mucus | | | | | | | | | | | | | | | | | | | | | | | | |
| Overinflat. Lungs-->barrel-shaped chest | | | | | | | | | | | | | | | | | | | | | | | | |
| Alveolar wall breakdown | | | | | | | | | | | | | | | | | | | | | | | | |
| Mucosal Pulmonary Edema | | | | | | | | | | | | | | | | | | | | | | | | |
| Ventilation-perfusion mismatch | X | X | | | | | | | | | | | | | | | | | | | | | | |
| Subepithelial Fibrosis (chronically) | | | | | | | | | | | | | | | | | | | | | | | | |
| Respiratory Muscle Fatigue | | | | | | | | | | | | | | | | | | | | | | | | |
| High small airway resistance | | | | | | | | | | | | | | | | | | | | | | | | |
| Hoarseness | | | | | | | | | | | | | | | | | | | | | | | | |
| | | | | | | | | | | | | | | | | | | | | | | | | |

Fig. 62E-1

Conditions and Sensors DETECTION OF PULMONARY DISEASES/DISORDERS

6201

| | Vent Gas | Vent Flow | Vent Pres | pH | Finger | Scale | Temp | Data Base | Direct Patient Query |
|---|---|---|---|---|---|---|---|---|---|
| CRM Sensors | | | | x | | | x | | |
| CPAP Sensors | x | x | x | | | | | | |
| External Non-CPAP/CRM | x | x | x | | x | x | x | x | x |

6204

6216-2

| Physiological Changes | Exhaled % O2 | Exhaled % CO2 | X | Expiratory Flow | Inspiratory Flow | X | Expiratory Pressure | Inspiratory Pressure | X | Blood pH | Relative Pulse Pressure | Blood pO2 | Weight | X | Core Temperature | X | Medications | History | X | Pain | Abnormal Breathing / Coughing | Duration of Symptoms | Falls | Other Symptoms |
|---|---|---|---|---|---|---|---|---|---|---|---|---|---|---|---|---|---|---|---|---|---|---|---|---|
| **Cardiovascular** | | | | | | | | | | | | | | | | | | | | | | | | |
| Pulmonary Hypertension | | | | | | | | | | | | | | | | | | | | | | | | |
| High Pulmonary Vascular Resistance | | | | | | | | | | | | | | | | | | | | | | | | |
| Tachycardia | | | | | | | | | | | | | | | | | | | | | | | | |
| Circulatory Collapse | X | X | | | | | | | | X | X | X | | | | | | | | | | | | |
| Pulsus Paradoxicus | | | | | | | | | | | X | | | | | | | | | | | | | |
| Syncope | | | | | | | | | | | | X | | | | | | | | | | | | |
| Hypertension | | | | | | | | | | | | | | | | | | | | | | | | |
| S3 Heart Sound | | | | | | | | | | | | | | | | | | | | | | | | |
| Split S2 Heart Sound | | | | | | | | | | | | | | | | | | | | | | | | |
| RV Hypertrophy | | | | | | | | | | | | | | | | | | | | | | | | |
| Systolic Murmur | | | | | | | | | | | | | | | | | | | | | | | | |
| | | | | | | | | | | | | | | | | | | | | | | | | |
| **General Systemic** | | | | | | | | | | | | | | | | | | | | | | | | |
| Fever | | | | | | | | | | | | | | | X | | | | | | | D | | D |
| Weight Loss | | | | | | | | | | | | | X | | | | | X | | | | D | | D |
| Weight Gain | | | | | | | | | | | | | X | | | | | | | | | D | | D |
| Night Sweats | | | | | | | | | | | | | | | ? | | | | | | | D | | D |
| Peripheral Edema | | | | | | | | | | | | | X | | | | | | | | | | | |
| High Hemoglobin | | | | | | | | | | | | | | | | | | | | | | | | |
| Fatigue | | | | | | | | | | | | | | | | | | | | | | D | | D |
| Joint Pain | | | | | | | | | | | | | | | | | | | | | | D | | D |
| Hypersomnolence | | | | | | | | | | | | | | | | | | | | | | D | | D |

DETECTION OF PULMONARY DISEASES/DISORDERS

Pulmonary Diseases/Disorders

6204

| Physiological Changes | Obstructive (COPD) | | | Restictive | | | Infectious | | | | | Pul Vasculature | | | | Pleural | | | Rhythm | | | | Other | | |
|---|---|---|---|---|---|---|---|---|---|---|---|---|---|---|---|---|---|---|---|---|---|---|---|---|---|
| | Chronic Bronchitis | Emphysema | Asthma | Sarcoidosis | Pulmonary Fibrosis | Pneumoconiosis | Bronchitis | Pneumonia | Brochiolitis | Tuberculosis | Bronchiectasis | Pulmonary Hypertension | Pulmonary Edema | Pulmonary Embolism | Atelectasis | Pleural Effusion | Pneumothorax | Hemothorax (See Pleural Effusion) | Apnea (obstructive & central) | Hypopnea (obstructive & central) | Cheyne-Stokes | Periodic Breathing | Lung Cancer | ARDS | x |
| **Dyspnea** | | | | | | | | | | | | | | | | | | | | | | | | | |
| Non-specific Dyspnea | X | X | X | X | X | X | | | | X | X | | X | X | X | | X | X | | | X | X | | | |
| Orthopnea | | | X | | | | | | | | | | X | | | | | | | | | | | | |
| Exertional Dyspnea | | X | | | X | | | | | | | X | X | X | | | | | | | | | | | |
| Paroxysmal Noctural Dyspnea | | | X | | | | | | | | | | X | | | | | | | | | | | | |
| | | | | | | | | | | | | | | | | | | | | | | | | | |
| **Blood / Respiratory Gases** | | | | | | | | | | | | | | | | | | | | | | | | | |
| Cyanosis | X | X | | | X | | | X | | | X | | X | | | | | | X | X | X | X | | | |
| Hypoxemia | X | X | | | X | | | | | | | X | X | X | X | | | X | X | X | X | X | | | |
| Hypercapnea | X | X | | | X | | | | | | | | | | X | | | X | X | X | X | X | | | |
| Low pCO2 | | | | | X | | | | | | | | | | | | | | X | X | X | | | | |
| Arterial acidosis | X | X | | | | | | | | | | | | | | | | | | | | | | | |
| High Alveolar-Arterial pO2 Diff | X | X | X | | | | | | | | | | | | | | | | | | | | | | |
| | | | | | | | | | | | | | | | | | | | | | | | | | |
| **Respiratory Sounds** | | | | | | | | | | | | | | | | | | | | | | | | | |
| Wheezing | | X | X | | | | | | X | | X | | X | | | X | | | | | | | | | |
| Crackles | X | X | | X | X | | X | | | X | | | X | | | | | | | | X | X | | | |
| Rhonchi | X | X | X | | | | X | | | | | | X | | | | | | | | | | | | |
| Fiction Rub | | | | | | | | | | | | | | X | | | | | | | | | | | |
| Attenuated Breath Sounds | X | X | X | | | | | | | | | | | | | | | | | | | | | | |
| Snoring | | | | | | | | | | | | | | | | X | | | X | X | X | X | | | |

Fig. 62F-2

DETECTION OF PULMONARY DISEASES/DISORDERS 6220-2

6204

| Physiological Changes | Chronic Bronchitis | Emphysema | Asthma | Sarcoidosis | Pulmonary Fibrosis | Pneumoconiosis | Bronchitis | Pneumonia | Brochiolitis | Tuberculosis | Bronchiectasis | Pulmonary Hypertension | Pulmonary Edema | Pulmonary Embolism | Atelectasis | Pleural Effusion | Pneumothorax | Hemothorax (See Pleural Effusion) | Apnea (obstructive & central) | Hypopnea (obstructive & central) | Cheyne-Stokes | Periodic Breathing | Lung Cancer | ARDS | x |
|---|---|---|---|---|---|---|---|---|---|---|---|---|---|---|---|---|---|---|---|---|---|---|---|---|---|
| Pulmonary Diseases/Disorders | COPD Obstructive | | | Restictive | | | Infectious | | | | | Pul Vasculature | | | | Pleural | | | Rhythm | | | | Other | | |
| | | | | | | | | | | | | | | | | | | | | | | | | | |
| **Pulmonary Function** | | | | | | | | | | | | | | | | | | | | | | | | | |
| Low FEV, FVC, FEV/FVC | X | X | X | | | | | | | | | | | | | | | | | | | | | | |
| Low FEF | | | X | | | | | | | | | | | | | | | | | | | | | | |
| High FRC, TLC | X | X | | | | | | | | | | | | | | | | | | | | | | | |
| High RV | | | X | | | | | | | | | | | | | | | | | | | | | | |
| High Lung Compliance | | X | | | | | | | | | | | | | | | | | | | | | | | |
| Slow Exhalation | X | X | X | | | | | | | | | | | | | | | | | | | | | | |
| Tachypnea | | X | X | | X | | | X | X | | | | X | | | X | | | | | | | | | |
| Shallow (Low Tidal Volume) Breathing | | X | | | X | | | X | | | | | X | | | | | | | | | | | | |
| High Minute Ventilation | X | X | | | | | | | | | | | | | | | | | | | | | | | |
| Respiratory Failure | | | | | | | | | | | | | | | | | | X | | | | | | | |
| Reduced Diffusion Capacity | X | X | | | X | | | | | | | | | | | | | | | | | | | | |
| | | | | | | | | | | | | | | | | | | | | | | | | | |

Fig. 62G-1

DETECTION OF PULMONARY DISEASES/DISORDERS 6222-1

6204

Pulmonary Diseases/Disorders: COPD; Obstructive; Restictive; Infectious; Pul Vasculature; Pleural; Rhythm; Other

| Physiological Changes | Chronic Bronchitis | Emphysema | Asthma | Sarcoidosis | Pulmonary Fibrosis | Pneumoconiosis | Bronchitis | Pneumonia | Brochiolitis | Tuberculosis | Bronchiectasis | Pulmonectasis | Pulmonary Hypertension | Pulmonary Edema | Pulmonary Embolism | Atelectasis | Pleural Effusion | Pneumothorax | Hemothorax (See Pleural Effusion) | Apnea (obstructive & central) | Hypopnea (obstructive & central) | Cheyne-Stokes | Periodic Breathing | Lung Cancer | ARDS |
|---|---|---|---|---|---|---|---|---|---|---|---|---|---|---|---|---|---|---|---|---|---|---|---|---|---|
| **Other Pulmonary** | | | | | | | | | | | | | | | | | | | | | | | | | |
| Hemoptysis | X | | | | | | X | X | | X | X | X | X | X | | | | | | | | | | | |
| Cough | X | X | X | X | X | X | | X | X | X | X | | X | | | | | | | | | | | | |
| Pleuritic Chest Pain | | | | | | | | | | X | | | | | | | | | | | | | | | |
| Local Inflammation | | | | | | | X | | | | | | | | | | | | | | | | | | |
| Excess Mucous Production | | | | | | | X | | | | | | | | | | | | | | | | | | |
| Chest Pain | | | | | | | X | | | | | X | | X | | X | X | X | | | | | | | |
| Respiratory Infection (slight. elev. WBC) | | X | | | | | X | X | X | X | X | | | | | | | | | | | | | | |
| Pulmonary Mucus | X | X | X | | | | | | | | | | | | | | | | | | | | | | |
| Overinflat. Lungs-->barrel-shaped chest | X | X | X | | | | | | | | | | | | | | | | | | | | | | |
| Alveolar wall breakdown | X | | | | | | | | | | | | | | | | | | | | | | | | |
| Mucosal Pulmonary Edema | | | X | | | | | | | | | | | | | | | | | | | | | | |
| Ventilation-perfusion mismatch | X | X | X | | | | | | | | | | | | | | | | | | | | | | |
| Subepithelial Fibrosis (chronically) | | | X | | | | | | | | | | | | | | | | | | | | | | |
| Respiratory Muscle Fatigue | | | | | | | | | | | | | | | | | | | | | | | | | |
| High small airway resistance | | X | | | | | | | | | | | | | | | | | | | | | | | |
| Hoarseness | | | | | | | | | | | | X | | | | | | | | | | | | | |
| | | | | | | | | | | | | | | | | | | | | | | | | | |

Fig. 62G-2

DETECTION OF PULMONARY DISEASES/DISORDERS
Pulmonary Diseases/Disorders 6222-2

6204

| COPD | | | | | | | | | | | | | | | | | | | | | | | | | |
|---|---|---|---|---|---|---|---|---|---|---|---|---|---|---|---|---|---|---|---|---|---|---|---|---|---|
| Obstructive | | | Restictive | | | Infectious | | | | | Pul Vasculature | | | | Pleural | | | Rhythm | | | | Other | | | |
| Chronic Bronchitis | Emphysema | Asthma | Sarcoidosis | Pulmonary Fibrosis | Pneumoconiosis | Bronchitis | Pneumonia | Brochiolitis | Tuberculosis | Bronchiectasis | Pulmonary Hypertension | Pulmonary Edema | Pulmonary Embolism | Atelectasis | Pleural Effusion | Pneumothorax | Hemothorax (See Pleural Effusion) | Apnea (obstructive & central) | Hypopnea (obstructive & central) | Cheyne-Stokes | Periodic Breathing | Lung Cancer | ARDS | x | Physiological Changes |
| | | | | | | | | | | | | | | | | | | | | | | | | | **Cardiovascular** |
| X | X | X | | X | | | | | | X | X | X | | | | | | | | | | | | | Pulmonary Hypertension |
| X | X | X | | | | | | | | X | | | | | | | | X | X | X | X | | | | High Pulmomary Vascular Resistance |
| | | X | | | | | X | | | | | | X | | X | | | X | X | X | X | | | | Tachycardia |
| | | | | | | | | | | | | | | | | | X | | | | | | | | Circulatory Collapse |
| X | X | X | | | | | | | | | | | | | | | | | | | | | | | Pulsus Paradoxicus |
| | | | | | | | | | | | X | X | X | | | | | | | | | | | | Syncope |
| | | | | | | | | | | | | | | | | | | X | X | X | | | | | Hypertension |
| | | | | | | | | | | | | X | | | | | | | | | | | | | S3 Heart Sound |
| | | | | | | | | | | | X | | | | | | | | | | | | | | Split S2 Heart Sound |
| | | | | | | | | | | | X | | | | | | | | | | | | | | RV Hypertrophy |
| | | | | | | | | | | | X | | | | | | | | | | | | | | Systolic Murmur |
| | | | | | | | | | | | | | | | | | | | | | | | | | |
| | | | | | | | | | | | | | | | | | | | | | | | | | **General Systemic** |
| | | | X | X | | X | X | X | X | | | | X | | | | | | | | | | | | Fever |
| | X | | X | X | | | | | X | X | | | | | | | | | | | | | | | Weight Loss |
| | | | | | | | | | | | | X | | | | | | | | | | | | | Weight Gain |
| | | | | X | | | | | X | | | | | | | | | | | | | | | | Night Sweats |
| X | X | | | X | | | | | | | X | | | | | | | | | | | | | | Peripheral Edema |
| X | X | | | | | | | | | | | | | | | | | | | | | | | | High Hemoglobin |
| | | | | X | | | | | | X | X | X | | | | | | X | X | | | | | | Fatigue |
| | | | X | X | | | | | | | | | | | | | | | | | | | | | Joint Pain |
| X | | | | | | | | | | | | | | | | | | X | X | X | | | | | Hypersomnolence |

DETECTION OF CARDIAC DISEASES/DISORDERS
Conditions and Sensors

6204

6240-1

| Physiological Changes | Right Ventricular Egram | | | | | | Left Ventricular Egram | | | | | | RA Egram | | |
|---|---|---|---|---|---|---|---|---|---|---|---|---|---|---|---|
| | RV R-wave Temporal Location | RV R-wave Morphology | RV R-wave Amplitude | RV T-wave Temporal Location | RV T-wave Morphology | RV QT Segment Elevation | LV R-wave Temporal Location | LV R-wave Morphology | LV R-wave Amplitude | LV T-wave Temporal Location | LV T-wave Morphology | LV QT Segment Elevation | RA P-wave Temporal Location | RA P-wave Morphology | RA P-wave Amplitude |
| **Caridiac** | | | | | | | | | | | | | | | |
| Heart Rate | D | | | | | | D | | | | | | D | | |
| Blood Pressure | | | | | | | | | | | | | | | |
| Pulse Pressure | | | | | | | | | | | | | | | |
| Ectopic Beat (PVC) Density | x | X | X | X | | | X | X | X | X | | | X | | |
| ST Segment Elevation | x | X | X | X | X | D | X | X | X | X | X | D | | | |
| Mitral Regurgitation | | | | | | | | | | | | | | | |
| Hypertrophy | | | X | | | | | | X | | | | | | |
| Chest Pain | | | | | | | | | | | | | | | |
| Stoke Volume | | X | | | | | | X | | | | | | | |
| Ventricular Contractility | | X | | | | | | X | | | | | | | |
| Pulse Alternans | | | | | | | | | | | | | | | |
| Syncope | | | | | | | | | | | | | | | |

Fig. 62I-1

DETECTION OF CARDIAC DISEASES/DISORDERS

Conditions and Sensors 6240-2

6204

| Physiological Changes | LA Egram | | | Accelerometer | | | | Transthoracic Impedance | | | | | | |
|---|---|---|---|---|---|---|---|---|---|---|---|---|---|---|
| | LA P-wave Temporal Location | LA P-wave Morphology | LA P-wave Amplitude | Body Motion | Heart Sounds | Respiration Sounds | Posture | Respiration Rate | Tidal Volume | Minute Ventilation | Inspiration Time | Exhalation Time | Heart Motion Morphology | DC Thoracic Impedance |
| **Caridiac** | | | | | | | | | | | | | | |
| Heart Rate | D | | | | | | | | | | | | D | |
| Blood Pressure | | | | | | | | | | | | | | |
| Pulse Pressure | | | | | | | | | | | | | | |
| Ectopic Beat (PVC) Density | X | | | | | | | | | | | | X | |
| ST Segment Elevation | | | | | | | | | | | | | | |
| Mitral Regurgitation | | | | | X | | | | | | | | | |
| Hypertrophy | | | | | | | | | | | | | X | |
| Chest Pain | | | | | | | | | | | | | | |
| Stoke Volume | | | | | | | | | | | | | X | |
| Ventricular Contractility | | | | | | | | | | | | | X | |
| Pulse Alternans | | | | | | | | | | | | | | |
| Syncope | | | | | | | | | | | | | | |

Fig. 62I-2

DETECTION OF CARDIAC DISEASES/DISORDERS

Conditions and Sensors

6204

| | Blood Pressure | | | | | Blood Gas | | | Vent Gas | | | pH |
|---|---|---|---|---|---|---|---|---|---|---|---|---|
| Physiological Changes | Systolic Blood Pressure | Diastolic Blood Pressure | Pulse Pressure | Wedge Pressure | Contractility (dP/dt) | Blood pO2 | Blood pCO2 | Arterial / Venous pO2 | Exhaled % O2 | Exhaled % CO2 | X | Blood pH |
| **Caridiac** | | | | | | | | | | | | |
| Heart Rate | | | | | | X | X | X | | | | |
| Blood Pressure | D | D | D | D | D | | | | | | | |
| Pulse Pressure | D | D | D | D | D | | | | | | | |
| Ectopic Beat (PVC) Density | | | | | | | | | | | | |
| ST Segment Elevation | | | | | | | | | | | | |
| Mitral Regurgitation | | | | | | | | | | | | |
| Hypertrophy | | | | | | | | | | | | |
| Chest Pain | | | | | | | | | | | | |
| Stoke Volume | X | X | X | | | | | | | | | |
| Ventricular Contractility | X | X | X | | | | | | | | | |
| Pulse Alternans | X | X | X | | | | | | | | | |
| Syncope | X | X | | | | X | | | | | | |

DETECTION OF CARDIAC DISEASES/DISORDERS

Conditions and Sensors

6204

| | Finger | | Scale | | Temp | | Data Base | | | Direct Patient Query | | | | |
|---|---|---|---|---|---|---|---|---|---|---|---|---|---|---|
| Physiological Changes | Relative Pulse Pressure | Blood pO2 | Weight | X | Core Temperature | X | Medications | History | X | Pain | Breathing | Duration of Symptoms | Falls | X |
| **Caridiac** | | | | | | | | | | | | | | |
| Heart Rate | | X | | | X | | X | X | | | | | | |
| Blood Pressure | | | | | | | X | X | | | | | | |
| Pulse Pressure | X | | | | | | X | X | | | | | | |
| Ectopic Beat (PVC) Density | | | | | | | X | X | | | | | | |
| ST Segment Elevation | | | | | | | X | X | | | | | | |
| Mitral Regurgitation | | | | | | | X | X | | | | | | |
| Hypertrophy | | | | | | | X | X | | | | | | |
| Chest Pain | | | | | | | X | X | | D | | D | | |
| Stoke Volume | X | | | | | | X | X | | | | | | |
| Ventricular Contractility | | | | | | | X | X | | | | | | |
| Pulse Alternans | X | | | | | | | | | | | | | |
| Syncope | | X | | | | | | | | | | D | D | |

DETECTION OF CARDIAC DISEASES/DISORDERS

Conditions and Sensors

6204

| Physiological Changes | Right Ventricular Egram: RV R-wave Temporal Location | RV R-wave Morphology | RV R-wave Amplitude | RV T-wave Temporal Location | RV T-wave Morphology | RV QT Segment Elevation | Left Ventricular Egram: LV R-wave Temporal Location | LV R-wave Morphology | LV R-wave Amplitude | LV T-wave Temporal Location | LV T-wave Morphology | LV QT Segment Elevation | RA Egram: RA P-wave Temporal Location | RA P-wave Morphology | RA P-wave Amplitude |
|---|---|---|---|---|---|---|---|---|---|---|---|---|---|---|---|
| | | | | | | | | | | | | | | | |
| **Pulmonary** | | | | | | | | | | | | | | | |
| Pulmonary Edema | | | | | | | | | | | | | | | |
| Pleural Effusion | | | | | | | | | | | | | | | |
| Tidal Volume | | | | | | | | | | | | | | | |
| Cough at Rest | | | | | | | | | | | | | | | |
| Dyspnea | | | | | | | | | | | | | | | |
| Respiration Rate | | | | | | | | | | | | | | | |
| Wheezing | | | | | | | | | | | | | | | |
| | | | | | | | | | | | | | | | |
| **General systemic** | | | | | | | | | | | | | | | |
| Central Apnea | X | | | | | | X | | | | | | X | | |
| Activity Level | X | | | | | | X | | | | | | X | | |
| $O_2$ Saturation | X | | | | | | X | | | | | | | | |
| Automonic Balance | X | | | | | | X | | | | | | X | | |
| Heart Rate Variability (HRV) | X | | | | | | X | | | | | | X | | |
| Heart Rate / Activity Profile | X | | | | | | X | | | | | | X | | |
| Chenye-Stokes Respiration | | | | | | | | | | | | | X | | |
| Weight | | | | | | | | | | | | | | | |

DETECTION OF CARDIAC DISEASES/DISORDERS
Conditions and Sensors

6204

| Physiological Changes | LA Egram | | | Accelerometer | | | | Transthoracic Impedance | | | | | | |
|---|---|---|---|---|---|---|---|---|---|---|---|---|---|---|
| | LA P-wave Temporal Location | LA P-wave Morphology | LA P-wave Amplitude | Body Motion | Heart Sounds | Respiration Sounds | Posture | Respiration Rate | Tidal Volume | Minute Ventilation | Inspiration Time | Exhalation Time | Heart Motion Morphology | DC Thoracic Impedance |
| | | | | | | | | | | | | | | |
| **Pulmonary** | | | | | | | | | | | | | | |
| Pulmonary Edema | | | | | | | | X | X | X | X | X | | X |
| Pleural Effusion | | | | | | | | X | X | X | X | X | | X |
| Tidal Volume | | | | | | | | | D | | | | | |
| Cough at Rest | | | | | | X | | | X | | X | X | | |
| Dyspnea | | | | X | | | | X | X | X | X | X | | |
| Respiration Rate | | | | | | | | D | | | | | | |
| Wheezing | | | | | | X | | | | | X | X | | |
| | | | | | | | | | | | | | | |
| **General systemic** | | | | | | | | | | | | | | |
| Central Apnea | X | | | | | X | | X | X | | | | | |
| Activity Level | X | | | X | | | | X | X | X | | | | |
| $O_2$ Saturation | | | | | | | | X | X | X | | | | |
| Automonic Balance | X | | | | | | | | | | | | X | |
| Heart Rate Variability (HRV) | X | | | | | | | X | X | X | | | | |
| Heart Rate / Activity Profile | X | | | X | | | | X | X | X | | | | |
| Chenye-Stokes Respiration | X | | | | | | | | | | | | | |
| Weight | | | | | | | | | | | | | | |

DETECTION OF CARDIAC DISEASES/DISORDERS

Conditions and Sensors

6204

| Physiological Changes | Blood Pressure | | | | | Blood Gas | | | Vent Gas | | pH | |
|---|---|---|---|---|---|---|---|---|---|---|---|---|
| | Systolic Blood Pressure | Diastolic Blood Pressure | Pulse Pressure | Wedge Pressure | Contractility (dP/dt) | Blood pO2 | Blood pCO2 | Arterial / Venous pO2 | Exhaled % O2 | Exhaled % CO2 | X | Blood pH |
| | | | | | | | | | | | | |
| **Pulmonary** | | | | | | | | | | | | |
| Pulmonary Edema | | | | | | X | X | X | | | | X |
| Pleural Effusion | | | | | | X | X | X | | | | |
| Tidal Volume | | | | | | | | | | | | |
| Cough at Rest | | | | | | | | | | | | |
| Dyspnea | | | | | | X | X | X | X | X | | X |
| Respiration Rate | | | | | | | | | | | | |
| Wheezing | | | | | | | | | | | | |
| | | | | | | | | | | | | |
| **General systemic** | | | | | | | | | | | | |
| Central Apnea | X | X | | | | | | | | | | |
| Activity Level | | | | | | | | | | | | |
| $O_2$ Saturation | | | | | | X | | X | X | | | |
| Automonic Balance | | | | | | | | | | | | |
| Heart Rate Variability (HRV) | | | | | | | | | | | | |
| Heart Rate / Activity Profile | | | | | | | | | | | | |
| Chenye-Stokes Respiration | X | X | | | | | | | | | | |
| Weight | | | | | | | | | | | | |

DETECTION OF CARDIAC DISEASES/DISORDERS

Conditions and Sensors

Finger | Scale | Temp | Data Base | Direct Patient Query

6204

| Physiological Changes | Relative Pulse Pressure | Blood pO2 | Weight | X | Core Temperature | X | Medications | History | X | Pain | Breathing | Duration of Symptoms | Falls | X |
|---|---|---|---|---|---|---|---|---|---|---|---|---|---|---|
| | | | | | | | | | | | | | | |
| **Pulmonary** | | | | | | | | | | | | | | |
| Pulmonary Edema | | X | X | | | | X | X | | | | | | |
| Pleural Effusion | | | | | | | | X | | D | | D | | |
| Tidal Volume | | | | | | | | | | | | | | |
| Cough at Rest | | | | | | | | | | | | | | |
| Dyspnea | | | | | | | | X | | | D | D | | |
| Respiration Rate | | | | | | | | | | | | | | |
| Wheezing | | | | | | | | | | | X | X | | |
| | | | | | | | | | | | | | | |
| **General systemic** | | | | | | | | | | | | | | |
| Central Apnea | | | | | | | | X | | | | | | |
| Activity Level | | | | | | | | | | | | | | |
| $O_2$ Saturation | | | | | | | | | | | | | | |
| Automonic Balance | | | | | | | | X | | | | | | |
| Heart Rate Variability (HRV) | | | | | | | | | | | | | | |
| Heart Rate / Activity Profile | | | | | | | | | | | | | | |
| Chenye-Stokes Respiration | | | | | | | | X | | | | | | |
| Weight | | | D | | | | | | | | | | | |

DETECTION OF CARDIAC DISEASES/DISORDERS

Diseases/Disorders

| Physiological Changes (6204) | Rhythm | | | | | CAD | | | Heart Failure | | | | | Hypertension | | | Other | | |
|---|---|---|---|---|---|---|---|---|---|---|---|---|---|---|---|---|---|---|---|
| | Bradycardia | Ventricular Tachy / Fib | Paroxymal Atrial Tachy / Fib | Chronic Atrial Tachy / Fib | X | Acute MI | Ischemia | X | Low Output | Congestion | X | X | Systolic | Diastolic | X | X | X | X | X |
| **Caridiac** | | | | | | | | | | | | | | | | | | | |
| Heart Rate | X | X | X | X | | X | X | | X | X | | | | | | | | | |
| Blood Pressure | | X | X | X | | X | X | | X | | | | X | X | | | | | |
| Pulse Pressure | | | X | X | | X | X | | X | | | | X | X | | | | | |
| Ectopic Beat (PVC) Density | X | X | X | X | | X | X | | | | | | | | | | | | |
| ST Segment Elevation | | | | | | X | X | | | | | | | | | | | | |
| Mitral Regurgitation | | X | X | X | | X | X | | X | | | | | | | | | | |
| Hypertrophy | | | | | | | | | X | | | | | | | | | | |
| Chest Pain | | | | | | X | X | | | | | | | | | | | | |
| Stoke Volume | | X | | | | | | | X | | | | | | | | | | |
| Ventricular Contractility | | X | | | | | | | X | | | | X | | | | | | |
| Pulse Alternans | | | | | | | | | X | | | | | | | | | | |
| Syncope | X | X | X | X | | X | | | X | | | | | | | | | | |

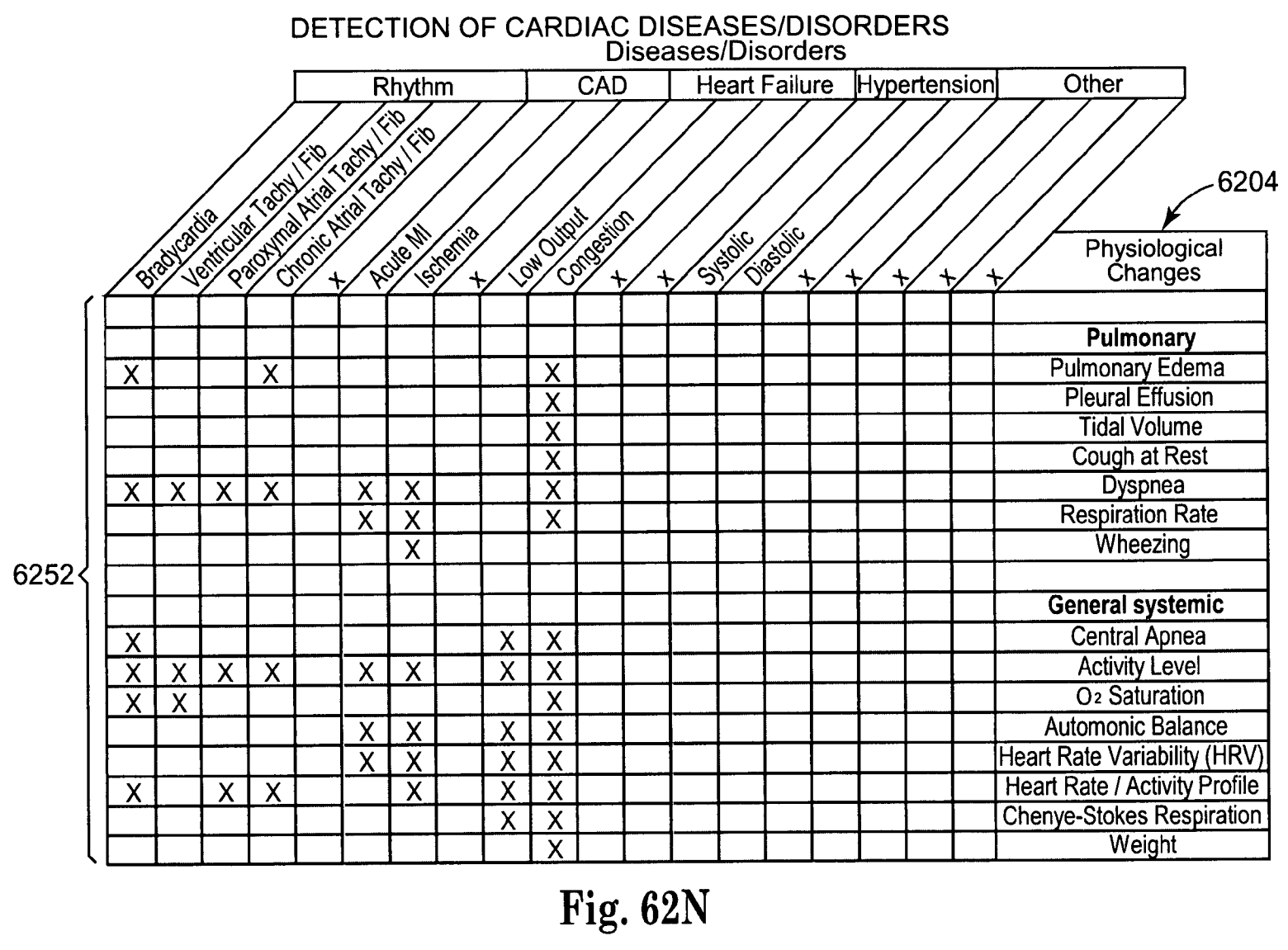

DETECTION OF CARDIAC DISEASES/DISORDERS

6252

6204

| Rhythm | | | | | CAD | | | Heart Failure | | | | Hypertension | | | Other | | | | |
|---|---|---|---|---|---|---|---|---|---|---|---|---|---|---|---|---|---|---|---|
| Bradycardia | Ventricular Tachy / Fib | Paroxymal Atrial Tachy / Fib | Chronic Atrial Tachy / Fib | x | Acute MI | Ischemia | x | Low Output | Congestion | x | x | Systolic | Diastolic | x | x | x | x | x | Physiological Changes |
| | | | | | | | | | | | | | | | | | | | |
| | | | | | | | | | | | | | | | | | | | **Pulmonary** |
| X | | | X | | | | | | X | | | | | | | | | | Pulmonary Edema |
| | | | | | | | | | X | | | | | | | | | | Pleural Effusion |
| | | | | | | | | | X | | | | | | | | | | Tidal Volume |
| | | | | | | | | | X | | | | | | | | | | Cough at Rest |
| X | X | X | X | | X | X | | | X | | | | | | | | | | Dyspnea |
| | | | | | X | X | | | X | | | | | | | | | | Respiration Rate |
| | | | | | | X | | | | | | | | | | | | | Wheezing |
| | | | | | | | | | | | | | | | | | | | |
| | | | | | | | | | | | | | | | | | | | **General systemic** |
| X | | | | | | | | X | X | | | | | | | | | | Central Apnea |
| X | X | X | X | | X | X | | X | X | | | | | | | | | | Activity Level |
| X | X | | | | | | | | X | | | | | | | | | | $O_2$ Saturation |
| | | | | | X | X | | X | X | | | | | | | | | | Automonic Balance |
| | | | | | X | X | | X | X | | | | | | | | | | Heart Rate Variability (HRV) |
| X | | X | X | | | X | | X | X | | | | | | | | | | Heart Rate / Activity Profile |
| | | | | | | | | X | X | | | | | | | | | | Chenye-Stokes Respiration |
| | | | | | | | | | X | | | | | | | | | | Weight |

Fig. 62N

Criteria Set for Assessment of Chronic Bronchitis

| Physiological Change or Symptom Associated with Chronic Bronchitis | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % CO2 | O2 Gas Sensor |
| | Expiratory Flow | Expiratory Flowmeter |
| | Inspiratory Flow | Inspiratory Flowmeter |
| Cyanosis | Exhaled % O2 | O2 Gas Sensor |
| Hypoxemia | Exhaled % O2 | O2 Gas Sensor |
| Hypercapnea | Exhaled % CO2 | CO2 Gas Sensor |
| Low pCO2 | Exhaled % CO2 | CO2 Gas Sensor |
| Arterial Acidosis | Exhaled % CO2 | CO2 Gas Sensor |
| High Aveolar-Arterial pO2 differential | Exhaled % O2 | O2 Gas Sensor |
| Low FEV, FVC, FEV/FVC | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| High, FRC, TLC | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Slow Exhalation | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Ventilation-Perfusion Mismatch | Exhaled % CO2 | CO2 Gas Sensor |
| | Exhaled % O2 | O2 Gas Sensor |

Figure 63B

Criteria Set for Assessment of Emphysema

| Physiological Change or Symptom Associated with Emphysema | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Exertional Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Cyanosis | Exhaled % O2 | O2 Gas Sensor |
| Hypoxemia | Exhaled % O2 | O2 Gas Sensor |
| Hypercapnia | Exhaled % CO2 | CO2 Gas Sensor |
| Arterial Acidosis | Exhaled % CO2 | CO2 Gas Sensor |
| High Aveolar-Arterial pO2 differential | Exhaled % O2 | O2 Gas Sensor |
| Low FEV, FVC, FEV/FVC | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| High, FRC, TLC | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| High Lung Compliance | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Slow Exhalation | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Ventilation-Perfusion Mismatch | Exhaled % CO2 | CO2 Gas Sensor |
| | Exhaled % O2 | O2 Gas Sensor |

Figure 63C

Criteria Set for Assessment of Asthma

| Physiological Change or Symptom Associated with Asthma | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Orthopnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Paroxysmal Nocturnal Dysnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| High Aveolar-Arterial pO2 differential | Exhaled % O2 | O2 Gas Sensor |
| Low FEV, FVC, FEV/FVC | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Low FEF | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| High RV | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Slow Exhalation | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Ventilation-Perfusion Mismatch | Exhaled % CO2 | CO2 Gas Sensor |
| | Exhaled % O2 | O2 Gas Sensor |

Figure 63D

Criteria Set for Assessment of Pulmonary Fibrosis

| Physiological Change or Symptom Associated with Pulmonary Fibrosis | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Exertional Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Cyanosis | Exhaled % O2 | O2 Gas Sensor |
| Hypoxemia | Exhaled % O2 | O2 Gas Sensor |
| Hypercapnia | Exhaled % CO2 | CO2 Gas Sensor |
| Low pCO2 | Exhaled % CO2 | CO2 Gas Sensor |

Figure 63E

Criteria Set for Assessment of Pulmonary Hypertension

| Physiological Change or Symptom Associated with Pulmonary Hypertension | Condition Used to Detect the Physiological Change or Symptom | Respiration Therapy Device Sensor Used to Sense Condition |
|---|---|---|
| Exertional Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Hypoxemia | Exhaled % O2 | O2 Gas Sensor |

Figure 63F

Criteria Set for Assessment of Pulmonary Edema

| Physiological Change or Symptom Associated with Pulmonary Edema | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Orthopnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Exertional Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Paroxysmal Nocturnal Dysnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Cyanosis | Exhaled % O2 | O2 Gas Sensor |
| Hypoxemia | Exhaled % O2 | O2 Gas Sensor |

Figure 63G

Criteria Set for Assessment of Pulmonary Embolism

| Physiological Change or Symptom Associated with Pulmonary Embolism | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Exertional Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Hypoxemia | Exhaled % O2 | O2 Gas Sensor |

Figure 63H

Criteria Set for Assessment of Atelectasis

| Physiological Change or Symptom Associated with Atelectasis | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Hypoxemia | Exhaled % O2 | O2 Gas Sensor |
| Hypercapnia | Exhaled % CO2 | CO2 Gas Sensor |

Figure 63I

Criteria Set for Assessment of Hemothorax

| Physiological Change or Symptom Associated with Hemothorax | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Hypoxemia | Exhaled % O2 | O2 Gas Sensor |
| Hypercapnia | Exhaled % CO2 | CO2 Gas Sensor |
| Respiratory Failure | Exhaled % CO2 | CO2 Gas Sensor |
| | Exhaled % O2 | O2 Gas Sensor |
| Circulatory Collapse | Exhaled % CO2 | CO2 Gas Sensor |
| | Exhaled % O2 | O2 Gas Sensor |

Figure 63J

Criteria Set for Assessment of Tuberculosis

| Physiological Change or Symptom Associated with Hemothorax | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Crackles | Duration of Symptoms | Patient Inquiry |
| | Abnormal Breathing/Coughing | Patient Inquiry |
| | Inspiration Time | Transthoracic Impedance |
| | Expiration Time | Transthoracic Impedance |
| | Respiration Sounds | Accelerometer |
| Hemoptysis | Duration of Symptoms | Patient Inquiry |
| | Abnormal Breathing/Coughing | Patient Inquiry |
| Cough | Duration of Symptoms | Patient Inquiry |
| | Abnormal Breathing/Coughing | Patient Inquiry |
| | Tidal Volume | Transthoracic Impedance |
| | Respiration Sounds | Accelerometer |
| Pleuritic Chest Pain | Duration of Symptoms | Patient Inquiry |
| | Pain | Patient Inquiry |
| | Exhalation Time | Transthoracic Impedance |
| | Inspiration Time | Transthoracic Impedance |
| | Minute Ventilation | Transthoracic Impedance |
| | Tidal Volume | Transthoracic Impedance |
| | Respiration Sounds | Accelerometer |
| | LV QT Segment Elevation | Left Ventricular Egram |
| | LV T wave Morphology | Left Ventricular Egram |
| | RV QT Segment Elevation | Right Ventricular Egram |
| | RV T wave Morphology | Right Ventricular Egram |

Figure 63K

PATIENT MONITORING, DIAGNOSIS, AND/OR THERAPY SYSTEMS AND METHODS

RELATED APPLICATIONS

This application claims the benefit of Provisional Patent Application Ser. No. 60/504,229, filed on Sep. 18, 2003, to which priority is claimed pursuant to 35 U.S.C. §119(e) and which is hereby incorporated herein by reference.

FIELD OF THE INVENTION

The invention relates to systems and methods providing patient monitoring, diagnosis and/or therapy.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. For example, heart failure (HF) is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

There are a number of diseases and disorders that primarily affect respiration, but also impact other physiological systems. Emphysema and chronic bronchitis are grouped together and are known as chronic obstructive pulmonary disease (COPD). Pulmonary system disease also includes tuberculosis, sarcoidosis, lung cancer, occupation-related lung disease, bacterial and viral infections, and other conditions.

Chronic obstructive pulmonary disease generally develops over many years, typically from exposure to cigarette smoke, pollution, or other irritants. Over time, the elasticity of the lung tissue is lost, and the lungs become distended, unable to expand and contract normally. As the disease progresses, breathing becomes labored, and the patient grows progressively weaker.

Disordered breathing is a respiratory system disorder that affects a significant percentage of patients between 30 and 60 years. Disordered breathing, including apnea and hypopnea, may be caused, for example, by an obstructed airway, or by derangement of the signals from the brain controlling respiration. Sleep disordered breathing is particularly prevalent and is associated with excessive daytime sleepiness, systemic hypertension, increased risk of stroke, angina and myocardial infarction. Disordered breathing can be particularly serious for patients concurrently suffering from cardiovascular deficiencies.

Various types of disordered respiration have been identified, including, apnea (interrupted breathing), hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Cheyne-Stokes respiration is particularly prevalent among heart failure patients, and may contribute to the progression of heart failure.

There are a number of cardiovascular system disorders that have secondary effects with respect to other physiological systems. When functioning properly, the human heart maintains its own intrinsic rhythm, and is capable of pumping an adequate amount of blood throughout the body's circulatory system. However, some people have abnormal cardiac rhythms, referred to as cardiac arrhythmias, that cause a decrease in cardiac output.

Bradycardia is a condition that involves a heart beat that is abnormally slow, causing insufficient blood supply to the body's tissues. Tachyarrhythmia occurs when the patient's cardiac rhythm is too fast. The excessively rapid cardiac contractions result in diminished blood circulation because the heart has insufficient time to fill with blood before contracting to expel the blood. Ventricular fibrillation is a particularly dangerous form of tachyarrhythmia, and may result in death within minutes if the heart's normal rhythm is not restored.

Because of the complex interactions between the cardiovascular, pulmonary and other systems, effective approaches to monitoring, diagnosis, and treatment of various disorders is needed. The present invention fulfills these and other needs, and addresses other deficiencies of prior art implementations and techniques.

SUMMARY OF THE INVENTION

The present invention is directed to systems and methods for monitoring, diagnosing, and/or treating a patient. Various embodiments of the invention are directed to systems and method configured to monitor, diagnose, and/or provide patient therapy using one or more individual medical procedures. Each of the individual medical procedures provide a particular monitoring, diagnosis or therapeutic function or set of functions. Each individual medical procedure may be implemented as a stand-alone system. Two or more of the individual medical procedures may be used in combination to provide more comprehensive patient monitoring, diagnosis and/or therapy. One or more functions of two or more individual medical procedures may be used in combination to enhance patient monitoring, diagnosis and/or therapy.

Various embodiments of the invention are directed to systems and methods configured to monitor, diagnose, and/or provide therapy using coordinated medical procedures. Coordinated medical procedures may involve cooperative operation of two or more of the individual processes. Coordinated medical procedures may also involve cooperative operation of one or more functions of two or more of the individual processes.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

According to various embodiments of the invention, a system may be implemented to include an implantable device configured to perform at least one cardiac-related function and a patient-external respiratory therapy device. A communication channel may be configured to facilitate communication between the implantable device and the respiratory therapy device. The implantable and respiratory therapy devices may be configured to operate cooperatively via the communication channel to provide one or more of patient monitoring, diagnosis, and therapy. The communication channel may be configured to facilitate uni-directional or bi-directional communication between the implantable device and the respiratory therapy device.

In one configuration, each of the implantable and respiratory therapy devices provides at least two of patient monitoring, diagnosis, and therapy. In another configuration, each of the implantable and respiratory therapy devices provides each of patient monitoring, diagnosis, and therapy.

The respiratory therapy device may be configured to coordinate one or more of initiation, modification, and termination of a function of the implantable device. The implantable device may be configured to coordinate one or more of initiation, modification, and termination of a function of the respiratory therapy device.

One or both of the implantable and respiratory therapy devices may comprise one or more sensors configured to detect one or more conditions affecting the patient. The implantable and respiratory therapy devices may be configured to provide one or more of the patient monitoring, diagnosis and therapy based at least in part on the one or more detected conditions.

The system may further include a drug delivery device. The drug delivery device may be controllable by one or both of the implantable and respiratory therapy devices.

The respiratory therapy device may comprises a positive airway pressure device. The respiratory therapy device may comprise a gas therapy device. The implantable device may comprise a cardiac rhythm management device.

In accordance with another embodiment, a system includes an implantable device configured to perform at least one cardiac-related function, a patient-external respiratory therapy device, a processing system external of the implantable and respiratory therapy devices, and a communication channel configured to facilitate communication between the processing system and at least one of the implantable device and the respiratory therapy device. The processing system may be communicatively coupled to the at least one of the implantable and respiratory therapy devices via the communication channel to provide one or more of patient monitoring, diagnosis, and therapy.

The communication channel may be configured to facilitate communication between the implantable device and the respiratory therapy device. The communication channel may be configured to facilitate uni-directional, bi-directional, or a combination of uni- and bi-directional communication between the processing system and one or both of the implantable and respiratory therapy devices.

The processing system may be configured to manage patient-related information. For example, the processing system may be implemented as a server-based patient information management system. The processing system may be configured to coordinate one or more of initiation, modification, and termination of a therapy deliverable by one or both of the implantable and respiratory therapy devices. The processing system may be configured to coordinate one or more of initiation, modification, and termination of a diagnostic procedure performed by one or both of the implantable and respiratory therapy devices.

The processing system may be configured to coordinate one or more of initiation, modification, and termination of a monitoring procedure performed by one or both of the implantable and respiratory therapy devices. One or both of the implantable and respiratory therapy devices may be configured to coordinate a function of the processing system. The processing system may be configured to remotely interrogate one or both of the implantable and respiratory therapy devices.

According to other embodiments, methods may involve providing a first set of medical procedures associated with a patient-external respiratory therapy device and providing a second set of medical procedures associated with an implantable device, the implantable device configured to perform at least one cardiac-related function. Methods may further involve coordinating, via communication between the implantable and respiratory therapy devices, one or more processes of the first and second sets of medical procedures, wherein the first and second sets of medical procedures involve at least one of patient monitoring, diagnosis, and therapy.

In accordance with other embodiments, method may involve providing a first set of medical procedures associated with a patient-external respiratory therapy device, and providing a second set of medical procedures associated with an implantable device, the implantable device configured to perform at least one cardiac-related function. Methods may further involve coordinating one or more processes of the first and second sets of medical procedures using a patient-external processing system, wherein the first and second sets of medical procedures involve at least one of patient monitoring, diagnosis, and therapy.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 63B-63K are criteria sets for assessing a presence of various non-rhythm pulmonary diseases in accordance with embodiments of the invention.

FIGS. 68A-8D are block diagrams systems that may be used for control of drug therapy in accordance with embodiments of the invention;

FIGS. 102-104 are signal flow diagrams illustrating pacing rate adjustment in accordance with embodiments of the invention;

FIG. 105 is a block diagram illustrating a controller that includes several different inputs to modify the rate at which pacing or other therapy is delivered based on disordered breathing detection in accordance with embodiments of the invention;

FIGS. 106 and 107 are graphs illustrating modification of a pacing rate in accordance with embodiments of the invention;

FIG. 108 is a graph illustrating a method of using at least one of coefficients a and b as a function of one or more previous cardiac intervals in accordance with embodiments of the invention;

FIGS. 109A and 109B are flowcharts depicting methods of classifying sleep stages according to embodiments of the invention;

FIG. 110 illustrates a block diagram of a system suitable for implementing a sleep stage classification method according to embodiments of the invention;

Figure 111:
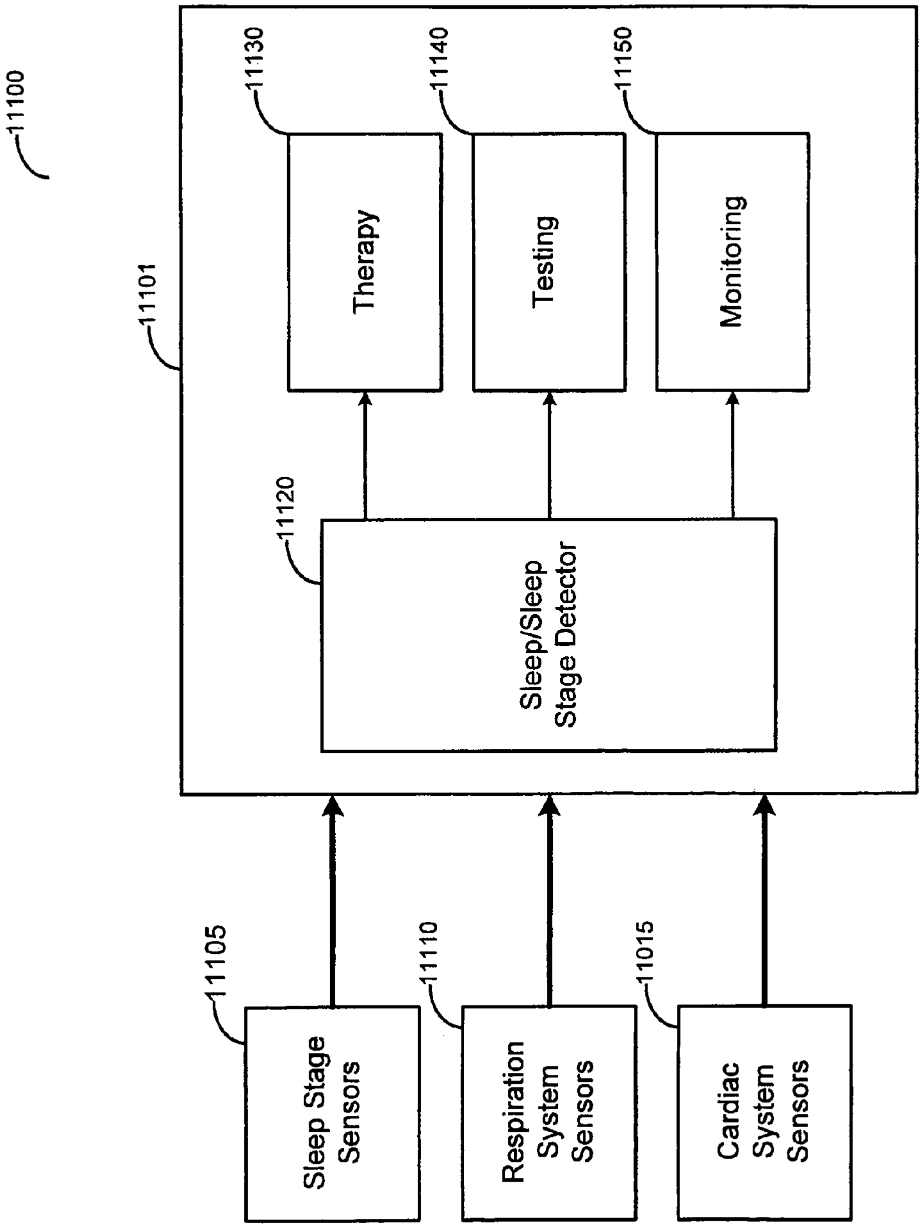
Figure 112:
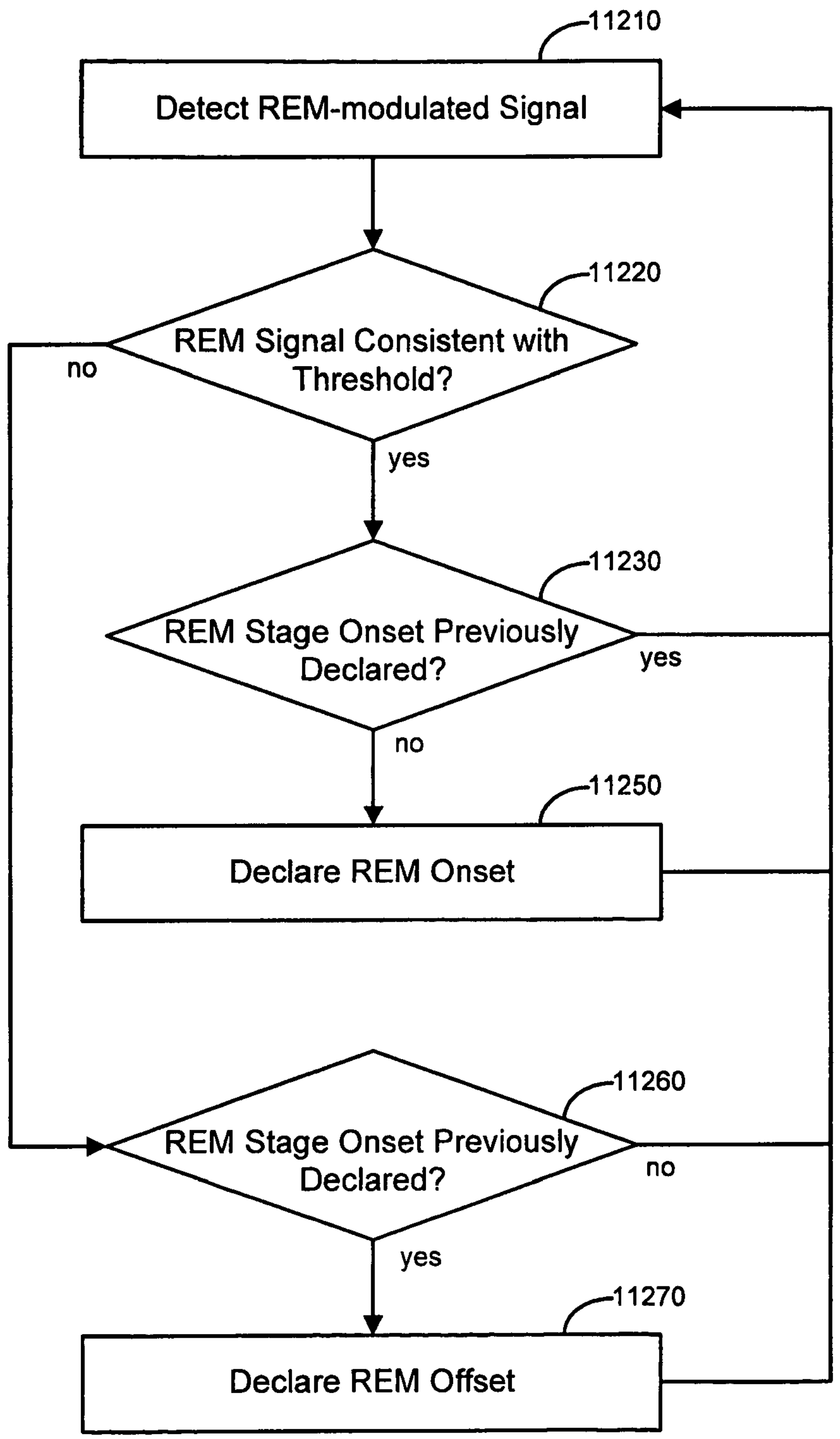
Figure 113:
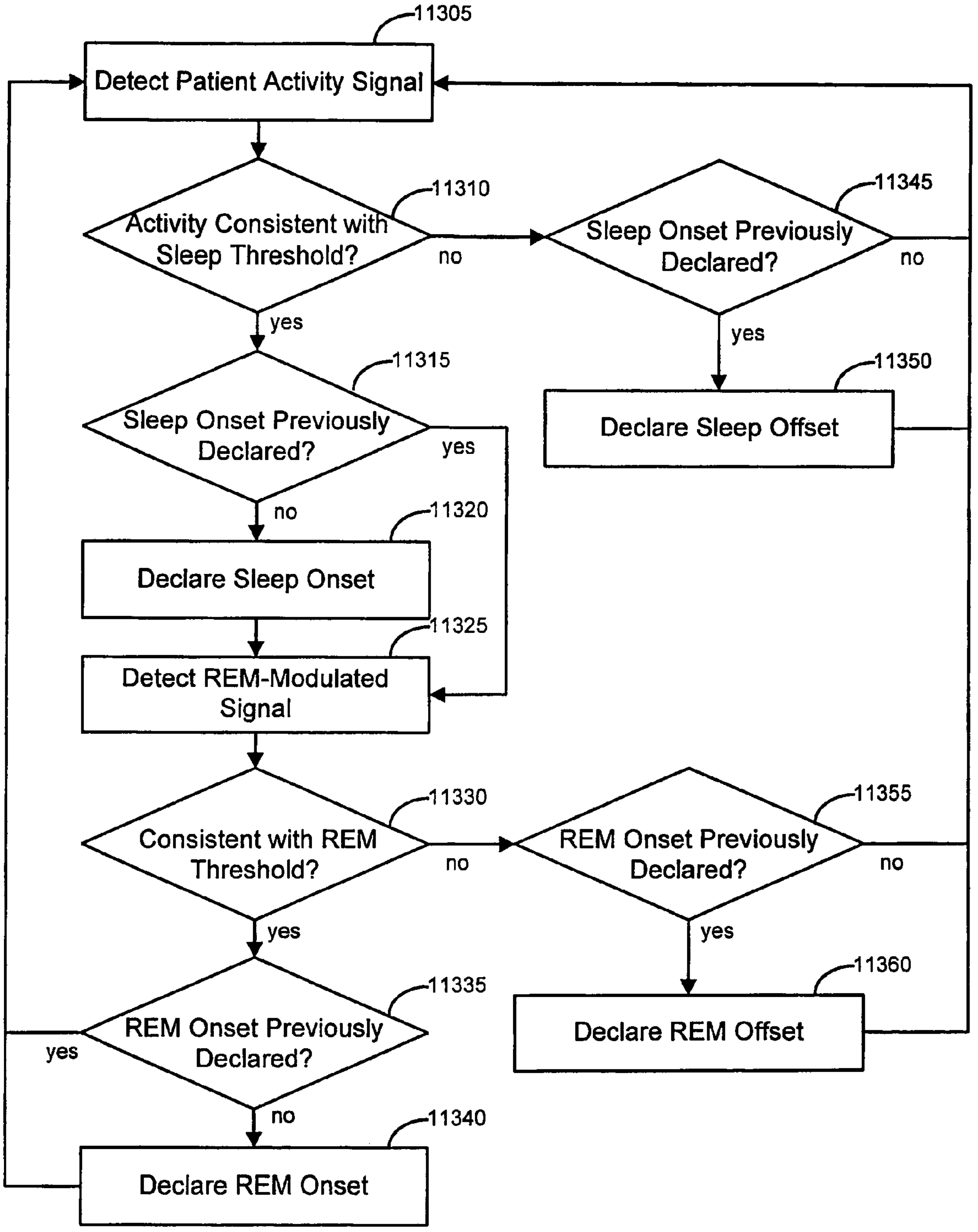
Figure 114:
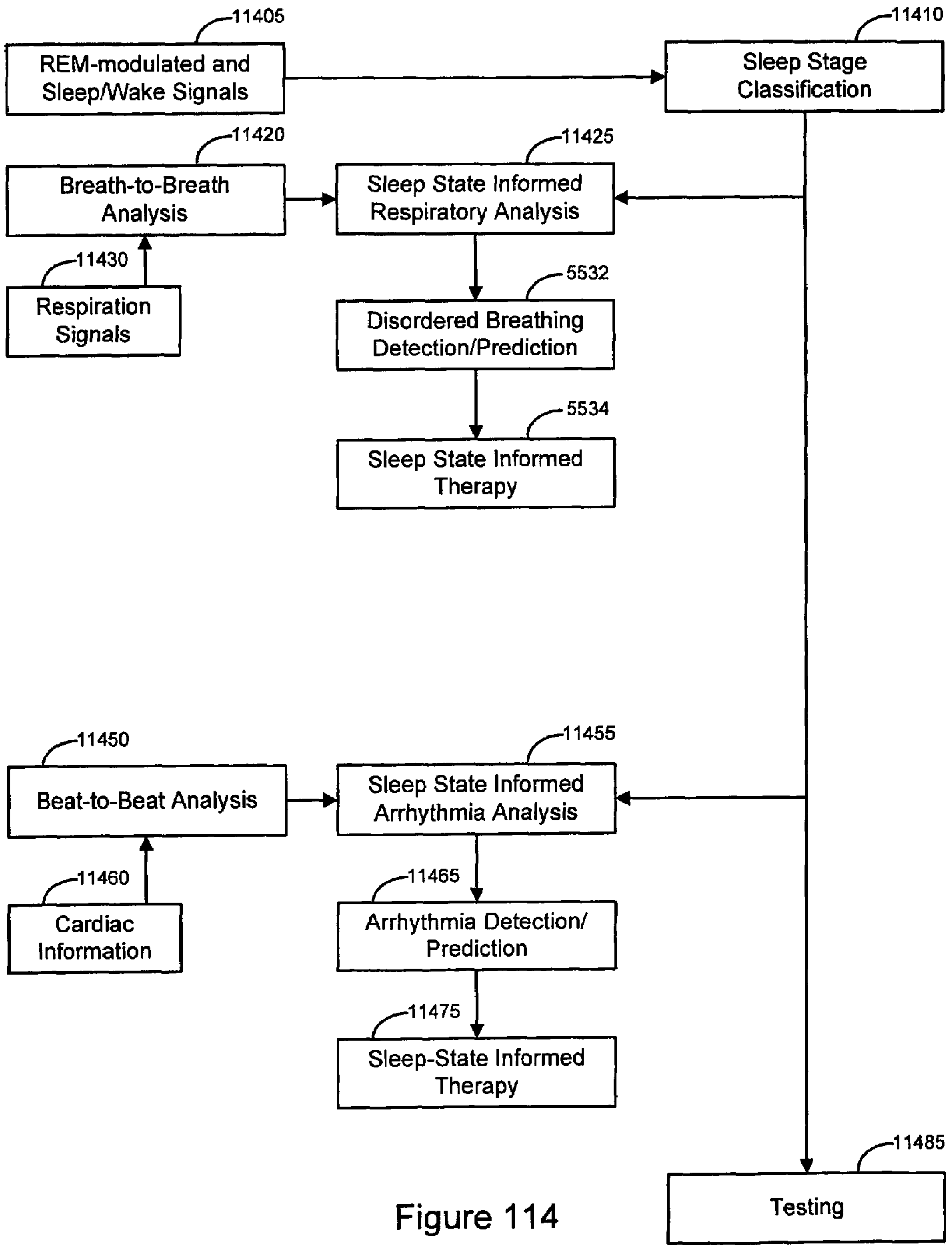
Figure 115:
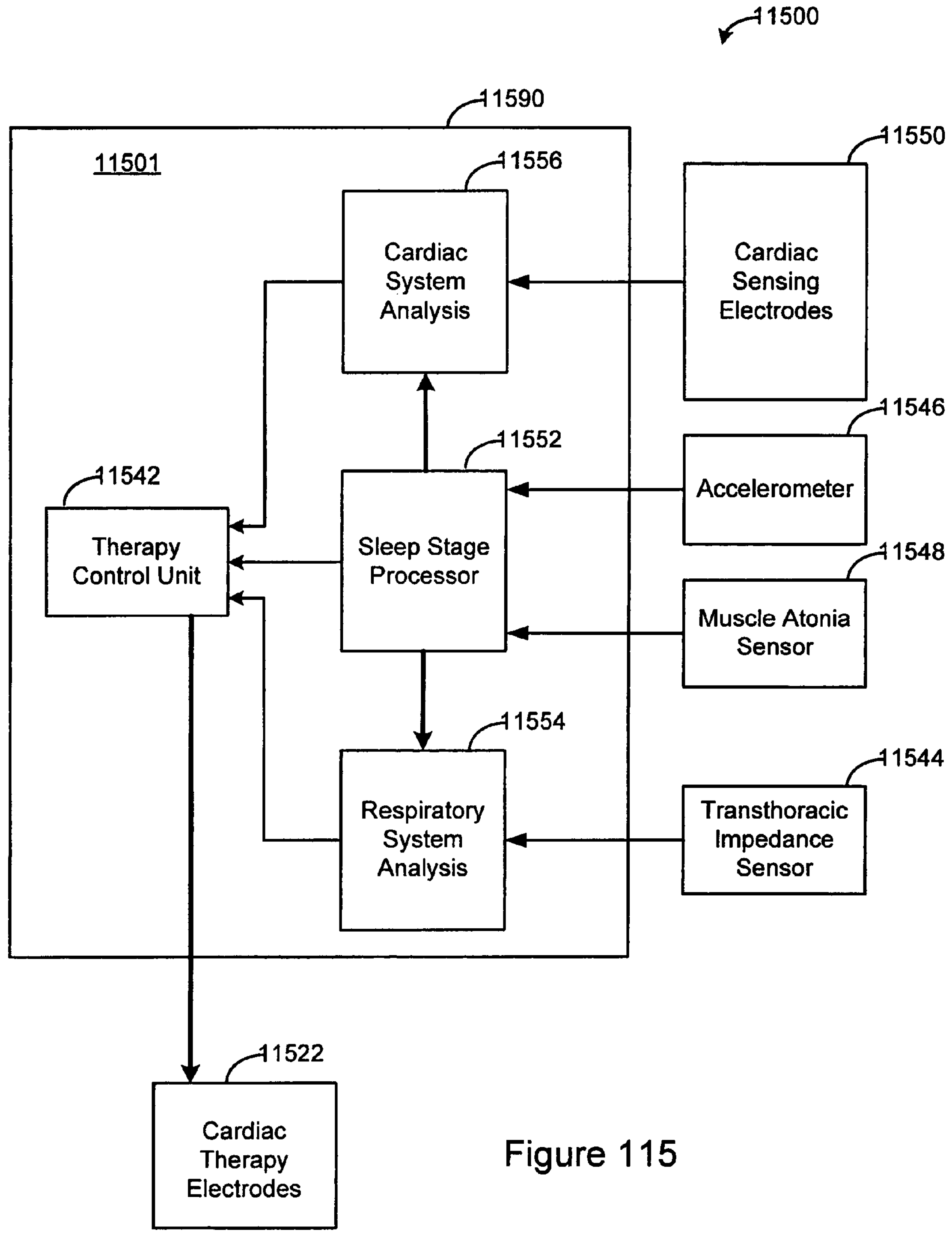

FIG. 111 presents a block diagram illustrating sleep stage discrimination circuitry configured according to embodiments of the invention;

FIGS. 112 and 113 are flowcharts illustrating methods of performing sleep stage classification in accordance with embodiments of the invention;

FIG. 114 is a process flow diagram illustrating a process for using sleep stage classification in cooperation with therapy delivery and testing in accordance with embodiments of the invention;

FIG. 115 illustrates a medical system that may be used to perform sleep stage informed therapy in accordance with embodiments of the invention; and FIGS. 116A-116D illustrate various configurations of a muscle atonia sensor mechanically coupled to an implanted medical device in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Methods, devices, and systems implementing a coordinated approach to patient monitoring, diagnosis, and/or therapy in accordance with the present invention may incorporate one or more of the features, structures, methods, or combinations thereof described herein below. For example, a medical system may be implemented to include one or more of the features and/or processes described below. It is intended that such a method, device, or system need not include all of the features and functions described herein, but may be implemented to include one or more selected features and functions that provide useful structures and/or functionality.

Disorders and diseases affecting the interdependent physiological systems of the human body may be more effectively diagnosed and treated using a coordinated approach. Various embodiments of the invention are implemented using medical systems employing one or a number of patient-external and/or patient-internal medical devices. Medical devices may communicate or otherwise operate in concert or in a stand-alone manner to provide more comprehensive patient monitoring, diagnosis, and therapy.

As referenced herein, the term "condition," denotes an attribute that may be sensed and/or measured based on a signal generated by a sensor or other input device of a respiratory therapy device or another medical device. The terms "symptom" and "physiological change" refer to a manifestation of a medical disease or disorder. Symptoms and/or physiological changes may be detectable based on a sensed presence of one or more physiological conditions and/or measured values associated with the one or more sensed physiological conditions. The terms "disease" and/or "disorder" are used to refer to a medical dysfunction that is characterizable by a collection of symptoms or physiological changes.

Figure 1A:
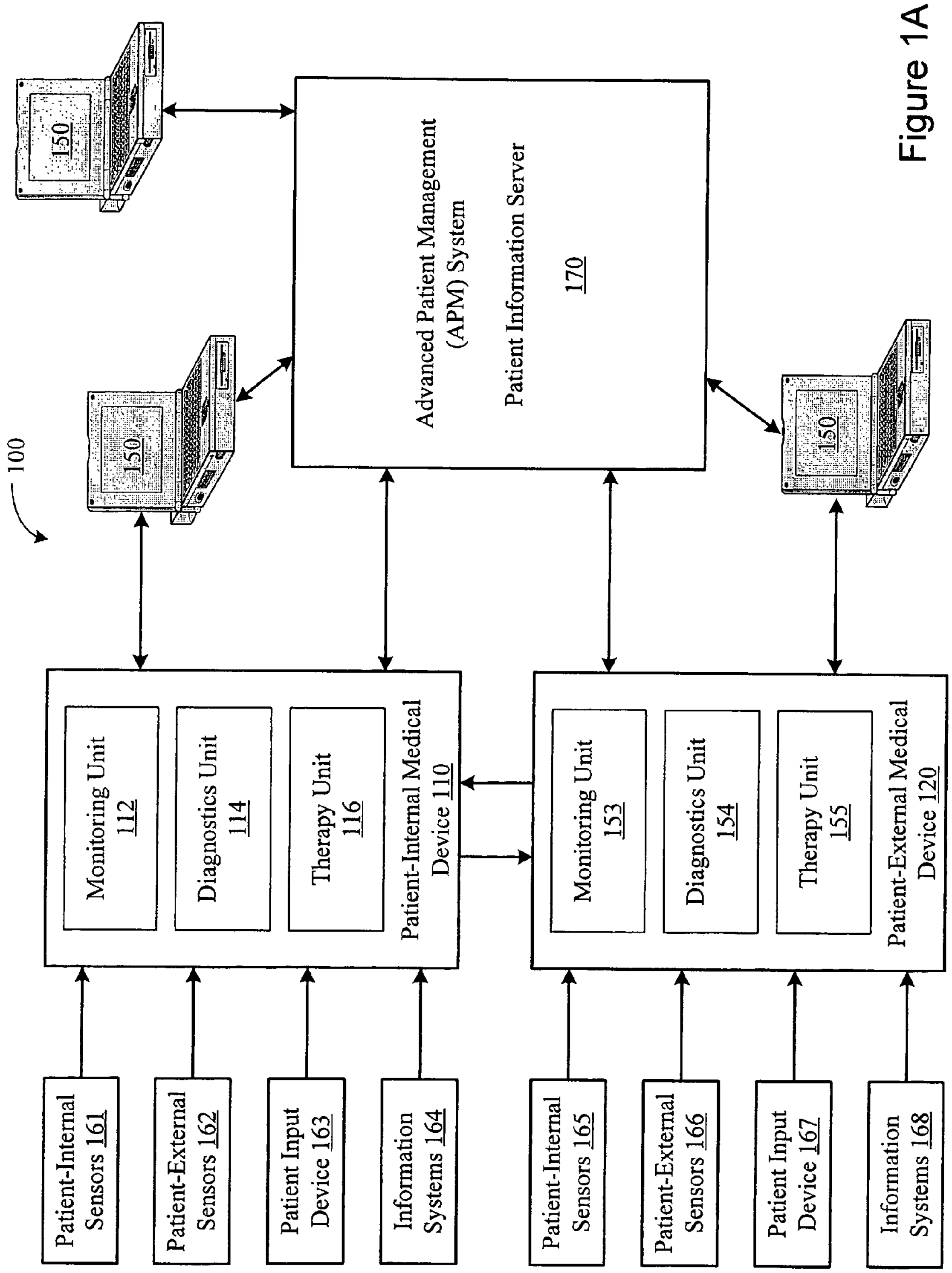
FIG. 1A is block diagram of a system for providing coordinated monitoring, diagnosis and therapy in accordance with embodiments of the invention.

FIG. 1A is a block diagram of a medical system 100 that may be used to implement coordinated patient monitoring, diagnosis, and/or therapy in accordance with embodiments of the invention. The medical system 100 may include, for example, one or more patient-internal medical devices 110 and one or more patient-external medical devices 120. Each of the patient-internal 110 and patient-external 120 medical devices may include one or more of a patient monitoring unit 112, 153, a diagnostics unit 114, 154, and/or a therapy unit 116, 155.

The patient-internal medical device 110 is typically a fully or partially implantable device that performs monitoring, diagnosis, and/or therapy functions. The patient-external medical device 120 performs monitoring, diagnosis and/or therapy functions external to the patient (i.e., not invasively implanted within the patient's body). The patient-external medical device 120 may be positioned on the patient, near the patient, or in any location external to the patient. It is understood that a portion of a patient-external medical device 120 may be positioned within an orifice of the body, such as the nasal cavity or mouth, yet can be considered external to the patient (e.g., mouth pieces/appliances, tubes/appliances for nostrils, or temperature sensors positioned in the ear canal).

The patient-internal and patient-external medical devices 110, 120 may be coupled to one or more sensors 141, 142, 145, 146, patient input devices 143, 147 and/or other information acquisition devices 144, 148. The sensors 141, 142, 145, 146, patient input devices 144, 147, and/or other information acquisition devices 144, 148 may be employed to detect conditions relevant to the monitoring, diagnostic, and/or therapeutic functions of the patient-internal and patient-external medical devices 110, 120.

The medical devices 110, 120 may each be coupled to one or more patient-internal sensors 141, 145 that are fully or partially implantable within the patient. The medical devices 110, 120 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 141 may be coupled to the patient-internal medical device 110 through internal leads. In one example, an internal endocardial lead system used to couple cardiac electrodes to an implantable pacemaker or other cardiac rhythm management device. One or more patient-internal sensors 141 may be equipped with transceiver circuitry to support wireless communications between the one or more patient-internal sensors 141 and the patient-internal medical device 110 and/or the patient-external medical device 120.

The patient-external sensors 142 may be coupled to the patient-internal medical device 110 and/or the patient-external medical device 120 through leads or through wireless connections. Patient-external sensors 142 preferably communicate with the patient-internal medical device 110 wirelessly. Patient-external sensors 146 may be coupled to the patient-external medical device 120 through leads or through a wireless link.

The medical devices 110, 120 may be coupled to one or more patient-input devices 143, 147. The patient-input devices are used to allow the patient to manually transfer information to the medical devices 110, 120. The patient input devices 143, 147 may be particularly useful for inputting information concerning patient perceptions, such as how well the patient feels, and information such as patient smoking, drug use, or other activities that are not automatically sensed or detected by the medical devices 110, 120.

The medical devices 110, 120 may be connected to one or more information systems 144, 148, for example, a database that stores information useful in connection with the monitoring, diagnostic, or therapy functions of the medical devices 110, 120. For example, one or more of the medical devices 110, 120 may be coupled through a network to a information system server that provides information about environmental conditions affecting the patient, e.g., the pollution index for the patient's location.

In one embodiment, the patient-internal medical device 110 and the patient-external medical device 120 may communicate through a wireless link between the medical devices 110, 120. For example, the patient-internal and patient-external devices 110, 120 may be coupled through a short-range radio link, such as Bluetooth or a proprietary wireless link. The communications link may facilitate uni-directional or bi-directional communication between the patient-internal 110 and patient-external 120 medical devices or particular units of medical devices 110, 120. Data and/or control signals may be transmitted between the patient-internal 110 and patient-external 120 medical devices to coordinate the functions of the medical devices 110, 120.

In another embodiment of the invention, the patient-internal and patient-external medical devices 110, 120 may be used within the structure of an advanced patient management system. Advanced patient management systems involve a system of medical devices that are accessible through various communications technologies. For example, patient data may be downloaded from one or more of the medical devices periodically or on command, and stored at a patient information server. The physician and/or the patient may communicate with the medical devices and the patient information server, for example, to acquire patient data or to initiate, terminate or modify therapy.

In the implementation illustrated in FIG. 1A, the patient-internal medical device 110 and the patient-external medical device 120 may be coupled through a wireless or wired communications link to a patient information server that is part of an advanced patient management system 170. The APM patient information server 170 may be used to download and store data collected by the patient-internal and patient-external medical devices 110, 120. Systems and methods involving advanced patient management techniques are further described in U.S. Pat. Nos. 6,336,903, 6,312,378, 6,270,457, and 6,398,728, hereby incorporated herein by reference.

Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

The data stored on the APM patient information server 170 may be accessible by the patient and the patient's physician through terminals 150, e.g., remote computers located in the patient's home or the physician's office. The APM patient information server 170 may be used to communicate to one or more of the patient-internal and patient-external medical devices 110, 120 to effect remote control of the monitoring, diagnosis, and/or therapy functions of the medical devices 110, 120.

In one scenario, the patient's physician may access patient data transmitted from the medical devices 110, 120 to the APM patient information server 170. After evaluation of the patient data, the patient's physician may communicate with one or more of the patient-internal or patient-external devices 110, 120 through the APM system 170 to initiate, terminate, or modify the monitoring, diagnostic, and/or therapy functions of the patient-internal and/or patient-external medical systems 110, 120.

The patient-internal and patient-external medical devices 110, 120 may not communicate directly, but may communicate indirectly through the APM system 170. In this embodiment, the APM system 170 may operate as an intermediary between two or more of the medical devices 110, 120. For example, data and/or control information may be transferred from one of the medical devices 110, 120 to the APM system 170. The APM system 170 may transfer the data and/or control information to another of the medical devices 110, 120.

In one scenario, the APM system may communicate directly with the patient-internal and/or patient-external medical devices 110, 120. The advanced patient management (APM) information server 170 may be used to download and store data collected by the patient-internal and patient-external medical devices 110, 120.

Figure 1B:
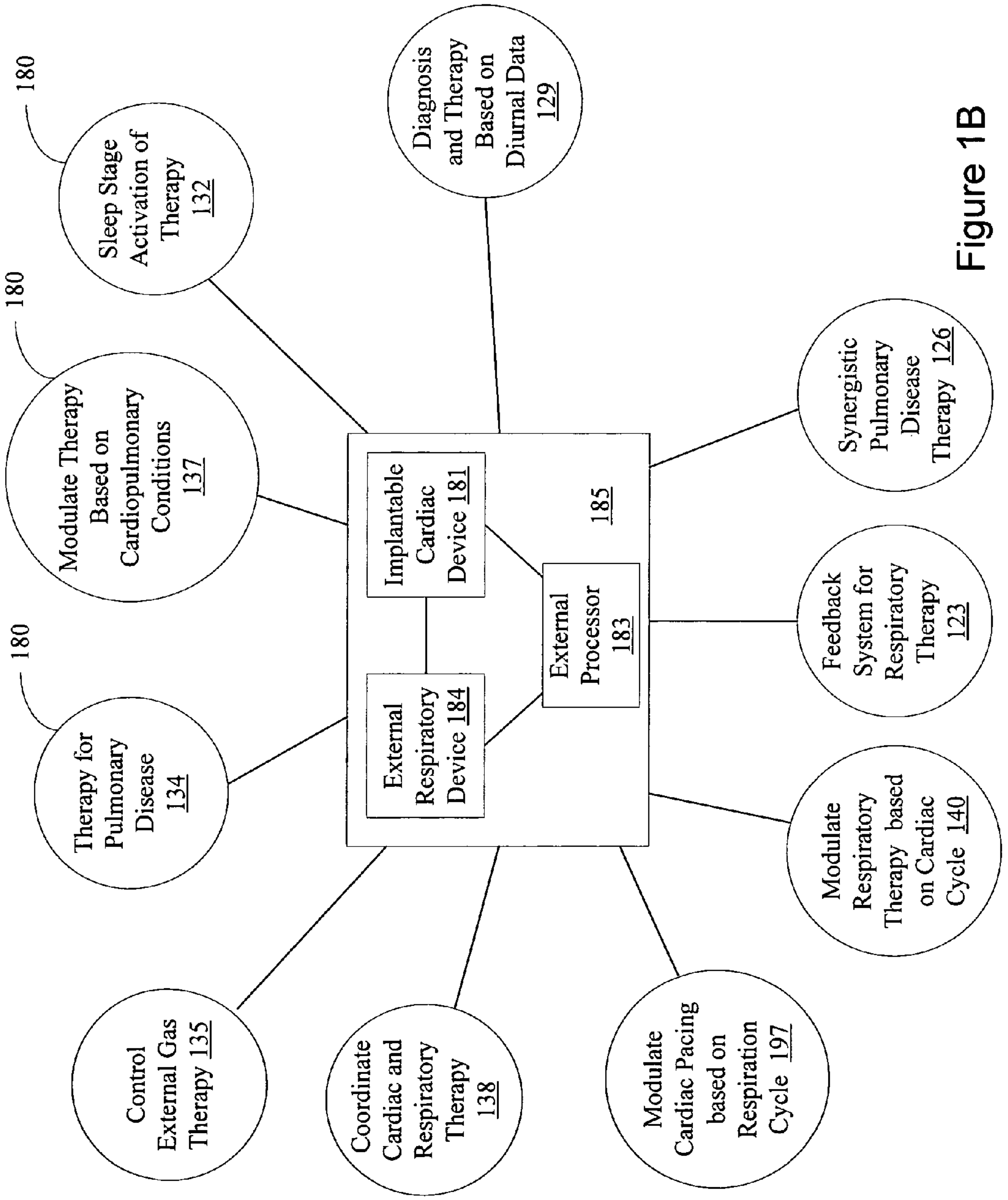
FIGS. 1B-1D illustrate various medical procedures that may be implemented by a coordinated medical system in accordance with embodiments of the invention.
Figure 1C:
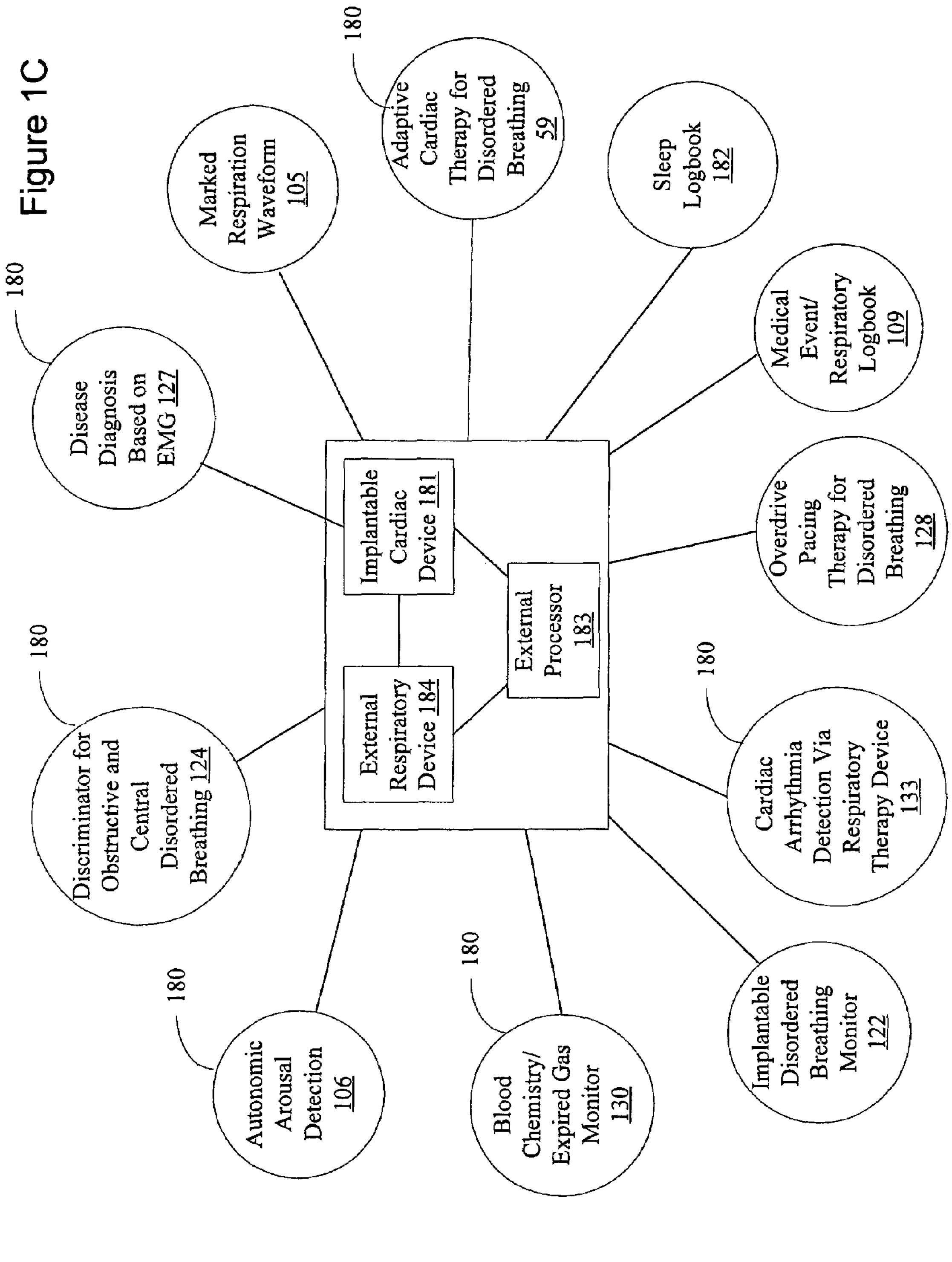
Figure 1D:
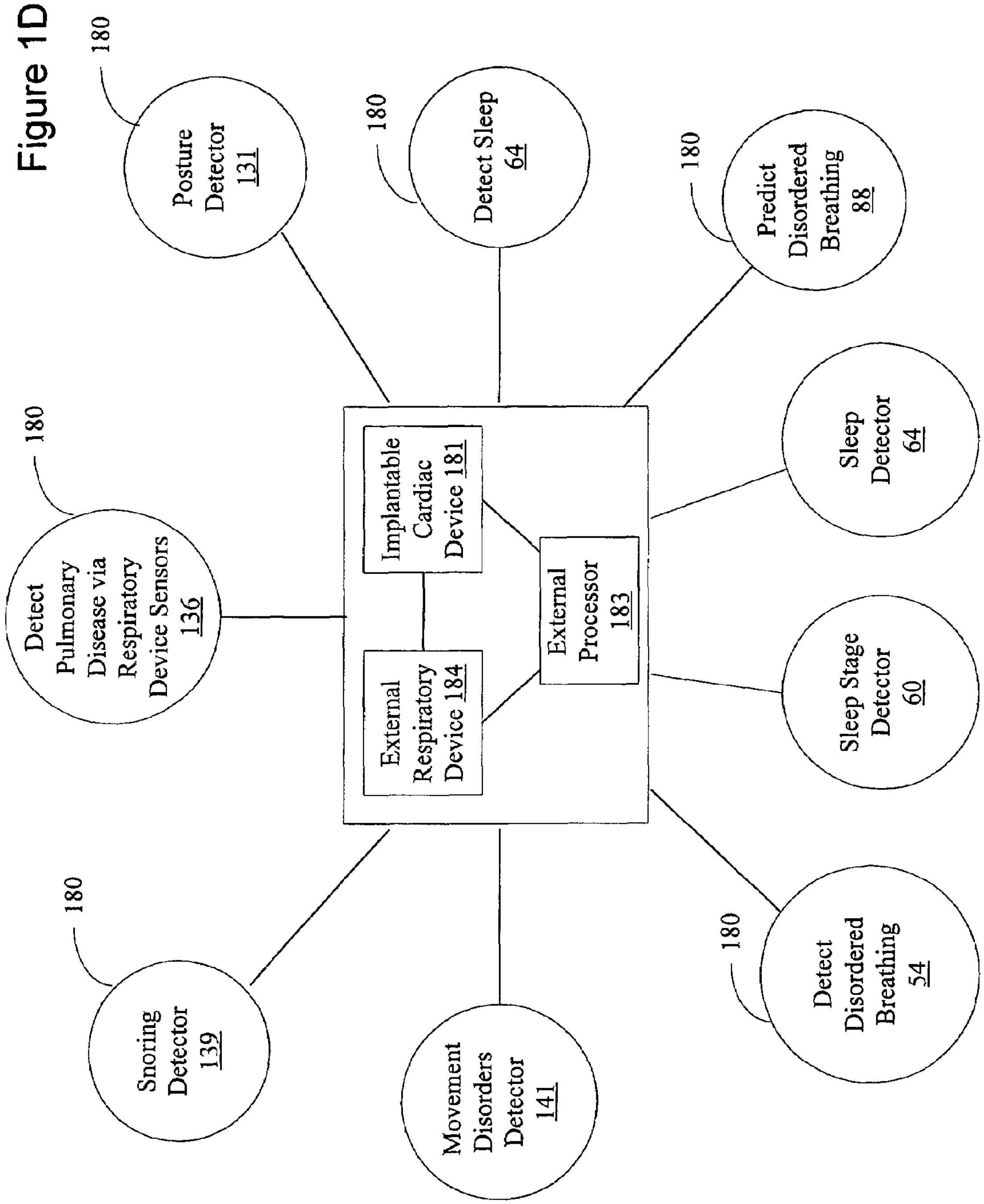

FIGS. 1B-1D illustrate various medical procedures that may be implemented by a coordinated medical system in accordance with embodiments of the invention. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve individual systems for performing the various medical procedures 180. Each of the procedures 180 may be implemented as a stand alone system or in combination with other individual medical procedures or systems 180, such as those described in FIGS. 1B-1D.

Other embodiments of the invention involve systems for providing coordinated patient monitoring, diagnosis and/or therapy that utilize one or more of the medical procedures 180. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

As indicated in FIG. 1A, one or both of the devices 110, 120 of the medical system 100 may include a monitoring unit 112, 153, a diagnostics unit 114, 154, and a therapy unit 116, 155. Each of these units 112, 114, 116, 153, 154, 155 may be used alone or in cooperation with other components of the medical system 100 to implement the various medical procedures 180.

Monitoring circuitry 112, 153 of one or both devices 110, 120 may include detection and/or monitoring functionality that may be employed to implement one or more processes of the medical procedures 180 indicated in FIG. 1B-1D involving monitoring and/or detection. For example, monitoring circuitry 112, 153 may be used in connection with on or more of sleep detection 54, sleep quality monitoring 58, sleep stage detection 60, marked respiratory waveform generation 105, medical event/respiratory event logbook generation 106, sleep logbook generation 184, monitoring of respiratory therapy 122, posture detection 131, cardiac event detection via the respiratory therapy device 133 snoring detection 139, and autonomic arousal detection 106.

Diagnosis circuitry incorporated in one or both devices 110, 120 may be used to implement processes of the one or more of the medical procedures 180 indicated in FIGS. 1B-1D that involve assessing a presence of diseases or disorders. For example, one or both diagnosis units 114, 153 maybe used in connection with one or more of pulmonary disease detection 136, disordered breathing detection 54, central and obstructive disordered breathing detection 124, detection of movement disorders 141, disease detection based on use of diurnal data 129, use of electromyogram for disease diagnosis 127, diagnosis based on blood chemistry/blood gas 130, and disease detection by synergistic use of respiratory therapy and cardiac devices 126.

Therapy delivery of therapy control circuitry incorporated in one or both devices 110, 120 may be used to implement processes of the one or more of the medical procedures 180 indicated in FIGS. 1B-1D that involve delivery or control of therapy For example, one or both therapy units 116, 155 maybe used in connection with one or more of adaptive cardiac therapy for disordered breathing 59, overdrive pacing for disordered breathing 128, therapy based on prediction of disordered breathing 103, respiratory therapy based on feedback from an implanted monitor 123, modification of therapy using detected cardiopulmonary conditions 137, automatic activation of therapy based on brain waves 132, modulation of external gas therapy 135, disordered breathing therapy using a combination of cardiac and respiratory therapies 138, modulation of respiration therapy based on cardiac cycle phase 141, modulation of cardiac pacing based on respiration cycle 197.

Figure 2A:
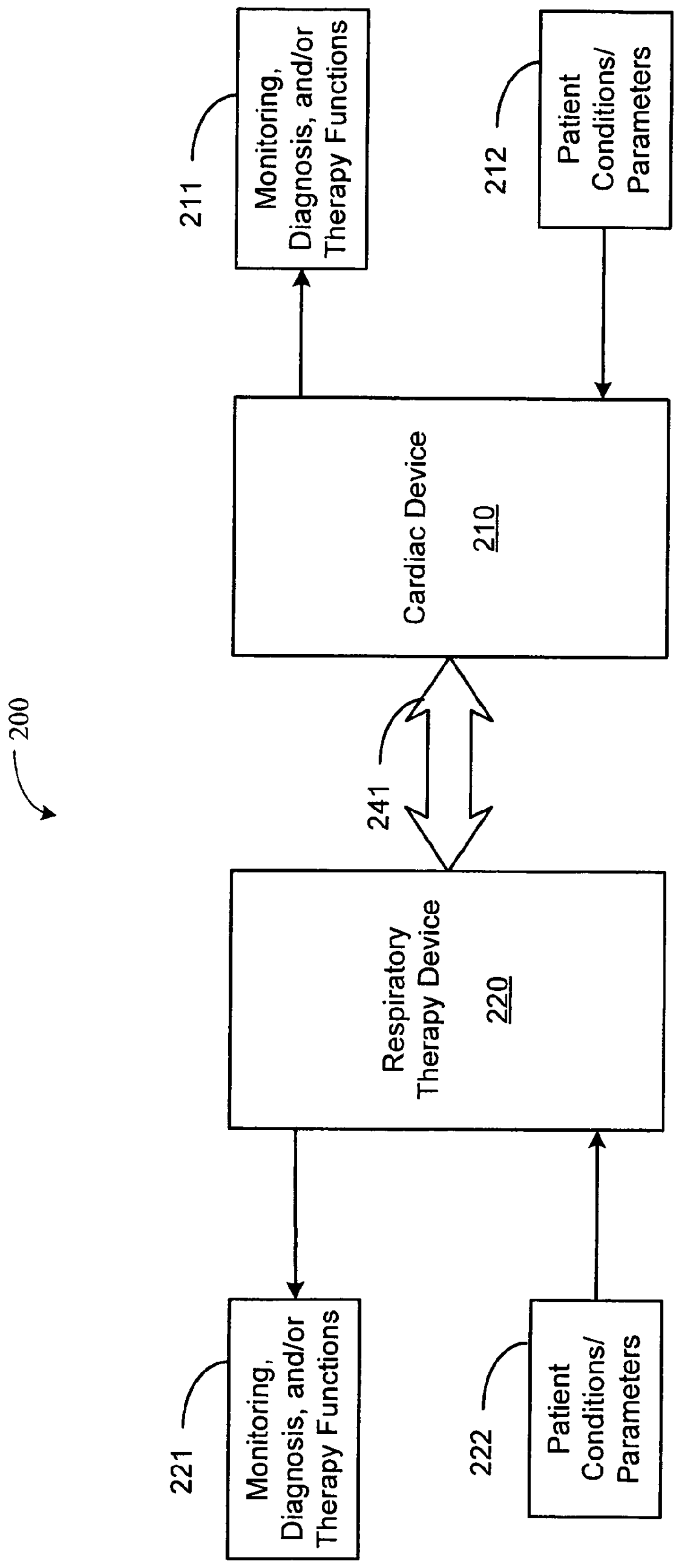
FIGS. 2A-2B are block diagrams of a coordinated system including a respiratory therapy device and an implantable device.
Figure 2B:
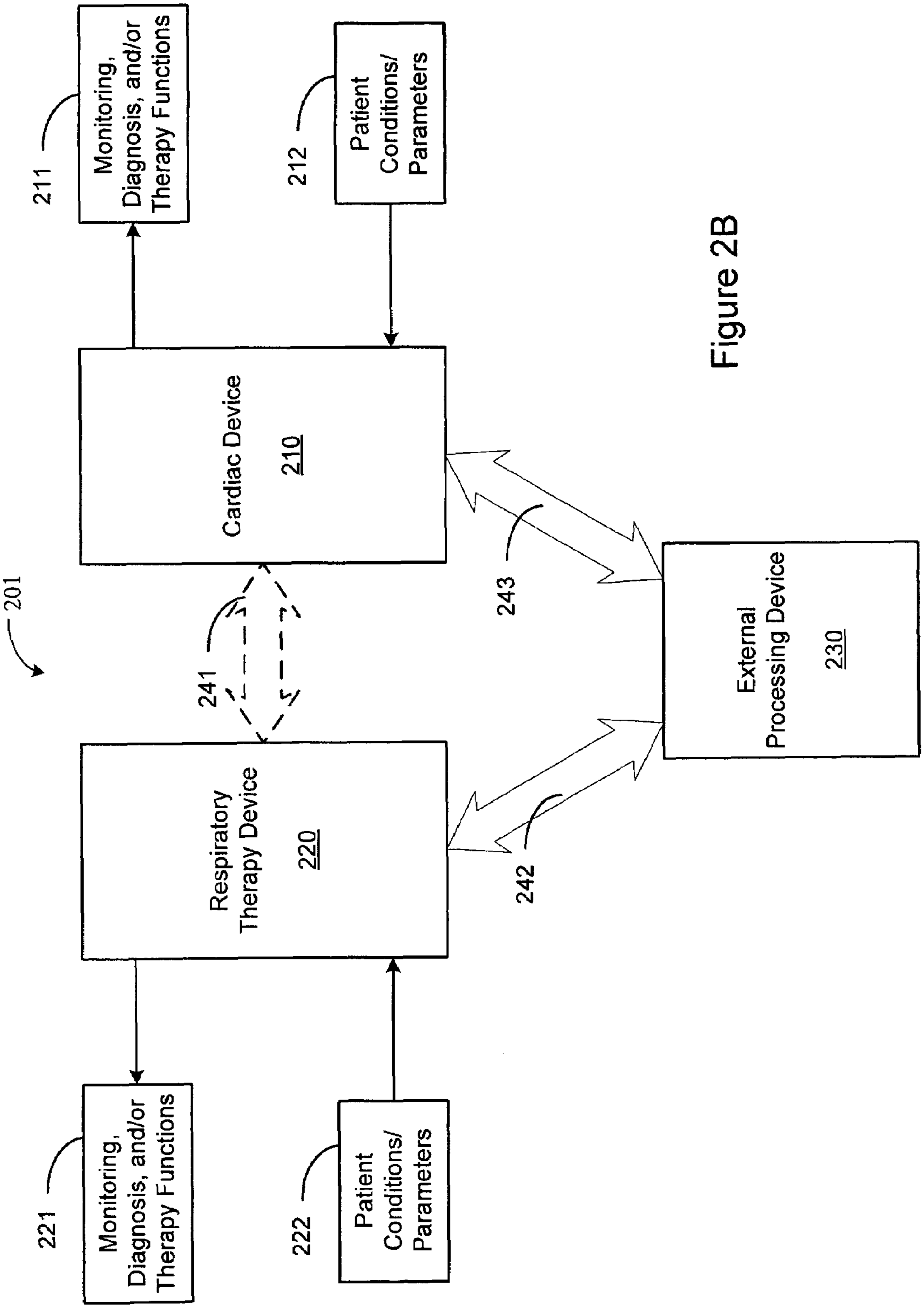

The block diagrams of FIGS. 2A and 2B provide examples of a coordinated monitoring, diagnosis and/or therapeutic system 200 in accordance with embodiments of the invention. Referring to FIG. 2A, the system 200 employs medical device 210 that may be fully or partially implantable. The medical device 210 performs at least one cardiac function. The implantable cardiac device 210 may be coupled to an array of data acquisition devices 212, including patient-internal sensors, patient-external sensors, patient input devices, and/or other information systems for sensing, detecting and/or measuring conditions or parameters affecting the patient and useful for the monitoring, diagnostic, and/or therapeutic functions of the coordinated system 200.

The system 200 employs a respiratory therapy device 220. The respiratory therapy device may be positioned on the patient, near the patient, or in any location external to the patient. It is understood that a portion of a respiratory therapy device 220 may be positioned within an orifice of the body, such as the nasal cavity or mouth, yet can be considered external to the patient (e.g., mouth pieces/appliances, tubes/appliances for nostrils, or temperature sensors positioned in the ear canal). The respiratory therapy device 220 may be coupled to an array of data acquisition devices 222, including patient-internal sensors, patient-external sensors, patient input devices, and/or other information systems for sensing, detecting and/or measuring conditions or parameters affecting the patient and useful for the monitoring, diagnostic, and/or therapeutic functions of the coordinated system 200.

Patient conditions or parameters may include both physiological and non-physiological contextual conditions affecting the patient. Physiological conditions may include a broad category of conditions associated with the internal functioning of the patient's physiological systems, including the cardiovascular, respiratory, nervous, muscle and other systems. Examples of physiological conditions include blood chemistry, patient posture, patient activity, respiration quality, sleep quality, among others.

Contextual conditions generally encompass non-physiological, patient-external or background conditions. Contextual conditions may be broadly defined to include, for example, present environmental conditions, such as patient location, ambient temperature, humidity, air pollution index. Contextual conditions may also include historical/background conditions relating to the patient, including the patient's normal sleep time and the patient's medical history, for example.

Table 1 provides a representative set of patient conditions that may be used in connection with a coordinated approach to patient monitoring, diagnostics, and/or therapy in accordance with embodiments of the invention. Table 1 also provides illustrative sensing methods that may be employed to sense the conditions. It will be appreciated that patient conditions and detection methods other than those listed in Table 1 may be used in connection with patient monitoring, diagnosis, and/or therapy and are considered to be within the scope of the invention.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |
| | Respiratory System | Snoring | Accelerometer Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | CO2 saturation | Blood analysis |
| | | O2 saturation | |
| | | Blood alcohol content | |
| | | Adrenalin | |
| | | Brain Natriuretic Peptide (BNP) | |
| | | C-Reactive Protein | |
| | | Drug/Medication/Tobacco use | |
| | Muscle System | Muscle atonia | EMG |
| | | Eye movement | EOG |
| | | Patient activity | Accelerometer, MV, etc. |
| | | Limb movements | Accelerometer, EMG |
| | | Jaw movements | Accelerometer, EMG |
| | | Posture | Multi-axis accelerometer |
| Contextual/ Non-Physiological | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | | Altitude | Altimeter |
| | | Location | GPS, proximity sensor |
| | | Proximity to bed | Proximity to bed sensor |
| | Historical/Background | Historical sleep time | Patient input, previously detected sleep onset times |
| | | Medical history | Patient input |
| | | Age | |
| | | Recent exercise | |
| | | Weight | |
| | | Gender | |
| | | Body mass index | |
| | | Neck size | |
| | | Emotional state | |
| | | Psychological history | |
| | | Daytime sleepiness | |
| | | Patient perception of sleep quality | |
| | | Drug, alcohol, nicotine use | |

One or both of the medical devices 210, 220 of FIG. 2A may include a monitoring unit, as previously described in connection with FIG. 1A, that processes signals from one or more of the sensors or other data acquisition devices. The monitoring unit may include processes to detect the occurrence of various events, including, for example, normal and/or abnormal physiological system events or condition, cardiovascular system events, a respiratory system events, muscle system events, nervous system event, and/or a sleep-related events. Other types of events may also be detected. For example, detection of a cardiovascular system event may involve detection of detect abnormal or unusual events of the cardiovascular system such as ventricular tachycardia or fibrillation. The detection of a cardiovascular system event may alternatively involve detection of normal cardiac beats or other events or conditions associated with the usual functioning of the heart.

Respiratory event detection may involve events or conditions associated with various respiratory system disorders, such as a disordered breathing event or a pulmonary congestion condition. Respiratory system event/condition detection may also be used to detect the inspiratory and expiratory phases of normal respiration cycles, for example.

Muscle system event/condition detection may involve detection of abnormal limb movements, such as those associated with periodic limb movement disorder (PLMD), for example. Muscle system event/condition detection may further be used to detect normal or abnormal conditions, such as normal muscle atonia associated with REM sleep or abnormal muscle tone of the upper airway associated with obstructive sleep apnea events. The muscle system event/condition detection may also be used, for example, to detect the level of patient activity. Patient activity information may be useful, for example, in assessing the overall activity level of the patient, or determining if the patient is asleep.

Detection of nervous system events may comprise, for example, detection arousals for sleep, or detection of brain wave activity events. Sleep-related events such as sleep onset, sleep offset, sleep stages, arousals from sleep sleep disordered breathing events, and nocturnal movements may be monitored in connecting with sleep quality assessment.

Information related to parameter or conditions affecting the patient may be stored in memory. The stored data may be transmitted to another component of the medical devices 210, 220 or to a separate device for storage, further processing, trending, analysis and/or display, for example. In one scenario, the stored data can be downloaded to a separate device periodically or on command. The stored data may be presented to the patient's health care professional on a real-time basis, or as a long-term, e.g., month long or year long, trend of daily measurements.

One or both of the devices 210, 220 may include the capability of assessing disease presence and/or diagnosing various diseases or disorders. The diagnostics capability of the medical devices 210, 220 may rely on information acquired and stored in memory over a period of time. Diagnostics or assessments of disease presence may involve evaluation of events or conditions detected by the monitoring/detection components of the devices 210, 220.

One or both medical devices 210, 220 may include the ability to deliver or control the delivery of therapy to a patient. In the example provided in FIG. 2A, the cardiac device 210 may deliver cardiac electrical stimulation therapy using a cardiac pulse generator and electrical stimulation electrodes.

The respiratory therapy device 220 may delivery any of a variety of respiration therapies, including, for example, continuous positive airway pressure (CPAP), bi-level positive airway pressure (bi-PAP), proportional positive airway pressure (PPAP), auto-titrating positive airway pressure, ventilation, gas, pharmacological agent, or oxygen therapies, among others.

One of the devices 210, 220 may partially or fully control the therapy delivered by the other device 220, 210. For example, the cardiac device 210 may control or aid in the control of therapy delivered by the respiratory device 220. The respiratory device 220 may control or aid in the control of therapy delivered by the cardiac device 210.

One or both of the medical devices 210, 220 may fully or partially control other therapy delivery devices or receive input from other sensors. For example, one or both of the medical devices 210, 220 may be used to control a drug therapy device, such as a drug pump, a controllable nebulizer, and/or electrically activated drug patch. In a further example, one or both of the medical devices 210, 220 may be used to control a nerve stimulation or muscle stimulation therapy device, such as a hypoglossal or phrenic nerve stimulation device.

In one implementation, illustrated in FIG. 2A, the medical system 200 includes a uni-directional or bidirectional communications channel 241 between the medical devices 210, 220. The communications channel 241 facilitates the cooperation between the medical devices 210, 220. The communications channel 241 may be implemented as a wireless link between the cardiac device 210 and the respiratory therapy device 220. The wireless communication channel 241 coupling the medical devices 210, 220 may utilize a variety of wireless protocols, including, for example, Bluetooth, IEEE 802.11, and/or a proprietary wireless protocol.

In another implementation, illustrated in FIG. 2B, the medical system 201 includes an external processor 230. The external processor 230 may comprise, for example, an advanced patient management system, as previously described. The external processor 230 may acquire patient conditions or parameters 232, store patient information, provide monitoring and/or diagnostic functionality 231, control therapy 231 delivered by the cardiac and/or respiratory devices 210, 220 and/or other therapy devices.

The external processor may be coupled to one or both of the cardiac and respiratory devices 210, 220 through wireless or wired communications channels 243, 242. In one implementation, the cardiac and respiratory devices 210, 220 may not communicate directly, but may communicate indirectly via the external processor 230.

Figure 3:
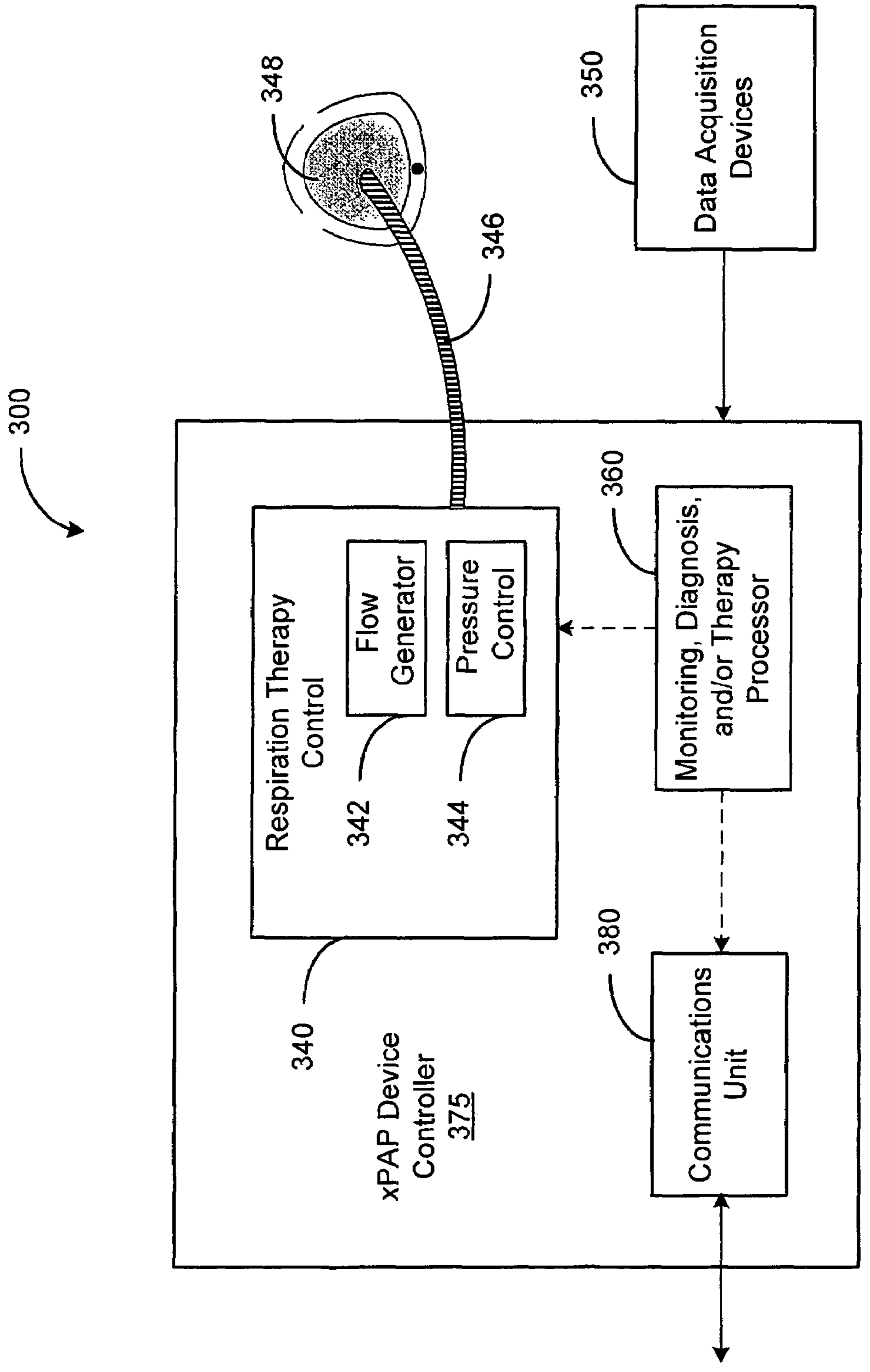
FIG. 3 is a block diagram of a respiratory therapy system that may be utilized in a coordinated system in accordance with embodiments of the invention.

FIG. 3 illustrates a respiratory therapy device 300 in accordance with embodiments of the invention. Respiratory therapy, such as gas therapy, oxygen therapy, CO2 therapy, positive airway pressure therapy, or other therapies provided to a patient through the pulmonary system, may mitigate a patient's suffering from a number of respiratory disorders. Some lung diseases, such as emphysema, sarcoidosis, and chronic obstructive pulmonary disorder, reduce lung function to the extent that supplemental oxygen is needed to continue normal bodily functions. For many patients with end stage lung disease, oxygen therapy allows the patients to get the oxygen they need, helps them be more active, and may also prevent or treat heart failure. All types of respiratory therapy devices are referred to generically herein as xPAP devices.

The respiratory therapy device 300 may include, for example, any of the positive airway pressure devices, including CPAP, bi-level positive airway pressure (bi-PAP), proportional positive airway pressure (PPAP), and/or autotitration positive airway pressure devices, for example. Continuous positive airway pressure (CPAP) devices deliver a set air pressure to the patient. The pressure level for the individual patient may be determined during a titration study. Such a study may take place in a sleep lab, and involves determination of the optimum airway pressure by a sleep physician or other professional. The CPAP device pressure control is set to the determined level. When the patient uses the CPAP device, a substantially constant airway pressure level is maintained by the device.

Autotitration PAP devices are similar to CPAP devices, however, the pressure controller for autotitration devices automatically determines the air pressure for the patient. Instead of maintaining a constant pressure, the autotitration PAP device evaluates sensor signals and the changing needs of the patient to deliver a variable positive airway pressure. Autotitration PAP and CPAP are often used to treat sleep disordered breathing, for example.

Bi-level positive airway pressure (bi-PAP) devices provide two levels of positive airway pressure. A higher pressure is maintained while the patient inhales. The device switches to a lower pressure during expiration. Bi-PAP devices are used to treat a variety of respiratory dysfunctions, including chronic obstructive pulmonary disease (COPD), respiratory insufficiency, and ALS or Lou Gehrig's disease, among others.

Respiratory therapy may be provided by a servo ventilation device. Servo ventilation devices provide airway pressure dependent on the respiration cycle stage. A servo ventilation device provides positive pressure on inhalation and negative pressure on exhalation.

The respiration therapy control unit 340, illustrated in this example as a positive airway device, includes a flow generator 342 that pulls in air through a filter. The flow generator 342 is controlled by the pressure control circuitry 344 to deliver an appropriate air pressure to the patient. Air flows through tubing 346 coupled to the respiratory device 300 and is delivered to the patient's airway through a mask 348. In one example, the mask 348 may be a nasal mask covering only the patient's nose. In another example, the mask 348 covers the patient's nose and mouth.

The respiratory device 300 includes a communications unit 380 for communicating with one or more separate devices, including patient-external and/or patient-internal monitoring, diagnostic and/or therapeutic devices.

The respiratory therapy device 300 may receive information from one or more data acquisition devices 350, e.g., sensors, patient input devices, and/or other information systems. The acquired information may be used to implement one or more monitoring, diagnostic and/or therapeutic functions 360 of the respiratory therapy device 300. In one example, a monitoring processor 360 may be used to store information related to one or more physiological or nonphysiological parameters acquired over a period of time. In another example, a diagnostics unit may assess the presence of a disease or disorder based on information acquired through use of the data acquisition devices and/or received via the communications channel 370 from a separate device. In yet a further example, therapy delivered by the respiratory therapy device 300 may be controlled by a therapy processor 360. Alternatively or additionally, the therapy processor 360 may control therapy delivered by remote device coupled to the respiratory therapy device 300 via the communications channel 370.

Figure 4A:
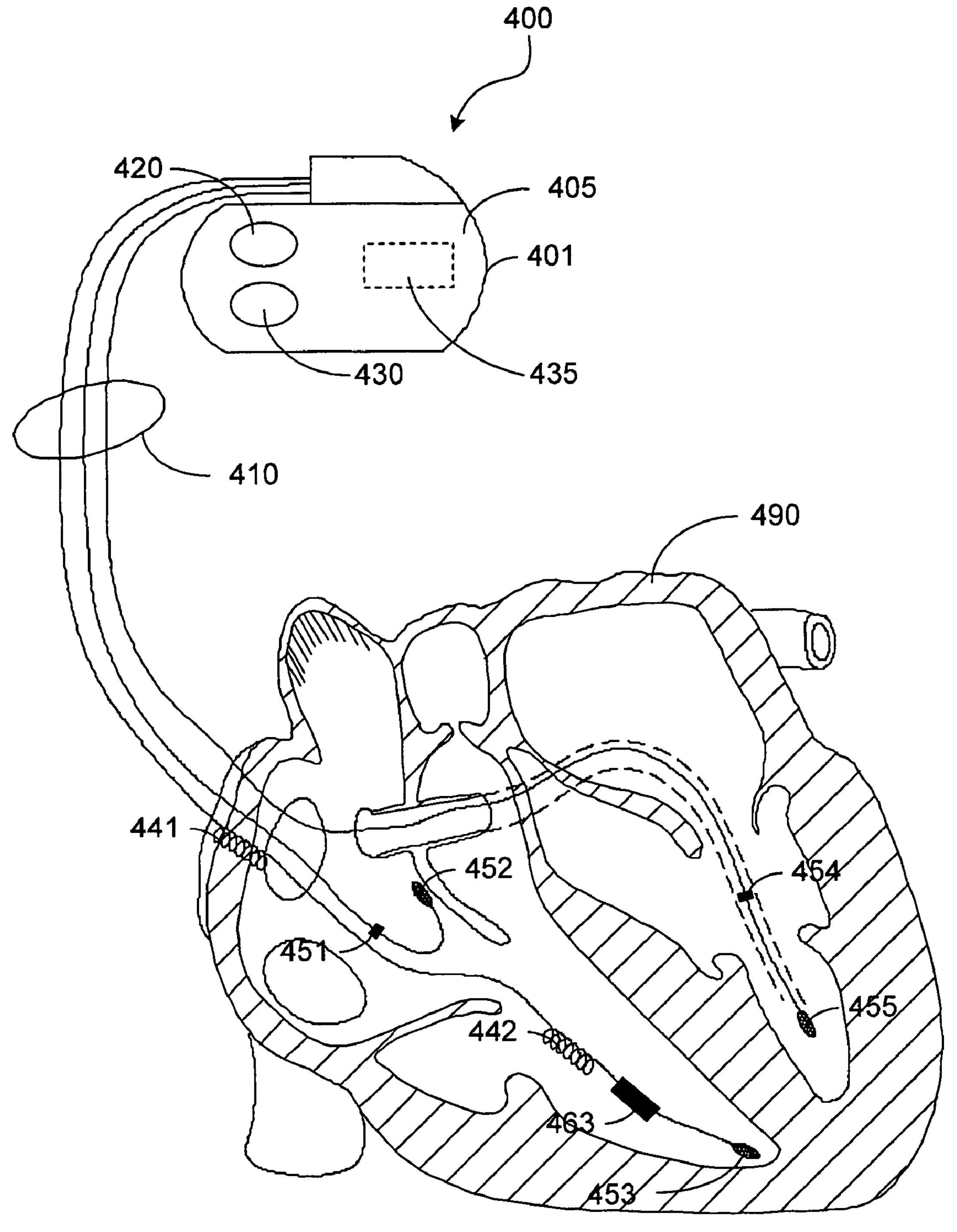
FIG. 4A is a partial view of an implantable device that may be utilized in a coordinated system in accordance with embodiments of the invention.

FIG. 4A is a partial view of an implantable cardiac device that may include circuitry for implementing coordinated monitoring, diagnosis and/or therapy in accordance with embodiments of the invention. In this example, the implantable device comprises a cardiac rhythm management device (CRM) 400 including an implantable electrical stimulation generator 405 electrically and physically coupled to an intracardiac lead system 410. Portions of the intracardiac lead system 410 are inserted into the patient's heart 490. The intracardiac lead system 410 includes one or more electrodes configured to sense electrical cardiac activity of the heart, deliver electrical stimulation to the heart, sense the patient's transthoracic impedance, and/or sense other physiological parameters, e,g, cardiac chamber pressure or temperature. Portions of the housing 401 of the pulse generator 405 may optionally serve as a can electrode.

Communications circuitry is disposed within the housing 401 for facilitating communication between the electrical stimulation generator 405 and remote devices having wireless communication functionality, such as a portable or bed-side communication station, patient-carried/worn communication station, or external programmer, for example. The wireless communications circuitry can also facilitate unidirectional or bidirectional communication with one or more implanted, external, cutaneous, or subcutaneous physiologic or non-physiologic sensors, patient-input devices and/or other information systems.

The housing 401 of the electrical stimulation generator 405 may optionally incorporate various sensors, including, for example, a motion sensor that may be programmed to sense various conditions. For example, the motion sensor may be optionally configured to sense snoring, patient activity level, and/or chest wall movements associated with respiratory effort, for example. In one example implementation, the motion detector may be implemented as an accelerometer positioned in or on the housing 401 of the electrical stimulation generator 405. If the motion sensor is implemented as an accelerometer, the motion sensor may also provide respiratory information, e.g. rales, coughing, and cardiac information, e.g. S1-S4 heart sounds, murmurs, and/or other acoustic information.

The lead system 410 of the CRM 400 may incorporate one or more electrodes used to sense transthoracic impedance. Transthoracic impedance sensing may be used to acquire the patient's respiration waveform, or other respiration-related information. Transthoracic impedance may be sensed using one or more intracardiac electrodes 441, 442, 451-455, 463 positioned in one or more chambers of the heart 490. The intracardiac electrodes 441, 442, 451-455, 463 may be coupled to impedance drive/sense circuitry positioned within the housing of the electrical stimulation generator 405.

In one implementation, impedance drive/sense circuitry disposed within the housing 401 generates a current that flows through the tissue between an impedance drive electrode 451 and a can electrode on the housing 401 of the electrical stimulation generator 405. The voltage at an impedance sense electrode 452 relative to the can electrode changes as the patient's transthoracic impedance changes. The voltage signal developed between the impedance sense electrode 452 and the can electrode is detected by the impedance sense circuitry disposed within the housing 401 of the electrical stimulation generator 405. Other locations and/or combinations of impedance sense and drive electrodes are also possible.

Figure 4B:
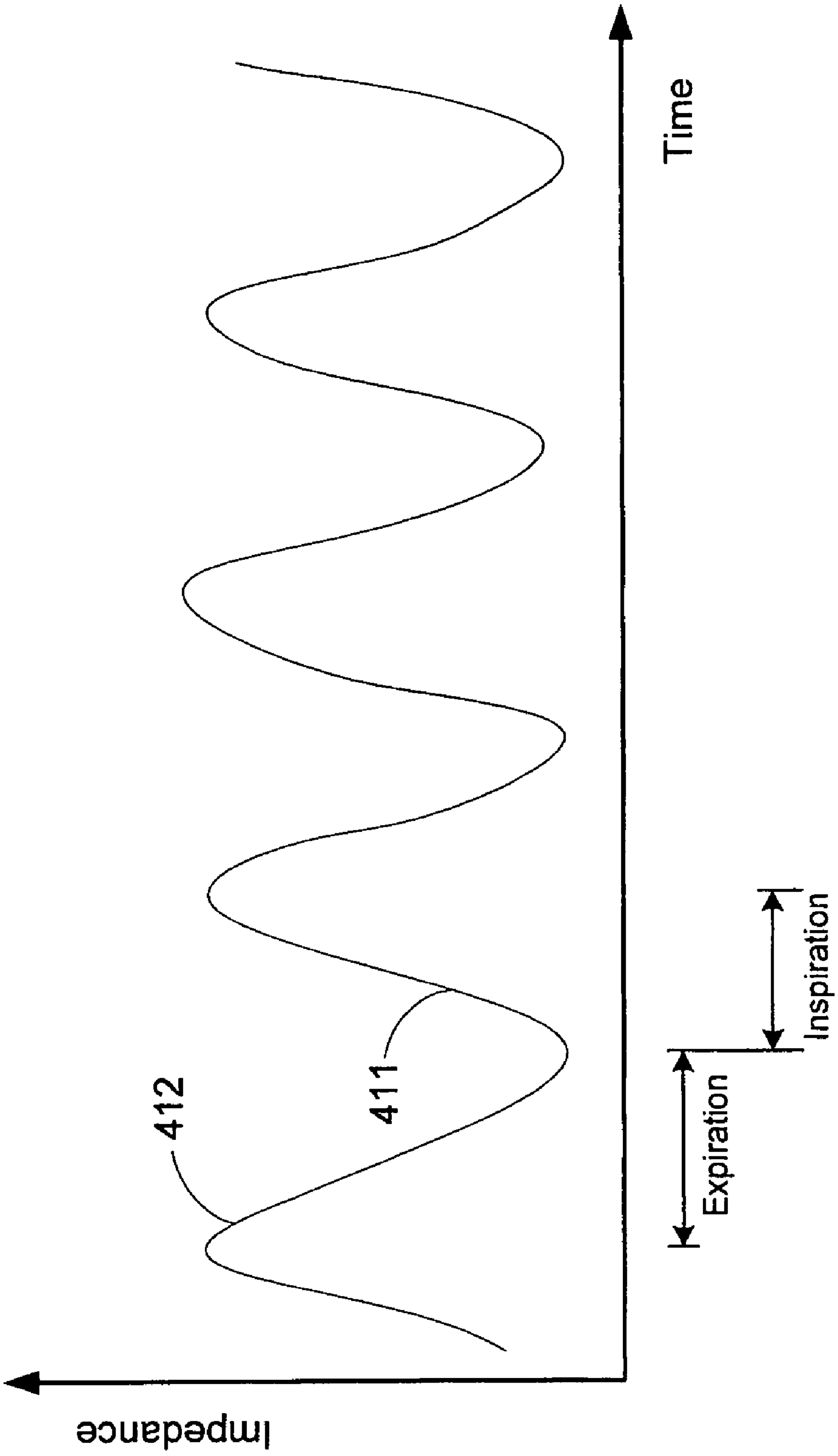
FIG. 4B illustrates a normal respiration pattern as represented by a transthoracic impedance sensor signal.

The voltage signal developed at the impedance sense electrode 452, illustrated in FIG. 4A, is proportional to the patient's transthoracic impedance and represents the patient's respiration waveform. The transthoracic impedance increases during respiratory inspiration and decreases during respiratory expiration. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration—expiration cycles without substantial interruptions, as indicated in FIG. 4B.

Returning to FIG. 4A, the lead system 410 may include one or more cardiac pace/sense electrodes 451-455 positioned in, on, or about one or more heart chambers for sensing electrical signals from the patient's heart 490 and/or delivering pacing pulses to the heart 490. The intracardiac sense/pace electrodes 451-455, such as those illustrated in FIG. 4A, may be used to sense and/or pace one or more chambers of the heart, including the left ventricle, the right ventricle, the left atrium and/or the right atrium. The lead system 410 may include one or more defibrillation electrodes 441, 442 for delivering defibrillation/cardioversion shocks to the heart 490.

As described above, the housing 401 of the electrical stimulation generator 405 may include circuitry for detecting cardiac arrhythmias and/or for controlling pacing and/or defibrillation therapy in the form of electrical stimulation pulses or shocks delivered to the heart through the lead system 410. Also disposed within the housing 401 may be various communications circuitry and monitoring, diagnostic, and/or therapy control circuitry that may be used to effect coordinated monitoring, diagnosis and/or therapy in accordance with embodiments of the invention.

In accordance with another embodiment, an implantable transthoracic cardiac sensing and/or stimulation (ITCS) device may be implemented to detect/monitor normal and abnormal cardiac and/or respiratory activity, and may be configured to deliver an appropriate therapy in response to abnormal activity or conditions. An ITCS device 500 of the present invention may be configured for monitoring, diagnosing, and/or treating cardiac and disordered breathing events/conditions. An ITCS device 500 is typically implemented to sense activity of both the cardiac system and the respiratory system. Using appropriate sensors, the ITCS device 500 may be implemented to detect and monitor a variety of disordered breathing conditions, including sleep and non-sleep related disordered breathing conditions. An ITCS device 500 may further be implemented to detect sleep, and may further be implemented to detect stages of patient sleep. An ITCS device 500 so implemented may be configured to perform a variety of sensing, monitoring, diagnosing, and/or therapy control/coordination functions, including those described herein and in the references respectively incorporated herein.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243 and commonly owned U.S. patent application Ser. No. 60/462,272, filed Apr. 11, 2003; U.S. Publication Nos. 2004/0230229; 2004/0230230; 2005/0004615; U.S. Pat. No. 7,570,997; and U.S. Publication No. 2004/0215240, all of which are incorporated herein by reference.

Figure 5A:
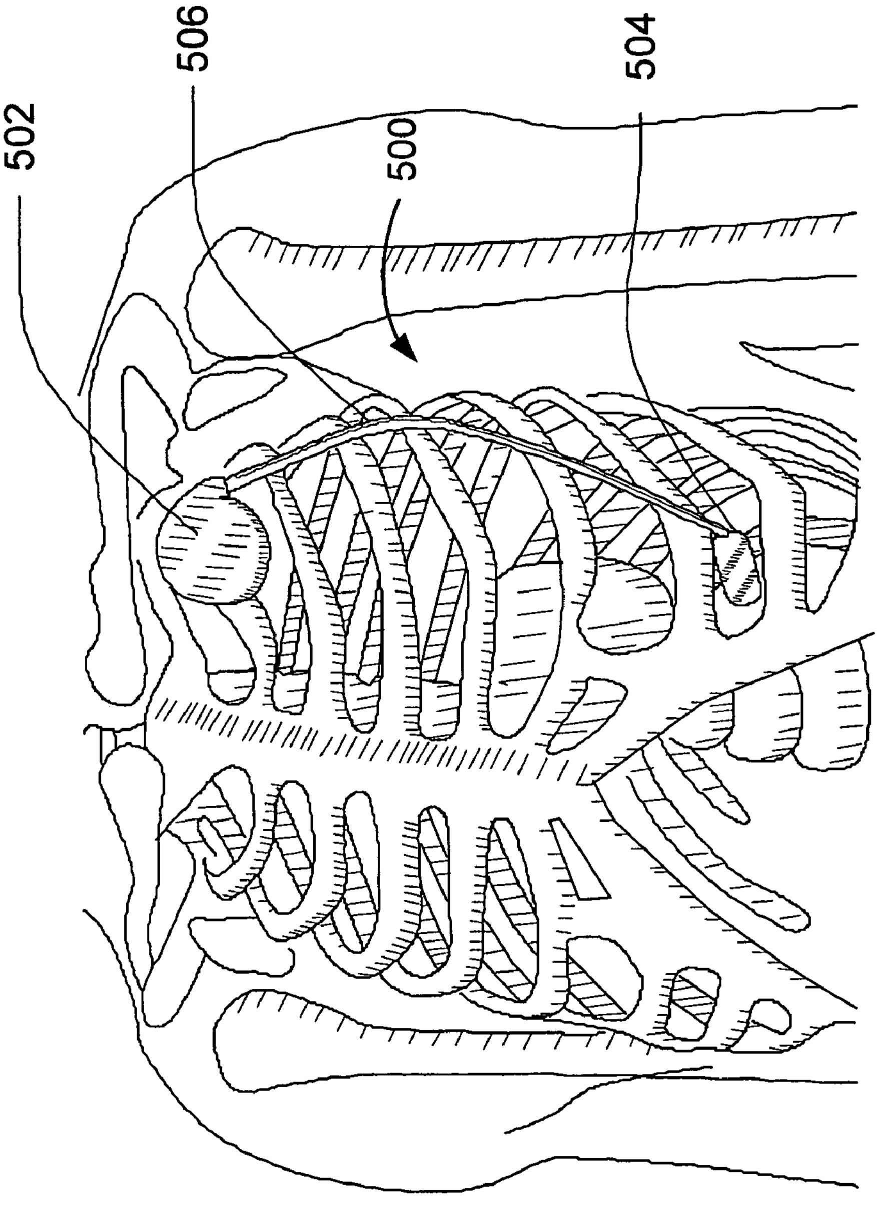
FIG. 5A is a view of a transthoracic cardiac sensing and/or stimulation device as implanted in a patient in accordance with an embodiment of the present invention.

FIG. 5A is a block diagram illustrating various components of an ITCS device 500 that provides for disordered breathing detection and/or treatment in accordance with embodiments of the present invention. In general terms, cardiac activity and disordered breathing (e.g., sleep disordered breathing and wakeful disordered breathing) may be detected, monitored, and/or treated with use of an ITCS device 500, such as the one shown in FIG. 5A. An ITCS device 500 may be implanted under the skin in the chest region of a patient. The ITCS device 500 may, for example, be implanted subcutaneously such that all or selected elements of the device are positioned on the patient's front, back, side, or other body locations suitable for sensing cardiac activity and delivering cardiac stimulation therapy. It is understood that elements of the ITCS device 500 may be located at several different body locations, such as in the chest, abdominal, or subclavian region with electrode elements respectively positioned at different regions near, around, or on the heart.

The primary housing (e.g., the active or non-active can) 502 of the ITCS device 500, for example, may be configured for positioning outside of the rib cage at an intercostal or subcostal location, within the abdomen, or in the upper chest region (e.g., subclavian location, such as above the third rib). In one implementation, one or more electrodes may be located on the primary housing 502 and/or at other locations (e.g., electrode 504) about, but not in direct contact with the heart, great vessels or coronary vasculature. A pulse generator and a cardiac stimulation controller are disposed in the primary housing 502. The cardiac stimulator controller determines and coordinates appropriate cardiac and/or respiratory therapy to be delivered to a patient, and the pulse generator produces the appropriate energy waveforms associated with a selected therapy. Also disposed in the primary housing 502 is a cardiac activity detector configured to detect normal and abnormal (e.g., arrhythmic) cardiac activity.

In a further implementation, one or more subcutaneous electrode subsystems or electrode arrays 504 may be used to sense cardiac activity and deliver cardiac stimulation energy in an ITCS device 500 configuration employing an active can or a configuration employing a non-active can. Electrodes (e.g., electrode 504) may be situated at anterior and/or posterior locations relative to the heart.

The ITCS device 500 depicted in FIG. 5A may be configured in a manner described herein or may have other configurations. An ITCS device 500 of the present invention may be implemented to include one or more of cardiac and/or respiratory detection/monitoring circuitry (e.g., for cardiac activity, breathing patterns such as from transthoracic impedance signals, heart sounds, blood gas/chemistry such as oxygen saturation and/or pH), cardiac and respiratory diagnostics circuitry, and cardiac and respiratory therapy circuitry. An ITCS device 500 of the present invention may be implemented to provide for upgradeability in terms of functionality and/or configuration. For example, an ITCS device 500 may be implemented as an upgradeable or reconfigurable cardiac/respiratory monitor or stimulation device.

An ITCS device 500 in accordance with embodiments of the present invention provides for patient breathing monitoring and disordered breathing detection and/or prediction. Such embodiments may further provide treatment for detected or predicted disordered breathing events or conditions, as determined by a therapy controller or in response to an externally generated command signal (such as received from an advanced patient management system or programmer). Detection and treatment of disordered breathing and/or respiratory conditions may be facilitated by use of an ITCS device 500 having appropriate sensing/detection/therapy delivery capabilities, or by cooperative use of an ITCS device 500 and an external programmer or an advanced patient management system via a communications interface.

With continued reference to FIG. 5A, the ITCS device 500 includes a housing 502 within which various cardiac and respiratory sensing, detection, processing, and energy delivery circuitry may be housed. Communications circuitry is disposed within the housing 502 for facilitating communication between the ITCS device 500 and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 502 is typically configured to include one or more electrodes (e.g., can electrode and/or indifferent electrode). Although the housing 502 is typically configured as an active can, it is appreciated that a non-active can configuration may be implemented, in which case at least two electrodes spaced apart from the housing 502 are employed.

In the configuration shown in FIG. 5A, a subcutaneous electrode 504 may be positioned under the skin in the chest region and situated distal from the housing 502. The subcutaneous and, if applicable, housing electrode(s) may be positioned about the heart at various locations and orientations, such as at various anterior and/or posterior locations relative to the heart. The subcutaneous electrode 504 is coupled to circuitry within the housing 502 via a lead assembly 506. One or more conductors (e.g., coils or cables) are provided within the lead assembly 506 and electrically couple the subcutaneous electrode 504 with circuitry in the housing 502. One or more sense, sense/pace or defibrillation electrodes may be situated on the elongated structure of the electrode support, the housing 502, and/or the distal electrode assembly (shown as subcutaneous electrode 504 in the configuration shown in FIG. 5A).

In one configuration, the lead assembly 506 is generally flexible and has a construction similar to conventional implantable, medical electrical leads (e.g., defibrillation leads or combined defibrillation/pacing leads). In another configuration, the lead assembly 506 is constructed to be somewhat flexible, yet has an elastic, spring, or mechanical memory that retains a desired configuration after being shaped or manipulated by a clinician. For example, the lead assembly 506 may incorporate a gooseneck or braid system that may be distorted under manual force to take on a desired shape. In this manner, the lead assembly 506 may be shape-fit to accommodate the unique anatomical configuration of a given patient, and generally retains a customized shape after implantation. Shaping of the lead assembly 506 according to this configuration may occur prior to, and during, ITCS device 500 implantation.

In accordance with a further configuration, the lead assembly 506 includes an electrode support assembly, such as an elongated structure that positionally stabilizes the subcutaneous electrode 504 with respect to the housing 502. In this configuration, the rigidity of the elongated structure maintains a desired spacing between the subcutaneous electrode 504 and the housing 502, and a desired orientation of the subcutaneous electrode 104/housing 502 relative to the patient's heart. The elongated structure may be formed from a structural plastic, composite or metallic material, and includes, or is covered by, a biocompatible material. Appropriate electrical isolation between the housing 502 and subcutaneous electrode 504 is provided in cases where the elongated structure is formed from an electrically conductive material, such as metal.

In one configuration, the electrode support assembly and the housing 502 define a unitary structure (e.g., a single housing/unit). The electronic components and electrode conductors/connectors are disposed within or on the unitary ITCS device 500 housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 502. The electrode support assembly includes mechanical and electrical couplings that facilitate mating engagement with corresponding mechanical and electrical couplings of the housing 502. For example, a header block arrangement may be configured to include both electrical and mechanical couplings that provide for mechanical and electrical connections between the electrode support assembly and housing 502. The header block arrangement may be provided on the housing 502 or the electrode support assembly. Alternatively, a mechanical/electrical coupler may be used to establish mechanical and electrical connections between the electrode support assembly and housing 502. In such a configuration, a variety of different electrode support assemblies of varying shapes, sizes, and electrode configurations may be made available for physically and electrically connecting to a standard ITCS device 500 housing 502.

It is noted that the electrodes and the lead assembly 506 may be configured to assume a variety of shapes. For example, the lead assembly 506 may have a wedge, chevron, flattened oval, or a ribbon shape, and the subcutaneous electrode 504 may include a number of spaced electrodes, such as an array or band of electrodes. Moreover, two or more subcutaneous electrodes 504 may be mounted to multiple electrode support assemblies 506 to achieve a desired spaced relationship amongst subcutaneous electrodes 504.

Figure 5B:
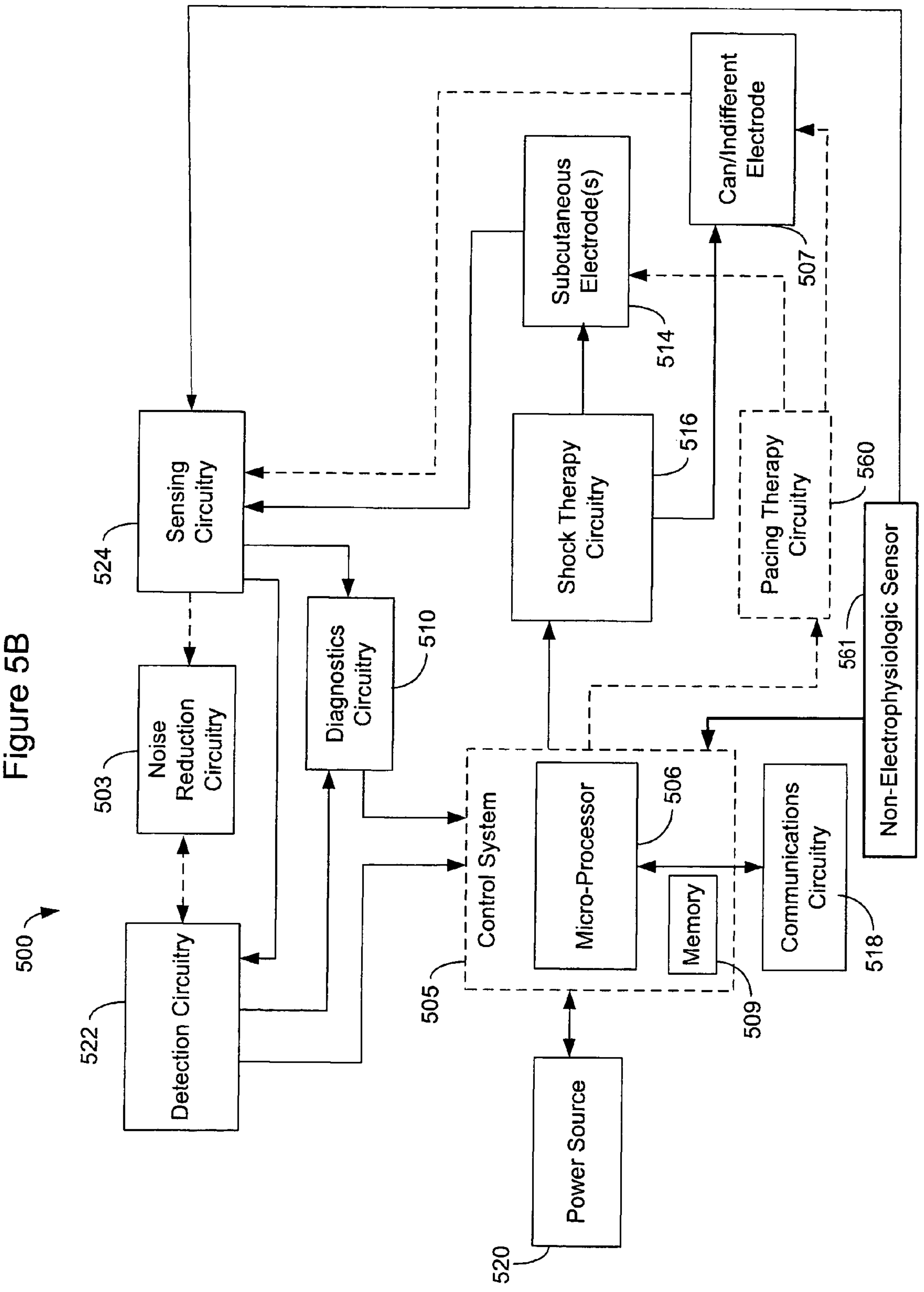
FIG. 5B is a block diagram illustrating various components of a transthoracic cardiac sensing and/or stimulation device in accordance with an embodiment of the present invention.

FIG. 5B is a block diagram depicting various components of an ITCS device 500 in accordance with one configuration. According to this configuration, the ITCS device 500 incorporates a processor-based control system 505 which includes a micro-processor 526 coupled to appropriate memory (volatile and non-volatile) 509, it being understood that any logic-based control architecture may be used. The control system 505 is coupled to circuitry and components to sense, detect, and analyze electrical signals produced by the heart and deliver electrical stimulation energy to the heart under predetermined conditions to treat cardiac arrhythmias. In certain configurations, the control system 505 and associated components also provide pacing therapy to the heart. The electrical energy delivered by the ITCS device 500 may be in the form of low energy pacing pulses, non-excitatory energy (e.g., sub-threshold stimulation energy) or high-energy pulses for cardioversion or defibrillation.

Cardiac signals are sensed using the subcutaneous electrode(s) 514 and the can or indifferent electrode 507 provided on the ITCS device 500 housing. Cardiac signals may also be sensed using only the subcutaneous electrodes 514, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 524, which includes sense amplification circuitry and may also include filtering circuitry and an analog-to-digital (A/D) converter. The sensed cardiac signals processed by the sensing circuitry 524 may be received by noise reduction circuitry 503, which may further reduce noise before signals are sent to the detection circuitry 522.

Noise reduction circuitry 503 may also be incorporated after sensing circuitry 522 in cases where high power or computationally intensive noise reduction algorithms are required. The noise reduction circuitry 503, by way of amplifiers used to perform operations with the electrode signals, may also perform the function of the sensing circuitry 524. Combining the functions of sensing circuitry 524 and noise reduction circuitry 503 may be useful to minimize the necessary componentry and lower the power requirements of the system.

In the illustrative configuration shown in FIG. 5B, the detection circuitry 522 is coupled to, or otherwise incorporates, noise reduction circuitry 503. The noise reduction circuitry 503 operates to improve the signal-to-noise ratio (SNR) of sensed cardiac signals by removing noise content of the sensed cardiac signals introduced from various sources. Typical types of transthoracic cardiac signal noise includes electrical noise and noise produced from skeletal muscles, for example.

Detection circuitry 522 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 522 to detect and verify the presence and severity of an arrhythmic episode.

The detection circuitry 522 communicates cardiac signal information to the control system 505. Memory circuitry 509 of the control system 505 contains parameters for operating in various sensing, defibrillation, and, if applicable, pacing modes, and stores data indicative of cardiac signals received by the detection circuitry 522. The memory circuitry 509 may also be configured to store historical ECG and therapy data, which may be used for various purposes and transmitted to an external receiving device as needed or desired.

In certain configurations, the ITCS device 500 may include diagnostics circuitry 510. The diagnostics circuitry 510 typically receives input signals from the detection circuitry 522 and the sensing circuitry 524. The diagnostics circuitry 510 provides diagnostics data to the control system 505, it being understood that the control system 505 may incorporate all or part of the diagnostics circuitry 510 or its functionality. The control system 505 may store and use information provided by the diagnostics circuitry 510 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 505 processes cardiac signal data received from the detection circuitry 522 and initiates appropriate tachyarrhythmia therapies to terminate cardiac arrhythmic episodes and return the heart to normal sinus rhythm. The control system 505 is coupled to shock therapy circuitry 516. The shock therapy circuitry 516 is coupled to the subcutaneous electrode(s) 514 and the can or indifferent electrode 507 of the ITCS device 500 housing. Upon command, the shock therapy circuitry 516 delivers cardioversion and defibrillation stimulation energy to the heart in accordance with a selected cardioversion or defibrillation therapy. In a less sophisticated configuration, the shock therapy circuitry 516 is controlled to deliver defibrillation therapies, in contrast to a configuration that provides for delivery of both cardioversion and defibrillation therapies.

In accordance with another configuration, an ITCS device 500 may incorporate a cardiac pacing capability in addition to cardioversion and/or defibrillation capabilities. As is shown in dotted lines in FIG. 5B, the ITCS device 500 may include pacing therapy circuitry 530, which is coupled to the control system 505 and the subcutaneous and can/indifferent electrodes 514, 507. Upon command, the pacing therapy circuitry delivers pacing pulses to the heart in accordance with a selected pacing therapy. Control signals, developed in accordance with a pacing regimen by pacemaker circuitry within the control system 505, are initiated and transmitted to the pacing therapy circuitry 530 where pacing pulses are generated. A pacing regimen may be modified by the control system 505.

A number of cardiac pacing therapies may be useful in a transthoracic cardiac monitoring and/or stimulation device. Such cardiac pacing therapies may be delivered via the pacing therapy circuitry 530 as shown in FIG. 5B. Alternatively, cardiac pacing therapies may be delivered via the shock therapy circuitry 516, which effectively obviates the need for separate pacemaker circuitry.

The ITCS device 500 shown in FIG. 5B is configured to receive signals from one or more physiologic and/or non-physiologic sensors. Depending on the type of sensor employed, signals generated by the sensors may be communicated to transducer circuitry coupled directly to the detection circuitry 522 or indirectly via the sensing circuitry 524. It is noted that certain sensors may transmit sense data to the control system 505 without processing by the detection circuitry 522.

Non-electrophysiological cardiac sensors 561 may be coupled directly to the detection circuitry 522 or indirectly via the sensing circuitry 524. Non-electrophysiological cardiac sensors 561 sense cardiac activity that is non-electrophysiological in nature. Examples of non-electrophysiological cardiac sensors 561 include blood oxygen sensors, transthoracic impedance sensors, blood volume sensors, acoustic sensors and/or pressure transducers, and accelerometers. Signals from these sensors are developed based on cardiac activity, but are not derived directly from electrophysiological sources (e.g., R-waves or P-waves). A non-electrophysiological cardiac sensor 561, as is illustrated in FIG. 5B, may be connected to one or more of the sensing circuitry 524, detection circuitry 522 (connection not shown for clarity), and the control system 505.

Communications circuitry 518 is coupled to the microprocessor 526 of the control system 505. The communications circuitry 518 allows the ITCS device 500 to communicate with one or more receiving devices or systems situated external to the ITCS device 500. By way of example, the ITCS device 500 may communicate with a patient-worn, portable or bedside communication system via the communications circuitry 518. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the ITCS device 500 via the communications circuitry 518. It is noted that physiologic or non-physiologic sensors equipped with wireless transmitters or transceivers may communicate with a receiving system external of the patient.

The communications circuitry 518 may allow the ITCS device 500 to communicate with an external programmer. In one configuration, the communications circuitry 518 and the programmer unit (not shown) use a wire loop antenna and a radio frequency telemetric link, as is known in the art, to receive and transmit signals and data between the programmer unit and communications circuitry 518. In this manner, programming commands and data are transferred between the ITCS device 500 and the programmer unit during and after implant. Using a programmer, a physician is able to set or modify various parameters used by the ITCS device 500. For example, a physician may set or modify parameters affecting sensing, detection, pacing, and defibrillation functions of the ITCS device 500, including pacing and cardioversion/defibrillation therapy modes.

Typically, the ITCS device 500 is encased and hermetically sealed in a housing suitable for implanting in a human body as is known in the art. Power to the ITCS device 500 is supplied by an electrochemical power source 520 housed within the ITCS device 500. In one configuration, the power source 520 includes a rechargeable battery. According to this configuration, charging circuitry is coupled to the power source 520 to facilitate repeated non-invasive charging of the power source 520. The communications circuitry 518, or separate receiver circuitry, is configured to receive RF energy transmitted by an external RF energy transmitter. The ITCS device 500 may, in addition to a rechargeable power source, include a non-rechargeable battery. It is understood that a rechargeable power source need not be used, in which case a long-life non-rechargeable battery is employed.

The components, functionality, and structural configurations depicted in FIGS. 5A-5E are intended to provide an understanding of various features and combination of features that may be incorporated in an ITCS device 500. It is understood that a wide variety of ITCS and other implantable cardiac monitoring and/or stimulation device configurations are contemplated, ranging from relatively sophisticated to relatively simple designs. As such, particular ITCS or cardiac monitoring and/or stimulation device configurations may include particular features as described herein, while other such device configurations may exclude particular features described herein.

In accordance with embodiments of the invention, an ITCS device 500 may be implemented to include a subcutaneous electrode system that provides for one or both of cardiac sensing and arrhythmia therapy delivery. According to one approach, an ITCS device 500 may be implemented as a chronically implantable system that performs monitoring, diagnostic and/or therapeutic functions. The ITCS device 500 may automatically detect and treat cardiac arrhythmias.

In one configuration, an ITCS device 500 includes a pulse generator and one or more electrodes that are implanted subcutaneously in the chest region of the body, such as in the anterior thoracic region of the body. The ITCS device 500 may be used to provide atrial and/or ventricular therapy for bradycardia and tachycardia arrhythmias. Tachyarrhythmia therapy may include cardioversion, defibrillation and anti-tachycardia pacing (ATP), for example, to treat atrial or ventricular tachycardia or fibrillation. Bradycardia therapy may include temporary post-shock pacing for bradycardia or asystole.

In one configuration, an ITCS device 500 according to one approach may utilize conventional pulse generator and subcutaneous electrode implant techniques. The pulse generator device and electrodes may be chronically implanted subcutaneously. Such an ITCS may be used to automatically detect and treat arrhythmias similarly to conventional implantable systems. In another configuration, the ITCS device 500 may include a unitary structure (e.g., a single housing/unit). The electronic components and electrode conductors/connectors are disposed within or on the unitary ITCS device 500 housing/electrode support assembly.

The ITCS device 500 contains the electronics and may be similar to a conventional implantable defibrillator. High voltage shock therapy may be delivered between two or more electrodes, one of which may be the pulse generator housing (e.g., can), placed subcutaneously in the thoracic region of the body.

Additionally or alternatively, the ITCS device 500 may also provide lower energy electrical stimulation for bradycardia therapy. The ITCS device 500 may provide brady pacing similarly to a conventional pacemaker. The ITCS device 500 may provide temporary post-shock pacing for bradycardia or asystole. Sensing and/or pacing may be accomplished using sense/pace electrodes positioned on an electrode subsystem also incorporating shock electrodes, or by separate electrodes implanted subcutaneously.

The ITCS device 500 may detect a variety of physiological signals that may be used in connection with various diagnostic, therapeutic or monitoring implementations in accordance with the present invention. For example, the ITCS device 500 may include sensors or circuitry for detecting pulse pressure signals, blood oxygen level, heart sounds, cardiac acceleration, and other non-electrophysiological signals related to cardiac activity. In one embodiment, the ITCS device 500 senses intrathoracic impedance, from which various respiratory parameters may be derived, including, for example, respiratory tidal volume and minute ventilation. Sensors and associated circuitry may be incorporated in connection with an ITCS device 500 for detecting one or more body movement or body position related signals. For example, accelerometers and GPS devices may be employed to detect patient activity, patient location, body orientation, or torso position.

The ITCS device 500 may be used within the structure of an APM system. APM systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management.

An ITCS device 500 according to one approach provides an easy to implant therapeutic, diagnostic or monitoring system. The ITCS system may be implanted without the need for intravenous or intrathoracic access, providing a simpler, less invasive implant procedure and minimizing lead and surgical complications. In addition, this system would have advantages for use in patients for whom transvenous lead systems cause complications. Such complications include, but are not limited to, surgical complications, infection, insufficient vessel patency, complications associated with the presence of artificial valves, and limitations in pediatric patients due to patient growth, among others. An ITCS system according to this approach is distinct from conventional approaches in that it may be configured to include a combination of two or more electrode subsystems that are implanted subcutaneously in the anterior thorax.

Figure 5C:
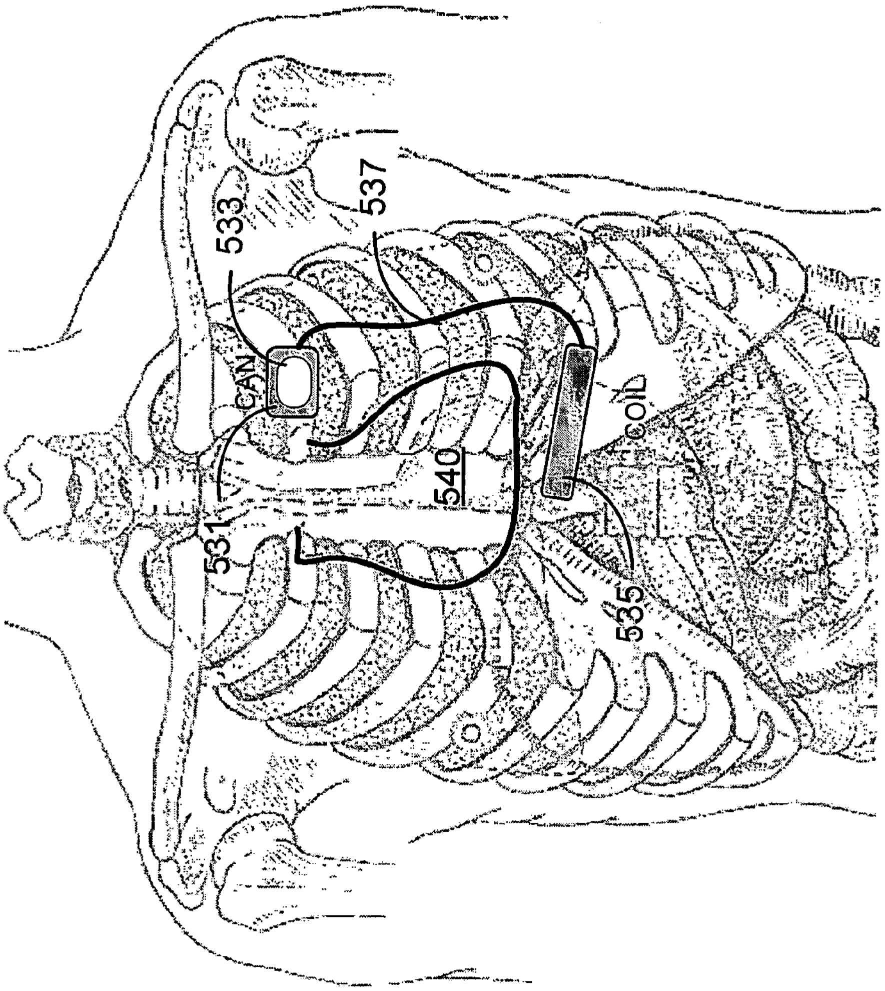
FIGS. 5C-5E are diagrams illustrating various components of a transthoracic cardiac sensing and/or stimulation device located in accordance with embodiments of the invention.

In one ITCS system configuration, as is illustrated in FIG. 5C, electrode subsystems of the ITCS system include a first electrode subsystem, including a can electrode 533, and a second electrode subsystem 535 that may include at least one coil electrode, for example. The second electrode subsystem 535 may include a number of electrodes used for sensing and/or electrical stimulation. In various configurations, the second electrode subsystem 535 may include a single electrode or a combination of electrodes. The single electrode or combination of electrodes including the second electrode subsystem 535 may include coil electrodes, tip electrodes, ring electrodes, multi-element coils, spiral coils, spiral coils mounted on non-conductive backing, and screen patch electrodes, for example. A suitable non-conductive backing material is silicone rubber, for example.

The can electrode 533 is located on the housing 531 that encloses the ITCS device 500 electronics. In one embodiment, the can electrode 533 includes the entirety of the external surface of housing 531. In other embodiments, various portions of the housing 531 may be electrically isolated from the can electrode 533 or from tissue. For example, the active area of the can electrode 533 may include all or a portion of either the anterior or posterior surface of the housing 531 to direct current flow in a manner advantageous for cardiac sensing and/or stimulation.

The housing 531 may resemble that of a conventional implantable ICD, is approximately 20-100 cc in volume, with a thickness of 0.4 to 2 cm and with a surface area on each face of approximately 30 to 100 $cm^2$. As previously discussed, portions of the housing may be electrically isolated from tissue to optimally direct current flow. For example, portions of the housing 531 may be covered with a non-conductive, or otherwise electrically resistive, material to direct current flow. Suitable non-conductive material coatings include those formed from silicone rubber, polyurethane, or parylene, for example.

FIG. 5C illustrates the housing 531 and can electrode 533 placed subcutaneously, superior to the heart 540 in the left pectoral region, which is a location commonly used for conventional pacemaker and defibrillator implants. The second electrode subsystem 535 may include a coil electrode mounted on the distal end of a lead body 537, where the coil is approximately 3-15 French in diameter and 5-12 cm in length. The coil electrode may have a slight preformed curve along its length. The lead may be introduced through the lumen of a subcutaneous sheath, through a common tunneling implant technique, and the second electrode subsystem 535, e.g., including a coil electrode, may be placed subcutaneously, deep to any subcutaneous fat and adjacent to the underlying muscle layer.

In this configuration, the second electrode subsystem 535 is located approximately parallel with the inferior aspect of the right ventricle of the heart 540, just inferior to the right ventricular free wall, with one end extending just past the apex of the heart 540. For example, the tip of the electrode subsystem 535 may extend less than about 3 cm and may be about 1-2 cm left lateral to the apex of the heart 540. This electrode arrangement may be used to include a majority of ventricular tissue within a volume defined between the housing 531 and the second electrode subsystem 535. In one configuration, a majority of the ventricular tissue is included within a volume associated with an area bounded by lines drawn between the distal and proximal ends of the second electrode subsystem 535 and the medial and lateral edges of the left pectoral can electrode 533.

In one example arrangement, the volume including a majority of ventricular tissue may be associated with a cross sectional area bounded by lines drawn between the ends of the electrode subsystems 533, 535 or between active elements of the electrode subsystems 533, 535. In one implementation, the lines drawn between active elements of the electrode subsystems 533, 535 may include a medial edge and a lateral edge of the can electrode 533, and a proximal end and a distal end of a coil electrode utilized within the second electrode subsystem 535. Arranging the electrode subsystems so that a majority of ventricular tissue is contained within a volume defined between the active elements of the electrode subsystems 533, 535 provides an efficient position for defibrillation by increasing the voltage gradient in the ventricles of the heart 540 for a given applied voltage between electrode subsystems 533, 535.

Figure 5D:
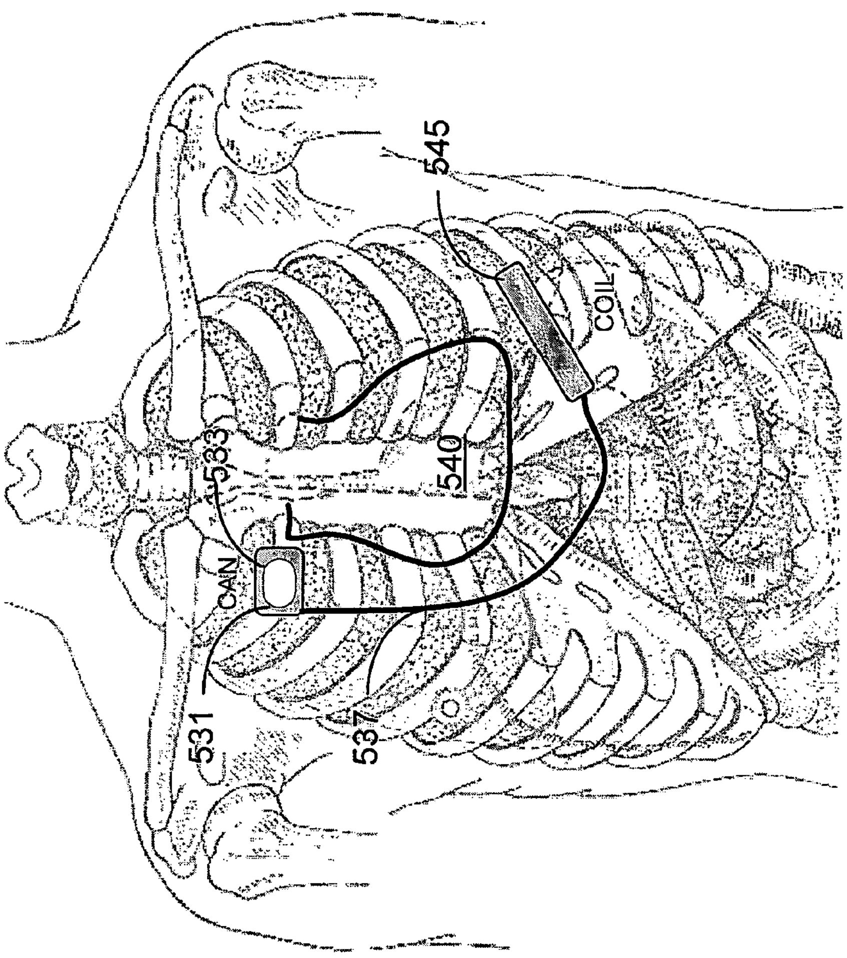

In a similar configuration, and as shown in FIG. 5D, the housing 531 including the can electrode 533 is placed in the right pectoral region. The second electrode subsystem 535 is located more laterally, to again include a majority of the ventricular tissue in a volume defined between the can electrode 533 and the second electrode subsystem 535.

Figure 5E:
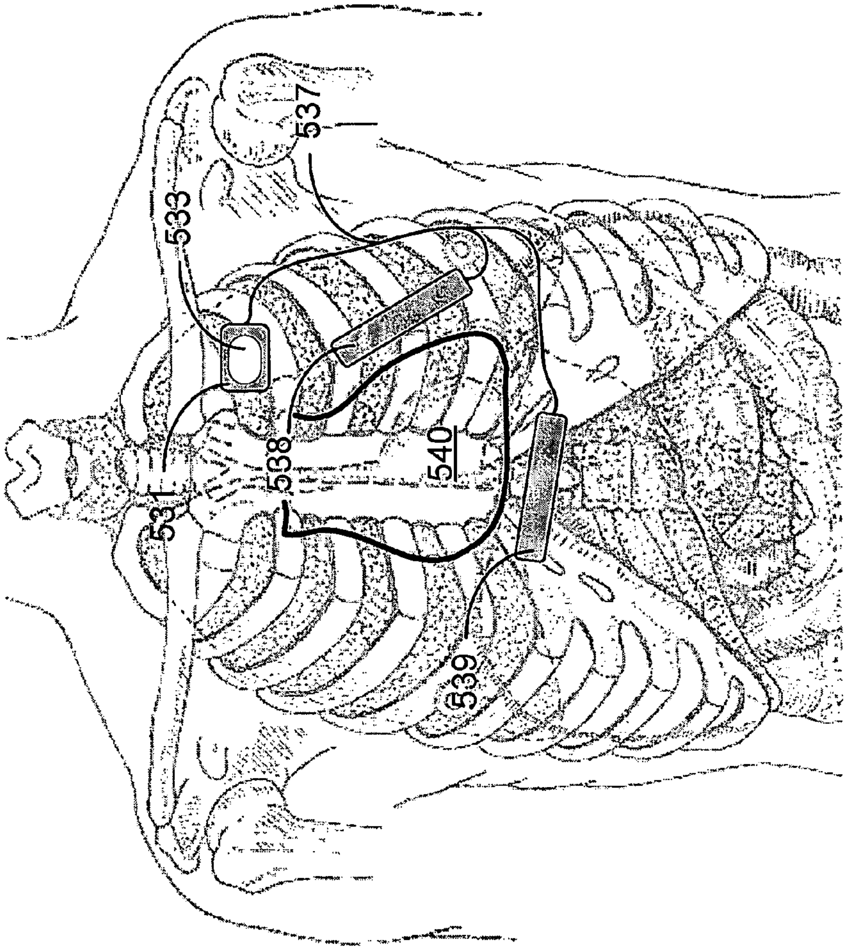

In a further configuration, and as shown in FIG. 5E, the ITCS device housing 531 containing the electronics (i.e., the can) is not used as an electrode. In this case, an electrode system including two electrode subsystems 538, 539 coupled to the housing 531 may be implanted subcutaneously in the chest region of the body, such as in the anterior thorax. The first and the second electrode subsystems 538, 539 are placed in opposition with respect to the ventricles of the heart 540, with the majority of the ventricular tissue of the heart 540 included within a volume defined between the electrode subsystems 538, 539. As illustrated in FIG. 5E, the first electrode system 538 is located superior to the heart 540 relative to a superior aspect of the heart 540, e.g., parallel to the left ventricular free wall. The second electrode system 539 is located inferior to the heart 540 and positioned in relation to an inferior aspect of the heart 540, e.g., parallel to the right ventricular free wall.

In this configuration, the first and the second electrode subsystems 538, 539 may include any combination of electrodes, including or excluding the can electrode, used for sensing and/or electrical stimulation. In various configurations, the electrode subsystems 538, 539 may each be a single electrode or a combination of electrodes. The electrode or electrodes including the first and second electrode subsystems 538, 539 may include any combination of one or more coil electrodes, tip electrodes, ring electrodes, multi-element coils, spiral coils, spiral coils mounted on non-conductive backing, and screen patch electrodes, for example.

Figure 5F:
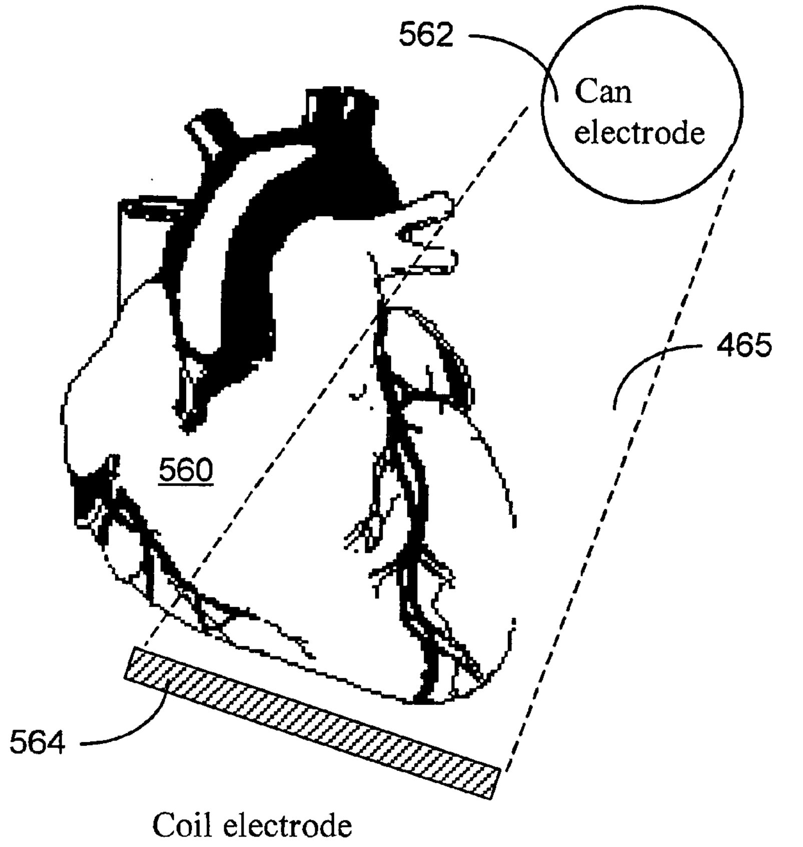
FIGS. 5F-5H are diagrams illustrating electrode subsystem placement relative to a heart in accordance with embodiments of the invention.
Figure 5G:
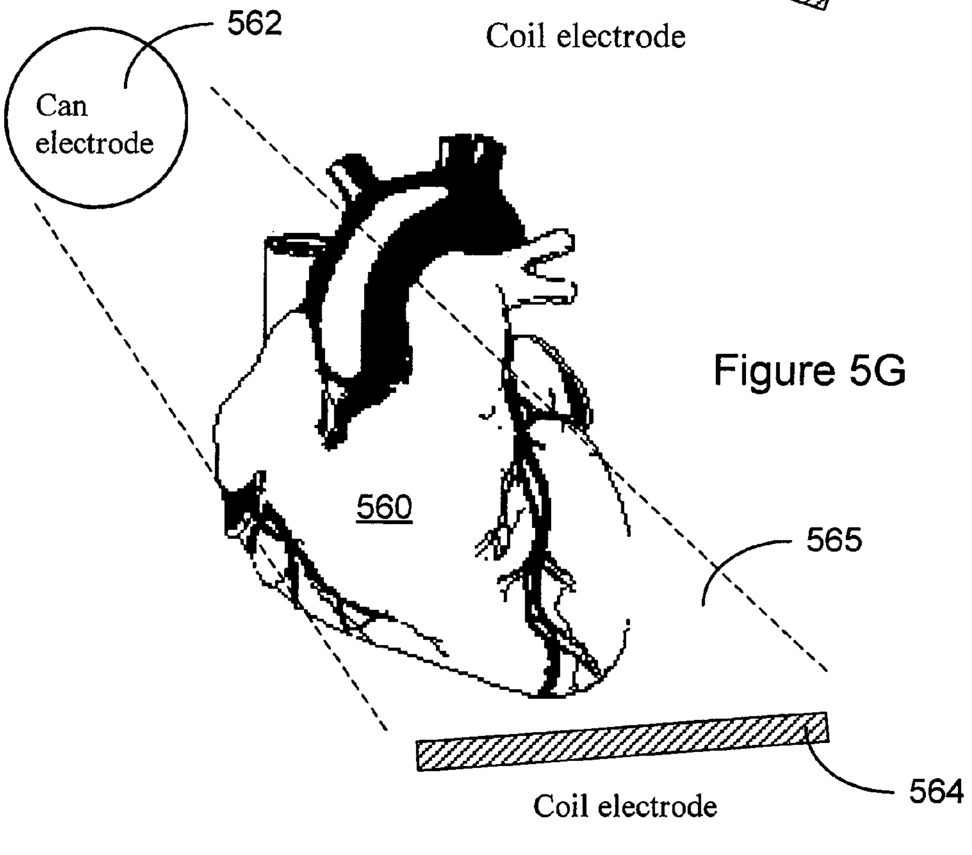
Figure 5H:
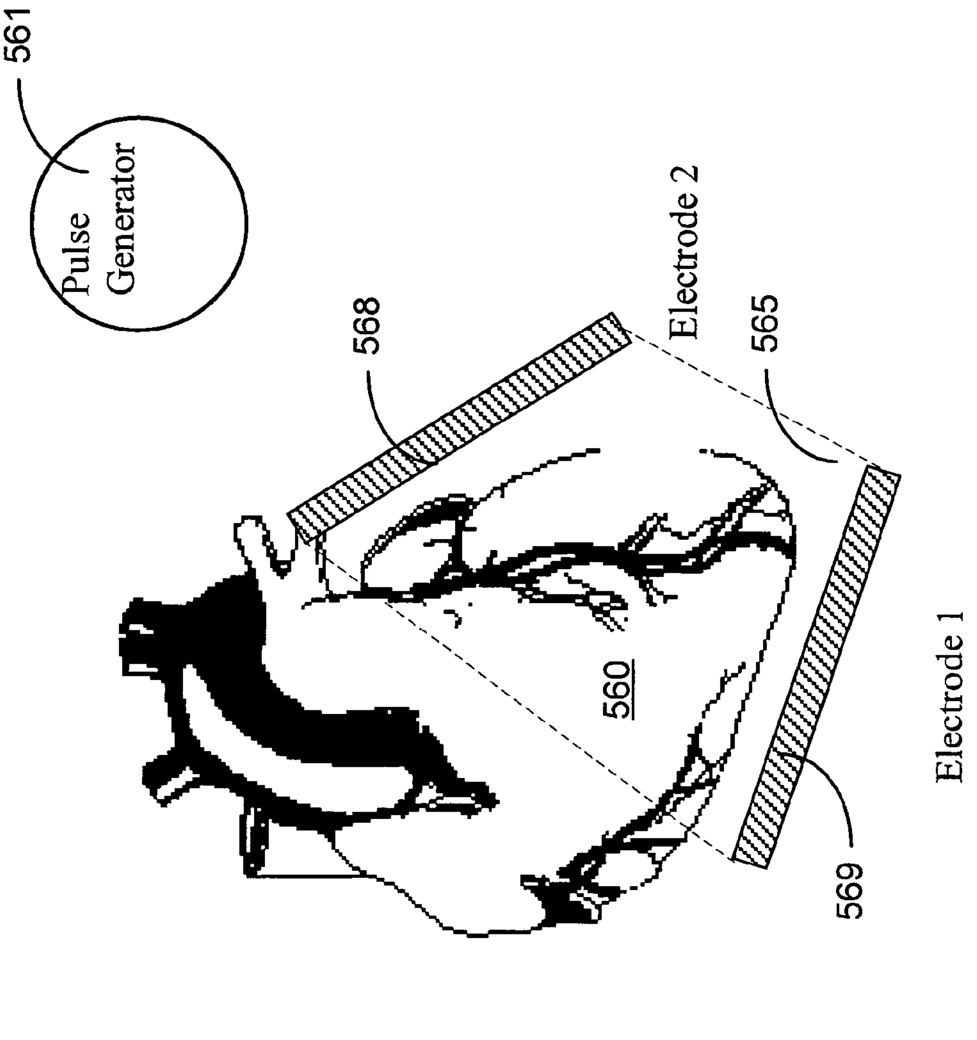

FIGS. 5F-5H provide additional detailed views of subcutaneous electrode subsystem placement considered particularly useful with ITCS devices incorporating disordered breathing detection in accordance with embodiments of the present invention. FIG. 5F illustrates first and second electrode subsystems configured as a can electrode 562 and a coil electrode 564, respectively. FIG. 5F illustrates the can electrode 562 located superior to the heart 560 in the left pectoral region and the coil electrode 564 located inferior to the heart 560, parallel to the right ventricular free wall of the heart 560.

The can electrode 562 and the coil electrode 564 are located so that the majority of ventricular tissue is included within a volume defined between the can electrode 562 and the coil electrode 564. FIG. 5F illustrates a cross sectional area 565 formed by the lines drawn between active elements of the can electrode 562 and the coil electrode 564. Lines drawn between active areas of the electrodes 562, 564, may be defined by a medial edge and a lateral edge of the can electrode 562, and a proximal end and a distal end of a coil electrode utilized as the second electrode subsystem 564. The coil electrode 564 extends a predetermined distance beyond the apex of the heart 560, e.g. less than about 3 cm.

A similar configuration is illustrated in FIG. 5G. In this embodiment, the can electrode 562 is placed superior to the heart 560 in the right pectoral region. The coil electrode 564 is located inferior to the heart. In one arrangement, the coil electrode is located relative to an inferior aspect of the heart 560, for example, the apex of the heart. The can electrode 562 and the coil electrode 564 are positioned so that the majority of ventricular tissue is included within a volume defined between the can electrode 562 and the coil electrode 564.

FIG. 5G illustrates a cross sectional area 565 formed by the lines drawn between active elements of the can electrode 562 and the coil electrode 564. Lines drawn between active areas of the electrodes 562, 564, may be defined by a medial edge and a lateral edge of the can electrode 562, and a proximal end and a distal end of a coil electrode utilized as the second electrode subsystem 564. The coil electrode 564 extends a predetermined distance beyond the apex of the heart 560, e.g. less than about 3 cm.

FIG. 5H illustrates a configuration wherein the pulse generator housing 561 does not include an electrode. In this implementation two electrode subsystems are positioned about the heart so that a majority of ventricular tissue is included within a volume defined between the electrode subsystems. According to this embodiment, the first and second electrodes are configured as first and second coil electrodes 568, 569.

The first coil electrode 568 is located superior to the heart 560 and may be located relative to a superior aspect of the heart, e.g., the left ventricular free wall. The second coil electrode 569 is located inferior to the heart 560. The second electrode 569 may be located in relation to an inferior aspect of the heart 560. In one configuration, the second electrode 569 is positioned parallel to the right ventricular free wall with a tip of the electrode 569 extending less than about 3 cm beyond the apex of the heart 560. As illustrated in FIG. 5H, the volume defined between the electrodes may be defined by the cross sectional area 565 bounded by lines drawn between active areas of the electrodes 568, 569.

Disordered Breathing Detection

According to various embodiments of the invention, detection of disordered breathing events may be used in connection with providing coordinated monitoring, diagnosis and/or therapy. In one embodiment, detection and assessment of disordered breathing is used to adapt (initiate, modify and/or terminate) therapy delivery. In another embodiment, disordered breathing events detected during and/or after therapy delivery may be used to assess the effectiveness of the disordered breathing therapy. In various implementations, some of which are described below, episodes of disordered breathing may be detected and classified by analyzing the patient's respiration patterns and/or other conditions associated with disordered breathing. Systems and methods directed to disordered breathing detection may be implemented to include selected features, functions, and/or structures described in commonly owned, U.S. Pat. No. 7,252,640, which is hereby incorporated herein by reference.

In accordance with one embodiment of the invention, the cardiac electrical therapy for disordered breathing may be adapted based on detected episodes of disordered breathing. In one scenario, one or more episodes of disordered breathing are detected and the cardiac electrical therapy is initiated or increased to treat the detected episodes. Adaptation of the therapy may continue, enabling the system to deliver a therapeutically appropriate therapy throughout the disordered breathing episode or episodes. If the system determines that the disordered breathing has mitigated or ceased, then the therapy may be reduced or terminated. Therapy may continue after the disordered breathing episode has stopped to prevent future occurrences of disordered breathing.

Table 1 provides a representative set of conditions affecting the patient that may be used to monitor and/or diagnose disordered breathing and/or to adapt a disordered breathing therapy. Table 1 also provides example sensing methods that may be employed to sense the conditions.

Detection of disordered breathing may involve detecting one or more conditions indicative of disordered breathing listed in Table 1. The patient conditions listed in Table 1 may be employed in a multi-sensor approach to detect and confirm episodes of disordered breathing. For example, the accuracy of a preliminary disordered breathing detection may be enhanced by verifying the patient is asleep, in bed, inactive, lying down, or that the present environmental conditions are associated with disordered breathing in the patient.

Table 2 provides examples of how a representative subset of the physiological and non-physiological conditions listed in Table 1 may be used in connection with disordered breathing detection.

TABLE 2

| Condition Type | Condition | Examples of how condition may be used in disordered breathing detection |
|---|---|---|
| Physiological | Heart rate | Decrease in heart rate may indicate disordered breathing episode.<br>Decrease in heart rate may indicate the patient is asleep. |
| | Heart rate variability | Disordered breathing causes heart rate variability to decrease. Changes in HRV associated with sleep disordered breathing may be observed while the patient is awake or asleep |
| | Ventricular filling pressure | May be used to identify/predict pulmonary congestion associated with respiratory disturbance. |
| | Blood pressure | Swings in on-line blood pressure measures are associated with apnea. Disordered breathing generally increases blood pressure variability - these changes may be observed while the patient is awake or asleep. |
| | Snoring | Snoring is associated with a higher incidence of obstructive sleep apnea and may be used to detect disordered breathing. |
| | Respiration pattern/rate | Respiration patterns including, e.g., respiration rate, may be used to detect disordered breathing episodes.<br>Respiration patterns may be used to determine the type of disordered breathing.<br>Respiration patterns may be used to detect that the patient is asleep. |
| | Patency of upper airway | Patency of upper airway is related to obstructive sleep apnea and may be used to detect episodes of obstructive sleep apnea. |
| | Pulmonary congestion | Pulmonary congestion is associated with respiratory disturbances. |

TABLE 2-continued

| Condition Type | Condition | Examples of how condition may be used in disordered breathing detection |
|---|---|---|
| | Sympathetic nerve activity | End of apnea associated with a spike in SNA. Changes in SNA observed while the patient is awake or asleep may be associated with sleep disordered breathing |
| | CO2 | Low CO2 levels initiate central apnea. |
| | O2 | O2 desaturation occurs during severe apnea/hypopnea episodes. |
| | Blood alcohol content | Alcohol tends to increase incidence of snoring & obstructive apnea. |
| | Adrenalin | End of apnea associated with a spike in blood adrenaline. |
| | BNP | A marker of heart failure status, which is associated with Cheyne-Stokes Respiration |
| | C-Reactive Protein | A measure of inflammation that may be related to apnea. |
| | Drug/Medication/ Tobacco use | These substances may affect the incidence of both central & obstructive apnea. |
| | Muscle atonia | Muscle atonia may be used to detect REM and non-REM sleep. |
| | Eye movement | Eye movement may be used to detect REM and non-REM sleep. |
| Non-physiological/ Contextual | Temperature | Ambient temperature may be a condition predisposing the patient to episodes of disordered breathing and may be useful in disordered breathing detection. |
| | Humidity | Humidity may be a condition predisposing the patient to episodes of disordered breathing and may be useful in disordered breathing detection. |
| | Pollution | Pollution may be a condition predisposing the patient to episodes of disordered breathing and may be useful in disordered breathing detection. |
| | Posture | Posture may be used to confirm or determine the patient is asleep. |
| | Activity | Patient activity may be used in relation to sleep detection. |
| | Location | Patient location may used to determine if the patient is in bed as a part of sleep detection. |

Episodes of disordered breathing are associated with acute and chronic physiological effects. Acute responses to disordered breathing may include, for example, negative intrathoracic pressure, hypoxia, arousal from sleep, and increases in blood pressure and heart rate. During obstructive apnea episodes, negative intrathoracic pressure may arise from an increased effort to generate airflow. Attempted inspiration in the presence of an occluded airway results in an abrupt reduction in intrathoracic pressure. The repeated futile inspiratory efforts associated with obstructive sleep apnea may trigger a series of secondary responses, including mechanical, hemodynamic, chemical, neural, and inflammatory responses.

Obstructive sleep apneas may be terminated by arousal from sleep several seconds after the apneic peak, allowing the breathing to resume. Coincident with arousal from sleep, surges in sympathetic nerve activity, blood pressure, and heart rate may occur. The adverse effects of obstructive apnea are not confined to sleep. Waking conditions such as sympathetic nerve activity and systemic blood pressure are increased. There may also be a sustained reduction in vagal tone, causing reduction in total heart rate variability during periods of wakefulness.

Central sleep apnea is generally caused by a failure of respiratory control signals from the brain. Central sleep apnea is a component of Cheyne-Stokes respiration (CSR), a respiration pattern primarily observed in patients suffering from chronic heart failure (CHF). Cheyne-Stokes respiration is a form of periodic breathing in which central apneas and hypopneas alternate with periods of hyperventilation causing a waxing-waning pattern of tidal volume. In some CHF patients, obstructive sleep apnea and central sleep apnea may coexist. In these patients, there may be a gradual shift from predominantly obstructive apneas at the beginning of the night to predominantly central apneas at the end of the night.

Several mechanisms may be involved in central apneas observed in patients suffering from chronic heart failure. According to one mechanism, increased carbon dioxide sensitivity in CHF patients triggers hyperventilation initiating a sleep apnea episode. Breathing is regulated by a negative feedback system that maintains the arterial partial pressure of carbon dioxide ($PaCO_2$) within limits. Changes in $PaCO_2$ lead to changes in ventilation wherein the greater the sensitivity to carbon dioxide, the greater the ventilatory response.

In patients with cardiopulmonary disorders, an increase in carbon dioxide sensitivity may minimize perturbations in $PaCO_2$, thus protecting them against the long-term consequences of hypercapnia, an excess of carbon dioxide in the blood. This protective mechanism may be advantageous while the patient is awake, however, the increased sensitivity to carbon dioxide may disrupt breathing during sleep.

During sleep, ventilation decreases and $PaCO_2$ levels increase. If the $PaCO_2$ level decreases below level referred to as the apneic threshold, ventilation ceases, central sleep apnea ensues, and $PaCO_2$ rises to previous levels.

In patients with increased sensitivity to carbon dioxide, the negative-feedback system that controls breathing initiates a large ventilatory response when $PaCO_2$ rises. The resultant hyperventilation, by driving the $PaCO_2$ level below the apneic threshold, results in central sleep apnea. As a result of the apnea, the $PaCO_2$ level rises again, leading to an increase in ventilation. In this way, cycles of hyperventilation and central apnea may recur throughout sleep.

The posture of CHF patients during sleep may also be implicated in triggering apnea. When CHF patients lie down, the prone posture may create central fluid accumulation and pulmonary congestion causing the patient to reflexively hyperventilate. Hyperventilation may initiate the cyclical pattern of hyperventilation-apnea described above.

Arousals are not necessarily required in central sleep apneas for the resumption of breathing at the termination of the apneic event. In central apnea, the arousals follow the initiation of breathing and may facilitate the development of oscillations in ventilation by recurrently stimulating hyperventilation and reducing $PaCO_2$ below the apneic threshold. Once triggered, the pattern of alternating hyperventilation and apnea is sustained by the combination of increased respiratory drive, pulmonary congestion, arousals, and apnea-induced hypoxia causing $PaCO_2$ oscillations above and below the apneic threshold. Shifts in the patient's state of consciousness, particularly with repeated arousals, may further destabilize breathing.

With the transition from wakefulness to NREM sleep, the waking neural drive to breathe is lost, and the threshold for a ventilatory response to carbon dioxide is increased. Therefore, if the patient's $PaCO_2$ level during wakefulness is below this higher sleeping threshold, the transition to NREM sleep may be accompanied by a transient loss of respiratory drive resulting in a central apnea. During the apnea, the $PaCO_2$ rises until it reaches the new higher threshold level and initiates breathing. If sleep becomes firmly established, regular breathing resumes. However, if an arousal should occur, the increased $PaCO_2$ level associated with sleep is now relatively too high for a state of wakefulness and will stimulate hyperventilation. Thus, although arousals terminate obstructive sleep apneas, arousals trigger the respiratory oscillations associated with central apneas, particularly Cheyne-Stokes respiration.

In addition to the acute responses to sleep disordered breathing, such as those discussed above, sleep disordered breathing is also associated with a number of secondary or chronic responses, including, for example, chronic decrease in heart rate variability (HRV) and blood pressure changes. Patients with central sleep apnea may have higher urinary and circulating norepinephrine concentrations and lower $PaCO_2$ during both sleep and wakefulness.

Acute responses to disordered breathing are associated with physiological conditions that are modulated during an ongoing disordered breathing event. Sensing conditions modulated by the acute responses to disordered breathing may be used to detect a disordered breathing event contemporaneously with the occurrence of the disordered breathing event. Chronic responses to disordered breathing may be modulated by an aggregation of disordered breathing events that occur over time. Chronic responses to disordered breathing may be used to determine if disordered breathing events have occurred.

Both acute and chronic responses to disordered breathing may be used to asses the efficacy and impact of disordered breathing therapy. In one implementation, a first subset of patient conditions may be used to detect disordered breathing, including presently occurring events, and/or an aggregation of events occurring over time. A second subset of patient conditions, possibly overlapping the subset used for disordered breathing detection, may be used to assess the disordered breathing therapy. For example, according to one embodiment, the efficacy of the therapy may be assessed and the therapy may be adapted to enhance the efficacy based on the assessment. In another embodiment, the therapy may be assessed to determine an impact of the therapy on the patient. The therapy may be adapted to reduce therapy impact of the therapy on the patient based on the assessment. In yet a further embodiment, the therapy may be adapted both to enhance therapy effectiveness and to reduce an impact of the therapy on the patient. Other constraints may be utilized for therapy adaptation, including, for example, preservation of useable device life, and/or avoidance of interactions between disordered breathing therapy and other therapies delivered to the patient.

Conditions used to assess therapy effectiveness may be different from, or the same as, conditions used to assess an impact of the therapy on the patient. Table 3 provides a representative set of conditions that may be used for therapy assessment.

TABLE 3

| Condition | Therapy Impact | Therapy Efficacy |
|---|---|---|
| Arousal-Based Sleep Fragmentation Measures | May be used to assess therapy impact during sleep. | |
| Restful sleep (Patient reported) | May be used to assess therapy impact during sleep. | |
| Discomfort (Patient reported) | May be used to assess therapy impact. | |
| Pacing algorithm interaction | May be used to assess therapy impact. | |
| Remaining useful life of therapy device | May be used to assess therapy impact. | |
| Disturbed Breathing-Based Measures | | May be used to analyze/assess efficacy of therapy to mitigate disordered breathing episodes. |
| Respiration quality (Patient reported) | | May be used to analyze/assess efficacy of therapy to mitigate disordered breathing episodes. |
| Heart rate variability (HRV) | | Disordered breathing causes heart rate variability to decrease. Therapy may be modified based on changes in HRV |
| Blood pressure | | Disordered breathing causes blood pressure increase |
| Sympathetic nerve activity (SNA) | | Changes in sympathetic nerve activity are caused by disordered breathing. Therapy may be adjusted based on the level of SNA |
| Blood chemistry | | A number of disordered breathing related changes may occur in a patient's blood chemistry, including, e.g., higher norepinephrine levels, and lower $PaCO_2$ |

It is understood that the patient conditions that may be used in connection with disordered breathing therapy, including detection of disordered breathing and/or therapy assessment, for example, are not limited to the representative sets listed in Tables 1-3 or those described herein. Further, although illustrative sensing methods for detecting the patient conditions listed above are provided, it is understood that the patient conditions may be detected using a wide variety of technologies. The invention is not limited to the particular conditions or the particular sensing technologies discussed herein in connection with the illustrative embodiments.

In one embodiment, episodes of disordered breathing may be detected by monitoring the respiratory waveform output of a transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 6:
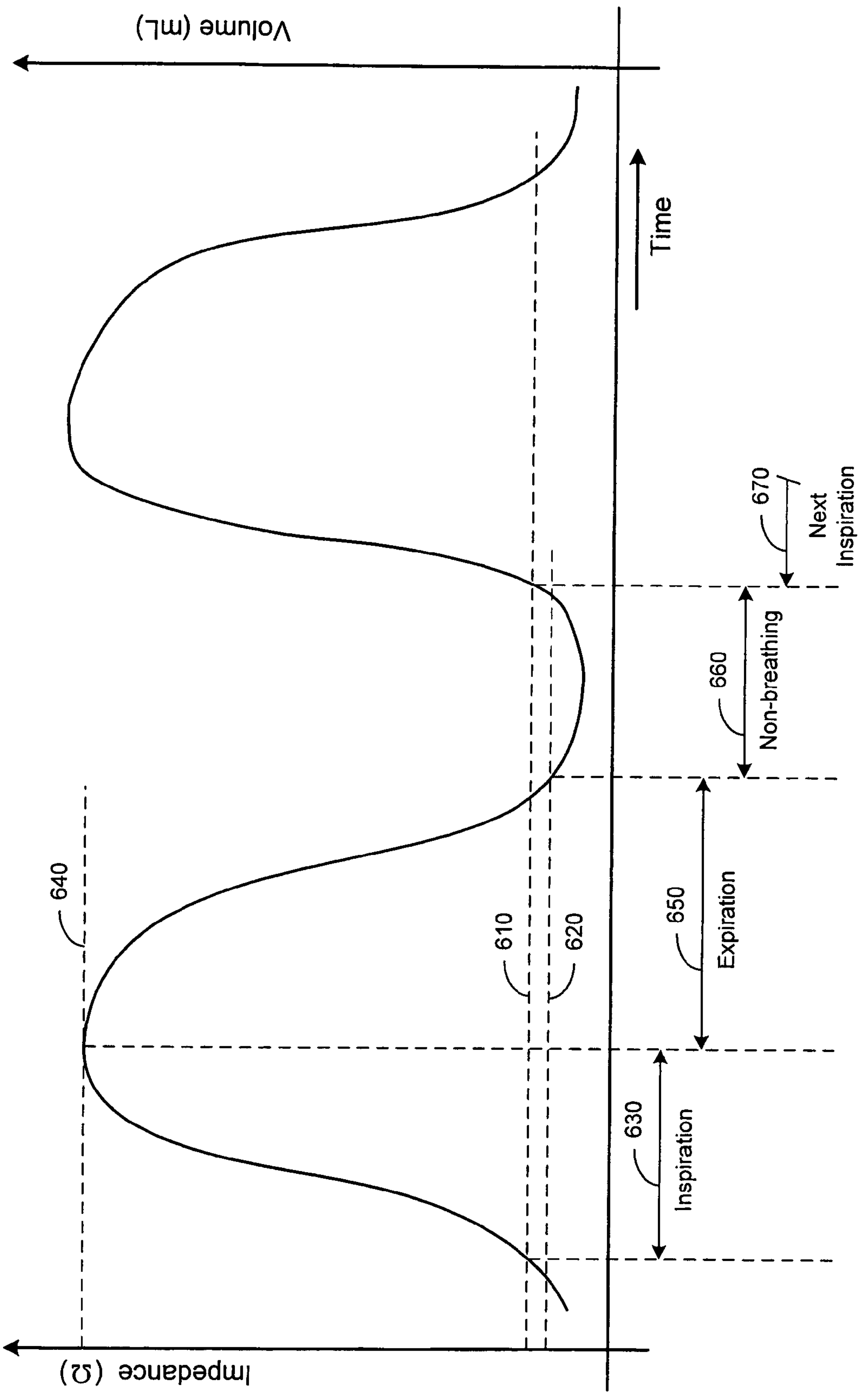
FIG. 6 illustrates respiration intervals used for disordered breathing detection according to embodiments of the invention.

In another embodiment, detection of disordered breathing involves defining and examining a number of respiratory cycle intervals. FIG. 6 illustrates respiration intervals used for disordered breathing detection according to an embodiment of the invention. A respiration cycle is divided into an inspiration period corresponding to the patient inhaling, an expiration period, corresponding to the patient exhaling, and a non-breathing period occurring between inhaling and exhaling. Respiration intervals are established using inspiration 610 and expiration 620 thresholds. The inspiration threshold 610 marks the beginning of an inspiration period 630 and is determined by the transthoracic impedance signal rising above the inspiration threshold 610. The inspiration period 630 ends when the transthoracic impedance signal is maximum 640. A maximum transthoracic impedance signal 640 corresponds to both the end of the inspiration interval 630 and the beginning of the expiration interval 650. The expiration interval 650 continues until the transthoracic impedance falls below an expiration threshold 620. A non-breathing interval 660 starts from the end of the expiration period 650 and continues until the beginning of the next inspiration period 670.

Figure 7:
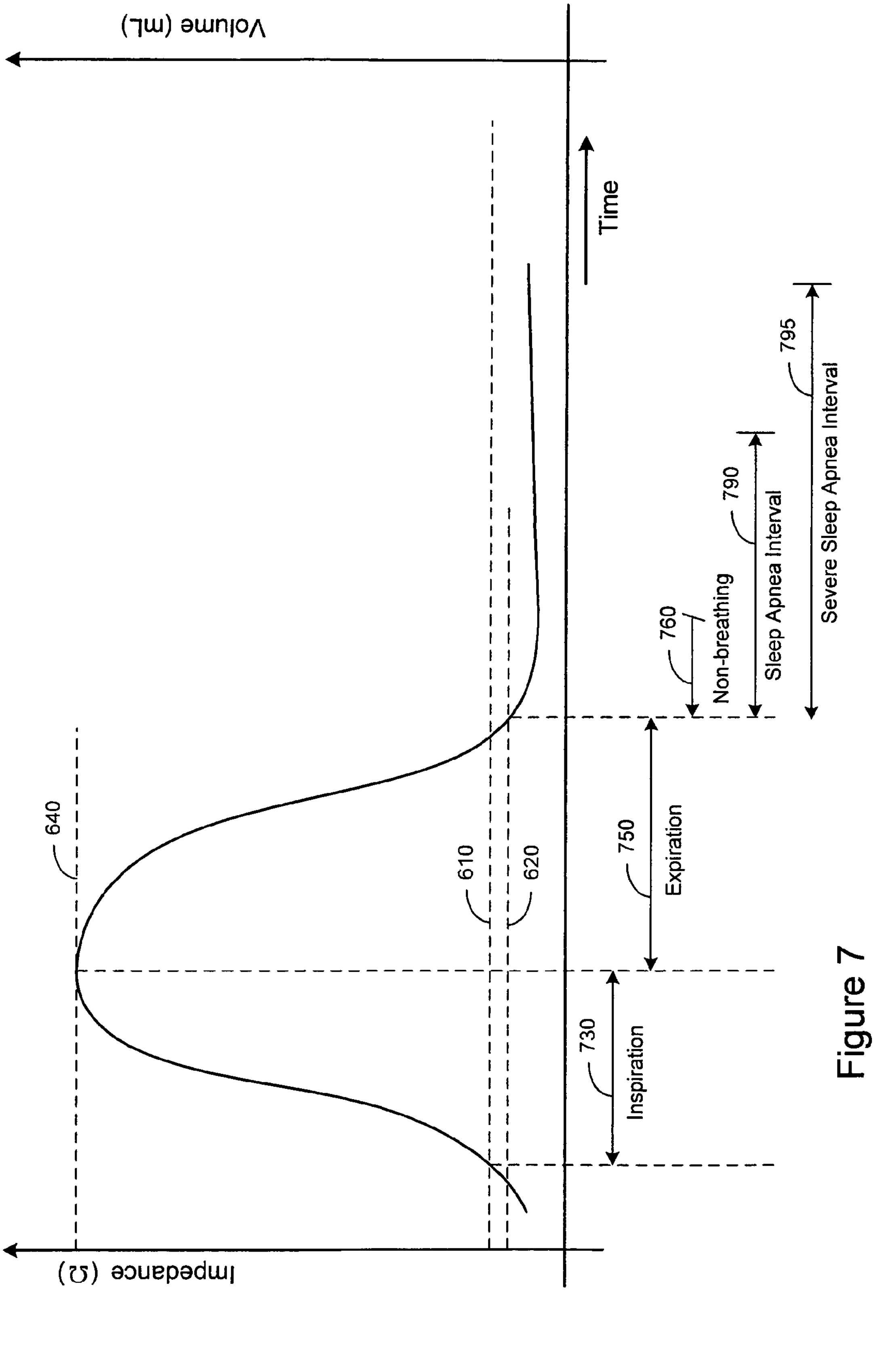
FIG. 7 illustrates respiration intervals used in detection of sleep apnea and severe sleep apnea according to embodiments of the invention.

Detection of sleep apnea and severe sleep apnea according to embodiments of the invention is illustrated in FIG. 7. The patient's respiration signals are monitored and the respiration cycles are defined according to inspiration 730, expiration 750, and non-breathing 760 intervals as described in connection with FIG. 6. A condition of sleep apnea is detected when a non-breathing period 760 exceeds a first predetermined interval 790, denoted the sleep apnea interval. A condition of severe sleep apnea is detected when the non-breathing period 760 exceeds a second predetermined interval 795, denoted the severe sleep apnea interval. For example, sleep apnea may be detected when the non-breathing interval exceeds about 10 seconds, and severe sleep apnea may be detected when the non-breathing interval exceeds about 20 seconds.

Figure 8A:
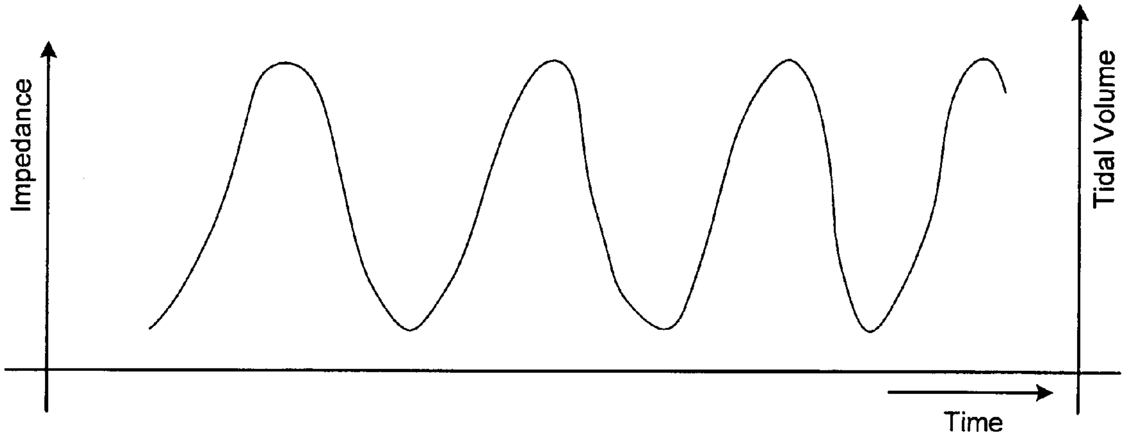
FIGS. 8A-B are graphs of respiration patterns that may be detected according to embodiments of the invention.
Figure 8B:
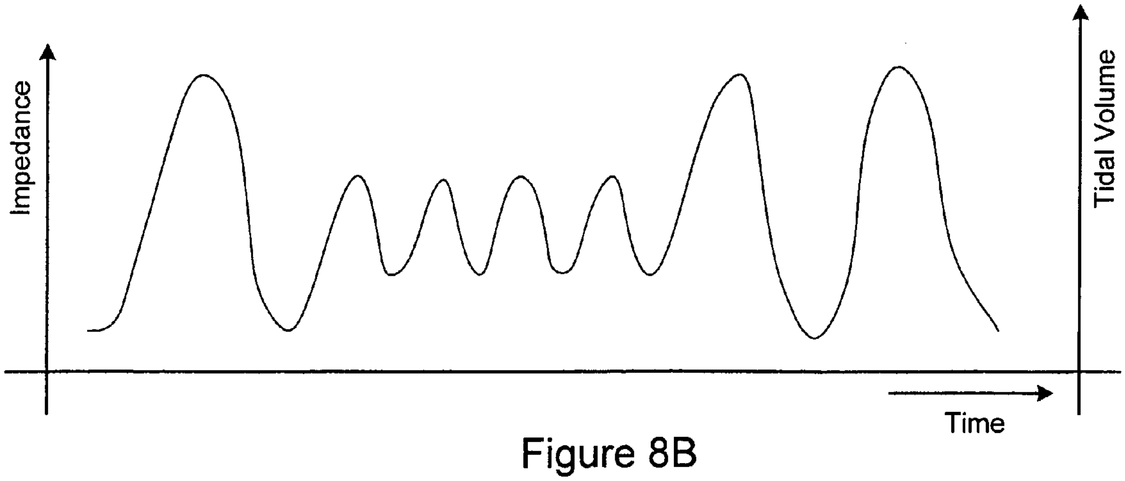

Hypopnea is a condition of disordered breathing characterized by abnormally shallow breathing. FIGS. 8A-8B are graphs of tidal volume derived from transthoracic impedance measurements. The graphs compare the tidal volume of a normal breathing cycle to the tidal volume of a hypopnea episode. FIG. 8A illustrates normal respiration tidal volume and rate. As shown in FIG. 8B, hypopnea involves a period of abnormally shallow respiration.

According to an embodiment of the invention, hypopnea is detected by comparing a patient's respiratory tidal volume to a hypopnea tidal volume threshold. The tidal volume for each respiration cycle is derived from transthoracic impedance measurements acquired in the manner described above. The hypopnea tidal volume threshold may be established using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

Figure 9:
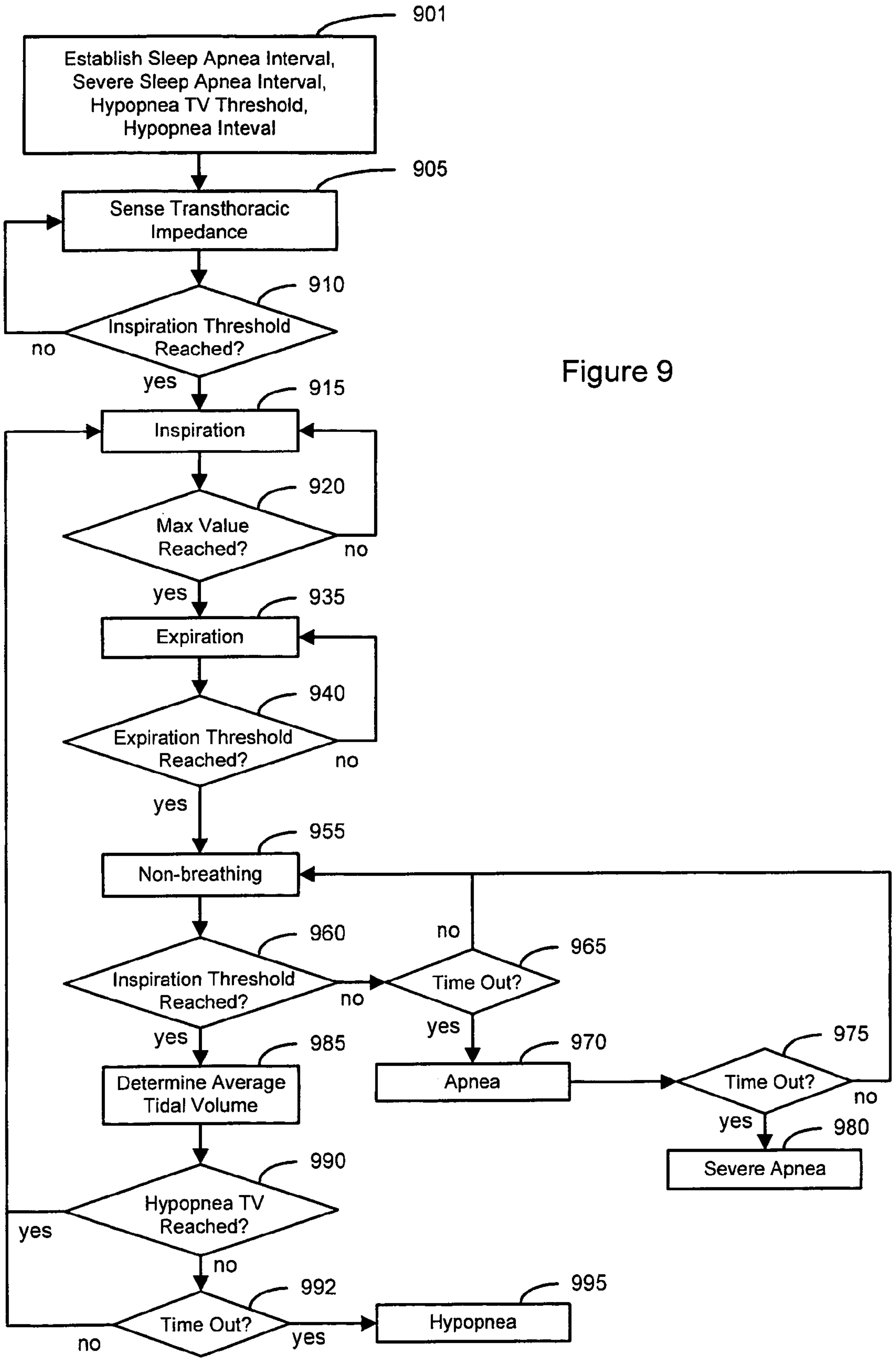
FIG. 9 is a flow chart illustrating a method of apnea and hypopnea detection according to embodiments of the invention.

FIG. 9 is a flowchart illustrating a method of apnea and/or hypopnea detection according to embodiments of the invention. Various parameters are established 901 before analyzing the patient's respiration for disordered breathing episodes, including, for example, inspiration and expiration thresholds, sleep apnea interval, severe sleep apnea interval, and hypopnea tidal volume threshold.

The patient's transthoracic impedance is measured 905 as described in more detail above. If the transthoracic impedance exceeds 910 the inspiration threshold, the beginning of an inspiration interval is detected 915. If the transthoracic impedance remains below 910 the inspiration threshold, then the impedance signal is checked 905 periodically until inspiration 915 occurs.

During the inspiration interval, the patient's transthoracic impedance is monitored until a maximum value of the transthoracic impedance is detected 920. Detection of the maximum value signals an end of the inspiration period and a beginning of an expiration period 935.

The expiration interval is characterized by decreasing transthoracic impedance. When the transthoracic impedance falls 940 below the expiration threshold, a non-breathing interval is detected 955.

If the transthoracic impedance does not exceed 960 the inspiration threshold within a first predetermined interval 965, denoted the sleep apnea interval, then a condition of sleep apnea is detected 970. Severe sleep apnea is detected 980 if the non-breathing period extends beyond a second predetermined interval 975, denoted the severe sleep apnea interval.

When the transthoracic impedance exceeds 960 the inspiration threshold, the tidal volume from the peak-to-peak transthoracic impedance is calculated, along with a moving average of past tidal volumes 985. The peak-to-peak transthoracic impedance provides a value proportional to the tidal volume of the respiration cycle. This value is compared 990 to a hypopnea tidal volume threshold. If the peak-to-peak transthoracic impedance is consistent with 990 the hypopnea tidal volume threshold for a predetermined time 992, then a hypopnea cycle is detected 995.

Additional sensors, such as motion sensors and/or posture sensors, may be used to confirm or verify the detection of a sleep apnea or hypopnea episode. The additional sensors may be employed to prevent false or missed detections of sleep apnea/hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern is detected as a disordered breathing episode based on the comparison.

Figure 10:
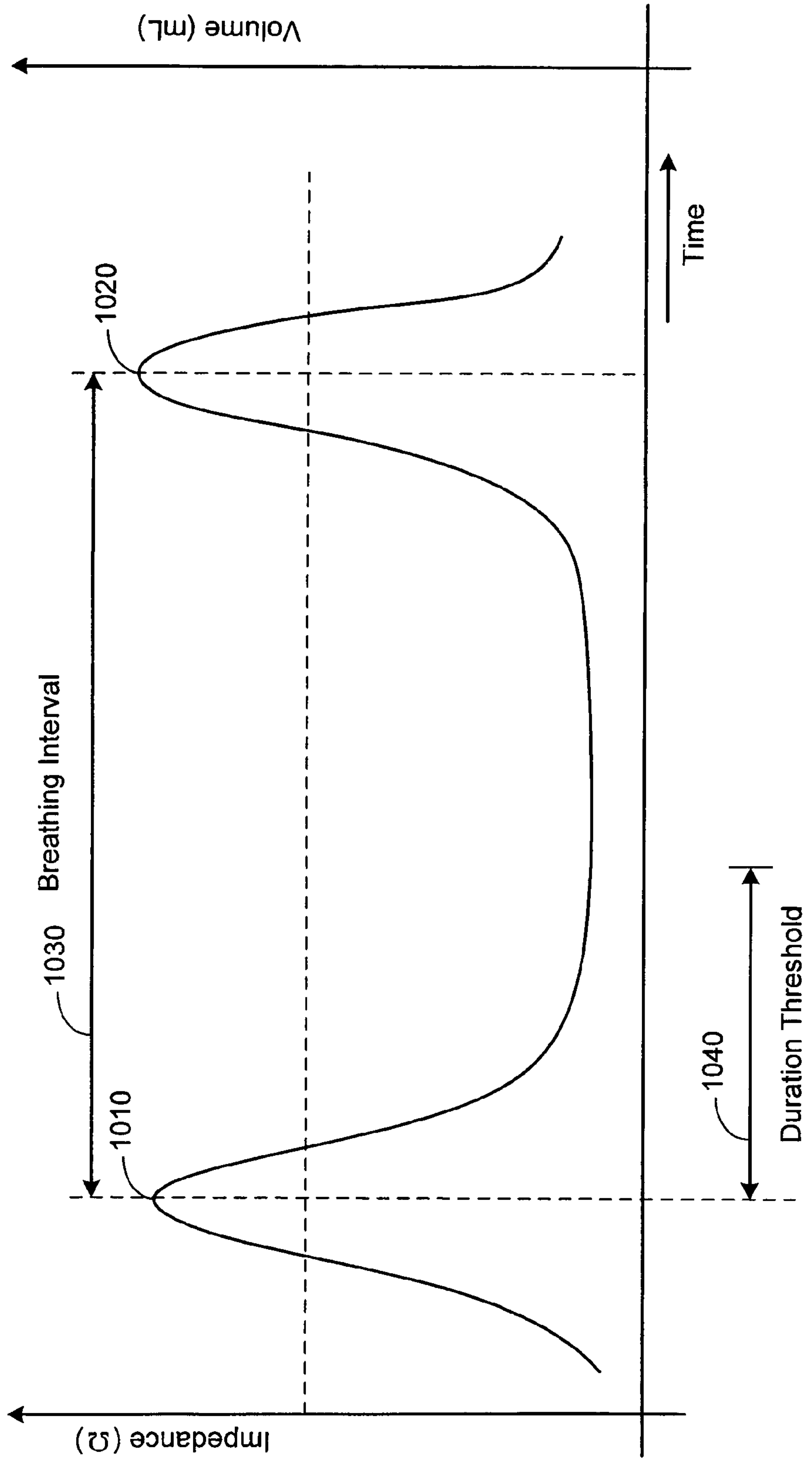
FIG. 10 is a graph illustrating a breathing interval according to embodiments of the invention.

According to principles of the invention, a breath interval is established for each respiration cycle. A breath interval represents the interval of time between successive breaths, as illustrated in FIG. 10. A breath interval 1030 may be defined in a variety of ways, for example, as the interval of time between successive maxima 1010, 1020 of the impedance signal waveform.

Detection of disordered breathing, in accordance with embodiments of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 10. Apnea represents a period of non-breathing. A breath interval 1030 exceeding a duration threshold 1040, comprises an apnea episode.

Hypopnea may be detected using the duration threshold and tidal volume threshold. A hypopnea event represents a period of shallow breathing. Each respiration cycle in a hypopnea event is characterized by a tidal volume less than the tidal volume threshold. Further, the hypopnea event involves a period of shallow breathing greater than the duration threshold.

Figure 11:
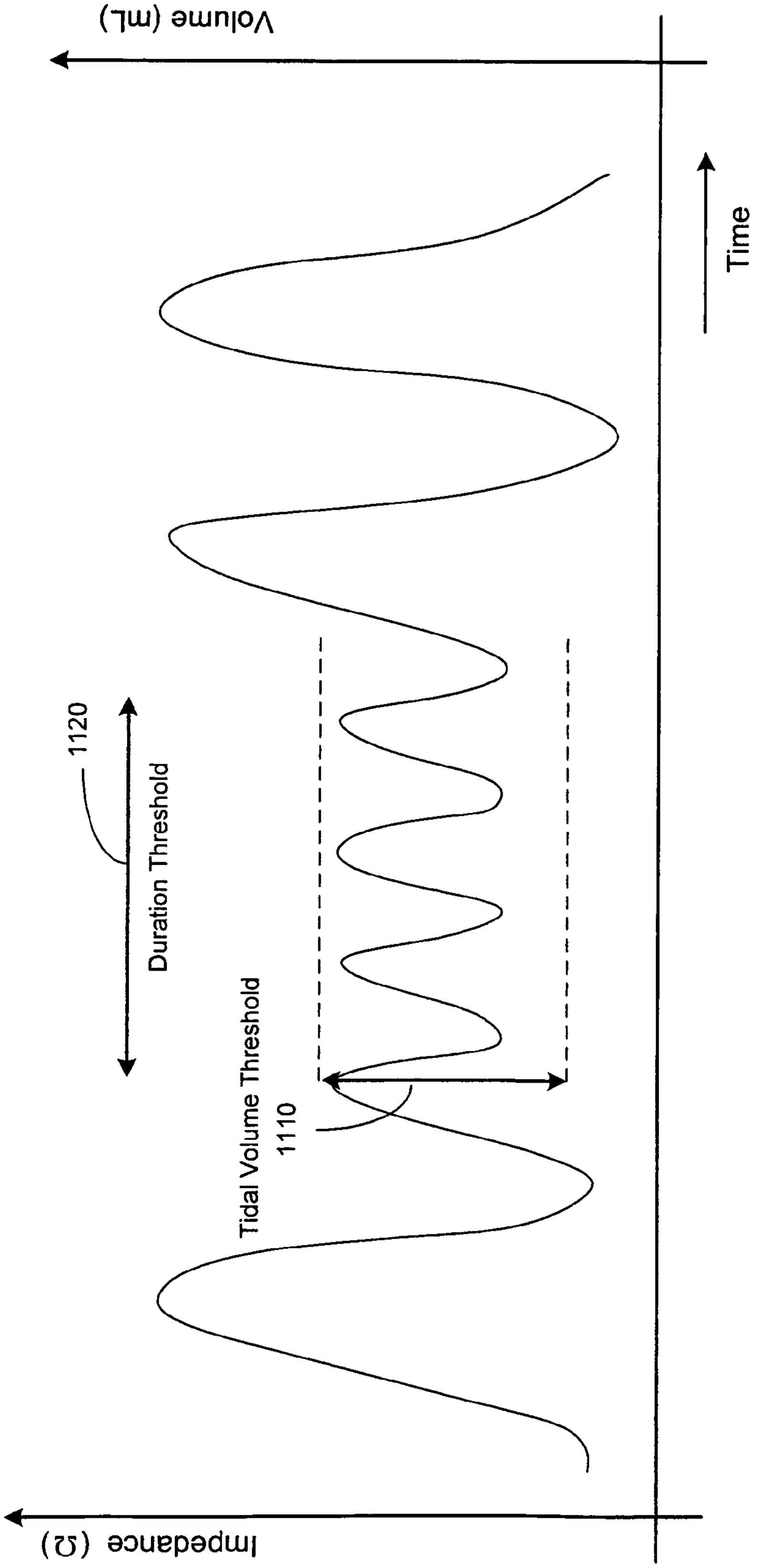
FIG. 11 is a graph illustrating a hypopnea detection approach in accordance with embodiments of the invention.

A hypopnea detection approach, in accordance with embodiments of the invention, is illustrated in FIG. 11. Shallow breathing is detected when the tidal volume of one or more breaths is below a tidal volume threshold 1110. If the shallow breathing continues for an interval greater than a duration threshold 1120, then the breathing pattern represented by the sequence of shallow respiration cycles, is classified as a hypopnea event.

Figure 12:
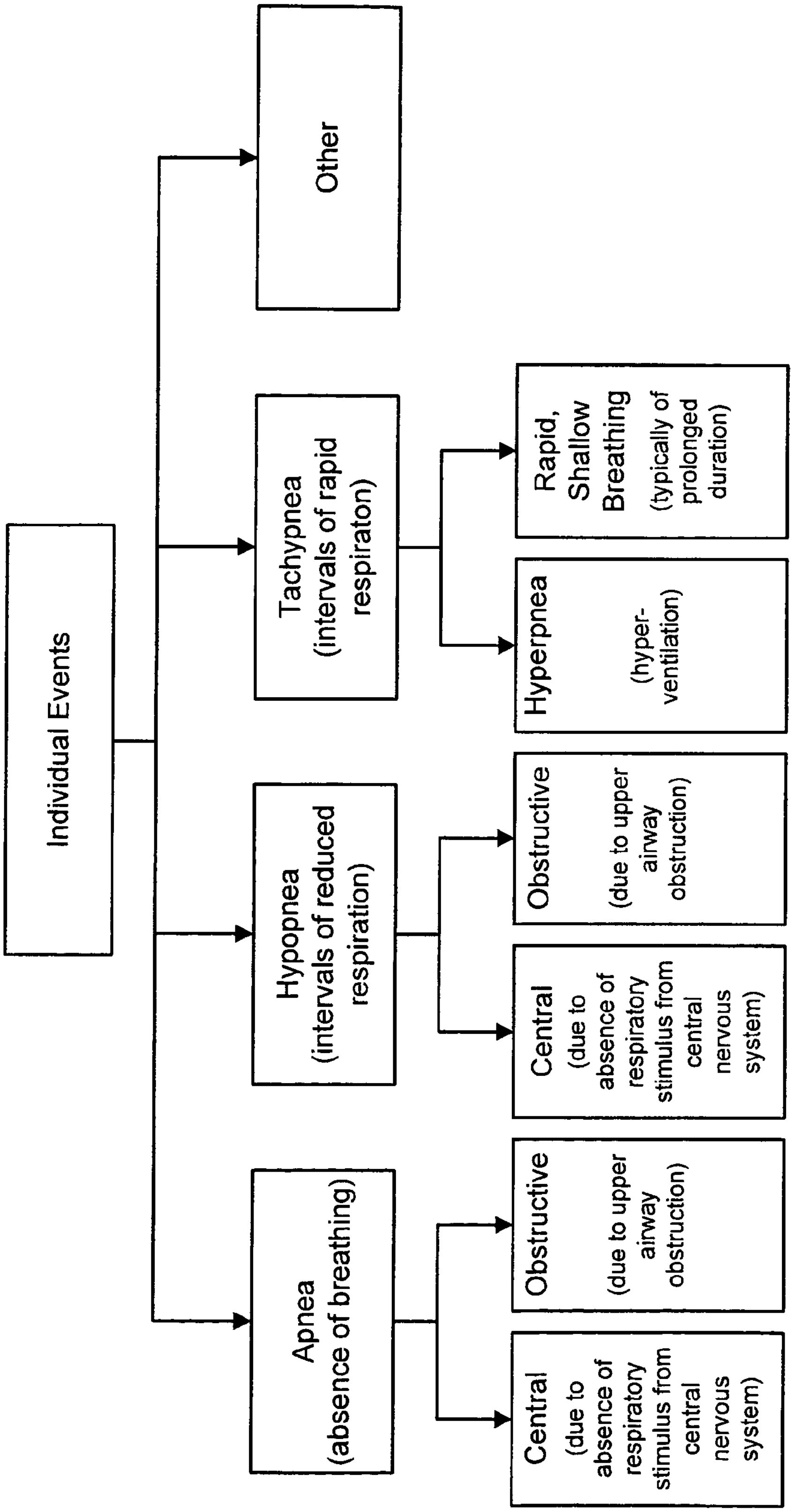
FIGS. 12-13 are charts illustrating nomenclature for individual disordered breathing events and combinations of disordered breathing events that can be addressed in accordance with embodiments of the invention, respectively.
Figure 13:
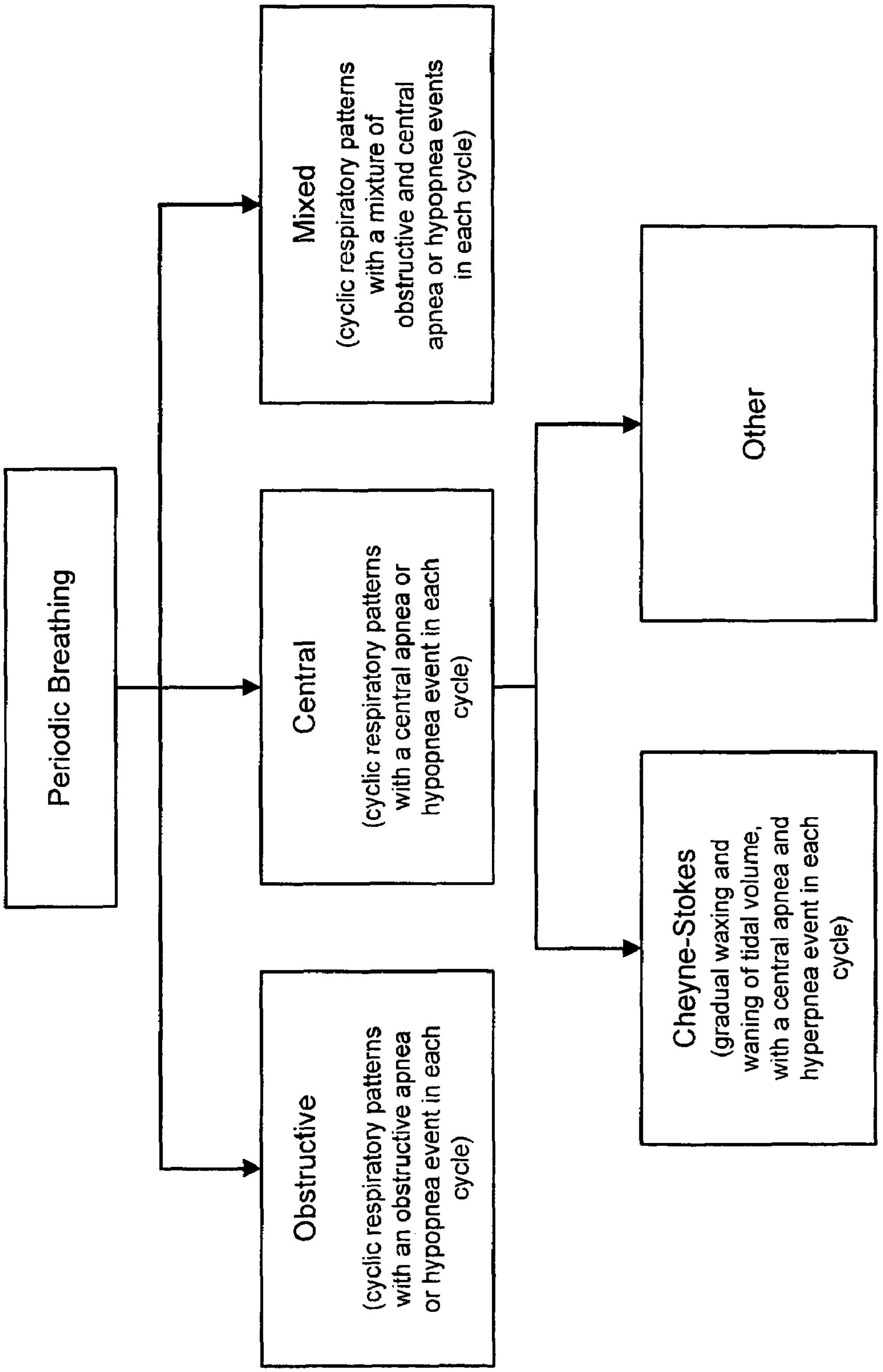

FIGS. 12 and 13 provide charts illustrating classification of individual disordered breathing events and series of periodically recurring disordered breathing events, respectively. As illustrated in FIG. 12, individual disordered breathing events may be grouped into apnea, hypopnea, tachypnea and other disordered breathing events. Apnea events are characterized by an absence of breathing. Intervals of reduced respiration are classified as hypopnea events. Tachypnea events include intervals of rapid respiration characterized by an elevated respiration rate.

As illustrated in FIG. 12, apnea and hypopnea events may be further subdivided as either central events, related to central nervous system dysfunction, or obstructive events, caused by upper airway obstruction. A tachypnea event may be further classified as a hyperpnea event, represented by hyperventilation, i.e., rapid deep breathing. A tachypnea event may alternatively be classified as rapid breathing, typically of prolonged duration.

FIG. 13 illustrates classification of combinations of periodically recurring disordered breathing events. Periodic breathing may be classified as obstructive, central or mixed. Obstructive periodic breathing is characterized by cyclic respiratory patterns with an obstructive apnea or hypopnea event in each cycle. Central periodic breathing involves cyclic respiratory patterns including a central apnea or hypopnea event in each cycle. Periodic breathing, illustrated in FIG. 14F, may also be of mixed origin. Mixed origin periodic breathing is characterized by cyclic respiratory patterns having a mixture of obstructive and central apnea events in each cycle. Cheyne-Stokes respiration, illustrated in FIG. 14G, is a particular type of periodic breathing involving a gradual waxing and waning of tidal volume and having a central apnea and hyperpnea event in each cycle. Other manifestations of periodic breathing are also possible. The various forms of disordered breathing may be determined based on the characteristic respiration patterns associated with particular types of disordered breathing.

Figure 14A:
FIGS. 14A-14E are graphs illustrating disordered breathing events comprising a mixture of apnea and hypopnea respiration cycles.
Figure 14B:
Figure 14C:
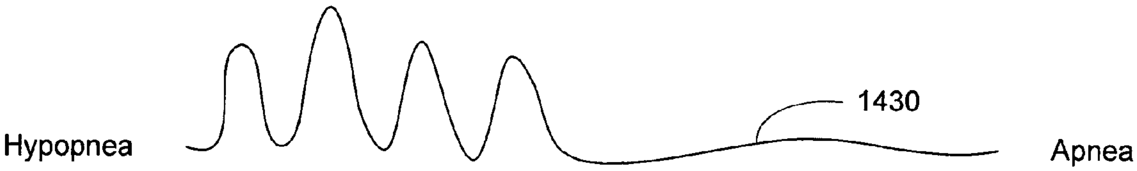
Figure 14D:
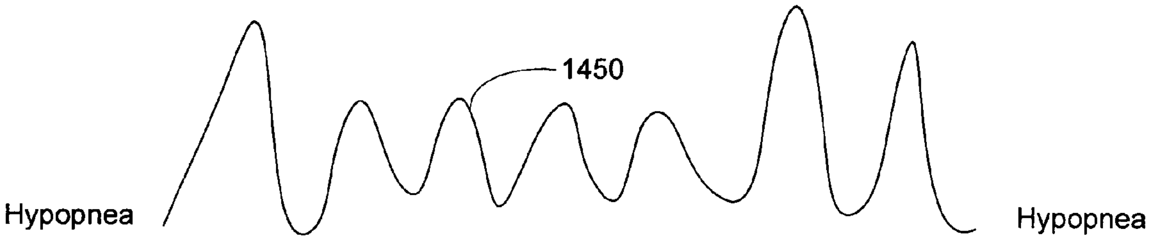
Figure 14E:
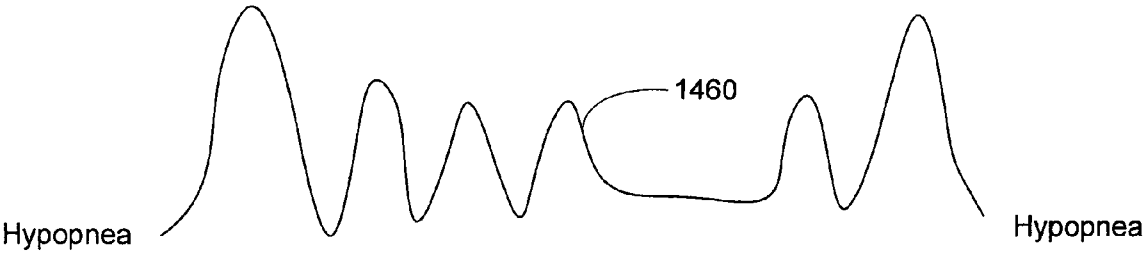
Figure 14F:
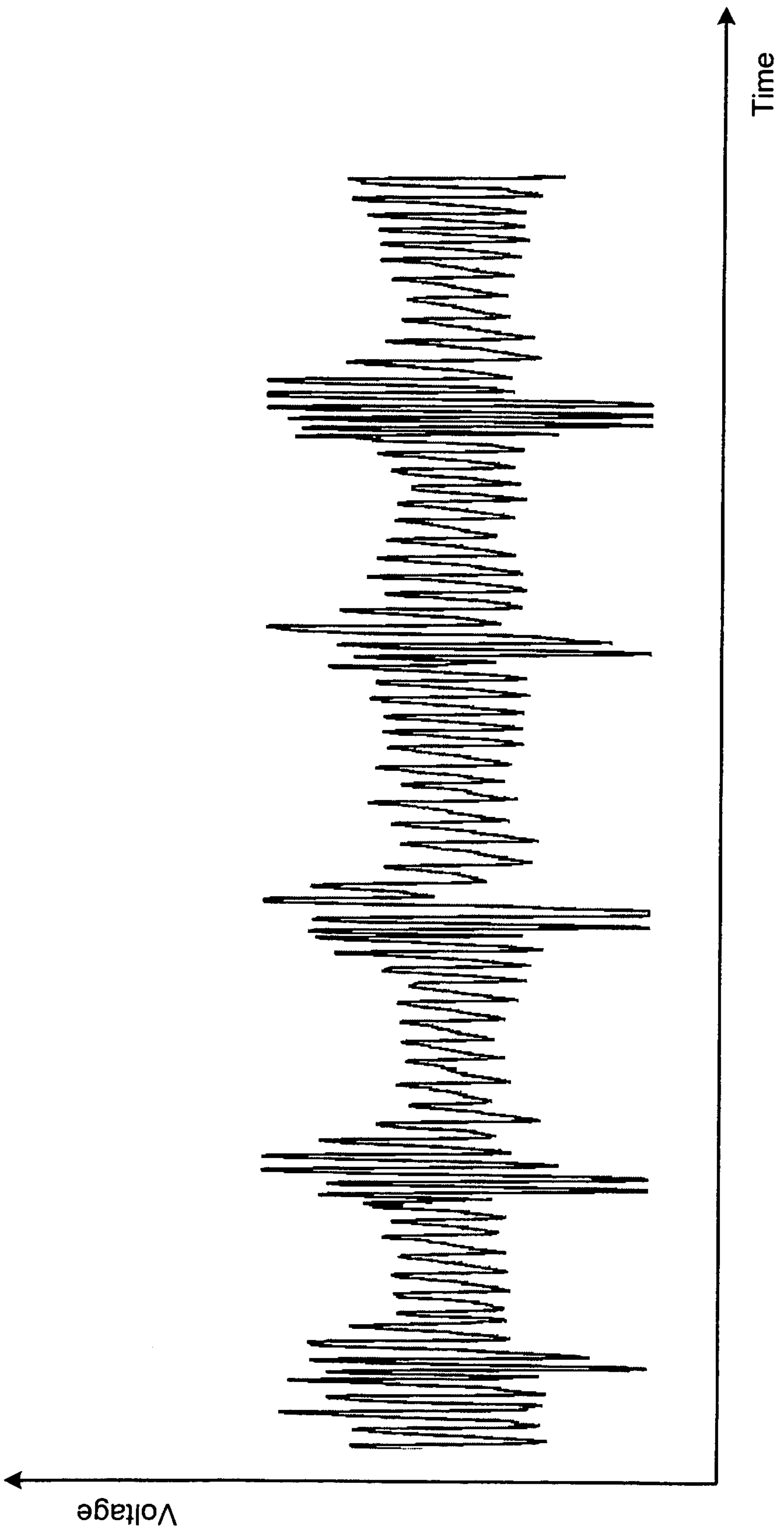
FIG. 14F is a graph illustrating a periodic breathing respiration pattern that may be detected according to embodiments of the invention.
Figure 14G:
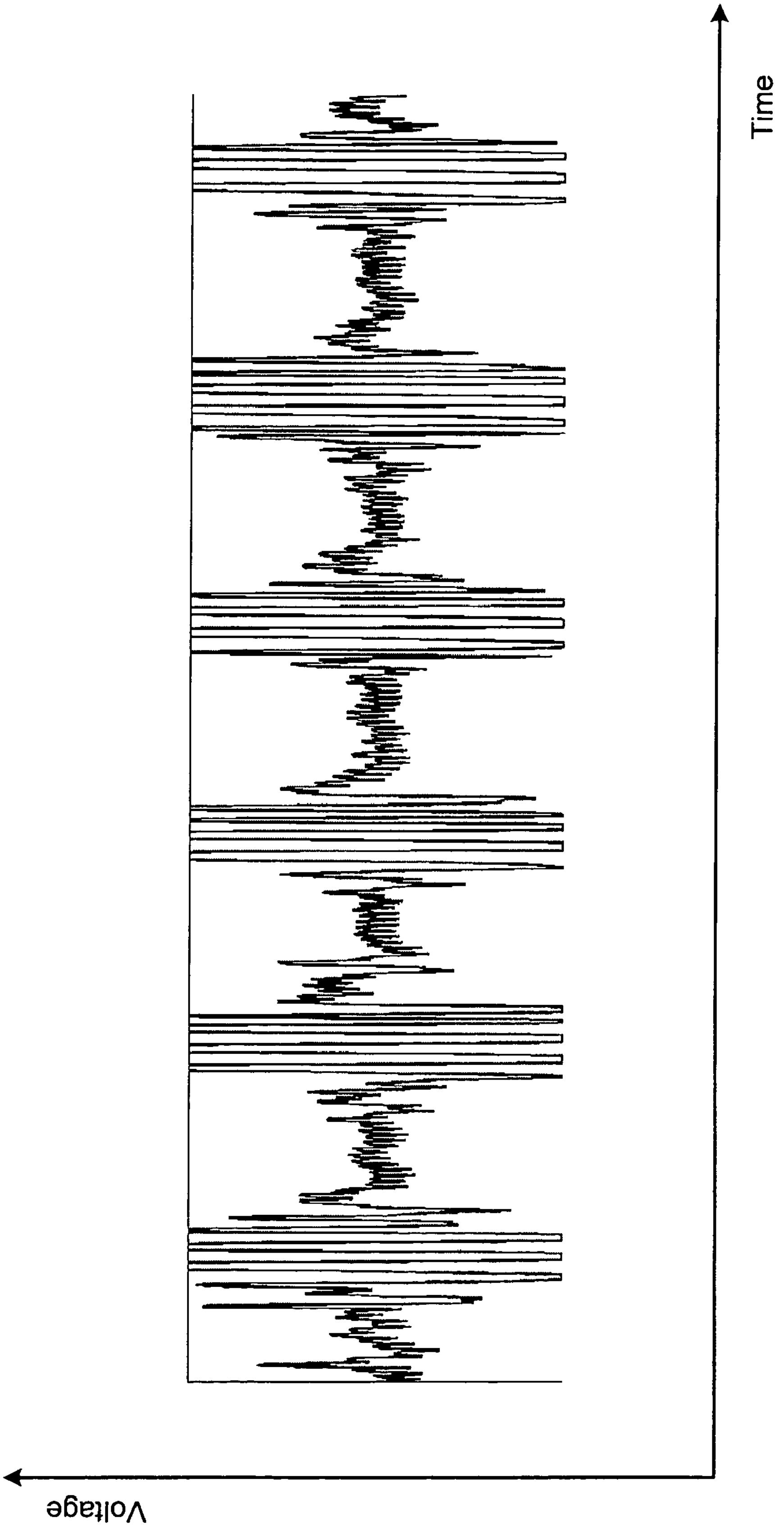
FIG. 14G is a graph illustrating a Cheyne-Stokes respiration pattern that may be detected according to embodiments of the invention.

As illustrated in FIGS. 14A-E, a respiration pattern detected as a disordered breathing episode may include only an apnea respiration cycle 1410 (FIG. 14A), only hypopnea respiration cycles 1450 (FIG. 14D), or a mixture of hypopnea and apnea respiration cycles 1420 (FIG. 14B), 1430 (FIG. 14C), 1460 (FIG. 14E). A disordered breathing event 1420 may begin with an apnea respiration cycle and end with one or more hypopnea cycles. In another pattern, the disordered breathing event 1430 may begin with hypopnea cycles and end with an apnea cycle. In yet another pattern, a disordered breathing event 1460 may begin and end with hypopnea cycles with an apnea cycle in between the hypopnea cycles.

Figure 15:
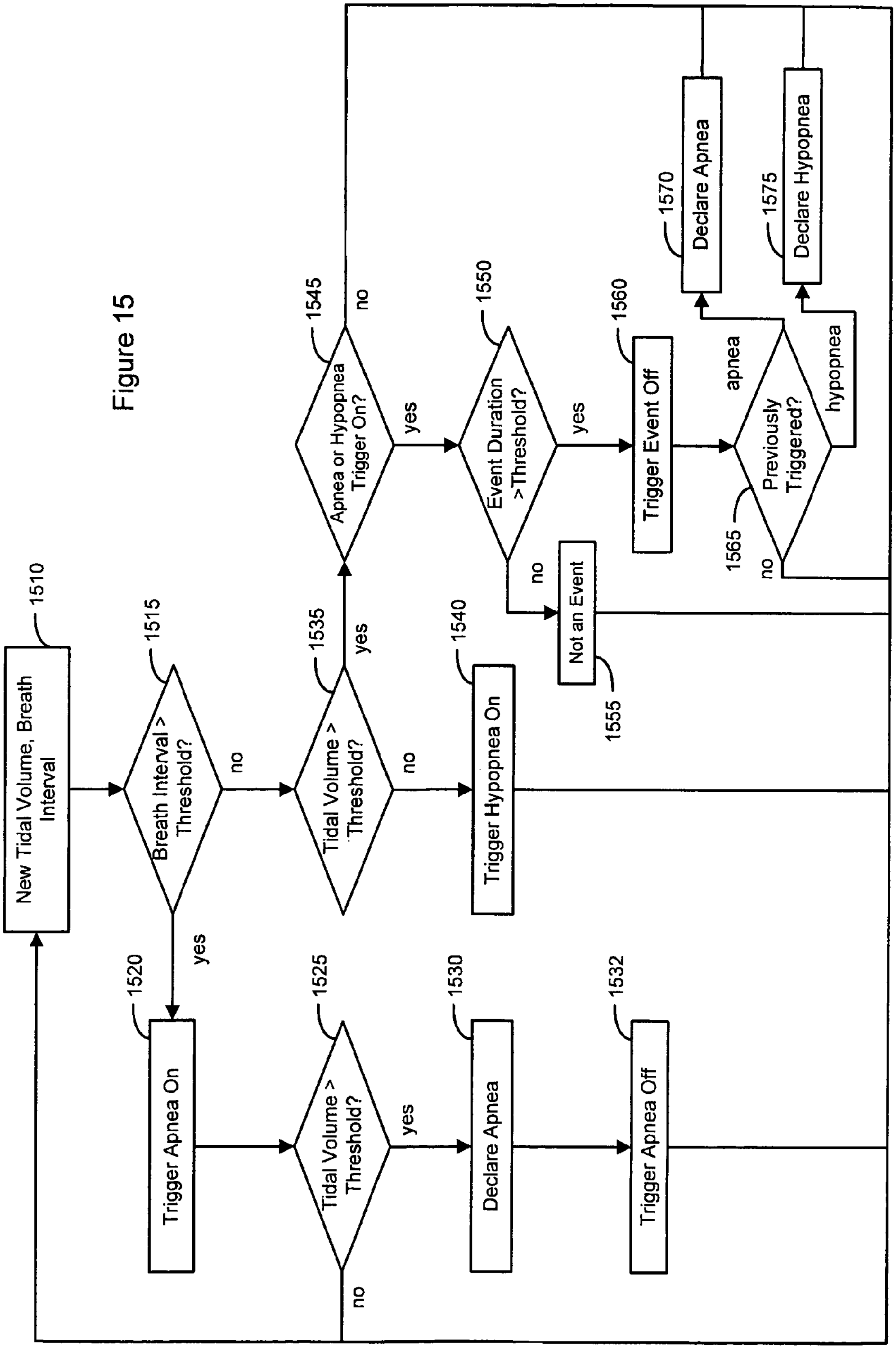
FIG. 15 is a flowchart of a method for detecting disordered breathing in accordance with an embodiment of the invention.

FIG. 15 is a flow graph of a method for detecting disordered breathing in accordance with embodiments of the invention. The method illustrated in FIG. 15 operates by classifying breathing patterns using breath intervals in conjunction with tidal volume and duration thresholds as previously described above. In this example, a duration threshold and a tidal volume threshold are established for determining both apnea and hypopnea breath intervals. An apnea episode is detected if the breath interval exceeds the duration threshold. A hypopnea episode is detected if the tidal volume of successive breaths remains less than the tidal volume threshold for a period in excess of the duration threshold. Mixed apnea/hypopnea episodes may also occur. In these cases, the period of disordered breathing is characterized by shallow breaths or non-breathing intervals. During the mixed apnea/hypopnea episodes, the tidal volume of each breath remains less than the tidal volume threshold for a period exceeding the duration threshold.

Transthoracic impedance is sensed and used to determine the patient's respiration cycles. Each breath 1510 may be characterized by a breath interval, the interval of time between two impedance signal maxima, and a tidal volume (TV).

If a breath interval exceeds 1515 the duration threshold, then the respiration pattern is consistent with an apnea event, and an apnea event trigger is turned on 1520. If the tidal volume of the breath interval exceeds 1525 the tidal volume threshold, then the breathing pattern is characterized by two respiration cycles of normal volume separated by a non-breathing interval. This pattern represents a purely apneic disordered breathing event, and apnea is detected 1530. Because the final breath of the breath interval was normal, the apnea event trigger is turned off 1532, signaling the end of the disordered breathing episode. However, if the tidal volume of the breath interval does not exceed 1525 the tidal volume threshold, the disordered breathing period is continuing and the next breath is checked 1510.

If the breath interval does not exceed 1515 the duration threshold, then the tidal volume of the breath is checked 1535. If the tidal volume does not exceed 1535 the tidal volume threshold, the breathing pattern is consistent with a hypopnea cycle and a hypopnea event trigger is set on 1540. If the tidal volume exceeds the tidal volume threshold, then the breath is normal.

If a period of disordered breathing is in progress, detection of a normal breath signals the end of the disordered breathing. If disordered breathing was previously detected 1545, and if the disordered breathing event duration has not exceeded 1550 the duration threshold, and the current breath is normal, then no disordered breathing event is detected 1555. If disordered breathing was previously detected 1545, and if the disordered breathing event duration has extended for a period of time exceeding 1550 the duration threshold, and the current breath is normal, then the disordered breathing trigger is turned off 1560. In this situation, the duration of the disordered breathing episode was of sufficient duration to be classified as a disordered breathing episode. If an apnea event was previously triggered 1565, then an apnea event is declared 1570. If a hypopnea was previously triggered 1565, then a hypopnea event is declared 1575.

Central/Obstructive Disordered Breathing Discrimination

Aspects of the invention are directed to methods and systems configured to monitor, diagnose, and/or provide patient therapy using one or more individual medical procedures involving discrimination between central and obstructive disordered breathing. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of this invention involving discrimination between central and obstructive disordered breathing are directed methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 124 (FIG. 1C) for discriminating between central and obstructive disordered breathing. The central/obstructive disordered breathing discrimination system 124 may be implemented as a stand alone system or in combination with other individual medical systems, such as those described in FIGS. 1B-1D.

Embodiments of the invention are directed to methods and systems for classifying the origin of disordered breathing events and/or discriminating between disordered breathing origin types. One embodiment of the invention involves a method for classifying disordered breathing in a patient. The method includes detecting a disordered breathing event and sensing motion associated with respiratory effort during he disordered breathing event. The disordered breathing event is classified based on the sensed motion. At least one of detecting the disordered breathing event, sensing the motion associated with respiratory effort, and classifying the disordered breathing event are performed at least in part implantably. Implantably performing an operation comprises performing the operation using a device that is partially or fully implantable within the patient's body.

In another embodiment of the invention, a disordered breathing classification system includes a disordered breathing detector configured to detect disordered breathing in a patient. A motion sensor is configured to sense the patient's motion associated with respiratory effort during the disordered breathing event. A disordered breathing classification processor is coupled to the motion sensor and the disordered breathing detector. The disordered breathing classification processor is configured to classify the disordered breathing event based on motion associated with respiratory effort. At least one of the disordered breathing detector, the motion sensor, and the disordered breathing classification processor is at least in part implantable.

Another embodiment of the invention involves a system 185 for providing coordinated patient monitoring, diagnosis and/or therapy that utilizes discrimination 124 of central and obstructive disordered breathing. The coordinated system may include, for example, an implantable cardiac device 181 and a patient-external respiratory therapy device 184. The system 185 may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy further includes a system 124 configured to discriminate between central and obstructive disordered breathing. The disordered breathing discrimination system 124 includes a disordered breathing detector configured to detect a disordered breathing event and a motion sensor configured to sense motion associated with respiratory effort of a patient during the disordered breathing event. The disordered breathing detector and the motion sensor are coupled to a disordered breathing classification processor. The disordered breathing classification processor is configured to classify the disordered breathing event based on the respiratory effort motion. At least one of the disordered breathing detector, the motion sensor, and the disordered breathing classification processor is at least in part implantable.

The implantable and respiratory therapy devices 181, 184 may operate cooperatively based on discrimination 124 between central and obstructive disordered breathing. For example, discrimination 124 between central and obstructive disordered breathing may allow the implantable and respiratory therapy devices 181, 184 to operate cooperatively to provide a first therapy to treat obstructive disordered breathing and a second therapy to treat central disordered breathing. Systems and methods directed to discrimination of central and obstructive disordered breathing events may be implemented to include selected features, functions, and/or structures described in commonly owned, U.S. Pat. No. 7,510,531, which is hereby incorporated herein by reference.

According to various implementations, disordered breathing events may be classified based on a patient's motion associated with respiratory effort during the disordered breathing event. For example, central apnea may be identified by insufficient respiration for at least about 10 seconds with insufficient respiratory effort. Obstructive apnea may be identified by insufficient respiratory inspiration for at least about 10 seconds accompanied by respiratory effort. Respiratory effort may be detected by sensing patient motion associated with respiratory effort during the disordered breathing event. The sensed motion may comprise motion of the patient's chest, abdomen, diaphragm, and/or other motion associated with respiratory effort.

Disordered breathing episodes may be classified as central disordered breathing, obstructive disordered breathing, or a combination of central and obstructive types. Various forms of disordered breathing that may be classified with respect to origin (central, obstructive, or mixed origin) may include, for example, apnea, hypopnea, hyperpnea, tachypnea, periodic breathing, Cheyne-Stokes respiration (CSR), and/or other forms of disordered breathing.

Figure 16A:
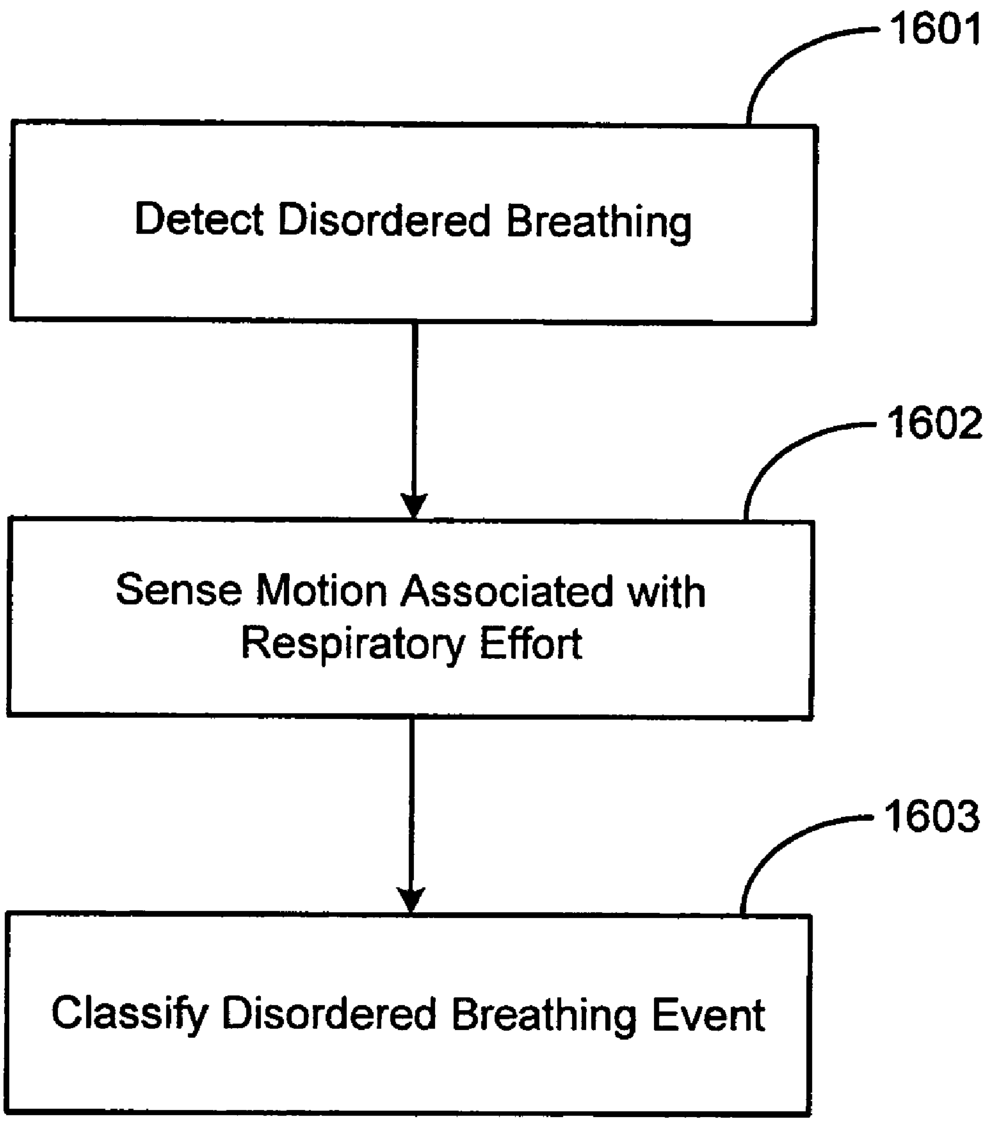
FIG. 16A is a flowchart of a method of classifying a disordered breathing event in accordance with embodiments of the invention.

FIG. 16A is a flowchart of a method of classifying a disordered breathing event in accordance with embodiments of the invention. The method involves detecting 1601 a disordered breathing event and sensing 1602 motion associated with respiratory effort during the disordered breathing event. Disordered breathing may be detected based on the patient's respiration patterns, or by other methods. Motion associated with respiratory effort may be involve chest wall motion, abdominal motion and/or other motions associated with respiratory effort. The disordered breathing event may be classified 1603 as central, obstructive, or a mixture of central and obstructive types based on the patient's movements associated with respiratory effort during the disordered breathing event.

In one scenario, the disordered breathing event may include both central and obstructive types. The disordered breathing event may be classified as a mixed central and obstructive disordered breathing event if central disordered breathing is classified during one portion of the disordered breathing event and obstructive disordered breathing is classified during another portion of the disordered breathing event.

Figure 16B:
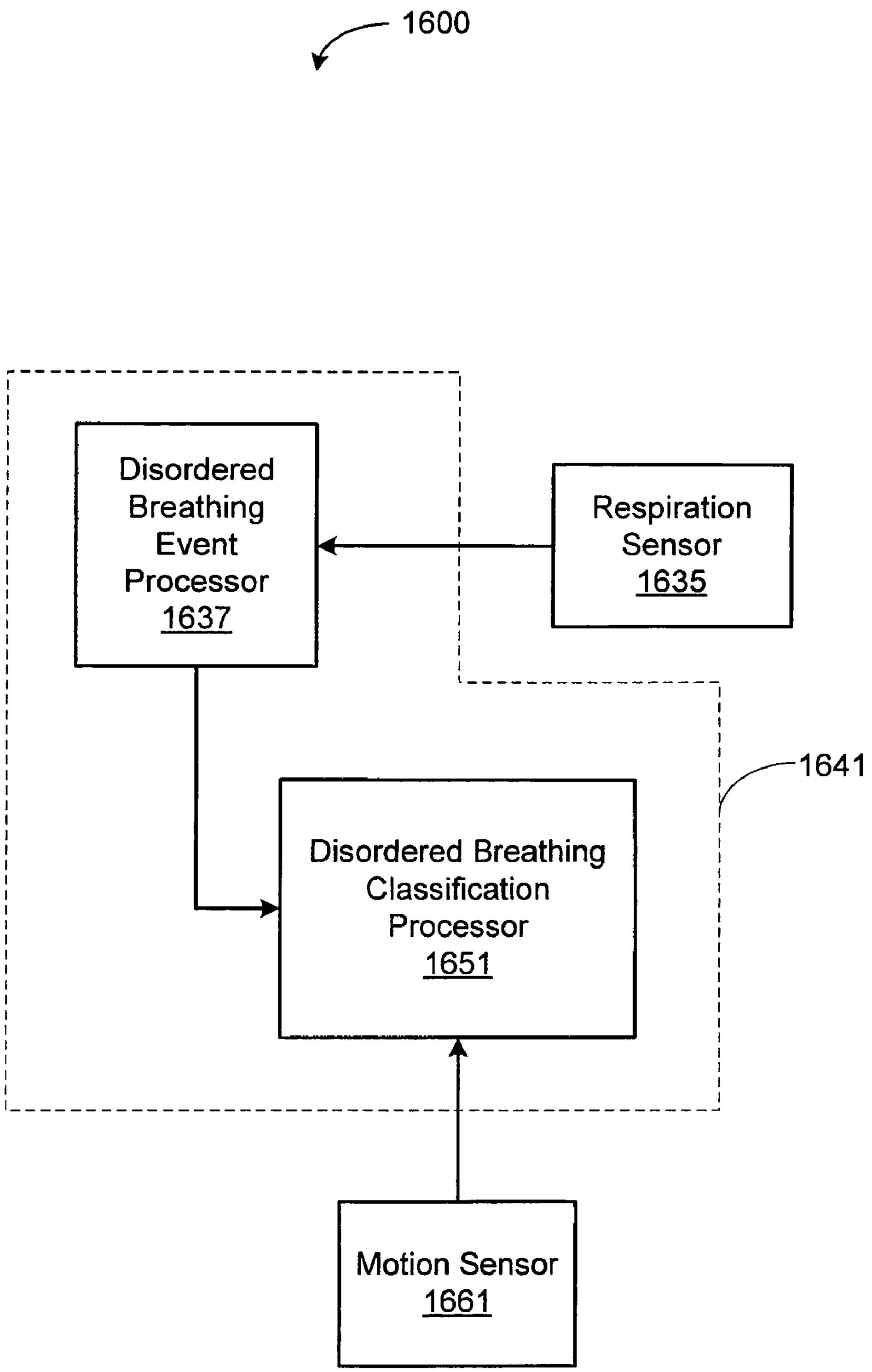
FIG. 16B is a block diagram of disordered breathing classification circuitry that may be implemented in accordance with embodiments of the invention.

FIG. 16B is a block diagram of disordered breathing classification circuitry 1600 for classifying disordered breathing in accordance with embodiments of the invention. The disordered breathing classification circuitry 1600 illustrated in FIG. 16B includes a disordered breathing classification processor 1651 that receives signals from a disordered breathing event detector 1637 and a motion sensor 1661.

The disordered breathing event detector 1637 received signals from at least one sensor 1635, e.g., a respiration sensor, for detecting a physiological signal indicative of disordered breathing. The disordered breathing event processor 1637 analyzes the sensor signals and may determine that a disordered breathing event is in progress based on the analysis.

In one implementation, the sensor 1635 generates a signal modulated by patient respiration. Such a signal may be generated, for example, by a transthoracic impedance sensor, an airflow meter, or by other sensing methods. A disordered breathing event may be detected based on the patient's breath intervals and/or tidal volume as described more fully herein.

The motion sensor 1661 may be configured to sense chest wall motion, abdominal motion, and/or other patient movement indicative of respiratory effort. The motion sensor 1661 generates a signal indicative of respiratory effort that is communicated to the disordered breathing classification processor 1651.

The sensors 1635, 1661 may comprise any number of patient-internal and/or patient-external sensors coupled through leads or wirelessly to other components of the disordered breathing classification circuitry 1600. In various embodiments, a signal indicative of the patient's respiration may be acquired using an implantable or patient-external transthoracic impedance sensor, blood oxygen sensor, microphone, flow meter, or by other patient-internal and/or patient-external sensing methods.

Sensing chest, abdominal, or other motion associated with respiratory effort may be accomplished using a patient-internal or patient-external sensing device. In one example, patient motion associated with respiratory effort may be sensed using an implanted or patient-external accelerometer. The accelerometer may be incorporated as a component of an implanted medical device, such as an implantable cardiac rhythm management system having functionality for delivering cardiac electrical therapy for disordered breathing.

In another example, motion associated with respiratory effort may be detected based on changes in an electromyogram (EMG) sensor signal. An EMG sensor may be positioned internally or externally to detect electrical activity of a patient's intercostal, pectoral and/or diaphragmatic muscles indicative of motion. In yet another example, motion associated with respiratory effort may be detected using a transthoracic impedance sensor. The patient's transthoracic impedance is modulated as the chest wall and/or abdomen moves during inspiratory attempts. Transthoracic impedance may be sensed using intracardiac electrodes, subcutaneous electrodes, or patient-external electrodes positioned at appropriate locations in, on, or about the patient's thorax.

A disordered breathing event may be classified as a central, obstructive or mixed type based on the based on the patient's respiratory efforts during disordered breathing episodes. The disordered breathing classification processor 1651 may discriminate between central and obstructive disordered breathing events using signals received from the motion sensor 1661 and the disordered breathing detector 1641. If patient motion associated with respiratory effort is of sufficient magnitude during disordered breathing, then the disordered breathing classification processor 1651 may determine that the disordered breathing event is obstructive in origin. If respiratory effort motion is insufficient during the disordered breathing event, then the disordered breathing classification processor 1651 may classify the disordered breathing event as central in origin. If the respiratory effort motion is sufficient during one portion of the disordered breathing episode, but is insufficient during another portion, then the disordered breathing classification processor 1651 may classify the episode as a mixture of central and obstructive types.

In one configuration, the disordered breathing classification circuitry 1600 may be fully patient-external. In another configuration, some functions of the disordered breathing classification circuitry may be implemented in an implantable device and other functions may be implemented as a patient external device. The implantable and the patient-external disordered breathing classification system components may be coupled through leads or a wireless communications link, such as through a Blue Tooth or a proprietary wireless communication link.

In yet another configuration, the disordered breathing classification circuitry 1600 may be fully implantable. Disordered breathing classification circuitry 1600 may be incorporated, for example, as a component of a cardiac device such as a pacemaker, defibrillator, cardiac resynchronizer, implantable cardiac monitor, or other implantable medical device.

Figure 16C:
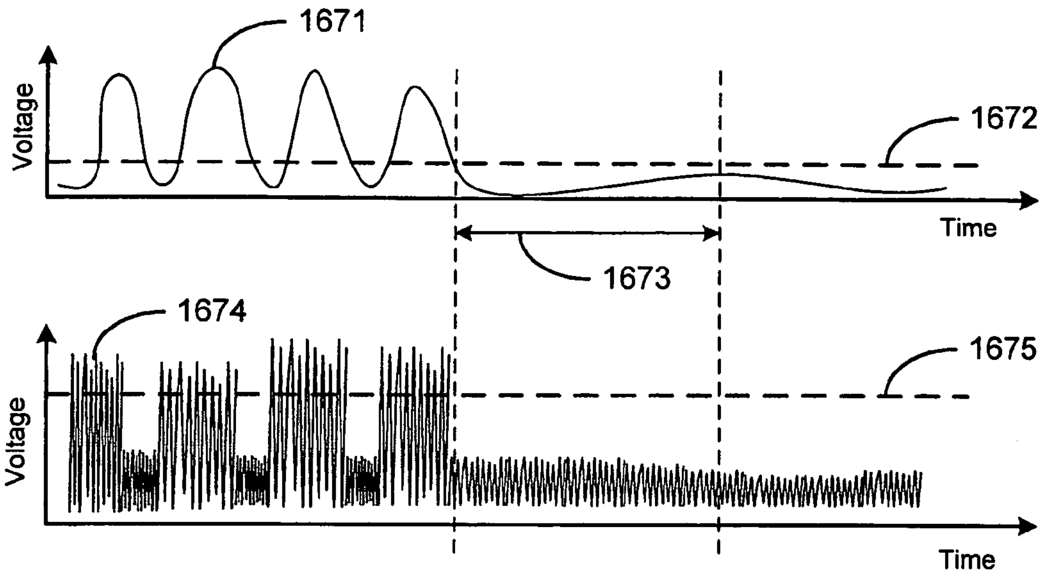
FIGS. 16C and 16D provide graphs of accelerometer signals representing chest wall motion for central and obstructive disordered breathing, respectively in accordance with embodiments of the invention.
Figure 16D:
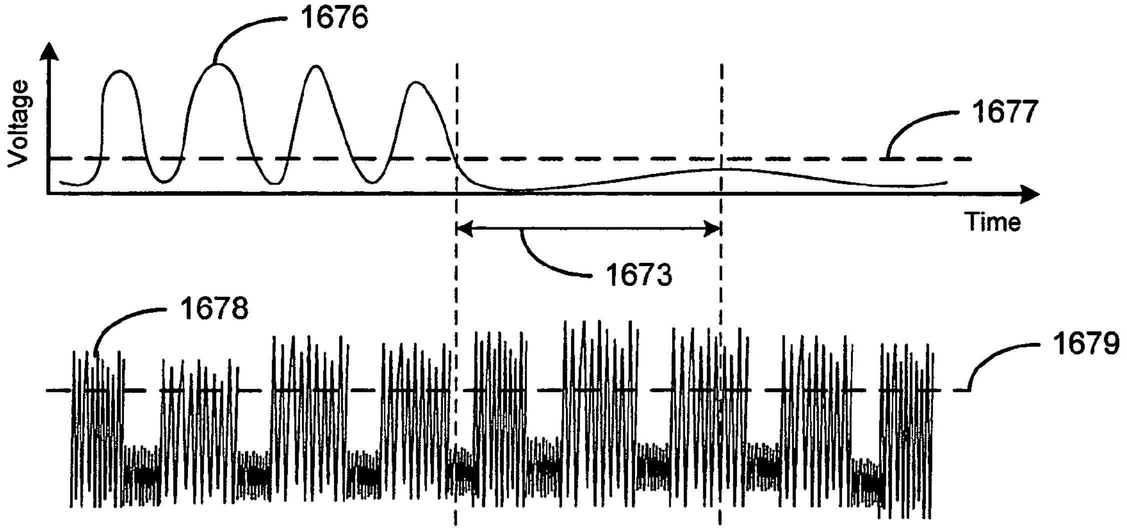

Classification of the disordered breathing event in accordance with the processes of the invention involves evaluating chest wall motion or other motion associated with respiratory effort. FIGS. 16C and 16D provide graphs of accelerometer signals representing chest wall motion for central and obstructive disordered breathing, respectively. As illustrated in FIG. 16C, apnea is detected when the transthoracic impedance signal 1671 remains below an inspiration threshold 1672 for a period of time greater than an apnea interval 1673, e.g., 10 seconds. In this example, the apnea event is a central apnea event and the signal 1674 from an accelerometer sensing the patient's chest wall motion also falls below a motion threshold 1675 during the period of non-respiration. The lack of chest wall motion indicates that the patient's breathing reflex is not being triggered by the central nervous system, indicative of a central disordered breathing event.

FIG. 16D illustrates the accelerometer signal and transthoracic impedance signal for an obstructive apnea event. Apnea is detected when the transthoracic impedance signal 1676 remains below an inspiration threshold 1677 for a period of time greater than an apnea interval 1673. In this example, the apnea event is an obstructive apnea event and the signal 1678 from an accelerometer sensing the patient's chest wall motion rises above a chest well motion threshold 1679 during the period of non-respiration. The chest wall motion indicates that the patient's breathing reflex is being triggered by the central nervous system, indicative of an obstructive disordered breathing event.

Figure 16E:
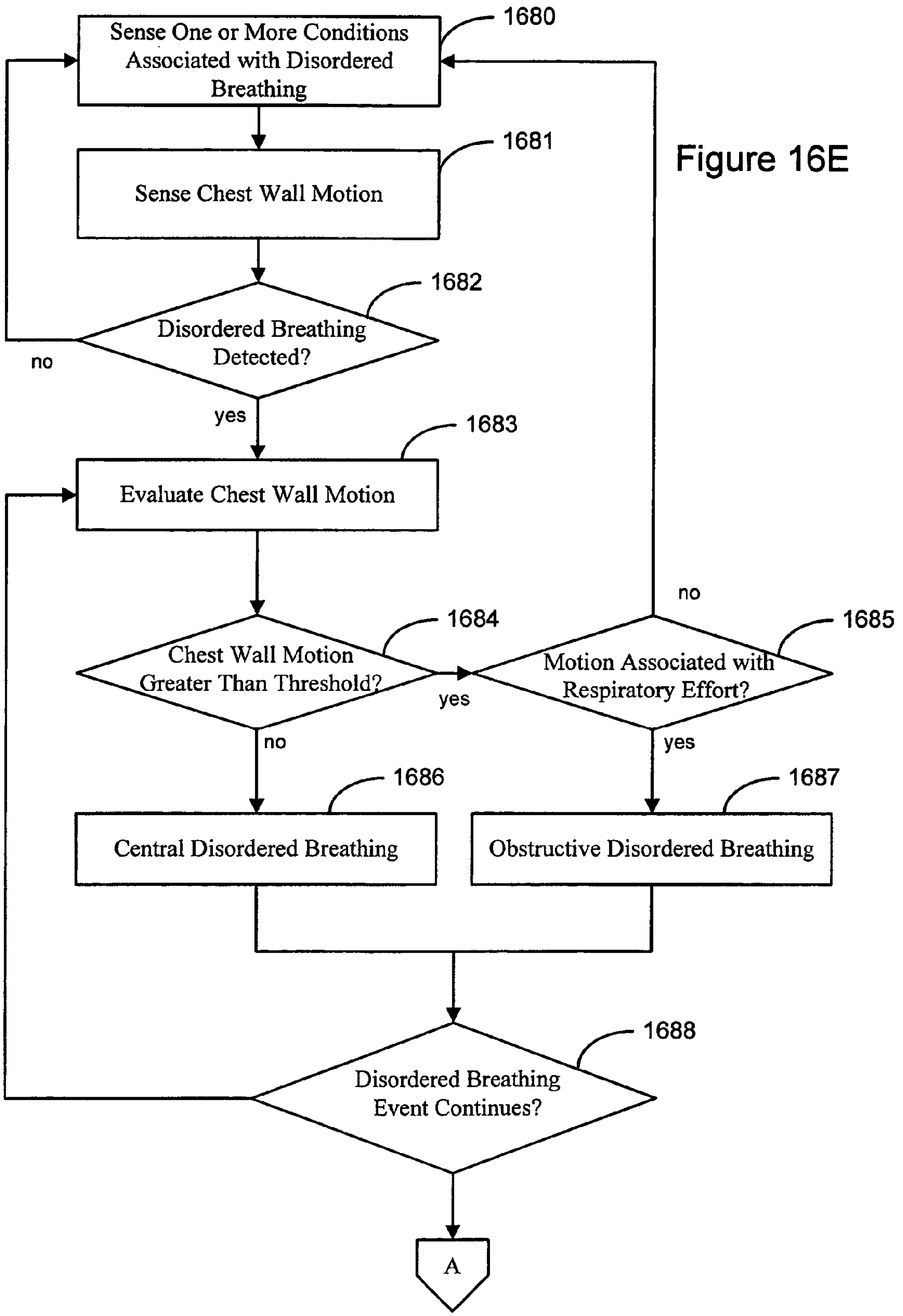
FIGS. 16E and 16F are flowcharts of a method for classifying disordered breathing events as central, obstructive or mixed events in accordance with embodiments of the invention.

FIG. 16E is a flowchart of a method for classifying disordered breathing events as central, obstructive or mixed events in accordance with embodiments of the invention. One or more conditions associated with disordered breathing are sensed 1680. For example, one or more of the conditions listed in Table 1 may be sensed to detect that a disordered breathing event is occurring. The patient's chest wall motion is sensed 1681 during the disordered breathing event.

If disordered breathing is detected 1682, then the chest wall motion signals are analyzed 1683 for obstructive/central origin discrimination. A parameter, e.g., average amplitude or frequency, of the signal produced by the motion sensor may be compared to a threshold. If the chest wall motion signal is not greater 1684 than a threshold, then the disordered breathing is classified 1686 as central disordered breathing. If the chest wall motion signal is greater than or equal to the threshold 1684 and the chest wall motion is associated with respiratory effort 1685, then the disordered breathing is classified 1687 as obstructive disordered breathing. For example, if chest wall motion from the accelerometer is synchronous with a reduced transthoracic impedance during a disordered breathing episode, then the concurrence of disordered breathing and chest wall motion indicates disordered breathing that is obstructive in origin.

If the disordered breathing event continues 1688, then chest wall motion continues to be sensed 1683. A second or subsequent portion of the disordered breathing event may have a different classification from the initial classification based on the presence or lack of motion associated with respiratory effort.

Figure 16F:
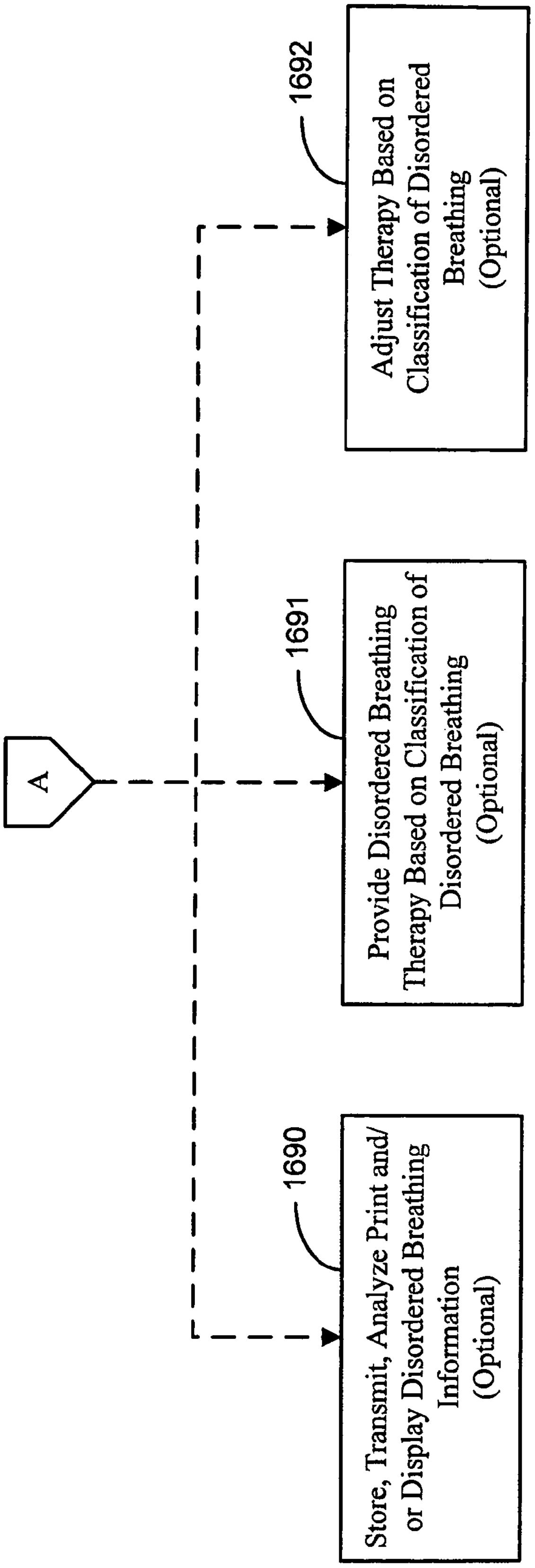

The flowchart of FIG. 16F follows from FIG. 16E and illustrates optional processes that may be implemented following classification of the disordered breathing event. Disordered breathing information may optionally be stored, transmitted, displayed, and/or printed 1690. For example, disordered breathing information may be stored over several weeks or months to enhance diagnosis of disordered breathing or other conditions, or to analyze disordered breathing trends and/or therapy effectiveness.

Additionally, or alternatively, classification of the origin of disordered breathing events may be used in connection with providing 1691 a therapy to treat the disordered breathing. Therapy for treating disordered breathing may involve cardiac electrical therapy, among other therapies. In one scenario, a first therapy regimen may be used to treat disordered breathing that is central in origin. A second therapy regimen may be used to treat disordered breathing that is obstructive in origin. The first and/or the second therapies may be initiated after the origin of the disordered breathing is determined.

Further, therapies other than disordered breathing therapy may be initiated, modified, or terminated 1692 based on the classification of disordered breathing. For example, as previously discussed, disordered breathing in the form of Cheyne-Stokes respiration is related to congestive heart failure and may be used to monitor the progression of CHF. As previously discussed, Cheyne-Stokes respiration is marked by periodic patterns of waxing and waning respiration interrupted by periods of central apnea. Characteristics of the disordered breathing experienced by the patient, e.g., origin, duration, and severity, may be used to initiate or adjust therapy, such as cardiac pacing therapy and/or cardiac resynchronization therapy, delivered to the patient.

In various embodiments of the invention described herein, discrimination between central and obstructive disordered breathing is based on sensing chest wall motion using an implanted motion sensor, e.g., an accelerometer. In other embodiments, a patient-external motion detector, such as a patient-external accelerometer, patient-external respiratory bands, transthoracic impedance sensor, or a mercury switch, may be used alone or in combination with other implanted or patient-external respiratory sensors and detection algorithms for central/obstructive disordered breathing classification.

In one example, a movement sensor, such as an accelerometer, is mounted inside an implantable CRM device to sense chest wall motions that are indicative of obstructive apnea. The output of the movement sensor may be used in combination with other sensors (such as trans-thoracic impedance) for classification of obstructive apnea. Multi-sensor pulse generators are products in a unique position to provide accurate long-term monitoring and prediction of the progression of disease in patients with disordered breathing. Discrimination between types of apnea events allows more accurate diagnosis, monitoring, and/or treatment of abnormal respiration patterns associated with CHF or sleep disordered breathing. Monitoring with discrimination between types of apnea may enable therapy improvements to counteract the effects of abnormal respiratory patterns.

Disordered Breathing Prediction

Aspects of the invention that include prediction of disordered breathing are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy including prediction of disordered breathing.

Other aspects of the invention are directed to methods and systems configured to monitor, diagnose, and/or provide therapy using coordinated medical procedures including disordered breathing prediction. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 88 (FIG. 1D) for predicting disordered breathing. The disordered breathing prediction system 88 may be implemented as a stand alone system or in combination with other individual medical systems, such as those described in FIGS. 1B-1D.

An embodiment of the invention involves an automated method of predicting disordered breathing in a patient. One or more conditions associated with disordered breathing are detected and compared to one or more sets of disordered breathing prediction criteria. Disordered breathing is predicted based on the comparison. At least one of comparing the conditions to the disordered breathing prediction criteria and predicting the disordered breathing is performed at least in part implantably.

In others embodiment of the invention, a method for predicting disordered breathing involves detecting one or more conditions predisposing a patient to disordered breathing. The predisposing conditions are compared to one or more sets of disordered breathing prediction criteria. Disordered breathing is predicted based on the comparison. At least one of comparing the predisposing conditions to the one or more sets of disordered breathing prediction criteria and predicting the disordered breathing is performed at least in part implantably.

Yet another embodiment of the invention involves detecting one or more precursor conditions associated with disordered breathing. The precursor conditions are compared to one or more sets of disordered breathing prediction criteria. Disordered breathing is predicted based on the comparison. At least one of comparing the precursor conditions to the one or more sets of disordered breathing prediction criteria and predicting the disordered breathing is performed at least in part implantably.

In a further embodiment of the invention, a medical device includes a detector system and a prediction engine. The detector system is configured to detect one or more conditions associated with disordered breathing. The prediction engine is coupled to the detector system and is configured to compare the one or more detected conditions to one or more sets of disordered breathing prediction criteria and to predict disordered breathing based on the comparison. The prediction engine includes at least one implantable component.

Another embodiment of the invention involves an automated disordered breathing prediction system. The system includes means for detecting one or more conditions associated with disordered breathing, means for comparing the detected one or more conditions to one or more sets of disordered breathing prediction criteria and means for predicting disordered breathing based on the comparison. At least one of the means for comparing and the means for predicting includes an implantable component.

In yet another embodiment of the invention, an automated system for predicting disordered breathing includes means for detecting conditions predisposing the patient to disordered breathing. The system further includes means for comparing the predisposing conditions to one or more sets of disordered breathing prediction criteria and means for predicting disordered breathing based on the comparison. At least one of the means for comparing the predisposing conditions to the one or more sets of prediction criteria, and the means for predicting disordered breathing includes an implantable component.

In yet a further embodiment of the invention, an automated system for predicting disordered breathing includes means for detecting precursor conditions associated with disordered breathing. The system further includes means for comparing the precursor conditions to one or more sets of disordered breathing prediction criteria and means for predicting disordered breathing based on the comparison. At least one of the means for comparing the precursor conditions to the one or more sets of disordered breathing prediction criteria and means for predicting disordered breathing includes an implantable component.

Another embodiment of the invention involves a system for providing coordinated patient monitoring, diagnosis and/or therapy that utilizes prediction 88 of disordered breathing. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to one embodiment, the system providing coordinated patient monitoring, diagnosis and/or therapy further includes a system 88 configured to predict disordered breathing. The disordered breathing prediction system 88 includes a detector system configured to detect conditions associated with disordered breathing and a prediction engine coupled to the detector system. The prediction engine is configured to compare the detected conditions to one or more sets of prediction criteria and predict the disordered breathing based on the comparison. The prediction engine includes at least one implantable component.

The implantable and respiratory therapy devices 181, 184 may operate cooperatively based on the predication 88 of disordered breathing. For example, implantable and respiratory therapy devices 181, 184 to operate cooperatively to provide monitoring and/or diagnosis based on the prediction of disordered breathing. In another example, the implantable and respiratory therapy devices 181, 184 may provide a coordinated therapy to treat the predicted disordered breathing. Systems and methods directed to prediction of disordered breathing may be implemented to include selected features, functions, and/or structures described in commonly owned, U.S. Pat. No. 7,396,333, which is hereby incorporated herein by reference. Systems and methods directed to therapy triggered by prediction of disordered breathing may be implemented to include selected features, functions, and/or structures described in commonly owned, U.S. Pat. No. 7,680,537, which is hereby incorporated herein by reference.

Figure 16G:
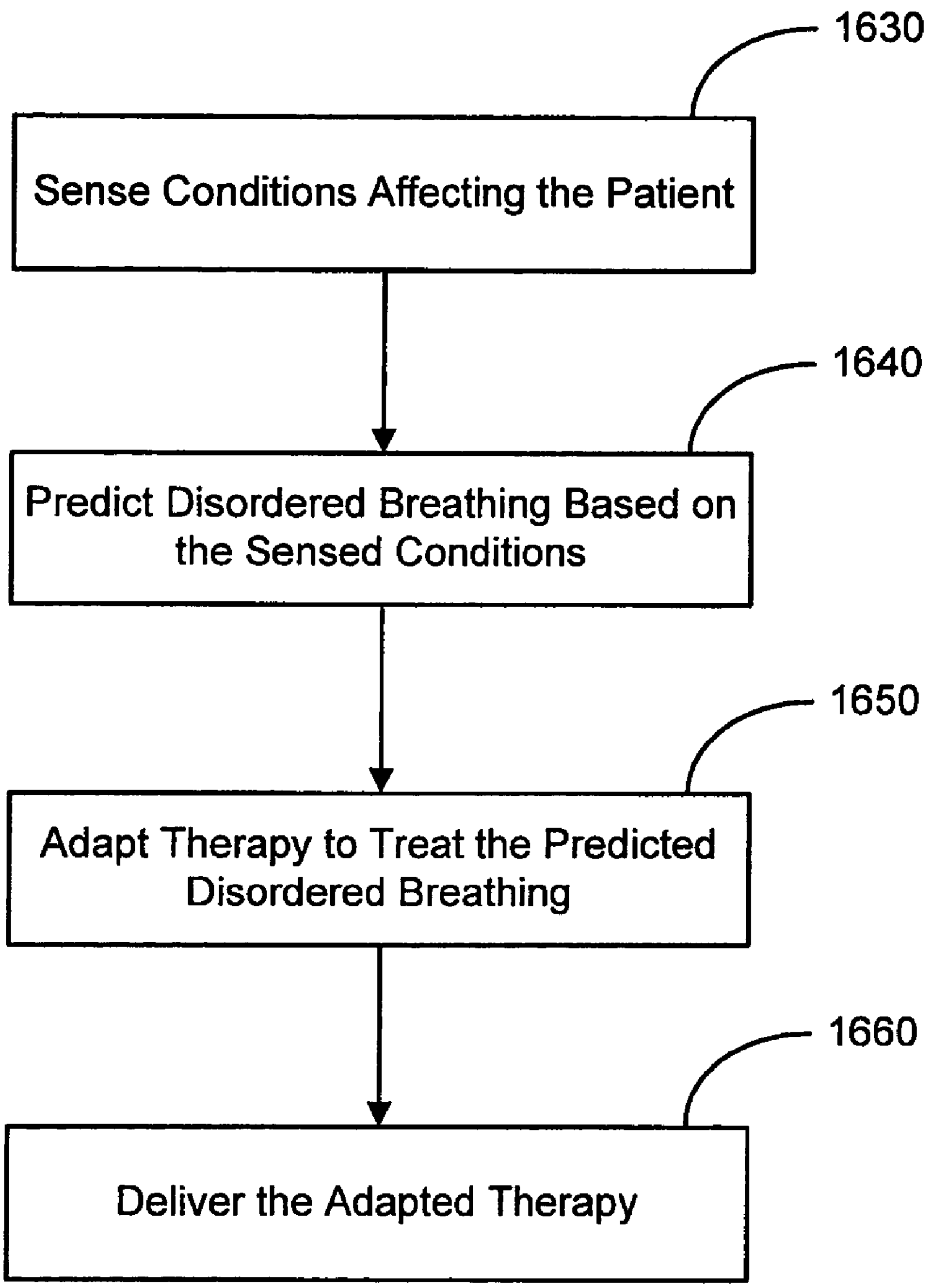
FIG. 16G is a flowchart illustrating a method for triggering disordered breathing therapy based on a prediction of disordered breathing according to embodiments of the invention.

The flowchart of FIG. 16G illustrates a method for triggering disordered breathing therapy based on a prediction of disordered breathing according to various embodiments of the invention. The method involves sensing 1630 one or more conditions predictive of disordered breathing and predicting disordered breathing 1640 based on the sensed conditions. Disordered breathing may be predicted, for example, by comparing the detected conditions to disordered breathing prediction criteria. A representative set of conditions that may be used to predict disordered breathing are listed in Table 1. The representative set of conditions listed in Table 1 is not exhaustive, and conditions other than those listed may be used to predict disordered breathing. If disordered breathing is predicted, therapy is adapted 1650 to treat the disordered breathing, e.g., reduce the severity of the disordered breathing or prevent the disordered breathing from occurring. The adapted therapy is delivered 1660 to the patient. One or more of sensing the conditions affecting the patient, predicting the disordered breathing based on the sensed conditions and delivering the therapy to treat the disordered breathing is performed as least in part implantably.

Figure 17:
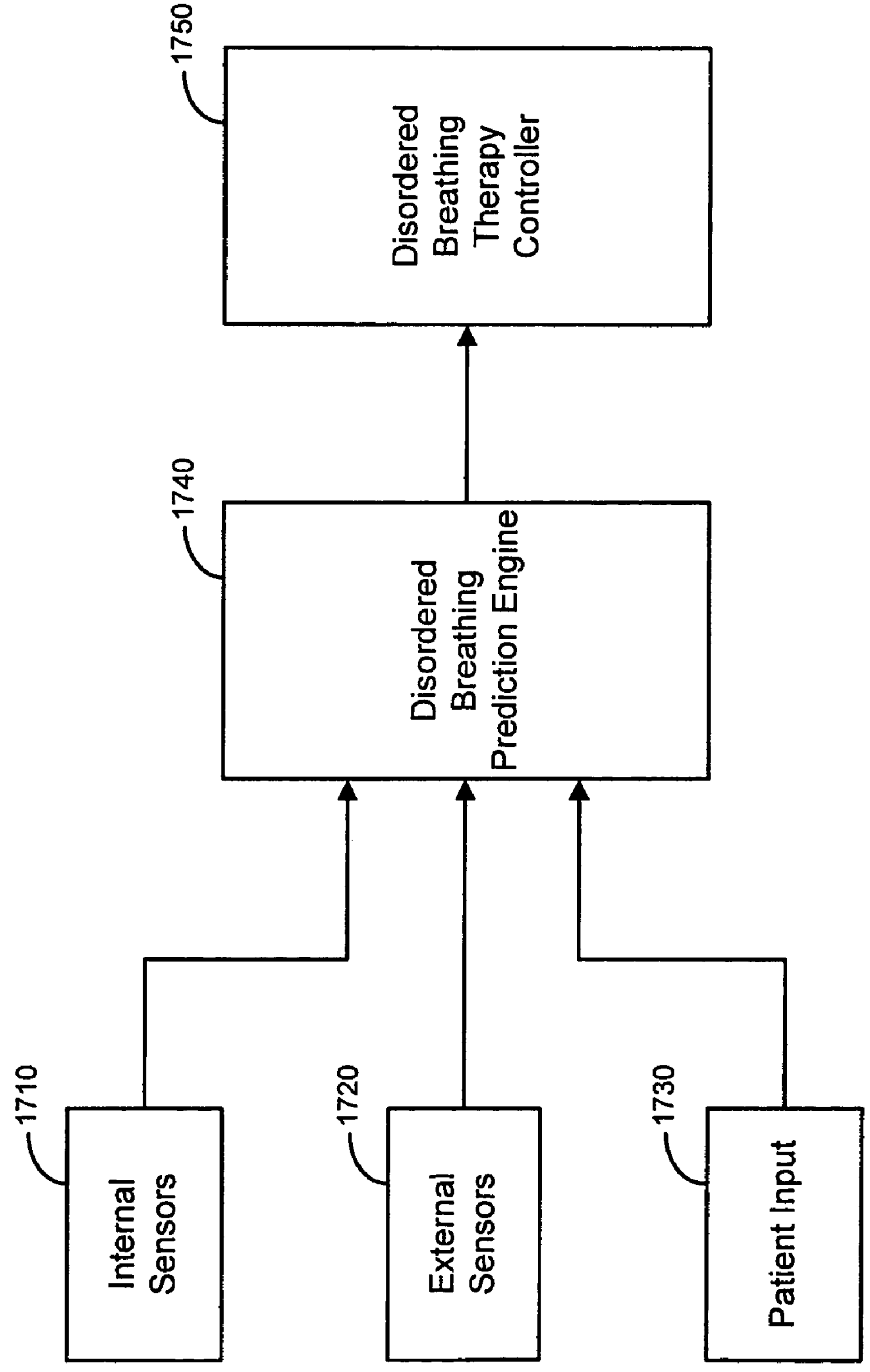
FIG. 17 is a block diagram of a disordered breathing therapy system including disordered breathing prediction functionality in accordance with embodiments of the invention.

FIG. 17 illustrates a block diagram of a disordered breathing therapy system configured in accordance with embodiments of the invention and including disordered breathing prediction functionality. The system may use patient-internal sensors 1710, implanted within the body of the patient, to detect physiological conditions. For example, the system may determine heart rate, heart rate variability, respiration cycles, tidal volume, and/or other physiological signals using an intracardiac electrocardiogram (EGM) signal detector and transthoracic impedance sensor that are part of an implanted cardiac rhythm management system such as a cardiac pacemaker or defibrillator.

The system may use patient-external sensors 1720 to detect physiological or non-physiological conditions. In one scenario, whether the patient is snoring may be useful in predicting disordered breathing. Snoring may be detected using an external microphone or an implanted accelerometer, for example. In another situation, temperature and humidity may be factors that exacerbate the patient's disordered breathing. Signals from temperature and humidity sensors may be used to aid in the prediction of disordered breathing.

Additionally, the system may use information input 1730 by the patient to inform the disordered breathing prediction system of one or more patient conditions. In various embodiments, the patient's medical history, self-described medication use, alcohol or tobacco use, day-time sleepiness, or perceptions of sleep quality over the past one or more sleep periods may be useful in connection with the disordered breathing prediction.

Signals from one or more of the patient-internal sensors 1710, patient-external sensors 1720, and patient input devices 1730 may be coupled to a disordered breathing prediction engine 1740 for prediction evaluation. In one implementation, the prediction engine 1740 may compare the patient conditions to one or more sets of disordered breathing criteria and predict disordered breathing based on the comparison. The prediction engine 1740 is coupled to a therapy controller 1750. If disordered breathing is predicted, the therapy controller 1750 delivers an appropriate therapy to the patient to mitigate the disordered breathing.

In one example, the patient conditions may be sensed and processed using implantable sensors 1710, and the prediction analysis and therapy delivery may be performed by a patient-external disordered breathing prediction engine 1740 and a patient-external therapy controller 1750. Some or all of the implantable sensors 1710 may have remote communication capabilities, such as a wireless proprietary or a wireless Bluetooth communications link. In this implementation, the wireless communications link couples the implantable sensor or sensors 1710 to the patient-external disordered breathing prediction engine 1740. Electrical signals representing patient conditions are produced by the implantable sensors 1710 and transmitted to the patient-external disordered breathing prediction engine 1740.

In another example, an implantable therapy device may incorporate a disordered breathing prediction engine 1740 and one or more patient-external sensors 1720. Signals representing the patient conditions may be transmitted from the patient-external sensors to the implanted prediction engine 1740 over a wireless communication link.

In a further example, the prediction engine may be a patient-external device coupled wirelessly to the therapy controller. Various combinations of wireless or wired connections between the patient-internal sensors 1710, patient-external sensors 1720, patient input devices 1730, the prediction engine 1740, and the therapy controller 1750 are possible.

The above examples provide a few of the many possible configurations that may be used to provide disordered breathing therapy based on the prediction of disordered breathing in accordance with various embodiments of the invention. It is understood that the components and functionality depicted in the figures and described herein can be implemented in hardware, software, or a combination of hardware and software. It is further understood that the components and functionality depicted as separate or discrete blocks/elements in the figures can be implemented in combination with other components and functionality, and that the depiction of such components and functionality in individual or integral form is for purposes of clarity of explanation, and not of limitation.

One subset of the detected patient conditions, such as the representative conditions listed in Table 1, may represent conditions that predispose the patient to disordered breathing. Predisposing conditions may be statistically associated with an onset of disordered breathing during the next few hours following the detection of the conditions leading to the disordered breathing prediction. Another subset of conditions may represent precursor conditions used to predict an imminent onset of disordered breathing that may occur within a time window measured in terms of a few minutes or seconds. Detection of patient conditions associated with disordered breathing and prediction of disordered breathing based on predisposing or precursor conditions is performed on real-time basis.

A subset of patient conditions may be used to verify or otherwise inform the disordered breathing prediction. In one example, information regarding sleep onset or sleep stage or state, e.g., REM or non-REM sleep, may be employed in prediction of sleep disordered breathing. A subset of the conditions listed in Table 1 may be used to detect whether the patient is asleep and to track the various stages of sleep. Another subset of the conditions may be employed to detect disordered breathing episodes, to classify disordered breathing episodes. Table 4 below provides examples of how some conditions listed in Table 1 may be used in disordered breathing prediction.

TABLE 4

| Condition | Examples of how condition is used in disordered breathing prediction |
|---|---|
| Heart rate | Decrease in heart rate may indicate disordered breathing episode. Decrease in heart rate may indicate the patient is asleep. |
| Heart rate variability | May be used to determine sleep state and reduction in heart rate variability is a chronic factor associated with disordered breathing. |
| Ventricular filling pressure | May be used to identify/predict pulmonary congestion associated with respiratory disturbance. |
| Blood pressure | Swings in on-line blood pressure measures are associated with apnea. |

TABLE 4-continued

| Condition | Examples of how condition is used in disordered breathing prediction |
|---|---|
| Snoring | Snoring is associated with a higher incidence of obstructive sleep apnea and may be used to detect disordered breathing. |
| Respiration signals/respiration patterns | Respiration patterns may be used to detect disordered breathing episodes.<br>Respiration patterns may be used to determine the type of disordered breathing.<br>Respiration patterns may be used to detect that the patient is asleep.<br>Hyperventilation may be used to predict disordered breathing.<br>Previous episodes of disordered breathing may be used to predict further episodes.<br>One form of disordered breathing may be used to predict another form of disordered breathing |
| Patency of upper airway | Patency of upper airway is related to obstructive sleep apnea and may be used to detect episodes of obstructive sleep apnea. |
| Pulmonary congestion | Pulmonary congestion is associated with respiratory disturbances. |
| Sympathetic nerve activity | End of apnea associated with a spike in SNA |
| CO2 saturation | Low CO2 levels initiate central apnea. |
| O2 saturation | O2 desaturation occurs during severe apnea/hypopnea episodes. |
| Blood alcohol content | Alcohol tends to increase incidence of snoring & obstructive apnea. |
| Adrenalin | End of apnea associated with a spike in blood adrenaline. |
| Brain Natriuretic Peptide (BNP) | A marker of heart failure status, which is associated with Cheyne-Stokes Respiration |
| C-Reactive Protein | A measure of inflammation that may be related to apnea. |
| Drug/Medication/ Tobacco use | These substances may affect the likelihood of both central & obstructive apnea. |
| Muscle atonia | Muscle atonia may be used to detect REM and non-REM sleep. |
| Eye movement | Eye movement may be used to detect REM and non-REM sleep. |
| Temperature | Ambient temperature may be a condition predisposing the patient to episodes of disordered breathing. |
| Humidity | Humidity may be a condition predisposing the patient to episodes of disordered breathing. |
| Pollution | Pollution may be a condition predisposing the patient to episodes of disordered breathing. |
| Posture | Posture may be used to determine if the patient is asleep and may predispose the patient to disordered breathing.<br>Posture may be a condition predisposing the patient to episodes of disordered breathing. |
| Activity | Patient activity may be used in relation to sleep detection. |
| Sleep stage | NREM sleep may be associated with a higher probability of DB |
| Location | Patient location may used to determine if the patient is in bed as a part of sleep detection. |

Figure 18:
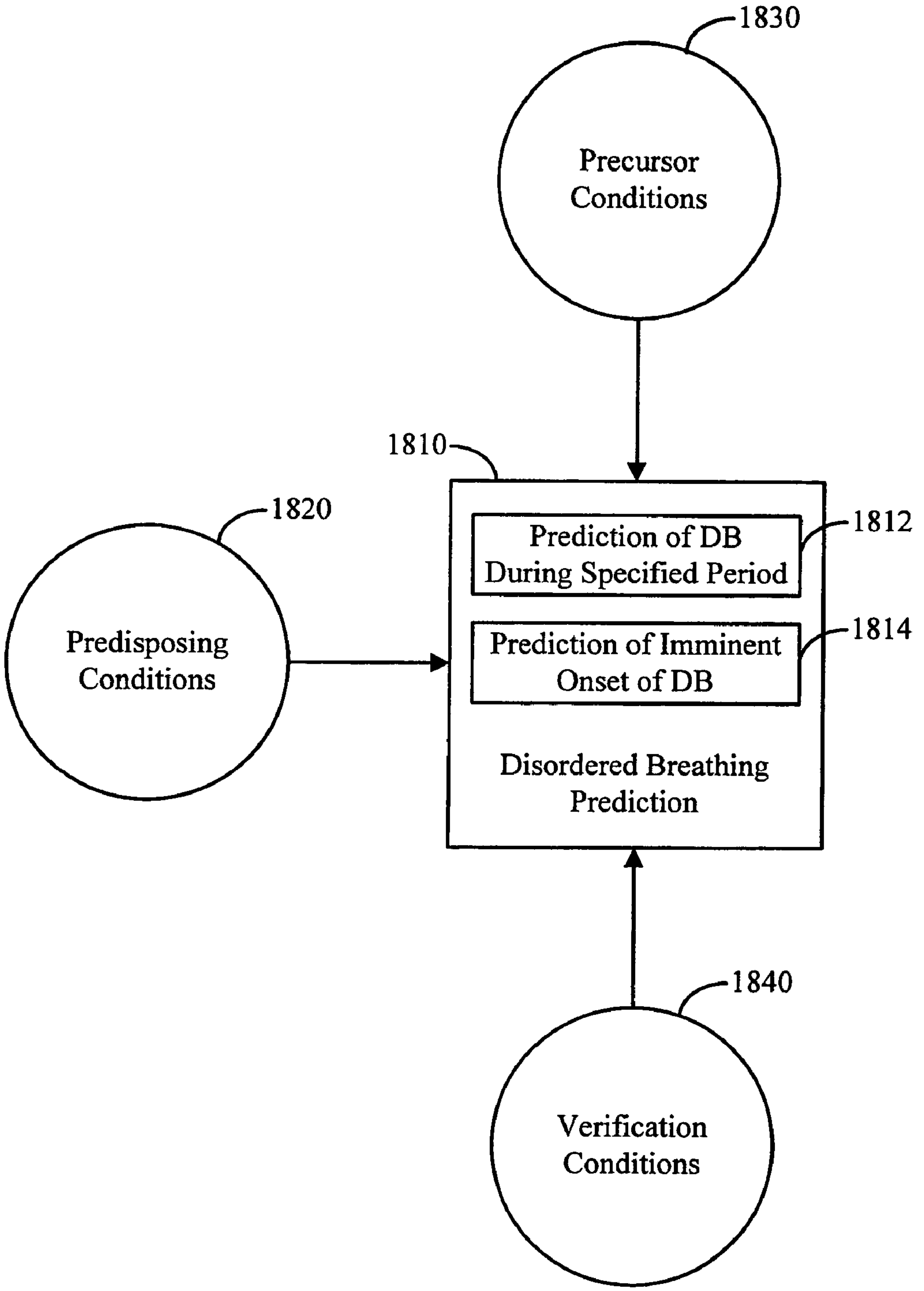
FIG. 18 is a diagram conceptually illustrating how conditions affecting the patient may be used in predicting disordered breathing in accordance with embodiments of the invention.

FIG. 18 conceptually illustrates how patient conditions such as those listed in Table 1 and/or 4 may be used in predicting disordered breathing 1810 according to embodiments of the invention. In one embodiment, the system tracks one or more of the conditions listed in Table 1, Table 4, or both, to predict disordered breathing. For example, over the course of a period of time, e.g., at least a 16 hour window preceding and including the patient's historical sleep time, the system may track one or more conditions to determine the presence and/or level of each particular condition.

In one implementation, the system tracks conditions that have been determined to predispose 1820 the patient to an attack of disordered breathing. Predisposing conditions represent patient conditions statistically associated with an onset of disordered breathing. The presence of one or more predisposing conditions may indicate that disordered breathing is likely to occur within the next time period, such as an eight hour period following the disordered breathing prediction, or during the current sleep period. For example, the predisposing conditions may include the air pollution index of the patient's environment downloaded from an air quality website, recent tobacco use reported by the patient, the degree of the patient's pulmonary congestion detected by an implanted transthoracic impedance sensor, as well as other predisposing conditions detected patient-internally and/or patient-externally.

Additionally, or alternatively, the system may use previous episodes of disordered breathing to determine that the patient is predisposed to further episodes of disordered breathing within particular time period, such as during a sleep period.

For example, previous episodes of disordered breathing during a first interval within the sleep period may be an indication that additional episodes are likely to occur in a second and subsequent interval within the same sleep period. In one example, the occurrence of a first type of disordered breathing may be used to predict a second type of disordered breathing. In another example, the periodicity of disordered breathing may be used to predict future episodes of disordered breathing.

The disordered breathing prediction engine may use the type, duration, frequency, and/or severity of the previous disordered breathing episodes to inform the disordered breathing prediction analysis. Quantification of the severity, frequency, and duration of disordered breathing may be accomplished using any of a number of disturbed breathing measures, including, for example, percent time in disordered breathing and the apnea/hypopnea index.

A further example of a condition predisposing a patient to hypopnea or apnea is body posture. A supine posture is more likely to result in obstruction of the upper airway and can be used to predict episodes of obstructive hypopnea and apnea. Posture and/or torso orientation sensing may be accomplished, for example, using an implantable multiaxis accelerometer.

As previously discussed, sleep disordered breathing is a prevalent form of disordered breathing. Thus, a patient may be more likely to experience episodes of disordered breathing when the patient is in bed sleeping. Thus, proximity to bed may be employed as a predisposing condition to disordered breathing. The disordered breathing therapy system may use a bed proximity sensor to detect that the patient is in bed. Bed proximity may be detected by placing a beacon transmitter on the patient's bed. Receiver circuitry on or in the patient, for example, incorporated in the patient's pacemaker, receives the beacon signal and determines that the patient is in bed.

Conditions that predispose the patient to disordered breathing 1820 are conditions that indicate the likelihood that one or more episodes of disordered breathing will occur during the next time period, such as over the course of the night or other sleep period. Based on predisposing conditions 1820, an onset of disordered breathing may be predicted 1812 to occur within a time window that may include several hours, for example, eight hours.

A second set of conditions, denoted herein as precursor conditions 1830, may be used to predict 1814 an impending onset of disordered breathing. Precursor conditions 1830 indicate that an episode of disordered breathing is imminent and will occur within a time window that may be measured in terms of minutes or seconds, for example. In one implementation, precursor conditions 1830 may be used to predict that an episode of disordered breathing will occur within the next 1800 seconds, for example.

In one embodiment, precursor conditions 1830 indicative of an impending onset of disordered breathing may include, for example, pre-apnea or pre-hypopnea conditions. In one implementation, changes in blood gas concentration, such as $CO_2$, may be causal to central apnea. Therefore, a precursor condition of pre-apnea in a particular patient may be detected when the patient's $CO_2$ level, as measured, for example, by a patient-external $CO_2$ sensor, falls below a selected level, indicating an impending onset of an apnea episode.

In another embodiment, a patient's heart rate variability may be significantly altered before, during, and after episodes of apnea. Heart rate variability may be used, for example, as a precursor condition to predict an impending episode of disordered breathing.

In yet another embodiment, a pre-apnea or pre-hypopnea condition may be detected by analyzing the patient's respiration patterns. Respiration cycles just prior to disordered breathing event, e.g., an apnea or hypopnea event, may exhibit a characteristic pattern. For example, an apnea event for many patients is preceded by a period of hyperventilation with a number of rapid, deep breaths. The pattern of hyperventilation may be detected by analyzing patient's transthoracic impedance signal to determine respiration rate and tidal volume.

Cheyne-Stokes respiration and some apnea/hypopnea episodes may exhibit a crescendo-decrescendo respiration pattern. The crescendo-decrescendo respiration pattern produces hyperventilation during the crescendo stage and hypoventilation during the decrescendo phase. Hyperventilation, secondary to pulmonary congestion, drives arterial partial pressure of carbon dioxide down. A decrease in arterial partial pressure of carbon dioxide below an apnea level may be a causal mechanism for central apnea. According to one embodiment of the invention, detection of an impending onset of disordered breathing may be implemented by detecting a series of increasing tidal volumes followed by a series of decreasing tidal volumes.

For some patients, disordered breathing occurs at regular intervals, allowing the periodicity of the disordered breathing episodes to be used as a precursor condition. If disordered breathing episodes of the patient occur at regular intervals, the next episode of disordered breathing may be predicted based on the time elapsed since the last episode was detected.

In addition, the occurrence of one form of disordered breathing may be used to predict another form of disordered breathing. For example, a patient may characteristically experience one or more episodes of obstructive sleep apnea during the first part of the night followed by central sleep apnea episodes during the later part of the night. In another example, one or more episodes of hypopnea may be used to predict future apnea episodes.

Snoring is an additional example of a pre-apnea or pre-hypopnea condition. In many, patient snoring, or more generally any abnormal airflow in the upper airway, which may be detectable via acoustic means, precedes more significant sleep disordered breathing conditions such as hypopnea or apnea. Precursor conditions 1830 may be analyzed individually, or in combination with one or more predisposing conditions 1820, to predict the impending onset of a disordered breathing episode.

The conditions and associated prediction criteria used for disordered breathing prediction may be highly patient specific. Conditions that are reliably predictors of disordered breathing in one patient may not be effective for another patient. Therefore, conditions used to predict disordered breathing and the respective prediction criteria are preferably based on patient-specific data.

A subset of patient conditions may be used to verify or confirm a prediction of disordered breathing. For example, before or after a prediction of disordered breathing is made, one or more verification conditions 1840 may be checked to confirm the prediction. The verification conditions, as well as the physiological and contextual conditions used to predict disordered breathing, may be highly patient specific.

In one example embodiment, a characteristic pattern of respiration is a reliable predictor of disordered breathing in a particular patient only when the patient is supine. If the prediction is made while the patient not supine, normal variations in respiration cycles in this particular patient may lead to an erroneous prediction of disordered breathing. Thus, before disordered breathing is predicted, a posture sensor signal is checked to verify that the patient is supine. If the patient is supine and the patient's respiration cycles are consistent with criteria indicating that disordered breathing is likely, the disordered breathing prediction is made.

In another example, the patient is known to suffer from episodes of apnea during sleep. The patient's sleep apnea may be predicted using a number of contextual and physiological conditions. The prediction of sleep apnea may be made after assessing that the patient's posture and location are consistent with sleep. Before a prediction of sleep apnea is made, the system confirms that the patient is lying down in bed by checking the signal from an implantable posture sensor and a bed proximity sensor.

Figure 19:
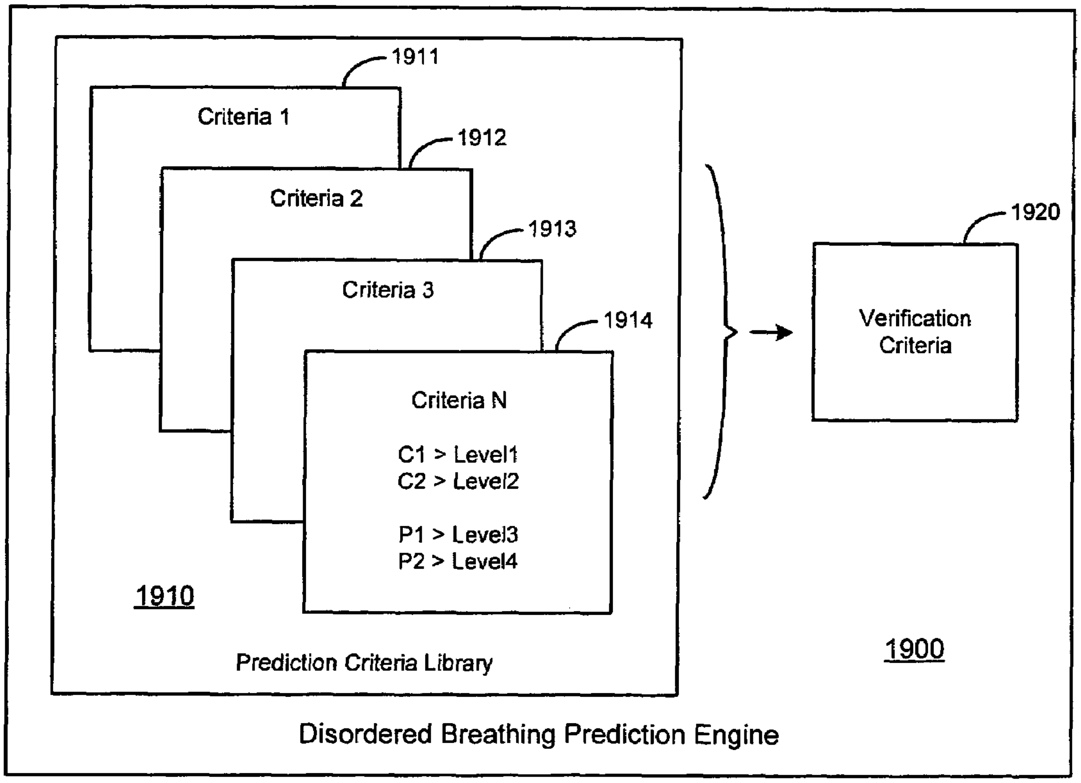
FIG. 19 is a diagram conceptually illustrating the operation of a disordered breathing prediction engine in accordance with embodiments of the invention.

The operation of a disordered breathing prediction engine 1900, according various to embodiments, is conceptually illustrated in the block diagram of FIG. 19. Periodically, one or more patient conditions are detected and compared to a library 1910 of prediction criteria. The prediction criteria library 1910 may incorporate one or more sets of prediction criteria 1911, 1912, 1913, 1914. Each of these sets of criteria may be compared to the detected patient conditions. If the criteria of a prediction criteria set 1911, 1912, 1913, 1914 are substantially consistent with the patient conditions, a preliminary disordered breathing prediction may be made.

In various embodiments, the prediction criteria sets 1911, 1912, 1913, 1914 represent one or more condition thresholds associated with an onset of disordered breathing. In one example embodiment, the level of one or more detected conditions may be compared to the prediction criteria sets 1911, 1912 1913, 1914. If the levels of the one or more conditions are substantially consistent with the thresholds specified in a prediction criteria set 1911, 1912, 1913, 1914, a preliminary prediction of disordered breathing may be made.

The examples that follow are described in terms of a condition being consistent with a prediction criteria when the condition exceeds a prediction criteria threshold. However, it will be understood that different threshold requirements may be defined for different conditions. For example, one condition may be defined to be consistent with a prediction criterion when the condition exceeds a prediction criterion threshold. Another condition may be defined to be consistent with a prediction criterion threshold when the condition falls below the threshold. In yet another example, a condition may be defined to be consistent with the prediction criterion when the condition falls within a specified range of values. Patient conditions may be compared to prediction criteria based on the timing, rate of change, or maximum or minimum value of the condition, for example.

In the example provided in FIG. 19, the prediction criteria N 1914 involves two contextual conditions, C1 and C2, and two physiological conditions, P1 and P2. In this particular example, if conditions C1, C2, P1, and P2 exceed levels Level1, Level2, Level3, and Level4, respectively, the patient may be likely to experience disordered breathing during the night. Therefore, when conditions C1, C2, and P1, P2 reach the levels specified in criteria N 1914, preliminary prediction of disordered breathing is made. One or more additional verification criteria 1920 may be used to confirm the preliminary predication of disordered breathing.

In another embodiment of the invention, the relationships between the detected conditions are analyzed to predict disordered breathing. In this embodiment, the disordered breathing prediction may be based on the existence and relative values associated with two or more patient conditions. For example, if condition A is present at a level of x, then condition B must also be present at a level of f(x) before a disordered breathing prediction is made.

In yet another embodiment of the invention, the estimated probability, $P(C_n)$, that disordered breathing will occur if a particular condition level is detected may be expressed as a function of the ratio of the number of times disordered breathing occurred within a selected time interval following the detection of the particular condition level to the total number of observed occurrences of the condition level. The probability that disordered breathing will occur, $P(C_n)$, is compared to a threshold probability level to make the disordered breathing prediction. Other methods of calculating the estimated probability are also possible.

The prediction of disordered breathing may be based on the convergence or divergence of a number of conditions occurring within the same time period. In this situation, a composite probability score may be computed as a combination of the individual probabilities. In one embodiment, the probabilities are combined by adding the condition probabilities after multiplying each of the condition probabilities by a weighting factor. For example, if the disordered breathing prediction is based on four substantially simultaneous conditions, $C_1$, $C_2$, $C_3$, and $C_4$, the total probability score $PS_T$ may be calculated as:

$$PS_T = A \times P(C_1) + B \times P(C_2) + C \times P(C_3) + D \times P(C_4), \quad [1]$$

where A, B, C, and D are scalar weighting factors that may be used to estimate the relative importance of each of the conditions $C_1$, $C_2$, $C_3$, and $C_4$. If the probability score exceeds a selected prediction criteria threshold, then disordered breathing is predicted.

Although the above process describes combining the estimated probabilities for each condition by adding each of the estimated probabilities, other methods are also possible. For example, a detected patient condition may operate against a prediction of disordered breathing. In this situation, the estimated probability, $P_n(C_n)$, that disordered breathing will not occur if a particular condition level is detected may be expressed as a function of the ratio of the number of times disordered breathing did not occur within a selected time interval following the detection of the particular condition level to the total number of observed occurrences of the condition level. This value may be subtracted from the total to determine the probability score. Non-linear methods of combining the estimated probabilities to arrive at a composite probability are also possible.

If the conditions affecting the patient are consistent with a prediction of disordered breathing, the prediction may be verified by comparing one or more verification conditions to verification criteria. If the verification conditions are consistent with the verification criteria, a prediction of disordered breathing is made.

In the embodiments described above, predictions of disordered breathing are based upon comparisons of one or more patient conditions to sets of prediction criteria. The initial data from which the initial prediction criteria sets are formed may be derived from past observations taken from population data, or from data collected from a particular patient. The initial prediction criteria sets may then be modified as additional data are collected from the patient.

In one embodiment, an estimated accuracy for the prediction criteria is updated for every prediction event. The estimated positive predictive value (PPV) for a prediction criteria set N may be expressed as:

$$PPV_N = \frac{TP}{TP + FP} \quad [2]$$

where TP (true positive) is the number of times the prediction criteria set successfully predicted disordered breathing, and FP (false positive) is the number of times the prediction criteria erroneously predicted disordered breathing.

If the estimated accuracy of prediction criteria set N, $PPV_N$, falls below a predetermined level, for example, 0.7, the prediction criteria set N may be modified. In one embodiment, a possible prediction criteria set is formed, for example, by modifying the threshold level of one or more of the conditions represented by the original prediction criteria set N. In one embodiment, each threshold in the original prediction criteria set N is modified by an incremental value, to make the prediction criteria set more accurate.

In another embodiment, conditions represented in the original prediction criteria set N are compared to the conditions that are present just prior to a disordered breathing occurrence to determine how the modification for the possible prediction criteria set should be implemented. For example, if the level of a particular condition just prior to the occurrence shows a relatively large variation just prior to the disordered breathing episode, but the levels of other conditions remain constant, then only the changing level may be modified in the possible prediction criteria set.

Each time the possible prediction criteria set is satisfied, no prediction of disordered breathing is made, however, the accuracy of the possible prediction criteria set is updated, for example, using an equation similar in form to Equation 2. If the accuracy of the possible prediction criteria set reaches a selected level, for example, 0.7, and the accuracy original prediction criteria set N remains below 0.7, the possible prediction criteria set may replace the original prediction criteria set N in the prediction criteria library.

According to various embodiments, new prediction criteria sets may be added to the prediction criteria library. In accordance with these embodiments, if a disordered breathing episode occurs without prediction, the levels of the detected patient conditions prior to the disordered breathing episode are saved as a possible prediction criteria set. Each time the possible prediction criteria set is satisfied, no prediction of disordered breathing is made, however, the accuracy of the possible prediction criteria set is updated, for example, using an equation similar in form to Equation 2. If the accuracy of the possible prediction criteria set reaches a selected level, for example, 0.7, the possible prediction criteria set may be added to the prediction criteria library.

The system may also be adjusted to provide increasingly sensitive disordered breathing prediction criteria sets, according to various embodiments. The estimated sensitivity for a prediction criteria set N may be expressed as:

$$Sensitivity_N = \frac{TP}{TP + FN} \quad [3]$$

where TP (true positive) is the number of times the prediction criteria successfully predicted disordered breathing, and FN (false negative) is the number of times the prediction criteria erroneously predicted that disordered breathing would not occur.

In one embodiment, if the prediction criteria accuracy for the prediction criteria set N becomes larger than a selected number, for example, 0.9, then the threshold levels of one or more of the conditions represented in the prediction criteria set N may be adjusted to provide enhanced sensitivity.

In one example, the threshold level of each condition represented in the prediction criteria set N is modified by an incremental value, thus making the prediction criteria set N more sensitive. In another embodiment, conditions represented in the prediction criteria set N are compared to the conditions that are present just prior to a disordered breathing occurrence to determine how the modification of the prediction criteria set N should be implemented. In yet another embodiment, a condition threshold level that is modified is based upon the relative importance of the condition in the overall prediction criteria. In another example, if the level of a particular condition is changing just prior to the occurrence of the disordered breathing episode, but the levels of other conditions remain constant, only the changing condition may be modified.

Following adjustment by any of the processes described above, the adjusted prediction criteria set may be designated as a possible prediction criteria set. Each time the possible prediction criteria set is satisfied, no prediction of disordered breathing is made, however, the accuracy of the possible prediction criteria set is updated, for example, using Equation 2 or 3. If the accuracy of a possible prediction criteria set reaches a selected level, for example, 0.7, the possible prediction criteria set may be added to the prediction criteria library.

The system may also be adjusted to provide improved specificity or a negative predictive value (NPV) of disordered breathing prediction criteria in a manner similar to the adaptive method described previously. Calculation of specificity and NPV for a prediction criteria N may be accomplished using equations 4 and 5 below.

$$Specificity_N = \frac{TN}{TN + FP} \quad [4]$$

$$NPV_N = \frac{TN}{TN + FN} \quad [5]$$

where TN (true negative) is the number of times the prediction criteria successfully predicted the absence of disordered breathing, FP (false positive) is the number of times the prediction criteria erroneously predicted disordered breathing and FN (false negative) is the number of times the prediction criteria erroneously predicted the absence of disordered breathing.

Figure 20:
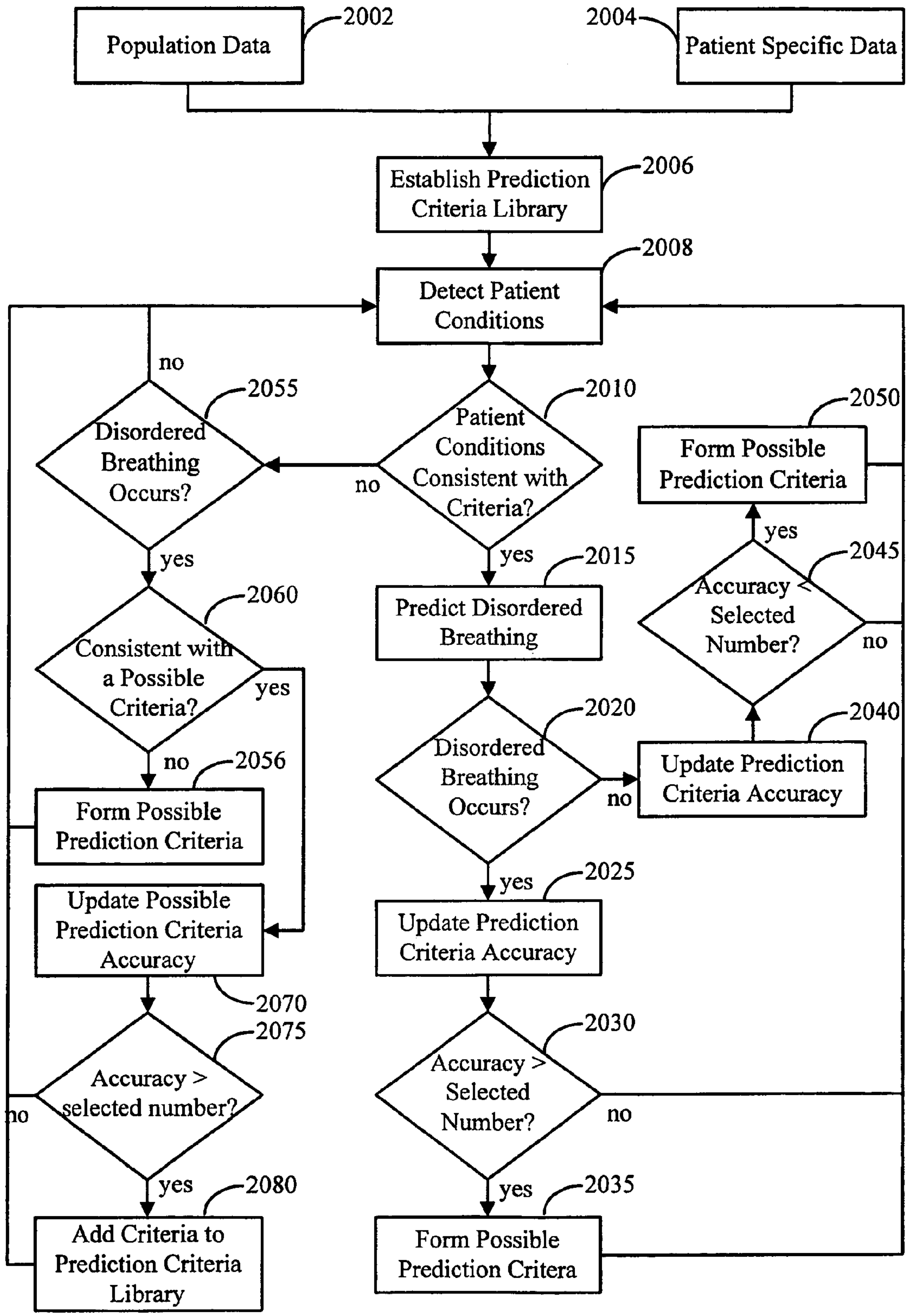
FIG. 20 is a flowchart illustrating a method for establishing and updating the prediction criteria library according to embodiments of the invention.

The flowchart of FIG. 20 illustrates a method for establishing and updating the prediction criteria library according to embodiments of the invention. Previous observations of disordered breathing may be assimilated from population data 2002 or from past observation of the specific patient 2004. One or more prediction criteria sets are determined and organized in a prediction criteria library 2006.

Conditions associated with disordered breathing are periodically detected 2008 and compared to the prediction criteria sets in the prediction criteria library. If the conditions are consistent 2010 with any of the prediction criteria sets in the library, then disordered breathing is predicted 2015. Within a selected time window following the disordered breathing prediction, the system determines if disordered breathing occurs 2020.

One illustrative approach to detecting disordered breathing involves monitoring a respiratory waveform output, for example, using a transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume fall below about 50% of the recent average tidal volume or other baseline tidal volume. When the patient's tidal volume falls further to an apnea threshold, e.g., about 10% of the recent average tidal volume, an apnea event is declared.

If disordered breathing occurs 2020, the prediction criteria accuracy of the prediction criteria set used for the disordered breathing prediction is updated 2025. If the updated prediction criteria accuracy is greater 2030 than a selected number, then a possible prediction criteria set is formed 2035. The possible prediction criteria set may be formed, for example, by substituting more sensitive condition levels when compared to the original prediction criteria set.

If disordered breathing is not detected 2020 following the prediction, then the prediction criteria set accuracy is updated 2040. If the prediction criteria set accuracy decreases 2045 below a selected number, then a possible prediction criteria set 2050 is formed. The possible prediction criteria set may be formed, for example, by substituting more stringent condition levels to produce a more accurate prediction.

If the detected patient conditions are not consistent 2010 with any of the prediction criteria sets in the prediction criteria library, disordered breathing is not predicted. Within a time window following the disordered breathing prediction, the system determines if disordered breathing occurs 2055. If disordered breathing occurs 2055, then the system checks to see if the patient conditions are consistent 2060 with any of the possible prediction criteria sets. If the patient conditions are not consistent 2060 with any of the possible prediction criteria sets, a possible prediction criteria set is formed 2056.

If the patient conditions are consistent 2060 with a possible criteria set, the possible prediction criteria set accuracy is updated 2070. If the possible prediction criteria accuracy increases beyond a selected number 2075, the possible prediction criteria set is added 2080 to the prediction criteria library.

Adaptation of Therapy

Aspects of the invention are directed to methods and systems configured to monitor, diagnose, and/or provide patient therapy using one or more individual medical procedures including adaptation of therapy based on therapy effectiveness and/or other factors. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that include adaptation of therapy are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

One embodiment of the invention involves an individual system 59 (FIG. 1B) that is configured to adapt therapy based on therapy effectiveness and/or other factors. Adaptation of therapy may be implemented in a stand alone system or in a combination of individual medical systems, such as those described in FIGS. 1B-1D.

Various embodiments of the invention involve methods and systems for providing an adaptive therapy for disordered breathing. In accordance with an embodiment of the invention, an automated method for providing disordered breathing therapy involves detecting disordered breathing and adapting a cardiac electrical therapy to mitigate the disordered breathing. The adapted therapy is delivered to the patient. At least one of detecting the disordered breathing, adapting the therapy to mitigate the disordered breathing, and delivering the therapy is performed at least in part implantably.

In accordance with a further embodiment of the invention, an automated method of providing disordered breathing therapy involves detecting disordered breathing and delivering a cardiac electrical therapy to mitigate the disordered breathing. The effectiveness of the therapy is assessed and therapy is adapted to enhance therapy efficacy. At least one of detecting the disordered breathing, delivering the therapy, evaluating the therapy, and adapting the therapy to enhance effectiveness, is performed at least in part implantably.

In accordance with yet another embodiment of the invention, an automated method for providing disordered breathing involves detecting disordered breathing and adapting a cardiac electrical therapy to mitigate the disordered breathing while adjusting an impact of the therapy on the patient. At least one of detecting the disordered breathing and adapting the therapy to mitigate the disordered breathing is performed at least in part implantably.

Yet another embodiment of the invention includes an automated medical device for providing disordered breathing therapy. The medical device includes a detector system configured to detect patient conditions. A disordered breathing detection system is coupled to the detector system and is configured to detect disordered breathing. A therapy control module is coupled to the disordered breathing detector system and is configured to adapt a cardiac electrical therapy to mitigate the disordered breathing. A therapy delivery system, coupled to the therapy control module, is configured to deliver the adapted therapy to the patient. At least one of the detector system, the disordered breathing detection system, the therapy control module, and the therapy delivery system includes an implantable component.

A further embodiment of the invention involves a disordered breathing therapy system. The system includes means for detecting disordered breathing and means for adapting a cardiac electrical therapy to mitigate the disordered breathing. The system further includes means for delivering the adapted therapy to the patient. At least one of the means for detecting disordered breathing, means for adapting a therapy to mitigate the disordered breathing, and means for delivering the adapted therapy includes an implantable component.

Another embodiment of the invention involves a system for providing therapy for disordered breathing. The system includes means for detecting disordered breathing and means for delivering a cardiac electrical therapy to the patient to mitigate the disordered breathing. The system further includes means for evaluating the effectiveness of the therapy and means for adapting the therapy to enhance the effectiveness of the therapy. At least one of the means for detecting the disordered breathing, the means for delivering the disordered breathing, the means for evaluating the effectiveness of the disordered breathing, and the means for adapting the disordered breathing to enhance effectiveness includes an implantable component.

Yet another embodiment of the invention includes means for detecting disordered breathing in a patient and means for adapting a cardiac electrical therapy to mitigate the disordered breathing while adjusting an impact of the therapy on the patient. The adapted therapy is delivered to the patient. At least one of the means for detecting the disordered breathing, the means for adapting a therapy to mitigate the disordered breathing, and the means for delivering the adapted therapy to the patient includes an implantable component.

Other embodiments of the invention are directed to methods and systems for adjusting cardiac pacing rate for disordered breathing therapy. Cardiac intervals between cardiac beats are obtained. A first indicated pacing interval is determined based at least on a cardiac interval duration and a previous value of the first indicated pacing interval. Cardiac pacing to mitigate disordered breathing is provided based on the first indicated pacing interval.

Another embodiment of the invention involves a system for delivering disordered breathing therapy including adaptive adjustment of pacing rate. The system includes a sensing circuit configured to sense cardiac beats. A controller is coupled to the sensing circuit. The controller is configured to determine a first indicated pacing interval based at least on a cardiac interval duration and a previous value of the first indicated pacing interval. A cardiac pacing circuit coupled to the controller is configured to provide cardiac pacing to mitigate disordered breathing based on the first indicated pacing interval.

Other embodiments of the invention involve a coordinated system for providing adaptive therapy. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy. Systems and methods directed to adaptive therapy for disordered breathing may be implemented to include selected features, functions, and/or structures described in commonly owned, U.S. Pat. No. 7,720,541, which is hereby incorporated herein by reference.

A disordered breathing therapy system may include a therapy assessment processor for assessing various parameters of the therapy. The therapy assessment processor may receive input from one or more of the patient-internal sensors patient-external sensors and/or other input devices capable of sensing conditions affecting the patient. The therapy assessment processor may also receive information from one or more of the cardiac arrhythmia detector sleep quality monitor sleep detector and/or disordered breathing detector/predictor. The therapy assessment processor may use the information acquired from one or more of these sources to adapt the therapy to achieve a therapeutic goal, for example, to adapt the therapy to achieve a level of effectiveness.

In one implementation, a therapeutic goal may involve terminating detected disordered breathing episodes and the disordered breathing therapy may be adapted to achieve this goal. Additionally, or alternatively, a therapeutic goal may involve terminating a disordered breathing episode and preventing further disordered breathing. In this example situation, the therapy regimen may be adapted to provide a first therapy to terminate the disordered breathing episode and provide a second preventative therapy to reduce or eliminate further disordered breathing episodes. The second preventative therapy may be adapted to reduce episodes of disordered breathing below a predetermined disordered breathing episode threshold. A disordered breathing episode threshold may be expressed, for example, in terms of an apnea/hypopnea index (AHI) or percent time in periodic breathing (% PB).

Figure 21:
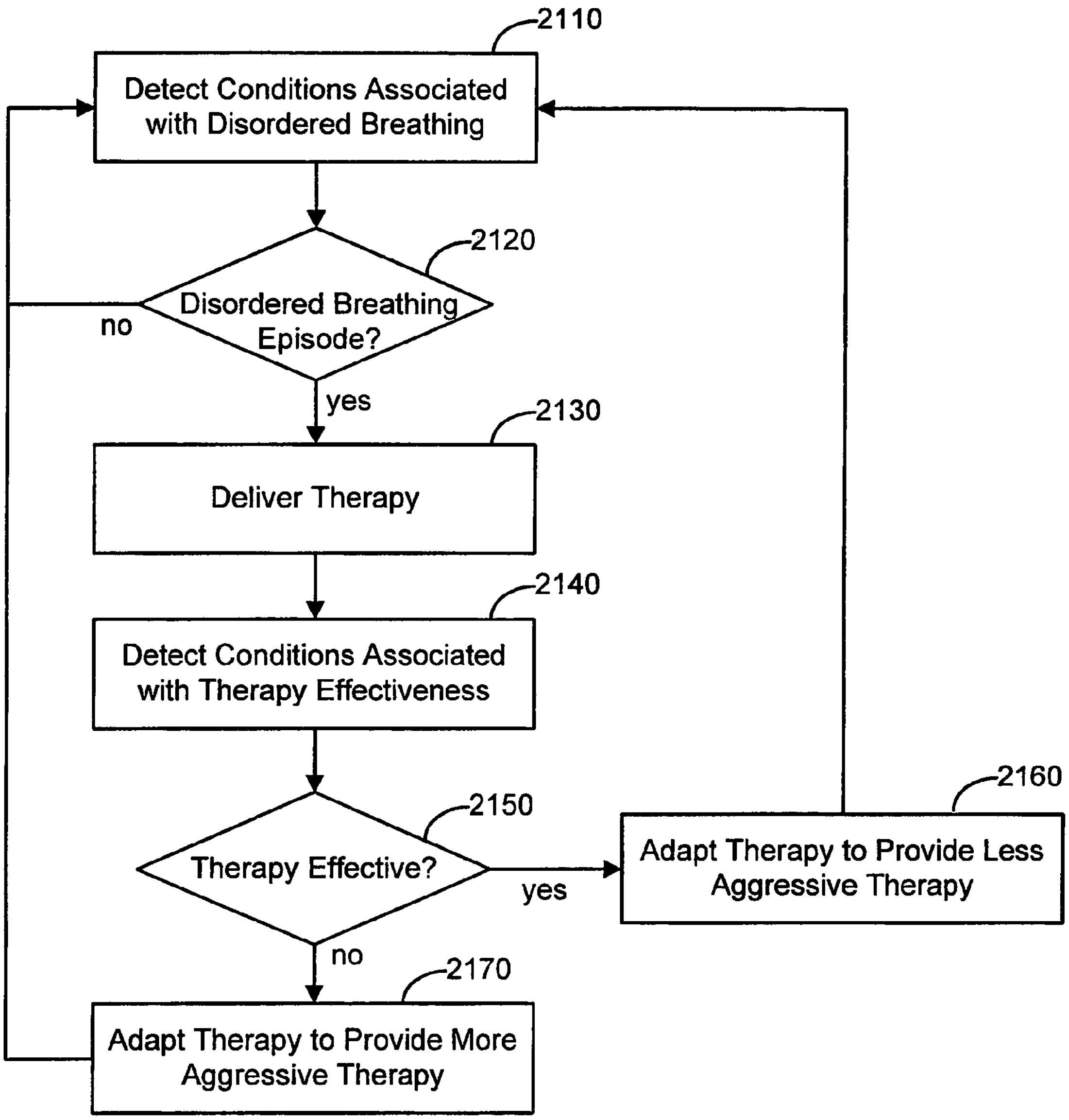
FIG. 21 is a flowchart illustrating a method of adapting a disordered breathing therapy according to embodiments of the invention.

FIG. 21 is a flowchart illustrating a method of adapting a disordered breathing therapy according to embodiments of the invention. The flowchart of FIG. 21 illustrates a method of adapting disordered breathing therapy to achieve a desired level of therapy efficacy. In this embodiment, a first set of conditions associated with disordered breathing is detected 2110 and used to determine if a disordered breathing episode is occurring. If disordered breathing is detected 2120, disordered breathing therapy is delivered 2130 to the patient to mitigate the disordered breathing. In one embodiment, the therapy delivered to the patient may include, for example, cardiac pacing at a rate in excess of an intrinsic rate, or in excess of a normally programmed rate, such as a normally programmed sleep rate.

Adapting the cardiac electrical therapy may also involve modifying the electrical stimulation energy with or without an increase in the pacing rate. Increased stimulation energy has been shown to produce higher cardiac contractility, which may be particularly beneficial for patients suffering from chronic heart failure. Loss of cardiac contractility is thought to initiate and drive the progression of heart failure, a disorder that is intertwined with Cheyne-Stokes respiration.

Further, adapting a cardiac electrical therapy to mitigate disordered breathing may involve adapting a therapy involving non-excitatory electrical stimulation of one or more heart chambers, e.g., the left and/or right ventricles, or other cardiac sites. Non-excitatory electrical stimulation may be delivered during absolute refractory periods of the cardiac tissue, for example, to improve cardiac contractility. The non-excitatory stimulation therapy may be used alone or in combination with the pacing to provide a comprehensive therapy regimen for patients with CHF and disordered breathing such as Cheyne-Stokes respiration.

In other embodiments, adapting the cardiac electrical therapy to mitigate disordered breathing may involve initiating a particular pacing regimen or switching from one pacing mode to another pacing mode. In one example, the cardiac pacing regimen may be switched from a dual-chamber pacing mode to a bi-ventricular or other resynchronization mode. In other examples, the pacing mode may be switched to a pacing mode that promotes atrial pacing, or promotes consistent ventricular pacing. In yet another example, the cardiac electrical therapy may involve initiating multi-site electrical stimulation to the heart or changing from one electrical stimulation site to another. The pacing mode may be switched from single chamber to multiple chambers, or the reverse. For example, a bi-ventricular mode may be switched to a left ventricular mode only. Alternatively, a single chamber mode, e.g., LV or RV, may be switched to a bi-ventricular mode. Other therapy regimens, involving various pacing modes, pacing sites, or non-excitatory electrical stimulations, are possible in connection with providing cardiac electrical therapy for disordered breathing. The type of cardiac electrical therapy beneficial to a patient is highly patient specific and may be determined based on the responses of a particular patient.

A second set of conditions associated with therapy effectiveness is sensed 2140 and used to assess the effectiveness of the therapy. The detected conditions used to assess the efficacy of the therapy and adapt the therapy to mitigate disordered breathing may represent one or more of the acute conditions associated with disordered breathing, e.g., detected episodes of interrupted breathing, hypoxia, arousals, negative intrathoracic pressure, blood pressure, and heart rate or blood pressure surges.

Additionally, or alternatively, the conditions used to assess therapy efficacy and adapt the cardiac electrical therapy may include one or more chronic conditions associated with disordered breathing, including, for example, decreased heart rate variability, increased blood pressure, chronic changes in sympathetic nerve activity, and changes in blood chemistry, such as increased levels of $PaCO_2$ and norepinephrine levels, among others.

In general, a therapeutic goal in the treatment of disordered breathing is to provide the least aggressive therapy that effectively mitigates, terminates or prevents the patient's disordered breathing or achieves a particular therapeutic goal associated with disordered breathing therapy. The disordered breathing therapy regimen may be enhanced by increasing the intensity or level of therapy to more effectively mitigate the disordered breathing. Alternatively, the disordered breathing therapy regimen may be enhanced by reducing the intensity or level of therapy while maintaining a desired decrease in the severity or frequency of disordered breathing episodes, thus reducing undesirable side effects from the therapy and extending the device lifetime.

If the therapy effectiveness is acceptable 2150, e.g., terminates or reduces the patient's disordered breathing or meets some other desired goal, then the therapy may be adapted 2160 to provide a less aggressive therapy, e.g., decreased pacing rate, decreased pacing energy, or altered pacing mode, as described above. If the therapy is not effective 2150, then the therapy may be adapted 2170 to enhance therapy efficacy by providing a more aggressive therapy, e.g., increased pacing rate, increased pacing energy, or pacing mode switch.

In one embodiment, therapy may be determined to be ineffective if disordered breathing continues unmitigated following therapy delivery. In this situation, the therapy may be adapted to provide a more aggressive therapy, for example, cardiac pacing at a higher rate. In another embodiment, if the disordered breathing decreases sufficiently in severity, or is otherwise sufficiently mitigated, the therapy may be enhanced by adapting the therapy to provide a less aggressive therapy, e.g., pacing at a lower rate or a decreased energy level. As previously discussed, a less aggressive therapy is preferable to reduce the risk of arousal, to avoid unnecessary stress on the patient's heart, and to prolong battery life, for example.

Figure 22:
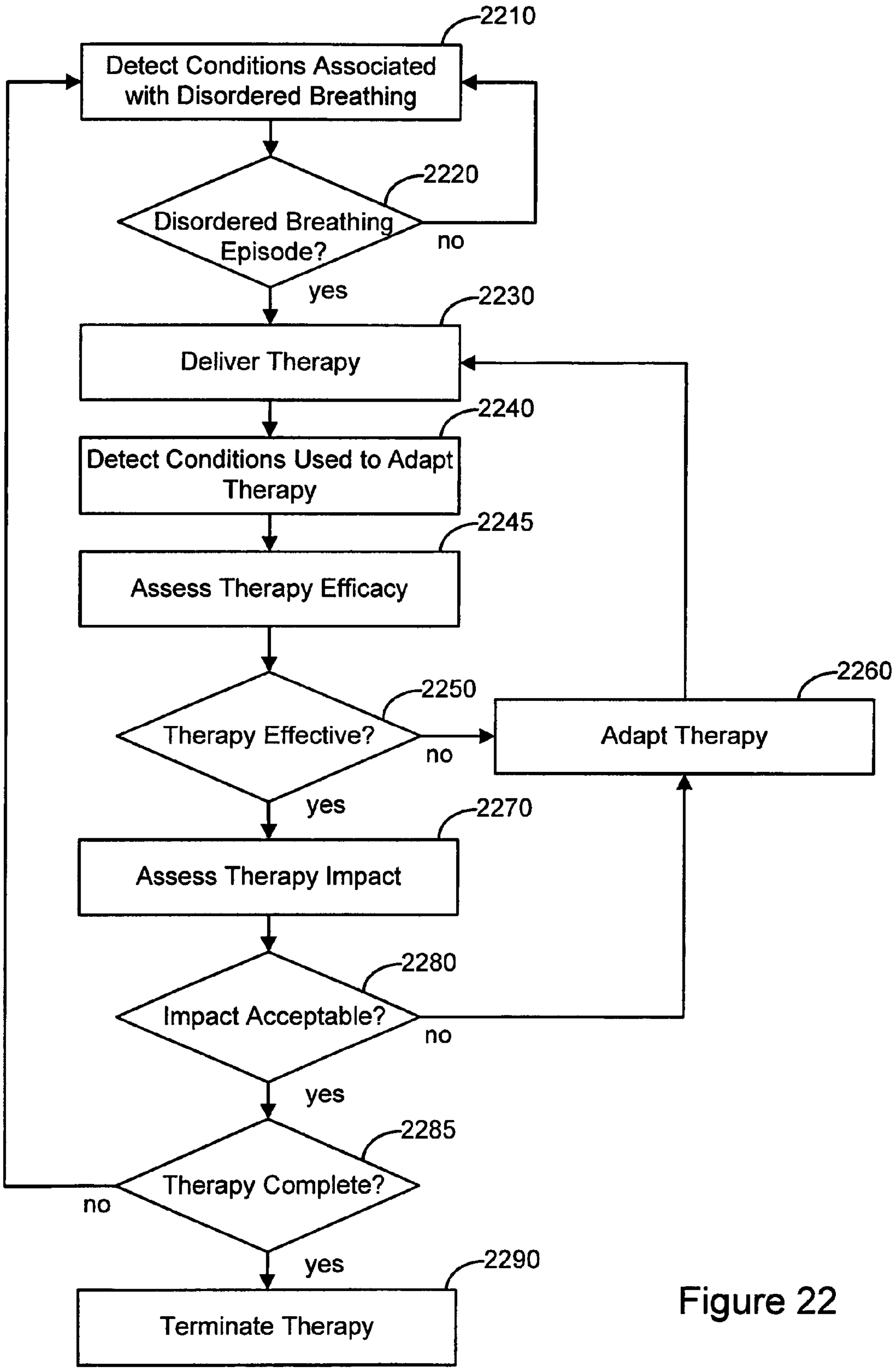
FIG. 22 is a flowchart illustrating a method of adapting a disordered breathing therapy taking into account both therapy effectiveness and therapy impact in accordance with embodiments of the invention.

The flowchart of FIG. 22 illustrates a method of adapting a disordered breathing therapy taking into account both therapy effectiveness and therapy impact in accordance with embodiments of the invention. In this example, a first set of conditions indicative of disordered breathing are sensed 2210 and used to determine if a disordered breathing episode is occurring. If disordered breathing is detected 2220, therapy is delivered 2230 to the patient to mitigate the disordered breathing.

A second set of conditions, possibly overlapping the first set, are sensed 2240 and used to adapt the therapy. Based on the second set of sensed conditions, therapy efficacy is assessed 2245. If the therapy efficacy is not acceptable 2250, then the therapy may be adapted 2260 to enhance therapy efficacy. If the therapy efficacy is acceptable 2250, then the impact of the therapy on the patient may be assessed 2270.

If the therapy impact on the patient is acceptable 2280, the system continues to deliver the therapy. When the therapy regimen is complete 2285, then therapy is terminated 2290.

If the therapy impact on the patient exceeds acceptable limits, the therapy impact is not acceptable 2280, and the therapy may be adapted 2260 to reduce the therapy impact. Various methods of assessing the impact of the therapy and determining if the therapy impact is acceptable are described herein.

The methods illustrated in the flow graphs of FIGS. 21 and 22 contemplate real-time monitoring of patient conditions allowing the therapy system to dynamically adjust the therapy regimen to accommodate the changing needs of the patient. In one configuration, the therapy may be adjusted during the period that therapy is delivered to the patient. In another configuration, the therapy may be adapted between disordered breathing episodes or from night-to-night based on assessment of the efficacy of therapy delivered in connection with one or more previously detected disordered breathing episodes.

Evaluation of the impact of disordered breathing therapy on the patient preferably takes into consideration the impact of disordered breathing therapy on the overall therapeutic goals for the patient, including cardiac pacing therapy goals and disordered breathing therapy goals. The disordered breathing therapy may involve a variety of therapy regimens implemented to achieve predetermined therapeutic goals. The effectiveness of the therapy, or the degree to which the therapy meets one or more therapeutic goals, may be assessed by detecting and analyzing episodes of disordered breathing that occur during therapy delivery, or during other periods, including periods of wakefulness.

For example, a therapeutic goal may involve terminating a disordered breathing episode and the disordered breathing therapy may be adapted to achieve this goal. Additionally, or alternatively, a therapeutic goal may involve terminating a disordered breathing episode and preventing further disordered breathing. In this example situation, the therapy regimen may be adapted to provide a first therapy to terminate the disordered breathing episode and provide a second preventative therapy to reduce or eliminate further disordered breathing episodes. The second preventative therapy may be adapted to reduce episodes of disordered breathing below a predetermined disordered breathing episode threshold. A disordered breathing episode threshold may be expressed, for example, in terms of an apnea/hypopnea index (AHI) or percent time in periodic breathing (% PB).

Sleep Quality Monitoring

Aspects of the invention that include sleep quality monitoring are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving sleep quality monitoring are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 58 (FIG. 1D) for monitoring sleep quality. The sleep quality monitor 58 may be implemented as a stand alone system or in combination with other individual medical systems, such as those described in FIGS. 1B-1D.

Various embodiments of present invention involve methods and systems for collecting sleep quality data and evaluating the sleep quality of a patient. An embodiment of the invention involves a method for collecting sleep quality data. The method includes detecting physiological and non-physiological conditions associated with the sleep quality of a patient and collecting sleep quality data based on the detected conditions. Collecting the sleep quality data may be performed at least in part implantably.

Another embodiment of the invention involves a method for evaluating sleep quality. In accordance with this method, one or more metrics associated with sleep are determined. One or more metrics associated with events that disrupt sleep are determined. A composite sleep quality metric is determined using the one or more metrics associated with sleep and the one or more metrics associated with events that disrupt sleep.

In yet another embodiment of the invention, a method for evaluating sleep quality includes detecting physiological and non-physiological conditions associated with the sleep quality of a patient and collecting sleep quality data based on the detected conditions. The sleep quality of the patient is evaluated using the collected data. At least one of collecting the sleep quality data and evaluating the sleep quality of the patient is performed at least in part implantably.

Another embodiment of the invention involves a method for evaluating sleep quality. One or more conditions associated with sleep quality of a patient are detected during a period of wakefulness. Sleep quality data is collected based on the detected conditions. The patient's sleep quality is evaluated using the collected sleep quality data. At least one of collecting the data and evaluating the sleep quality is performed at least in part implantably.

A further embodiment of the invention involves a medical device including a detector system configured to detect physiological and non-physiological conditions associated with sleep quality and a data collection system for collecting sleep quality data based on the detected conditions. The data collection system includes an implantable component.

Yet another embodiment of the invention relates to a medical device configured to evaluate sleep quality. The medical device includes a detector system configured to detect physiological and non-physiological conditions associated with the sleep quality of a patient. A sleep quality processor, coupled to the detection system, is configured to determine metrics based on the detected conditions. The metrics include one or more metrics associated with sleep, one or more metrics associated with events that disrupt sleep, and at least one composite sleep quality metric based on the one or more metrics associated with sleep and the one or more metrics associated with events that disrupt sleep.

In another embodiment of the invention, a medical device for assessing sleep quality includes a detector unit configured to detect physiological and non-physiological conditions associated with sleep quality and a sleep quality data collection unit configured to collect sleep quality data based on the detected conditions. A data analysis unit coupled to the data collection unit evaluates sleep quality based on the collected sleep quality data. At least one of the data collection unit and the data analysis unit includes an implantable component.

A further embodiment of the invention involves a system for collecting sleep quality data. The system includes means for detecting physiological and non-physiological conditions associated with sleep quality and means for collecting sleep quality data based on the detected conditions. The means for collecting the sleep quality data includes an implantable component.

Another embodiment of the invention involves a system for providing coordinated patient monitoring, diagnosis and/or therapy that utilizes sleep quality data. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a system 58 configured to collect and/or evaluate sleep quality data. The sleep quality collection and/or evaluation system comprises a detector system configured to detect physiological and non-physiological conditions associated with sleep quality of a patient. A data collection system is coupled to the detector system and is configured to collect sleep quality data based on the detected conditions. A data analysis system is coupled to the data collection system and is configured to evaluate the sleep quality using the collected sleep quality data, wherein at least one of the data collection system and the data analysis system includes an implantable component. The implantable device and the patient external respiratory device are configured to work in cooperation to collect and/or use the sleep quality data. Systems and methods directed to sleep quality data collection and evaluation may be implemented to include selected features, functions, and/or structures described in commonly owned, co-pending U.S. Publication No. 2005/0042589, which is hereby incorporated herein by reference.

Superficially, sleep may viewed as a monolithic event that is characterized by a period of unconsciousness. If examined in greater detail, sleep periods may be described as involving a series of events or stages. For example, sleep is typically divided into various stages of sleep, including rapid eye movement (REM) sleep and non-REM (NREM) sleep. Non-REM sleep may be further subdivided into stage 1, stage 2 and stage 3 non-REM sleep, for example.

In accordance with various embodiments of the invention, conditions related to sleep quality, e.g., sleep fragmentation and/or other arousal-based measures, patient-reported restful sleep, and patient-reported discomfort during therapy delivered during sleep, among other sleep quality factors, may be used to assess the impact of the therapy on the patient. A therapy assessment processor may assess therapy impact based on sleep quality using information acquired by a sleep quality monitor. For example, if a patient is receiving effective disordered breathing therapy and has low sleep fragmentation, reports restful sleep with no discomfort, the therapy effectiveness may be relatively high and the adverse effects of the therapy on the patient may be relatively low. If sleep fragmentation unrelated to disordered breathing episodes is relatively high, or if the patient reports discomfort or feeling tired after sleeping, these conditions may indicate that the disordered breathing therapy is causing sleep disturbances and/or other undesirable effects.

Because disordered breathing generally occurs during sleep, it may be particularly important to assess sleep quality during disordered breathing therapy delivery. It is undesirable to provide therapy that eliminates the disordered breathing but increases sleep fragmentation. In such a situation, the disordered breathing therapy may exacerbate the adverse effects produced by the respiratory disturbances. Thus, it may be preferable to assess the impact of the therapy on the patient and adjust the therapy to improve sleep quality. Sleep fragmentation and sleep disruptions may also occur if disordered breathing therapy is ineffective and disordered breathing occurs during sleep. Therefore, a therapy impact assessment based on detected sleep quality and/or patient-reported restful sleep may preferably take into account an assessment of therapy effectiveness.

Sleep quality assessments depend upon acquiring sleep-related data, including the patient's typical sleep patterns and the physiological, environmental, contextual, emotional, and other conditions affecting the patient during sleep. Diagnosis of sleep disorders and assessment of sleep quality often involves the use of a polysomnographic sleep study at a dedicated sleep facility. However, such studies are costly, inconvenient to the patient, and may not accurately represent the patient's typical sleep behavior. In a polysomnographic sleep study, the patient is instrumented for data acquisition and observed by trained personnel. Sleep assessment in a laboratory setting presents a number of obstacles in acquiring an accurate picture of a patient's typical sleep patterns. For example, spending a night in a sleep laboratory typically causes a patient to experience a condition known as "first night syndrome," involving disrupted sleep during the first few nights in an unfamiliar location. In addition, sleeping while instrumented and observed may not result in a realistic perspective of the patient's normal sleep patterns.

Further, polysomnographic sleep studies provide an incomplete data set for the analysis of some sleep disorders, including, for example, sleep disordered breathing. A number of physiological conditions associated with sleep disordered breathing are detectable during periods of wakefulness, e.g., decreased heart rate variability, elevated sympathetic nerve activity, norepinephrine concentration, and increased blood pressure variability. Collection of data during periods of sleep and/or during periods of wakefulness may provide a more complete picture of the patient's sleep quality.

Various aspects of sleep quality, including number and severity of arousals, sleep disordered breathing episodes, nocturnal limb movements, and cardiac, respiratory, muscle, and nervous system functioning may provide important information for diagnosis and/or therapy delivery. An initial step to sleep quality evaluation is an accurate and reliable method for discriminating between periods of sleep and periods of wakefulness. Further, acquiring data regarding the patient's sleep states or stages, including sleep onset, termination, REM, and NREM sleep states, and arousal events, including autonomic arousals may be used in connection sleep quality assessment. For example, the most restful sleep occurs during stages 3 and 4 non-REM sleep. One indicator of sleep quality is the percentage of time a patient spends in these sleep stages. Knowledge of the patient's sleep patterns may be used to diagnose sleep disorders and/or adjust patient therapy, including, e.g., cardiac or respiratory therapy. Trending disordered breathing episodes, arousal episodes, and other sleep quality aspects may be helpful in determining and maintaining appropriate therapies for patients suffering from disorders ranging from snoring to chronic heart failure.

The present invention involves methods and systems for acquiring sleep quality data and using the sleep quality data to assess the effectiveness and/or impact of disordered breathing therapy delivered to the patient. Methods of the invention involve sensing conditions associated with the sleep quality of the patient including physiological and/or non-physiological conditions. Data related to the patient's sleep quality is collected based on the sensed conditions. Sensing for conditions affecting the patient and related to sleep quality may occur during periods of wakefulness and/or during periods of sleep. Sensing the conditions associated with sleep quality and/or collecting the sleep quality data may be performed using a device having a component that is at least in part implantable.

A representative set of the conditions associated with sleep quality is listed in Table 1. Patient conditions used to evaluate sleep quality may include, for example, both physiological and non-physiological (i.e., contextual) conditions.

Each of the conditions listed in Table 1 may serve a variety of purposes in evaluating sleep quality. For example, a subset of the conditions may be used to detect whether the patient is asleep and to track the various stages of sleep and arousal incidents. Another subset of the conditions may be used to detect disordered breathing episodes. Yet another subset may be used to detect abnormal limb movements. In one implementation, some or all of the listed conditions may be collected over a relatively long period of time and used to analyze long term sleep quality trends. Trending may be used in connection with an overall assessment of sleep quality and diagnosis and treatment of sleep-disordered breathing, movement disorders, and/or other sleep disorders.

Table 5 provides examples of how some physiological and non-physiological conditions may be used in connection with sleep quality assessment.

TABLE 5

| Condition Type | Condition | Examples of how condition is used in sleep quality assessment |
|---|---|---|
| Physiological | Heart rate | Decrease in heart rate may indicate disordered breathing episode.<br>Decrease in heart rate may indicate the patient is asleep. |
| | Heart rate variability | May be used to determine sleep state.<br>Changes in heart rate variability, detected during periods of sleep or wakefulness, may indicate that the patient suffers from sleep disordered breathing. |
| | QT interval | May be used to detect sleep apnea. |
| | Ventricular filling pressure | May be used to identify/predict pulmonary congestion associated with respiratory disturbance. |
| | Blood pressure | Variation in blood pressure is associated with apnea. |
| | Snoring | Associated with a higher incidence of obstructive sleep apnea and may be used to detect disordered breathing. |
| | Respiration pattern | May be used to detect disordered breathing episodes.<br>May be used to determine the type of disordered breathing.<br>May be used to detect sleep. |
| | Patency of upper airway | Related to obstructive sleep apnea and may be used to detect episodes of obstructive sleep apnea. |
| | Pulmonary congestion | Associated with respiratory disturbances. |
| | Sympathetic nerve activity (SNA) | Apnea termination is associated with a spike in SNA.<br>SNA activity may be elevated during periods of wakefulness if the patient experiences sleep disordered breathing. |
| | Electroencephalogram (EEG) | May be used to determine sleep stages, including REM and NREM sleep stages |
| | CO2 saturation | Low CO2 levels may indicate initiation of central apnea. |
| | O2 saturation | O2 desaturation occurs during severe apnea/hypopnea episodes. |
| | Blood alcohol content | Alcohol tends to increase the incidence of snoring & obstructive apnea. |
| | Adrenalin | End of apnea associated with a spike in blood adrenaline. |
| | Brain Natriuretic Peptide (BNP) | A marker of heart failure status, which is associated with Cheyne-Stokes Respiration. |
| | C-Reactive Protein | A measure of inflammation that may be related to apnea. |
| | Drug/Medication/ Tobacco use | These substances may affect incidence of both central & obstructive apnea. |
| | Muscle atonia | Muscle atonia may be used in connection with detection of REM and non-REM sleep. |
| | Eye movement | Eye movement may be used in connection with detection of REM and non-REM sleep. |
| | Activity | May be used to detect sleep and patient well being. |
| | Limb movements | May be used to detect abnormal limb movements during sleep. |
| Non-physiological | Ambient Temperature | Ambient temperature may predispose the patient to episodes of disordered breathing during sleep. |
| | Humidity | Humidity may predispose the patient to episodes of disordered breathing during sleep. |
| | Pollution | Pollution may predispose the patient to episodes of disordered breathing during sleep. |
| | Posture | Posture may be used to determine if the patient is asleep.<br>Posture may predispose the patient to disordered breathing. |
| | Time | Used to establish historical sleep time. |
| | Ambient noise level | Noise level may affect sleep quality. |
| | Location | Patient location may used to determine if the patient is in bed as a part of sleep detection. |
| | Altitude | Altitude may predispose the patient to episodes of disordered breathing and may affect sleep quality. |
| | Barometric Pressure | Barometric pressure may predispose the patient to episodes of disordered breathing. |
| | Proximity to bed | May be used to determine if patient is in bed. |
| | Historical sleep time | May be used in connection with sleep detection. |
| | Medical history | History of medical disorders, e.g., CHF, that are associated with disordered breathing such as Cheyne-Stokes respiration. |
| | Age | Age is associated with increased risk of disordered breathing, RLS and other sleep disruptive disorders. |
| | Weight | Associated with sleep disordered breathing, e.g., obstructive sleep apnea. |
| | Gender | |
| | Obesity | |
| | Neck size | |
| | Patient reported drug, alcohol, nicotine use | Patient drug, alcohol and nicotine use may affect sleep quality. |
| | Psychological history | Psychological factors, e.g., clinical depression may be associated with insomnia. |
| | Emotional state | Emotional state, e.g., stress, anxiety, euphoria, may affect sleep quality. |

TABLE 5-continued

| Condition Type | Condition | Examples of how condition is used in sleep quality assessment |
|---|---|---|
| | Daytime sleepiness Patient perceptions of sleep quality | May be used to evaluate sleep quality. |

Figure 23:
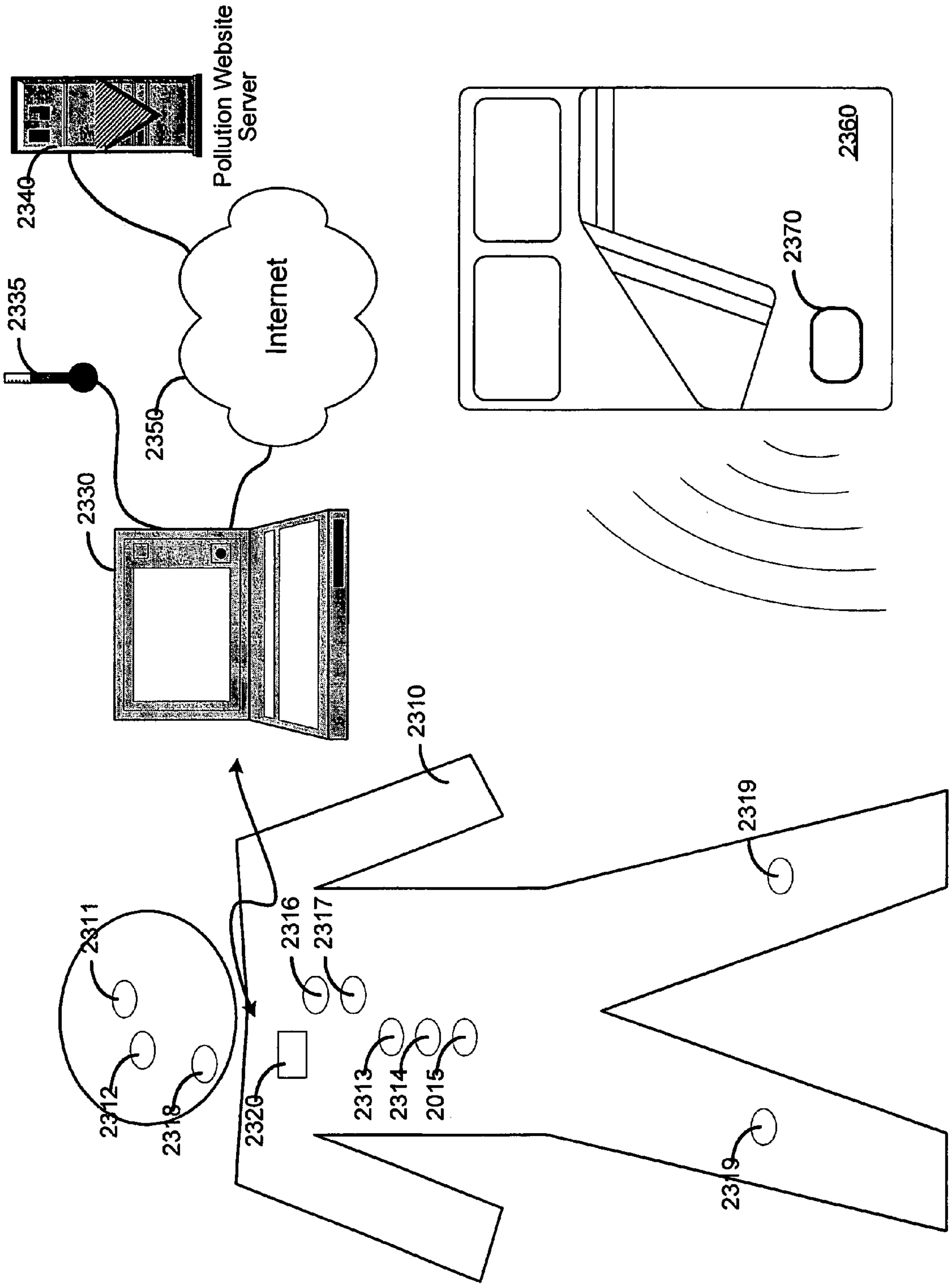
FIG. 23 illustrates a patient instrumented with a sleep quality monitor according to embodiments of the invention.

FIG. 23 illustrates a patient 2310 instrumented with a sleep quality monitor according to embodiments of the invention. The sleep quality monitor 2320 collects sleep quality data from the patient using a number of sensors 2311-2319. In one configuration, the collected data is analyzed by a therapy assessment processor that may be an integrated component of an implantable disordered breathing therapy system. The collected sleep quality data may be downloaded to a patient-external device 2330 for storage, analysis, or display.

In the implementation illustrated in FIG. 23, the implantable sleep quality monitor 2320 is coupled to a number of sensors 2311-2319. In this example, the sensors include an EGM sensor 2316 for detecting heart rate and heart rate variability conditions. A transthoracic impedance sensor 2317 is used to detect the respiration conditions of the patient, including, for example, minute ventilation, respiration rate, and tidal volume. An activity detector, e.g., accelerometer, 2315 may be used to detect patient activity conditions. The sleep quality monitor 2320 senses patient conditions including the patient's posture and location using a posture sensor 2314 and a proximity to bed sensor 2313, respectively. The sleep quality monitor 2320 senses the patient's brain activity using EEG sensors 2311 and the patient's eye movements using EOG sensors 2312. Jaw and limb movements are sensed using accelerometers attached to the patient's jaw 2318 and legs 2319.

In this application, the sleep quality monitor 2320 is configured to track the patient's heart rate, heart rate variability, minute ventilation, respiration rate, tidal volume, posture, proximity to bed, brain activity, eye movements, jaw movements and leg movements. At periodic intervals, the sleep quality monitor 2320 samples signals from the sensors and stores data regarding the detected conditions in memory circuitry within the sleep quality monitor 2320. The sleep quality monitor 2320 may additionally access an external input unit 2330 to detect patient reported conditions, for example, recent tobacco and medication use by the patient. Further, the sleep quality data monitor 2320 may monitor conditions using one or more external sensors. In the illustrated example, a thermometer 2335 is coupled through the external programmer 2330 and a pollution website 2340 is accessible to the sleep quality monitor 2320 through the internet 2350.

The sleep quality monitor 2320 may operate to acquire data during periods of both sleep and wakefulness. It may be beneficial, for example, to track changes in particular conditions measured during periods of wakefulness that are associated with sleep disordered breathing. For example, some patients who suffer from sleep apnea experience changes in heart rate variability, blood pressure variability, and/or sympathetic nerve activity during periods of wakefulness. Detection and analysis of the physiological changes attributable to sleep disorders and measurable during the time the patient is awake provides a more complete picture of sleep quality.

In another example, the patient's sleep quality may be evaluated by determining the patient's activity level while the patient is awake. The activity level of the patient during the day may provide important information regarding the patient's sleep quality. For example, if the patient is very inactive during periods of wakefulness, this may indicate that the patient's sleep is of inadequate quality or duration. Such information may also be used in connection with assessing the efficacy of a particular sleep disorder therapy and/or adjusting the patient's sleep disorder therapy. Patient activity information may be sensed for example, for example, using an accelerometer and/or transthoracic impedance sensor disposed within or on an implantable device. Collection of patient activity information may be performed over a period of time. Assessment of the patient activity data may indicate changes in the patient's well-being as indicated by a drop in activity level.

In another example, the patient's sleep quality may be evaluated by determining the patient's activity level while the patient is awake. The activity level of the patient during the day may provide important information regarding the patient's sleep quality. For example, if the patient is very inactive during periods of wakefulness, this may indicate that the patient's sleep is of inadequate quality or duration. Such information may also be used in connection with assessing the efficacy of a particular sleep disorder therapy and/or adjusting the patient's sleep disorder therapy. Methods and systems for determining the patient's activity level and generally assessing the well-being of a patient are described in commonly owned U.S. Pat. No. 6,021,351 which is incorporated herein by reference.

The sleep quality monitor 2320 may calculate one or more sleep quality metrics quantifying the patient's sleep quality. A representative set of the sleep quality metrics include, for example, sleep efficiency, sleep fragmentation, number of arousals per hour, denoted the arousal index (AI).

The sleep quality monitor 2320 may also compute one or more metrics quantifying the patient's disordered breathing, such as the apnea hypopnea index (AHI) providing the number of apneas and hypopneas per hour, and the percent time in periodic breathing (% PB).

Further, metrics associated with sleep movement disorders may also be determined by the sleep quality monitor 2320. Such metrics may include, for example, a general sleep movement disorder index (MDI) representing the number of abnormal movements arising from movement disorders such as restless leg syndrome, periodic limb movement disorder and bruxism per hour. In addition, specific indices may be calculated for each type of movement disorder, e.g., a bruxism index (BI) characterizing the number of jaw movements per hour, a RLS index (RLSI) characterizing the number of restless leg syndrome episodes per hour, and a PLM index (PLMI) characterizing the number of periodic limb movements experienced by the patient per hour.

In addition, percentage of sleep time during which the patient experiences movement disorders (% MD) may be calculated. Specific metrics relating to the percentage of time during which the patient experiences bruxism (% B), restless leg syndrome (% RLS), and periodic leg movement disorder (% PLMD) may also be determined.

Further, sleep summary metrics may be computed, either directly from the collected patient condition data, or by combining the above-listed sleep quality and sleep disorder metrics. In one embodiment, a composite sleep disordered respiration metric (SDRM) may be computed by combining the apnea hypopnea index AHI and the arousal index AI. The composite sleep disordered respiration metric (SDRM) may be computed as a linear combination of the AHI and AI as follows:

$$SDRM=c_1*AHI+c_2*AI \quad [6]$$

where $c_1$ and $c_2$ are constants chosen to balance the relative contributions of respiratory and arousal effects on sleep disturbance. The AHI may be monitored by performing disordered breathing detection based on transthoracic impedance measurements as previously described. The AI may be estimated, for example, by monitoring the patient activity, minute ventilation, and posture sensors for body motion indicating sleep termination or arousal. A more sensitive measure of arousal may be made using EEG signals. In this implementation, the constant $c_2$ may be adjusted to reflect the increased sensitivity to arousal.

In another embodiment, an undisturbed respiration sleep time (URST) or undisturbed respiration sleep efficiency (URSE) may be computed based on the amount of time the patient spends asleep in bed without respiratory disturbance.

The URST or URSE metrics may be determined using three parameters: total time in bed (TIB), total time asleep (TA), and combined sleep time duration in disturbed respiration (STDR). Time in bed may be determined by a combination of posture sensing and sensing the proximity of the patient to bed. The posture condition of the patient may determined, for example, using an implantable multiaxis accelerometer sensor.

The patient's total time in bed (TIB) may be determined using a proximity to bed sensor. The proximity to bed sensor may use a receiver in the sleep quality monitor 2320 for receiving signals transmitted from a beacon 2370 located at the patient's bed 2360. If the proximity to bed receiver detects a signal of sufficient strength from the proximity to bed beacon 2370, then the receiver detects that the patient is in bed 2360.

Total time asleep (TA) may be determined using the sleep detection method described in more detail above. The total sleep time in disturbed respiration (STDR) may be determined, for example, based on detection of sleep and disordered breathing using the sleep and disordered breathing detection methods described above.

The patient's undisturbed respiration sleep time (URST) is calculated as:

$$URST=TA-STDR \quad [7]$$

where TA=total time asleep and STDR=sleep time in disturbed breathing.

The undisturbed respiration sleep efficiency (URSE) in percent is calculated $$URSE=100*URST/TIB \quad [8]$$

where URST=undisturbed respiration sleep time and TIB=total time in bed.

Similar metrics may be calculated for movement disorders generally, or for specific movement disorders, e.g., RLS, PLMD, or bruxism. For example, the composite RLS, PLMD, and bruxism metrics, RLSM, PLMDM, and BM, respectively, may be calculated using equations similar in form to equation 6 above:

$$RLSM=c_1*RLSI+c_2*AI \quad [9]$$

where RLSI=number of restless leg movement syndrome episodes per hour, AI=number of arousals per hour, and $c_1$ and $c_2$ are constants chosen to balance the relative contributions of abnormal movement and arousal effects on sleep disturbance.

$$PLMDM=c_1*PLMDI+c_2*AI \quad [10]$$

where PLMDI=number of periodic leg movement syndrome episodes per hour, AI=number of arousals per hour, and $c_1$ and $c_2$ are constants chosen to balance the relative contributions of abnormal movement and arousal effects on sleep disturbance.

$$BM=c_1*BMI+c_2*AI \quad [11]$$

where BMI=number of bruxism movement episodes per hour, AI=number of arousals per hour, and $c_1$ and $c_2$ are constants chosen to balance the relative contributions of abnormal movement and arousal effects on sleep disturbance.

The patient's undisturbed movement sleep time (UMST) and undisturbed movement sleep efficiency (UMSE) may be calculated for each movement related disorder separately or in combination using equations similar in form to equations 2 and 3, above.

In addition, a composite sleep disorder index SDI quantifying the combined effect of both respiratory and movement disorders may be computed by combining the apnea hypopnea index (AHI), the movement disorder index (MDI), and the arousal index (AI).

A sleep disturbance index (SDI) may be computed as a linear combination of the AHI, and the combined disorder index $DI_C$. The combined disorder index may include both abnormal breathing and movement components. For example, the sleep disturbance index SDI is characterizable by the equation:

$$SDI=c_4*DI_C+c_3*AI, \quad [12]$$

where $DI_C$ is a combined disorder index of the form:

$$DI_C=c_{41}*DI_1+c_{42}*DI_2 \quad [13]$$

In equation 12, $c_4$ and $c_3$ are constants chosen to balance the relative contributions of the combined disorder and arousal effects, respectively. The disorder index, $DI_C$, may be used to characterize the effects of one or more sleep disorders, including, e.g., disorders associated with disturbed respiration and/or abnormal movements. The combined disorder index may represent only one disorder index, or may be a linear combination of two or more sleep disorder indices, e.g., the apnealhypopnea index (AHI) and the abnormal movement disorder index (MDI). The constants $c_{41}$ and $c_{42}$ may be used as weighting factors associated with particular disorder indices.

The patient's undisturbed sleep time (UST) may be calculated:

$$UST=TA-STSD \quad [14]$$

where TA=total time asleep and STSD=sleep time spent in sleep disorders.

The undisturbed sleep efficiency (USE) in percent may be calculated:

$$USE=100*UST/TIB \quad [15]$$

where UST=undisturbed sleep time and TIB=total time in bed.

Sleep quality metrics, such as those described above, or other metrics, may be acquired and analyzed using the sleep quality data collection and analysis unit 2320. Sleep quality metrics, in addition to raw or processed data based on physiological and non-physiological conditions may determined periodically, e.g., daily, and stored or transmitted to another device. Such data can be presented to the patient's health care professional on a real-time basis, or as a long-term, e.g., month long or year long, trend of daily measurements.

The health care professional may access the data during clinic visits via programmer interrogation of the implanted device, through occasional or periodic trans-telephonic device interrogations, or through an automatic or "on-demand" basis in the context of an advanced patient management system. The health care professionals may use the sleep quality indicator trends alone or in conjunction with other device-gathered or clinical data to diagnose disorders and/or adjust the patient's device or medical therapy as needed to improve the patient's quality of sleep.

Cardiac Pacing for Disordered Breathing

Aspects of the invention that include cardiac pacing for disordered breathing are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of this invention involving cardiac pacing for disordered breathing are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 128 (FIG. 1C) for treating disordered breathing using cardiac pacing. The system for treating disordered breathing using cardiac pacing may be implemented as a stand alone system or in combination with other individual medical systems, such as those described in FIGS. 1B-1D.

Embodiments of the present invention are directed to systems and methods for treating disordered breathing using cardiac pacing. Various embodiments of present invention involve methods and systems for providing disordered breathing therapy. One embodiment of the invention provides a method for delivering disordered breathing therapy. Cardiac intervals between cardiac beats are obtained. A first indicated pacing interval is determined based at least one cardiac interval duration and a previous value of the first indicated pacing interval. Cardiac pacing to mitigate disordered breathing is provided based on the first indicated pacing interval.

Another embodiment of the invention involves a system for delivering disordered breathing therapy. The system includes a sensing circuit configured to sense cardiac beats. A controller is coupled to the sensing circuit. The controller is configured to determine a first indicated pacing interval based on at least one cardiac interval duration and a previous value of the first indicated pacing interval. A cardiac pacing circuit coupled to the controller is configured to provide cardiac pacing to mitigate disordered breathing based on the first indicated pacing interval.

Another embodiment of this invention involves a system for providing coordinated patient monitoring, diagnosis and/or therapy that utilizes cardiac pacing for disordered breathing. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 183 operate cooperatively via the communication channel to provide one or more of patient monitoring, diagnosis, and therapy.

According to this embodiment, the system providing coordinated patient monitoring, diagnosis and/or therapy includes a system 128 configured to deliver cardiac pacing for disordered breathing. The disordered breathing therapy system 128 includes a sensing circuit configured to sense cardiac beats. A controller is coupled to the sensing circuit. The controller is configured to determine a first indicated pacing interval based on at least one cardiac interval duration and a previous value of the first indicated pacing interval. A cardiac pacing circuit coupled to the controller is configured to provide cardiac pacing to mitigate disordered breathing based on the first indicated pacing interval. Systems and methods directed to rate regularization of cardiac pacing for disordered breathing therapy may be implemented to include selected features, functions, and/or structures described in commonly owned, U.S. Pat. No. 7,336,996, which is hereby incorporated herein by reference.

In various implementations, disordered breathing therapy may comprise overdrive pacing. Overdrive pacing comprises pacing one or more heart chambers at a rate higher than an intrinsic rate. In accordance with embodiments of the invention, therapy to mitigate disordered breathing involves overdrive cardiac pacing of one or more atria and/or one or more ventricles as treatment for disordered breathing.

When operating in the overdrive pacing mode, a cardiac rhythm management device may deliver pacing pulses at a pacing preference (PP) rate that is a small amount above the intrinsic heart rate. If intrinsic beats are detected, the PP rate may be increased until it becomes slightly faster than the intrinsic heart rate of the sensed beat. The PP rate may then be gradually decreased to search for the intrinsic heart rate. After an intrinsic beat is sensed, the PP rate may be increased until the pacing rate is a small amount above the intrinsic heart rate.

In one implementation, a CRM device may be switched to operate in the overdrive pacing mode upon detection or prediction of disordered breathing. In another implementation, the CRM device may be switched to operate in the overdrive pacing mode following a determination that the patient is asleep. In yet another implementation, characteristics of the disordered breathing are used to develop an indicated pacing interval. The description that follows involves atrial overdrive pacing in the AAI(R) or DDD(R) modes. It will be appreciated that similar techniques may be implemented to effect ventricular overdrive pacing in the VVI(R) mode or overdrive pacing in a biventricular mode.

Figure 100:
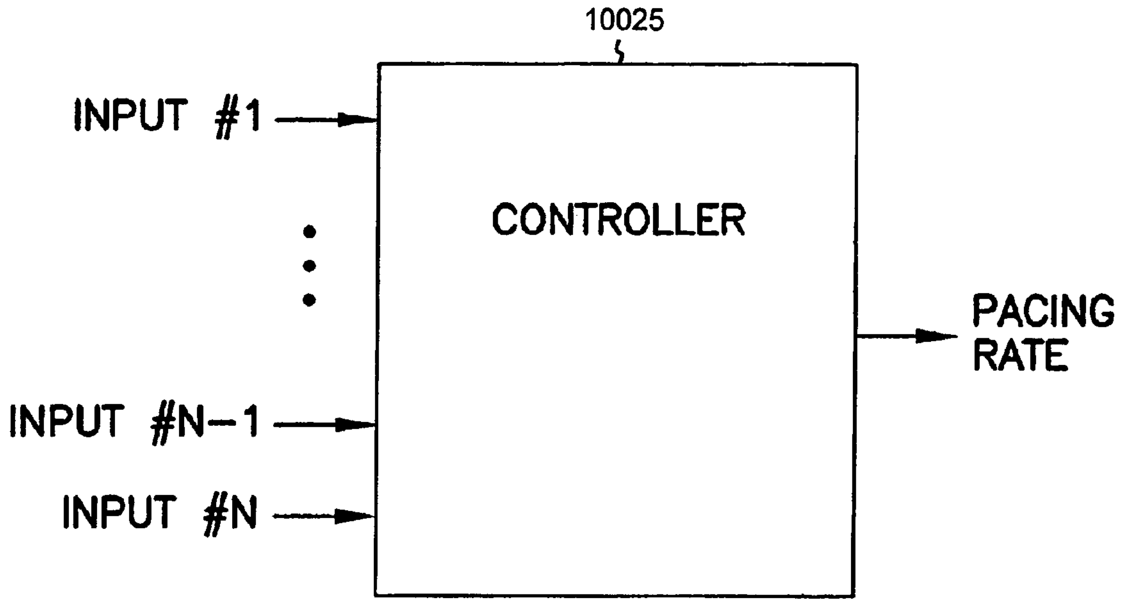
FIGS. 100 and 101 are block diagrams illustrating a controller configured to receive one or more inputs for modifying the rate at which cardiac pacing for disordered breathing is delivered in accordance with embodiments of the invention.

FIG. 100 is a block diagram illustrating a pacemaker controller 10025 in accordance with embodiments of the invention. The pacemaker controller 10025 uses signals from several different inputs to modify the rate at which pacing or other therapy is delivered. For example, Input #1 may provide information about atrial heart rate, Input #2 may provide information about ventricular heart rate, Input #3 may provide an accelerometer-based indication of activity, and Input #4 may provide an impedance-based indication of respiration, such as minute ventilation. Based on at least one of these and/or other inputs, controller 10025 provides an output indication of pacing rate as a control signal delivered to a therapy delivery circuit, such as to one or more of an atrial therapy delivery circuit and a ventricular therapy delivery circuit.

Various methods and systems for implementing impedance measurements in a cardiac rhythm management device are described in commonly owned U.S. Pat. Nos. 6,463,326, 6,161,042, 6,076,015 which are incorporated herein by reference.

Atrial and ventricular therapy delivery circuits issue pacing pulses based on one or more such control signals received from controller 10025. Control of the pacing rate may be performed by controller 10025, either alone or in combination with peripheral circuits or modules, using software, hardware, firmware, or any combination of the like. The software embodiments provide flexibility in how inputs are processed and may also provide the opportunity to remotely upgrade the device software while still implanted in the patient without having to perform surgery to remove and/or replace the device.

In various embodiments, a CRM device provides cardiac pacing therapy to treat disordered breathing. The CRM device obtains intervals between successive sensed or evoked atrial beats. The CRM device computes a new first indicated pacing interval based at least in part on the duration of a cardiac interval and a previous value of the first indicated pacing interval. In various implementations, the cardiac interval duration used to compute the new first indicated pacing interval may comprise a previous cardiac interval duration or a most recent cardiac interval duration. The CRM device provides pacing therapy delivered at a rate corresponding to the inverse of the duration of the first indicated pacing interval.

Figure 101:
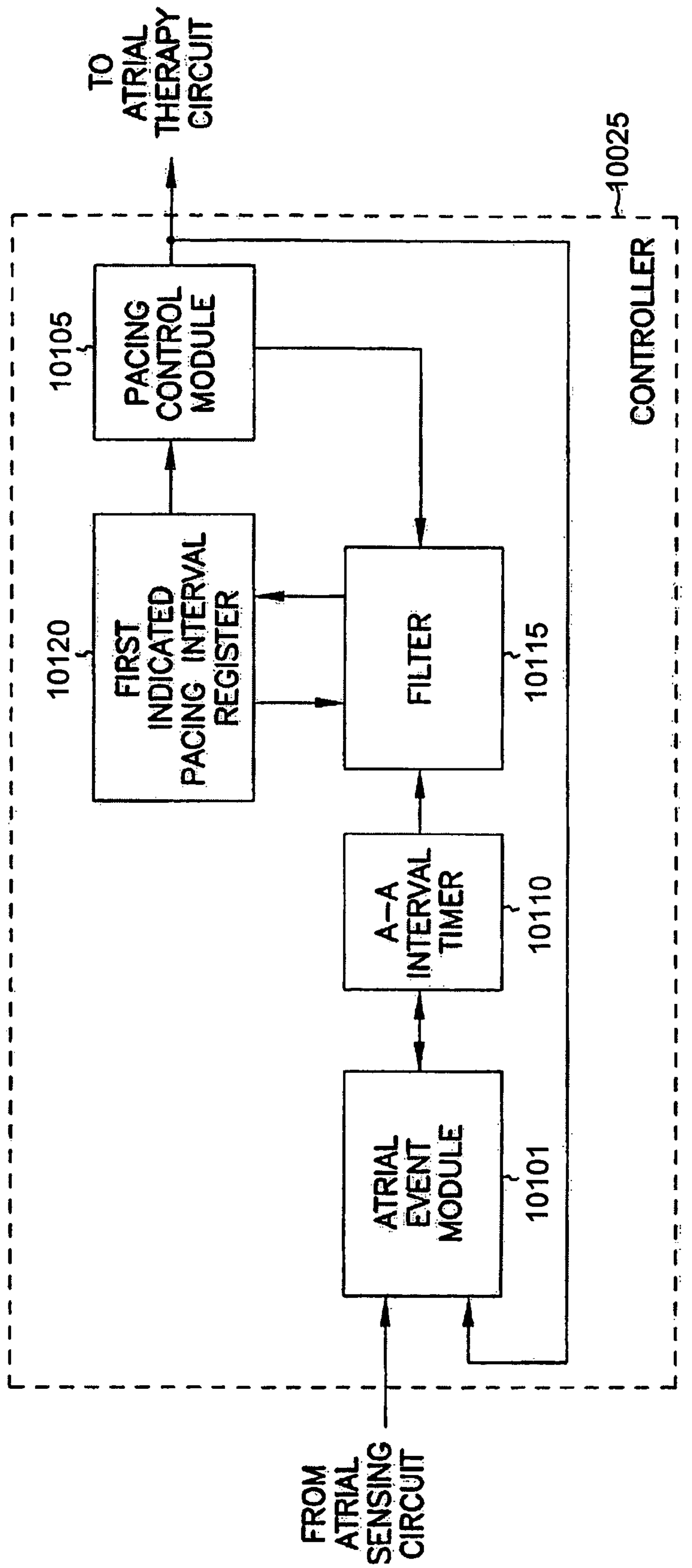

FIG. 101 is a block diagram illustrating one conceptualization of portions of the controller 10025 used to effect overdrive pacing for disordered breathing therapy in accordance with embodiments of the invention. The description that follows involves atrial overdrive pacing in the AAI(R) or DDD(R) modes. It will be appreciated that similar techniques may be implemented to effect ventricular overdrive pacing in the VVI(R) mode or overdrive pacing in a biventricular mode.

At least one signal from an atrial sensing circuit is received by atrial event module 501, which recognizes the occurrence of atrial events included within the signal. Such events are also referred to as "beats," "activations," "depolarizations," "P-waves," or "contractions." Atrial event module 10101 may detect intrinsic events (also referred to as sensed events) from the signal obtained from atrial sensing circuit. Atrial event module 10101 may also detect evoked events (resulting from a pace) either from the signal obtained from atrial sensing circuit, or preferably from an atrial pacing control signal obtained from pacing control module 10105, which also triggers the delivery of a pacing stimulus by atrial therapy circuit. Thus, atrial events include both intrinsic/sensed events and evoked/paced events.

A time interval between successive atrial events, referred to as an A-A interval, is recorded by a first timer, such as A-A interval timer 10110. A filter 10115 computes a "first indicated pacing interval," i.e., one indication of a desired time interval between atrial events or, stated differently, a desired atrial heart rate. The first indicated pacing interval is also referred to as an atrial pacing preference (APP) indicated pacing interval. In various embodiments, filter 10115 includes an averager, a weighted averager, a median filter, an infinite impulse (IIR) filter, a finite impulse response (FIR) filter, or any other analog or digital signal processing circuit providing the desired signal processing described more particularly below.

In one embodiment, filter 10115 computes a new value of the first indicated pacing interval (also referred to as the APP-indicated pacing interval) based on the duration of the most recent A-A interval recorded by timer 10110 and on a previous value of the first indicated pacing interval stored in first indicated pacing interval register 10120. Register 10120 is then updated by storing the newly computed first indicated pacing interval in register 10120. Based on the first indicated pacing interval stored in register 10120, pacing control module 10105 delivers control signals to atrial therapy circuit for delivering therapy, such as pacing stimuli, at the APP-indicated atrial heart rate corresponding to the inverse of the duration of the first indicated pacing interval.

Figure 102:
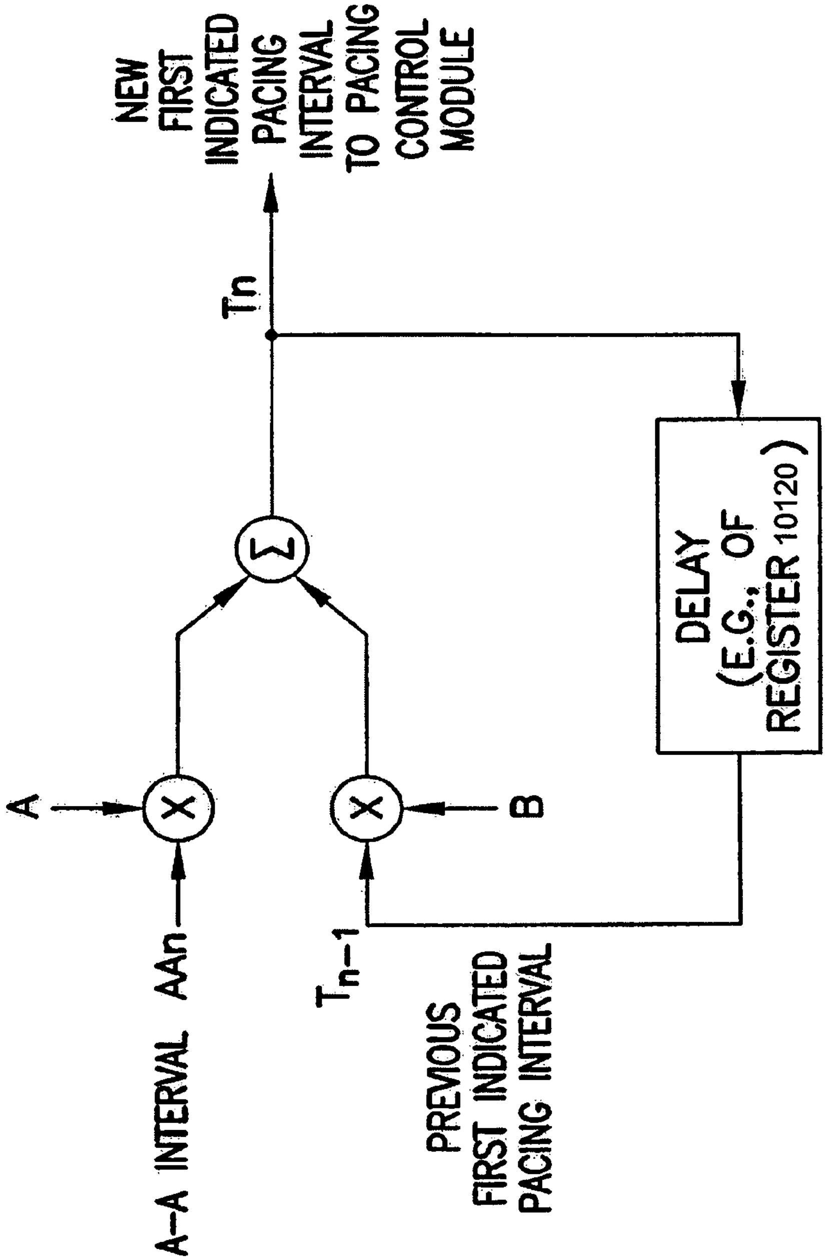

FIG. 102 is a signal flow diagram illustrating one embodiment of operating filter 10115. Upon the occurrence of a sensed or evoked atrial beat, timer 10110 provides filter 10115 with the duration of the A-A interval concluded by that beat, which is referred to as the most recent A-A interval ($AA_n$). Filter 10115 also receives the previous value of the first indicated pacing interval ($T_{n-1}$) stored in register 10120. The most recent A-A interval $AA_n$ and the previous value of the first indicated pacing interval $T_{n-1}$ are each scaled by respective constants A and B, and then summed to obtain a new value of the first indicated pacing interval ($T_n$), which is stored in register 10120 and provided to pacing control module 10105. In one embodiment, the coefficients A and B are different values, and are either programmable, variable, or constant.

If no atrial beat is sensed during the new first indicated pacing interval $T_n$, which is measured as the time from the occurrence of the atrial beat concluding the most recent A-A interval $AA_n$, then pacing control module 10105 instructs atrial therapy circuit to deliver an atrial pacing pulse upon the expiration of the new first indicated pacing interval $T_n$. In one embodiment, operation of the filter is described by $T_n=A\cdot AA_n+B\cdot T_{n-1}$, where A and B are coefficients (also referred to as "weights"), $AA_n$ is the most recent A-A interval duration, and $T_{n-1}$ is the previous value of the first indicated pacing interval.

From these examples, it can be seen that the first indicated pacing interval can be calculated using either a sensed or paced terminating event and using either a sensed or paced initiating event.

Initialization of filter 10115 includes seeding the filter by storing, in register 10120, an initial interval value. In one embodiment, register 10120 is initialized to an interval value corresponding to a lower rate limit (LRL), i.e., a minimum rate at which pacing pulses are delivered by device. Register 10120 could alternatively be initialized with any other suitable value.

In one embodiment, operation of filter 10115 is based on whether the beat concluding the most recent A-A interval $AA_n$ is a sensed/intrinsic beat or a paced/evoked beat. In this embodiment, the pacing control module 10105, which controls the timing and delivery of pacing pulses, provides an input to filter 10115 that indicates whether the most recent A-A interval $AA_n$ was concluded by an evoked beat initiated by a pacing stimulus delivered by CRM device, or was concluded by an intrinsic beat sensed by atrial sensing circuit.

In general terms, if the most recent A-A interval $AA_n$ is concluded by a sensed/intrinsic beat, then filter 10115 provides a new first indicated pacing interval $T_n$ that is adjusted from the value of the previous first indicated pacing interval $T_{n-1}$. For example, the new first indicated pacing interval $T_n$ may be decreased by an amount that is based at least partially on the duration of the most recent A-A interval $AA_n$ and on the duration of the previous value of the first indicated pacing interval $T_{n-1}$. If, however, the most recent A-A interval $AA_n$ is concluded by a paced/evoked beat, then filter 10115 may provide a new first indicated pacing interval $T_n$ that is increased from the value of the previous first indicated pacing interval $T_{n-1}$. For example, the new first indicated pacing interval $T_n$ may be increased by an amount that is based at least partially on the duration of the most recent A-A interval $AA_n$ and on the duration of the previous value of the first indicated pacing interval $T_{n-1}$. If no atrial beat is sensed during the new first indicated pacing interval $T_n$, measured as the time from the occurrence of the atrial beat concluding the most recent A-A interval $AA_n$, then pacing control module 10105 may instruct the atrial therapy circuit to deliver an atrial pacing pulse upon the expiration of the new first indicated pacing interval $T_n$.

Figure 103:
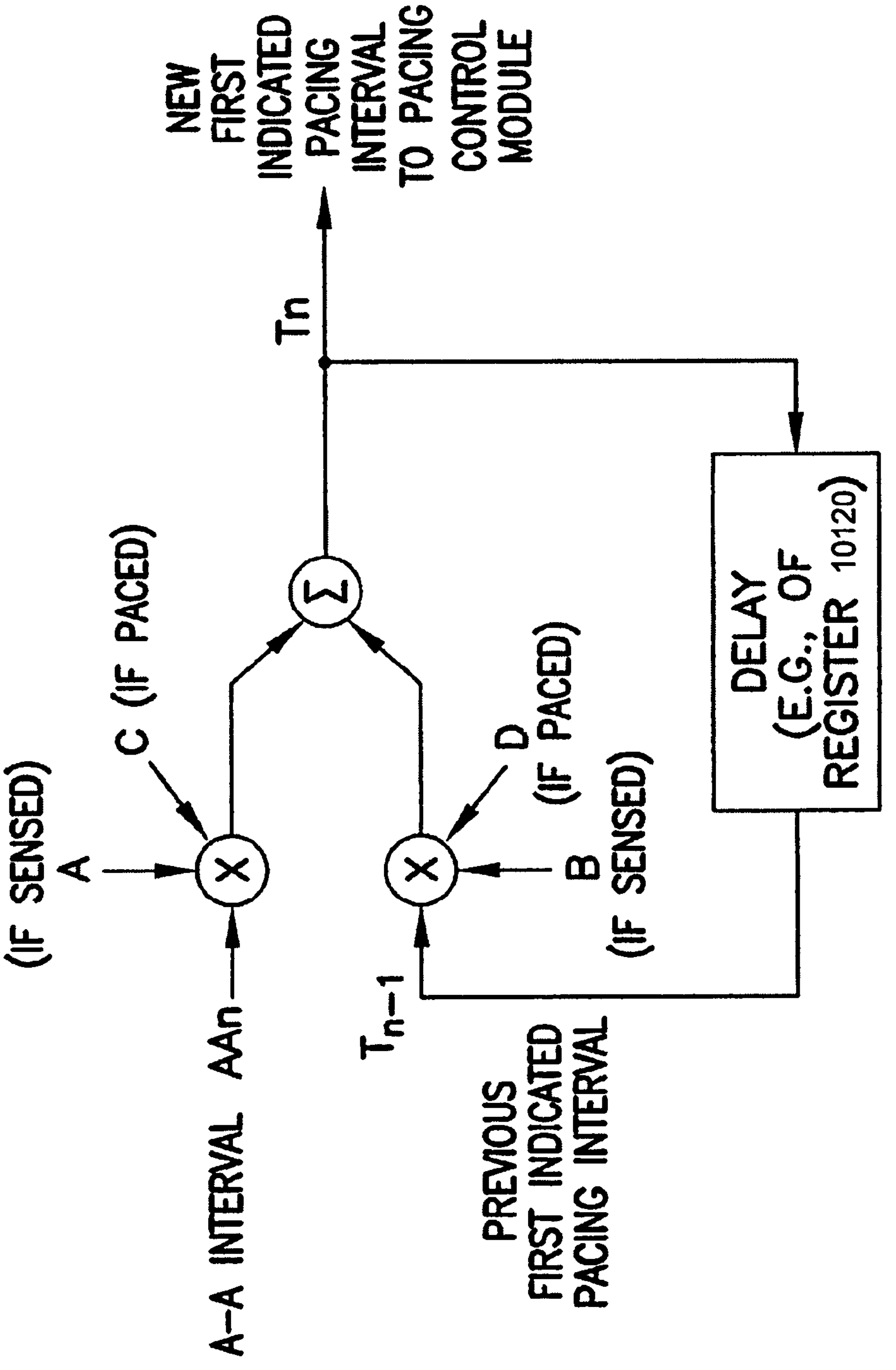

FIG. 103 is a signal flow diagram illustrating another conceptualization of operating filter 10115, with certain differences from FIG. 102 more particularly described below. In this embodiment, the pacing control module 10105, which controls the timing and delivery of pacing pulses, provides an input to filter 10115 that indicates whether the most recent A-A interval $AA_n$ was concluded by an evoked beat initiated by a pacing stimulus delivered by the CRM device, or was concluded by an intrinsic beat sensed by a trial sensing circuit.

If the most recent A-A interval $AA_n$ was concluded by an intrinsic beat, then the most recent A-A interval, $AA_n$, and the previous value of the first indicated pacing interval, $T_{n-1}$, are each scaled by respective constants A and B, and then summed to obtain the new value of the first indicated pacing interval $T_n$, which is stored in register 10120 and provided to pacing control module 10105. Alternatively, if the most recent A-A interval $AA_n$ was concluded by an evoked/paced beat, then the most recent A-A interval $AA_n$ and the previous value of the first indicated pacing interval $T_{n-1}$ are each scaled by respective constants C and D, and then summed to obtain the new value of the first indicated pacing interval $T_n$, which is stored in register 10120 and provided to pacing control module 10105. In one embodiment, the coefficients C and D are different from each other, and are either programmable, variable, or constant. In a further embodiment, the coefficient C is a different value from the coefficient A, and/or the coefficient D is a different value than the coefficient B, and these coefficients are either programmable, variable, or constant. In another embodiment, the coefficient D is the same value as the coefficient B.

In one embodiment, operation of filter 10115 is described by $T_n=A\cdot AA_n+B\cdot T_{n-1}$, if $AA_n$ is concluded by an intrinsic beat, and is described by $T_n=C\cdot AA_n+D\cdot T_{n-1}$, if $AA_n$ is concluded by a paced beat, where A, B, C and D are coefficients (also referred to as "weights"), $AA_n$ is the most recent A-A interval duration, $T_n$ is the new value of the first indicated pacing interval, and $T_{n-1}$ is the previous value of the first indicated pacing interval. If no atrial beat is sensed during the new first indicated pacing interval $T_n$, which is measured as the time from the occurrence of the atrial beat concluding the most recent A-A interval $AA_n$, then pacing control module 10105 instructs atrial therapy circuit to deliver an atrial pacing pulse upon the expiration of the new first indicated pacing interval $T_n$.

Figure 104:
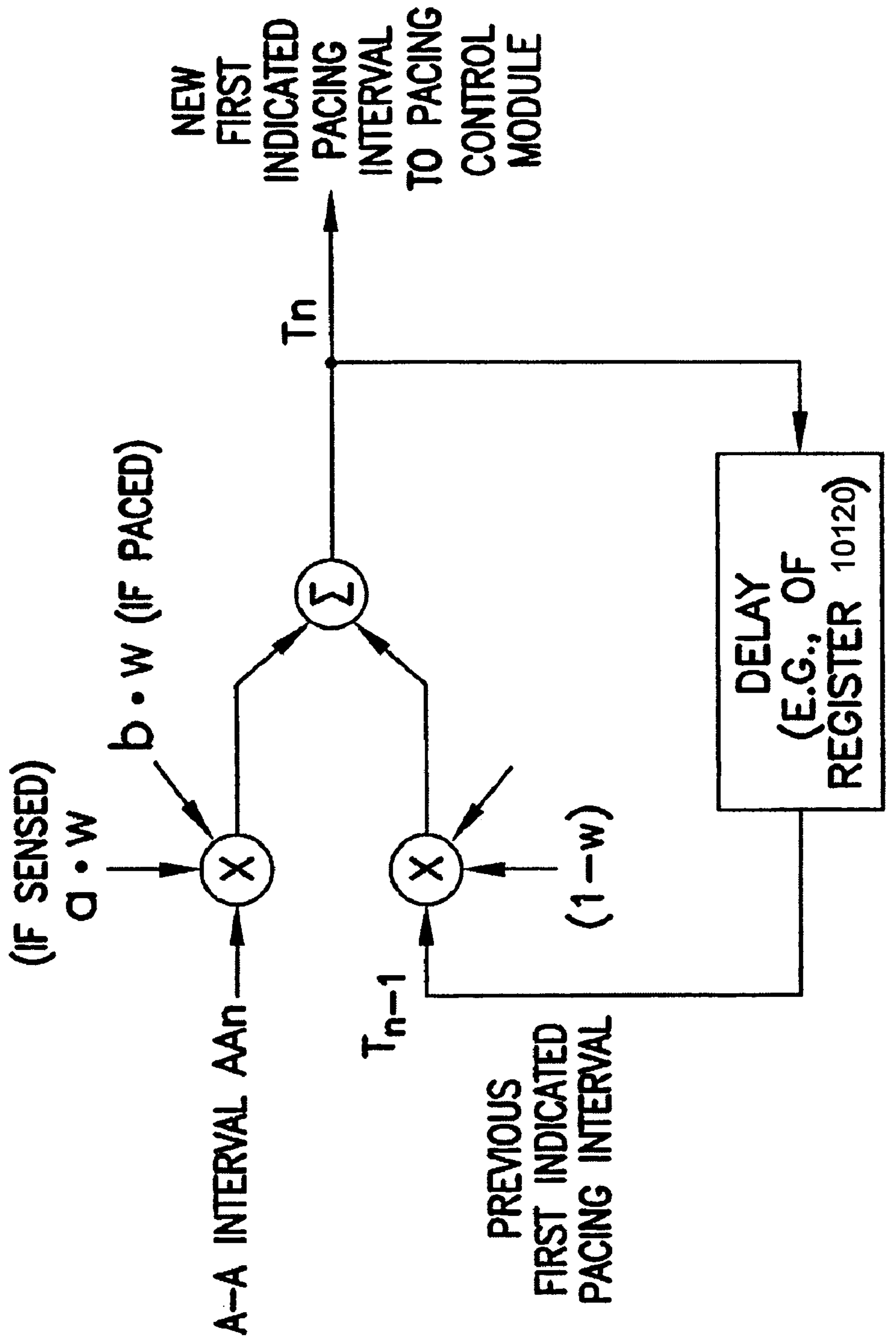

Another approach to operating filter 10115 is illustrated in the signal flow graph of FIG. 104. In this embodiment, the coefficients A, B, C, and D can be more particularly described using an intrinsic coefficient (a), a paced coefficient (b), and a weighting coefficient (w). In one such embodiment, $A=a\cdot w$, $B=(1-w)$, $C=b\cdot w$, and $D=(1-w)$. In one example, operation of the filter 10115 is described by $T_n=a\cdot w\cdot AA_n+(1-w)\cdot T_{n-1}$, if $AA_n$ is concluded by an intrinsic beat, otherwise is described by $T_n=b\cdot w\cdot AA_n+(1-w)\cdot T_{n-1}$, if $AA_n$ is concluded by a paced beat.

If no atrial beat is sensed during the new first indicated pacing interval $T_n$, which is measured as the time from the occurrence of the atrial beat concluding the most recent A-A interval $AA_n$, then pacing control module 10105 instructs atrial therapy circuit to deliver an atrial pacing pulse upon the expiration of the new first indicated pacing interval $T_n$. In one embodiment, the coefficients a and b are different from each other, and are either programmable, variable, or constant.

The above-described parameters (e.g., A, B, C, D, a, b, w) are stated in terms of time intervals (e.g., $AA_n$, $T_n$, $T_{n-1}$). However, an alternate system may produce results in terms of rate, rather than time intervals, without departing from the present method and apparatus. In one embodiment, weighting coefficient w, intrinsic coefficient a, and paced coefficient b, are variables. Different selections of w, a, and b, will result in different operation of the present method and apparatus. For example, as w increases the weighting effect of the most recent A-A interval $AA_n$ increases and the weighting effect of the previous first indicated pacing rate $T_{n-1}$ decreases. In one embodiment, $w=1/16=0.0625$. In another embodiment, $w=1/32$. Another possible range for w is from $w=1/2$ to $w=1/1024$. A further possible range for w is from about 0 to about.1. Other values of w, which need not include division by powers of two, may be substituted without departing from the present method and apparatus.

In one embodiment, intrinsic coefficient a, is selected to be less than (or, alternatively, less than or equal to) 1.0. In one example, the intrinsic coefficient a is selected to be lesser in value than the pacing coefficient b. In one embodiment, a may be about.0.6 and b may be about 1.5. In another embodiment, a=1.0 and b=1.05. One possible range for a is from a=0.6 to a=1.0, and for b is from b=1.05 to b=1.5. The coefficients may vary without departing from the present method and apparatus.

In one embodiment, for $a<1.0$, filter 10115 provides a new first indicated pacing interval $T_n$ that is at least slightly shorter than the expected intrinsic A-A interval being measured by timer 10115. Thus, filter 10115 operates to promote atrial pacing by increasing the APP-indicated rate until it becomes slightly faster than the intrinsic atrial rate. The APP-indicated rate is then gradually decreased to search for the underlying intrinsic atrial heart rate. After a sensed atrial beat, the APP filter 10115 again increases the APP indicated pacing rate until it becomes faster than the intrinsic atrial rate by a small amount. As a result, most atrial heart beats are paced, rather than sensed.

The overdrive pacing as described above, or as implemented in connection with pacing one or more ventricles may be provided as therapy for disordered breathing. Additionally, such pacing therapy may be activated upon detection or prediction of disordered breathing. For example, pacing may occur at a programmed rate until a disordered breathing episode is detected. After detection of disordered breathing, the CRM device may switch to overdrive pacing to mitigate the disordered breathing.

In another example, the CRM may deliver pacing at a programmed rate until patient conditions indicate that disordered breathing is likely to occur. After disordered breathing is predicted, the CRM may deliver overdrive pacing to prevent or mitigate episodes of disordered breathing.

Although disordered breathing may occur while the patient is awake, it is most likely to occur during sleep. In another example, the CRM may be equipped with a sleep detection system. The CRM may switch from pacing at a programmed rate to overdrive pacing when the CRM detects that the patient is asleep or when the CRM detects a particular sleep state, e.g., non-REM sleep.

Figure 105:
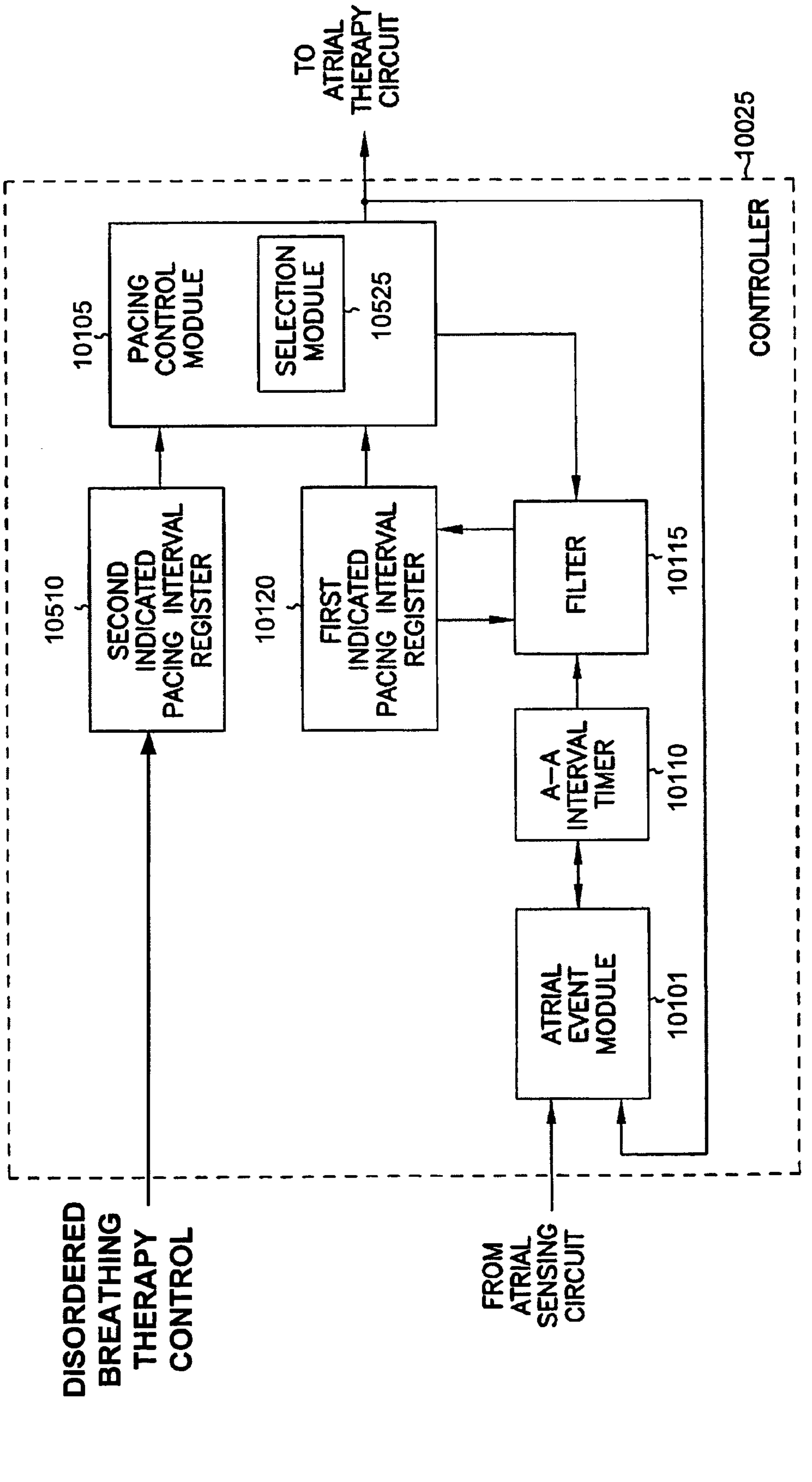

FIG. 105 is a block diagram illustrating generally, by way of example, but not by way of limitation, another conceptualization of portions of controller 10025, with certain differences from FIG. 101 more particularly described below. In FIG. 105, controller 10025 receives from a disordered breathing therapy control circuit a control signal indicating an overdrive pacing rate for disordered breathing therapy. The signal may be based, for example, on the severity, duration, frequency or type of disordered breathing experienced by the patient, or by other factors, such as therapy interaction and/or patient comfort. In one example, the control signal may be based on a disordered breathing index, such as an apnea/hypopnea index. The disordered breathing therapy pacing rate is expressed in terms of a second indicated pacing interval stored in register 3910.

Pacing control module 10105 delivers a control signal, which directs atrial therapy circuit to deliver a pacing pulse, based on either (or both) of the first or second indicated pacing intervals, stored in registers 10120 and 3910, respectively. In one embodiment, pacing control module 10105 includes a selection module 3915 that selects between the new first indicated pacing interval $T_n$ and the second indicated pacing interval that is modulated by disordered breathing conditions.

In one embodiment, selection module 10525 selects the shorter of the first and second indicated pacing intervals as the selected indicated pacing interval $S_n$. If no atrial beat is sensed during the selected indicated pacing interval $S_n$, which is measured as the time from the occurrence of the atrial beat concluding the most recent A-A interval $AA_n$, then pacing control module 10105 instructs atrial therapy circuit to deliver an atrial pacing pulse upon the expiration of the selected indicated pacing interval $S_n$.

In general terms, for this embodiment, the atrium is paced at the higher of the disordered breathing therapy rate and the APP-indicated rate. If, for example, the patient is experiencing no disordered breathing or only mild disordered breathing, the disordered breathing therapy rate is lower than the patient's intrinsic rate, then atrial pacing pulses will be delivered at the APP-indicated rate, which is typically slightly higher than the patient's intrinsic atrial heart rate. But if, for example, the patient is experiencing more significant disordered breathing, so that the disordered breathing therapy rate is higher than the APP-indicated rate, then pacing pulses generally will be delivered at the disordered breathing therapy rate. In an alternative embodiment, the pacing rate is determined by blending the disordered breathing therapy rate and the APP-indicated rate, rather than by selecting the higher of these two indicated rates (i.e., the shorter of the first and second indicated pacing intervals). In one such example, selection module 10525 applies predetermined or other weights to the first and second indicated pacing intervals to compute the selected pacing interval $S_n$.

Figure 106:
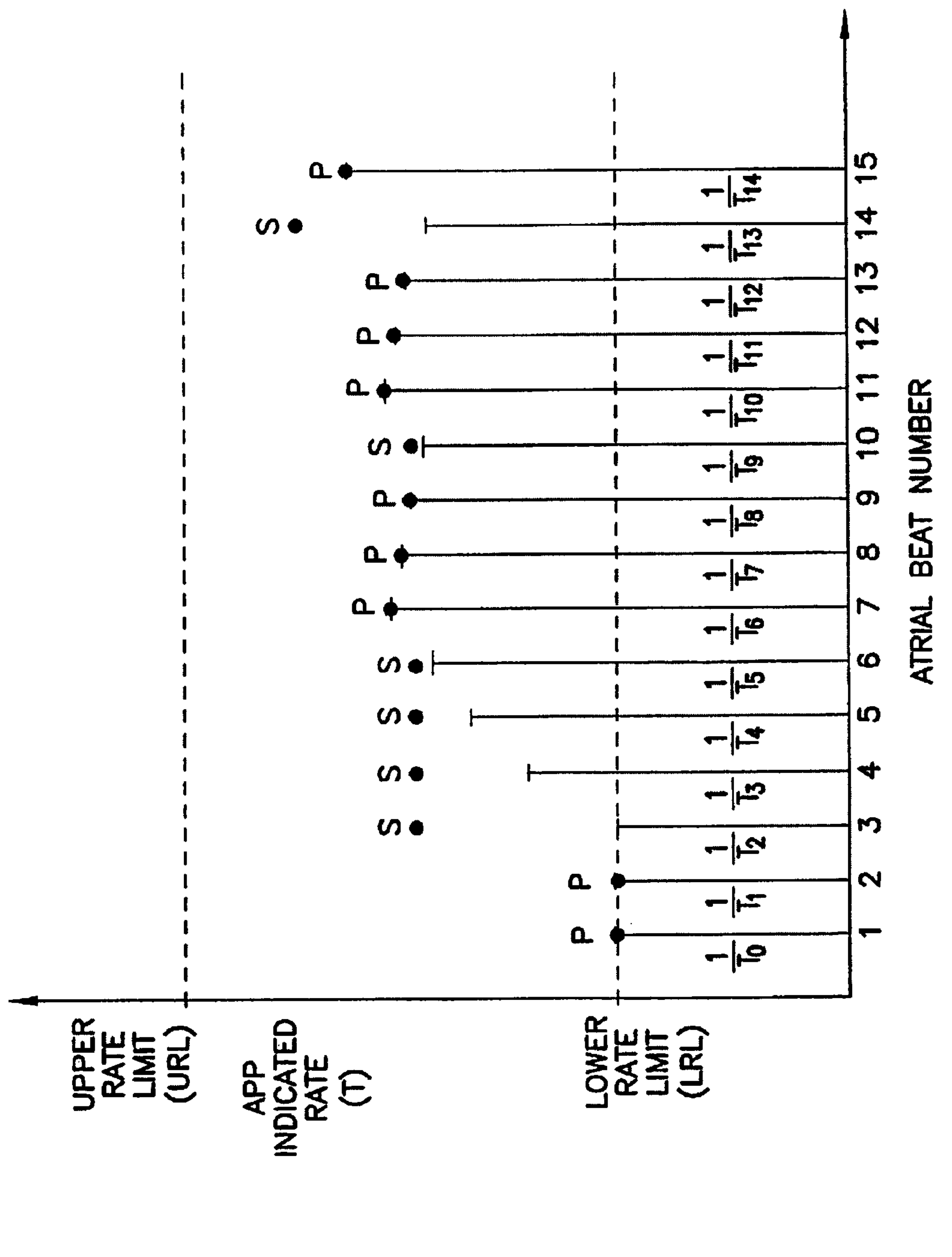

FIG. 106 is a graph illustrating generally, by way of example, but not by way of limitation, one embodiment of an APP-indicated rate for successive atrial heart beats for one mode of operating filter 10115. As discussed above, the APP-indicated rate is simply the frequency, between atrial heart beats, associated with the first indicated pacing interval. Stated differently, the APP indicated rate is inversely related to the duration of the first indicated pacing interval. If pacing is based solely on the APP indicated rate, pacing control module 10105 directs atrial therapy circuit to issue a pacing pulse after the time since the last atrial beat equals or exceeds the first indicated pacing interval. However, as described above, in certain embodiments, pacing control module 10105 directs atrial therapy circuit to issue a pacing pulse based on factors other than the APP indicated rate, for example, based on the severity of disordered breathing experienced by the patient.

In the example illustrated in FIG. 106, a first paced atrial beat, indicated by a "P" was issued upon expiration of the first indicated pacing interval (i.e., the APP indicated pacing interval) $T_0$, as computed based on a previous atrial beat. In one embodiment, the new APP indicated pacing interval $T_1$ is computed based on the duration of most recent A-A interval $AA_n$ and a previous value of the APP indicated pacing interval $T_0$, as discussed above. In FIG. 106, the new APP indicated pacing interval $T_1$ corresponds to a lower rate limit (LRL) time interval. In one embodiment, as illustrated in FIG. 106, the allowable range of the APP indicated pacing interval is limited so that the APP indicated pacing interval does not exceed the duration of the LRL time interval, and so that the APP indicated pacing interval is not shorter than the duration of an upper rate limit (URL) time interval.

In the example of FIG. 106, the second atrial beat is also paced upon expiration of the APP indicated pacing interval $T_1$. In one embodiment, the new APP indicated pacing interval $T_2$ is computed based on the duration of most recent A-A interval $AA_2$ and a previous value of the APP indicated pacing interval, $T_1$, as discussed above. The first and second atrial beats are paced beats because the APP indicated atrial heart rate is higher than the underlying intrinsic atrial heart rate.

The third atrial beat is sensed well before expiration of the APP indicated pacing interval $T_2$, such that no pacing pulse is issued. For the sensed third atrial beat, filter 10115 computes the new APP indicated pacing interval $T_3$ as being shorter in duration relative to the previous APP indicated pacing interval $T_2$.

The fourth, fifth, and sixth atrial beats are sensed before expiration of the APP indicated pacing interval $T_3$, $T_4$, and $T_5$, respectively. For each of the sensed fourth, fifth, and sixth atrial beats, filter 10115 computes a new APP indicated pacing interval as being shorter in duration relative to the previous APP indicated pacing interval.

At the time of the seventh atrial beat, the APP indicated heart rate has increased above the underlying intrinsic atrial heart rate, such that the seventh atrial beat is paced upon expiration of the APP indicated pacing interval $T_6$. Because the seventh atrial beat is paced, rather than sensed, the new APP indicated pacing interval $T_7$ is computed as being longer than the previous APP indicated pacing interval $T_6$.

Similarly, the eighth and ninth atrial beats are each paced upon expiration of the corresponding APP indicated pacing interval, i.e., $T_7$, and $T_8$, respectively. Each APP indicated pacing interval $T_7$, and $T_8$ is longer than the corresponding previous APP indicated pacing interval, i.e., $T_6$, and $T_7$, respectively. In this way, the APP indicated atrial heart rate is gradually decreased to search for the underlying intrinsic atrial heart rate.

At the time of the tenth atrial beat, the APP indicated heart rate has been lowered sufficiently to allow the sensing of the tenth atrial beat. The tenth atrial beat is sensed before expiration of the APP indicated pacing interval $T_9$, such that no pacing pulse is issued. For the sensed tenth atrial beat, filter 10115 computes the new APP indicated pacing interval $T_{10}$ as being shorter in duration relative to the previous APP indicated pacing interval $T_9$.

The eleventh atrial beat is paced upon expiration of the APP indicated pacing interval $T_{10}$. For the paced eleventh atrial beat, filter 10115 computes the new APP indicated pacing interval $T_{11}$ as being longer in duration relative to the previous APP indicated pacing interval $T_{10}$. Similarly, the twelfth and thirteenth atrial beats are each paced upon expiration of the corresponding APP indicated pacing interval, i.e., $T_{11}$, and $T_{12}$, respectively. Each APP indicated pacing interval $T_{12}$, and $T_{13}$ is longer than the corresponding previous APP indicated pacing interval, i.e., $T_{11}$, and $T_{12}$, respectively. In this way, the APP indicated atrial heart rate is gradually decreased to find the underlying intrinsic atrial heart rate.

The fourteenth atrial beat is sensed before expiration of the APP indicated pacing interval $T_{13}$, such that no pacing pulse is issued. For the sensed fourteenth atrial beat, filter 10115 computes the new APP indicated pacing interval $T_{14}$ as being shorter in duration relative to the previous APP indicated pacing interval $T_{13}$.

The fifteenth atrial beat is paced upon expiration of the APP indicated pacing interval $T_{14}$. For the paced fifteenth atrial beat, filter 10115 computes the new APP indicated pacing interval $T_{15}$ as being longer in duration relative to the previous APP indicated pacing interval $T_{14}$.

The intrinsic coefficient a of filter 10115 controls the "attack slope" of the APP indicated heart rate as the APP indicated heart rate increases because of sensed intrinsic beats. The paced coefficient b of filter 10115 controls the "decay slope" of the APP indicated heart rate as the APP indicated heart rate decreases during periods of paced beats. In one embodiment, in which a<1.0 and b>1.0, decreasing the value of a further beneath 1.0 increases the attack slope such that the APP indicated rate increases faster in response to sensed intrinsic beats, while decreasing the value of b toward 1.0 decreases the decay slope such that the APP indicated rate decreases more slowly during periods of paced beats. Conversely, for a<1.0 and b>1.0, increasing the value of a toward 1.0 decreases the attack slope such that the APP indicated rate increases more slowly in response to sensed intrinsic beats, while increasing the value of b from 1.0 increases the decay slope such that the APP indicated rate decreases more quickly during periods of paced beats.

In one embodiment, for a<1.0 and b>1.0, decreasing both a and b increases the APP indicated rate such that the APP indicated rate is higher above the mean intrinsic rate. Because the APP indicated rate is higher, variability in the intrinsic heart rate is less likely to result in sensed events. On the other hand, for a<1.0 and b>1.0, increasing both a and b decreases the APP indicated rate such that it is closer to, the mean intrinsic rate. Because the APP indicated rate is closer to the mean intrinsic rate, the same degree of variability in the intrinsic heart rate is more likely to result in sensed events. Thus, by adjusting the coefficients of filter 10115, as discussed above, it is possible to obtain more intrinsic beats than paced beats for a particular degree of variability in the patient's heart rate.

In one embodiment, these coefficients are programmable by the user, such as by using remote programmer. In another embodiment, the user selects a desired performance parameter (e.g., desired degree of overdrive pacing, desired attack slope, desired decay slope, etc.) from a corresponding range of possible values, and CRM device automatically selects the appropriate combination of coefficients of filter 10115 to provide a filter setting that corresponds to the selected user-programmed performance parameter, as illustrated generally by Table 6. Other levels of programmability or different combinations of coefficients may also be used.

TABLE 6

Example of Automatic Selection of Aspects of Filter Setting Based on a User-Programmable Performance Parameter.

| User-Programmable Performance Parameter | Intrinsic Coefficient a | Paced Coefficient b |
|---|---|---|
| 1 (Less Aggressive Attack/Decay) | 1.0 | 1.05 |
| 2 | 0.9 | 1.2 |
| 3 | 0.8 | 1.3 |
| 4 | 0.7 | 1.4 |
| 5 (More Aggressive Attack/Decay) | 0.6 | 1.5 |

FIG. 106 illustrates that sensed atrial beats increase the APP indicated rate by an amount that is based on the sensed atrial heart rate. Thus, for an abrupt and large increase in sensed atrial rate, the APP indicated rate will increase faster than for a slower and smaller increase in sensed atrial heart rate. However, increases in the APP indicated rate do not depend solely on the sensed atrial heart rate. Instead, such increases in the APP indicated heart rate also depend on the previous value of the APP indicated heart rate. This provides a smoothing function so that the APP indicated heart rate is not overly sensitive to a single extremely premature atrial beat, changes in the atrial rate are more gradual, and the degree of such rate changes is programmably adjustable, as described above. Moreover, in one embodiment, filter 10115 operates continuously to provide continuous rate adjustment based on the APP indicated rate.

Figure 107:
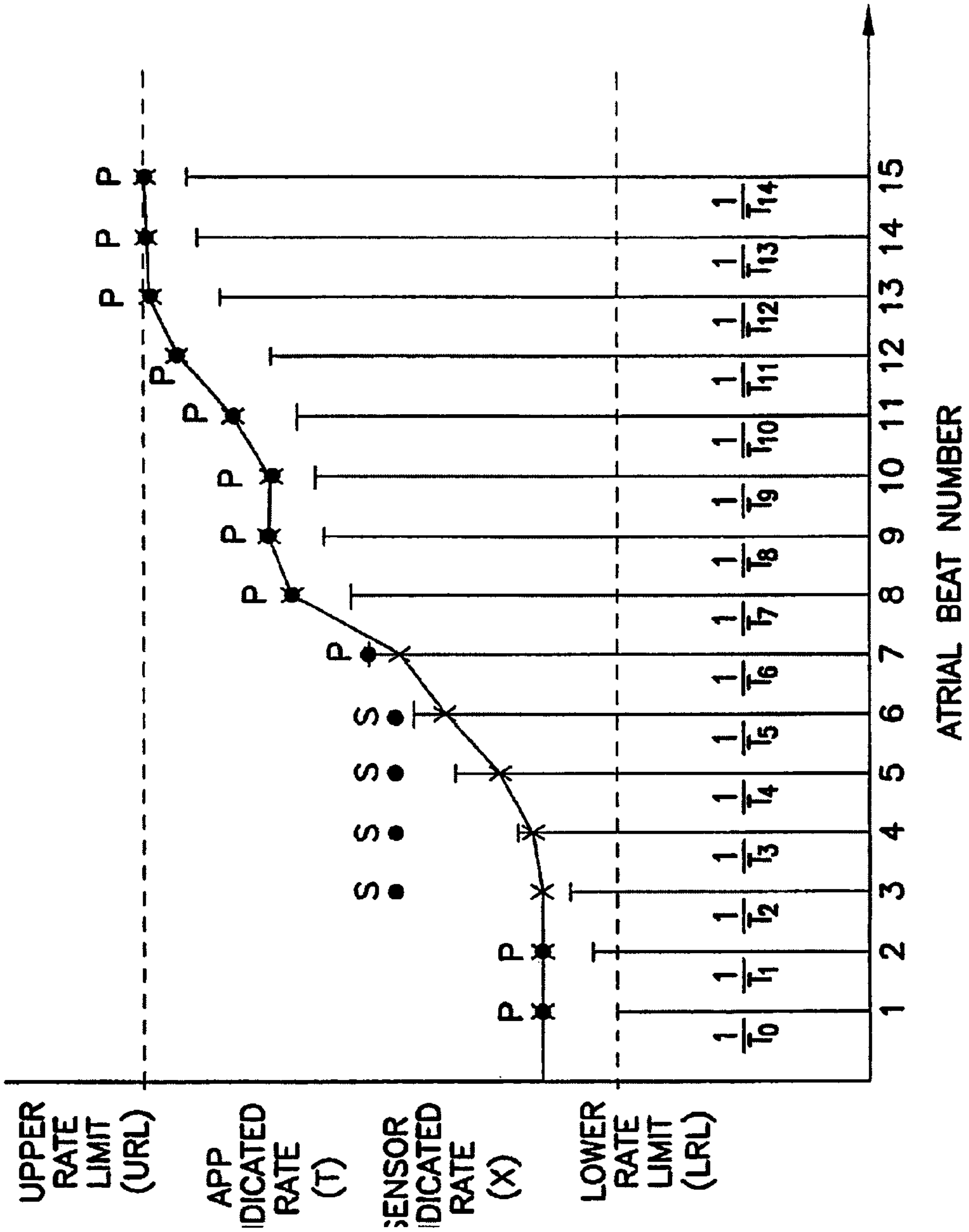

FIG. 107 is a graph illustrating generally, by way of example, but not by way of limitation, one embodiment of selecting between more than one indicated pacing interval. FIG. 107 is similar to FIG. 106 in some respects, but FIG. 107 includes a second indicated pacing interval. In one embodiment, the first indicated pacing interval is the APP indicated pacing interval, described above, and the second indicated pacing interval is a disordered breathing therapy pacing interval, based on the severity, frequency, duration, type, or other parameter of disordered breathing experienced by the patient.

In one embodiment, a selected indicated pacing interval is based on the shorter of the first and second indicated pacing intervals. Stated differently, CRM device provides pacing pulses at the higher indicated pacing rate. In the example illustrated in FIG. 107, the first and second beats and the eighth through fifteenth beats are paced at the disordered breathing therapy indicated rate, because it is higher than the APP indicated atrial rate and the intrinsic (sensed) atrial rate. The third, fourth, fifth and sixth atrial beats are sensed intrinsic beats that are sensed during the shorter of either of the APP and sensor indicated pacing intervals. The seventh beat is paced at the APP indicated rate, because it is higher than the disordered breathing therapy indicated rate, and because no intrinsic beat is sensed during the APP indicated interval $T_6$. In this embodiment, the ranges of both the sensor indicated rate and the APP indicated rate are limited so that they do not extend to rates higher than the URL or to rates lower than the LRL. In one embodiment, the above-described equations for filter 10115 operate to increase the APP indicated rate toward the disordered breathing therapy indicated rate when the sensor indicated rate is greater than the APP indicated rate, as illustrated by first through third and eighth through fifteenth beats in FIG. 107. In an alternate embodiment, however, $T_n=b\cdot w\cdot AA_n+(1-w)\cdot T_{n-1}$, if $AA_n$ is concluded by a APP indicated paced beat, and $T_n=T_{n-1}$ if $AA_n$ is concluded by a disordered breathing therapy indicated paced beat, thereby leaving the APP indicated rate unchanged for disordered breathing therapy indicated paced beats. In one embodiment, the LRL and the URL are programmable by the user, such as by using remote programmer.

In one embodiment, filter 10115 includes variable coefficients such as, for example, coefficients that are a function of heart rate (or its corresponding time interval). In one example, operation of the filter 10115 is described by $T_n=a\cdot w\cdot AA_n+(1-w)\cdot T_{n-1}$, if $AA_n$ is concluded by an intrinsic beat, otherwise is described by $T_n=b\cdot w\cdot AA_n+(1-w)\cdot T_{n-1}$, if $AA_n$ is concluded by a paced beat, where at least one of a and b are linear, piecewise linear, or nonlinear functions of one or more previous A-A intervals such as, for example, the most recent A-A interval, $AA_n$.

Figure 108:
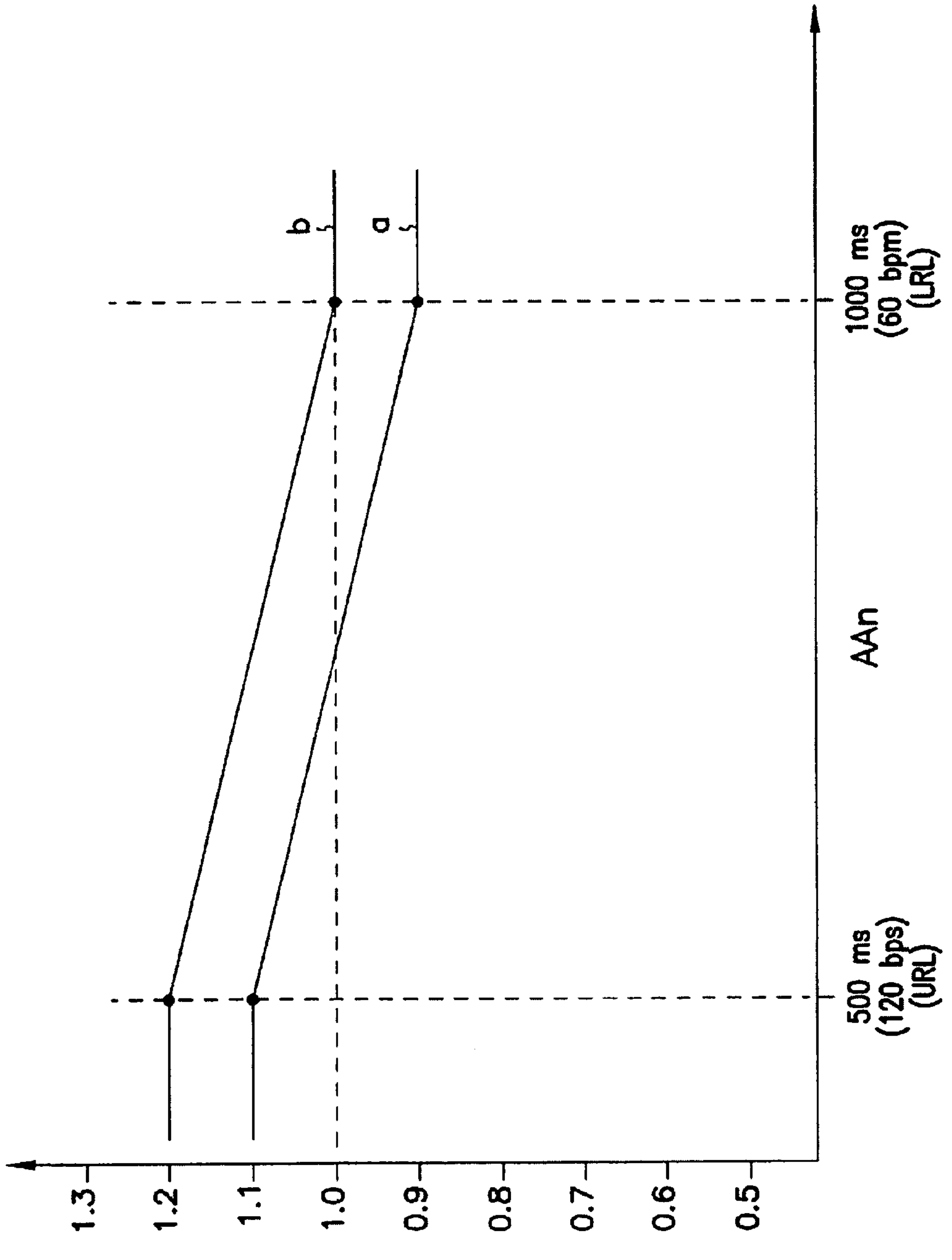

FIG. 108 is a graph illustrating generally, by way of example, but not by way of limitation, one embodiment of using at least one of coefficients a and b as a function of one or more previous A-A intervals such as, for example, the most recent A-A interval, $AA_n$. In one such example, a is less than 1.0 when $AA_n$ is at or near the lower rate limit (e.g., 1000 millisecond interval or 60 beats/minute), and a is greater than 1.0 when $AA_n$ is at or near the upper rate limit (e.g., 500 millisecond interval or 120 beats/minute). For a constant b, using a smaller value of a at lower rates will increase the pacing rate more quickly for sensed events; using a larger value of a at higher rates increases the pacing rate more slowly for sensed events. In another example, b is close to 1.0 when $AA_n$ is at or near the lower rate limit, and b is greater than 1.0 when $AA_n$ is at or near the upper rate limit. For a constant a, using a smaller value of b at lower rates will decrease the pacing rate more slowly for paced events; using a larger value of b at higher rates decreases pacing rate more quickly for paced events.

The above-described system provides, among other things, a cardiac rhythm management system including an atrial pacing preference (APP) filter for promoting atrial pacing. The APP filter controls the timing of delivery of atrial pacing pulses. The atrial pacing preference pacing may be initiated upon detection or prediction of disordered breathing, for example, to provide overdrive pacing to terminate or mitigate occurrences of disordered breathing.

The atrial pacing pulses are delivered at a first indicated pacing rate, i.e., the APP-indicated rate, that is typically at a small amount above the intrinsic atrial heart rate. For sensed beats, the APP indicated pacing rate is increased until it becomes slightly faster than the intrinsic atrial heart rate. The APP-indicated pacing rate is then gradually decreased to search for the underlying intrinsic atrial heart rate. Then, after a sensed atrial beat, the APP filter again increases the APP indicated pacing rate until it becomes faster than the intrinsic atrial rate by a small amount. As a result, most atrial heart beats are paced, rather than sensed.

Although the preceding discussion contemplates providing atrial overdrive pacing for disordered breathing therapy, similar processes for providing ventricular overdrive pacing or bi-ventricular overdrive pacing may be implemented. The pacing rate may be adjusted based on characteristics of the disordered breathing experienced by the patient. For example, the overdrive pacing may be modulated by the type, severity, frequency, and/or duration of the disordered breathing.

Further, the smoothed pacing rate may be limited. For example, the pacing rate may be capped or limited before therapy is delivered. In another implementation, the intrinsic input interval may be limited to some predetermined value. The predetermined may be set by the physician or may be determined from other variables. By limiting the input intrinsic interval, the output pacing rate is limited. Limiting the smoothed pacing rate may be useful in managing atrial fibrillation or flutter, for example. Methods and systems for providing rate regularization for atrial and ventricular pacing that may be used to implement disordered breathing therapy in accordance with embodiments of the present invention are described in commonly owned U.S. Pat. Nos. 6,351,669, 6,353,759, and 6,285,907, which are incorporated herein by reference.

Sleep Detection

Aspects of the invention that include sleep detection are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that include sleep detection are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 64 (FIG. 1D) for detecting sleep. The sleep detection system 64 may be implemented as a stand alone system or in combination with other individual medical systems, such as those described in FIGS. 1B-1D.

In various embodiments of the invention, a device for detecting sleep includes a first sensor for sensing a first sleep-related signal and a second sensor for sensing a second sleep-related signal, wherein the first and the second sleep-related signals are indicative of sleep. A sleep detector coupled to the first and the second sensors is configured to adjust a sleep threshold associated with the first sleep-related signal using the second sleep-related signal. The sleep detector detects a sleep condition by comparing the first sleep-related signal with the adjusted threshold. A component of one or more of the sleep detector, first sensor, and second sensor is implantable.

In accordance with another embodiment of the present invention, a method for sleep detection involves adjusting a sleep threshold associated with a first sleep-related signal using a second sleep-related signal. The first sleep-related signal is compared to the adjusted threshold and sleep is detected based on the comparison.

Yet another embodiment of the invention includes means for adjusting a sleep threshold of a first sleep-related signal using a second sleep-related signal, means for comparing the first sleep-related signal to the adjusted threshold, and means for detecting sleep based on the comparison.

In further embodiment of the invention, a method for detecting sleep includes sensing a plurality of sleep-related signals. A relationship is defined between at least two of the sleep-related signals, the relationship associated with sleep detection. Sleep is detected using the sleep-related signal relationship. At least one of the sensing and detecting is performed at least in part implantably.

Other embodiments of the invention involve a system for providing coordinated patient monitoring, diagnosis and/or therapy that utilizes sleep detection. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a sleep detection unit 64. The sleep detection unit 64 includes a first sensor configured to sense a first sleep-related signal and a second sensor configured to sense a second sleep-related signal. Sleep detection circuitry coupled to the first and the second sensors is configured to adjust a sleep threshold associated with the first sleep-related signal using the second sleep-related signal, and to detect a sleep condition by comparing the first sleep-related signal with the adjusted threshold, wherein one of the first sensor, second sensor and sleep detector comprises an implantable component, and wherein the implantable cardiac device and the patient-external respiratory therapy device are configured to operate cooperatively based on the detected sleep condition.

The implantable and respiratory therapy devices 181, 184 may operate cooperatively based on sleep detection. For example, a first therapy may be delivered by the patient-external respiratory therapy system while the patient is asleep. A second therapy may be delivered by the implantable cardiac device while the patient is awake. Thus, the therapy burden may be shifted from one device to another device based on the detection of sleep.

Various embodiments of the invention involve the use of sleep information to adapt therapy for disordered breathing. A disordered breathing therapy system, may include a sleep detector. The sleep detector may include circuitry for detecting sleep onset and offset, sleep stages, including REM and non-REM sleep stages, and arousals from sleep, including autonomic arousals.

Collecting information related to sleep involves discriminating between a state of sleep and a state of wakefulness. One method of detecting sleep involves comparing one or more detected physiological conditions to thresholds indicative of sleep. When the detected conditions are consistent with thresholds indicating sleep, then sleep onset is declared. For example, decreased patient activity is a condition associated with sleep. When the patient's activity falls below a predetermined threshold, the system declares the onset of sleep. When the patient's activity rises above the threshold, the system declares the end of sleep. In a similar manner, a number of patient conditions, such as heart rate, respiration rate, brain wave activity, etc., may be compared individually or collectively compared to thresholds or other indices to detect sleep.

A method for detecting sleep in accordance with embodiments of the invention involves adjusting a sleep threshold associated with a first patient condition using a second patient condition. The first patient condition is compared to the adjusted threshold to determine if the patient is asleep or awake.

Figure 24:
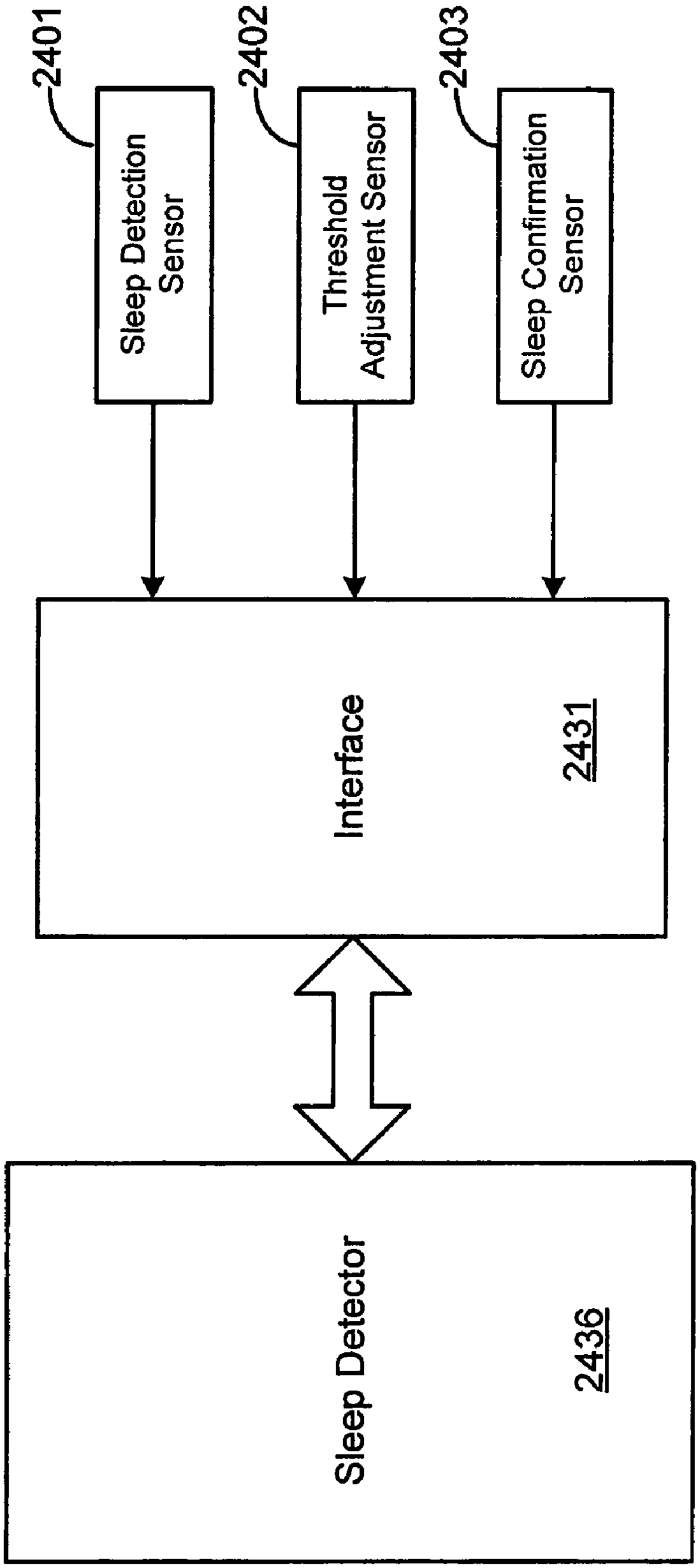
FIG. 24 is a block diagram of a sleep detector that may be used in connection with a therapy system for disordered breathing in accordance with embodiments of the invention.

FIG. 24 illustrates a sleep detector that may be used in connection with a therapy system for disordered breathing. The sleep detector 2436 uses a number of sensors 2401, 2402, 2403 to sense sleep-related patient conditions. A representative set of sleep-related conditions include, for example, patient activity, patient location, posture, heart rate, QT interval, eye movement, respiration rate, transthoracic impedance, tidal volume, minute ventilation, brain activity, muscle tone, body temperature, time of day, and blood oxygen level.

According to embodiments of the invention, a first sleep-related condition detected using a sleep detection sensor 2401 is compared to a sleep threshold for detecting the onset and termination of sleep. A second sleep-related condition, detected using a threshold adjustment sensor 2402, is used to adjust the sleep threshold. Although the example described herein involves one sleep detection sensor 2401 and one threshold adjustment sensor 2402, any number of thresholds or other indices corresponding to a number of sleep detection sensors may be used. Furthermore, conditions detected using any number of adjustment sensors may be used to adjust the thresholds or indices of a plurality of sleep detection signals. Additional sleep-related signals derived from one or more confirmation sensors 2403 may optionally be used to confirm the onset or termination of the sleep condition.

Signals derived from the sensors 2401, 2402, 2403 are received by interface circuitry 2431 that may include, for example, amplifiers, signal processing circuitry, and/or A/D conversion circuitry for processing each sensor signal. The interface circuitry 2431 may further include sensor drive circuitry required to activate the sensors 2401, 2402, 2403.

The sleep detector 2436 is configured to compare the level of a first sleep-related condition detected using the sleep detection sensor 2401 to a sleep threshold adjusted by a second sleep-related condition detected using the threshold adjustment sensor 2402. A determination of sleep onset or sleep termination may be made by the sleep detector 2436 based on the comparison. The onset or termination of sleep may optionally be confirmed using patient conditions derived using a sleep confirmation sensor 2403.

Figure 25:
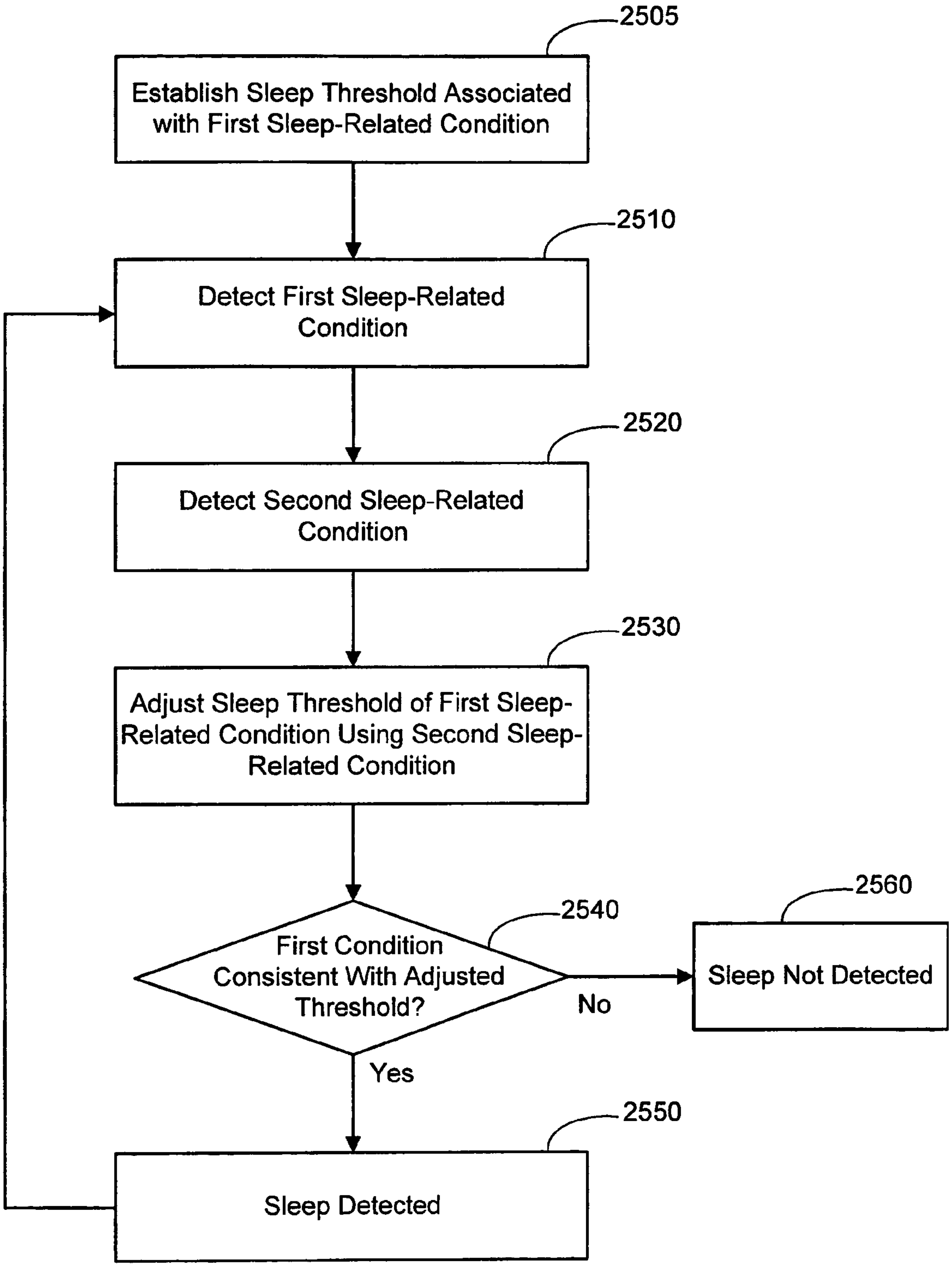
FIG. 25 is a flowchart illustrating a method of detecting sleep according to embodiments of the invention.

FIG. 25 is a flowchart illustrating a method of detecting sleep according to embodiments of the invention. A sleep threshold associated with a first sleep-related patient condition is established 2505. The sleep threshold may be determined from clinical data of a sleep threshold acquired using a group of subjects, for example. The sleep threshold may also be determined using historical data taken from the particular patient for whom the sleep condition is to be detected.

First and second sleep-related conditions are detected 2510, 2520. The first and the second sleep-related conditions may be detected using sensors implanted in the patient, attached externally to the patient or located remote from the patient, for example. The first and the second sleep-related conditions may include any condition associated with sleep and are not limited to the representative sleep-related conditions listed above.

The sleep threshold established for the first sleep-related condition is adjusted using the second sleep-related condition 2530. For example, if the second sleep-related condition indicates a high level of activity that is incompatible with a sleep state, the sleep threshold of the first sleep-related condition may be adjusted downward to require sensing a decreased level of the first sleep-related condition before a sleep condition is detected.

If the first sleep-related condition is consistent with sleep according to the adjusted sleep threshold 2540, sleep is detected 2550. If the first sleep-related condition is not consistent with sleep using the adjusted sleep threshold sleep is not detected 2560. After either sleep is detected or not detected, the first and the second sleep-related conditions continue to be detected 2510, 2520 and the threshold adjusted 2530 allowing further evaluation of the sleep state.

Figure 26:
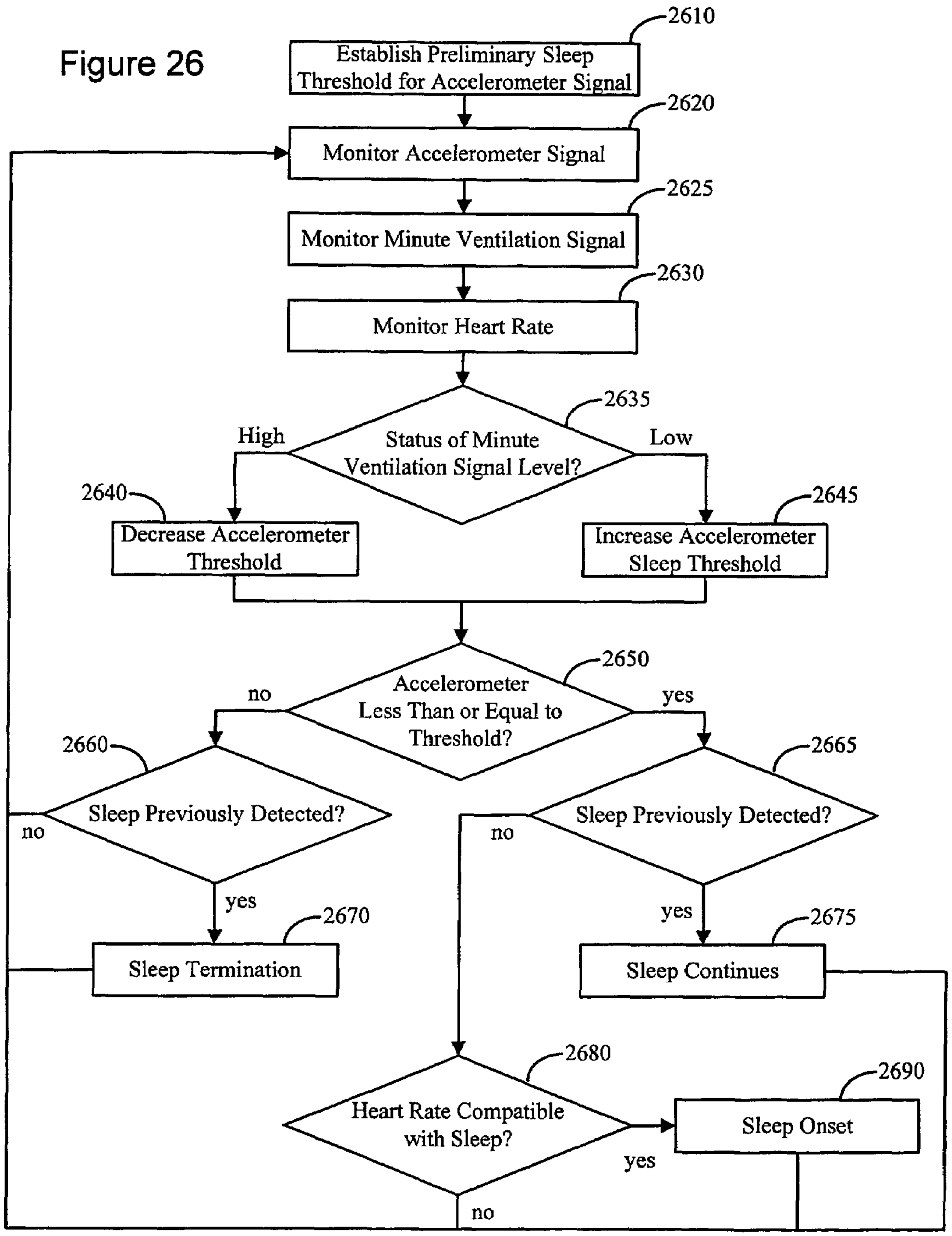
FIG. 26 is a flowchart illustrating a method for detecting sleep using accelerometer and minute ventilation signals according to embodiments of the invention.

The flow chart of FIG. 26 illustrates a method for detecting sleep using accelerometer and minute ventilation (MV) signals according to embodiments of the invention. In the method illustrated in FIG. 26, an accelerometer and a minute ventilation sensor are used to detect patient activity and patient respiration conditions, respectively. A preliminary sleep threshold is determined 2610 with respect to the patient activity condition sensed by the accelerometer. The preliminary sleep threshold may be determined from clinical data derived from a group of subjects or from historical data taken from the patient over a period of time.

The activity condition of the patient is monitored 2620 using an accelerometer that may be incorporated in an implantable cardiac rhythm management system. Alternatively, the accelerometer may be attached externally to the patient. The patient's MV condition is monitored 2625, for example, using a transthoracic impedance sensor. A transthoracic impedance sensor may be implemented as a component of an implantable CRM device.

In this embodiment, the patient's activity represents the sleep detection condition and is compared to the sleep threshold. The patient's MV is used as the threshold adjustment condition to adjust the sleep threshold. In addition, in this example, the patient's heart rate is monitored 2630 and used to provide a sleep confirmation condition.

The sleep threshold adjustment is accomplished using the patient's MV condition to adjust the activity sleep threshold. If the patient's MV condition is low relative to an expected MV level associated with sleep, the activity sleep threshold is increased. Similarly, if the patient's MV level is high relative to an expected MV level associated with sleep, the activity sleep threshold is decreased. Thus, when the patient's MV level is high, less activity is required to make the determination that the patient is sleeping. Conversely when the patient's MV level is relatively low, a higher activity level may result in detection of sleep. The use of two sleep-related conditions to determine the patient's sleep state enhances the accuracy of sleep detection over previous methods.

Various signal processing techniques may be employed to process the raw sensor signals. For example, a moving average of a plurality of samples of the sensor signals may be calculated. Furthermore, the sensor signals may be amplified, filtered, digitized or otherwise processed.

If the MV level is high 2635 relative to an expected MV level associated with sleep, the activity sleep threshold is decreased 2640. If the MV level is low 2635 relative to an expected MV level associated with sleep, the activity sleep threshold is increased 2645.

If the patient's activity level is less than or equal to the adjusted sleep threshold 2650, and if the patient is currently not in a sleep state 2665, then the patient's heart rate is checked 2680 to confirm that the patient is asleep. If the patient's heart rate is compatible with sleep 2680, then sleep onset is determined 2690. If the patient's heart rate is incompatible with sleep, then the patient's sleep-related conditions continue to be monitored.

If the patient's activity level is less than or equal to the adjusted sleep threshold 2650 and if the patient is currently in a sleep state 2665, then a continuing sleep state is determined 2675 and the patient's sleep-related conditions continue to be monitored for sleep termination to occur.

If the patient's activity level is greater than the adjusted sleep threshold 2650 and the patient is not currently in a sleep state 2660, then the patient's sleep-related conditions continue to be monitored until sleep onset is detected 2690. If the activity level is greater than the adjusted sleep threshold 2650 and the patient is currently in a sleep state 2660, then sleep termination is detected 2670.

Figure 27:
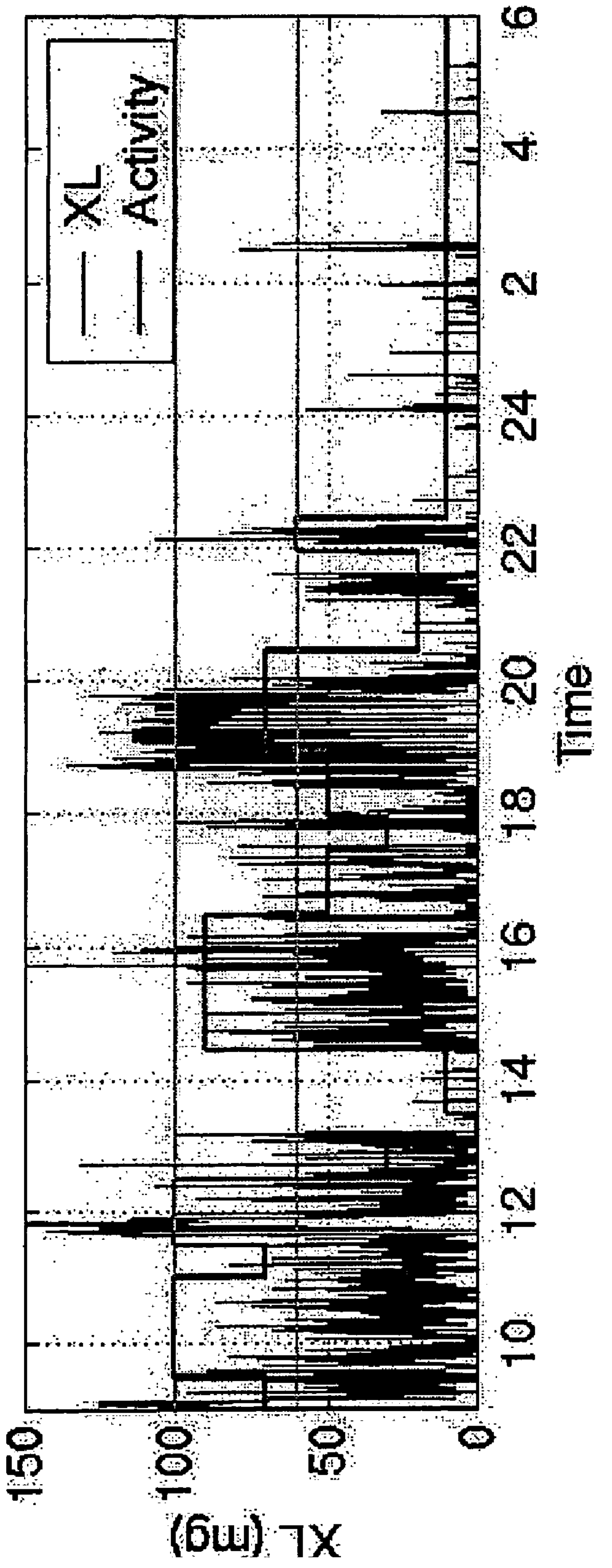
FIGS. 27 and 28 are graphs illustrating a patient's activity and heart rate, respectively.
Figure 28:
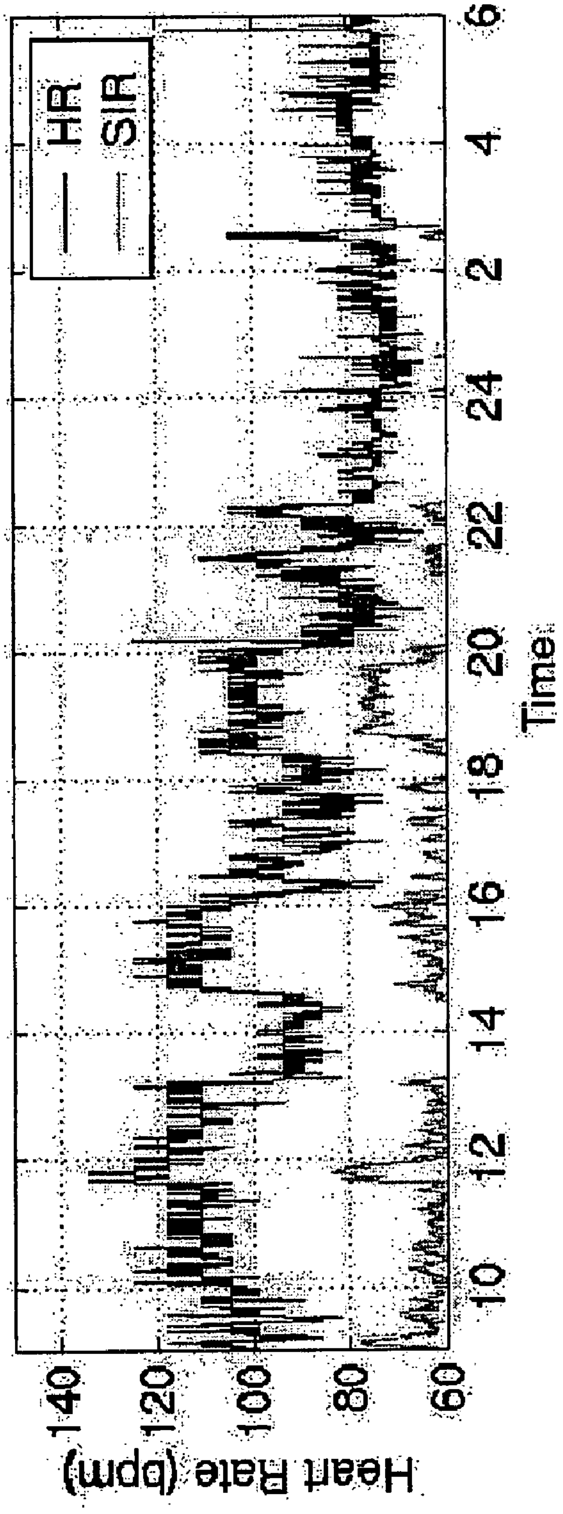

The graphs of FIGS. 27-30 illustrate the adjustment of the activity sleep threshold. The relationship between patient activity and the accelerometer and MV signals is trended over a period of time to determine relative signal levels associated with sleep. The graph of FIG. 27 illustrates the patient's activity as indicated by an accelerometer. The patient's heart rate (HR) and sensor indicated heart rate (SIR) for the same period are shown in the graph of FIG. 28. The accelerometer signal indicates a period of sleep associated with a relatively low level of activity beginning slightly before 23:00 and continuing through 6:00. The patient's heart rate appropriately tracks the activity level indicated by the accelerometer indicating a similar period of decreased heart rate corresponding to sleep. The signal level of the accelerometer during known periods of sleep may be used to establish a threshold for sleep detection.

Figure 29:
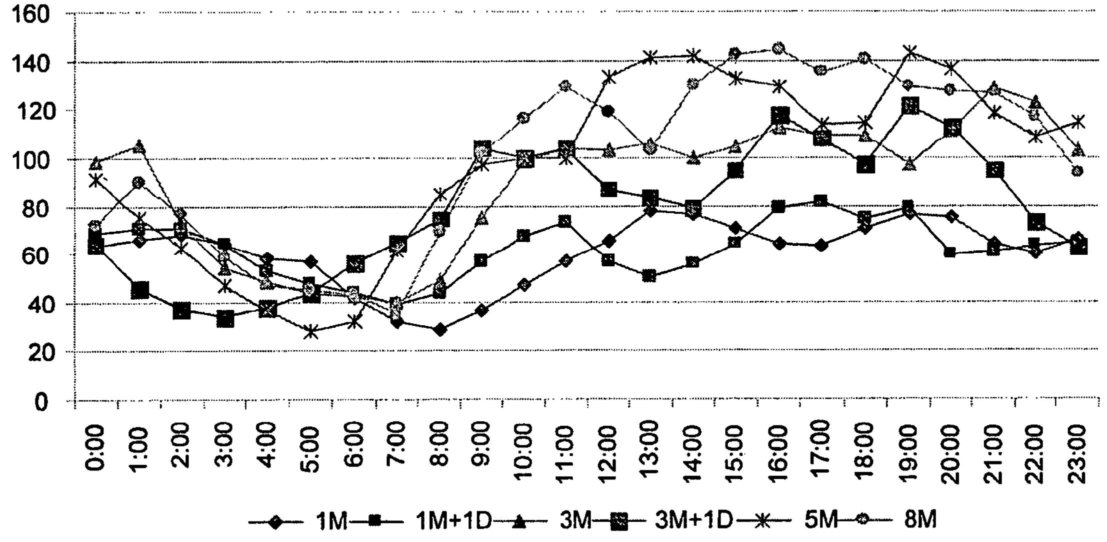
FIG. 29 is a graph of the patient's minute ventilation signal.

FIG. 29 is a graph of the patient's minute ventilation signal over time. Historical data of averaged minute ventilation is graphed to indicate variations over a 24 hour period. MV data is shown for averages of 1 month to 8 months. The minute ventilation data may be used to determine the minute ventilation signal level associated with sleep. In this example, a composite minute ventilation graph using the historical data presents a roughly sinusoidal shape with the relatively low minute ventilation levels occurring during the period approximately from hours 21:00 through 8:00. The decreased minute ventilation level is associated with periods of sleep. The minute ventilation level associated with sleep is used to implement sleep threshold adjustment.

Figure 30:
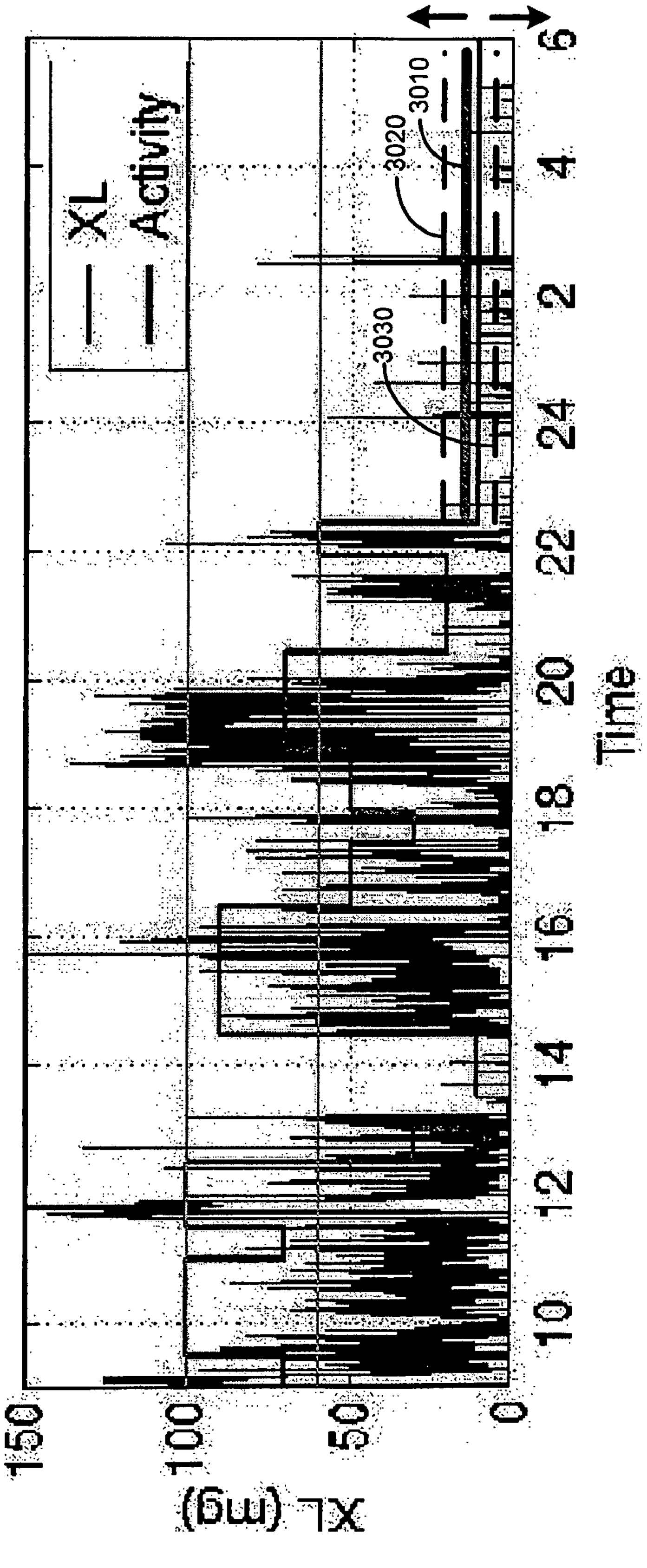
FIG. 30 illustrates adjustment of the activity sleep threshold in accordance with embodiments of the invention.

FIG. 30 illustrates adjustment of the activity sleep threshold using the MV data. The initial sleep threshold 3010 is established using the baseline activity data acquired as discussed above. If the patient's MV level is low relative to an expected MV level associated with sleep, the activity sleep threshold is increased 3020. If the patient's MV level is high relative to an expected MV level associated with sleep, the activity sleep threshold is decreased 3030. When the patient's MV level is high, less activity detected by the accelerometer is required to make the determination that the patient is sleeping. However, if the patient's MV level is relatively low, a higher activity level may result in detection of sleep. The use of two sleep-related signals to establish and adjust a sleep threshold enhances the accuracy of sleep detection over previous methods.

Additional sleep-related conditions may be sensed and used to improve the sleep detection method described above. For example, a posture sensor may be used to detect the posture of the patient and used to confirm sleep. If the posture sensor signal indicates an upright posture, then the posture sensor signal may be used to override a determination of sleep using the sleep detection and threshold adjustment conditions. Other conditions may also be used in connection with sleep determination or confirmation, including the representative set of sleep-related conditions indicated above. In another example, a proximity to bed sensor may be used alone or in combination with a posture sensor to detect that the patient is in bed and is lying down.

A sleep detection system may detect sleep onset, termination, arousals as well as the sleep stages, including REM and non-REM sleep. REM sleep may be discriminated from NREM sleep, for example, by examining one or more signals indicative of REM, e.g., muscle atonia, rapid eye movements, or EEG signals. Various conditions indicative of sleep state may be detected using sensors, e.g., electroencephalogram (EEG), electrooculogram (EOG), or electromyogram (EMG) sensors, coupled through wired or wireless connections to the sleep detection circuitry. The sleep detection circuitry may analyze the various patient conditions sensed by the sensors to track the patient's sleep through various sleep states, including REM and NREM stages.

Sleep Stage Detection

Aspects of the invention that include sleep stage detection are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving sleep stage detection are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 060 (FIG. 1D) for detection sleep stage. The sleep detector 60 may be implemented as a stand alone system or in combination with other individual medical systems, such as those described in FIGS. 1B-1D.

Various embodiments of the invention are directed to classifying various sleep states. In one embodiment of the invention, a method involves sensing sleep-related conditions and using the detected sleep-related signals to classify one or more sleep states of a patient. The sleep-related conditions include at least one REM-modulated condition and at least one condition associated with a sleep-wake status of the patient. Classifying the one or more sleep states is performed at least in part implantably.

Another embodiment of the invention involves sensing a REM-modulated condition and using the REM-modulated condition to classify one or more sleep states. Classifying the one or more sleep states is performed at least in part implantably.

In a further embodiment of the invention, a medical system includes a detector system, having a sensor configured to sense a condition associated with REM sleep. The medical system further includes a classification system coupled to the sensor system and configured to classify one or more sleep states based on the condition associated with REM sleep. The classification system includes an implantable component.

In yet another embodiment of the invention, a medical system involves means for detecting conditions related to sleep, including a condition associated with a sleep-wake status of a patient and a condition associated with REM sleep. The system further includes means for classifying one or more sleep states based on the detected conditions. The means for classifying includes an implantable component.

In a further embodiment, a medical system includes means for sensing a condition associated with REM sleep and means for classifying a one or more sleep states based on the detected condition associated with REM sleep. The means for classifying the one or more sleep states includes an implantable component.

Another embodiment of the invention involves a system for providing coordinated patient monitoring, diagnosis and/or therapy that utilizes sleep stage classification 60. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy further includes a system 60 configured to detect sleep stage. The sleep stage system includes a detector system comprising a sensor configured to detect a condition associated with REM sleep. A classification system is coupled to the detector system and configured to classify one or more sleep stages based on the one or more sleep-related conditions. The classification system includes an implantable component. The implantable cardiac device and the patient-external respiratory device operate cooperatively based on the sleep stage classification. Systems and methods directed to sleep state classification may be implemented to include selected features, functions, and/or structures described in commonly owned, co-pending U.S. Publication No. 2005/0043652, which is hereby incorporated herein by reference.

Sleep and its various states have been linked to an increase in respiratory and cardiac disorders, particularly for patients with cardiopulmonary disorders. For example, some epidemiologic studies note a peak incidence of sudden cardiac death around 5 to 6 am. One explanation for this peak suggests an association between the incidence of sudden death and episodes of rapid eye movement (REM) sleep, morning wakening or arousal. The mechanism eliciting fatal arrhythmia may be related to the intense phasic sympathetic modulation of the cardiovascular system during the REM state or morning wakening.

Non-REM sleep may also be linked to an increased likelihood of cardiac arrhythmia. Some patients are predisposed to nocturnal cardiac paroxysms associated with surges in vagal activity. Because non-REM sleep is associated with conditions of "vagal dominance," characterized by lower heart rate and low-to-high frequency power ratios, non-REM sleep may be implicated in these nocturnal arrhythmias.

Sleep may also be associated with increased respiratory disruptions. Variations in disease, medication, etiology, and phenotype may all contribute to a patient's sleep state propensities to cardiac or respiratory disorders. Sleep stage classification may be used to provide more effective therapy, better diagnostic information, and improved prognostic and preventive therapy capabilities. Sleep stage classification in concert with therapy may result in improved therapy management for both cardiac and respiratory conditions, such as those described above. Tracking physiological changes during sleep may also provide a mechanism for improved diagnosis of sleep-related disorders.

Diagnostic testing or therapeutic device testing may be advantageously performed during sleep or during particular sleep stages. Diagnostic testing may involve, for example, assessing the patient's autonomic integrity during sleep and the possible use of REM episodes as a surrogate for stress testing. Performing diagnostic procedures during sleep recognizes opportunities afforded by sleep or particular sleep stages to routinely perturb the cardiovascular system under controlled conditions to assess the patient's autonomic response.

Therapeutic device testing, such as AVI search, capture threshold, and cardiac template acquisition, may also be performed during sleep. Sleep provides a period of time to perform such therapeutic device tests while the patient's activity is low, resulting in more effective and consistent testing conditions.

Various embodiments of the invention involve sensing a physiological condition associated with REM sleep and using the REM condition to classify the patient's sleep stages. REM-modulated conditions represent a group of physiological conditions that change during REM sleep and may be used to discern REM sleep from non-REM periods. REM sleep, as indicated by its name, is characterized by rapid bursts of eye movements, intense brain activity, and a general state of atonia, or skeletal muscle paralysis.

Various embodiments of the invention exploit the marked loss of skeletal muscle tone during REM to produce a REM-modulated signal. In this implementation, sensing a REM-modulated signal involves sensing the patient's skeletal muscle tone. Other REM-modulated signals may be used to detect REM sleep, including, for example, eye movement and brain wave activity. A representative set of sensors that may be used to sense REM-modulated signals include, for example, electroencephalogram (EEG) electrodes for detecting brain activity, electrooculogram (EOG) sensors for detecting eye movement, sensors for detecting muscle atonia, including electromyogram (EMG) sensors, strain gauge sensors, piezoelectric sensors, mechanical force sensor, or other transducers.

Sensing a condition associated with REM sleep may be used to discern REM sleep periods from non-REM periods. Sleep stage classification may be further enhanced by detecting a condition associated with a sleep-wake status of the patient, the condition associated with the sleep-wake status indicating whether the patient is asleep or awake.

According to embodiments of the invention, a sleep stage classification approach involves sensing sleep-related conditions, including at least one condition modulated by the sleep-wake status of the patient and a REM-modulated condition. The condition modulated by the sleep-wake status of the patient represents a condition that may be used to discriminate between periods of sleep and periods of wakefulness or arousal. Discriminating between periods of sleep and periods of wakefulness may be accomplished, for example, by sensing patient activity. According to this approach, if the patient's activity level is relatively low, e.g., below a sleep threshold, then the patient is determined to be asleep. The level of patient activity may be detected using an accelerometer, heart rate sensor, respiratory minute ventilation (MV) sensor or other types of sensors, for example.

Information derived from the REM-modulated condition may be used in combination with information related to the patient's sleep-wake status. This technique may be used to determine, for example, sleep onset and sleep offset, the duration and degree of arousals from sleep, and to classify sleep stages including REM and non-REM states.

In accordance with embodiments of the invention, a sleep stage classification processor receives the outputs of the one or more sensors configured to sense signals associated with the sleep-related conditions. The sleep stage processor may perform sleep stage classification on a real-time basis, or may process previously acquired and stored sensor data in a batch mode to retrospectively classify the sleep stages of one or more sleep periods.

Sleep stage classification may involve an adaptive approach, wherein the sleep stage processor learns the physiological responses of a patient in various sleep stages. The learned responses may be used to enhance the accuracy and/or sensitivity of the sleep stage classification. Adaptive sleep stage classification may involve monitoring the changes in one or more physiological signals over a period of time and adjusting thresholds used for determining sleep onset, sleep offset, and various sleep stages to accommodate the drift or other changes in the sleep-related signals.

In one configuration, one or more of the sensors used to detect the sleep-related conditions, e.g., the REM-modulated condition and/or the condition associated with the patient's sleep-wake status, may be implantable, or may utilize an implantable component. In another configuration, the sleep stage processor may be partially or fully implantable. In other configurations, both the sensors and the sleep stage processor may be implantable or use implantable components.

As previously discussed, sleep stage classification may be useful in coordinating sleep stage informed therapy delivery to treat various disorders and to perform sleep stage informed testing and monitoring. In one example implementation, cardiac therapy may be triggered during particular sleep stages to reduce the likelihood of cardiac arrhythmia during vulnerable sleep periods. In a similar manner, sleep stage classification may be used to trigger disordered breathing therapy to preclude or reduce episodes of sleep-disordered breathing.

Figure 109A:
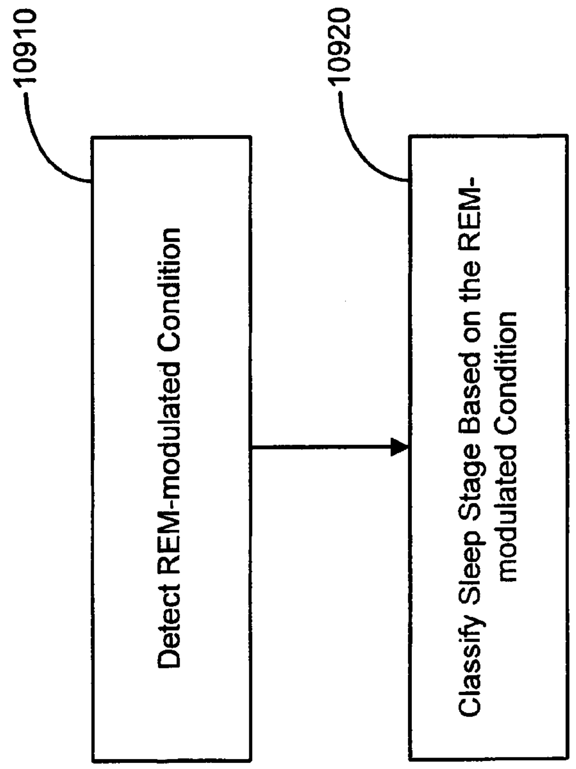

The flow graph of FIG. 109A depicts a method of classifying sleep stages according to embodiments of the invention. A REM-modulated condition e.g., brain activity, eye movement, and/or muscle atonia, is detected 10910 and is used to classify 10920 the patient's sleep stage. Using the detected REM-modulated condition, the system may determine that the patient is in a REM sleep stage or in a non-REM period, for example.

Figure 109B:
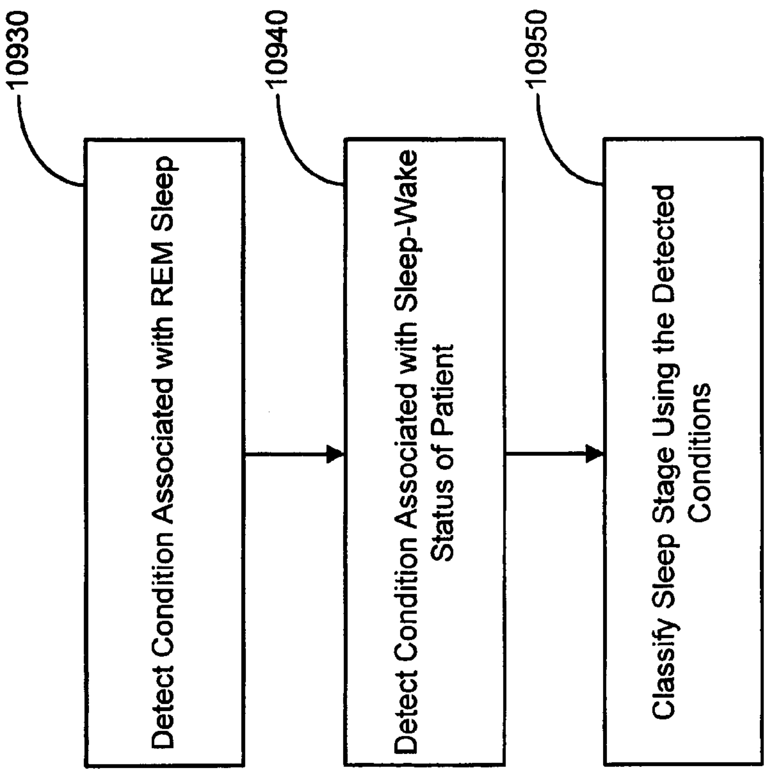

Another method for classification of sleep stages in accordance with embodiments of the invention is illustrated in the flow graph of FIG. 109B. The method involves detecting sleep-related conditions including at least one REM-modulated condition 10930 and at least one condition 10940 associated with a sleep-wake status of the patient. Sleep stage classification is performed 10950 based on the detected conditions.

Figure 110:
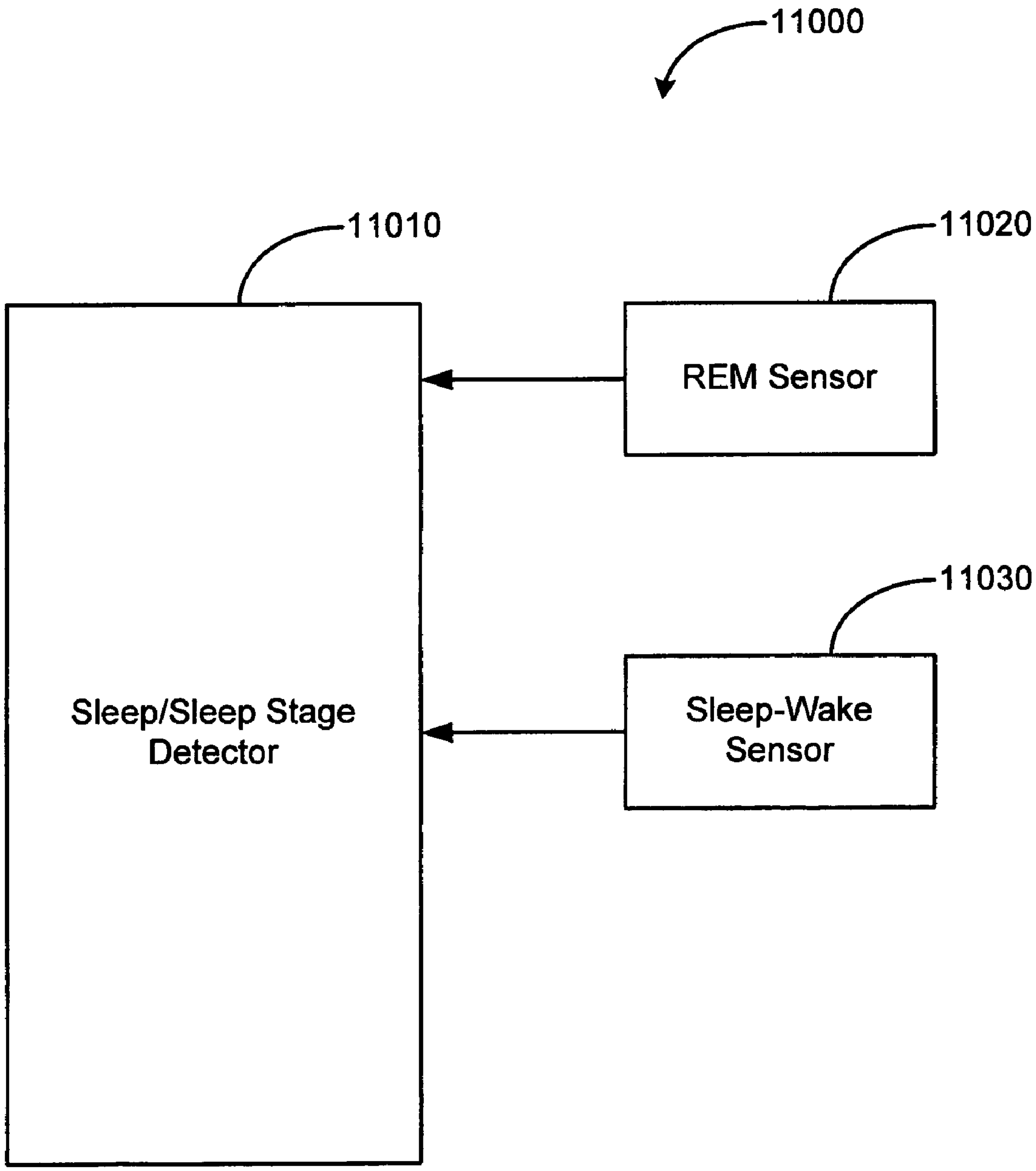

A block diagram of a system 11000 suitable for implementing a sleep stage classification method according to embodiments of the invention is illustrated in FIG. 110. The sleep stage classification system 11000 may include one or more sensors 11030 used to sense a physiological signal associated with the sleep-wake status of the patient. In one example implementation, the sleep-wake sensor 11030 may be responsive to patient activity. When the patient's activity falls below a threshold, the patient is considered to be asleep. When the patient's activity rises above the activity threshold, the patient is considered to be awake. Other methods of detecting whether the patient is asleep or awake are also possible.

The system further includes a REM sensor 11020 sensitive to a REM-modulated physiological condition. REM sleep detection may be implemented by comparing the output of a skeletal muscle tone sensor to a threshold, for example. When the REM sensor output indicates loss of muscle tone consistent with a REM sleep threshold, the patient is determined to be in REM sleep. The sleep-wake sensor 11030 and the REM sensor 11020 may optionally be used in cooperation with additional sensors employed to detect additional sleep-related conditions. The additional sleep-related conditions may be used to augment the accuracy, sensitivity, or other functional capabilities, of the sleep stage classification system 11000. For example, a patient posture or torso orientation sensor may be used in combination with a patient activity sensor to provide enhanced detection of the sleep-wake status of the patient. If the patient's activity is low, as indicated by the output of a patient activity sensor, and the patient is lying down, as indicated by the output of a torso orientation sensor, then the combination of the two conditions may allow for more accurate sleep onset detection.

The REM sensor 11020, the sleep-wake status sensor 11030, and any additional sensors are coupled to a sleep/sleep stage detector 11010 that detects and processes the sensor outputs. The sleep/sleep stage detector 11010 may use outputs from the sleep-wake sensor 11930 and the REM sensor 11020 to determine if the patient is awake or asleep, to determine the duration and degree of arousals from sleep, to classify sleep stages including REM and non-REM states, and to determine the duration of various sleep stages, for example.

In one embodiment, one or both the REM sensor 11020 and the sleep-wake sensor 11930 are positioned external to the patient and the sleep/sleep stage detector 11010 is implantable or includes an implantable component. In another embodiment, one or both the REM sensor 11020 and the sleep-wake sensor 11030 are fully or partially implantable and the sleep/sleep stage detector 11010 is positioned externally to the patient. In yet another embodiment, the REM sensor 11020, sleep-wake sensor 11030, and the sleep/sleep stage detector 11010 all include implantable components or are fully implantable.

Components of the sleep stage classification system 11000 may employ wireless communications. For examples, the REM sensor 11020 and sleep-wake sensor 11030 may be coupled to the sleep/sleep stage detector 11010 using a wireless communications link. In one example, some or all of the sensors 11020, 11030 use remote communication capabilities, such as a wireless proprietary or a wireless Bluetooth communications link.

The sleep/sleep stage detector 11010 may adaptively classify sleep stages by learning patient responses in connection with various sleep stages. In one example, the sleep/sleep stage detector 11010 may perform sleep stage classification by comparing sensor signal levels to predetermined thresholds. Initial thresholds may be established using clinical data derived from a group of individuals, or using patient-specific data. After initial thresholds have been established, the sleep/sleep stage detector 11010 may update the thresholds to provide more sensitive and/or more accurate sleep stage classification based on data acquired from the patient over time. A sleep stage threshold may be updated by a recent history of the sensor output level associated with a particular sleep stage. This process may involve collecting data over time to determine the sleep patterns of the patient and adjusting the thresholds based on the sleep patterns. By this process, initially established thresholds, e.g., sleep onset threshold for an accelerometer output, or REM sleep threshold for an EMG sensor output, may be modified as additional data is acquired from the patient regarding the relationship between the sensor output levels and patient's sleep stage.

FIG. 111 presents a block diagram illustrating sleep stage discrimination circuitry 11100 utilizing a sleep stage classification system implemented in accordance with embodiments of the invention. Sleep stage discrimination circuitry 11100 may be employed, for example, to perform sleep stage informed diagnostic monitoring and/or diagnostic testing to assess the capabilities of the patient's physiological systems. Such diagnostic monitoring or testing may involve one or more physiological systems, including, for example, the cardiac and respiratory systems. Additionally, or alternatively, the sleep stage discrimination circuitry 11100 may be used to provide sleep stage informed therapy to a patient, for example, cardiac rhythm therapy, respiratory therapy, or other types of therapy enhanced by sleep stage classification. Further, the sleep stage discrimination circuitry 11100 may be used to perform sleep stage informed therapeutic device testing. Uses of the sleep stage discrimination circuitry 11100 may be purely or predominantly diagnostic, purely or predominantly therapeutic, or may include a combination of therapeutic and diagnostic operations.

The sleep stage discrimination circuitry 11100 includes a medical device 11101 coupled to a variety of sensors 11105, 11110, 11115. The sensors 11105, 11110, 11115 provide physiological information used in connection with sleep stage classification and the therapeutic and/or diagnostic operations performed by the medical device 11101. The sleep stage sensors 11105 include a sensor capable of detecting a REM-modulated condition, such as skeletal muscle atonia. Additional sleep stage sensors, including one or more sensors indicative of the sleep-wake status of the patient, e.g., a patient activity sensor, may also be used.

The medical device 11101 may also be coupled to sensors 11110, 11115 configured to detect one or more aspects of the patient's physiological systems, including, for example, the cardiac and/or respiratory functions of a patient. In various configurations, the medical system 11100 may monitor, test, or provide therapy to the patient, including cardiac and/or respiratory therapy. In one implementation, cardiac sensors 11115, e.g., cardiac electrodes, may be used to sense the electrical activity of the heart. The cardiac system sensors may comprise patient-internal or patient-external cardiac electrodes electrically coupled to the patient's heart tissue, for example.

The medical device 11101 may be coupled to one or more respiratory system sensors 11110 capable of detecting conditions associated with the respiratory functions of the patient. In one embodiment, the respiratory functions of the patient may be monitored using a transthoracic impedance sensor. Transthoracic impedance tracks the patient's respiratory effort, increasing upon respiratory inspiration and decreasing upon respiratory expiration. The transthoracic impedance signal may be used to determine the patient's respiration tidal volume (TV), minute ventilation (MV), and/or other respiratory parameters, for example. Sensors other than, or in addition to, the cardiac and respiration system sensors described herein may be used to detect cardiac and/or respiration functions of the patient.

The sleep/sleep stage detector 11120 uses information from the sleep stage sensors 11105 to determine the states of the patient's sleep, including, for example, sleep onset, termination, REM and non-REM states. Information generated by the sleep/sleep stage detector 11120 may be used by other components of the medical device 11101 to provide therapy, testing, and/or monitoring coordinated with the patient's sleep stage.

Sleep stage information may be provided to a therapy module 11130 coupled to the sleep/sleep stage detector 11120. The therapy module 11130 controls the delivery of sleep stage informed therapy to the patient. For example, cardiac therapy may be coordinated using sleep stage classification information to provide cardiac arrhythmia therapy during REM or other proarrhythmic sleep periods. Sleep stage classification may also be used, for example, in connection with delivery of sleep informed therapy to preclude or reduce episodes of disordered breathing while the patient is asleep. Other types of therapy may also be enhanced using sleep stage classification.

The sleep/sleep stage detector 11120 may be coupled to a monitoring unit 11150 configured to collect and store historical data acquired from the sleep stage sensors 11105, respiratory system sensors 11110, the cardiac system sensors 11115, and/or other components of the medical device 11101. The monitoring unit 11150 may track one or more patient conditions and provide data used in the analysis of various physiological processes. The monitoring module 11150 may collect data useful in assessing trends of various physiological systems. Trending data may be used in combination with sleep stage classification to identify gradual changes in the patient's physiological conditions, especially those altered by sleep, or by particular sleep stages.

A testing module 11140 may be implemented within the medical device 11101 to control diagnostic tests and/or to control device testing to maintain or improve the operation of the medical device 11101. Information from the sleep/sleep stage detector 11120 is used by the testing module 11140 to ensure that diagnostic and/or device testing appropriately coincides with a sleep or waking state of the patient, or to a particular state of sleep.

Diagnostic testing may be employed to investigate the functioning of one or more of the patient's physiological systems. Diagnostic testing may include changing one or more parameters of the patient's therapy, e.g., cardiac rhythm therapy, and assessing the impact of the change on the patient. For example, the patient's therapy regime may be altered during sleep, or during a particular sleep stage, to determine the effect of the change on the patient.

A diagnostic testing methodology may use sleep stage classification to determine the general behavior of the patient's physiological responses in connection with various sleep stages. Such a process may involve determining the patient's intrinsic responses to normal variations in physiologic processes. In addition, the patient's evoked physiological responses to device-based stimuli may also be determined.

In one implementation of sleep coordinated diagnostic testing, non-REM sleep may present an opportunity to perform automatic or physician activated diagnostic testing under relatively controlled circumstances. The medical device 11101 may perform diagnostic testing during non-REM sleep when the patient's activity is low. In one configuration, the medical device 11101 may modify or implement a particular cardiac pacing regimen during a non-REM period to determine the effect of such modification on the patient's cardiac system.

In addition to diagnostic testing, various device testing procedures may preferably be conducted while the patient's activity is low, such as during non-REM sleep. For example, a medical device 11101 providing cardiac rhythm management therapy may perform device testing to improve or modify a pacing regimen during the non-REM sleep state. In one implementation, a pacemaker may perform tests during non-REM sleep to optimize a pacing escape interval, such as the AV delay of a dual chamber or bi-ventricular device. In another example, a pacemaker may adjust pacing energy levels based on a capture threshold test performed during non-REM sleep. In yet another embodiment, a cardiac rhythm management system may use non-REM sleep as an opportune period of low patient activity to acquire or update cardiac waveform morphological templates used to identify various cardiac arrhythmias.

The flow graph of FIG. 112 illustrates a method of performing sleep stage classification in accordance with embodiments of the invention. The method involves detecting 11210 at least one REM-modulated signal, e.g., a signal modulated by muscle atonia. If the REM-modulated signal is consistent 11220 with a predetermined REM sleep threshold, then the system determines if REM sleep onset has previously been declared 11230. If REM sleep onset was not previously declared 11230, then the system declares REM sleep onset 11250.

If the REM-modulated signal is not consistent 11220 with the predetermined REM sleep threshold and REM sleep onset was previously declared 11260, then REM sleep offset is declared 11270. If the REM-modulated signal is not consistent 11220 with the REM sleep threshold and REM onset was not previously declared 11260, the system continues to sense 11210 the REM-modulated signal to detect REM sleep onset.

The flow graph of FIG. 113 illustrates a method of using a sleep-wake condition in combination with a REM-modulated condition to classify sleep stages according to embodiments of the invention. According to this implementation, the system determines sleep onset and sleep offset by comparing a patient activity signal to a threshold. Various methods of sleep onset and sleep offset detection, for example, the methodologies described herein may be used in connection with the sleep stage classification approaches of the present invention.

The method illustrated in FIG. 113 involves determining REM sleep onset and offset using a REM-modulated signal. REM sleep periods may be classified as intervals between REM onset and offset. Non-REM sleep periods may be classified as intervals between sleep onset and offset that are not classified as REM sleep.

A signal related to the activity level of the patient, e.g., accelerometer signal, is detected 11305 and compared 11310 to a predetermined sleep threshold. If the patient's activity level is consistent 11310 with the sleep threshold, and if sleep onset was previously declared 11315, the system detects 11325 a REM-modulated signal. If the patient's activity level is not consistent 11310 with a sleep threshold and if sleep onset was previously declared 11345, then sleep offset is declared 11350. If the patient's activity level is consistent 11310 with the sleep threshold and if sleep onset was not previously declared 11315, the system declares sleep onset 11320 and senses 11325 the REM-modulated signal.

If the REM-modulated signal level is consistent 11330 with a REM sleep threshold, and REM sleep onset 11335 was not previously declared, then REM sleep onset is declared 11340. If the REM-modulated signal level is not consistent 11330 with the REM sleep threshold and REM onset was previously declared 11355, then REM sleep offset is declared 11360.

Using the method illustrated in FIG. 113, sleep onset, offset, REM, and non-REM sleep may be detected. Periods of REM and/or non-REM sleep may be advantageously used in connection with a number of diagnostic and therapeutic operations, as previously discussed. FIG. 114 is a process flow diagram illustrating a process for using sleep stage classification in cooperation with therapy delivery and testing in accordance with embodiments of the invention.

As presented in the process flow diagram of FIG. 114, the system detects 11460 cardiac signals and analyzes 11450 the cardiac signals on a beat-to-beat basis. Beat-to-beat cardiac signal analysis 11450 may be used to perform arrhythmia detection 11465 based on rate and/or morphological analysis techniques, for example. Depending on the type of arrhythmia detected, if any, an appropriate therapy 11475 may be delivered to the heart. In one implementation, bradycardia pacing therapy may be delivered to the heart to maintain the patient's rhythm at a hemodynamically sufficient rate. In other examples, a variety of tiered tachyarrhythmia therapies, including, for example, anti-tachycardia pacing, cardioversion, and/or defibrillation may be available to treat detected cardiac tachyarrhythmias.

The illustrative system utilizes REM-modulated and sleep/wake condition signals 11405 for sleep stage classification 11410. Sleep stage classification 11410 may be used in cooperation with the beat-to-beat cardiac signal analysis 11450 to implement sleep stage informed arrhythmia analysis 11455, thus augmenting the delivery of cardiac arrhythmia therapy 11475. In one example, bradycardia pacing therapy may be enhanced by the ability to switch to a lower pacing rate when the patient is determined to be asleep. Such a procedure may be advantageous, for example, both to increase the device lifetime and to reduce stress on the heart. In a further example, preventive arrhythmia therapy 11475 may be delivered during sleep or based on prediction of future arrhythmic events, e.g., upon detection of a pro-arrhythmic sleep stage 11465. In one example, preventive arrhythmia therapy may be delivered to prevent tachyarrhymias known to occur more frequently during REM sleep or during arousal from sleep.

Sleep stage classification may also be used in connection with therapy to terminate or prevent sleep-disordered breathing. Various therapies may be implemented to treat sleep-disordered breathing, including maintaining continuous positive air pressure to prevent collapse of tissue into the respiratory passage, electrical stimulation of nerves or muscles, and cardiac pacing therapy, for example. Because disordered breathing is more likely to occur when the patient is asleep, disordered breathing detection or prediction 11432 may be augmented by employing sleep stage informed respiratory analysis 11425 in accordance with embodiments of the present invention.

Detection of disordered breathing may be accomplished by detecting 11430 respiration signals representing the patient's breathing cycles and analyzing each breath 11420. In one implementation, disordered breathing, including, e.g., hypopnea and apnea, may be detected 11432 by monitoring the respiratory waveform output produced by a transthoracic impedance sensor.

When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Another method of detecting 11432 disordered breathing involves analyzing the patient's respiratory patterns. According to this method, the patient's respiratory cycle is divided into several periods, including, inspiration, expiration, and non-breathing periods. The inspiration, expiration, and non-breathing respiratory periods are analyzed for patterns consistent with various types of disordered breathing.

As described herein, sleep-disordered breathing may be predicted based on a number of patient conditions that increase the likelihood of disordered breathing. Conditions that predispose the patient to disordered breathing include, for example, air pollution, alcohol use, and pulmonary congestion, among other conditions. In addition to predisposing conditions that make disordered breathing more likely, various precursor conditions may be used to determine that a disordered breathing episode is imminent. For example, blood chemistry, hyperventilation, and the regular periodicity of previous disordered breathing episodes may be used to predict an imminent onset of disordered breathing. If disordered breathing is detected or predicted 11432, an appropriate therapy 11434 may be provided to terminate or prevent the disordered breathing.

Sleep stage classification 11410 may also be used to identify preferable periods of time for performing 11485 various testing procedures, including, for example, diagnostic testing and/or testing of therapeutic device parameters. In various implementations, sleep stage informed diagnostic testing may allow testing to assess the patient's autonomic integrity. Sleep stage classification may further allow the use of REM episodes as a surrogate for stress testing, and recognition of opportunities to routinely perturb the cardiovascular system under controlled conditions.

Sleep stage classification also provides an opportunity to test one or more parameters of a therapeutic device while the patient's activity is low. Such testing may involve, for example, capture threshold testing for a cardiac pacing device and cardiac signal morphology template acquisition to be used in connection with cardiac arrhythmia detection. Thus, sleep stage classification may be used to provide more effective therapy, better diagnostic information, and improved prognostic and predictive capabilities.

FIG. 115 illustrates a medical system that may be used to perform sleep stage informed therapy in accordance with embodiments of the invention. The block diagram of FIG. 115 shows the medical system 11500 divided into functional blocks. It will be appreciated by those skilled in the art that there exist many possible configurations in which these functional blocks can be arranged and implemented. The example depicted in FIG. 115 is one possible functional arrangement.

FIG. 115 illustrates an implantable cardiac pulse generator 11501 enclosed in a housing 11590 and configured to provide therapy for cardiac arrhythmia. Various cardiac electrical therapies, including therapy for disordered breathing and cardiac rhythm therapies, including bradycardia pacing, anti-tachycardia pacing, defibrillation, and cardioversion, may be implemented in cooperation with sleep stage classification in accordance with embodiments of the invention.

Optionally, the medical device 11500 may also be configured to detect respiratory disorders, e.g., sleep-disordered breathing, and to provide therapy to mitigate the respiratory disorders. Disordered breathing therapy, including cardiac pacing and/or other types of disordered breathing therapy, such as continuous positive air pressure (CPAP), nerve stimulation, muscle stimulation or other therapy for treating disordered breathing, may be controlled or provided by components of the cardiac pulse generator 11501.

Although FIG. 115 depicts a sleep stage classification system implemented in a cardiac pulse generator 11501, it is understood that configurations, features, and combinations of features described in the disclosure may be implemented in a number of medical devices. Sleep stage classification may be implemented in connection with various diagnostic and therapeutic devices and such embodiments and features are not limited to the particular devices described herein.

Further, although various embodiments involve devices or systems having an implantable control system and implantable sensors, it is understood that therapy or diagnostic systems utilizing the sleep stage classification methodologies of the present invention may be configured so that the control system or components of the control system are arranged externally to the patient. The sensors and the control system, and in particular the patient sleep stage classification system, may involve patient-external components, patient-internal components or a combination of patient-external and patient-internal components.

In the embodiment illustrated in FIG. 115, the implantable pulse generator 11501 includes circuitry for providing cardiac rhythm therapy 11542 to treat various arrhythmic conditions. Cardiac arrhythmia therapy is implemented by detecting electrical signals produced by the heart, analyzing the signals for arrhythmia, and providing an appropriate therapy to terminate or reduce the arrhythmia. The pulse generator 11501 is coupled to a cardiac lead system having sensing and therapy electrodes 11550, 11522 electrically coupled to the patient's heart. The cardiac lead system sensing and therapy electrodes 11550, 11522 may include one or more electrodes positioned in or around the heart as well as one or more electrodes positioned on the housing 11590 or header of the pulse generator 11501. In one arrangement, the electrodes used for sensing are also used for therapy delivery. In another arrangement, a set of therapy electrodes different from the sensing electrodes is used.

Cardiac signals sensed by sensing electrodes 11550 of the cardiac lead system are coupled to an arrhythmia analysis unit 11556 configured to identify cardiac arrhythmias. The arrhythmia analysis unit 11556 may use information derived from a sleep stage processor 11552 to provide sleep stage informed arrhythmia detection. If cardiac arrhythmia is detected, the therapy unit 11542 may provide a number of therapies to treat the detected arrhythmia.

The cardiac therapy may include pacing therapy controlled to treat cardiac rhythms that are too slow. In this situation, the therapy unit 11542 controls the delivery of periodic low energy pacing pulses to one or more heart chambers through pacing electrodes of the cardiac lead system 11550. The pacing pulses ensure that the periodic contractions of the heart are maintained at a hemodynamically sufficient rate.

The cardiac therapy may also include therapy to terminate tachyarrhythmia, wherein the heart rhythm is too fast. The arrhythmia analysis unit 11556 detects and treats episodes of tachyarrhythmia, including tachycardia and/or fibrillation. The arrhythmia analysis unit 11556 recognizes cardiac rhythms consistent with various types of tachyarrhythmia. When tachyarrhythmia is identified, the therapy unit 11522 may deliver high energy electrical stimulation to the heart through defibrillation electrodes of the cardiac lead system 11550 to terminate the arrhythmia.

Implementation of an appropriate cardiac therapy may be augmented using sleep stage classification determined by the sleep stage processor 11552 in accordance with embodiments of the invention. As previously discussed, sleep stage classification may be used to determine an optimal arrhythmia therapy. In one example implementation, cardiac therapy may be triggered by signals from the sleep stage processor 11552 to prevent cardiac arrhythmia during REM or other proarrhythmic sleep periods. In another example, the lower rate limit of a bradycardia pacing regimen may be modified when the sleep stage processor 11552 indicates that the patient is asleep.

The sleep stage processor 11552 performs sleep stage classification based on one or more sleep-related signals, including at least one REM-modulated signal. In the illustrative embodiment of FIG. 115, a muscle atonia sensor 11548, for example, a EMG sensor, provides a REM-modulated signal to the sleep stage processor 11552. Additionally, a signal responsive to the patient's activity may be used in combination with the REM-modulated signal to augment sleep stage classification. In the example implementation illustrated in FIG. 115, the patient activity signal is provided by an accelerometer 11546.

The medical device 11500 may optionally include components for performing respiratory system analysis 11554. In one embodiment, the patient's respiration patterns may be analyzed with knowledge of the patient's sleep stage to determine an appropriate therapy to mitigate detected episodes of disordered breathing or to prevent the occurrence of sleep-disordered breathing.

A transthoracic impedance sensor 11544 may be implemented to produce a signal representing the patient's respiration cycles. A respiration analysis unit 11554 uses sleep stage information provided by the sleep stage processor 11552 in analyzing the patient's respiration patterns to detect episodes of sleep-disordered breathing. Based on sleep stage classification, respiration analysis, and, optionally, cardiac system analysis, cardiac electrical stimulation therapy may be delivered to the patient through the cardiac electrodes 11522 to mitigate or prevent disordered breathing, including sleep apnea, hypopnea, or other forms of disordered breathing. According to one embodiment, preventive therapy for disordered breathing may be initiated if the sleep stage classification processor indicates the patient is asleep, or upon detection of a particular sleep stage.

FIGS. 116A-D illustrate various configurations of a muscle atonia sensor mechanically coupled to an implanted medical device 11600, such as an implantable pacemaker or implantable cardioverter/defibrillator in accordance with embodiments of the invention. The implantable medical device 11600 may include a housing 11620 enclosing the medical device circuitry and a header 11610 for coupling a lead system 11660 to the circuitry of the medical device 11600.

Figure 116B:
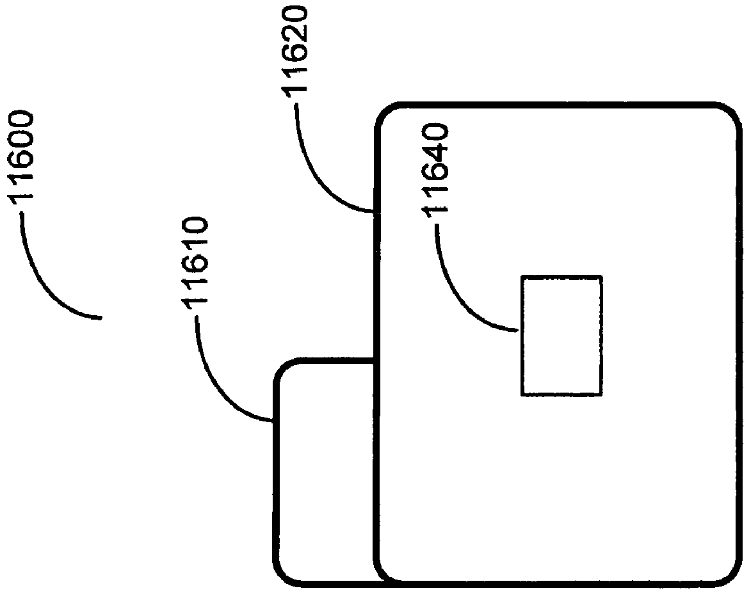
Figure 116A:
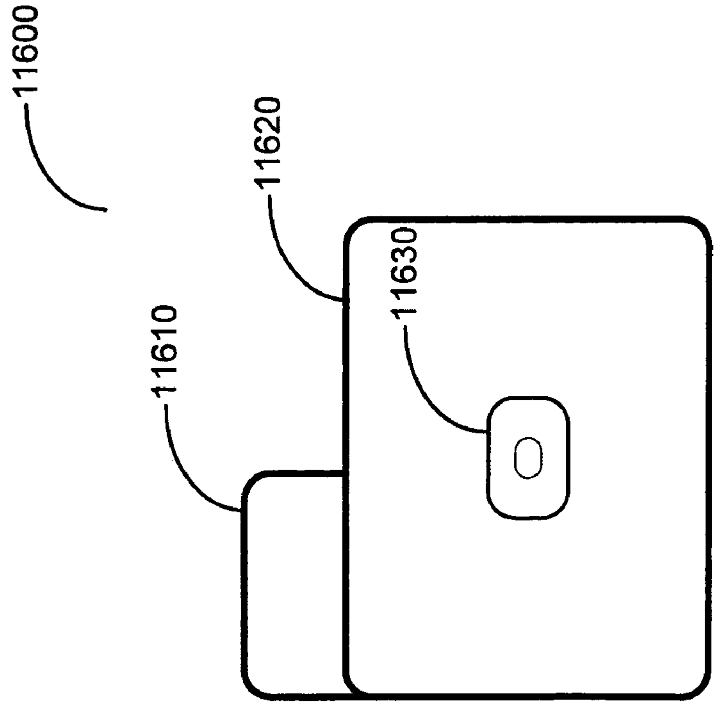
Figure 116D:
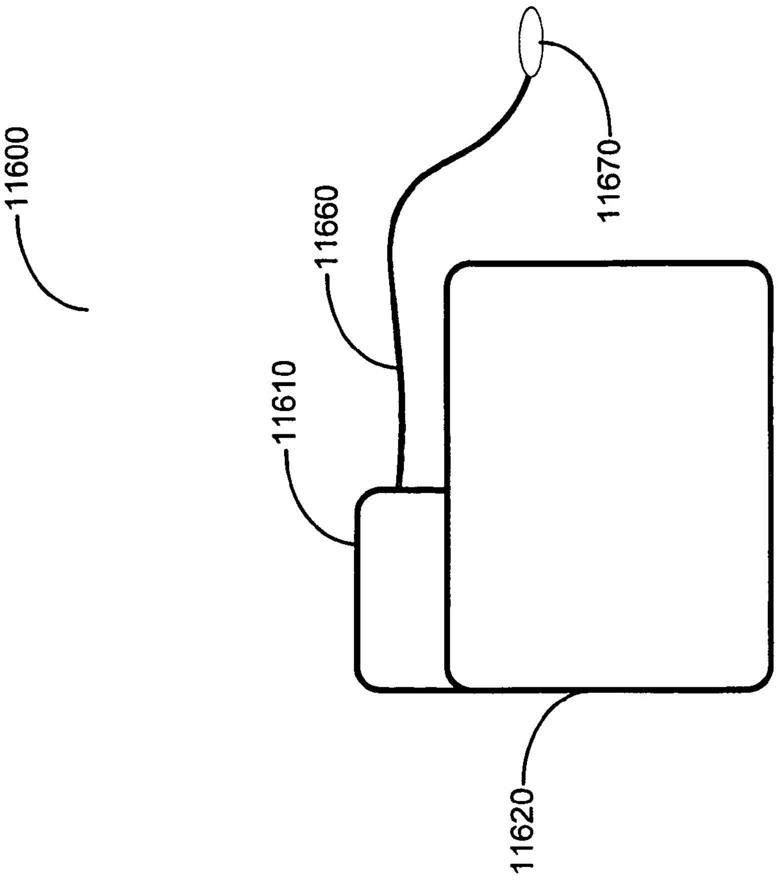
Figure 116C:
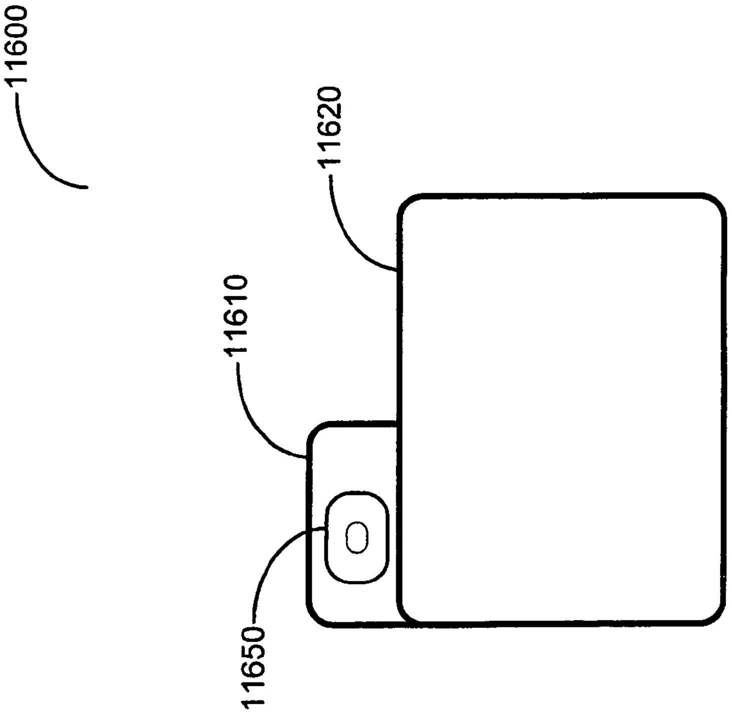

A muscle atonia sensor may be implemented, for example, using an electromyogram (EMG) electrode 11630 or force responsive sensor 11640 positioned on the housing 11620 of the medical device 11600 as illustrated in FIGS. 116A and 116B, respectively. FIG. 116C illustrates a muscle atonia sensor 11650 positioned on the header 11610 of the medical device 11600. Alternatively, a muscle atonia sensor 11670, e.g., EMG electrode or strain gauge, may be positioned on the lead system 5760 or may be coupled to the medical device 11600 through a catheter or lead system 11660, as illustrated in FIG. 116D.

Detection of Autonomic Arousal

Aspects of the invention that include autonomic arousal detection are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving automatic arousal detection are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 106 (FIG. 1C) configured to detect autonomic arousal events. The autonomic arousal detector 106 may be implemented as a stand alone system or in combination with other individual medical systems, such as those described in FIGS. 1B-1D.

Various embodiments are directed to systems and methods for detecting arousals of a patient during sleep. One embodiment of the invention is directed to a method for acquiring sleep information including autonomic arousal events. The method involves sensing one or more physiological conditions modulated by a patient's autonomic arousal response. Autonomic arousal events occurring during sleep are detected based on the one or more sensed signals. At least one of sensing the physiological signals and detecting the autonomic arousal events is performed at least in part implantably.

Another embodiment of the invention is directed to a method for acquiring sleep-related information. An arousal signal modulated by changes in muscle tone associated with autonomic arousal is sensed using a sensor disposed on an implantable therapy device. Autonomic arousal events are detected based on the arousal signal.

Yet a further embodiment of the invention involves a method for detecting arousals from sleep. One or both of a signal modulated by brainwave activity associated with an autonomic arousal response and a signal modulated by changes in muscle tone associated with the autonomic arousal response are generated. Autonomic arousal events are detected, using an implantable device, based on at least one of the brainwave signal and the muscle tone signal.

Another embodiment of the invention involves a system for detecting autonomic arousal events. The system includes an implantable therapy device and one or more sensors mechanically coupled to the implantable therapy device. The sensors are configured to sense one or more physiological conditions modulated by a patient's autonomic arousal response. An arousal detector is coupled to the sensor and is configured to detect autonomic arousal events based on the sensed physiological conditions.

In accordance with another embodiment of the invention, a system detects autonomic arousal events occurring during sleep. The system includes one or more sensors configured to sense one or more physiological conditions associated with a patient's autonomic arousal response. An implantable arousal detector is coupled to the one or more sensors. The arousal detector is configured to detect autonomic arousal events based on the one or more physiological conditions.

One embodiment of the invention is directed to a medical system detecting autonomic arousal events occurring during sleep. The system includes one or more sensors configured to sense one or more physiological conditions associated with a patient's autonomic arousal response. The system also includes an implantable arousal detector coupled to the one or more sensors. The arousal detector is configured to detect autonomic arousal events based on the one or more physiological conditions.

Other embodiments of the invention involve a system for providing coordinated patient monitoring, diagnosis and/or therapy that utilizes autonomic arousal detection 106 The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes an autonomic arousal detector 106 coupled to one or both of the implantable device and the patient external respiratory device. The autonomic arousal detector comprises one or more sensors configured to sense one or more physiological conditions associated with a patient's autonomic arousal response. The autonomic arousal detector also includes an implantable arousal detector coupled to the one or more sensors, the arousal detector configured to detect autonomic arousal events based on the one or more physiological conditions. The implantable device and the patient external respiratory device are configured to operate cooperatively using the detected autonomic arousal events.

The implantable and respiratory therapy devices 181, 184 may operate cooperatively to detect autonomic arousal events. For example, sensors of the respiratory therapy device may sense the one or more physiological conditions associated with autonomic arousal response. The sensed information may be transmitted to an arousal detector disposed within a housing of the implantable device. Systems and methods directed to autonomic arousal detection may be implemented to include selected features, functions, and/or structures described in commonly owned, co-pending U.S. Publication No. 2005/0076908, which is hereby incorporated herein by reference.

One indicator of sleep quality is the number of arousals experienced during sleep. An arousal is an event that occurs during sleep and may be identified based on changes in EEG signals during non-REM sleep and changes in EEG and EMG signals during REM sleep. Arousal events may or may not culminate in wakefulness. The patient may experience an arousal event during sleep and never wake up.

In one implementation, arousal from sleep has been identified, for example, based on a shift in the patient's EEG signal to a higher frequency for a specified period of time during non-REM sleep assuming sleep has been previously detected. Arousals during REM sleep have been identified by the EEG arousal defined above in addition to changes in an electromyogram (EMG) signal or body movements. Arousals, as identified based on changes in EEG signals, encompass activation of the patient's autonomic nervous system.

Activation of the patient's autonomic nervous system during sleep may be used to identify arousal events referred to herein as an autonomic arousal event. Autonomic arousal events may be identified by an autonomic arousal response involving transient activation of the patient's autonomic nervous system. The autonomic arousal response may or may not result in detectable changes to the patient's EEG signal.

Autonomic arousal events comprise transient changes during sleep that affect autonomic physiological parameters such as heart rate, blood pressure, cardiac output, peripheral vasoconstriction, sympathetic nerve traffic, and arteriole size, among other conditions. For example, an autonomic arousal event may be detected based on a change of about 4 mm Hg increase in systolic blood pressure and/or about a 4 beat per minute increase in heart rate. As previously mentioned, autonomic arousal events begin during sleep and may or may not result in wakefulness. Thus, the patient may experience a number of autonomic arousal events while asleep without achieving a waking state. Nevertheless, these autonomic arousal events disrupt the patient's sleep and degrade sleep quality.

Information about the autonomic arousal events may be stored in memory, and/or transmitted to a separate device for printing or display. Information about the autonomic arousal events may be used to diagnose sleep disorders and/or adjust patient therapy, such as cardiac stimulation therapy, drug therapy, neural stimulation therapy, and/or respiration therapy. Trending sleep information including autonomic arousal events and correlating the sleep information with sleep disorder events may be helpful in determining and maintaining appropriate therapies for patients suffering from a range of sleep disorders.

Many sleep disorder events, e.g., disordered breathing events and movement disorder events, are followed by autonomic arousal events. These autonomic arousals disrupt the normal sleep pattern and may be involved in causing chronic hypertension. The autonomic arousal response may be visible on signals generated by electroencephalogram (EEG) sensors, electromyogram (EMG) sensors, and/or other sensors sensitive to autonomic nervous system changes.

In accordance with embodiments of the present invention, information related to the patient's autonomic arousal response may be collected and/or analyzed. The identification of autonomic arousal events may be used for a variety of purposes, including detecting and/or verifying sleep disorder events, trending the number of arousals per night, and developing various indices such as an arousal index and/or a composite index based on arousals and sleep disorder events. The arousal information may be collected and used in the evaluation of sleep and/or sleep disorders.

Frequent arousals are indicative of a number of medical disorders, including sleep disorders such as sleep disordered breathing. Frequent arousals of the sympathetic nervous system may lead to chronic hypertension or other medical problems. The ability to detect individual and/or aggregate arousals may be used in diagnosing various medical disorders, including disordered breathing. If the patient receives therapy to treat disordered breathing, then the ability to count and trend arousals also provides information regarding therapy efficacy. For example, if arousals decline after therapy is delivered, then it may be assumed that the therapy provides an effective treatment for the disordered breathing. Further, detection of an arousal following delivery of therapy may be used to provide feedback for therapy control.

Methodologies may involve using arousal information in combination with disordered breathing information. For example, the system may provide the capability of discriminating between disordered breathing events that cause arousals and disordered breathing events that do not cause arousals. The detection of arousals may allow trending of arousals that occur during sleep. The disordered breathing events that are followed by arousals are considered to be the most disruptive, because repeated arousals prevent the patient from receiving a restful sleep. Some patients continue to experience disordered breathing events during an aroused status. It may be desirable to ignore disordered breathing events that occur during an aroused state. The ability to detect an arousal and ignore subsequently detected disordered breathing events during arousal may improve the accuracy of disordered breathing indices, e.g., apnea/hypopnea index.

An arousal detection system may comprise, for example, a sensor that generates a signal modulated by changes in muscle tone associated with autonomic arousal. Such a signal may be generated, for example, using an electromyogram sensor or a strain gauge positioned in contact with or near skeletal muscle, such as the pectoral muscle. The sensor may be disposed on an implantable device such as an implantable cardiac rhythm management system, e.g., a pacemaker, defibrillator, cardiac monitor, cardiac resynchronizer, or the like.

Other sensors may be used in connection with arousal detection in addition to or instead of the muscle tone sensor. For example, an accelerometer may be employed to detect patient movement correlated to arousal. An electrogram or other cardiac sensor may be used to detect various cardiac parameters associated with arousal. For example, heart rate increases upon arousal, the AV delay decreases upon arousal, and heart rate variability is modified by autonomic tone changes associated with arousal. Cardiac output increases during arousal, as may be measured via an impedance sensor. Blood pressure, measured, for example, by a lead-based pressure gauge, is modulated by arousal and may be utilized in arousal detection. Peripheral arterial tonography may be used in arousal detection. Arteriole size, which may be measured by photoplethysmography, decreases upon arousal due to sympathetic nervous system activation. Sympathetic nerve traffic modulated by arousal may be sensed using microelectrodes coupled to an implantable device.

In accordance with one embodiment, an arousal detector includes circuitry configured to detect changes in the patient's nervous system. The changes may comprise sympathetic and/or parasympathetic nervous system changes. The arousal detector may be configured to detect the presence of individual arousal events, the presence of aggregate arousals, or the presence of both individual and aggregate arousals.

For example, in one implementation, the sensors may sense conditions that are modulated contemporaneously with an arousal event. In this implementation, the system may detect an individual arousal event during or slightly after the occurrence of the arousal event, for example. In another implementation, the sensors may be sensitive to conditions that are modulated by the aggregate effect of multiple arousal events that occur over a period of time. In such an implementation, detection of individual arousals may or may not occur. The sensors may detect changes in physiological conditions that are caused by the occurrence of multiple arousals. The changes in the physiological conditions are used by the arousal detector to determine that multiple arousal events that have occurred over a period of time. A representative set of conditions indicative of the occurrence of multiple arousal events over a period of time may include, heart rate variability, blood pressure, AV-delay, arteriole size, sympathetic nerve activity, among others. This list is not exhaustive and other conditions may be sensed by the system to determine the occurrence of multiple arousal events.

The arousal detection system ay include functionality for evaluating the arousal information and/or determining values or indices using the arousal information. For example, the arousal detection system ay determine the number of arousals occurring within a sleep period, or other specified time period. The therapy assessment processor 260 may determine an arousal index (arousals detected per unit time), an apnea/hypopnea index (apneas or hypopneas detected per unit time), or other indices. Further, the arousal detection system may evaluate the sleep disorder events to determine if arousals are associated with the sleep disorder events. For example, if an arousal is detected within a predetermined time period after a sleep disorder event is detected, the arousal may be associated with the sleep disorder event. Using this process, arousals from sleep that are associated with sleep disorder events can be discriminated from arousals from sleep that are not associated with sleep disorder events.

In one application the number of arousals may be counted and used to calculate an arousal index to quantify the number of arousals experienced by the patient per unit time. Arousal information may be used to determine a number of sleep quality indices. The arousal information may be used in diagnosing and treating a variety of disorders, including nocturnal sleep disorders, such as sleep disordered breathing, and other conditions. The ability to count and trend these arousals provides diagnostic information regarding patient status with respect to the disorders. For example, autonomic arousals are associated with causing hypertension. A presence of hypertension may be determined or predicted based on arousal information, such as a trend of arousal events over time. Trending arousals may be used to improve therapy used to treat sleep disorders.

Arousals fracture sleep staging, leading to disrupted sleep, and as a consequence, daytime sleepiness. An arousal will bring a patient out of REM sleep or deep sleep (stage 3-4), and bring them temporarily to a waking state. As a consequence, the amount of REM and deep sleep is limited, since the patient has to go back through Stage 1-2 sleep before they enter REM or deep sleep.

In one configuration, arousal information may be used by a therapy controller disposed within an implantable therapy device, for initiating, terminating, or adjusting therapy. Alternatively, the arousal information may be transmitted to the APM system or other remote device for automatic or physician conducted analysis. The APM system may transmit control signals to the implanted device to initiate, terminate or modify therapy delivered by the implanted device. For example, arousal feedback information may be used by an APM system, an implantable cardiac device, to provide closed-loop control of the therapy using arousal information feedback.

In one implementation, detection of arousals involves evaluating signals generated by sensors for a characteristic signature of autonomic arousal. Autonomic arousal responses, as detected using EEG sensors and EMG sensors, are illustrated in the graph of FIG. 31.

Figure 31:
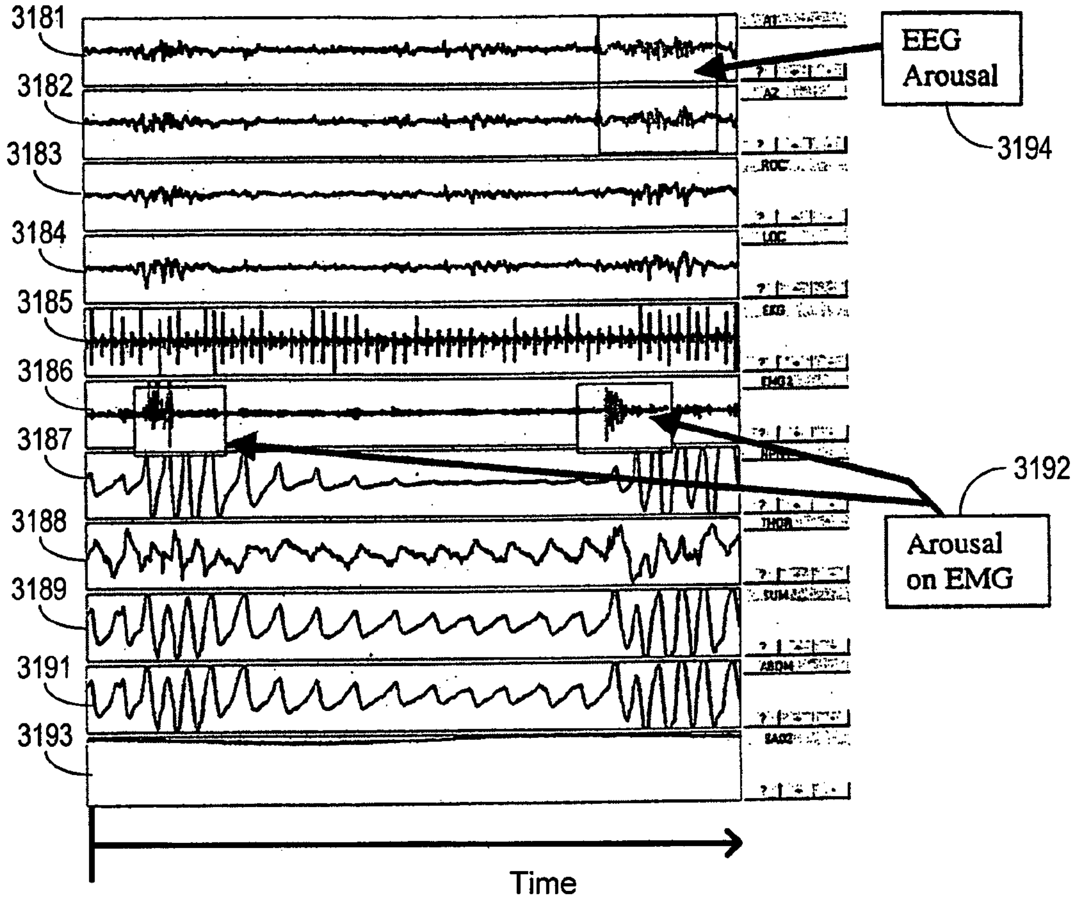
FIG. 31 are graphs of autonomic arousal responses which may be utilized by the disordered breathing therapy system in accordance with embodiments of the invention.

Referring now to FIG. 31, a sleep study sensor array output is illustrated including an apnea event terminating in an arousal. Arousal detection may be implemented using implantable sensors capable of detecting changes in the sympathetic or parasympathetic nervous system. These changes may be either short-term (i.e., changes associated with individual arousals) or long-term (i.e., aggregate effect of multiple arousals). A short-term effect of arousal includes, for example, the activation of sympathetic nerve activities. Sympathetic or parasympathetic changes, or the changes of autonomic balance can be assessed, for example, by heart rate variability (HRV), which can be detected using a device configured to sense cardiac activity, changes in heart rate, and/or changes in AV conduction.

In the graphs of FIG. 31, the abscissa of all the graphs is the same time period during the sleep analysis of a patient. The ordinate of each of the graphs is the signal amplitude of the respective sensor. Traces 3181, 3182, 3183, and 3184 are the top, second, third, and fourth traces respectively, plotted from sensors adapted to produce electroencephalogram (EEG) signals. Evident in all four traces, but particularly pointed out in traces 3181 and 3182 is a characteristic signature of an EEG signal indicative of arousal 3194. A trace 3185 provides an electrocardiogram (EKG) of the heart beats during the time period of the graph. A trace 3186 provides an electromyogram defining muscular movement during the time period of the graph. Particularly evident in the trace 3186 is a characteristic signature of an EMG signal indicative of arousal 3192.

Traces 3187, 3188, 3191, and 3189 illustrate various parameters related to respiration. Trace 3187 is nasal pressure, 3188 is thoracic effort, 3191 is abdominal effort, and 3189 is the sum of the thoracic and abdominal effort. Trace 3193 depicts the blood oxygen saturation level of the patient. Pulmonary activity may be sensed through the use of internal sensors, such as impedance sensors and/or minute ventilation sensors described further below.

In accordance with aspects of the present invention, arousal detection may be used in connection with detection of sleep disorders, such as disordered breathing. Sleep disordered breathing may cause the patient to arouse from sleep frequently during a sleep period. Thus arousals from sleep follow the sleep disorder event. In one configuration, arousal detection may be used as a surrogate for direct detection of the disordered condition. For example, in systems that do not have a respiration sensor capable of detecting disrupted respiration, arousal detection may be used as a surrogate for detecting disrupted respiration. Information from the arousal detector may be used to separate sleep disorder events, e.g., apnea, hypopnea, followed by arousal versus those terminated without arousal. The sleep disorder events that are followed by arousal are considered to be the most disruptive, as these arousals interrupt the normal course of sleep and prevent the patient from receiving a full sleep cycle each night. Detecting these types of sleep disorder events enhances the specificity of sleep disorder event detection and guides diagnosis and/or therapy.

The arousal information may be used to modify therapy for sleep disorder events such as disordered breathing. In various implementations, the arousal information and/or disordered breathing information may be used to modify disordered breathing therapy delivered to the patient.

For example, cardiac electrical therapy may be provided by an implanted therapy device. Detection of disordered breathing may be used to initiate the cardiac electrical therapy. Detection of arousal, indicating the end of the disordered breathing event, may be used to terminate the electrical stimulation therapy, for example.

In another example, cardiac electrical therapy may be provided, and the number of arousals monitored. If the cardiac electrical therapy causes an excessive number of arousals, then the cardiac electrical therapy may be adjusted or terminated.

In another example, an APM system may receive information about sleep disorder events from the disordered breathing detector/predictor 258 (FIG. 2) and/or arousal information from the arousal detector. The information may be automatically evaluated by the APM system, or may be evaluated by the patient's physician. The APM system may be used to transmit control signals to an implanted device to initiate, terminate or modify the therapy delivered to the patient.

In various configurations, an EMG sensor may be positioned on a housing or header of an implantable device, such as a cardiac rhythm management device, or may be located on a catheter or lead coupled to the cardiac rhythm management device. An EMG sensor located on a device positioned in the pectoral region provides access to skeletal muscle that may be exploited to detect arousal.

Figure 32:
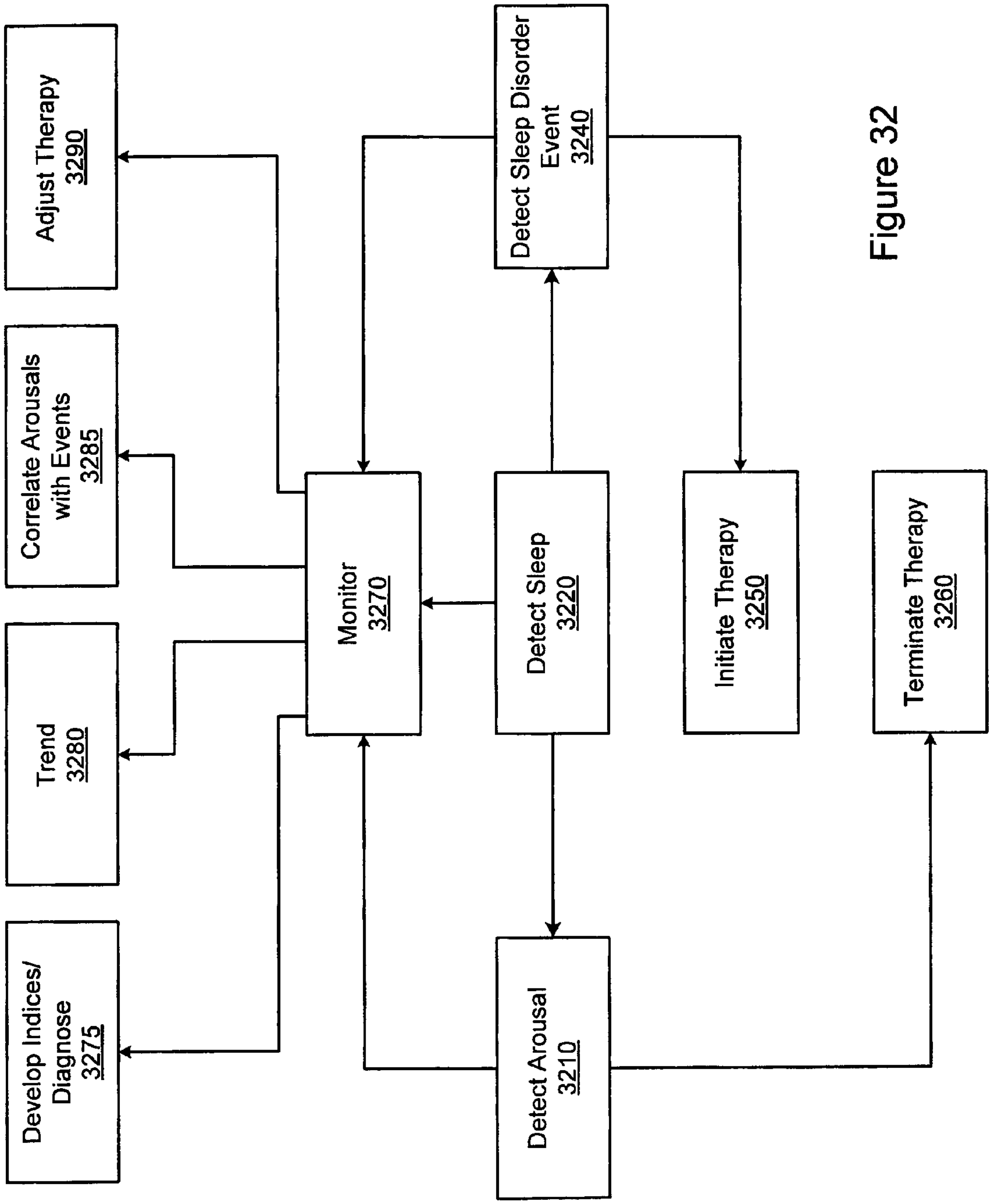
FIG. 32 depicts a flow diagram illustrating various optional processes that may be implemented in connection with arousal detection according to embodiments of the invention.

FIG. 32 depicts a flow diagram illustrating various optional processes that may be implemented in connection with arousal detection according to embodiments of the invention. Detection of sleep 3220 may be used to inform the arousal detection process 3210 and the sleep disorder event detection process 3240. Information about sleep, sleep disorder events, and arousals from sleep are monitored 3270. The information may be used to diagnose sleep-related disorders and/or other disorders 3275, calculate arousal and sleep disorder indices, develop trend information 3280, correlate arousals with sleep disorder events 385, and/or adjust therapy delivered to the patient 3290. Upon detection of a sleep disorder event 3240, e.g., sleep disordered breathing, therapy to mitigate the sleep disorder event may be initiated 3250. Arousal detection 3210 signals the end of the sleep disorder event, and therapy may be terminated 3260 following detection of arousal from sleep.

Figure 33:
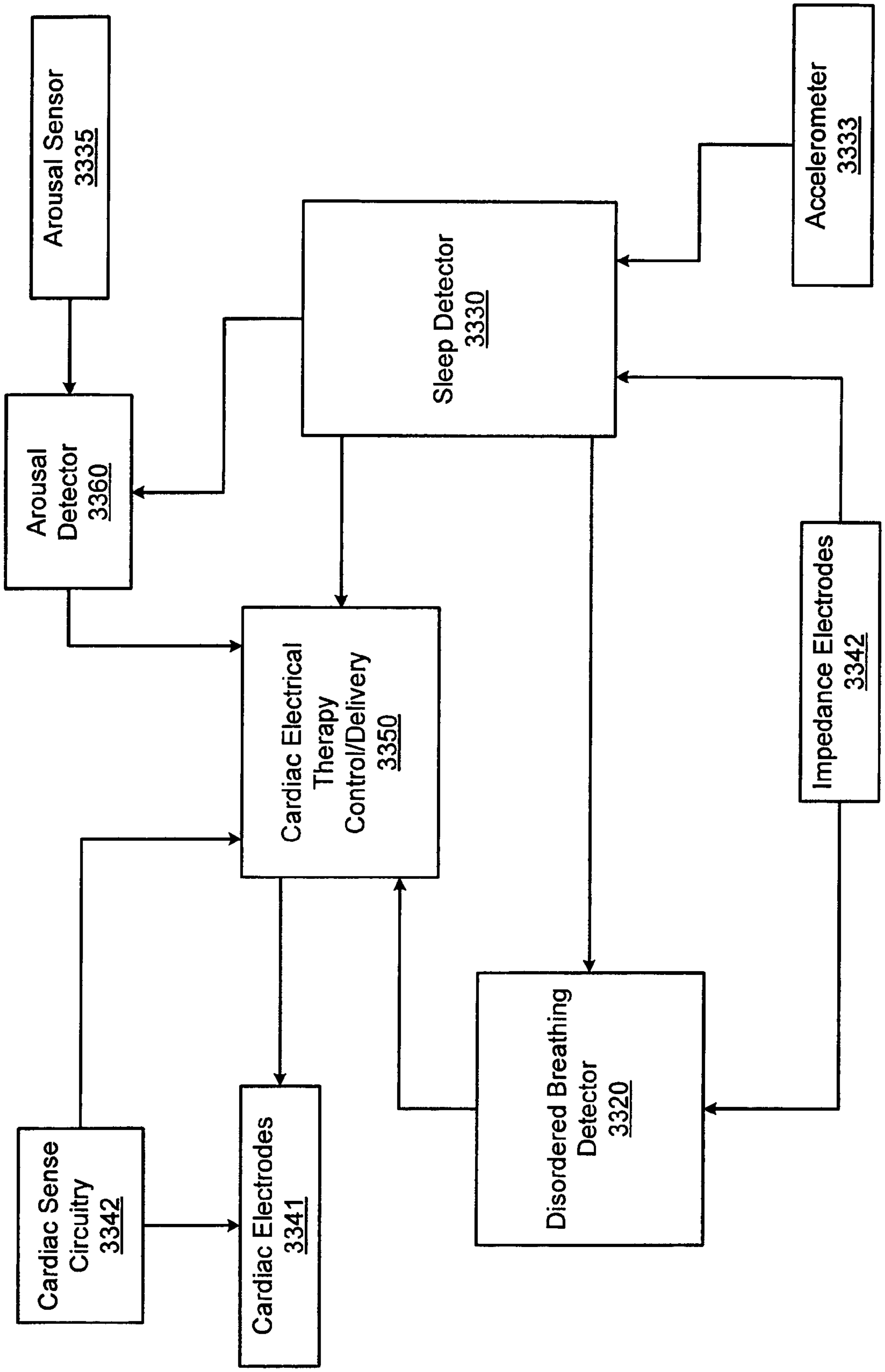
FIG. 33 is a block diagram of a cardiac rhythm management (CRM) system suitable for implementing an arousal detection methodology in accordance with embodiments of the present invention.

FIG. 33 is a block diagram of an arousal detector that is implemented in cooperation with a cardiac rhythm management (CRM) system such as a pacemaker and/or cardioverter/defibrillator with functionality to deliver cardiac electrical stimulation for disordered breathing in accordance with an embodiment of the invention. The system may be partially or completely implantable.

Cardiac sense circuitry 3342, cardiac electrical stimulation control and delivery circuitry 3350, disordered breathing detector 3320, arousal detector 3360, and sleep detector 3330 are arranged within a housing that is hermetically sealed and suitable for implanting within the patient, such as within the pectoral region of the patient's chest. An accelerometer 3333 configured to detect patient activity may also be incorporated within the housing. An EMG sensor is implemented as an arousal sensor 3335 and is disposed on the housing so that the EMG sensor 3335 is positioned in contact with or near skeletal muscle, such as the pectoral muscle. An intracardiac lead system includes cardiac electrodes 3341 for electrically coupling to the patient's heart and one or more transthoracic impedance electrodes 3342 for generating a respiration signal.

The sleep detector 3330 uses the patient activity signal generated by the accelerometer 3333 and the respiration signal generated by the transthoracic impedance electrodes 3342 to determine if the patient is asleep or awake.

The disordered breathing detector 3320 detects disordered breathing events based on the patient's respiration patterns, as described more fully above. The arousal detector 3360 compares the EMG signal to a characteristic arousal signature and detects arousal based on the comparison. Disordered breathing detection and arousal detection may be enhanced using sleep/wake information provided by the sleep detector 3330.

In one embodiment, the CRM provides cardiac electrical stimulation the to one or more heart chambers as therapy for disordered breathing. The cardiac electrical therapy control unit 3350 may utilize signals from the sleep detector 3330, disordered breathing detector 3320, and arousal detector 3360 to initiate, terminate, and/or adjust the cardiac electrical stimulation therapy for disordered breathing. For example, the therapy control unit 3350 may initiate a process for treating disordered breathing episodes when the sleep detector 3330 determines that the patient is asleep.

In one scenario, the therapy control unit 3350 may initiate cardiac electrical stimulation, e.g., cardiac overdrive pacing, to treat disordered breathing upon detection of a disordered breathing event during sleep. In another scenario, the therapy control unit 3350 may initiate cardiac electrical stimulation to treat disordered breathing when sleep is detected. The therapy control unit 3350 may adjust the cardiac electrical stimulation when a disordered breathing event is detected during sleep. If an arousal is detected, then the therapy control unit 3350 may terminate or adjust the cardiac electrical stimulation therapy for disordered breathing.

Marked Respiratory Waveform

Aspects of the invention that include generation of a marked respiratory waveform are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that involve a marked respiratory waveform are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 105 (FIG. 1C) for generating a marked respiratory waveform. The marked respiratory waveform system 105 may be implemented as a stand alone system or in combination with other individual medical systems, such as those described in FIGS. 1B-1D.

Various embodiments of the invention are directed to characterizing respiration using a marked respiration waveform. In accordance with one embodiment, a method for characterizing respiration includes acquiring a respiration waveform. One of more characteristics associated with the patient's respiration are detected. A marked respiration waveform is generated using the respiration waveform and one or more symbols indicating the one or more characteristics associated with the patient respiration. At least one of acquiring the respiration waveform, detecting the one or more characteristics associated with the respiration, and generating the marked respiration waveform is performed at least in part implantably.

Another embodiment of the invention involves a system for characterizing patient respiration. The system includes a respiration waveform sensor configured to acquire a respiration waveform. A respiration processor is configured to determine one or more characteristics associated with the respiration. A waveform generator is coupled to the respiration waveform sensor and the respiration processor. The waveform generator is configured to generate a marked respiration waveform comprising the respiration waveform and symbols indicating the one or more characteristics associated with the respiration. At least one of the respiration waveform sensor, the respiration processor, and the waveform generator includes an implantable component.

Other embodiments of the invention involve a system providing coordinated patient monitoring, diagnosis and/or therapy that generates and/or uses a marked respiration waveform. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a system for characterizing respiration using a marked respiration waveform. The marked respiration waveform is coupled to at least one of the implantable device and the patient external respiratory device.

The marked respiration waveform system 105 includes a respiration waveform sensor configured to acquire a respiration waveform and a respiration processor configured to determine one or more characteristics associated with the respiration. A waveform generator is coupled to the respiration waveform sensor and the respiration processor. The waveform generator is configured to generate a marked respiration waveform comprising the respiration waveform and symbols indicating the one or more characteristics associated with the respiration. At least one of the respiration waveform sensor, the respiration processor, and the waveform generator comprises an implantable component. The implantable device and the patient external respiratory device are configured to operate cooperatively to generate or use the marked respiration waveform. Systems and methods directed to patient respiration characterization may be implemented to include selected features, functions, and/or structures described in commonly owned, U.S. Pat. No. 7,678,061, which is hereby incorporated herein by reference.

Figure 34:
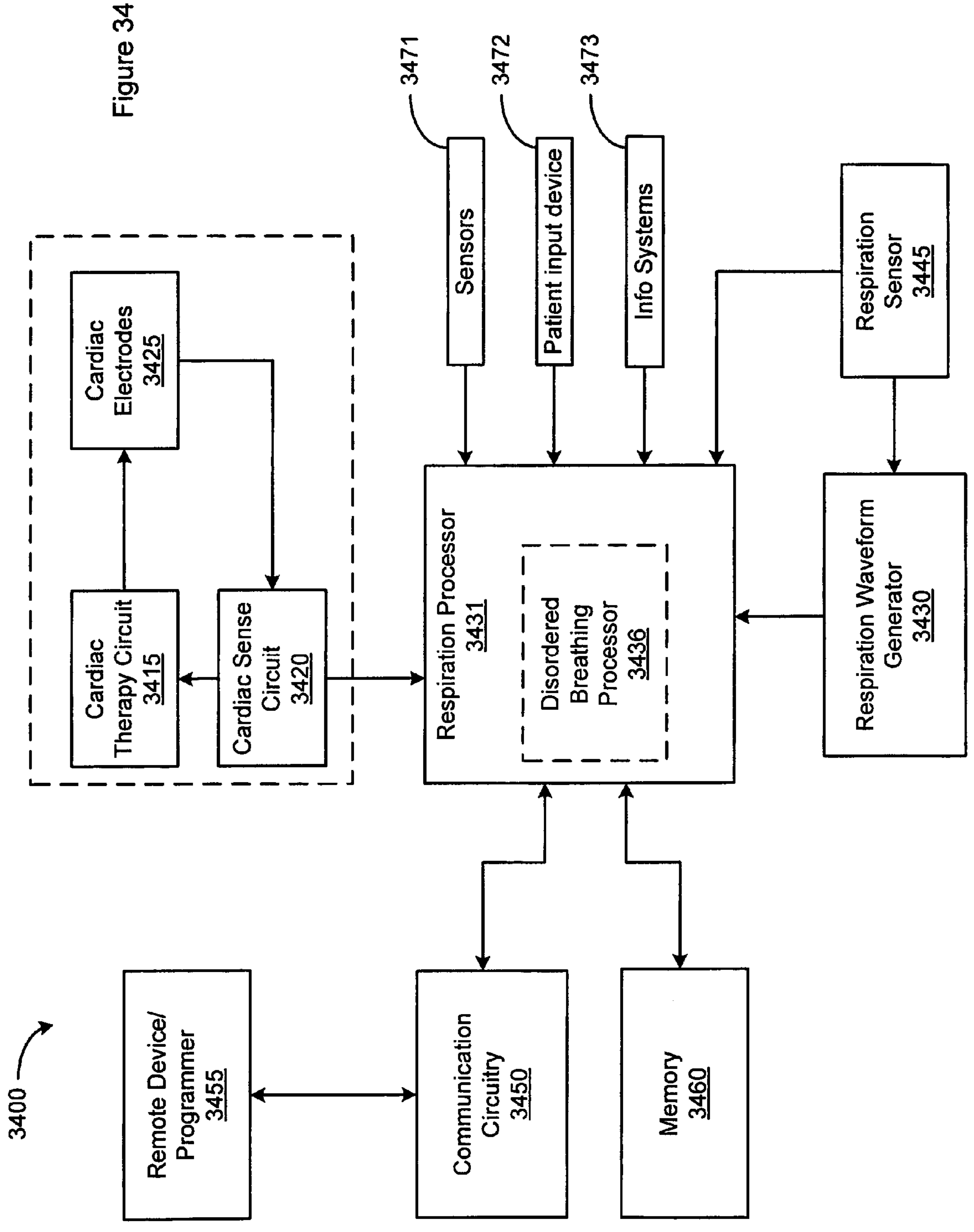
FIG. 34 is a block diagram of a medical system including a cardiac device that may be used to characterize patient respiration in accordance with embodiments of the invention.

FIG. 34 is a block diagram of a medical system 3400 including patient-external or fully or partially implantable a medical device 3400 incorporating a marked respiration waveform system in accordance with embodiments of the invention. The medical device 3400 may optionally include a cardiac therapy circuit 3415 and a cardiac sense circuit 3420 coupled through a lead system to cardiac electrodes 3425. The cardiac electrodes 3425, illustrated in FIG. 34 may be used to electrically couple to the patient's heart for sensing electrical cardiac signals and/or delivering therapy to the heart in the form of electrical stimulation energy, e.g., pacing pulses and/or defibrillation/cardioversion shocks as more fully described herein.

The medical system 3400 incorporates a system for generating marked respiration waveforms. In the embodiment illustrated in FIG. 34, respiration waveforms are acquired based on signals generated by a respiration sensor 3445. In a preferred embodiment, the respiration sensor comprises a transthoracic impedance sensor. Other methods of acquiring a respiration waveform are also possible. Such methods may include, for example, the use of patient-external respiratory bands, respiration flowmeter measurements, implantable or patient-external breath sound detection, blood oxygen levels, and/or other processes.

Various respiration-related conditions affecting the patient may be acquired using the cardiac electrodes 3425, sensors 3471, patient input devices 3472 and/or other information systems 3473. The sensors 3471 may comprise patient-internal and/or patient-external sensors coupled through leads or wirelessly to the respiration processor 3431. The patient input device 3472 allows the patient to input information relevant to respiration conditions. For example, the patient input device 3472 may be particularly useful for inputting information concerning patient-known information, such as information related to patient smoking, drug use, or other activities or perceptions that are not automatically sensed or detected.

The respiration processor 3431 may be coupled to other information systems 3473, such as network-connected servers. The respiration processor 3431 may access the information systems 3473 to acquire information about conditions that may affect patient respiration. In one implementation, the respiration processor 3431 accesses the information systems 3473 to acquire information about conditions correlated to, or otherwise associated with, an increased or decreased incidence of disordered breathing in the patient. For example, the respiration processor 3431 may access an air quality website to acquire the ambient pollution index. In this scenario, a particular level of pollution may be correlated to in increased likelihood of disordered breathing.

Signals from the respiration sensor 3445 and/or signals produced by one or more additional sensors or devices 3471, 3425, 3472, 3473, may be used by the respiration processor 3431 to detect one or more characteristics related to patient respiration. The respiration characteristics are used to generate a marked respiration waveform.

In one embodiment, the respiration characteristics may include parameters associated with the respiration waveform morphology, such as peak inspiration, expiration slope, or inspiration slope. The respiration characteristics may include a variety of physiological and/or non-physiological conditions. For example, the respiration characteristics may include parameters derived from the respiration waveform, e.g., respiration rate, tidal volume, minute ventilation, or breath intervals. Additionally or alternatively, the respiration characteristics may include symptoms and/or physiological conditions derived from the respiration waveform, e.g., dyspnea, pulmonary congestion. The respiration characteristics may include non-physiological, contextual conditions such as pollution, ambient temperature, and/or humidity. The respiration characteristics may also include parameters characterizing disordered breathing, such as duration, severity, frequency, and type of disordered breathing.

In another embodiment, the respiration characteristics may include conditions associated with respiration, including, for example, physiological conditions and/or contextual, non-physiological conditions. Table 1 provides examples of patient conditions that may be used in connection with generation of a marked respiration waveform in accordance with embodiments of the invention. Table 1 also provides illustrative sensing methods that may be employed to sense the conditions. The list provided in Table 1 is not exhaustive and additional or different conditions may be used.

Respiration-related conditions that may be used to generate a marked respiration waveform may include, for example, both physiological and non-physiological (contextual) conditions affecting the patient. Physiological conditions may include a broad category of conditions associated with the internal functioning of the patient's physiological systems, including the cardiovascular, respiratory, nervous, muscle and other systems. Examples of physiological conditions include blood chemistry, patient posture, patient activity, respiration patterns, blood pressure, among others.

The respiration processor 3431 may optionally include a disordered breathing processor 3436 for detecting disordered breathing episodes, including, for example, episodes of central and/or obstructive disordered breathing including apnea, hypopnea, Cheyne-Stokes respiration, or other types of disordered breathing. The disordered breathing processor 3436 may also determine various characteristics of the disordered breathing episodes, such as the severity, frequency, duration, and other characteristics of the disordered breathing. The occurrences of disordered breathing and/or disordered breathing characteristics may be indicated in the marked respiration waveform.

Figure 35A:
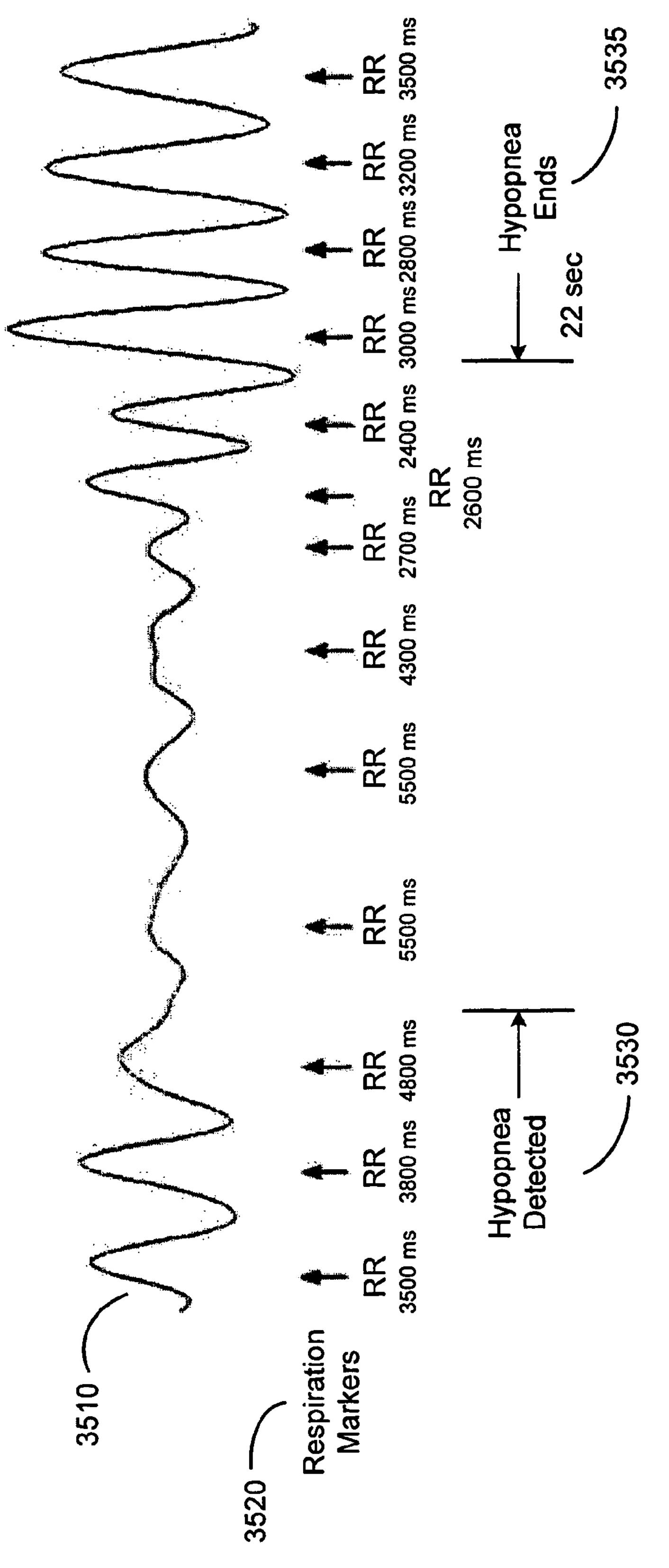
FIG. 35A illustrates a marked respiration waveform in accordance with embodiments of the invention.

The respiration waveform generator 3430 uses the acquired respiration waveform, the respiration characteristics derived from the respiration waveform, and/or the other conditions associated with respiration to generate a marked respiration waveform. The marked respiration waveform comprises the respiration waveform and one or more symbols or other indicators associated with the presence of various respiration waveform characteristics and/or respiration-related conditions. As illustrated in FIG. 35A, the symbols may be displayed at positions relative to the marked respiration waveform to indicate the timing of the respiration characteristics and/or conditions.

The medical system 3400 may acquire one or more additional waveforms representative of physiological and/or non-physiological conditions affecting the patient. The marked respiration waveform may be displayed along with the one or more additional waveforms. The additional waveforms may be time aligned with the respiration waveform to facilitate comparison, such as the ECG and respiration waveforms depicted in FIG. 35B.

The medical system 3400 may include a memory circuit 3460 used to store information related to respiration waveforms, including for example, information related to detected respiration characteristics, respiration-related conditions and/or marked or unmarked respiration waveform data. Stored information may be transmitted by communication circuitry 3450 to a remote device 3455, such as a remote device programmer, a patient management server, or other computing device through a wireless or wired communications link.

As illustrated in FIG. 35A, the marked respiration waveform 3510 may comprise respiratory symbols positioned at locations relative to the respiration waveform to indicate the time of occurrence of respiration events, and the time of occurrence of various respiration conditions and/or characteristics. In the example depicted in FIG. 35A, the respiration waveform 3510 is marked with minute ventilation symbols 3520 denoting peaks on the waveform and apnea markers 3530, 3535 denoting when an apnea event is detected 3530 and when the apnea event ends 3535. In addition, other symbols indicating respiration characteristics and/or disordered breathing characteristics described above may be used to annotate the respiration waveform. The marked respiration waveform information may be stored, transmitted, printed and/or displayed on a display device to allow the patient's physician to view respiratory disturbances and/or other characteristics. Generation of a marked respiration waveform allows a clinician to view respiration disturbances and to determine that respiration events were properly detected. Further, the marked respiration waveform may be used to guide diagnosis and therapy.

Figure 35B:
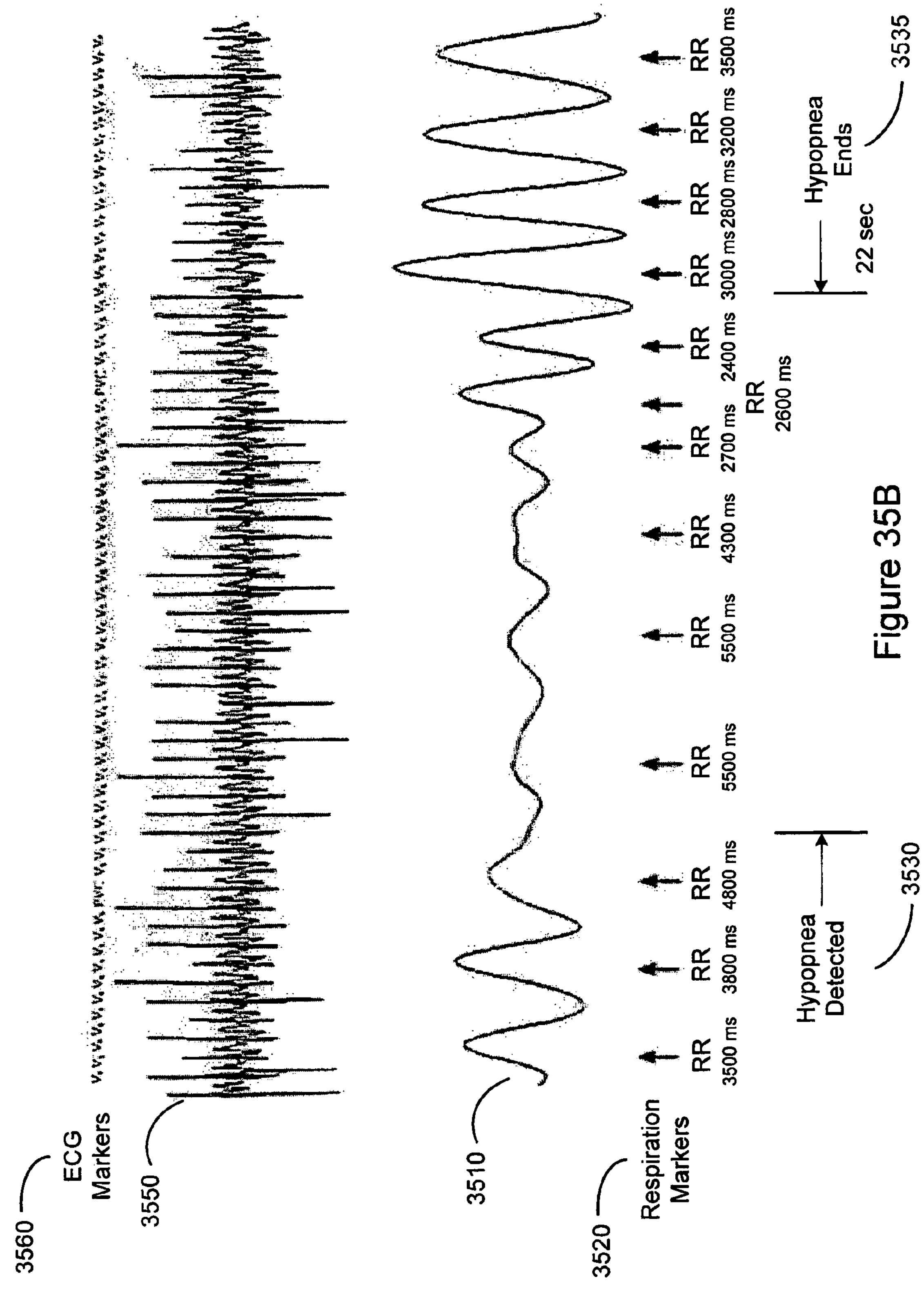
FIG. 35B illustrates a marked respiration waveform including respiration and ECG graphs in accordance with embodiments of the invention.

FIG. 35B provides an illustration of a marked respiration waveform in accordance with embodiments of the invention including respiration and electrocardiogram (ECG) graphs. The respiration waveform and ECG graph, such as the one depicted in FIG. 35B, may be produced, for example, by a medical device having a transthoracic impedance sensor and intracardiac EGM electrodes.

As illustrated in FIG. 35B, the marked respiration waveform may present one or more additional waveforms. The additional waveforms may include, for example, waveforms depicting patient activity, posture, blood gas, blood pressure, and/or other waveforms. In FIG. 35B, an ECG is shown above respiratory waveform 3510. The ECG is time-aligned with respiration waveform 3510 and can be marked with indicators corresponding to the occurrence of breathing events, cardiac events, and/or other events. Displaying marked respiration waveforms and other waveforms related to patient conditions allows the patient's physician to verify, for example, that a disordered breathing event was properly detected. This confirmation may be used to enhance diagnosis and/or therapy. Symbols indicating characteristics and/or conditions related to the cardiovascular, respiratory and/or other physiological systems provide further diagnostic information for physicians. For example, annotated waveforms allow a physician to evaluate the impact of respiration events on other physiological systems.

Medical Event Logbook

Aspects of the invention a medical event logbook are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving a medical event logbook are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 109 (FIG. 1C) for providing a medical event logbook. The medical event logbook system 109 may be implemented as a stand alone system or in combination with other individual medical systems, such as those described in FIGS. 1B-1D.

Embodiments of the invention relate to acquiring and organizing information related to medical events affecting the patient into a logbook. One embodiment of the invention involves a method for organizing medical information. The method involves detecting or predicting a respiratory event of a patient. Responsive to the detection or prediction of the respiratory event, collection of medical information associated with the respiratory event is initiated. The medical information is collected and organized as a respiratory event log entry. At least one of detecting or predicting the respiratory event, collecting the medical information and organizing the medical information is performed implantably.

In accordance with another embodiment of the invention, a method for accessing medical information involves collecting medical information associated with respiratory events. The collection of medical information associated with respiratory events includes initiating, responsive to the detection or prediction of the respiratory event, collection of medical information associated with each respiratory event. The medical information is collected and organized a respiratory logbook. A user interface is provided for accessing the respiratory logbook. At least one of detecting or predicting the respiratory event, collecting the medical information and organizing the medical information is performed implantably.

Another embodiment of the invention involves a method for organizing respiratory information associated with medical events. Responsive to the detection and/or prediction of a medical event, the system initiates collection of respiratory information associated with the medical event. The respiratory information is collected and organized as a medical event log entry. At least one of detecting or predicting the medical event, collecting the respiratory information and organizing the respiratory information is performed implantably.

In accordance with a further embodiment of the invention, a method for accessing respiratory information associated with medical events of a patent involves collecting and organizing respiratory information associated with medical events. Collection of the respiratory information is implemented by initiating, responsive to the detection or prediction of a medical event, collection of respiratory information associated with each medical event. The respiratory information is collected and organized in a medical event logbook. A user interface provides access to the medical event logbook. At least one of detecting or predicting the medical event, collecting the respiratory information and organizing the respiratory information is performed implantably.

Yet another embodiment involves a method for organizing medical event information. According to this method, a medical event is predicted. The system collects information associated with conditions affecting the patient prior to the occurrence of the medical event. The medical event is detected, and the system collects information during the medical event. The collected information is organized as a medical event log entry. At least one of detecting the medical event, predicting the medical event, collecting the respiratory information and organizing the respiratory information is performed implantably.

In accordance with another embodiment of the invention, a medical event logbook system includes an event detector configured to detect or predict a medical event. A data acquisition unit is coupled to the event detector and is configured to collect, responsive to the detection or prediction of the medical event, respiratory information associated with the medical event. The system also includes processor configured to organize the acquired respiratory information as a medical event log entry. At least one of the event detector, the data acquisition unit, and the processor includes an implantable component. In accordance with a further embodiment, a respiratory event logbook system includes an event detector configured to detect or predict a respiratory event affecting the patient. A data acquisition unit is coupled to the event detector and is configured to collect medical information associated with the respiratory event responsive to the detection or prediction of the respiratory event. The system includes a processor configured to organize the collected medical information associated with the respiratory event as a respiratory event log entry. At least one of the event detector, the data acquisition unit, and the processor includes an implantable component.

Other embodiments of the invention involve a system for providing coordinated patient monitoring, diagnosis and/or therapy that generates or utilizes a medical event logbook. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a medical event logbook 109 coupled to at least one of the implantable device and the patient external respiratory therapy device. The medical event logbook is configured to acquire and organize data related to medical events. The medical event logbook includes an event detector configured to detect or predict a medical event affecting the patient. A data acquisition unit is coupled to the event detector. The data acquisition unit is configured to collect respiratory information associated with the medical event responsive to the detection or prediction of the medical event. A processor, coupled to the data acquisition unit, is configured to organize the collected respiratory information associated with the medical event as a medical event log entry. The implantable device and the patient external respiratory device are configured to operate cooperatively to generate or utilize the medical event logbook.

Other embodiments of the invention involve a system for providing coordinated patient monitoring, diagnosis and/or therapy that generates or utilizes a respiratory event logbook. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a respiratory event logbook 109 coupled to at least one of the implantable device and the patient external respiratory therapy device. The respiratory event logbook is configured to acquire and organize data related to medical events. The respiratory event logbook includes an event detector configured to detect or predict a respiratory event affecting the patient. A data acquisition unit is coupled to the event detector. The data acquisition unit is configured to collect medical information associated with the respiratory event responsive to the detection or prediction of the respiratory event. A processor, coupled to the data acquisition unit, is configured to organize the collected medical information associated with the respiratory event as a respiratory event log entry. The implantable device and the patient external respiratory device are configured to operate cooperatively to generate or utilize the respiratory event logbook. The implantable and respiratory therapy devices 181, 184 may operate cooperatively to acquire, organize or use information associated with the respiratory event logbook and/or the medical event logbook. Systems and methods directed to a medical event logbook may be implemented to include selected features, functions, and/or structures described in commonly owned, co-pending U.S. Publication No. 2005/0080348, which is hereby incorporated herein by reference.

Figure 36A:
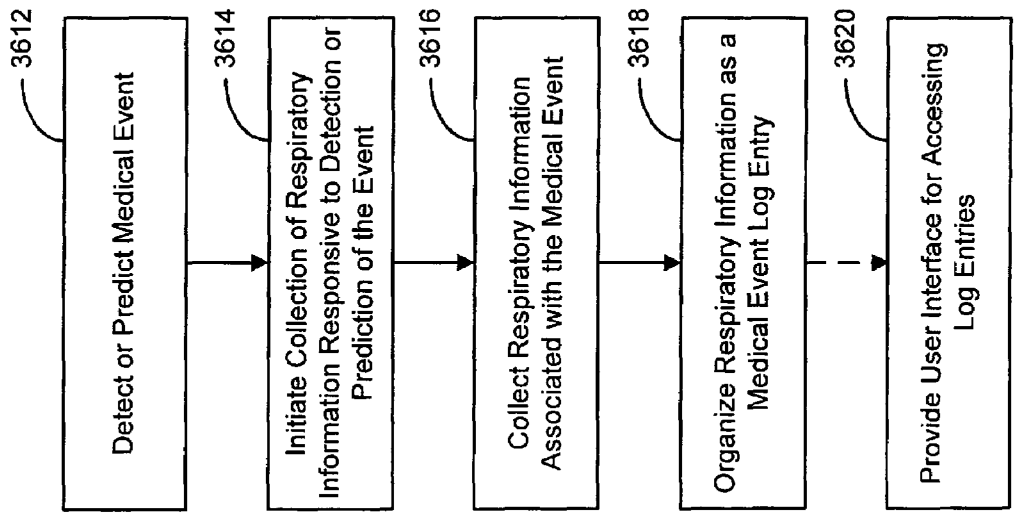
FIGS. 36A-36B a re flowcharts of methods for acquiring and organizing information as event log entries in accordance with embodiments of the invention.

FIG. 36A is a flowchart illustrating a method of acquiring and organizing respiratory information collected in response to a medical event. The medical event may involve various types of events affecting one or more of the respiratory system, cardiovascular system, nervous system, muscle systems, and/or other physiological systems or combinations of physiological systems of the patient. The system implementing the method may be programmable to detect or predict a particular type of event, for example, a cardiac event, such as cardiac arrhythmia or an ectopic beat. The system may collect information about one or more respiratory parameters during, before and/or after the medical event.

In response to the detection or prediction 3612 of the medical event, collection 3614 of respiratory information for the medical event logbook entry is initiated. In some embodiments, the respiratory information is collected 3616 during the event. In other embodiments, the respiratory information is collected 3616 during the event and during a time period proximate to the event. Information may be collected during the event, during a period of time preceding the event, and/or during a period of time following the event. In some embodiments, the information may be collected prior to the prediction or detection of the event.

To facilitate collection of respiratory information preceding the prediction or detection of the event, respiratory conditions may be monitored, e.g., on a continuous or periodic basis, and stored in a temporary buffer. Temporary storage is required to provide information prior to the event prediction or detection, e.g., onset data. The size of the temporary storage buffer may vary according to the medical events for which onset data is desired. Due to the varied nature of onset data requirements and the reality of limited storage in the system, the system may allow different onset data lengths and different sampling rates for the temporarily stored data. In the preferred embodiment the system would use a circular buffer to store the temporary data such that the oldest data is replaced by the newest data.

Once initiated, collection of respiratory information, which may involve storage of the information in long term memory, may be performed on a substantially continuous basis, or it may be performed periodically. Long term storage of data acquired periodically may be beneficial when the event is relatively prolonged, such an in the case of a disease or disorder that may linger for several days or weeks. The type of data collected, data collection frequency, and/or data collection intervals may be selectable by the user. Further, the system may be programmable to use different data collection regimens under different conditions over the course of the event. For example, the system may be programmable to collect data more frequently during sleep or during particular stages of the disease progression, for example. The system may be programmed to collect data on a continuous basis during some time intervals, and periodically during other time intervals, for example.

Collecting information preceding the event facilitates enhanced identification of conditions that may be used to detect or predict the occurrence of future events. For example, acquiring information preceding a medical event allows for the identification and assessment of physiological conditions present immediately before and leading up to the medical event. The identification of precursor conditions for medical events may facilitate increased sensitivity and/or accuracy in detecting or predicting occurrences of the future events.

The acquired respiratory information is organized 3618 as a medical event log entry. A medical event logbook may comprise a number of entries, each entry corresponding to a separate medical event. The medical events represented in the medical event logbook may comprise, for example, cardiovascular system events, nervous system events, respiratory system events, or any other medical events affecting the patient. The event entries included in medical event log may be organized according to various categories, including for example, event type, event time/date, order of occurrence of the event, therapy provided to treat the event, among other categories. The selection of categories used to organize the information may be programmable by the user. The organized information may be stored in long term memory, displayed, printed, and/or transmitted to a separate device. In one approach, the medical event comprises a cardiac event. Respiratory information collected before, during and/or after the cardiac event may be stored as a log entry in a cardiac arrhythmia logbook, for example.

In one embodiment of the invention, the collected information for the events is optionally accessible 3620 through an interactive user interface. Selection of events to the accessed may involve a hierarchical selection menu, or other selection method, for example. In one implementation, the user may select a log entry from the menu by activating an input mechanism. Upon selection of the log entry, the user interface may provide graphical or textual depictions of the collected respiratory information associated with the medical event.

Figure 36B:
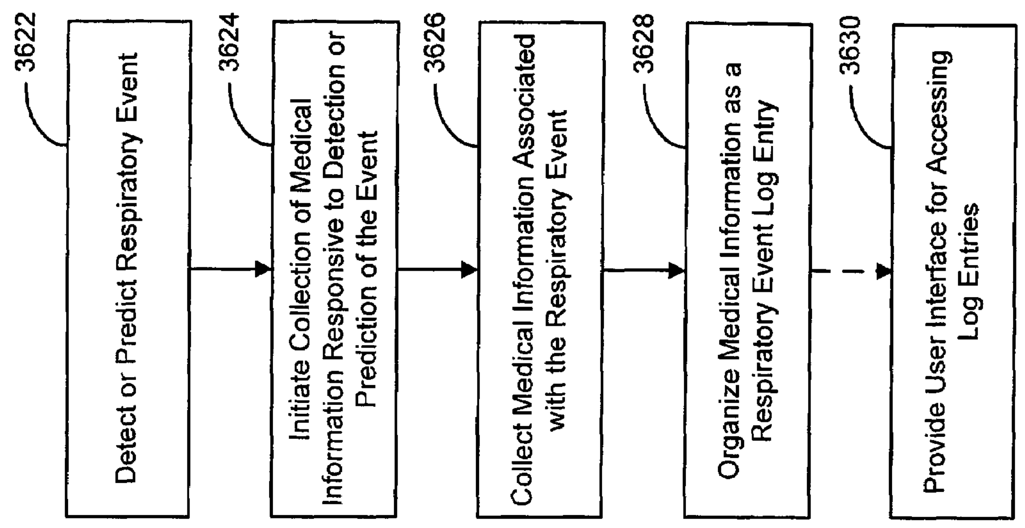

FIG. 36B is a flow chart for an embodiment involving collecting medical information associated with a respiratory event. The respiratory event may be detected or predicted 3622. The event may include any detectable or predictable respiratory event, such as disordered breathing (apnea, hypopnea, tachypnea), coughing and/or breathing irregularities associated with pulmonary diseases and disorders such as asthma, pulmonary edema, chronic obstructive pulmonary disease, and/or pleural effusion, among others.

In response to the detection or prediction 3622 of the respiratory event, collection 3624 of medical information for the respiratory event logbook entry is initiated. The medical information may be collected 3624 during the event and/or during a time period proximate to the event. Information may be collected during the event, during a period of time preceding the event, and/or during a period of time following the event. In some embodiments, the information may be collected prior to the prediction or detection of the respiratory event.

To facilitate collection of medical information preceding the prediction or detection of the respiratory event, the medical information may be monitored, e.g., on a continuous or periodic basis, and stored in a temporary buffer. Temporary storage is required to provide information prior to the event prediction or detection, e.g., onset data. The duration of the temporary storage may vary according to the respiratory events for which onset data is desired. For example, temporary storage of about one minute may be sufficient to understand onset conditions for an obstructive an apnea event whereas temporary storage of about one day may be required to understand onset conditions for an asthma event.

Due to the varied nature of onset data requirements and the reality of limited storage in the system, the system may allow different onset data lengths and different sampling rates for the temporarily stored data. In a preferred embodiment, the system uses a circular buffer to store the temporary data such that the oldest data is replaced by the newest data.

Once initiated, collection of respiratory information, which may involve storage of the information in long term memory, may be performed on a substantially continuous basis, or it may be performed during discrete intervals. Long term collection of data on a periodic basis may be beneficial when the event is relatively prolonged, such an in the case of a disease or disorder that may linger for several days or weeks. Various collection parameters, such as the type of data collected, data collection frequency, and/or data collection intervals may be selectable by the user. Further, the system may be programmable to use different data collection regimens under different conditions over the course of the event. For example, the system may be programmed to collect data more frequently during sleep or during particular stages of the disease progression, for example. The system may be programmed to collect data on a substantially continuous basis during some time intervals, and periodically during other time intervals, for example.

Collecting medical information preceding the respiratory event facilitates enhanced identification of conditions that may be used to detect or predict the occurrence of future events. For example, acquiring information preceding the event affecting patient respiration allows for the identification and assessment of physiological conditions present immediately before and leading up to the event. In one scenario, the patient may experience a period of hyperventilation prior to an apnea event. Collecting respiratory information prior to the apnea event allows the identification of hyperventilation as a precursor condition. The identification of precursor conditions for apnea facilitate increased sensitivity and/or accuracy in detecting or predicting future occurrences of apnea.

Additionally, or alternatively, medical information preceding the respiratory event may provide insight into conditions that predispose the patient to certain respiratory events. Acquiring information preceding the event may provide allow identification of the triggering or causal factors of the event. For example, an asthma attack may be induced by increased exercise or a sudden change in ambient temperature, e.g., the patient moving from a warmer location to a colder location. Collection of medical information preceding the asthma attack allows the factors that precipitate the respiratory event to be identified. Such information may be used to enhance the detection and/or prediction of future events.

Information collected following the event may be used to assess the acute effects of the event. Episodes of disordered breathing, for example, may be associated with acute physiological effects, including negative intrathoracic pressure, hypoxia, and arousal from sleep. Such effects may be detectable for a period of time following the respiratory event.

For example, obstructive sleep apneas are typically terminated by arousal from sleep that occurs several seconds after the apneic peak, allowing the resumption of airflow. Coincident with arousal from sleep, and continuing for some period of time after termination of the event, surges in sympathetic nerve activity, blood pressure, and heart rate occur.

During obstructive apnea events, the effort to generate airflow increases. Attempted inspiration in the presence of an occluded airway results in an abrupt reduction in intrathoracic pressure. The repeated futile inspiratory efforts associated with obstructive sleep apnea may trigger a series of secondary responses, including mechanical, hemodynamic, chemical, neural, and inflammatory responses. Collection of data following obstructive sleep apnea events may be used to determine the presence and/or severity of the secondary responses to obstructive apnea events. The post-event information enhances the ability to evaluate the impact of the secondary responses upon the patient.

As previously described, obstructive sleep apnea events are typically terminated by arousal from sleep. However, arousals are not usually required for the resumption of breathing in central sleep apnea events. In the case of central apnea events, the arousals follow the initiation of breathing. Arousals following central apnea events may facilitate the development of oscillations in ventilation by recurrently stimulating hyperventilation and reducing $PaCO_2$ below the apneic threshold. Once triggered, the pattern of alternating hyperventilation and apnea may be sustained by the combination of increased respiratory drive, pulmonary congestion, arousals, and apnea-induced hypoxia causing $PaCO_2$ oscillations above and below the apneic threshold. Shifts in the patient's state of consciousness, particularly with repeated arousals, may further destabilize breathing. Collecting information during central apnea events and before and/or after the occurrence of the events may allow identification of the oscillations associated with central apnea.

The collected medical information, which may be stored in long term memory, transmitted, printed and/or displayed is organized as a respiratory logbook entry 3628. The medical information may include various physiological and non-physiological data. For example, respiratory system data, cardiovascular system data, nervous system data, posture, activity, medical history data, environmental data (temperature, altitude, air quality) and other types of medical information may be organized as a respiratory logbook entry. The respiratory logbook entry may be stored, transmitted, printed and/or displayed.

A respiratory event logbook may comprise a number of entries, each entry corresponding to a separate respiratory event. The event entries included in medical event log may be organized according to various categories, including for example, event type, event time/date, order of occurrence of the event, therapy provided to treat the event, among other categories. The selection of categories used to organize the information may be programmable by the user. The organized information may be stored in long term memory, displayed, printed, and/or transmitted to a separate device.

The collected information for the events may be optionally accessible 3630 through an interactive user interface. The interactive user interface may provide access to one or more log entries through activation of a selection process, involving a hierarchical selection menu, or other selection method, for example. In one implementation, the user may select a log entry from the menu by activating an input mechanism. Upon selection of the log entry, the user interface may provide graphical or textual depictions of the collected respiratory information associated with the medical event.

Relating to both FIGS. 36A and 36B, the event information of the logbook may be stored in long term memory using various storage methodologies. For example, the logbook may utilize a flat file system, hierarchical database, relational database, or distributed database. Data for a group of events may be analyzed and/or summarized in various formats. Graphical and/or textual summary information may be displayed on the user interface and/or otherwise communicated to the user. For example, histograms, trend graphs, and/or other analytical tools or formats may be generated based on the logbook event entries. A logbook display may have the ability to display trends of the patient's apnea/hypopnea index, histograms of number of apneas/hypopneas and/or obstructive/central events per night, sleep stage diagram (shows the stage of sleep for each night), heart rate trend during the night, oxygen saturation trend during the night.

In various embodiments, collection of medical information may be initiated responsive to prediction of a medical event. In this scenario, information may be collected prior to the prediction of the medical event, prior to the detection of the medical event, during the event, and/or following the event.

Figure 37:
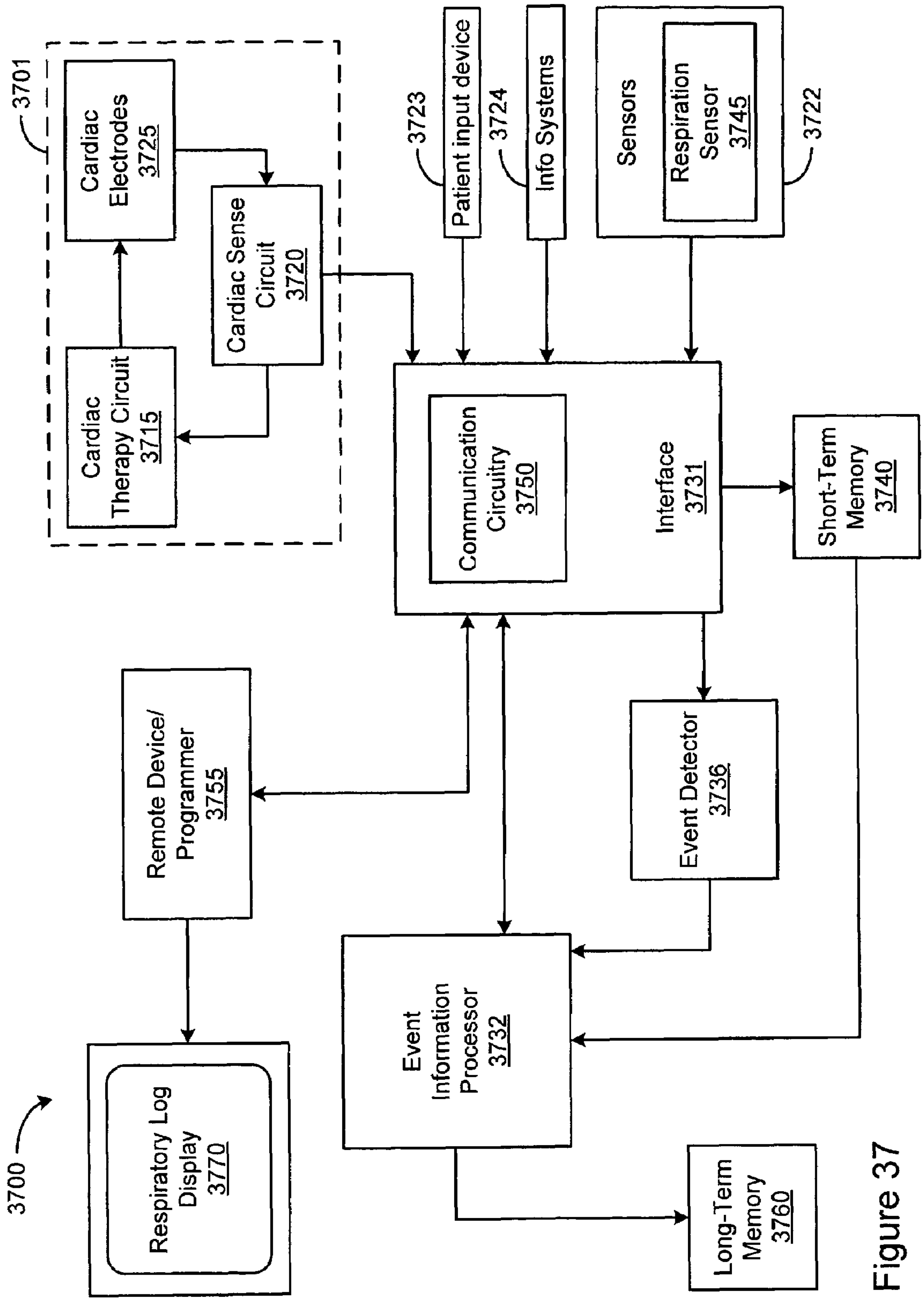
FIG. 37 is a block diagram of a respiratory logbook system in accordance with embodiments of the invention.

FIG. 37 is a block diagram of a logbook system 3700 in accordance with embodiments of the invention. The respiratory logbook system 3700 implements an event-driven method of collecting and organizing data related to events affecting patient respiration.

Various patient conditions may be monitored through sensors 3722, patient input devices 3723, and/or information systems 3724. Data associated with patient conditions may be stored in short term memory 3740. One or more of the patient conditions may be used by event detection circuitry 3736 to detect or predict the occurrence of an event affecting respiration. Detection or prediction of an event affecting respiration initiates the long term storage of information associated with the event by the event information processor 3732 into the long term memory 3760. For example, the event information processor 3732 may collect information supplied by one or more of the sensors 3722, patient input devices 3723, and information systems 3724 before, during, and/or after the detection and/or prediction of the event. The collected information associated with each event is organized as a respiratory logbook entry in the respiratory logbook. The respiratory logbook, or portions thereof, may be stored in long term memory 3760, transmitted to a remote device 3755, and/or displayed on a display device 3770.

The embodiment illustrated in FIG. 37 includes a respiration sensor 3745 that senses a physiological condition modulated by patient respiration. In one embodiment, the respiration sensor may comprise a transthoracic impedance sensor. Other methods of sensing respiration are also possible. Such methods may include, for example, the use of patient-external respiratory bands, respiration flowmeter measurements, implantable or patient-external breath sound detection, blood oxygen levels, and/or other processes. The respiration sensor 3745 may be used, for example, to acquire a respiration waveform before, during, and/or after an event affecting the patient respiration. The respiration waveform may be a component of the respiratory log entry for the event.

Information about various conditions affecting the patient and associated with the event may be acquired using sensors 3722, patient input devices 3723 and/or other information systems 3724. The sensors 3722 may comprise patient-internal and/or patient-external sensors coupled through leads or wirelessly to the interface 3731 of the respiratory logbook system 3700. The sensors may sense various physiological and/or non-physiological conditions affecting patient respiration or other physiological systems. The patient input device 3723 allows the patient to input information relevant to conditions affecting the patient that may be useful in generating a respiratory event log. For example, the patient input device 3723 may be particularly useful for acquiring information known to the patient, such as information related to patient smoking, drug use, recent exercise level, and/or other patient activities, perceptions and/or symptoms. The information provided by the patient-input device may include patient-known information relevant to the event affecting respiration that is not automatically sensed or detected by the respiratory logbook system 3700.

The respiratory logbook system 3700 may also include one or more information systems 3724 such as a remote computing device and/or a network-based server. The event information processor 3732 may access the information systems 3724 to acquire information from databases and/or other information sources stored on or generated by the remote computing devices and/or servers. The information acquired from the information system s 3724 may be recorded in the respiratory logbook along with other information relevant to the event affecting respiration. In one exemplary implementation, the respiratory logbook system 3700 may access an internet connected air quality server to collect data related to environmental conditions, such as an ambient pollution index. In another implementation, the respiratory logbook system 3700 may access the patient's medical history through a patient information server.

The sensors 3722, patient input devices 3723, and information systems 3724 are coupled to other components of the respiratory logbook system 3700 through interface circuitry 3731. The interface 3731 may include circuitry for energizing the sensors 3722 and/or for detecting and/or processing signals generated by the sensors. The interface 3731 may include, for example, driver circuitry, amplifiers, filters, sampling circuitry, and/or A/D converter circuitry for conditioning the signals generated by the sensors.

The interface 3731 may also include circuitry 3750 for communicating with the patient input device 3723, information systems 3724, a device programmer 3755, an APM system (not shown), or other remote devices. Communication with the patient input device 3723, information systems 3724 and/or a remote device programmer 3755 and/or other remote devices may be implemented using a wired connection or through a wireless communication link, such as a Bluetooth or other wireless link. The communication circuitry 3750 may also provide the capability to wirelessly communicate with various sensors, including implantable, subcutaneous, cutaneous, and/or non-implanted sensors.

The respiratory logbook system 3700 may optionally be implemented as a component of a medical device that includes a therapy system, such as a cardiac rhythm management system 3701. The cardiac rhythm management system 3701 may include cardiac electrodes 3725 electrically coupled to the patient's heart. Cardiac signals sensed by cardiac sense circuitry 3720 may be used in the detection and treatment of various anomalies of the heart rhythm. Anomalous heart rhythms may include, for example, a rhythm that is too slow (bradycardia), a heart rhythm that is too fast (tachycardia), and/or a heart rhythm that involves insufficiently synchronized contractions of the atria and/or ventricles, a symptom of congestive heart failure.

If an arrhythmia is detected by the cardiac rhythm management system, then a cardiac therapy circuit 3715 may deliver cardiac therapy to the heart in the form of electrical stimulation pulses, such as pacing and/or cardioversion/defibrillation pulses. The cardiac signals and/or cardiac conditions, e.g., arrhythmia conditions, derived or detected through the use of the cardiac signals may be associated with an event affecting respiration. The cardiac information associated with the event may be acquired and organized by the respiratory logbook system 3700.

Figure 38:
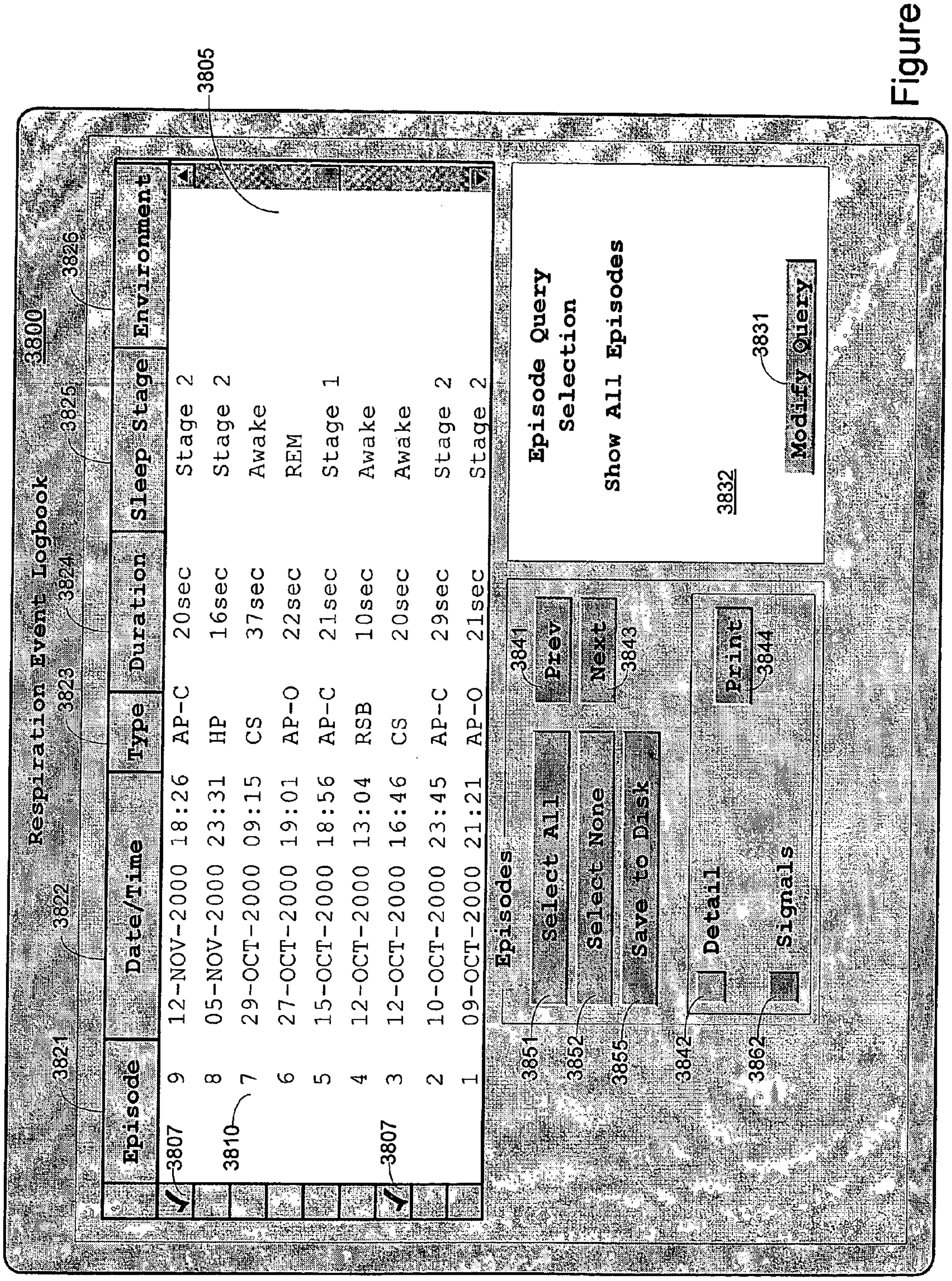
FIG. 38 illustrates an exemplary depiction of a user interface display that may be used with a respiratory logbook system in accordance with embodiments of the invention.

A user interface may be used to view and/or access the respiratory logbook information. FIG. 38 illustrates an exemplary depiction of a user interface display 3800. An area 3805 of the display may be used to provide textual or graphical information about respiratory events. As illustrated in FIG. 38, a menu 3810 of respiratory events may be presented and may enable the user to access additional information related to the respiratory event. The menu 3810 may provide a summary of parameters associated with the events contained in the respiratory logbook. As illustrated in FIG. 38, one or more summary parameter headings, such as episode number 3821, date/time 3822, type 3823, duration 3824, sleep stage 3825, and/or environment 3826, among other parameter headings, may be presented at the top of the menu 3810 or in another convenient location. The summary parameter headings 3821-3826 may be programmable, and additional or alternative parameter headings to those depicted in FIG. 38 may be selected, for example.

The type parameter 3823 may contain abbreviations for various respiratory events. For example AP-C and AP-O may abbreviate central and obstructive apneas respectively, HP abbreviates a hypopnea, CS abbreviates Cheyne-Stokes respiration and RSB abbreviates rapid-shallow breathing.

The respiratory events displayed as menu items in the menu 3810 may be selected by a user according to episode number, date/time, duration, type, number, or by other criteria. The menu items may be selected for display based on various criteria ranges and/or thresholds. For example, in the example screen illustrated in FIG. 38, different groups of events selected as menu items may be selected by activating the modify query button 3831. The modify query button 3831 and other buttons illustrated on the display may be voice activated, activated through touching the display screen, or by operating a keyboard or pointing device, for example.

In one implementation, activation of the modify query button 3831 initiates a dialog session that allows the user to select respiratory events to be presented in the menu according various criteria such as by date/time, duration, type, number, or by other criteria ranges or thresholds. In one example, the user may select all apnea events to be presented as menu items. In another example, the user may select all events that occurred between a first date and a second date. In yet another example, the user may select all events that occurred while the patient experienced certain environmental conditions, e.g., ambient temperature range and/or humidity range. In yet another example, the user may choose to select all events of the respiratory logbook. The selection criteria may be displayed in an episode query selection area 3832 of the display. The episode query selection area 3832 in the depiction of a respiratory logbook display shown in FIG. 38 indicates that all episodes have been selected to be displayed as menu items.

The menu 3810 allows the user to choose respiratory events for which additional textual and/or graphical information is displayed. The additional information provides more detailed information about the selected events beyond the summary information presented in the menu 3810. In the exemplary illustration depicted in FIG. 38, the selections are indicated by check marks 3807 beside the selected respiratory events. For convenience, the display may include a select all button 3851 and/or a select none button 3852. Activation of the select all button 3851 causes all events in the menu 3810 to be selected. Activation of the select none button 3852 causes all events in the menu 3810 to be deselected.

Following selection of one or more episodes in the menu, activation of the detail button 3842 causes detailed textual information associated with a selected event to be presented on the display screen. The detail information may be displayed in the area of the screen 3805 previously occupied by the menu 3810, for example. The user may scroll back and forth through the textual information for the one or more selected events using the prev button 3841 and the next button 3843. The textual information may be printed upon activation of the print button 3844, or may be saved to a disk, or other storage medium, through activation of the save to disk button 3855.

Graphical information associated with the selected events may be displayed upon activation of the signals button 3862. In one implementation, a respiration waveform acquired during, before and/or after a selected event may be displayed in the area 3805 of the display previously used for the menu 3810. Waveforms of other parameters, e.g., cardiac rhythm, patient activity, may additionally or alternatively be displayed. In one implementation, a marked waveform may be displayed. For example, a marked respiration waveform may include the respiration waveform acquired before, during, and after the event, along with one or more symbols aligned with the respiration waveform to indicate the occurrence of one or more conditions. The symbol may provide a numerical value or a textual description associated with the respiration characteristic, e.g., average respiration rate, expiratory slope, etc. In one example, various characteristics of disordered breathing events including quantifiable characteristics, such as episode duration, blood oxygen saturation, disordered breathing type, and/or other detected characteristics may also be displayed along with the respiration waveform. A user may scroll through the waveforms associated with the selected events using the prev and next buttons 3841, 3843.

Figure 39A:
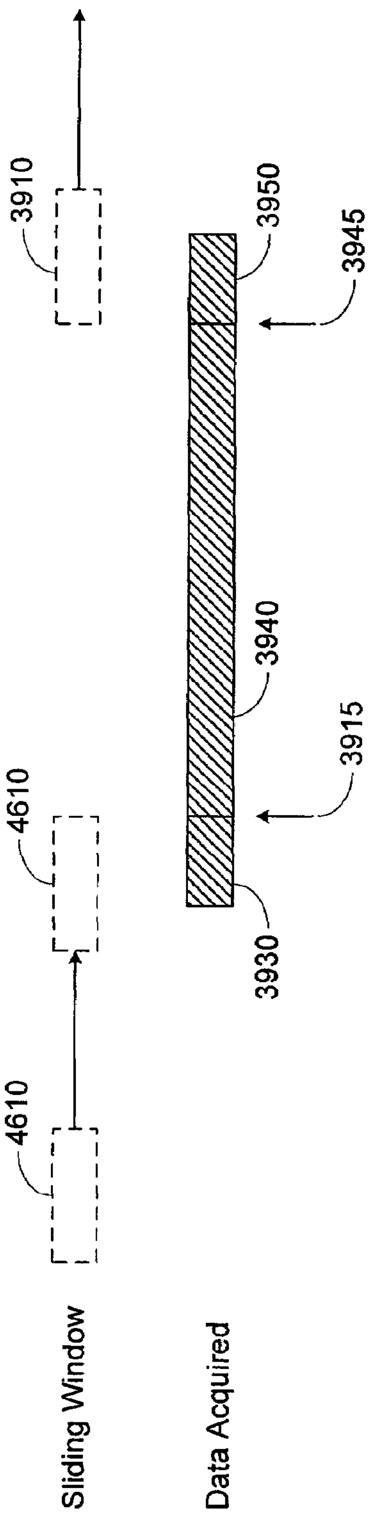
FIG. 39A provides a timing diagram illustrating the acquisition of respiration logbook information for a detected event affecting respiration in accordance with embodiments of the invention.

FIG. 39A provides a timing diagram illustrating the acquisition of respiratory logbook information for a detected event affecting respiration in accordance with embodiments of the invention. The respiratory logbook system senses and stores in a temporary buffer a sliding scale window 3910 of one or more patient conditions, such as those listed in Tables 1-3. The selection of information that is sensed and stored may be programmable by the physician. The selection of the information to be acquired may be based on the patient's medical history. For example, if the patient suffers from sleep apnea, or another form of disordered breathing, the respiratory logbook would preferably be programmed to sense conditions associated with disordered breathing. Conversely, if the patient suffers from chronic obstructive pulmonary disorder, a different set of conditions from those used for disordered breathing could be sensed.

If an event affecting respiration is detected 3915, then pre-event information 3930 acquired prior to the event is stored. Information is collected and stored during 3940 the event. Upon detection that the event has terminated 3945, post-event information 3950 is collected and stored for a period of time after the termination of the event. The event and post-event information 3940, 3950 may be acquired on a continuous basis, or the information may be acquired during discrete intervals. After the post-event information 3950 is collected, the acquired information 3930, 3940, 3950 is organized as a logbook entry. The respiratory logbook system begins sensing for the next event.

Figure 39B:
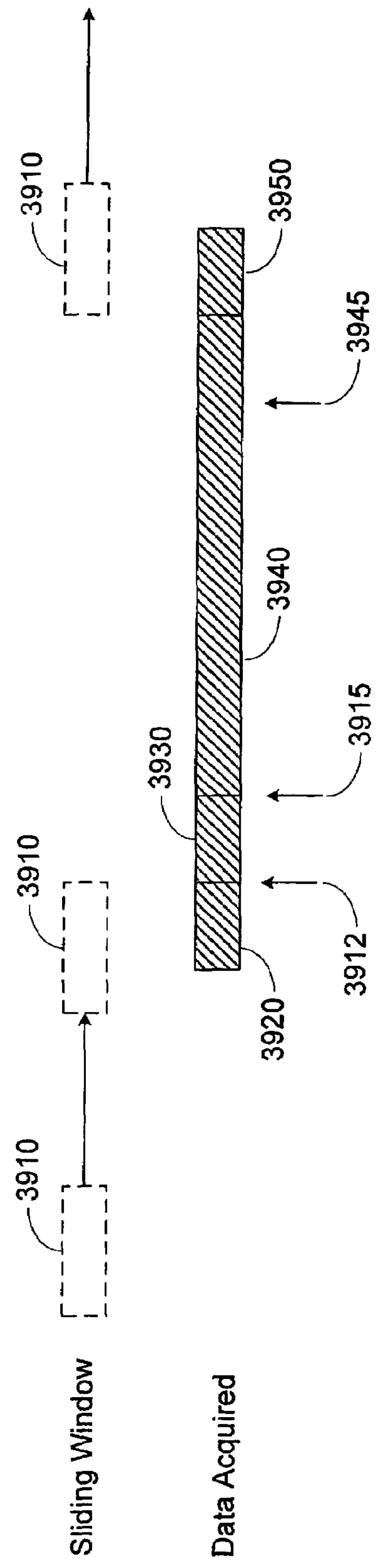
FIG. 39B provides a timing diagram illustrating the acquisition of respiratory logbook information for a predicted event affecting respiration in accordance with embodiments of the invention.

FIG. 39B provides a timing diagram illustrating the acquisition of respiratory logbook information for a predicted event affecting respiration in accordance with embodiments of the invention. The respiratory logbook system senses and stores in a temporary buffer a sliding scale window 3910 of one or more patient conditions, such as those listed in Tables 1-3. The conditions that are sensed and stored are programmable and may be selected based on the patient's medical history. For example, the information sensed and stored may include information that has been effectively used to predict the one or more types of events affecting the patient's respiration. If an event affecting respiration is predicted 3912, then pre-prediction information 3920 is acquired and stored. When the event affecting respiration is detected 3915, then pre-event information 3930 acquired prior to the event is stored. Information 3940 is collected and stored during the event. Upon detection that the event has terminated 3945, information 3950 is collected and stored for a period of time after the termination of the event. The pre-event, event and post-event information 3930, 3940, 3950 may be acquired on a continuous basis, or the information may be acquired during discrete intervals. After the post-event information 3940 is collected, the acquired information 3920, 3930, 3940, 3950 is organized as a logbook entry. The respiratory logbook begins sensing for the next event.

Sleep Logbook

Aspects of the invention that include a sleep logbook are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving a sleep logbook are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 182 (FIG. 1C) for acquiring and organizing information related to sleep in a logbook format. The sleep logbook system 182 may be implemented as a stand alone system or in combination with other individual medical systems, such as those described in FIGS. 1B-1D.

Embodiments of the invention are directed to methods and systems for organizing information related to sleep and/or events occurring during sleep. One embodiment of the invention involves an automated method for collecting and organizing information associated with sleep. The method includes detecting sleep and acquiring information associated with sleep. The acquired information is organized as a sleep logbook. At least one of detecting sleep, acquiring the information associated with sleep, and organizing the acquired information is performed at least in part implantably.

Another embodiment involves a method for organizing sleep-related information. The method includes acquiring information associated with one or more sleep periods. The information associated with the one or more sleep periods is organized as a sleep logbook. A user interface is provided for accessing the sleep logbook.

In another embodiment of the invention, a sleep logbook system provides organized sleep information. The sleep logbook includes a sleep detector configured to detect sleep. A data acquisition unit acquires sleep information related to sleep. A processor is coupled to the sleep detector and the data acquisition unit. The processor organizes the acquired sleep information as a sleep logbook entry. At least one of the sleep detector, the data acquisition unit, and the processor includes an implantable component.

Other embodiments of the invention involve a system for providing coordinated patient monitoring, diagnosis and/or therapy utilizing a sleep logbook 182. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy further includes a sleep logbook system configured to collect and organize information related to sleep. The sleep logbook system includes a sleep detector configured to detect sleep. The sleep logbook system also includes a data acquisition unit configured to acquire information related to sleep. A processor is coupled to the sleep detector and the data acquisition unit. The processor is configured to organize the acquired sleep information as a sleep logbook entry. The implantable and respiratory therapy devices 181, 184 work cooperatively to implement or use the sleep logbook. Systems and methods directed to a sleep logbook may be implemented to include selected features, functions, and/or structures described in commonly owned, U.S. Pat. No. 7,572,225, which is hereby incorporated herein by reference.

Sleep quality assessments depend upon acquiring sleep-related data, including the patient's typical sleep patterns and the physiological, environmental, contextual, emotional, and other conditions affecting the patient during sleep. Diagnosis of sleep disorders and assessment of sleep quality often involves the use of a polysomnographic sleep study at a dedicated sleep facility. However, such studies are costly, inconvenient to the patient, and may not accurately represent the patient's typical sleep behavior. In a polysomnographic sleep study, the patient is instrumented for data acquisition and observed by trained personnel. Sleep assessment in a laboratory setting presents a number of obstacles in acquiring an accurate picture of a patient's typical sleep patterns. For example, spending a night in a sleep laboratory typically causes a patient to experience a condition known as "first night syndrome," involving disrupted sleep during the first few nights in an unfamiliar location. In addition, sleeping while instrumented and observed may not result in a realistic perspective of the patient's normal sleep patterns.

Further, polysomnographic sleep studies provide an incomplete data set for the analysis of some sleep disorders, including, for example, sleep disordered breathing. A number of physiological conditions associated with sleep disordered breathing are detectable during periods of wakefulness, e.g., decreased heart rate variability, elevated sympathetic nerve activity, norepinephrine concentration, and increased blood pressure variability. Collection of data during periods of sleep and/or during periods of wakefulness may provide a more complete picture of the patient's sleep quality.

Various aspects of sleep quality, including the number and severity of arousals, sleep disordered breathing episodes, and nocturnal limb movements. Further, cardiac, respiratory, muscle, and nervous system functioning may provide important information for diagnosis and/or therapy delivery. An initial step to sleep quality evaluation is an accurate and reliable method for discriminating between periods of sleep and periods of wakefulness. Further, acquiring data regarding the patient's sleep states or stages, including sleep onset, termination, REM, and NREM sleep states may be used in connection sleep quality assessment. For example, the most restful sleep occurs during stages 3 and 4 NREM sleep. One indicator of sleep quality is the percentage of time a patient spends in these sleep stages. Knowledge of the patient's sleep patterns may be used to diagnose sleep disorders and/or adjust patient therapy, including, e.g., cardiac or respiratory therapy. Trending disordered breathing episodes, arousal episodes, and other sleep quality aspects may be helpful in determining and maintaining appropriate therapies for patients suffering from disorders ranging from snoring to congestive heart failure.

Figure 40:
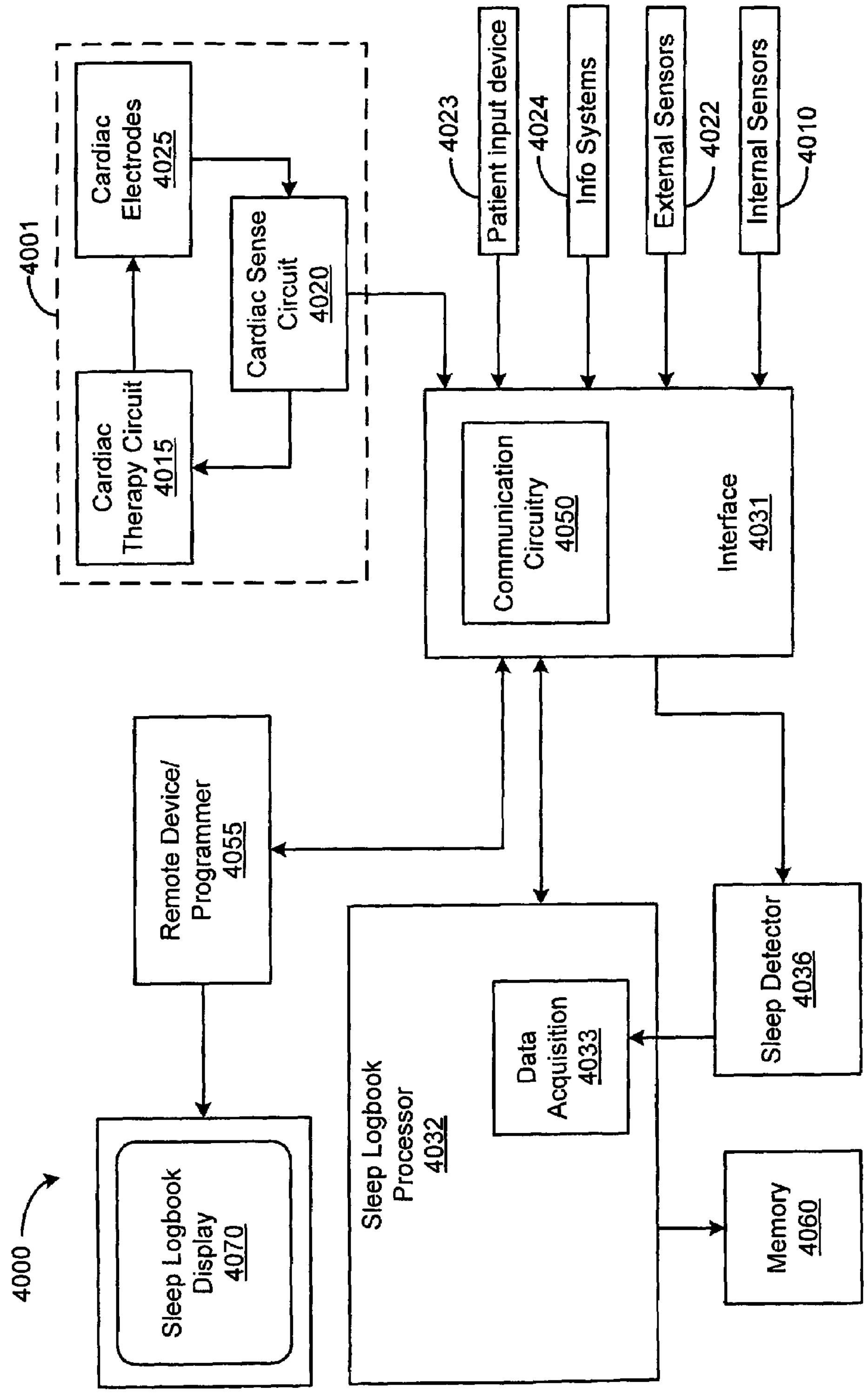
FIG. 40 is a block diagram of a sleep logbook system in accordance with embodiments of the invention.

FIG. 40 is a block diagram of a sleep logbook system 4000 in accordance with embodiments of the invention. In this exemplary embodiment, the system includes sleep logbook functionality provided along with a cardiac rhythm management. This embodiment is particularly useful for patients benefiting from cardiac pacing and/or defibrillation support through an implantable cardiac pulse generator.

Various patient conditions associated with sleep may be monitored through sensors 4010, 4022, patient input devices 4023, and/or information systems 4024. One or more of the patient conditions may be used by sleep detection circuitry 4036 to detect the onset and/or offset of sleep. Detection of sleep onset initiates the collection of information associated with the sleep period by the data acquisition unit 4033 of a sleep logbook processor 4032. For example, the data acquisition unit 4033 may collect information supplied by one or more of the sensors 4010, 4022, patient input devices 4023, and information systems 4024 before, during, and/or after the sleep period. The collected information associated with each sleep period is organized as a sleep logbook entry in the sleep logbook. The sleep logbook, or portions thereof, may be stored in memory 4060, transmitted to a remote device 4055, and/or displayed on a display device 4070.

The embodiment illustrated in FIG. 40 may include, for example, a respiration sensor that senses a physiological condition modulated by patient respiration. In one embodiment, the respiration sensor may comprise an implantable transthoracic impedance sensor. Other methods of sensing respiration are also possible. Such methods may include, for example, the use of patient-external respiratory bands, respiration flowmeter measurements, implantable or patient-external breath sound detection, blood oxygen levels, and/or other processes. The respiration sensor may acquire information used in the detection of sleep onset and offset, as described in greater detail below. Additionally or alternatively, respiration sensing may be used, for example, to acquire a respiration waveform before, during, and/or after an event affecting the patient respiration. The respiration waveform may be a component of the sleep logbook entry.

Information about various conditions associated with and/or occurring during sleep may be acquired using sensors 4010, 4022, patient input devices 4023 and/or other information systems 4024. The sensors may comprise patient-internal 4010 and/or patient-external 4022 sensors coupled through leads or wirelessly to the interface 4031 of the sleep logbook system 4000. The sensors 4010, 4022 may sense various physiological and/or non-physiological conditions. The patient input device 4023 allows the patient to input information relevant to conditions affecting the patient that may be useful in generating a sleep log. For example, the patient input device 4023 may be particularly useful for acquiring information known to the patient, such as information related to patient smoking, drug use, recent exercise level, and/or other patient activities, symptoms, or perceptions, including patient perceptions of daytime sleepiness and/or sleep quality. The information provided by the patient-input device may include patient-known information that is not automatically sensed or detected by the sleep logbook system 4000.

The sleep logbook system 4000 may also include one or more information systems 4024 such as a remote computing device and/or a network-based server. The event information processor 4032 may access the information systems 4024 to acquire information from databases and/or other information sources stored on or generated by the remote computing devices and/or servers. The information acquired from the information systems 4024 may be recorded in the sleep logbook along with other information relevant to the event affecting sleep. In one exemplary implementation, the sleep logbook system 4000 may access an internet connected air quality server to collect data related to environmental conditions, such as an ambient pollution index. In another implementation, the sleep logbook system 4000 may access the patient's medical history through a patient information server.

The sensors 4010, 4022, patient input devices 4023, and information systems 4024 are coupled to other components of the sleep logbook system 4000 through interface circuitry 4031. The interface 4031 may include circuitry for energizing the sensors 4010, 4022 and/or for detecting and/or processing signals generated by the sensors. The interface 4031 may include, for example, driver circuitry, amplifiers, filters, sampling circuitry, and/or A/D converter circuitry for conditioning the signals generated by the sensors.

The interface 4031 may also include circuitry 4050 for communicating with the patient input device 4023, information systems 4024, a device programmer 4055, an APM system (not shown), or other remote devices. Communication with the patient input device 4023, information systems 4024 and/or a remote device programmer 4055 and/or other remote devices may be implemented using a wired connection or through a wireless communication link, such as a Bluetooth or other proprietary wireless link. The communication circuitry 4050 may also provide the capability to wirelessly communicate with various sensors, including implantable, subcutaneous, cutaneous, and/or external sensors.

The sleep logbook functionality may optionally be provided in a medical device that includes a therapy system, such as an implantable cardiac rhythm management system 4001. The cardiac rhythm management system 4001 may include cardiac electrodes 4025 electrically coupled to the patient's heart. Cardiac signals sensed by cardiac sense circuitry 4020 may be used in the detection and treatment of various anomalies of the heart rhythm. Anomalous heart rhythms may include, for example, a rhythm that is too slow (bradycardia), a heart rhythm that is too fast (tachycardia), and/or a heart rhythm that involves insufficiently synchronized contractions of the atria and/or ventricles, a symptom of congestive heart failure.

If an arrhythmia is detected by the cardiac rhythm management system, then a cardiac therapy circuit 4015 may deliver cardiac therapy to the heart in the form of electrical stimulation pulses, such as pacing and/or cardioversion/defibrillation pulses. The cardiac signals and/or cardiac conditions, e.g., arrhythmia conditions, derived or detected through the use of the cardiac signals may be associated with sleep. The cardiac information associated with sleep may be acquired and organized by the sleep logbook system 4000.

Figure 41:
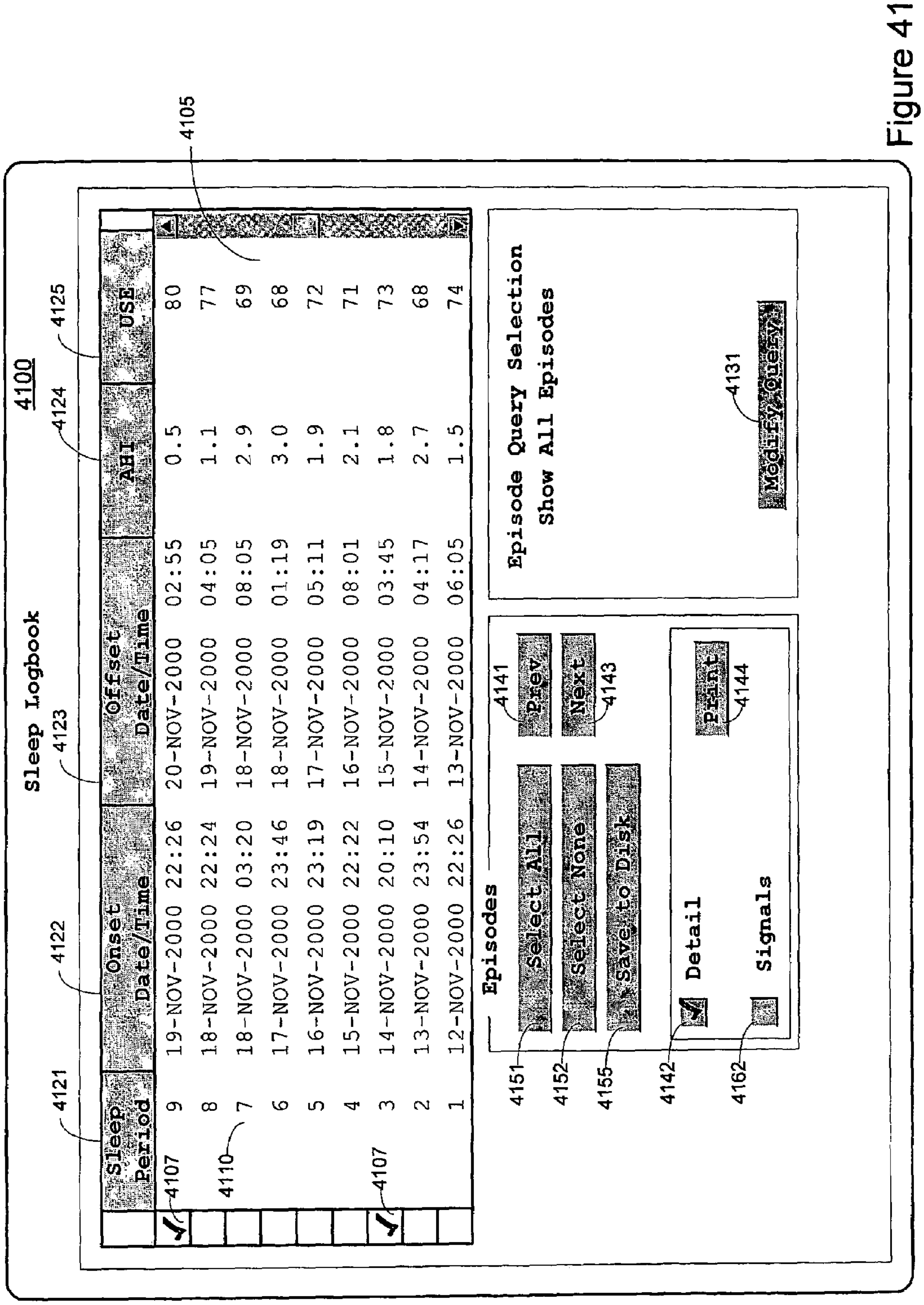
FIG. 41 illustrates an exemplary depiction of a user interface display that may be used with a sleep logbook system in accordance with embodiments of the invention.

A user interface may be used to view and/or access the sleep logbook information. FIG. 41 illustrates an exemplary depiction of a user interface display 4100. An area 4105 of the display may be used to provide textual or graphical information about sleep. As illustrated in FIG. 41, a menu 4110 of sleep periods may be presented and may enable the user to access additional information related to the sleep periods and/or to sleep disorder events occurring during the sleep periods. The menu 4110 may provide a summary of parameters associated with sleep periods contained in the sleep logbook. As illustrated in FIG. 41, one or more summary parameter headings, such as sleep period 4121, onset date/time 4122, offset date/time 4123, apnea/hypopnea index (AHI) 4124, uninterrupted sleep efficiency 4125, among other parameter headings, may be presented at the top of the menu 4110 or in another convenient location. The summary parameter headings 4121-4125 may be programmable, and additional or alternative parameter headings to those depicted in FIG. 41 may be selected.

The sleep periods displayed as menu items in the menu 4110 may be selected by a user according to episode number, date/time, duration, or by other criteria such as by one or more sleep quality indices. Additionally or alternatively, the menu items may reflect one or more sleep disorder events, e.g., movement disorder events and/or disordered breathing events. The menu items may be selected for display based on various criteria ranges and/or thresholds. For example, in the example screen illustrated in FIG. 41, different groups of sleep periods selected as menu items may be selected by activating the modify query button 4131. In an alternate scenario, different groups of sleep disorder events selected as menu items may be selected by activating the modify query button 4131. The modify query button 4131 and other buttons illustrated on the display may be voice activated, activated through touching the display screen, or by operating a keyboard or pointing device, for example.

In one implementation, activation of the modify query button 4131 initiates a dialog session that allows the user to select sleep periods and/or sleep disorder events to be presented in the menu according various criteria such as by date/time, duration, type, sleep quality metrics, or by other criteria parameters. In one example, the user may select all sleep periods having an uninterrupted sleep efficiency (USE) metric below a threshold to be presented as menu items. In another example, the user may select all sleep periods between a first date and a second date. In yet another example, the user may select all sleep disorder events of a particular type that occurred while the patient experienced certain environmental conditions, e.g., ambient temperature range and/or humidity range. In yet another example, the user may choose to select all sleep periods or all sleep disorder events represented in the sleep logbook. The selection criteria may be displayed in an episode query selection area 4132 of the display. The episode query selection area 4132 in the depiction of a sleep logbook display shown in FIG. 41 indicates that all sleep periods have been selected to be displayed as menu items.

The menu 4110 allows the user to choose sleep periods for which additional textual and/or graphical information is displayed. The additional information provides more detailed information about the selected periods beyond the summary information presented in the menu 4110. In the exemplary illustration depicted in FIG. 41, the selections are indicated by check marks 4107 beside the selected sleep periods. For convenience, the display may include a select all button 4151 and/or a select none button 4152. Activation of the select all button 4151 causes all sleep periods in the menu 4110 to be selected. Activation of the select none button 4152 causes all sleep periods in the menu 4110 to be deselected.

Following selection of one or more sleep periods in the menu, activation of the detail button 4142 causes detailed textual information associated with a selected sleep period to be presented on the display screen. The detail information may be displayed in the area of the screen 4105 previously occupied by the menu 4110, for example. The user may scroll back and forth through the textual information for the one or more selected sleep periods using the prev button 4141 and the next button 4143. The textual information may be printed upon activation of the print button 4144, or may be saved to a disk, or other storage medium, through activation of the save to disk button 4155.

Graphical information associated with the selected sleep periods may be displayed upon activation of the signals button 4162. In one implementation, a respiration waveform acquired during all or a portion of a selected sleep period may be displayed in the area 4105 of the display previously used for the menu 4110. In one implementation, a respiration waveform may be acquired before, during and/or after respiration events that occur during sleep. Waveforms of other parameters, e.g., cardiac rhythm, patient activity, may additionally or alternatively be displayed. In one implementation, a marked waveform may be displayed. For example, a marked respiration waveform may include the respiration waveform along with one or more symbols aligned with the respiration waveform to indicate the occurrence of one or more conditions. The symbols may provide a numerical value or a textual description associated with the respiration characteristic, e.g., average respiration rate, expiratory slope, etc. In one example, various characteristics of disordered breathing events including quantifiable characteristics, such as episode duration, blood oxygen saturation, disordered breathing type, and/or other detected characteristics may also be displayed along with the respiration waveform. A user may scroll through the waveforms associated with the selected events using the prev and next buttons 4141, 4143.

Snoring Detection Systems and Methods

Aspects of the invention that include snoring detection are directed to methods and systems configured to monitor, diagnose, and/or provide patient therapy using one or more individual medical procedures. Each of the circles 180 illustrated in FIGS. 42B-42D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that include snoring detection are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of, the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Systems and methods may provide for snoring detection to determine, predict, and/or verify the presence of sleep disordered breathing. According to various embodiments, snoring sounds generated by a patient are detected. The presence of sleep disordered breathing is determined using the detected snoring sounds. In other embodiments, snoring is detected from disturbances in a respiration or airflow signal.

Snoring sounds or snoring-related respiration/airflow disturbances may be detected internally of the patient or externally of the patient. Determining presence of sleep disordered breathing may be performed internally or externally of the patient. Determining presence of sleep disordered breathing may include computing a snoring index developed from the detected snoring. Sleep apnea may be detected using the snoring index. Sleep apnea may be verified using internal or external sensors. In one approach, sleep disordered breathing is detected, such as by use of a minute ventilation sensor, and presence of the sleep disordered breathing may be confirmed using the detected snoring.

Embodiments of methods of detecting snoring in a patient involve generating a signal modulated by snoring and detecting snoring based on the generated signal, wherein at least one of generating the signal and detecting snoring is performed using a component disposed in or on a cardiac rhythm management device. Modulating the signal by snoring and detecting snoring may be performed implantably, such as by using a sensor disposed in or on a pulse generator housing. The sensor may alternately or additionally be disposed in or on a lead system coupled to a pulse generator, in or on a header of a pulse generator, coupled to a cardiac rhythm management system, mechanically coupled to an external respiration therapy device, or disposed in or on a respiratory mask. Detecting snoring may involve using circuitry disposed in or on a cardiac rhythm management device, which may further deliver a therapy to mitigate the detected snoring, and/or detect sleep disordered breathing based on the detected snoring, and/or deliver a therapy to treat the detected disordered breathing.

According to other embodiments, systems may include a sensor configured to sense snoring generated by a patient and a processor coupled to the sensor. The processor algorithmically determines presence of sleep disordered breathing using the sensed snoring. The sensor may include one or more of an accelerometer, a microphone, a pressure transducer, a subsonic sensor, a respiration sensor, or a vibration or motion sensor. The sensor may be implemented for patient-external sensing of the snoring or on or within an implantable sensing device. The processor may be disposed within an implantable medical device (e.g., CRM device). Systems may further include a positive airway pressure (CPAP) device communicatively coupled to one or both of the sensor and the processor. Sleep disordered breathing may be verified using the CPAP device.

Systems and methods that employ snoring detection 139 (FIG. 1D) may be implemented as a stand-alone system or in combination with other individual medical systems, such as those described in FIGS. 1B-1D. Various embodiments involve a system for providing coordinated patient monitoring, diagnosis and/or therapy that utilizes snoring detection 139. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

The implantable and respiratory therapy devices 181, 184 may operate cooperatively based on detected snoring. For example, detection of snoring and/or severity of snoring may allow the implantable and respiratory therapy devices 181, 184 to operate cooperatively to provide a therapy to treat patient snoring and/or sleep apnea associated with the detected snoring. Systems and methods directed to snoring detection may be implemented to include selected features, functions, and/or structures described in commonly owned, U.S. Pat. No. 7,532,934, which is hereby incorporated herein by reference.

Embodiments are directed to one or more of sensing, detection, and treatment of snoring using an at least partially implantable device. Snoring information is useful in disordered breathing detection, verification, and/or prediction, such as for detecting or prediction of apnea events. Snoring detection is also useful independent of disordered breathing, to treat the snoring itself. Snoring may lead to insomnia, arousals from sleep, marital discord, and wake-time sleepiness. Snoring detection in accordance with the present invention may also be used to treat the snoring, such as by modulating the pressure of a continuous positive airway pressure (CPAP) device to reduce the snoring, for example.

An internal or external snore sensor, such as a vibration sensor, respiration sensor, airflow sensor, accelerometer or microphone, may be coupled to a patient-internal medical device (PIMD), such as a cardiac rhythm management (CRM) device, or a respiration therapy device. In some embodiments, the snore sensor may be configured as a patient-external device, possibly mounted on a respiratory mask, for example. Information from the snore sensor is wirelessly transmitted to the PIMD device.

In other embodiments, the snore sensor may be associated with an implanted device, such as an accelerometer positioned within or on the housing of an PIMD device, or on the PIMD lead system. A snore detector in the PIMD device may receive signals from the patient-external and/or patient-internal snore sensor, and may generate one or more snore indices, based on the frequency, severity and/or other characteristics of snoring incidents, for example. A snore index may be used, for example, to determine if a patient is at risk for daytime fatigue and sleepiness due to excessive nighttime snoring indicating sleep disordered breathing.

In further embodiments, an airflow sensor may be associated with an implanted device, such as a transthoracic impedance sensor mounted on the lead system of a PIMD device. The snore detector in the PIMD device may be configured to algorithmically detect snoring using the transthoracic impedance signal, and may be configured to generate one or more snoring indices. For example, airflow may be measured, such as by use of transthoracic impedance or external airflow sensing, and snoring may be determined using the airflow measurement.

Detection of the snore severity, as measured by a severity snore index, may be used to test for risk of vascular disease such as hypertension. A snore index also may be used in connection with disordered breathing detection and/or prediction. One or more snore indices may be stored, trended, displayed and/or transmitted to another device.

Figure 42A:
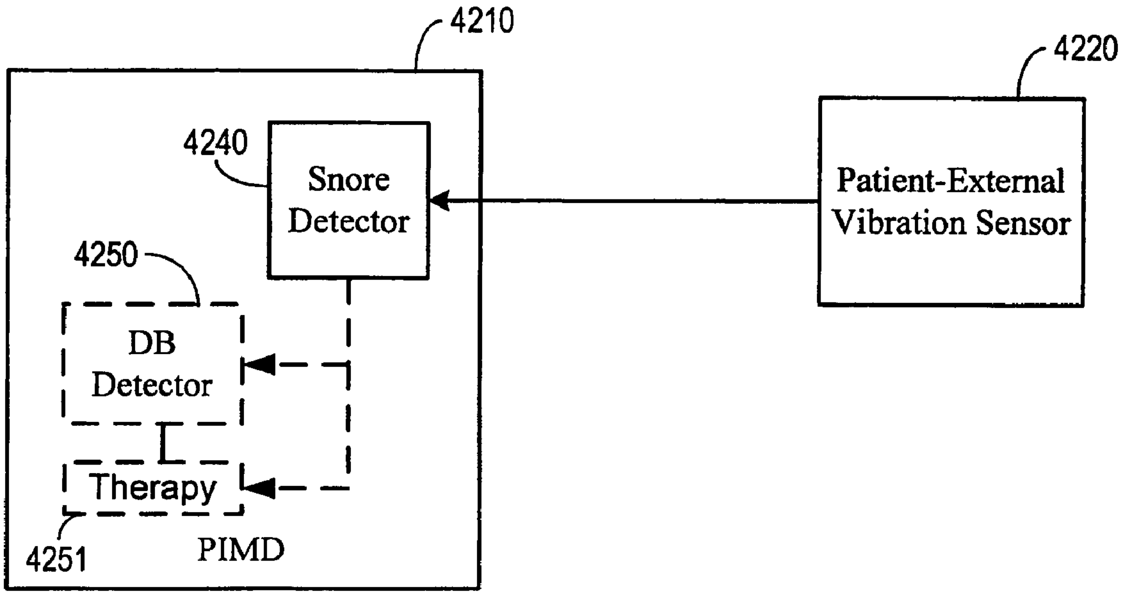
FIGS. 42A and 42B are block diagrams of implantable systems implementing snoring detection and therapy features in accordance with embodiments of the present invention.
Figure 42B:
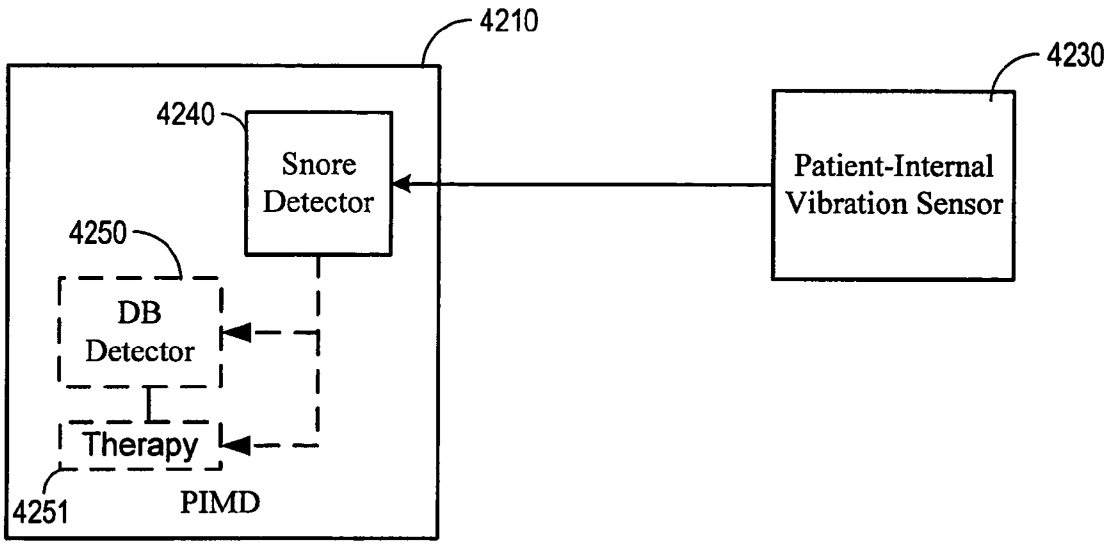
Figure 42C:
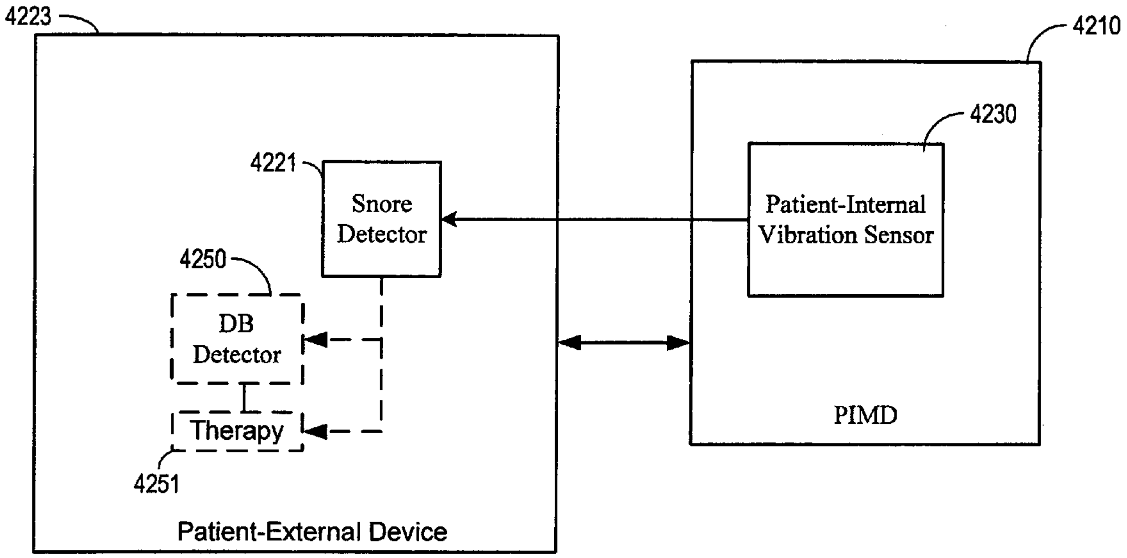
FIGS. 42C and 42D are block diagrams illustrating embodiments of the present invention with a snore detector in a patient-external configuration.
Figure 42D:
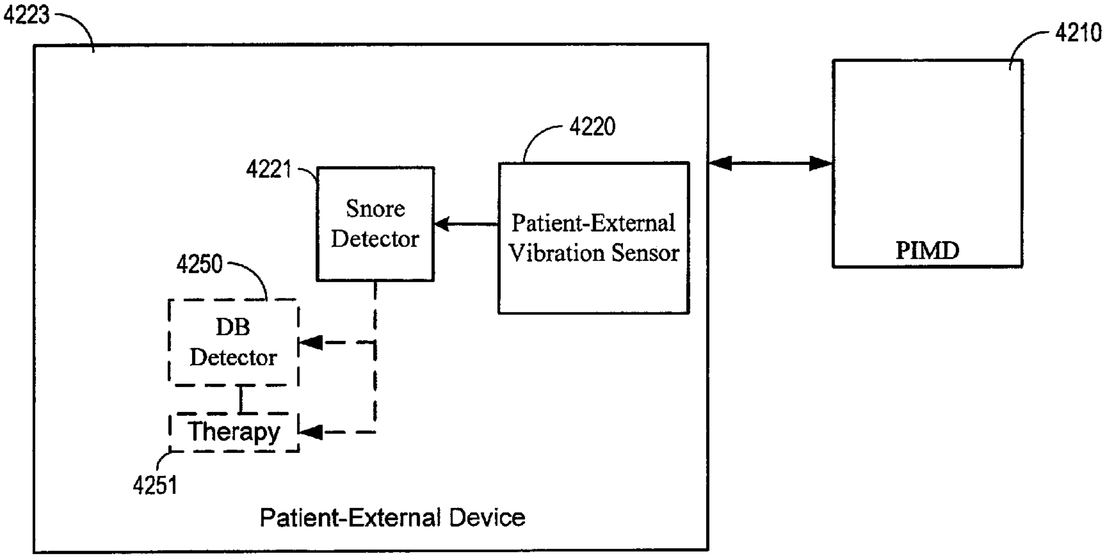

FIGS. 42A and 42B illustrate embodiments of the present invention involving snoring detection using an implantable device. The processes and systems exemplified by these embodiments may be implemented alone or in combination with one or more processes and systems exemplified by other embodiments described herein to provide a coordinated approach to patient monitoring, diagnosis, and/or therapy.

In various embodiments, a snore sensor may be implantable, partially implantable, or patient-external. The snore sensor may be coupled to detection circuitry directly, coupled through wiring, and/or coupled wirelessly. The sensor may be incorporated into a lead, such as a cardiac pacing lead.

In accordance with embodiments of the invention, illustrated in FIGS. 42A and 42B, a snore sensor 4220 (FIG. 42A) and 4230 (FIG. 42B), such as an accelerometer or microphone, is coupled to a PIMD device 4210 and used for snoring detection. In one embodiment (FIG. 42A), the snore sensor 4220 is a patient-external device, possibly mounted on a CPAP mask housing, for example. Information from the snore sensor 4220 is wirelessly transmitted to the PIMD device 4210.

In another embodiment (FIG. 42B), the snore sensor 4230 is an implanted device, such as, for example, an accelerometer or a transthoracic impedance sensor positioned within or on the housing of the PIMD device 4210, or on a PIMD lead system (not shown). For example, the low frequency sounds produced by snoring can be detected using a PIMD accelerometer, such as an accelerometer used in connection with rate adaptive pacing or posture sensing, for example. By way of further example, disturbances in a transthoracic impedance sensor signal indicative of snoring may be detected.

According to a further embodiment, the snore sensor 4220/4230 may be implemented as an airflow sensor configured to sense airflow disturbances indicative of snoring. The snore sensor 4220/4230 may be implemented as an internal or an external airflow sensor. For example, the snore sensor 4230 may be implemented as an external airflow sensor, which may be provided on a CPAP mask, and configured to sense patient snoring.

A snore detector 4240 in the PIMD device 4210 receives signals from the patient-external snore sensor 4220 and/or patient-internal snore sensor 4230, and may generate one or more snore indices, based on the frequency, severity and/or other characteristics of snoring incidents, for example. Snoring detection in accordance with embodiments of the invention may be used alone, or in combination with other sensors, to detect and/or verify occurrences of disordered breathing. For example, detection of periodic snorts may indicate an episode of obstructive sleep apnea.

The snoring methodology described herein may be used in cooperation with a multi-sensor system. Snore information may be used in combination with information from other patient-internal and/or patient-external sensors to confirm the detection of disordered breathing. In accordance with the present invention, any number or all of snoring sensor(s), snoring detector(s), disordered breathing detector(s), and disordered breathing prediction device(s) may be implantable, partially implantable, or patient-external, as long as at least one element is at least partially implantable. In one approach, an initial detection of a disordered breathing episode may be made by an optional disordered breathing detector 4250 based on respiration patterns detected using a transthoracic impedance sensor. Snore information may be used alone, or in combination with other sensor signals, to confirm the initial detection of disordered breathing.

In another example, an initial detection of a disordered breathing episode may be made by a CPAP device using a respiration signal acquired from sensors on the CPAP mask. The CPAP device may communicate with the PIMD device 4210 for confirmation of disordered breathing. Based on snoring information obtained and evaluated in the PIMD device 4210, the PIMD device 4210 may confirm or refute the occurrence of disordered breathing and respond accordingly, such as through a change of settings, alarm, or other action.

In another implementation, detection of snoring may be used to modulate CPAP pressure, allowing auto-titration of CPAP pressure therapy through snoring detection. Detection of snoring may indicate that the CPAP pressure is insufficient to open the patient's airways. In accordance with an embodiment of the invention, a CPAP mounted microphone may be used to detect snoring. Based on detection of snoring, or based on snoring characteristics, e.g., the snore index, CPAP pressure may be modulated. For example, the snore index may be compared to a threshold. If the snore index is beyond the threshold, the CPAP pressure may be increased. In another example, CPAP therapy pressure may be adjusted as a function of the snore index. In a further embodiment, optional therapy circuitry 4251 may be used to provide therapy to, for example, reduce snoring, correct disordered breathing, improve patient hemodynamics, or other therapy.

FIGS. 42C and 42D illustrate embodiments of the present invention with a snore detector 4221 in a patient-external configuration 4223. The snore detector 4221 may be coupled to the PIMD device 4210 wirelessly, for example. The snore sensor may be an internal snore sensor 4230 (FIG. 42C) or a patient-external snore sensor 4220 (FIG. 42D), such as of a type previously described. Similarly to the snore detector 4221, the disordered breathing detector 4250, and therapy circuitry 4251 may be implemented in either or both of patient-external and internal configurations, as well as cooperate with the PIMD device 4210 for coordinated and/or combined therapy.

Posture Detection System

Aspects of the invention that include detection of patient posture are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that involve posture detection are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

One embodiment of the invention involves an individual system 131 (FIG. 1D) for detecting patient posture. The posture detection system 131 may be implemented as a stand alone system or in combination with other individual medical systems, such as those described in FIGS. 1B-1D.

Embodiments of the invention relate to detection of patient posture. One embodiment of the invention involves a posture detection system including an implantable cardiac device and a patient-external respiratory therapy device. The implantable cardiac device and the patient-external respiratory therapy device are coupled by a communications channel configured to transfer at least posture information between the implantable cardiac device and a patient-external respiratory therapy device.

According to one aspect of the invention, the patient-external respiratory therapy device includes components of the posture detector. For example, the posture detector may be positioned on the respiratory mask or the respiratory mask strap. In another example, the posture detector may be positioned on the patient's body and communicatively coupled to a control unit of the respiratory therapy device through a lead. The patient-external respiratory therapy device transmits posture information to the implantable cardiac device.

According to another aspect of the invention, the implantable cardiac device includes components of the posture detector. The implantable cardiac device transmits posture information to the patient-external respiratory therapy device.

Another embodiment of the invention involves a posture detection method. The posture detection method includes detecting posture using a sensor of a patient-external respiratory therapy device or a sensor of an implantable cardiac device. The posture information is transmitted between the patient-external respiratory therapy device and the implantable cardiac device.

According to various aspects of the invention, the posture information may be used to adjust therapy delivered to the patient. The therapy adjusted may include a therapy delivered by the implantable device, or by the external respiratory therapy device. In one implementation, the implantable device delivers a cardiac electrical stimulation therapy and the cardiac electrical stimulation therapy is adjusted based on patient posture. Alternatively, or additionally, therapy delivered by the respiratory therapy device may be modified using the posture information.

Another embodiment of the invention involves a system for providing coordinated patient monitoring, diagnosis and/or therapy system 131 that utilizes patient posture detection. The coordinated system includes, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a system 131 configured to detect patient posture. The posture detection system 131 includes an implantable cardiac device, a patient-external respiratory therapy device and a communications channel between the implantable cardiac device and the a patient-external respiratory therapy device. The communications channel is configured to transfer information between the implantable cardiac device and the patient-external therapy respiratory device, where at least one of the implantable cardiac device and the patient-external respiratory therapy device includes one or more components of a posture detector. The communications channel is configured to at least transfer posture information between the implantable cardiac device and the patient-external respiratory therapy device. Systems and methods directed to posture detection may be implemented to include selected features, functions, and/or structures described in commonly owned, U.S. Pat. No. 7,664,546, which is hereby incorporated herein by reference.

Posture detection may involve, for example, determining a positional orientation of the patient's body or the positional orientation of a portion of the patient's body, such as the patient's torso. Posture detection includes discriminating between a horizontal, recumbent or supine position and a vertical or upright position, determining an inclination of a portion of the patient's body, and or determining if the patient is lying on his or her side, back, or front. Knowledge of patient posture may be used by the implantable device to diagnose various patient disorders and/or to adjust patient therapy, for example. A supine posture is more likely to result in obstruction of the upper airway and can be used to predict episodes of obstructive hypopnea and apnea, for example.

Discriminating between a recumbent and an upright position of the patient's body is useful in connection with determining if a patient is asleep or awake. Patient posture can be used as an indicator or verifier that a patient is sleeping. Diagnosis of various conditions, e.g., sleep apnea, may be enhanced with knowledge of the patient's sleep state. Thus, a patient may be diagnosed as having sleep disordered breathing if breathing interruptions occur while a patient is sleeping, as indicated by patient posture during the disordered breathing episodes.

The position of the patient's body, such as the inclination of the upper torso, may predispose the patient to various medical disorders, including disorders affecting the respiratory, cardiopulmonary, and/or cardiovascular systems. Information about patient position may be evaluated with respect to the detection of various disorders to determine if an association between patient position and a particular disorder is present.

Knowledge of patient posture may enhance therapy delivery. Therapy may be adjusted to provide a more appropriate therapy based on whether the patient is asleep or awake. For example, a cardiac pacing rate may be decreased from a waking rate to a lower sleeping rate to account for the decreased hemodynamic need of the patient during sleep.

Some patients suffer from a number of disorders that are treated with multiple therapy devices. For example, a patient suffering from cardiac and respiratory problems may receive therapy from an implantable cardiac rhythm management system, e.g., a bi-ventricular pacing device for synchronizing ventricular contractions, and an external respiratory therapy device. Using therapy devices in a coordinated manner provides opportunities for enhanced monitoring, diagnosis and/or therapy delivery. Various embodiments described herein are directed to a posture sensor disposed on a respiratory therapy mask. Information related to patient posture is transmitted to an implantable device, such as a cardiac therapy device.

Figure 43:
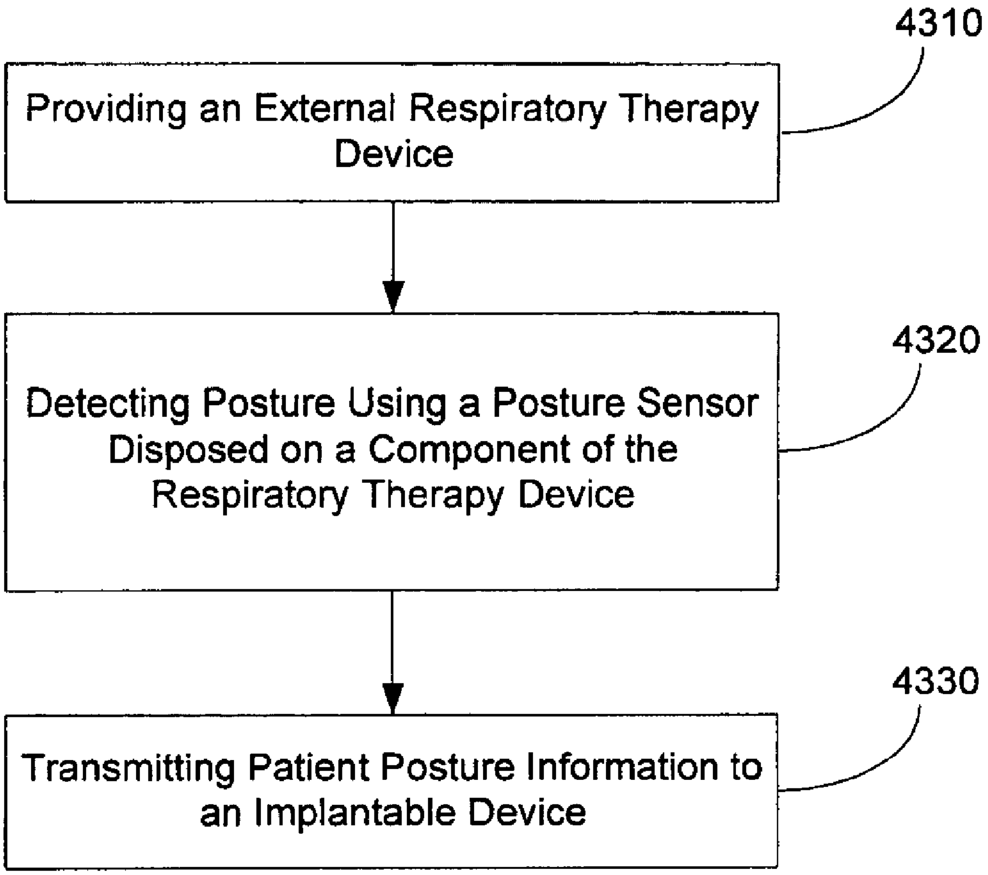
FIG. 43 is a flow chart of a method for posture detection in accordance with embodiments of the invention.

FIG. 43 is a flowchart of a method for determining patient posture. At least one of a patient-external respiratory device and an implantable device include 4310 a posture detector. The posture detector, which may be positioned on a component of the respiratory therapy device, within an implantable housing of the implantable device, or in other locations, acquires 4320 patient posture information. The posture information is transmitted 4330 to between the patient-external respiratory device and the implantable device.

In a one configuration, the posture detector is coupled by a wire lead to the controller unit of the respiratory therapy device. Communications circuitry positioned within the controller unit wirelessly transmits the posture information, possibly along with other relevant information, to the implantable device. In another configuration, the circuitry for wirelessly transmitting the posture information to the implantable device is disposed with the posture sensor on the respiratory mask or mask strap, for example.

In another configuration, the posture detector is disposed within a housing of an implantable device. Communications circuitry positioned within the implantable device housing wirelessly transmits the posture information to the control unit of the respiratory therapy device, possibly along with other relevant information.

In yet another configuration, the posture information may be relayed from one device to another device through a patient information server, such as is used in an advanced patient management system.

Figure 44:
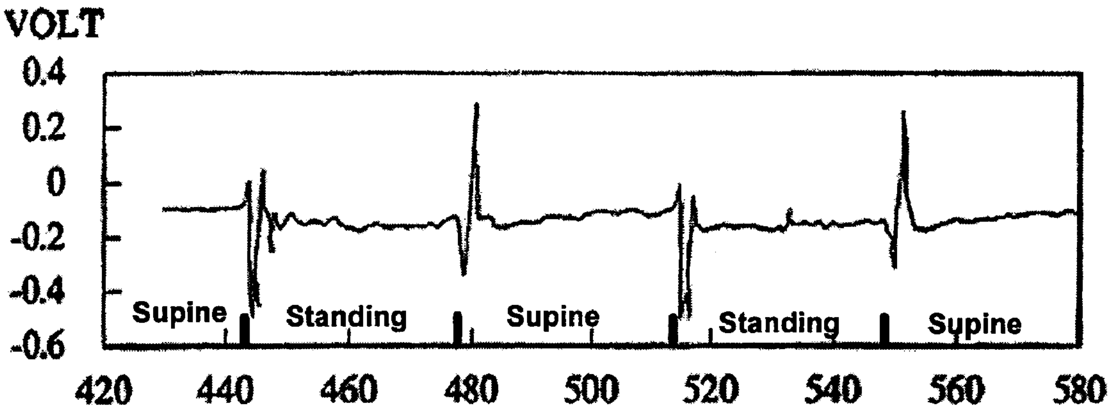
FIG. 44 is a graph representative of accelerometer signals associated with a patient moving from a standing to supine or supine to standing position.

Posture sensing may employ various types of sensors, including, for example, multiaxis accelerometers, inclination sensors, magnetometers, mercury-type switches, or other sensing methodologies. In one implementation, an accelerometer is used as a posture sensor. FIG. 44 is a waveform signal generated by an accelerometer that indicates patient posture. When a patient moves from a supine position to an upright position, the accelerometer produces fluctuating waveform signals. When a patient is supine and moves to an upright standing position, a negative change in voltage on the waveform occurs, e.g. from 0 Volts to −0.5 Volts. When a patient is in the standing position and moves to a supine position, a positive change in voltage on the waveform occurs, e.g. from 0 Volts to 0.25 Volts.

FIGS. 45A-45D are diagrams illustrating medical systems 4500 with posture detection functionality in accordance with embodiments of the invention. The medical system 4500 includes a respiratory therapy device 4510 communicatively coupled to a CRM system 4550. Delivery of cardiac electrical stimulation therapy provided by the CRM system 4550, e.g., bradycardia pacing, tachycardia pacing, cardiac resynchronization pacing and/or cardioversion/defibrillation, is controlled by a cardiac therapy control unit 4555 disposed within the housing of the CRM system.

The respiratory therapy device 4510 may comprise for example, a positive airway pressure (CPAP) device, a nebulizer, ventilator, or other type of respiration therapy device. For the purposes of describing FIGS. 45A-45D, the respiratory therapy device 4510 is considered to be a CPAP device. The CPAP device includes a respiratory therapy control unit 4511, respiratory mask 4520, and tubing 4515 coupling the respiratory mask 4520 to the control unit 4511. Respiratory therapy pressure is controlled by circuitry 4526 within the control unit 4511. The respiratory therapy control unit 4511 develops an airway pressure delivered to the patient through the respiratory mask 4520 via tubing 4515. Various methodologies and systems for implementing CPAP therapies are described in U.S. Pat. Nos. 5,245,995 and 5,199,424, which are incorporated herein by reference.

The respiratory mask 4520 is held in place over the patient's nose and/or mouth using a strap 4521 or other type of securing structure. In one embodiment, illustrated in FIG. 45A, a posture detector 4525 is positioned on a component of the CPAP device, preferably on the mask 4520 or mask strap 4521. With the posture detector 4525 positioned on the mask 4520 or mask strap 4521, the sensor produces signals modulated by changes in the position of the patient's torso and/or head. The posture detector 4525 is coupled to the respiratory therapy control unit 4510 through a lead extending from the mask assembly 4520, 4521.

Figure 45A:
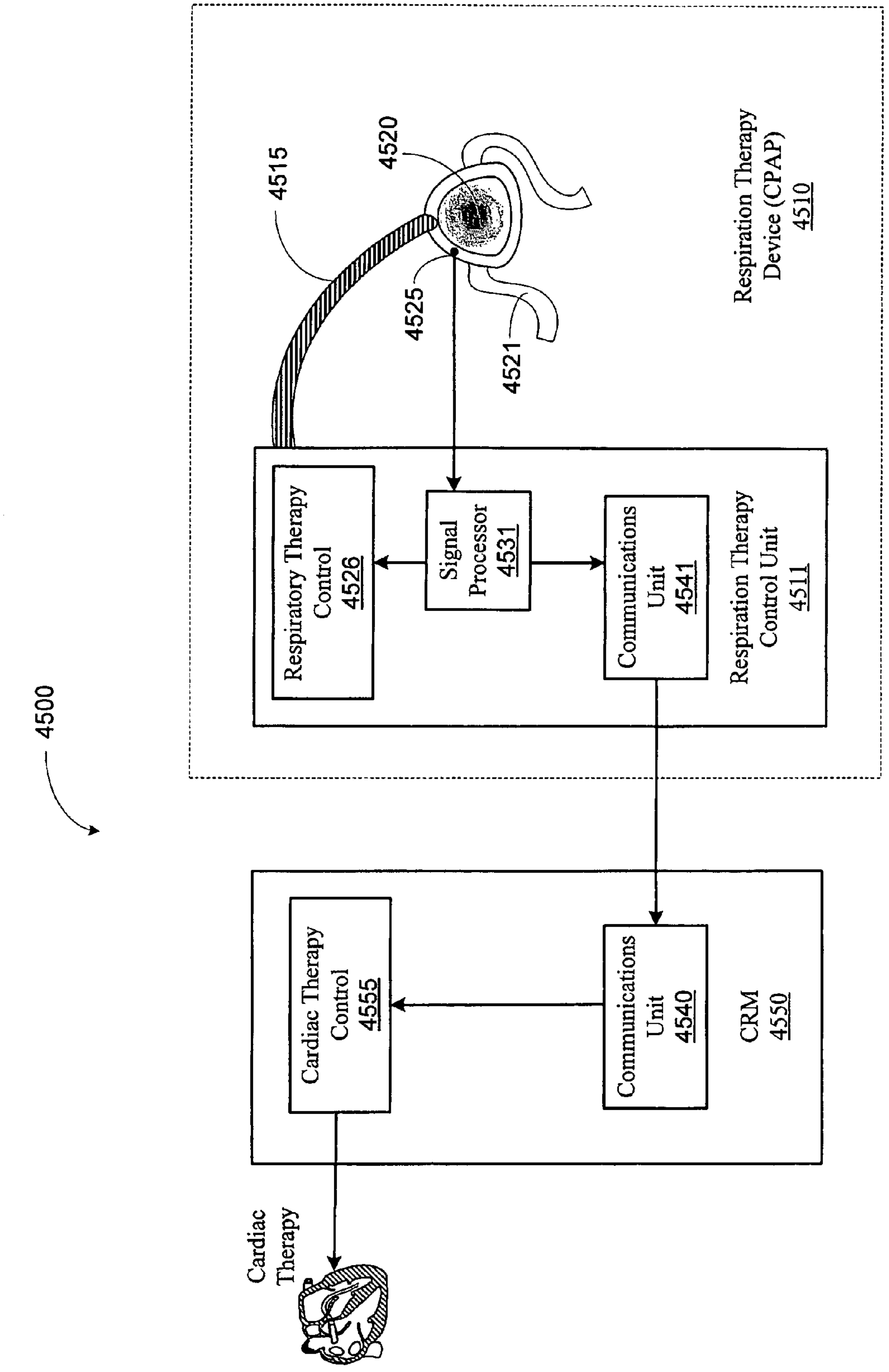
FIGS. 45A-45D are block diagrams illustrating medical systems with posture detection functionality in accordance with embodiments of the invention.
Figure 45B:
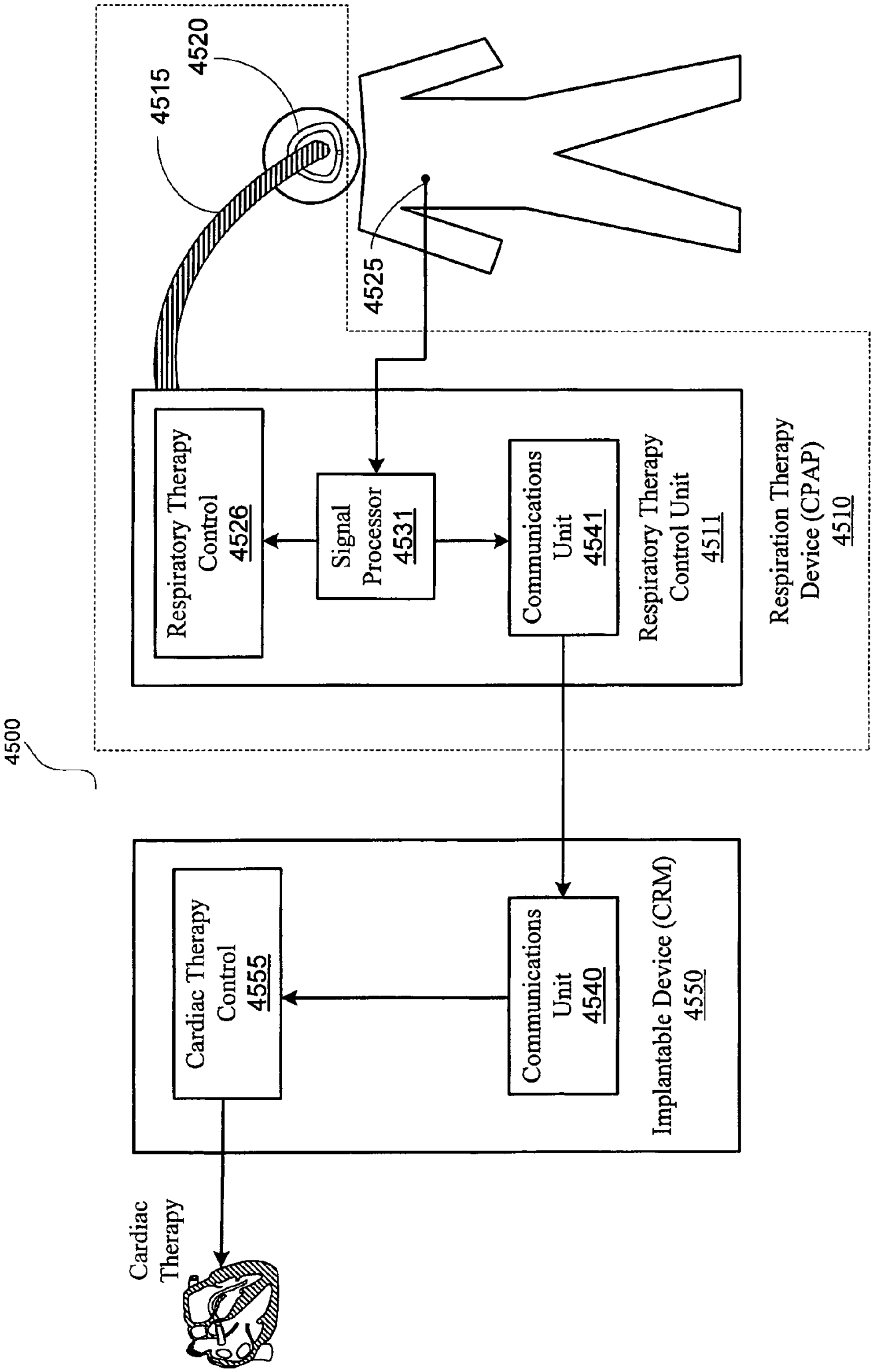

In another embodiment, illustrated in FIG. 45B, one or more posture detectors 4525 are positioned on or near the patient so that changes in the patient's posture are detectable by an accelerometer or other sensor used for sensing patient position. The posture detectors 4525 may be positioned on or near the patient's head, chest, abdomen, or other appropriate location of the patient's body. The posture detector 4525 may be communicatively coupled to the respiratory therapy unit 4510 through a wire lead or through a wireless communications link.

The respiratory therapy unit includes a signal processor 4531 for energizing the posture detector 4525 and/or receiving the signals from the posture detector 4525. Compatible communications units 4541, 4540 of the CPAP 4510 and CRM 4550 devices establish a wireless communication channel between the CPAP device 4510 and the CRM device 4550. Posture information is transmitted over the wireless communications channel 4540, 4541 from the CPAP device 4510 to the CRM device 4550.

Figure 45C:
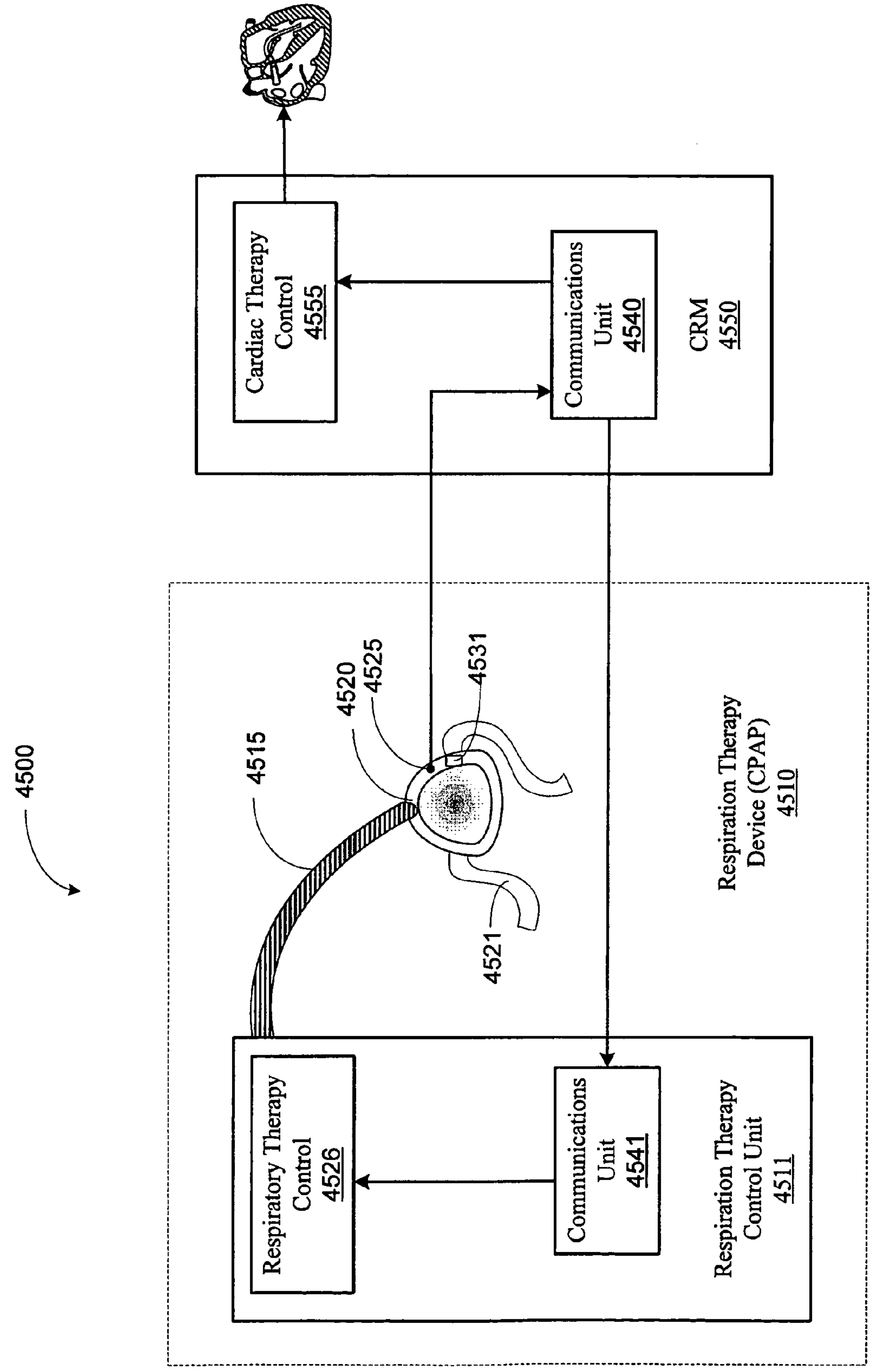

In a further embodiment, illustrated in FIG. 45C, a signal processing circuitry 4531, including circuitry for wireless communication is positioned along with the posture detector 4525 on the respiratory mask 4520 or mask strap 4521. In one configuration, the posture detector and processing circuitry 4525, 4531 are configured to detect patient posture and wirelessly communicate posture information to the implantable device 4550. Posture information may also be transferred between the implantable device 4550 and the respiratory therapy device 4510. In another configuration (not shown), the posture detector and associated circuitry 4525, 4531 detect patient posture and wirelessly communicate the posture information to the respiratory therapy device 4510.

Figure 45D:
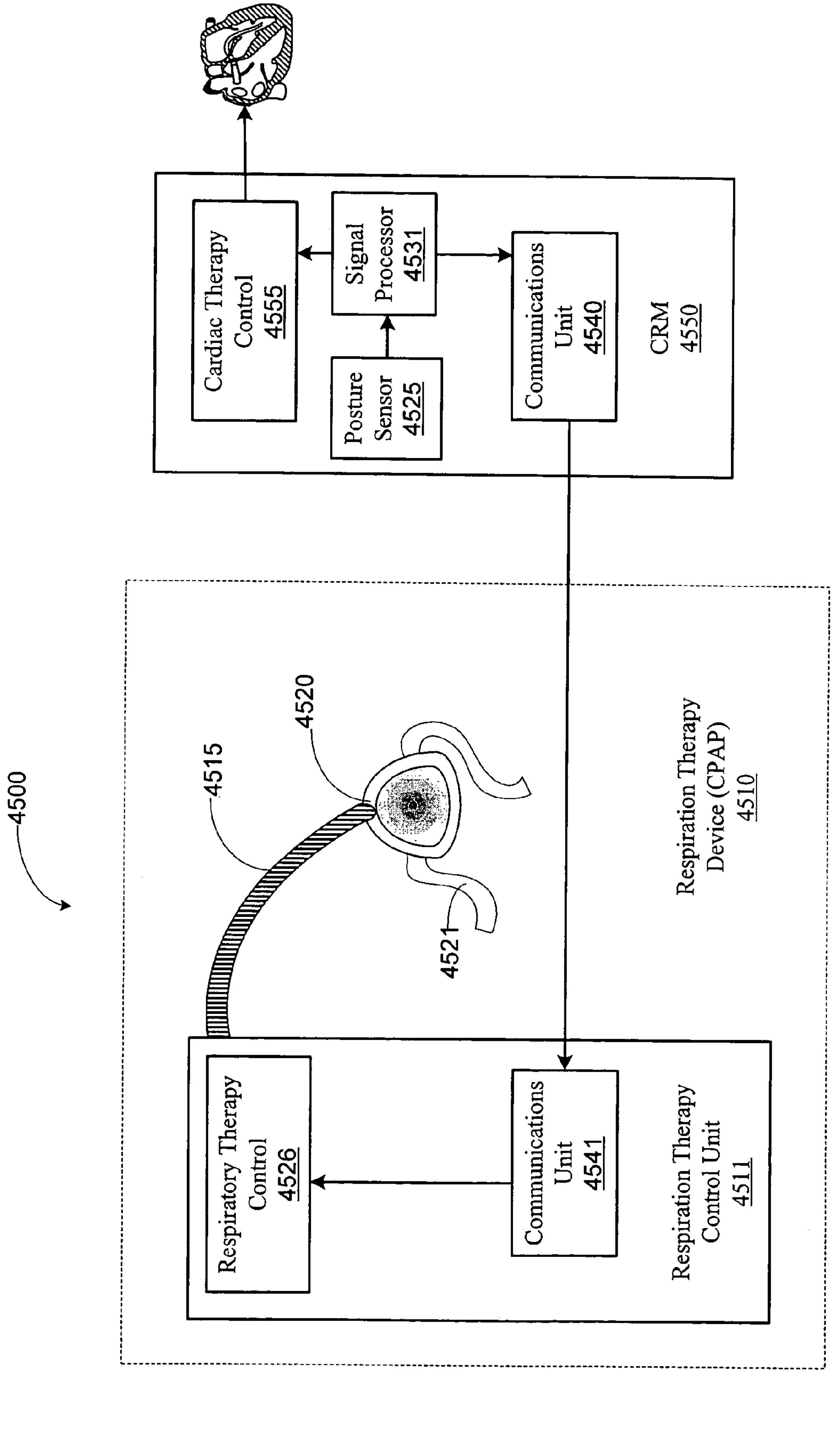

FIG. 45D illustrates another embodiment of a posture detection system. In this embodiment, the implantable device 4550 includes the posture sensor 4525 and associated circuitry 4531. The posture detector 4525 may comprise, for example, an accelerometer or other sensor disposed within or on an implantable housing or other component of the implantable device 4550. The posture information may be transmitted form the implantable device 4550 to the external respiratory therapy device 4510.

The CRM device 4550 may utilize the received posture information for diagnostic or therapeutic purposes. For example, as previously discussed, the CRM device 4550 may use the posture information to detect or confirm sleep. The posture information may also be used in connection with detecting or predicting disordered breathing. Further posture information may be used by the CPAP device 4510 or the CRM device 4550 to correlate patient posture, e.g., particular patient positions or torso inclinations, to episodes of disordered breathing. Correlation of patient posture to detected disordered breathing episodes may be used to enhance detection or prediction of subsequent episodes of disordered breathing. Methods of detecting disordered breathing using a CPAP device are described in previously incorporated U.S. Pat. Nos. 5,245,995 and 5,199,424.

Posture information may be used by the implantable cardiac device 450 to initiate, modify or terminate a therapy delivered by the CRM device to the patient. For example, based on the posture information, the CRM device may decrease or increase a pacing rate, switch from a uni-ventricular pacing mode to a bi-ventricular pacing mode or the reverse, initiate, modify or terminate cardiac electrical stimulation therapy for disordered breathing. The CPAP device 4510 may also utilize the received posture information to adjust the external respiratory therapy delivered by the CPAP device 4510.

Figure 46:
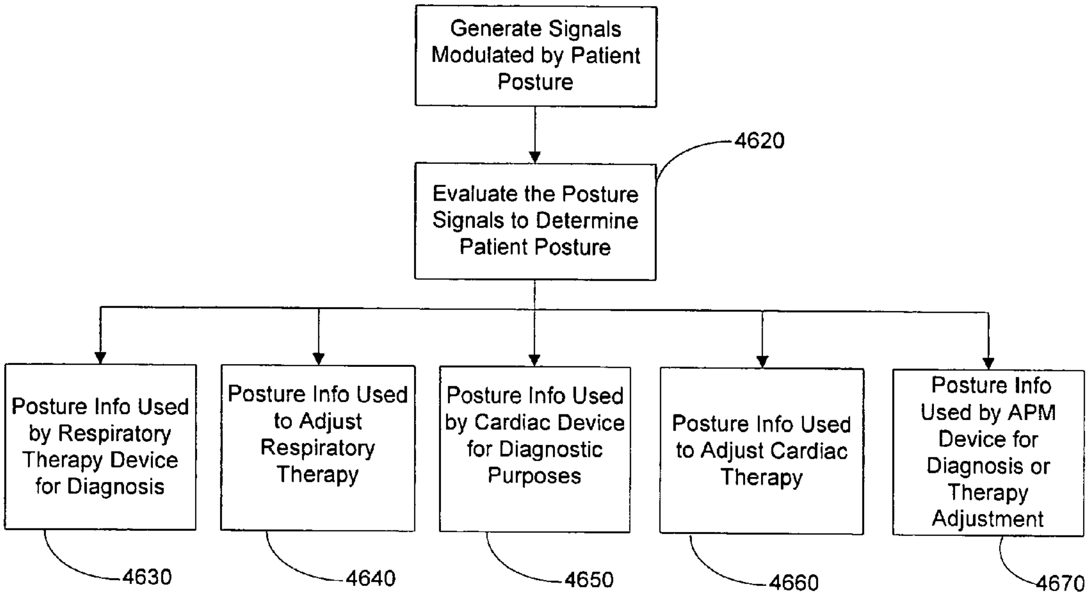
FIG. 46 is a flow chart of uses for posture detection in accordance with the invention.

FIG. 46 is a process flow diagram illustrating various uses for posture information in accordance with the present invention. A posture sensor coupled to a respiratory therapy device generates signals 4610 modulated by patient posture. The signals are evaluated 4620 to determine various aspects of patient posture. For example, evaluation of the posture sensor signals may provide information about the patient position, such as whether the patient is recumbent or upright, the inclination of the patient's torso, whether the patient is lying on his or her back, left side, right side, or front, and/or other posture or position-related information.

The posture information is transmitted to an implantable device, such as a pacemaker or other implantable cardiac device. The posture information may be used to detect or verify sleep. Additionally or alternatively, the posture information may be used, to diagnose 4630 or predict various disorders of the patient, such as disordered breathing, or for other purposes. The implantable CRM device may use the posture information to adjust 4640 cardiac electrical stimulation therapy delivered to the patient.

The posture information may also be used by the respiratory therapy device. The respiratory therapy device may use the posture information to detect or verify sleep, to diagnose 4650 or predict episodes of disordered breathing. The posture information may be used respiratory therapy device to modify 4660 the therapy delivered by the respiratory therapy device.

The implantable device, respiratory therapy device, or both may be coupled to an APM system. Posture information may be relayed to the APM system. The APM system may store the posture information, use 4670 the posture information to monitor the patient, diagnose various disorders affecting the patient, and/or to adjust patient therapy. The APM system may transmit the posture information to a variety of other devices connected through the APM system.

Cardiac Electrical Activity Detected Via Respiratory Therapy Device

Aspects of the invention that include use of an external respiratory therapy device to detect cardiac electrical activity are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving cardiac detection via a respiratory therapy device are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 133 (FIG. 1C) for detecting cardiac electrical activity using a respiratory therapy device. The cardiac electrical activity detection system 133 via a respiratory therapy device may be implemented as a stand alone system or in combination with other individual medical systems, such as those described in FIGS. 1B-1D.

Various embodiments are directed to methods and systems for detecting cardiac electrical activity using an external respiratory therapy device. In accordance with one embodiment, a medical system includes one or more cardiac electrodes configured to sense cardiac electrical activity. The cardiac electrodes are coupled to an external respiratory therapy device. The cardiac electrical activity is used to generate an electrocardiogram (ECG) signal.

In accordance with another embodiment of the invention, a system includes sensors coupled to an external respiratory therapy device. The sensors are configured to sense electrical activity of a heart. A cardiac event detector is coupled to the one or more sensors and is configured to detect one or more cardiac events based on the sensed cardiac electrical activity.

Another embodiment of the invention involves a method for generating an electrocardiogram (ECG) signal. Cardiac electrical activity is sensed using one or more cardiac electrodes coupled to an external respiratory therapy device. The ECG signal is generated based on the sensed cardiac electrical activity.

A further embodiment involves detecting cardiac events. The method includes sensing cardiac electrical activity using one or more cardiac electrodes coupled to an external respiratory therapy device. The cardiac events are detected based on the sensed, cardiac electrical activity.

Another embodiment of the invention involves a system for providing coordinated patient monitoring, diagnosis and/or therapy that utilizes an external respiratory therapy system 133 to detect cardiac electrical activity. The coordinated system includes, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy further includes a system 133 configured to detect electrical activity of a heart using a respiratory therapy device. The cardiac electrical activity detection system 133 includes one or more sensors coupled to an external respiratory therapy device configured to sense electrical activity of a heart and to generate a cardiac electrical signal based on the sensed electrical activity. The system further includes a cardiac event detector coupled to the one or more sensors configured to detect one or more cardiac events based on the sensed electrical activity. Systems and methods directed to detection of cardiac activity using an external respiratory therapy device may be implemented to include selected features, functions, and/or structures described in commonly owned, U.S. Pat. No. 7,364,547, which is hereby incorporated herein by reference.

Treatment of respiratory disorders may involve the use of an external respiratory therapy device. Respiratory therapy devices may include a respiratory mask assembly that fits over the patient's nose and/or face and directs a flow of gas to the patient. The mask assembly is connected through a tube to a control unit that controls the flow of air or other gas to the patient. Sensors on the mask, in the control unit, or elsewhere may facilitate control of the respiratory therapy delivered to the patient.

External respiratory therapy devices are often used to treat breathing disorders, such as sleep disordered breathing. Sleep apnea is a common form of sleep disordered breathing and is characterized by periods of interrupted breathing during sleep. Apnea and other types of disordered breathing may be caused blockage of the airway due to prolapse of soft tissue into the throat (obstructive apnea) and/or by derangement of the central nervous system signals controlling the breathing reflex. The cessation of breathing may occur repeatedly during sleep, sometimes hundreds of times a night and sometimes for a minute or longer. Respiratory therapy for sleep disordered breathing typically involves the use of an external respiratory device during the night. The external respiratory therapy device delivers positive airway pressure to the patient. The positive air pressure acts as a pneumatic splint, keeping the patient's airway open and reducing episodes of disordered breathing.

Patient's suffering from respiratory disorders may concurrently experience cardiac dysfunction. Sleep apnea and cardiac arrhythmia are common comorbidities. Further, Cheyne-Stokes respiration is frequently observed in patients with congestive heart failure. Cheyne-Stokes respiration in congestive heart failure patients is associated with poor prognosis and may be used to track the progression of the disease. Cardiac arrhythmias have been associated with the hypoxia or autonomic arousal from sleep disordered breathing.

Although cardiac conditions and respiratory disorders are commonly found in combination, monitoring and/or treatment of the disorders is generally accomplished using separate medical devices. Respiratory disorders such as disordered breathing have traditionally been treated using the above-described external respiratory therapy devices. Monitoring cardiac conditions such as cardiac arrhythmia may be accomplished using a patient worn or carried monitor, for example, a Holter monitor, having electrodes attached to the patient's chest for detecting cardiac electrical activity. Cardiac conditions such as arrhythmia and congestive heart failure may also be monitored and/or treated using an implantable cardiac rhythm management (CRM) system.

The nightly use of an external respiratory therapy device by the patient provides an opportunity to detect and/or diagnose cardiac disorders in addition to respiration disorders. Embodiments of the invention involve the use of cardiac sensors used in cooperation with a respiratory therapy device to provide coordinated patient monitoring, diagnosis and/or therapy. The cardiac sensors sense cardiac electrical activity used to generate an electrocardiogram signal. Further embodiments of the invention involve detecting cardiac arrhythmia based on the sensed cardiac electrical activity.

Figure 47A:
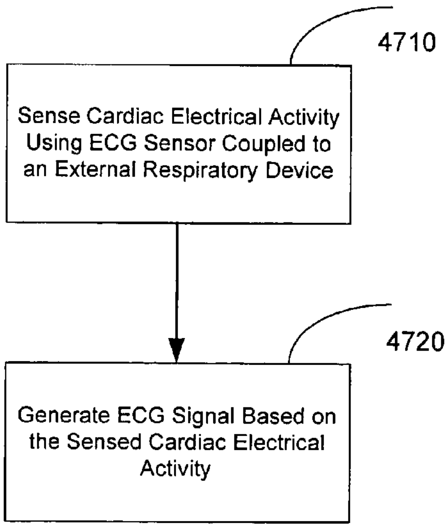
FIGS. 47A and 47B are flowcharts of methods involving the use of electrodes coupled to an external respiratory therapy device in accordance with embodiments of the invention.
Figure 47B:
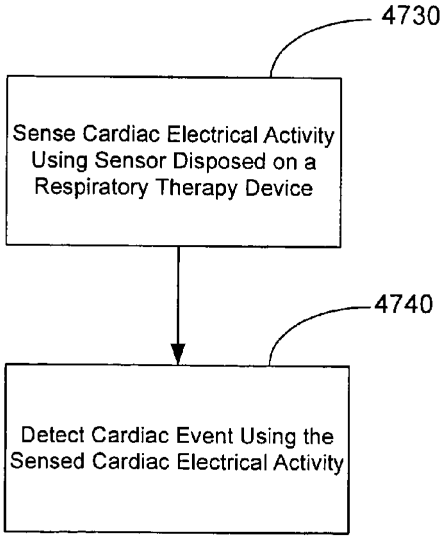

FIGS. 47A and 47B are flowcharts illustrating methods of using a cardiac electrical activity sensor disposed on a respiratory therapy device in accordance with embodiments of the invention. One or more electrodes are disposed 4710, 4730 on a respiratory therapy device in locations that facilitate sensing cardiac electrical activity. The electrodes may be positioned on a respiratory mask, mask strap, or in other locations of the respiratory therapy device from which cardiac signals can be sensed. In one embodiment, the sensed cardiac electrical activity is used 4720 to generate an electrocardiogram (ECG) signal. In another embodiment, the sensed cardiac electrical activity signal is used 4740 to detect arrhythmia.

FIGS. 48A-48F illustrate various embodiments for sensing cardiac activity and generating ECG signals using electrodes coupled to an external respiratory therapy device. In some embodiments, cardiac electrodes disposed on the mask of an external respiratory device sense cardiac signals. Circuitry coupled to the electrodes generates an ECG waveform. The ECG waveform generating circuitry coupled to the electrodes may be disposed on the mask, within the CPAP controller, or in another location.

In the illustrative examples presented herein, the external respiratory therapy device is configured as a continuous positive airway pressure (CPAP) device 4820 including a controller 4820, tubing 4822, and respiratory mask apparatus 4824. Any type of external respiratory therapy device other than CPAP can alternatively be used, such as bi-level positive airway pressure devices, auto titrating positive airway pressure devices, nebulizers, respirators, ventilators, and other external respiratory therapy devices. The CPAP controller 4820 develops a positive air pressure that is delivered to the patient's airway through tubing 4822 and mask assembly 4824. The positive airway pressure provided by the respiratory therapy device 4800 acts as a pneumatic splint keeping the patient's airway open and reducing the severity and/or number of occurrences of disordered breathing due to airway obstruction.

A typical CPAP device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example. The term CPAP will be used herein as a generic term for any device using forms of positive airway pressure (and negative pressure when necessary), whether continuous or otherwise.

In some embodiments (FIGS. 48A-48D), the one or more cardiac electrodes 4826 are mechanically coupled to the respiratory therapy device 4800. The electrodes 4826 may be positioned on the mask assembly 4824 of the external respiratory device 4800. For example, electrodes 4826 may be positioned on the mask, mask strap, or other appropriate location on the mask assembly in a location that facilitates sensing cardiac electrical activity. The mask assembly 4824 serves to hold the electrodes 4826 in place while the external respiration therapy is delivered to the patient.

In some configurations, the electrodes 4826 are coupled to an ECG processor 4821 that uses the cardiac signals sensed by the electrodes 4826 to generate an ECG waveform. The ECG processor 4821 may be disposed, for example, within or on the CPAP controller unit. The electrodes 4826 may be coupled to the ECG processor 4821 through a wire lead 4860.

In some implementations, the ECG processor 4821 may be positioned proximate the electrodes 4826, for example, on the respiratory mask assembly. This configuration facilitates generation of an ECG waveform that may be transmitted via a wireless communications link 4870 to the CPAP controller 4820 or other medical devices 4830.

The ECG waveform generated by the ECG processor 4821 may be printed on a printing device, displayed on a display device 4831, stored in memory, and/or analyzed by circuitry disposed within the CPAP controller 4820 and/or the cooperating medical device 4830.

If the patient uses the external respiratory therapy device regularly, for example each night, data acquisition via the electrodes 4826 coupled to the external respiratory device 4800 allows a significant amount of information about the patient's cardiac functioning to be collected during each sleep period. In some implementations, the cooperating medical device 4830 may comprise a patient-worn or patient-carried device. In other implementations, the medical device 4830 may comprise an implantable device, for example, an implantable monitor or implantable therapy device.

In some embodiments (FIGS. 48C and 48D), the ECG processor 4821 may be disposed within the medical device 4830. The medical device 4830 may additionally include circuitry for storing and/or analyzing the ECG signals. Information about the ECG signals may be downloaded from the medical device 4830 to an external device for display, analysis, or storage, for example.

In one configuration, the electrodes 4826 may be communicatively coupled to the external device 4830 through a wire lead 4860. In another configuration, additional circuitry, e.g., amplifiers and/or transmitter circuitry, may be used to provide a wireless link 4870 between the cardiac electrodes 4826 and the device 4830.

Figure 48A:
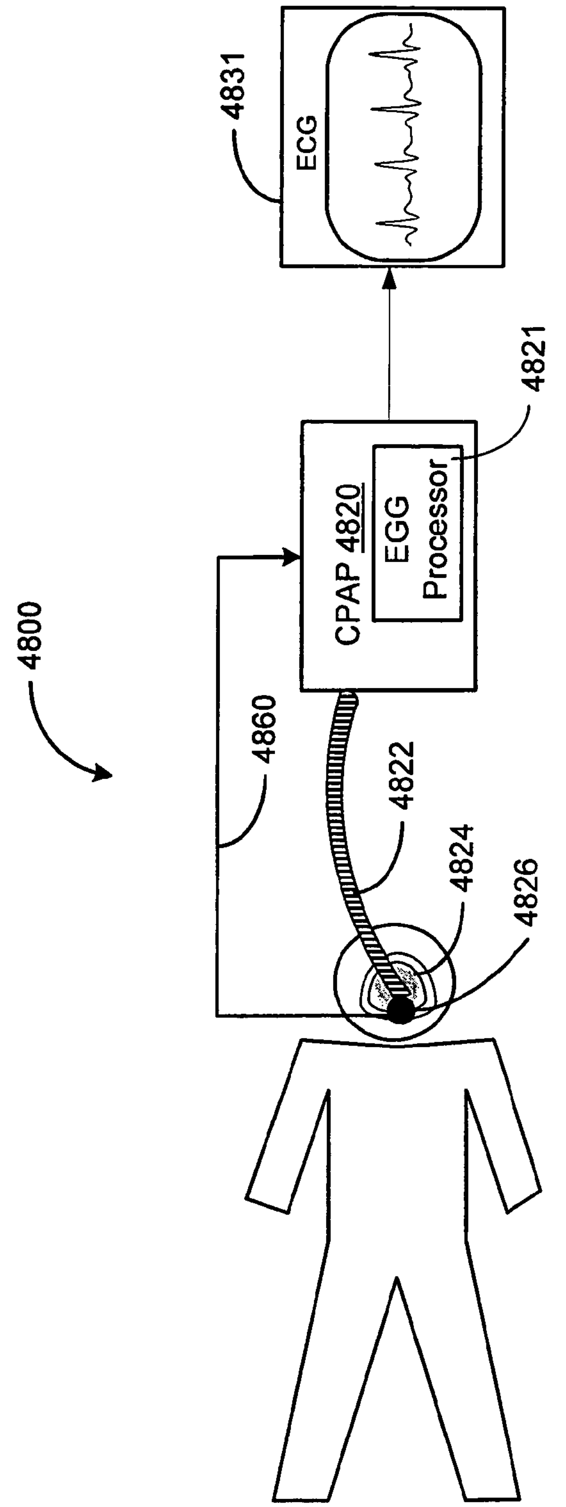
FIGS. 48A-48D are block diagrams of external respiratory therapy devices having one or more electrodes mechanically coupled to the respiratory therapy mask assembly and used in connection with generating electrocardiogram (ECG) signals in accordance with embodiments of the invention.
Figure 48B:
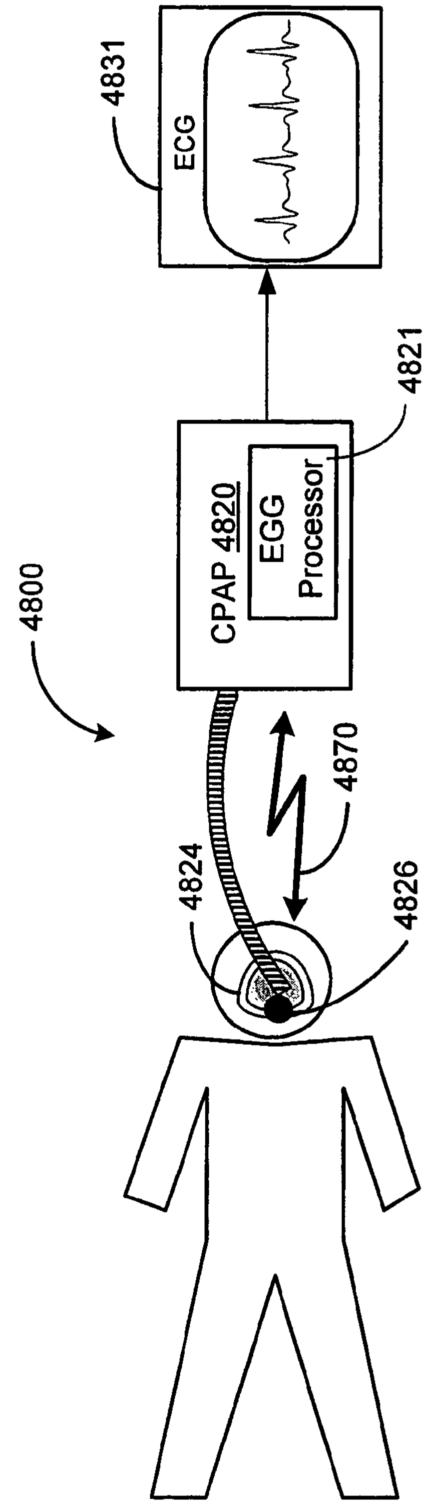
Figures 48C, 48D:
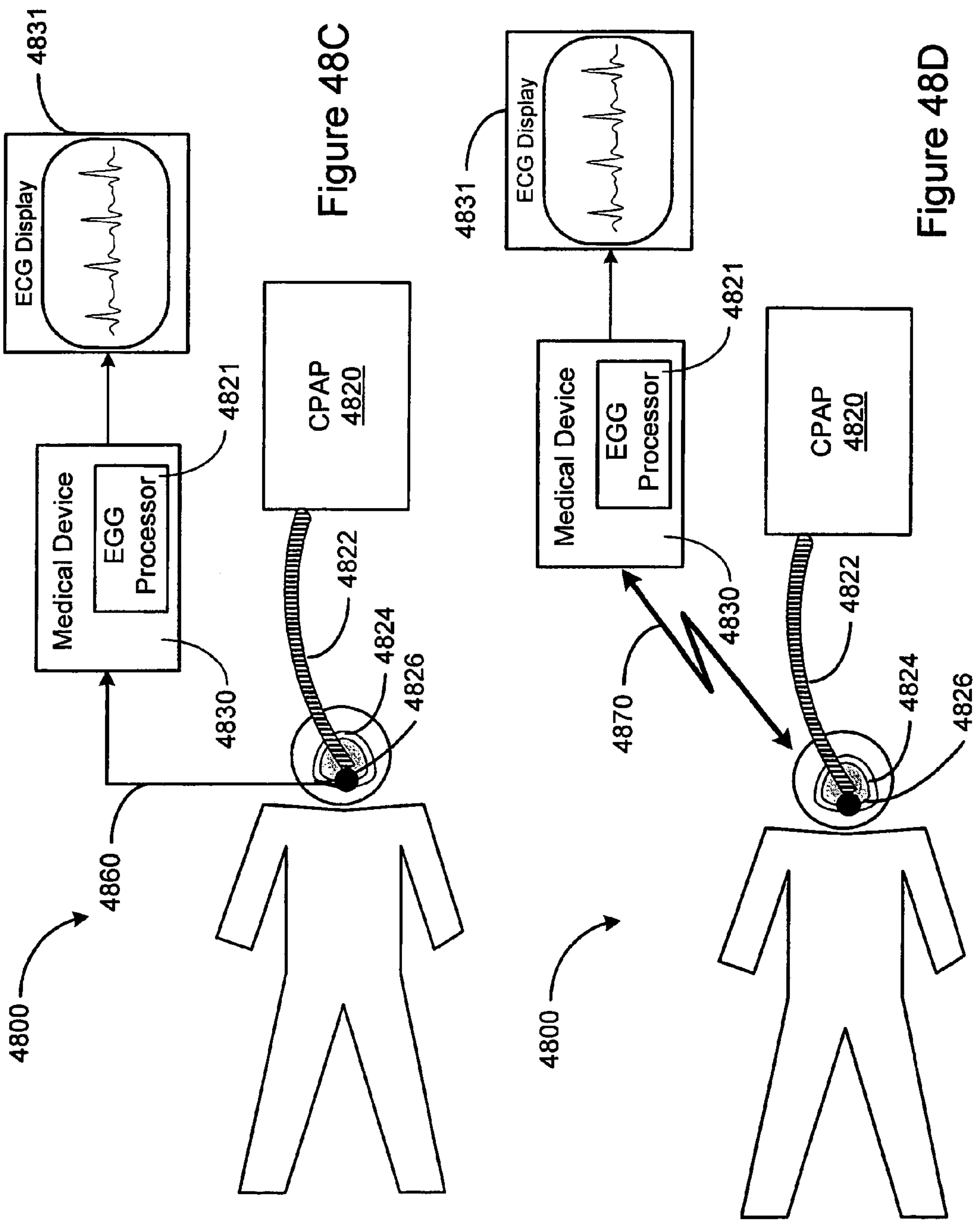
Figure 48E:
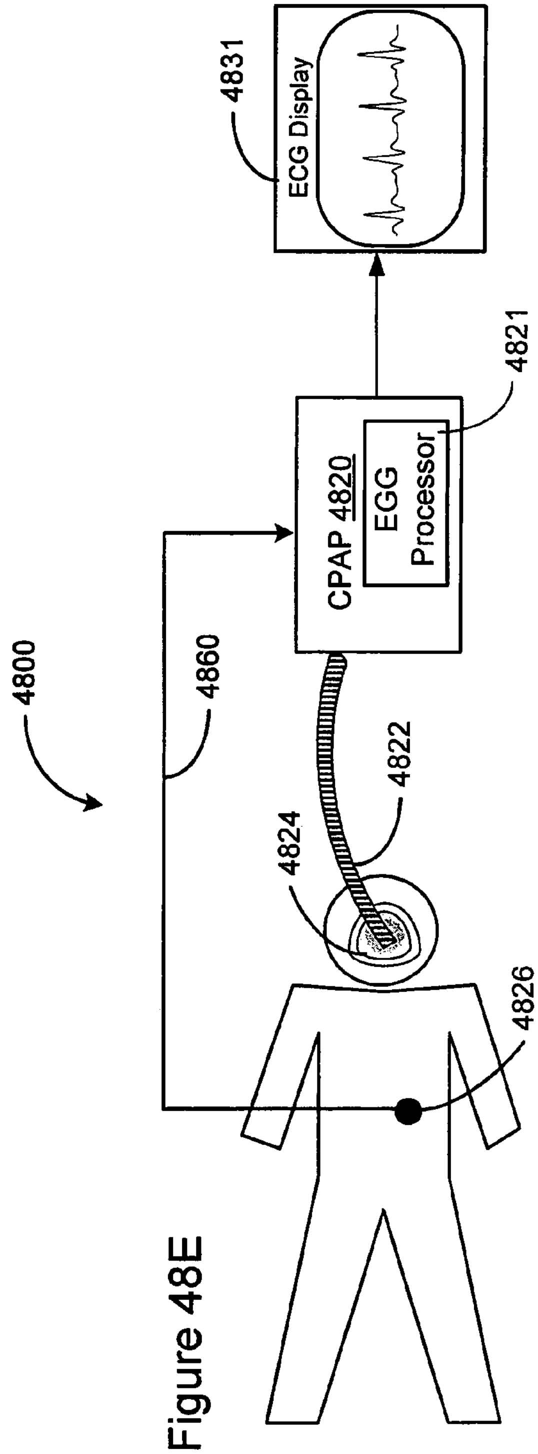
FIGS. 48E-48F are block diagrams of external respiratory therapy devices having one or more electrodes communicatively coupled to the respiratory therapy device controller and used in connection with generating ECG signals in accordance with embodiments of the invention.
Figure 48F:
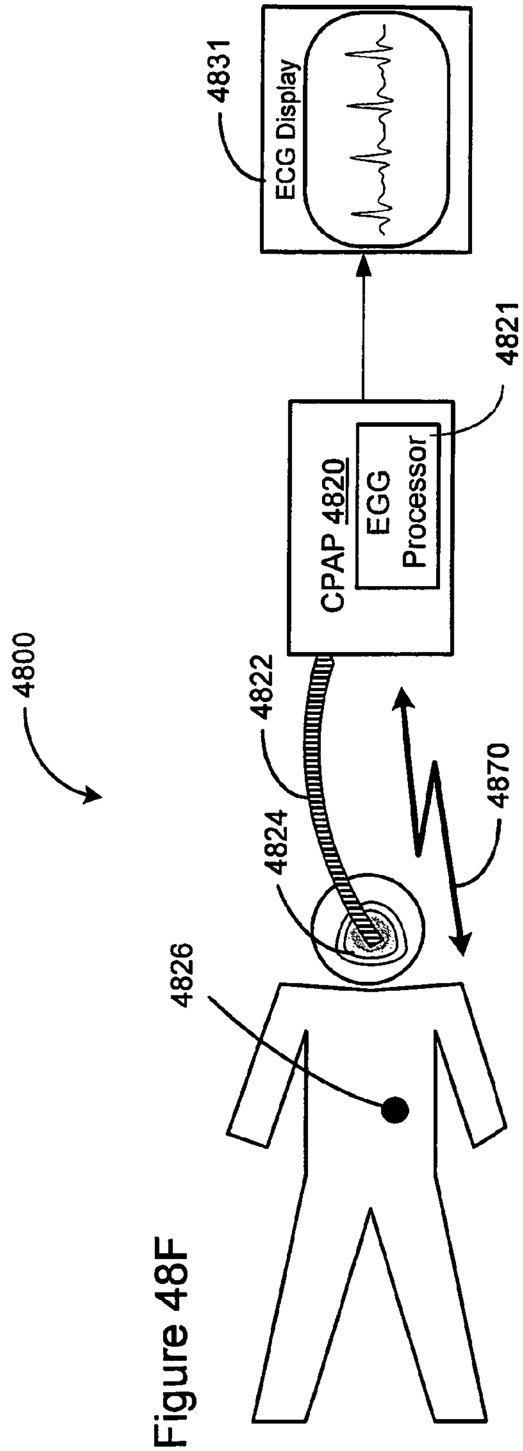
Figure 48G:
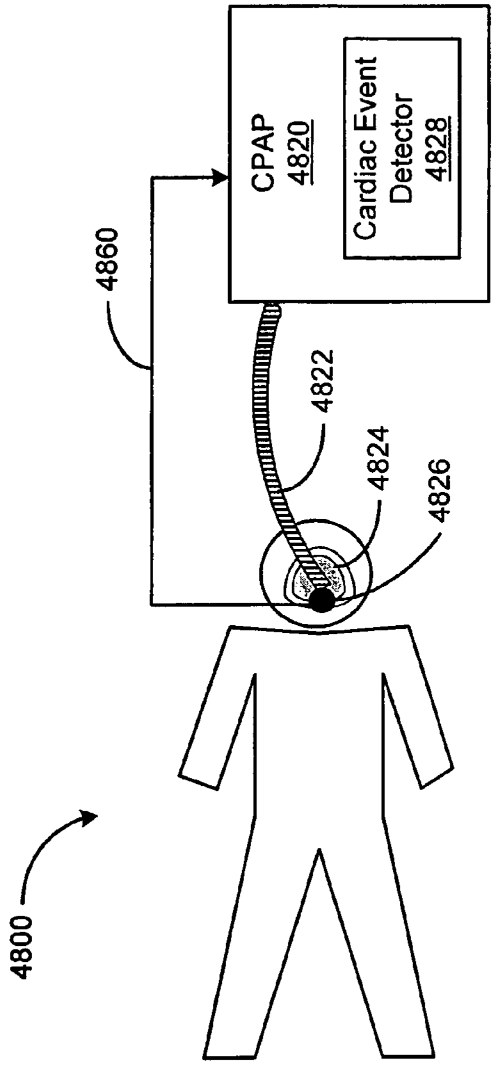
FIGS. 48G-48J are block diagrams of external respiratory therapy devices having one or more electrodes mechanically coupled to the respiratory therapy mask assembly and used in connection with detecting cardiac events in accordance with embodiments of the invention.
Figure 48H:
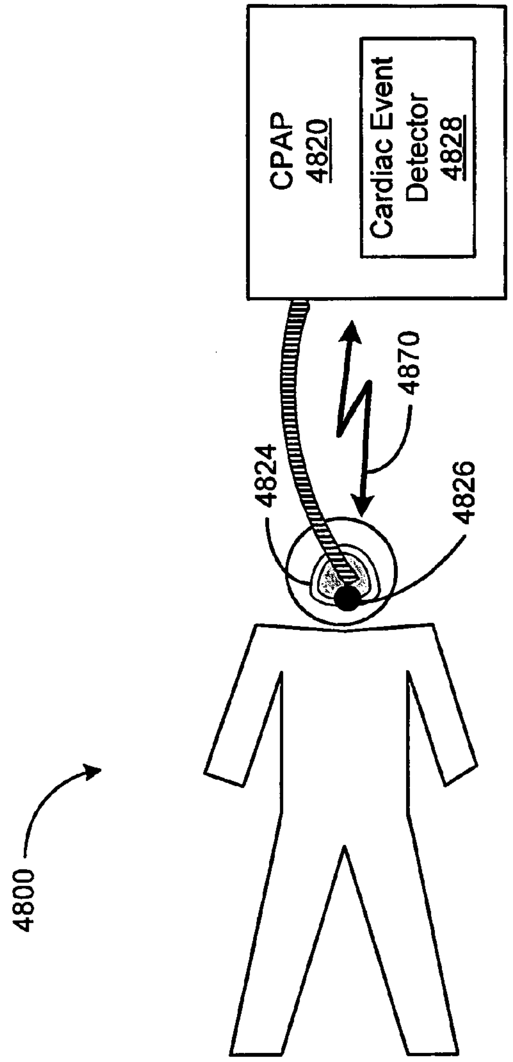

In some embodiments (FIGS. 48E and 48F), one or more cardiac electrodes 4826 may be positioned on the patient's chest, or another location suitable for sensing cardiac electrical activity. The cardiac electrodes may be communicatively coupled to the external respiratory device 4800. For example, the sensors may be communicatively coupled to the CPAP controller 4820 through a wire lead 4860 (FIG. 48E). Alternatively, additional circuitry may be situated proximate the electrodes to facilitate communication with the CPAP controller 4820 through a wireless communications link 4870 (FIG. 48F).

FIGS. 48G-48L illustrate embodiments of the invention involving cardiac event detection using one or more cardiac electrodes 4826 coupled to an external respiratory therapy device 4800. In some embodiments (FIGS. 48G-48J), the electrodes 4826 are mechanically coupled to the respiratory mask apparatus 4824. The respiratory mask apparatus 4824 serves as a support for the electrodes 4826 positioning the electrodes against the patient's face to facilitate sensing cardiac electrical activity. The electrodes 4826 are coupled to an external or implantable cardiac event detector 4828 through wired 4860 or wireless 4870 connections. In some embodiments (FIGS. 48G and 48H), the cardiac event detector 4828 is disposed within or on the CPAP controller 4820 housing. In other embodiments (FIGS. 48I and 48J), cardiac event detector 4828 circuitry is separate from the CPAP controller 4820.

Figure 48I:
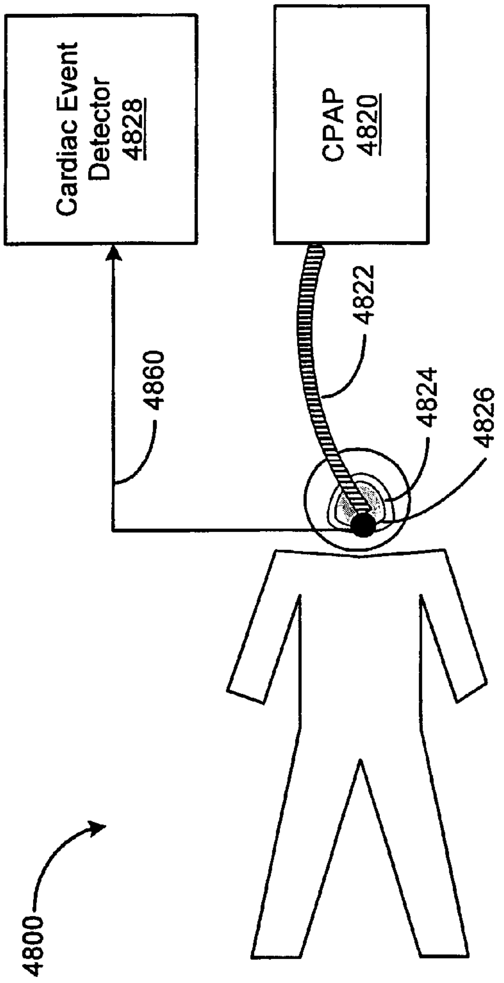
Figure 48J:
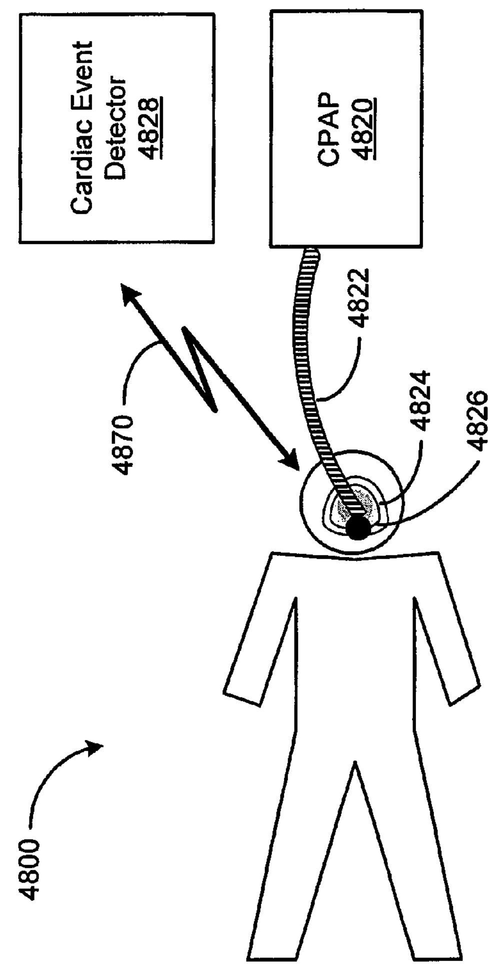
Figure 48K:
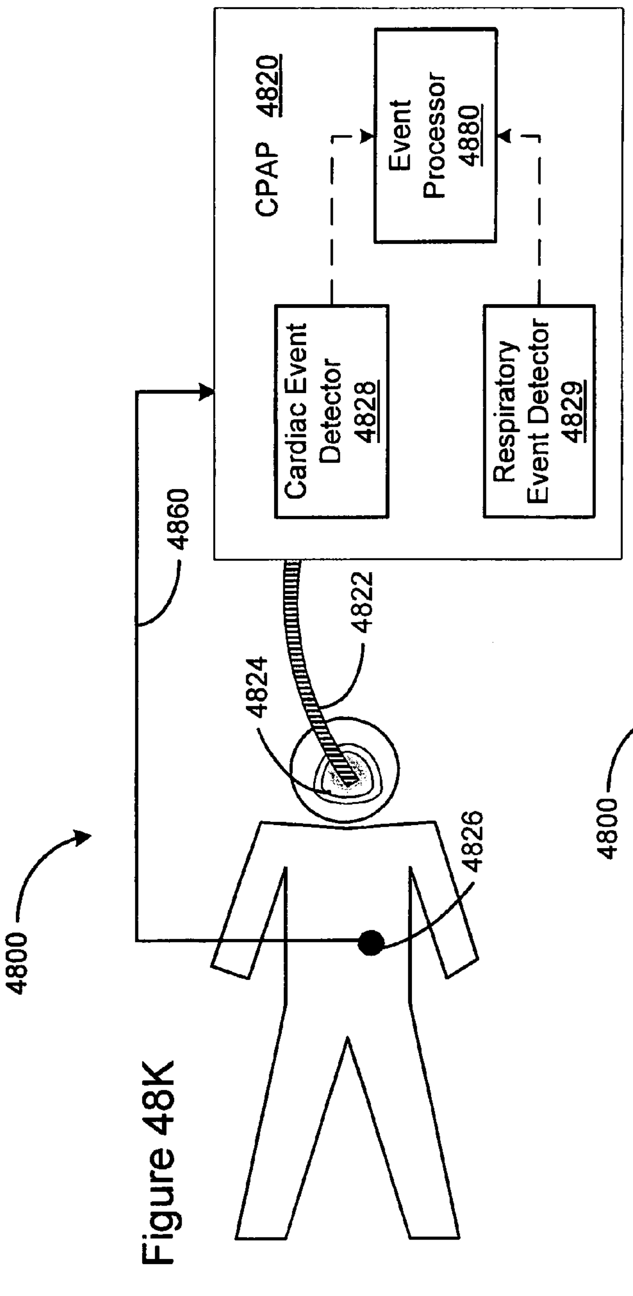
FIGS. 48K-48L are block diagrams of external respiratory therapy devices having one or more electrodes communicatively coupled to the respiratory therapy device controller and used in connection with detection of cardiac events in accordance with embodiments of the invention.
Figure 48L:
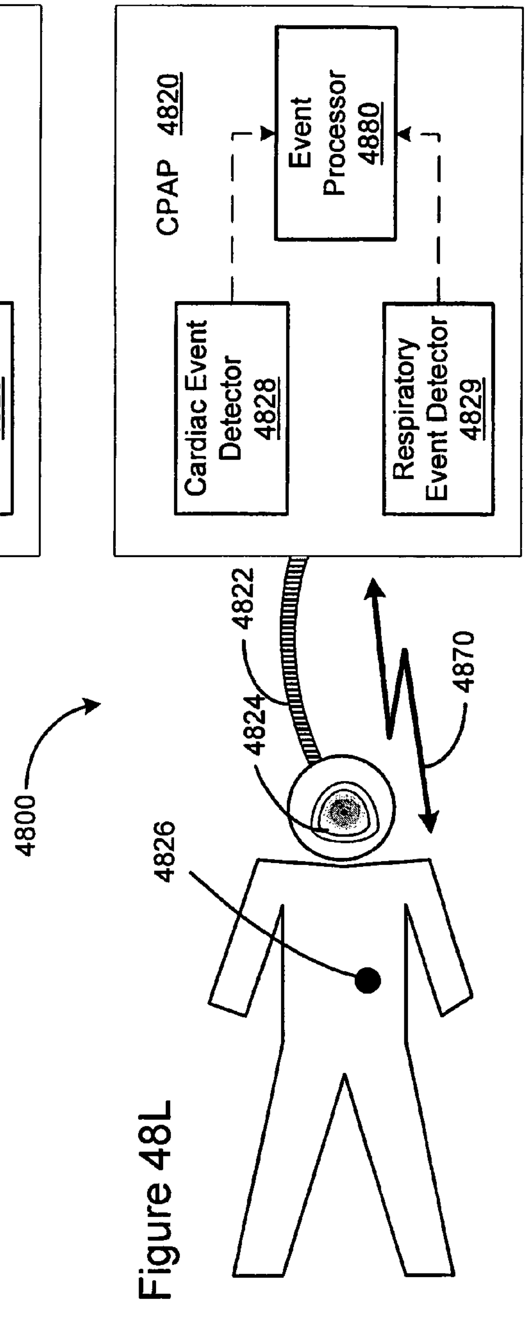

FIGS. 48K and 48L illustrate embodiments of the invention wherein one or more cardiac electrodes 4826 are positioned on the patient's chest or other location suitable for sensing cardiac electrical activity. The electrodes are coupled to a cardiac event detector 4828 of an external respiratory therapy device 4800. The electrodes 4826 may be coupled to the cardiac event detector 4828 through a wire lead 4860 or through a wireless connection 4870.

The CPAP device 4820 may optionally include a respiratory event detector 4829. In accordance with one implementation, the respiratory event detector may be used to provide feedback for therapy control. For example, CPAP therapy may be initiated or adjusted based on the presence, absence, severity, frequency and/or duration of disordered breathing events detected by the respiratory event detector.

If a respiratory event detector is included, the respiratory event detector and the cardiac event detector may be coupled to an event processor 4880. The event processor 4880 may be used to detect physiological events, including events affecting one or more of the cardiac and pulmonary systems based on inputs from the cardiac and respiratory event detectors. The cardiac event detector, respiratory event detector and/or event processor may be employed to detect various cardiac and/or respiratory dysfunctions, including, for example, bradycardia, tachycardia, including atrial tachyarrhythmia, ventricular tachyarrhythmia and ventricular fibrillation, myocardial ischemia, and/or myocardial infarction. The event processor may compare occurrences of respiratory and cardiac events including one or more of the timing, severity, type, and occurrence rate of the respiratory and cardiac events and detect the physiological events based on these and/or other factors.

The cardiac event detection circuitry illustrated, for example, in FIGS. 48I and 48J may be implemented in a patient carried or patient worn device, or in an implantable device such as a cardiac defibrillator or pacemaker.

Figure 48M:
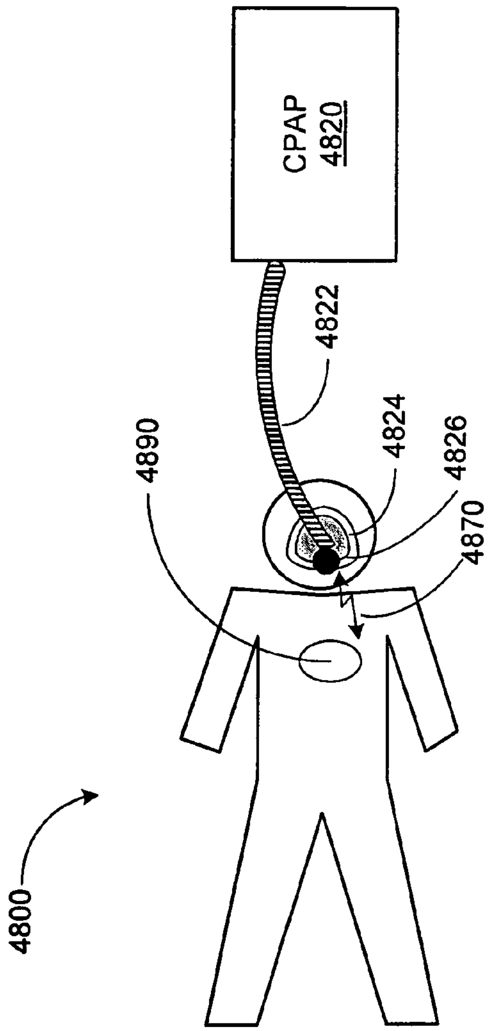
FIGS. 48M-48N are block diagrams of an external respiratory therapy device having cardiac electrodes communicatively coupled to an implantable medical device in accordance with embodiments of the invention.

FIG. 48M illustrates an embodiment of the invention wherein one or more cardiac electrodes 4826, and circuitry used to establish a wireless communications link 4870, are disposed on the CPAP mask assembly 4824. In FIG. 48M, signals sensed by the cardiac electrodes are transmitted to an implantable device 4890, bypassing the CPAP controller 4820.

The implantable device 4890 may comprise, for example, an implantable therapy device, such as an implantable electrical stimulation device or implantable drug pump. The implantable device may comprise an implantable monitor. In one implementation, the implantable device 4890 may comprise an implantable pacemaker, defibrillator, cardioverter, cardiac resynchronizer, or other cardiac therapy devices that receives the ECG signals. In another implementation, the implantable device 4890 may comprise an implantable loop recorder, such as a subcutaneous ECG recorder. The implantable device may include a cardiac event detector that analyzes the ECG signals to detect cardiac events including cardiac arrhythmia, ischemia, and/or myocardial infarction.

Figure 48N:
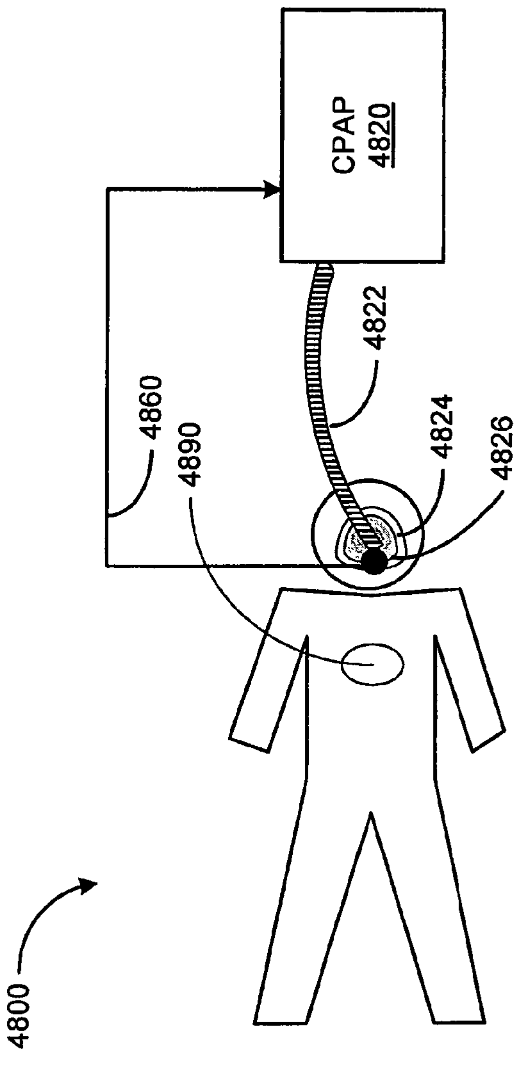

FIG. 48N illustrates an embodiment wherein the cardiac electrodes 4826 are coupled to the CPAP device 4820 through a wire lead. Signals received by the CPAP device 4820 may be wirelessly transmitted to the implantable device 4890 for storage, analysis or for other purposes.

Figure 49A:
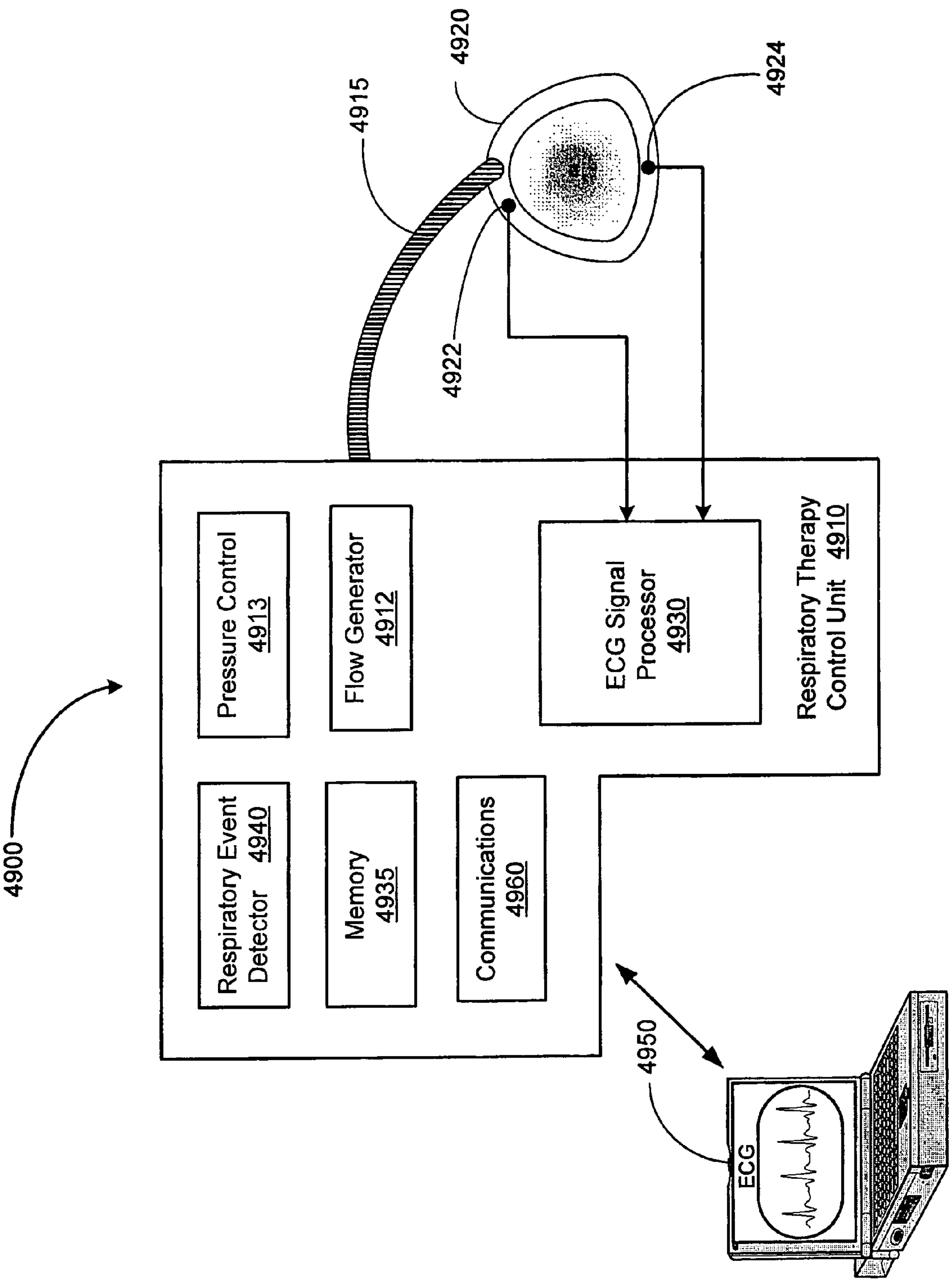
FIG. 49A is a block diagram of an external respiratory therapy device including one or more electrodes mechanically coupled to the respiratory therapy mask assembly and a respiratory therapy controller incorporating an ECG signal processor in accordance with embodiments of the invention.
Figure 49B:
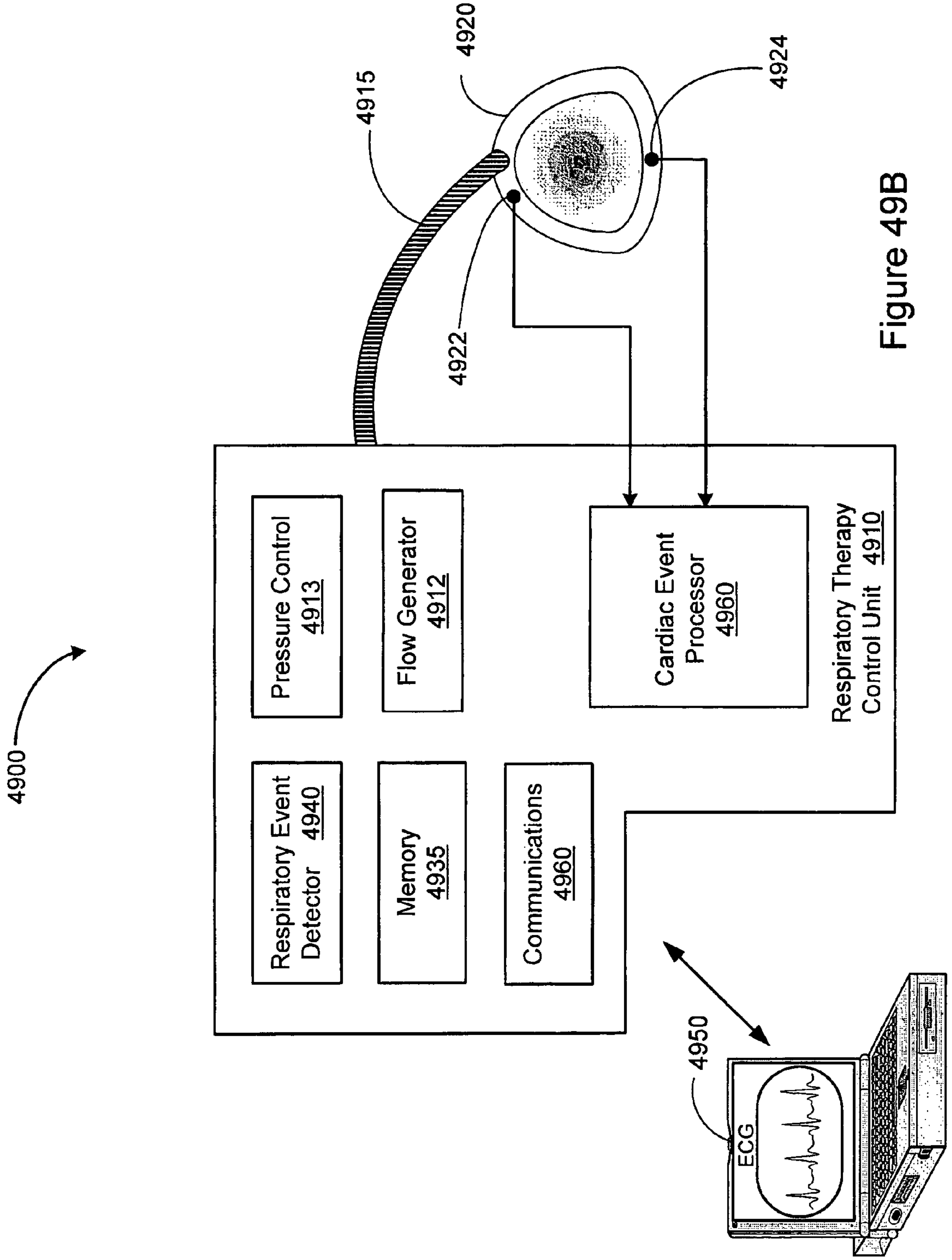
FIG. 49B is a block diagram of an external respiratory therapy device including one or more electrodes mechanically coupled to the respiratory therapy mask assembly and a respiratory therapy controller incorporating cardiac event detector in accordance with embodiments of the invention.

FIGS. 49A and 49B are block diagrams of a medical system including an external respiratory therapy device that may be used in connection with sensing cardiac electrical activity. FIG. 49A illustrates an embodiment that are directed to generating an electrocardiogram signal in accordance embodiments of the invention. FIG. 49B illustrates an embodiment that uses the sensed electrical cardiac activity to detect arrhythmia.

FIGS. 49A and 49B depict block diagrams of a CPAP device 4900 having cardiac sensing capabilities in accordance with the present invention. The CPAP device includes a CPAP controller 4910, tubing 4915, and mask assembly 4920. The CPAP controller unit may include a respiratory event detector 4940 configured to detect disordered breathing episodes, such as sleep apnea and/or hypopnea. Detection of disordered breathing may be used to initiate or adjust respiratory therapy delivered to the patient.

The CPAP controller unit 4910 includes flow generator 4912 that pulls in air through a filter. The flow generator 4912 is controlled by the pressure control circuitry 4913 to deliver an appropriate air pressure to the patient. Air flows through tubing 4915 coupled to the CPAP device 4910 and is delivered to the patient's airway through the mask assembly 4920. The CPAP controller 4910 may be coupled through communications circuitry 4960 to other computing devices 4950, such as a programmer or patient management server to facilitate storage, evaluation and/or display of the cardiac information.

In embodiments of the present invention, the mask apparatus 4920 may comprise a nasal mask covering only the patient's nose. In other configurations the mask covers the patient's nose and mouth. One or more cardiac electrodes may be coupled to the CPAP device 4900. For example, the one or more cardiac electrodes 4922, 4924 may be incorporated on the respiratory therapy mask 4920. However, the one or more cardiac electrodes 4922, 4924 can be positioned in another location of the respiratory therapy device that facilitates acquisition of a cardiac signal and. For example, electrodes 4922 can be incorporated in a respiratory mask strap (not shown).

As illustrated in FIG. 49A, the cardiac electrodes 4922, 4924 are communicatively coupled to signal processing circuitry 4930 within the CPAP controller 4910. The cardiac activity information is used to generate an electrocardiogram signal. The ECG signal can be used by the CPAP control unit 4910 to control the external respiratory therapy delivered to the patient. Additionally or alternatively, the ECG signal can be stored in memory 4935, used to generate an ECG display or printout, and/or evaluated for diagnostic or therapeutic purposes.

FIG. 49B illustrates a block diagram of an embodiment of the invention that involves detection of cardiac arrhythmia. In this configuration, cardiac electrodes 4922, 4924 positioned on the respiratory mask 4920, sense cardiac electrical activity. The electrodes 4922, 4924 are coupled to an arrhythmia detector 4960 disposed within a housing of the respiratory therapy control unit 4910. The cardiac event detector 4960 uses the cardiac electrical activity sensed by the electrodes 4922, 4924 to detect cardiac events, such as bradycardia, ventricular tachyarrhythmia, ventricular fibrillation, and/or other arrhythmic events. In one implementation, the cardiac event detector 4960 may evaluate the cardiac electrical activity to determine heart rate and detect arrhythmia based on heart rate. In another implementation, the arrhythmia detector 4960 may analyze the morphology of the cardiac electrical activity signal and detect arrhythmia based on the morphology of the cardiac electrical activity signal. Other methods of arrhythmia detection are possible.

Figure 50:
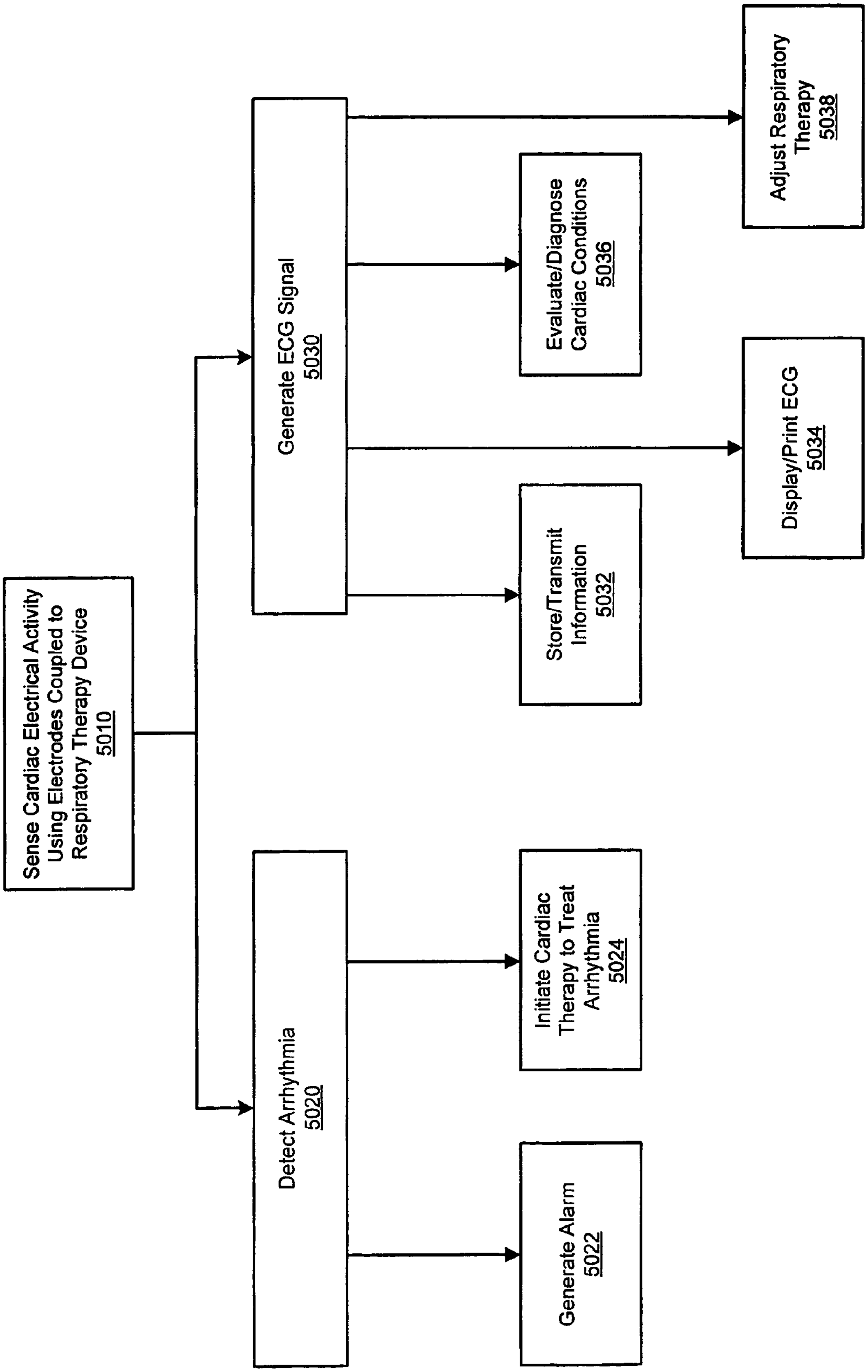
FIG. 50 is a process flow diagram illustrating various optional processes that may be implemented using one or more electrodes coupled to an external respiratory therapy device.

FIG. 50 illustrates various optional processes that may be facilitated using cardiac electrodes coupled to a respiratory therapy device. Cardiac electrical activity is sensed using electrodes coupled to an external respiratory therapy device 5010. According to one aspect of the invention, the sensed cardiac activity may be used to detect arrhythmia 5020. If arrhythmia is detected, an alarm may be generated 5022, such as an audible or visual alarm. The alarm may include various tones or signals to indicate more than one type of arrhythmic condition, for example. In one implementation, the alarm may involve wireless communication with a remote device, such as a cell phone or pager, for example.

The sensed cardiac activity may be used to generate 5030 an ECG signal. The ECG signal may be stored and/or transmitted 5032 to a separate device. For example, the ECG signal may be transmitted to a patient management server for further analysis. The ECG waveform may be displayed 5034 on a display device or printed. The ECG signal may be used to initiate cardiac therapy 5024 to treat an arrhythmia.

Detected cardiac events and detected respiratory events may also be analyzed to determine relationships between cardiac and respiratory events. The results of this comparison may be displayed, stored, transmitted or used to modify cardiac or respiratory therapy.

Acquisition of ECG signals over a period of time may be used to trend cardiac conditions and/or diagnose 5036 cardiac dysfunction, for example. Further, the ECG signals may be evaluated may be used to adjust 5038 the patient's therapy, such as the external respiratory therapy delivered to the patient.

The ECG signal may be analyzed to detect morphological characteristics and/or cardiac timing measurements indicative of heart status including, for example, RR interval, PP interval, AV interval, PR interval, QT interval and/or ST elevation. The ECG signal may be used to determine statistics derived from heart rates, such as heart rate variability and various cardiac timing measurements, including RR timings and AV delay timing. Various cardiac events and/or other indications of heart status may be determined based on the ECG signal, including arrhythmia, myocardial ischemia, and/or other events. These analyses may be used to identify patient's cardiac condition and adjust therapy.

Implantable Monitor for External Respiratory Therapy

Aspects of the invention that include implantably monitoring external breathing therapy are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving implantable monitoring of external respiratory therapy are directed to methods and systems configured to monitor, diagnose, and/or provide therapy using coordinated medical procedures. Coordinated medical procedures may involve cooperative operation of two or more of the individual processes 180. Coordinated medical procedure may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

One embodiment of the invention involves an individual system 122 (FIG. 1C) for implantably monitoring external respiratory therapy delivered to a patient. The respiratory therapy monitoring system 122 may be implemented as a stand alone system or in combination with other individual medical systems, such as those described in FIGS. 1B-1D.

Embodiments of the invention are directed to methods and systems for monitoring therapy delivered to a patient. An embodiment of the invention involves a method for implantably monitoring a patient-external respiration therapy delivered to the patient. The method includes sensing one or more conditions associated with patient-external breathing therapy. The patient-external respiration therapy is monitored by an implantable device based on the sensed conditions.

In accordance with another embodiment of the invention, a medical system, includes a sensing system configured to sense conditions associated with a patient-external breathing therapy. The system also includes an implantable monitoring device, coupled to the sensing system. The implantable monitoring device is configured to monitor the patient-external breathing therapy based on the one or more sensed conditions.

Another embodiment of the invention involves a system for providing coordinated patient monitoring, diagnosis and/or therapy that utilizes system 122 sensed conditions to monitor patient-external breathing therapy. The coordinated system includes, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a system 122 configured to monitor external breathing therapy based on sensed conditions. The monitoring system 122 includes a sensing system configured to sense conditions associated with a patient-external breathing therapy and an implantable monitoring device. The implantable monitoring device is coupled to the sensing system and is configured to monitor the patient-external breathing therapy based on the one or more sensed conditions. Systems and methods directed to implantably monitoring external breathing therapy may be implemented to include selected features, functions, and/or structures described in commonly owned, U.S. Pat. No. 7,468,040, which is hereby incorporated herein by reference.

Breathing disorders may be more effectively monitored and/or treated using a coordinated approach. Various embodiments of the invention are implemented using medical systems employing two or more patient-external and/or patient-internal medical devices. The medical devices may communicate or otherwise operate in concert to provide more comprehensive patient monitoring for external breathing therapy.

A number of disorders are treated using external breathing therapy devices. For example, rhythm related breathing disorders such as sleep apnea, hypopnea may be treated with a positive airway pressure device. Asthma may be treated with a nebulizer. Various diseases affecting the pulmonary system may be treated with gas or oxygen therapy. Embodiments of the invention are directed to methods and systems utilizing an implantable device to monitor parameters associated with an external breathing therapy delivered to the patient. External breathing therapy may be delivered by various types of patient-external respiratory therapy devices, including, for example, nebulizers, respirators, ventilators, external gas therapy devices and/or positive airway pressure devices.

A typical continuous positive airway pressure (CPAP) device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example.

The parameters monitored by the monitoring system may include therapy effectiveness, impact of the therapy on the patient, therapy usage, compliance with a prescribed usage and/or therapy interactions, for example. In various embodiments described herein, sensors coupled to the implantable monitoring device sense conditions used to monitor therapy parameters. For example, the sensed conditions may be used to evaluate the effectiveness of the breathing therapy the impact of the therapy on the patient and/or therapy interactions between the external breathing therapy and other therapies delivered to the patient. The external breathing therapy may be adjusted to enhance therapy effectiveness, to reduce an impact of the therapy and/or to reduce therapy interactions.

The implantable device may monitor the patient's use of the external breathing therapy and/or compliance with a prescribed usage of the breathing therapy, for example.

The implantable device may transmit information about the sensed conditions and/or the monitored parameters to the external breathing therapy device. The information may be used by the external breathing therapy device to automatically adjust the breathing therapy delivered to the patient. The information may be transmitted, either by the implantable device, or by the external breathing therapy device, to a patient management system. Advanced patient management (APM) systems involve a system of medical devices that are accessible through various communications technologies. Medical information may be transmitted to a remote patient management server from the various medical devices. The medical information may be analyzed and used to diagnose and/or monitor disease progression, to determine appropriate therapies for the patient, and/or for other medical purposes.

Information acquired by the monitoring device, including information associated with the sensed conditions and/or the parameters of the breathing therapy, may be evaluated to facilitate diagnosis and/or therapy adjustment. The information transmitted to the patient management system may be used for diagnostic purposes related to the breathing disorder affecting the patient, for example. The patient management system may adjust breathing therapy delivery based on the information. In one implementation, the patient management system transmits control signals to the breathing therapy device to adjust the breathing therapy. Further, the patient and/or the patient's physician may access the information through the patient management system.

Figure 51:
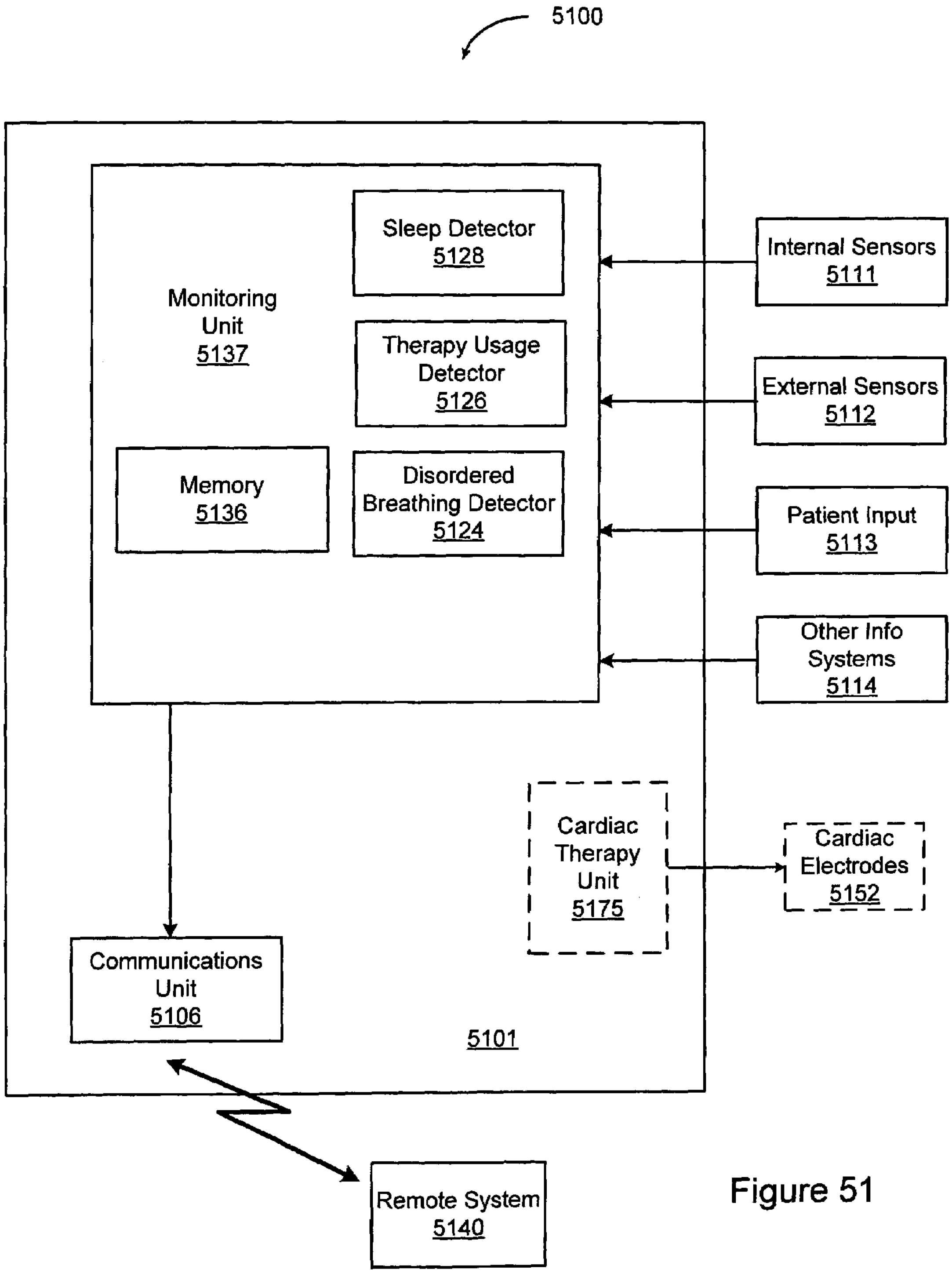
FIG. 51 is a block diagram of a patient-external respiratory therapy device that may be used to provide breathing therapy monitored by an implantable device in accordance with embodiments of the invention.

The block diagram of FIG. 51 illustrates an example of medical system 5100 including a fully or partially implantable device 5101 that may be used to monitor breathing therapy delivered by an external device in accordance with embodiments of the invention. The system 5100 employs a medical device 5101 that may be coupled to an array of data acquisition devices, including patient-internal sensors 5111, patient-external sensors 5112, patient input devices 5113, and/or other information systems 5114 as described herein.

Conditions used to monitor parameters of the breathing therapy may include both physiological and non-physiological contextual conditions affecting the patient. Table 1 above provides a representative set of patient conditions that may be used to monitor breathing therapy in accordance with embodiments of the invention. Table 1 also provides illustrative sensing methods that may be employed to sense the conditions. It will be appreciated that patient conditions and detection methods other than those listed in Table 1 above may be used and are considered to be within the scope of the invention.

The implantable device 5101 of FIG. 51 includes a monitoring unit 5137 that processes signals received from the sensors, 5111, 5112, patient input devices 5113, and/or other information system 5114. The monitoring unit 5137 may include one or more a detection units 5124, 5126, 5128 that detect the occurrence of various physiological events. For example, the monitoring unit 5137 may include one or more of a disordered breathing detector 5124, a sleep detector 5128, and/or a therapy usage detector 5126. Other event detection components may also be included in the monitoring unit 5137. The monitoring unit 5137 may include circuitry used to calculate various indices, such as AHI, % PB, arousals per unit time, and/or other indices that can be used to evaluate therapy efficacy, therapy impact and/or other parameters. The monitoring unit 5137 may compare the patient's therapy usage to a prescribed therapy to determine therapy compliance.

The disordered breathing detector 5124 may be coupled to a respiration sensor, for example, and used to detect disordered breathing events based on the inspiratory and expiratory phases of the patient's respiration cycles, for example. The sleep detector 5128 may analyze various inputs from the patient-internal sensors 5111, patient-external sensors 5112, patient input devices 5113, and/or other information systems 5114 to detect sleep-related events, including, for example, sleep onset, sleep offset, sleep stages, and arousals from sleep.

The therapy usage detector may detect the proximity of the patient to the external breathing device, to determine therapy usage. In another example, the therapy usage detector may analyze the patient's respiration waveform to determine therapy usage.

The monitoring unit 5137 may operate in cooperation with a memory 5136. The memory 5136 may store information derived from signals produced by the patient-internal sensors 5111, patient-external sensors 5112, patient input devices 5113, and/or other information systems 5114. The memory 5136 may also store information about detected events, e.g., sleep and disordered breathing events, and/or information related to calculated indices characterizing various events such as sleep and/or disordered breathing events. The stored data, along with other information related to the breathing therapy may be transmitted to another component of the medical device 5101 or to a separate device 5140 for storage, further processing, trending, analysis, printing and/or display, for example. In one scenario, the stored data can be downloaded to a separate device periodically or on command. The stored data may be presented to the patient's health care professional on a real-time basis, or as a long-term, e.g., month long or year long, trend of daily measurements.

The medical device 5101 may optionally include a therapy unit. In various examples provided herein, the medical device 5101 is a cardiac device configured to deliver cardiac electrical stimulation therapy using a cardiac pulse generator 5175 and electrical stimulation electrodes 5152.

The medical device 5101 may further include a communications unit 5106 that controls communications between the medical device 5101 and other devices or systems. For example, the communications unit 5106 may be used to provide wireless or wired communications links between the medical device 5101 and one or more of the patient-internal sensors 5111, patient-external sensors 5112, patient input devices 5113, and information systems 5114.

The communications unit 5106 may also facilitate communications between the medical device 5101 and a remote device 5140 such as the patient-external breathing therapy device, a programmer, and/or an APM system. The wireless connections coupling the medical device 5101 to various other devices and systems may utilize a variety of wireless protocols, including, for example, Bluetooth, IEEE 802.11, and/or a proprietary wireless protocol.

Detecting the onset, termination, duration, stages, and quality of sleep experienced by a patient may be employed in connection with monitoring breathing therapy. Patients suffering from sleep apnea, or other types of sleep disordered breathing, are generally treated with breathing therapy only during periods of sleep. Monitoring the sleep disordered breathing therapy may involve determining when the patient is asleep and/or monitoring arousals and/or various sleep stages.

In addition, monitoring patient sleep may be used to assess an impact of breathing therapy on the patient. Therapy impact information may be used to determine an appropriate breathing therapy for the patient. The implantable monitoring device may include a sleep detector 5128 for detecting when the patient is asleep and the various stages of sleep. Various methods of sleep detection implementable in an implanted device involve sensing one or more conditions associated with sleep. The sleep-related conditions may be compared to a threshold to determine if the patient is asleep.

The sleep-related conditions may be derived from patient-external or implantable sensors and analyzed by a sleep detector located in the implantable monitoring device or by circuitry within the APM communication unit (i.e., a supervisor device that co-ordinates diagnostics between various sensors. In one implementation proximity to bed, sleep detection may be implemented in an implantable cardiac rhythm management system configured as a pacemaker/defibrillator as an ITCS device.

Sleep detection may involve sensing one or more conditions indicative of sleep. A representative set of sleep-related conditions include body movement, heart rate, QT interval, eye movement, respiration rate, transthoracic impedance, tidal volume, minute ventilation, body posture, brain activity, cardiac activity, muscle tone, body temperature, time of day, historical sleep times, blood pressure, and blood gas concentration, proximity to bed, for example.

Sleep may be detected by comparing levels of the one or more sleep-related conditions to one or more sleep thresholds. For example, sleep may be detected by based on the patient's heart rate. When the patient's heart rate decreases below a sleep threshold, the patient may be determined to be asleep. Sleep may also be detected base on the patient's activity. If the patient's activity decreases below a sleep threshold, then the patient may be determined to be asleep. Another method of detecting sleep involves monitoring the patient's minute ventilation. If the patient's minute ventilation falls below a sleep threshold, then the patient may be determined to be asleep.

Sleep may be detected by comparing multiple sleep-related conditions to multiple thresholds. For example, the patient may be determined to be asleep if the patient's activity, sensed by an accelerometer, falls below an activity sleep threshold and the patient's heart rate, sensed by cardiac electrodes, falls below a heart rate sleep threshold.

Sleep may also be detected using one sleep-related condition to modify the sleep threshold of another sleep-related condition. A first sleep-related condition may be sensed. The level of the sleep-related condition may be compared to a sleep threshold to determine the onset and termination of sleep. A second sleep-related condition may be used to adjust the sleep threshold. Additional sleep-related conditions may optionally be sensed to confirm the onset or termination of the sleep condition.

A sleep detector 5128 (FIG. 51) may be configured to compare the levels of one or more sleep-related conditions to one or more thresholds. In one implementation, the one sleep related condition may be compared to a sleep threshold or other index to detect sleep. In another implementation, multiple sleep-related conditions may be compared to multiple thresholds or indices. In a further implementation, one or more of the sleep-related conditions may be used to adjust the sleep thresholds or indices. Furthermore, the onset or termination of sleep may be confirmed using an additional number of sleep-related conditions.

One or more sleep-related conditions may be sensed using implantable sensors and/or patient-external sensors, for example. In one embodiment, patient activity may be compared to a sleep threshold to determine when the patient is asleep. A low level of activity is indicative that the patient is sleeping. Patient activity may be sensed, for example, using an accelerometer positioned on or in the housing of an implantable cardiac device, or in another convenient location. The accelerometer signal may be correlated with activity level or workload.

A second sleep-related condition may be used to adjust the sleep threshold. In one embodiment, the patient's minute ventilation is used to adjust the sleep threshold. The patient's respiration may be sensed using a transthoracic impedance sensor. Transthoracic impedance may be used to derive various parameters associated with respiration, including, for example, tidal volume and/or minute ventilation. A transthoracic impedance sensor may be integrated into an implantable cardiac device with intracardiac electrodes, for example. Impedance driver circuitry generates a current that flows through the blood between the impedance drive electrode and a can electrode on the housing of the cardiac device. The voltage at an impedance sense electrode relative to the can electrode changes as the transthoracic impedance changes.

Figure 52A:
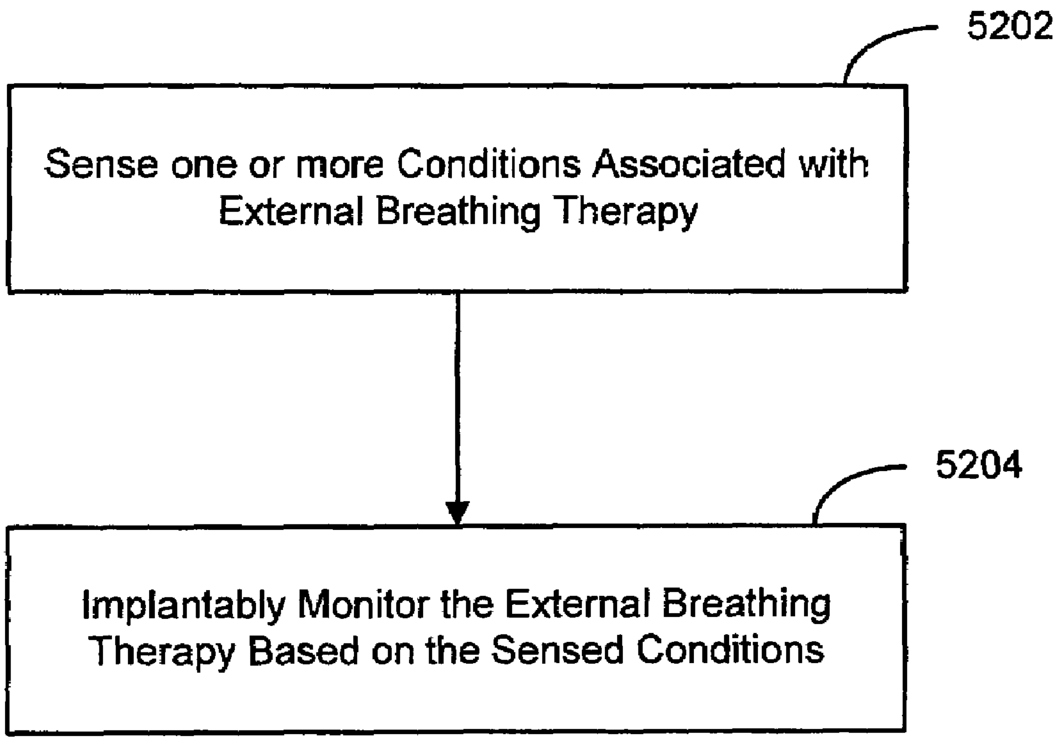
FIGS. 52A-52E are flowcharts illustrating methods of implantably monitoring an externally delivered breathing therapy in accordance with embodiments of the invention.

FIGS. 52A-E are flowcharts illustrating methods related to implantably monitoring external breathing therapy in accordance with various embodiments of the invention. As illustrated in the flowchart of FIG. 52A, a method for monitoring external breathing treatment involves sensing 5202 one or more conditions associated with patient-external breathing therapy and implantably monitoring 5204 the patient-external breathing therapy based on the one or more sensed conditions. The sensed conditions are used to monitor one or more parameters of the patient-external breathing therapy, such as the patient's compliance with the external breathing therapy, the effectiveness of the external breathing therapy, the impact of the external breathing therapy on the patient, and/or other conditions.

The parameters monitored by the implantable device, and the conditions sensed to monitor the breathing therapy parameters can be programmable. The implantable device may acquire information used to monitor the breathing therapy parameters continuously or during selected periods of time. For example, if the patient suffers from sleep disordered breathing, the implantable device may acquire information associated with the breathing therapy after detecting that the patient is asleep.

Figure 52B:
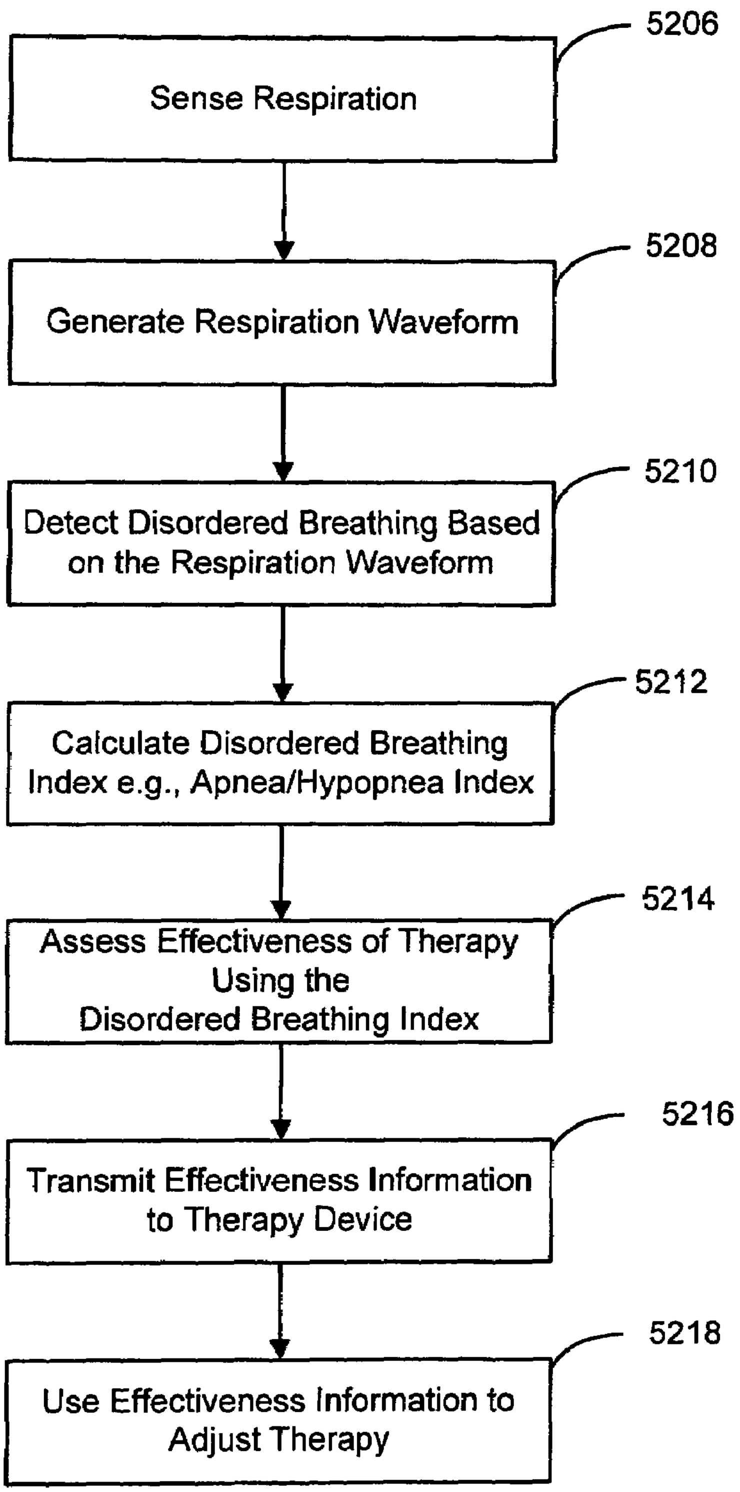

Information acquired by the implantable device based on the sensed conditions may be stored, displayed, printed, trended and/or transmitted from the implantable device to another device, such as a patient-external device, implantable device, therapy device, device programmer, and/or advanced patient management server. Information associated with the monitored parameters, e.g., therapy usage, may be stored, displayed, printed, trended, and/or transmitted from the implantable device to another device FIG. 52B is a flowchart illustrating a method for monitoring the effectiveness of an externally delivered breathing therapy using an implantable device. The patient's respiration is sensed 5206 and a respiration waveform is generated 5208. The sensed respiration waveform is used by the implantable device to detect 5210 disordered breathing events. An apnea/hypopnea index (AHI) is calculated 5212 based on the detected disordered breathing events. The AHI is used to assess the effectiveness 5214 of the breathing treatment. A lower AHI may indicate a more effective breathing treatment than a relatively higher AHI, for example. The therapy effectiveness information may be transmitted 5216 to the external breathing therapy device and/or to an APM server. The therapy effectiveness data may be used 5218 by the external breathing therapy device, or by the APM device, for example, to adjust the external breathing therapy. The therapy adjustment may be performed automatically by the APM or by the external breathing therapy device. The therapy adjustment may be performed manually by the patient's physician based on the effectiveness information.

External breathing therapy may be inconvenient to use and uncomfortable to the patient. As a result, the patient may limit the use of the therapy. For example, if the use of the breathing therapy interferes with the patient's ability to sleep, the patient may stop using the breathing therapy, or may use the breathing therapy infrequently. The patient may not keep track of how frequently he or she uses the breathing therapy and may not be able to accurately report breathing therapy compliance to the physician.

Figure 52C:
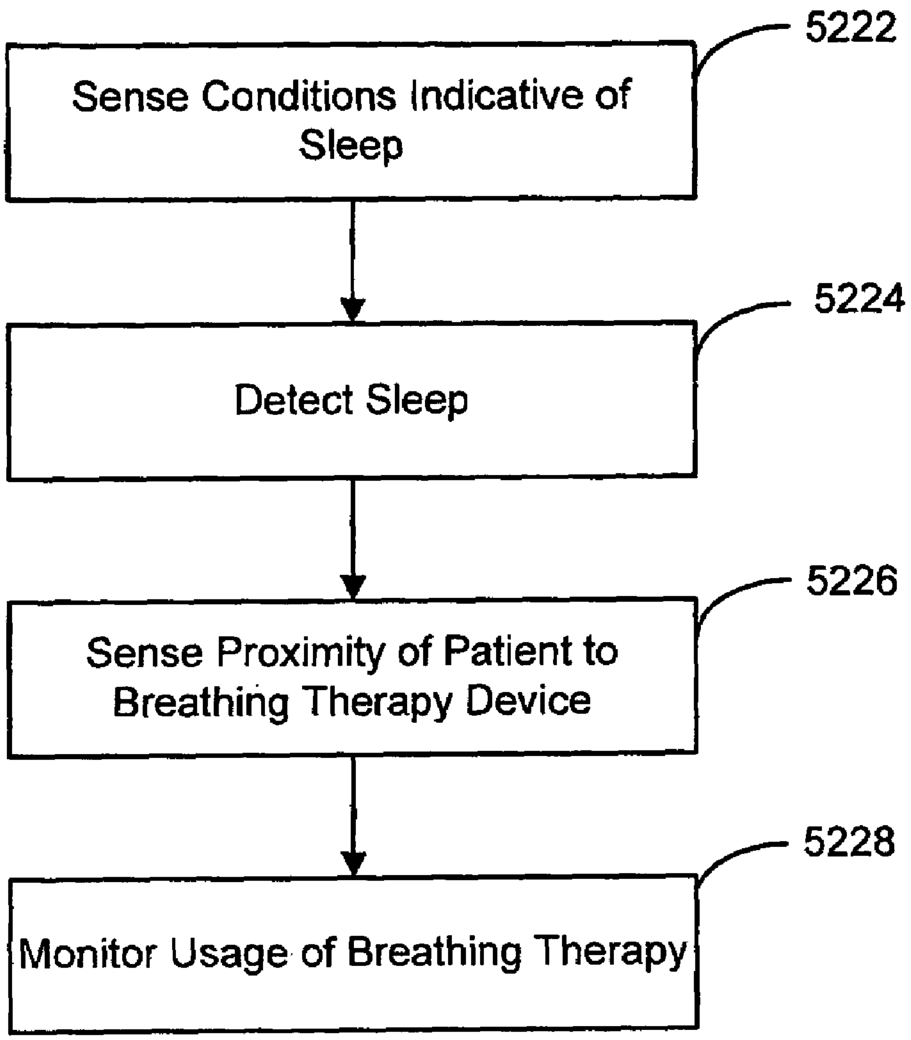

FIG. 52C is a flowchart of a method for implantably monitoring a patient's usage of the external breathing therapy. In this example, usage of an external breathing therapy for sleep disordered breathing is determined based on the patient's proximity to the external breathing therapy device during sleep. As illustrated in FIG. 52C, one or more conditions indicative of sleep may be sensed 5222. The implantable device detects 5224 sleep based on the sensed sleep-related conditions. The proximity of the patient to the external breathing therapy device is sensed 5226.

The proximity of the patient to the external breathing therapy device may be determined using a transmitter coupled to the external breathing therapy device and a receiver in the implantable monitoring device. If the patient is near the external breathing therapy device, the receiver receives a signal broadcast by the transmitter. The transmitter may be located on a bedside unit of the external breathing therapy device, or on the respiratory mask of the external breathing therapy device, for example.

The implantable device monitors 5228 the patient's usage of external breathing therapy based on the proximity of the patient to the external breathing therapy device during sleep. Other methods of determining patient usage of the external breathing therapy device may also be implemented. For example, the morphology of the patient's respiration waveform during external breathing therapy may be detectably different from the patient's respiration waveform when therapy is not being delivered. The implantable device may sense the patient's respiration and monitor usage of the external breathing therapy device based on evaluation of the patient's respiration waveform.

The implantable device may monitor patient compliance with respect to a prescribed breathing therapy. The implantable device may transmit information related to the patient compliance to an external device, such as a patient management device accessible to the patient and/or the patient's physician. The information may be used to alert to the patient and/or to the patient's physician when the patient's compliance with the prescribed breathing therapy drops below a threshold level.

Figure 52D:
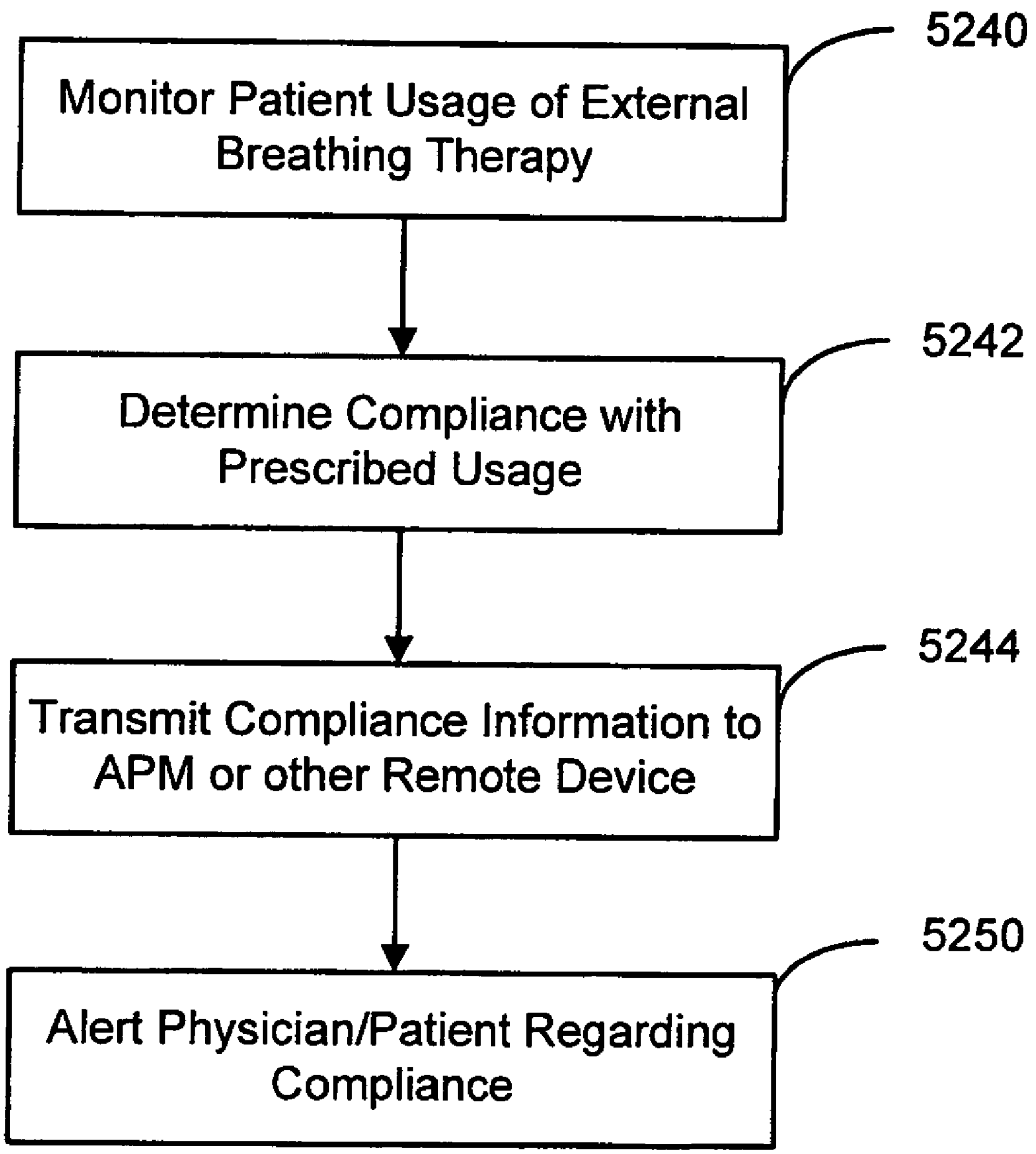

FIG. 52D is a flowchart of a method for implantably monitoring patient compliance with a prescribed breathing therapy in accordance with embodiments of the invention. Breathing therapy is delivered to the patient using a patient external device. The patient's use of externally delivered breathing therapy is monitored 5240 using an implantable device.

In one implementation, the implantable device may monitor patient use of the breathing therapy may by sensing the proximity of the patient to the breathing therapy unit. According to this approach, if the patient is within a selected proximity range of the patient-external breathing therapy unit, then the patient is assumed to be using the breathing therapy.

Figure 52E:
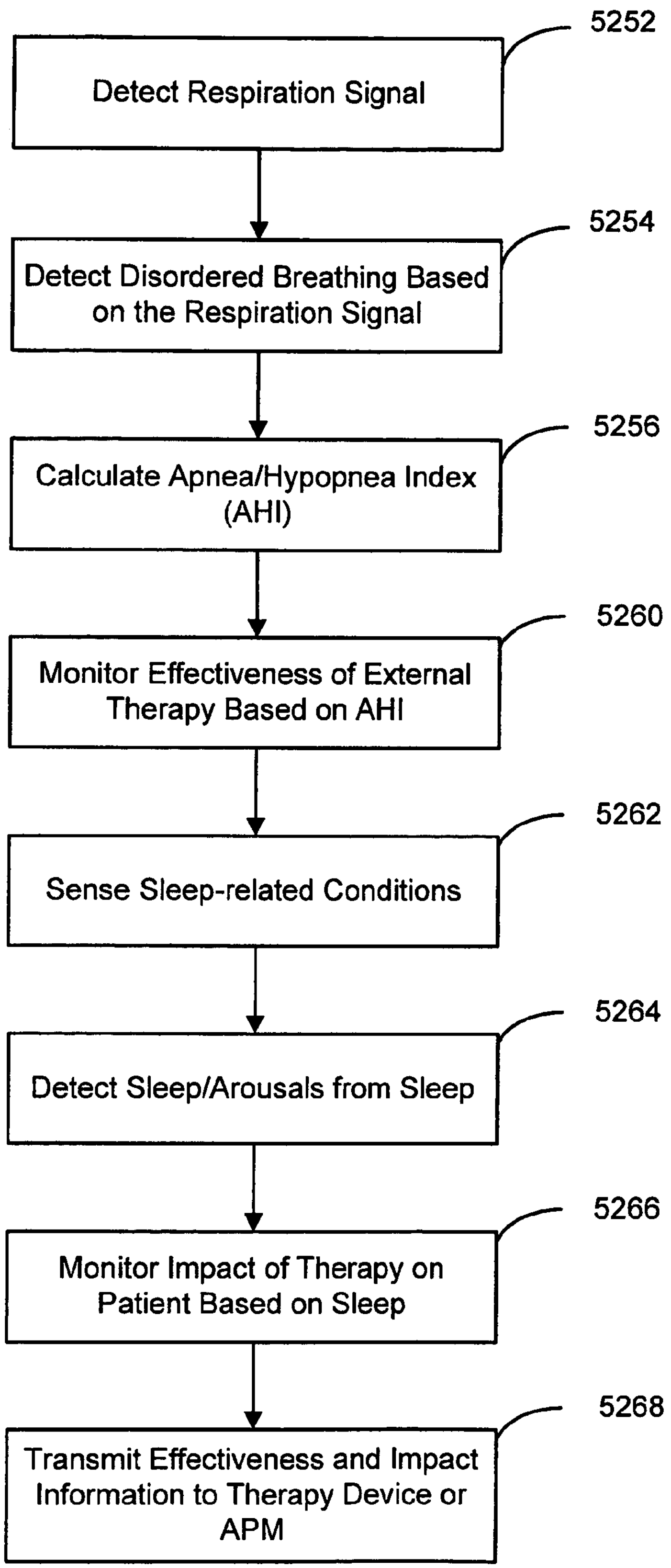
Figure 52F:
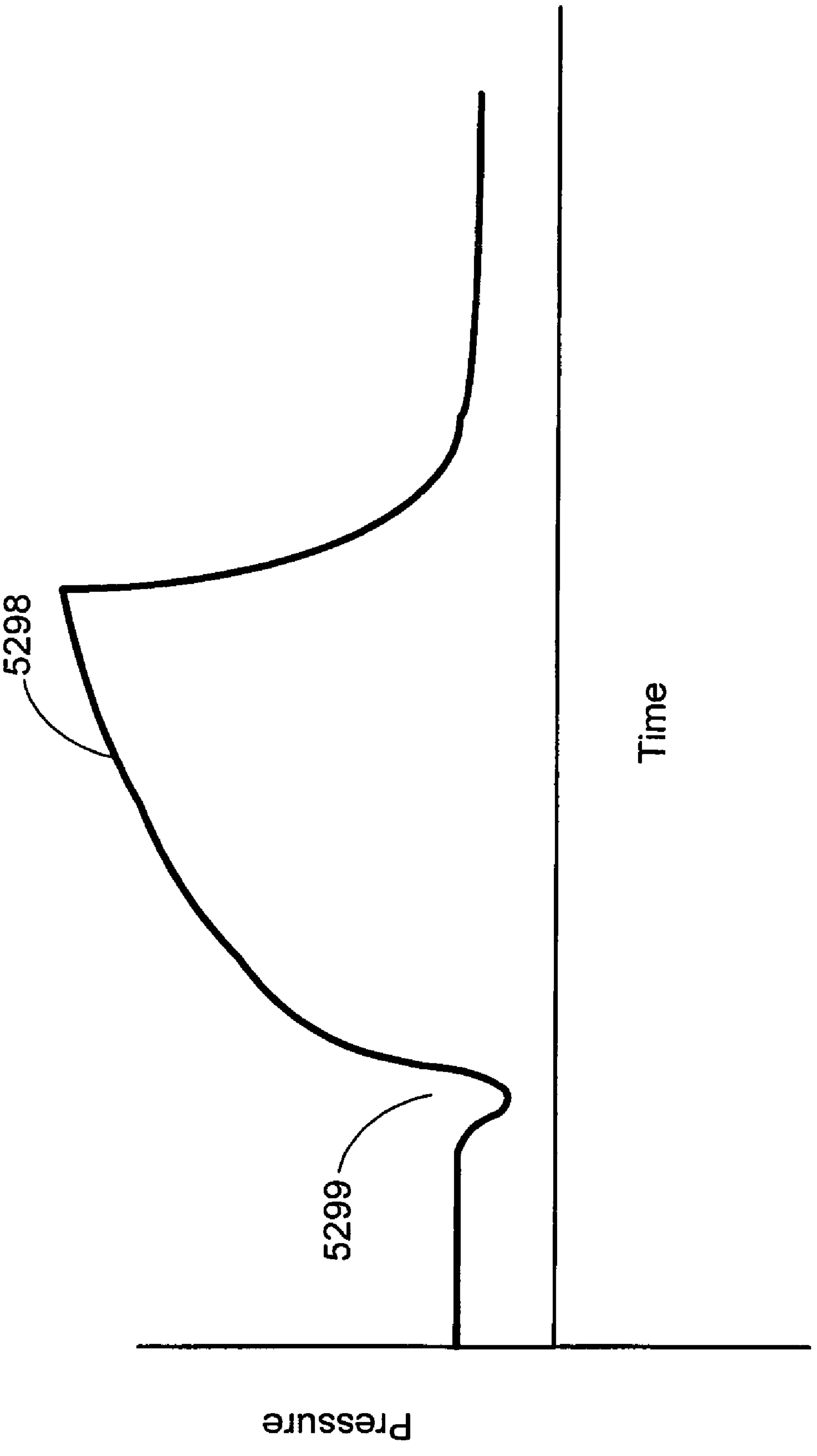
FIG. 52F is a graph of respiratory pressure with respect to time illustrating a respiratory pressure notch observable when a patient is using a breathing therapy device.

Another approach to monitoring patient compliance with breathing therapy involves analyzing the respiratory waveform of the patient. For example, the implantable device may sense the transthoracic impedance of the patient to determine the patient's respiratory waveform. The patient's use of the breathing therapy may be determined by detecting features of the respiratory waveform indicative of breathing therapy usage. In one scenario, use of the breathing therapy may be determined by comparing the morphology of a patient's respiratory waveform during therapy to the morphology of the patient's respiratory waveform without therapy. The patient's respiratory waveforms with and without therapy may be compared to detect features that indicate usage. For example, the patient may be determined to be using the breathing therapy if the patient's respiratory waveform exhibits a pressure notch indicative of flow controlled breathing therapy usage. FIG. 52F illustrates a graph of respiratory pressure 5298 with respect to time. The notch 5299 on the pressure graph indicates that the patient is using the breathing therapy device.

In another example, patient compliance with the prescribed breathing therapy may be determined based on night to night changes in therapy effectiveness. For example, if the therapy effectiveness stays constant or changes slowly over the course of several nights, it may be determined that the patient is using the breathing therapy as prescribed. Usage of the therapy may be determined by using a baseline of therapy effectiveness developed over several nights. If the therapy effectiveness drops significantly from the baseline, then the patient may have stopped using the therapy device.

Returning to FIG. 52D, information related to the patient's use of the breathing therapy may be collected and/or evaluated by the implantable device, including, for example, the times the patient used the breathing therapy, the duration of the usage, the frequency of usage, and/or other information. The patient's compliance with a prescribed breathing therapy may be determined 5242 by comparing the actual use to the prescribed use. In one scenario, the compliance determination may be performed by the implantable device. In another scenario, information related to the patient use of the breathing therapy may be transmitted 5244 to a remote device, such as the breathing therapy device or a patient management device, where the analysis is performed. The patient and/or the patient's physician may be alerted 5250 to the patient's compliance with the breathing therapy. In one scenario, the patient and/or the patient's physician may be alerted if the patient's compliance decreases below a threshold value. The patient may be reminded to use the breathing therapy. If patient compliance is low, the physician and/or the patient may adjust the therapy to increase breathing therapy compliance.

In accordance with one embodiment, the breathing therapy may be implantably monitored for therapy effectiveness and impact to the patient. The flowchart of FIG. 52E illustrates an example method involving the use of a monitoring device configured as a component of an implantable cardiac device to monitor breathing therapy delivered by a continuous positive airway pressure (CPAP) device. In this example, therapy for sleep disordered breathing is delivered to the patient using a continuous positive airway pressure (CPAP) device. The effectiveness of the breathing therapy and the impact of the therapy on the patient are monitored by an implantable cardiac device.

Sensors coupled to the implantable monitoring device sense one or more patient conditions related to therapy effectiveness. For example, the respiration of the patient may be sensed 5252 and the monitoring device may detect 5254 disordered breathing episodes based on the respiration signal. The monitoring device may monitor therapy effectiveness by monitoring the severity, frequency and/or duration of sleep disordered breathing episodes experienced by the patient. In one implementation, the monitoring device may calculate 5256 an apnea/hypopnea index (AHI) and/or a percent time in periodic breathing (% PB) indicative of the frequency of disordered breathing episodes. The effectiveness of the CPAP therapy may be monitored 5260 based on the calculated indices. If the AHI and/or % PB are relatively low, the breathing therapy may be determined to be effective.

A CPAP device typically includes a respiratory mask, e.g., a nasal or facial mask, worn by the patient to facilitate delivery of air or other gas to the patient's airway. The respiratory mask may be inconvenient and/or uncomfortable for the patient to wear and may keep the patient awake. Further, delivery of positive airway pressure may disturb the patient, inhibit sleep, and/or cause the patient to arouse frequently. Sleep disturbances may be more frequent and/or severe if the CPAP therapy pressure is too high. Information about these side effects of the breathing therapy may be helpful in tailoring a therapy regimen for the patient. The monitoring device may monitor the impact of the CPAP therapy on the patient based on one or more sensed conditions indicative of the impact of the therapy on the patient.

In one example, the one or more sensed conditions 5262 relate to sleep and may be used to detect 5264 sleep and/or arousals from sleep. The monitoring unit implemented in an implantable cardiac device may monitor 5266 the impact of the CPAP therapy on the patient by monitoring the patient's sleep. For example, the monitoring unit may monitor the total time the patient spends sleeping, the number of arousals experienced by the patient in one night, and/or the depth of the arousals. In one implementation the cardiac device may calculate the number of arousals experienced by the patient per hour (A/h).

The therapy effectiveness and impact information may be transmitted 5268 to the CPAP device and/or an APM server. The information may be used to automatically or manually adjust the therapy delivered to the patient. For example, if the AHI is high, the breathing therapy pressure may be adjusted upward to provide a more effective therapy. If the patient experiences an arousal rate, e.g., A/h, greater than a threshold without experiencing sleep disordered breathing episodes, the therapy may be determined to be too aggressive. The breathing therapy pressure may be adjusted downward to provide a disordered breathing therapy that is more comfortable to the patient and allows the patient to sleep with fewer interruptions.

Feedback System for Sleep Disordered Breathing Therapy

Aspects of the invention that include disordered breathing therapy feedback are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving a feedback system for disordered breathing therapy are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

One embodiment of the invention involves an individual system 123 (FIG. 1B) for developing feedback using monitored conditions for controlling sleep disordered breathing therapy. The sleep disordered breathing therapy feedback system 123 may be implemented as a stand alone system or in combination with other individual medical systems, such as those described in FIGS. 1B-1D.

Various embodiments of present invention involve methods and systems for developing and providing feedback information for sleep disordered breathing therapy. In accordance with one embodiment, a method of controlling sleep disordered breathing therapy includes monitoring one or more patient conditions using a monitoring device having circuitry disposed within an implantable housing. Feedback information for controlling sleep disordered breathing therapy is developed based on the one or more monitored conditions. The feedback information is provided to a device delivering therapy to treat sleep disordered breathing. The housing of the therapy device is separate from the implantable housing of the monitoring device.

In accordance with another embodiment of the invention, a method of adjusting sleep disordered breathing therapy includes monitoring one or more patient conditions using a monitoring device having circuitry disposed within an implantable housing. Feedback information for controlling sleep disordered breathing therapy is developed based on the one or more monitored conditions. The feedback information is provided to a device delivering therapy to treat sleep disordered breathing. The housing of the therapy device is separate from the implantable housing of the monitoring device. The sleep disordered breathing therapy is adjusted using the feedback information.

Yet another embodiment of the invention involves a medical system for controlling sleep disordered breathing therapy. The medical system includes a monitoring unit having components disposed within an implantable housing. The monitoring unit is configured to monitor one or more patient conditions. A processor is coupled to the monitoring unit. The processor is configured to provide feedback information related to sleep disordered breathing therapy delivered to a patient based on the one or more monitored conditions. Components of a therapy device delivering the disordered breathing therapy are disposed within a therapy device housing. The therapy device housing is separate from the implantable housing of the monitoring device.

A further embodiment of the invention involves a medical system for providing sleep disordered breathing therapy. The medical system includes a monitoring unit having components disposed within an implantable housing. The monitoring unit configured to monitor one or more patient conditions. The system also includes a therapy device having components disposed within a housing that is separate from the implantable housing of the monitoring device. The therapy device is configured to deliver sleep disordered breathing therapy. A processor is coupled to the monitoring unit and the therapy device. The processor is configured to provide feedback information related to the sleep disordered breathing therapy based on the one or more patient conditions.

Another embodiment of the invention involves a system for providing coordinated patient monitoring, diagnosis and/or therapy system that utilizes feedback of sensed conditions for controlling sleep disordered breathing therapy. The coordinated system includes, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a system 123 configured to develop feedback based on sensed conditions associated with disordered breathing therapy. The disordered breathing therapy feedback system 123 includes a monitoring unit having components disposed within an implantable housing, the monitoring unit configured to monitor one or more patient conditions, and a processor coupled to the monitoring unit. The processor is configured to provide feedback information related to sleep disordered breathing therapy delivered to a patient based on the one or more monitored conditions, wherein components of a therapy device delivering the disordered breathing therapy are disposed within a therapy device housing and the therapy device housing is separate from the implantable housing of the monitoring device.

The implantable and respiratory therapy devices 181, 184 may operate cooperatively based on system 123 feedback information from delivered respiratory therapy. For example, system 123 feedback information from delivered respiratory therapy may allow the implantable and respiratory therapy devices 181, 184 to operate cooperatively to adjust sleep disordered breathing therapy. Systems and methods directed to feedback for sleep disordered breathing therapy may be implemented to include selected features, functions, and/or structures described in commonly owned, U.S. Pat. No. 7,469,697, which is hereby incorporated herein by reference.

Sleep disordered breathing disorders may be more effectively monitored and/or treated using a coordinated approach. Various embodiments of the invention are implemented using medical systems employing two or more patient-external and/or patient-internal medical devices. The medical devices may communicate or otherwise operate in concert to provide more comprehensive patient monitoring for disordered breathing.

Embodiments of the invention are directed to methods and systems utilizing an implantable device to monitor conditions associated with sleep disordered breathing. Feedback for controlling sleep disordered breathing therapy is provided based on the monitored conditions. Various types of therapy have been used to treat sleep disordered breathing. Positive airway pressure devices, e.g., continuous positive airway pressure (CPAP) devices are among the most frequently used mechanical respiration therapy devices employed for treating sleep disordered breathing. Sleep disordered breathing has also been treated using muscle and/or nerve stimulation therapy. For example, a treatment for obstructive sleep apnea involves compensating for the decreased muscle activity by electrical activation of the tongue muscles. The hypoglossal (HG) nerve innervates the protrusor and retractor tongue muscles. In one approach, an appropriately applied electrical stimulation to the hypoglossal nerve, for example, may prevent backward movement of the tongue, thus preventing the tongue from obstructing the airway.

Central sleep apnea may also be treated by phrenic nerve pacing, also referred to as diaphragmatic pacing. Phrenic nerve pacing uses an electrode implanted in the chest to stimulate the phrenic nerve. The phrenic nerve is generally known as the motor nerve of the diaphragm. It runs through the thorax, along the heart, and then to the diaphragm. Diaphragmatic pacing involves the use of electronic stimulation of the phrenic nerve to control the patient's diaphragm and induce a respiratory cycle. Pacing the phrenic nerve may be accomplished by surgically placing a nerve cuff on the phrenic nerve, and then delivering an electric stimulus. The electric stimulus of the phrenic nerve then causes the diaphragm to induce a respiratory cycle.

Recently, cardiac pacing therapy has been used as a therapy for disordered breathing. Cardiac pacing therapy may be implemented using an implanted electrical pulse generator coupled to endocardiac leads inserted into one or more heart chambers. Cardiac pacing for sleep disordered breathing treatment may include pacing one or more heart chambers, and may involve pacing at a rate above a lower rate limit during sleep and/or during episodes of disordered breathing, for example.

Drug therapy may also be used to treat disordered breathing. Drugs may be delivered to the patient through one or more automatically controllable drug delivery devices, e.g., a drug pump, a controllable nebulizer, or an electrically activated drug patch, for example.

Figure 53:
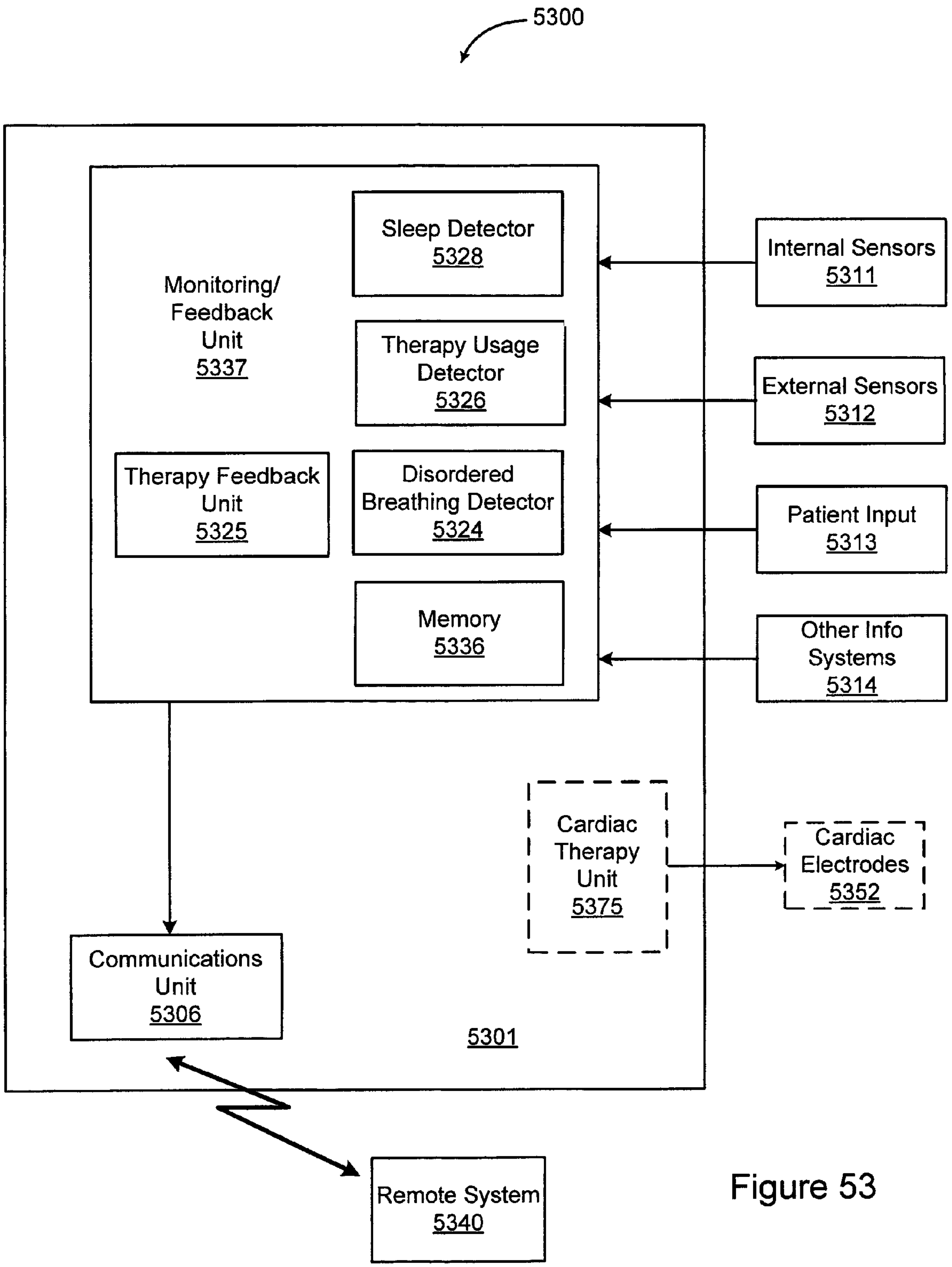
FIG. 53 is a block diagram of an implantable medical device including a cardiac therapy pulse generator that may be used to monitor patient conditions in accordance with embodiments of the invention.

The block diagram of FIG. 53 illustrates an example of medical system 5300 including a fully or partially implantable device 5301 that may be used to monitor patient conditions and to develop feedback information for a device delivering sleep disordered breathing therapy in accordance with embodiments of the invention. The medical device 5301 that may be coupled to an array of data acquisition devices, including patient-internal sensors 5311, patient-external sensors 5312, patient input devices 5313, and/or other information systems 5314 as described in more detail above.

Patient conditions monitored by the implantable device may include both physiological and non-physiological contextual conditions affecting the patient. Table 1 above provides a representative set of patient conditions that may be monitored by the device 5301 in accordance with embodiments of the invention. Table 1 also provides illustrative sensing methods that may be employed to sense the conditions. It will be appreciated that patient conditions and detection methods other than those listed in Table 1 may be used and are considered to be within the scope of the invention.

The implantable device 5301 of FIG. 53 includes monitoring circuitry 5337 for processing signals received from the sensors, 5311, 5312, patient input devices 5313, and/or other information system 5314. The monitoring circuitry 5337 may include one or more a detection units 5324, 5326, 5328 that detect the occurrence of various physiological events. For example, the circuitry 5327 may include one or more of a disordered breathing detector 5324, a sleep detector 5328, and/or a therapy usage detector 5326. Other event detection components may also be included. The monitoring circuitry 5327 may be used to calculate various indices, e.g., AHI, % PB, and/or arousals per unit time, used for evaluating therapy efficacy, and/or therapy impact. The monitoring circuitry 5327 may compare the patient's therapy usage to a prescribed therapy to determine therapy compliance. The monitoring circuitry 5327 communicates with a therapy feedback unit 5325 that develops feedback information based on the monitored conditions, the detected events, and/or the calculated indices.

In one exemplary implementation, the disordered breathing detector 5324 may be coupled to a respiration sensor. The disordered breathing detector 5324 may use the respiration signal developed by the respiration sensor to detect disordered breathing events based on the inspiratory and expiratory phases of the patient's respiration cycles, for example. The sleep detector 5328 may analyze various inputs from the patient-internal sensors 5311, patient-external sensors 5312, patient input devices 5313, other information systems 5314 to detect sleep-related events, including, for example, sleep onset, sleep offset, sleep stages, and arousals from sleep.

The monitoring circuitry 5327 includes a memory 5336 for storing information derived from signals produced by the patient-internal sensors 5311, patient-external sensors 5312, patient input devices 5313, and/or other information systems 5314. The memory 5336 may also store information about detected events, e.g., sleep and disordered breathing events, and/or information related to calculated indices characterizing various events such as sleep and/or disordered breathing events. The stored data may be transferred to the feedback unit 5325 and used to develop feedback information to control disordered breathing therapy. The stored data may be retrieved by another component of the medical device 5301 for later use, or may be transmitted to a separate device 5340 for storage, further processing, trending, analysis and/or display, for example. In one scenario, the stored data can be downloaded to a separate device periodically or on command. The stored data may be presented to the patient's health care professional on a real-time basis, or as a long-term, e.g., month long or year long, trend of daily measurements.

The medical device 5301 may optionally include a therapy unit. In some examples described herein, the medical device 5301 comprises a cardiac therapy device configured to deliver cardiac electrical stimulation therapy using a cardiac pulse generator 5375 and electrical stimulation electrodes 5352.

The medical device 5301 may further include a communications unit 5306 that controls communications between the medical device 5301 and other devices or systems. For example, the communications unit 5306 may be used to provide wireless or wired communications links between the medical device 5301 and one or more of the patient-internal sensors 5311, patient-external sensors 5312, patient input devices 5313, and information systems 5314.

The communications unit 5306 may also facilitate communications between the medical device 5301 and a remote device 5340 such as the sleep disordered breathing therapy device, a programmer, and/or an APM system. The wireless connections coupling the medical device 5301 to various other devices and systems may utilize a variety of wireless protocols, including, for example, Bluetooth, IEEE 802.11, and/or a proprietary wireless protocol.

Detecting the onset, termination, duration, stages, and quality of sleep experienced by a patient may be employed in connection with monitoring patient conditions and providing feedback for sleep disordered breathing therapy. Patients suffering from sleep apnea, or other types of sleep disordered breathing, may be treated with for sleep disordered breathing only during periods of sleep. Monitoring patient conditions and/or development of feedback information may involve determining if the patient is asleep and/or detecting various sleep-related processes, such as arousals from sleep and/or REM or non-REM sleep stages.

In addition, patient sleep may be monitored and information associated with patient sleep may be used to assess an impact of breathing therapy on the patient. Therapy impact data may be used to develop feedback information used to adjust the therapy. The implantable monitoring device 5301 may include a sleep detector 5328 for detecting when the patient is asleep and various stages and/or processes of sleep. Various methods of sleep detection implementable in an implanted device involve sensing one or more conditions indicative of sleep. The sleep-related conditions may be compared to a threshold to determine if the patient is asleep.

The sleep-related conditions may be sensed or derived using patient-external or implantable sensors and analyzed by a sleep detector of the implantable monitoring device or by circuitry within the APM communication unit (i.e., a supervisor device that co-ordinates diagnostics between various sensors. For example, sleep detection may be implemented in an implantable cardiac rhythm management system configured as a pacemaker/defibrillator or an ITCS device.

Sleep detection may involve sensing one or more conditions indicative of sleep. A representative set of sleep-related conditions include body movement, heart rate, QT interval, eye movement, respiration rate, transthoracic impedance, tidal volume, minute ventilation, body posture, brain activity, cardiac activity, muscle tone, body temperature, time of day, historical sleep times, blood pressure, and blood gas concentration, proximity to bed, for example.

Sleep may be detected by comparing levels of the one or more sleep-related conditions to one or more sleep thresholds. For example, sleep may be detected by monitoring the patient's heart rate. When the patient's heart rate decreases below a sleep threshold, the patient may be determined to be asleep. Sleep may also be detected by monitoring the patient's activity. If the patient's activity decreases below a sleep threshold, then the patient may be determined to be asleep. Another method of detecting sleep involves monitoring the patient's minute ventilation. If the patient's minute ventilation falls below a sleep threshold, then the patient may be determined to be asleep.

Sleep may be detected by comparing multiple sleep-related conditions to multiple thresholds. For example, the patient may be determined to be asleep if the patient's activity, sensed by an accelerometer, falls below an activity sleep threshold and the patient's heart rate, sensed by cardiac electrodes, falls below a heart rate sleep threshold.

Sleep may also be detected using one sleep-related condition to modify the sleep threshold of another sleep-related condition. A first sleep-related condition may be sensed. The level of the sleep-related condition may be compared to a sleep threshold to determine the onset and termination of sleep. A second sleep-related condition may be used to adjust the sleep threshold. Additional sleep-related conditions may optionally be sensed to confirm the onset or termination of the sleep condition.

A sleep detector 5328 (FIG. 53) may be configured to compare the levels of one or more sleep-related conditions to one or more thresholds. In one implementation, the one sleep related condition may be compared to a sleep threshold or other index to detect sleep. In another implementation, multiple sleep-related conditions may be compared to multiple thresholds or indices. In a further implementation, one or more of the sleep-related conditions may be used to adjust the sleep thresholds or indices. Furthermore, the onset or termination of sleep may be confirmed using an additional number of sleep-related conditions.

The sleep-related conditions may be sensed using implantable sensors and/or patient-external sensors, for example. In one embodiment, patient activity may be compared to a sleep threshold to determine when the patient is asleep. A low level of activity is indicative that the patient is sleeping. Patient activity may be sensed, for example, using an accelerometer positioned on or in the housing of an implantable cardiac device, or in another convenient location. The accelerometer signal may be correlated with activity level or workload.

A second sleep-related condition may be used to adjust the sleep threshold. In one embodiment, the patient's minute ventilation is used to adjust the sleep threshold. The patient's respiration may be sensed using a transthoracic impedance sensor. Transthoracic impedance may be used to derive various parameters associated with respiration, including, for example, tidal volume and/or minute ventilation. A transthoracic impedance sensor may be integrated into an implantable cardiac device with intracardiac electrodes, for example. Impedance driver circuitry generates a current that flows through the blood between the impedance drive electrode and a can electrode on the housing of the cardiac device. The voltage at an impedance sense electrode relative to the can electrode changes as the transthoracic impedance changes.

Figure 54A:
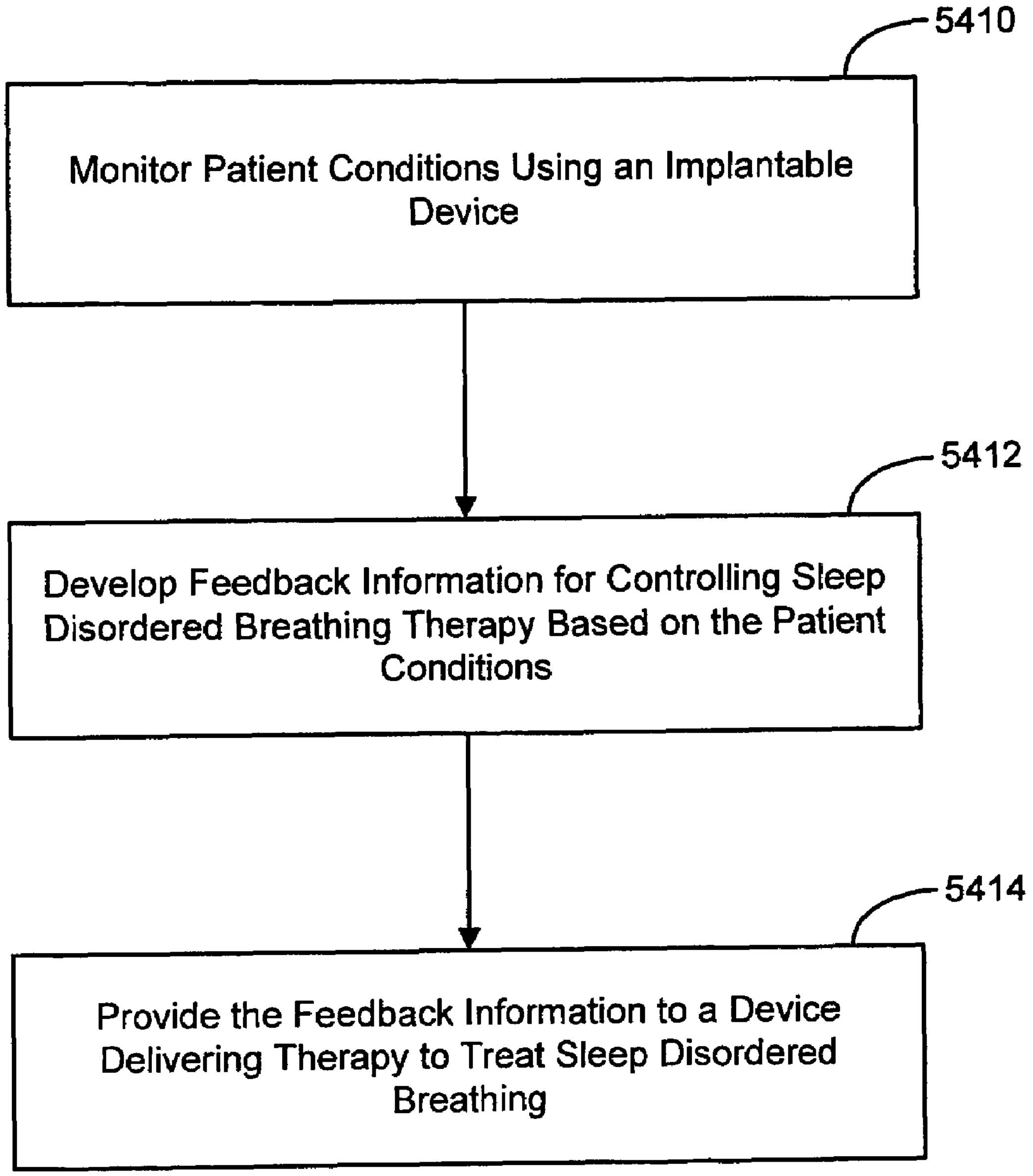
FIGS. 54A-54F are flowcharts illustrating methods that involve implantably monitoring patient conditions to develop feedback control information for sleep disordered breathing therapy in accordance with embodiments of the invention.
Figure 54B:
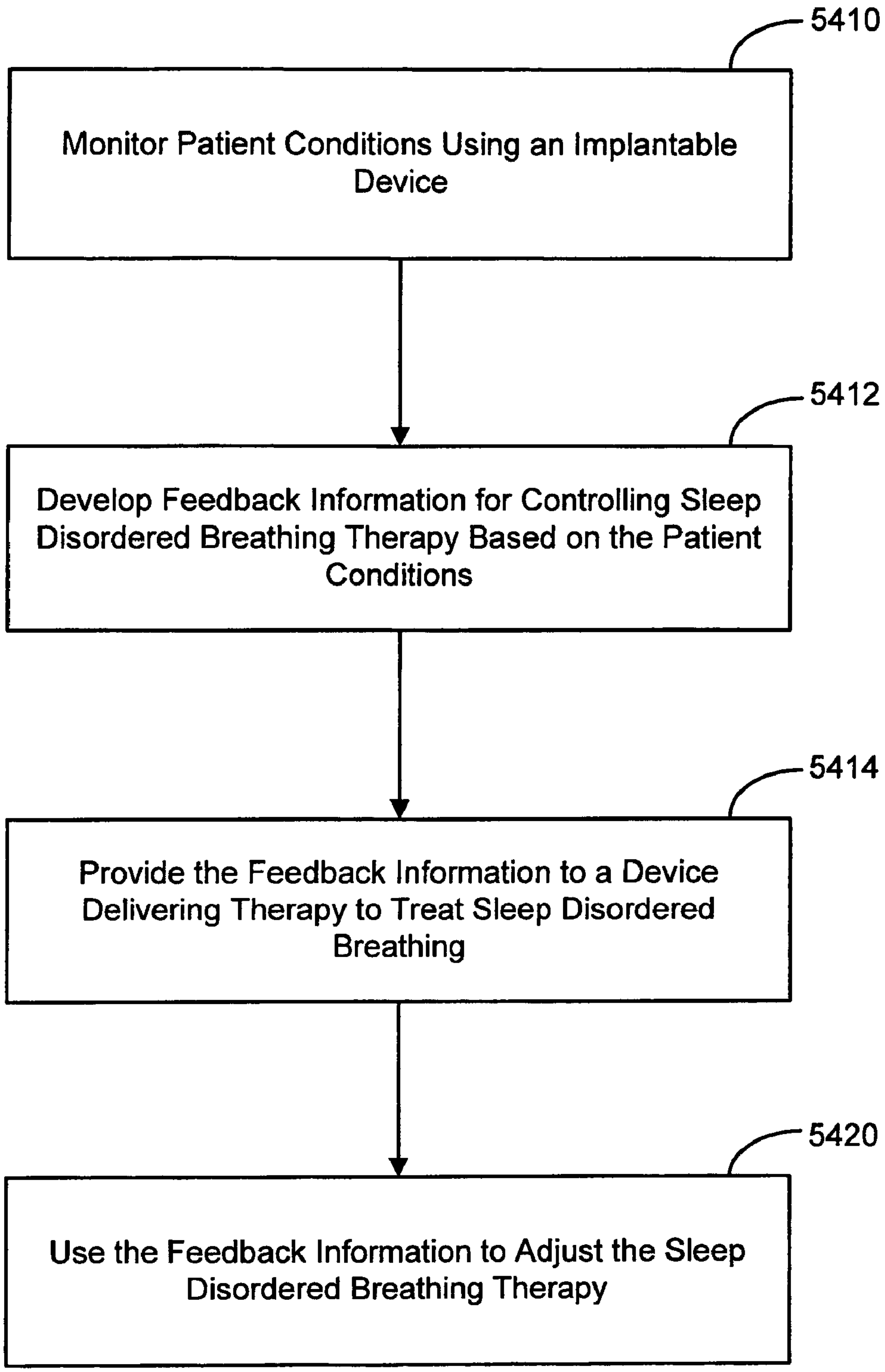

As illustrated in the flowchart of FIGS. 54A and 54B, embodiments of the invention are directed to monitoring 5410 one or more patient conditions using an implantable monitoring device. Feedback information is developed 5412 based on the monitored conditions. The feedback information is provided 5414 to a device delivering therapy to treat sleep disordered breathing. The monitoring device and the therapy device have separate housings. Components of the monitoring device are disposed within an implantable housing. The therapy device may comprise a housing that is implantable or patient-external. The feedback information may be used to adjust 5420 (FIG. 54B) the sleep disordered breathing therapy. The feedback information may comprise control signals indicating the sleep disordered breathing therapy should be initiated, modified, or terminated.

In one implementation, the feedback control signals are provided to the therapy device by the monitoring unit. Therapy adjustment based on the feedback information is made automatically by the therapy device. In other implementations, information related to the monitored conditions is transmitted from the monitoring device to a physician or medical decision network.

In one scenario, the medical decision network may develop the feedback control signals and transmit the feedback control signals to the therapy device. In another scenario, a physician may determine the feedback adjustments to be made to the therapy and may operate a programmer or other device to transfer the feedback control information to the therapy device.

In various implementations, the implantable device may monitor one or more patient conditions indicative of the severity of sleep disordered breathing events, the effectiveness of the sleep disordered breathing therapy, and/or the impact of the therapy on the patient. The implantable device may monitor conditions indicative of interactions between the sleep disordered breathing therapy and other therapies delivered to the patient. Based on the monitored conditions, feedback information is provided to the therapy device. The feedback information may be used to adjust the therapy to enhance therapy effectiveness, to reduce an impact of the therapy, to avoid or reduce therapy interactions, and/or to accomplish other therapeutic goals.

In one embodiment, the implantable device may develop the feedback information and transmit the feedback information directly to the sleep disordered breathing therapy device. The feedback information may be used by the therapy device to automatically adjust the therapy delivered to the patient. In another embodiment, both the implantable monitoring device and the therapy device may be communicatively coupled to a separate medical device, such as a device programmer or patient management system.

In one approach, the implantable device may transmit information about the sensed patient conditions to the separate medical device. The separate medical device may develop the feedback information. The feedback information and/or information related to the monitored conditions may be printed, displayed and/or stored. The feedback information may be used to manually or automatically adjust the sleep disordered breathing therapy. For example, the separate medical device may transmit the feedback information to the therapy device. The feedback information may be used by the therapy device to automatically adjust the sleep disordered breathing therapy.

In another approach, the feedback information may be developed by the monitoring device based on the sensed conditions. The feedback information may be transmitted from the monitoring device to the therapy device through the separate medical device. The feedback information may be used by the therapy device to automatically adjust the sleep disordered breathing therapy.

Figure 54C:
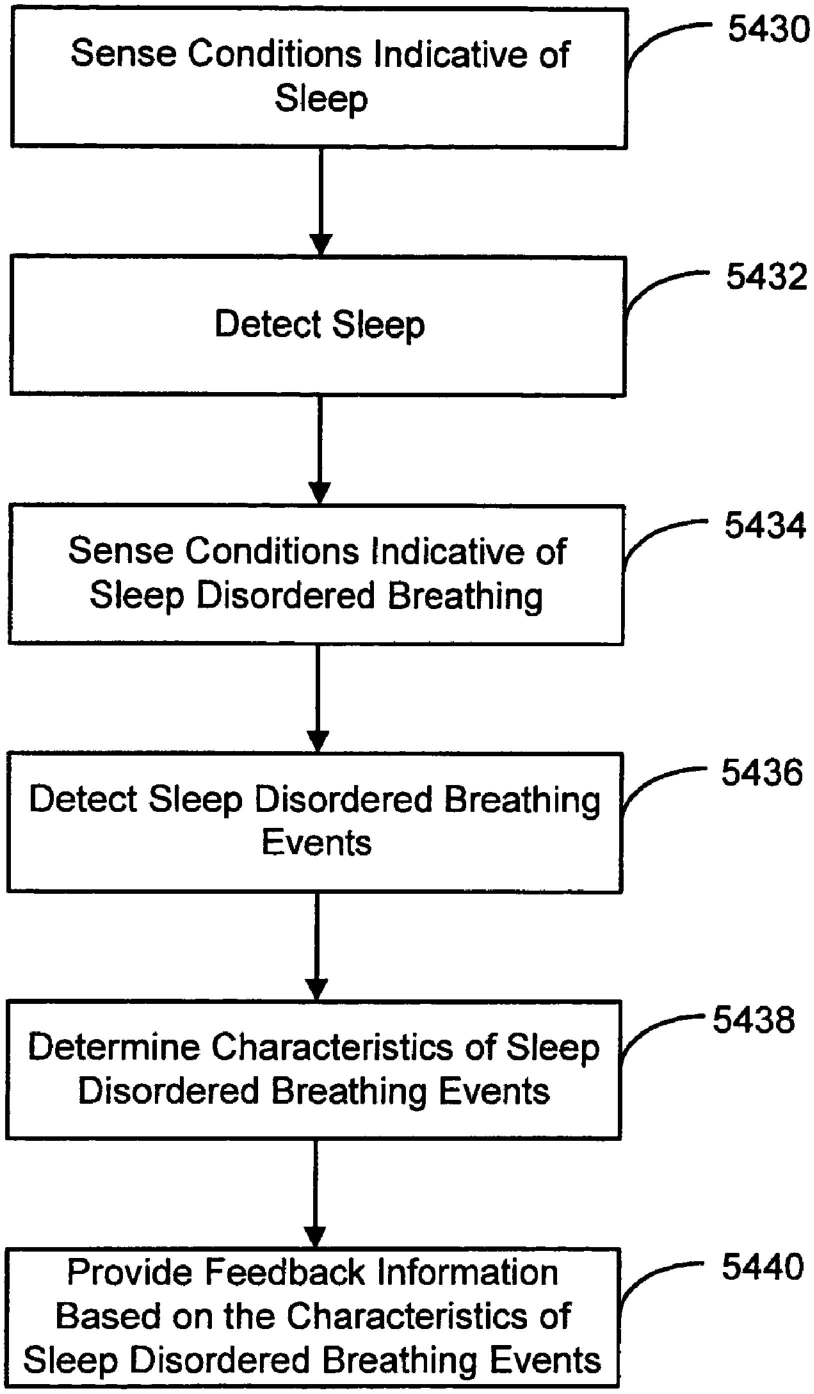

The flowchart of FIG. 54C illustrates a method of providing feedback information in accordance with an embodiment of the invention. The monitoring device senses 5430 one or more patient conditions associated with sleep. Sleep is detected 5432 based on the sleep-related conditions. The monitoring device senses 5434 one or more conditions associated with disordered breathing during sleep. One or more disordered breathing events occurring during sleep are detected 5436. Characteristics of the sleep disordered breathing events, such as, severity, frequency, and/or duration, may be determined 5438. Determination of the one or more characteristics of the sleep disordered breathing events may involve calculation of one or more indices characterizing the disordered breathing events. The indices may include, for example, an apnea/hypopnea index (AHI) and/or a percent time in periodic breathing (% PB), among other indices. Feedback information is provided 5440 to a device delivering therapy for sleep disordered breathing based on the one or more characteristics of the sleep disordered breathing events.

Figure 54D:
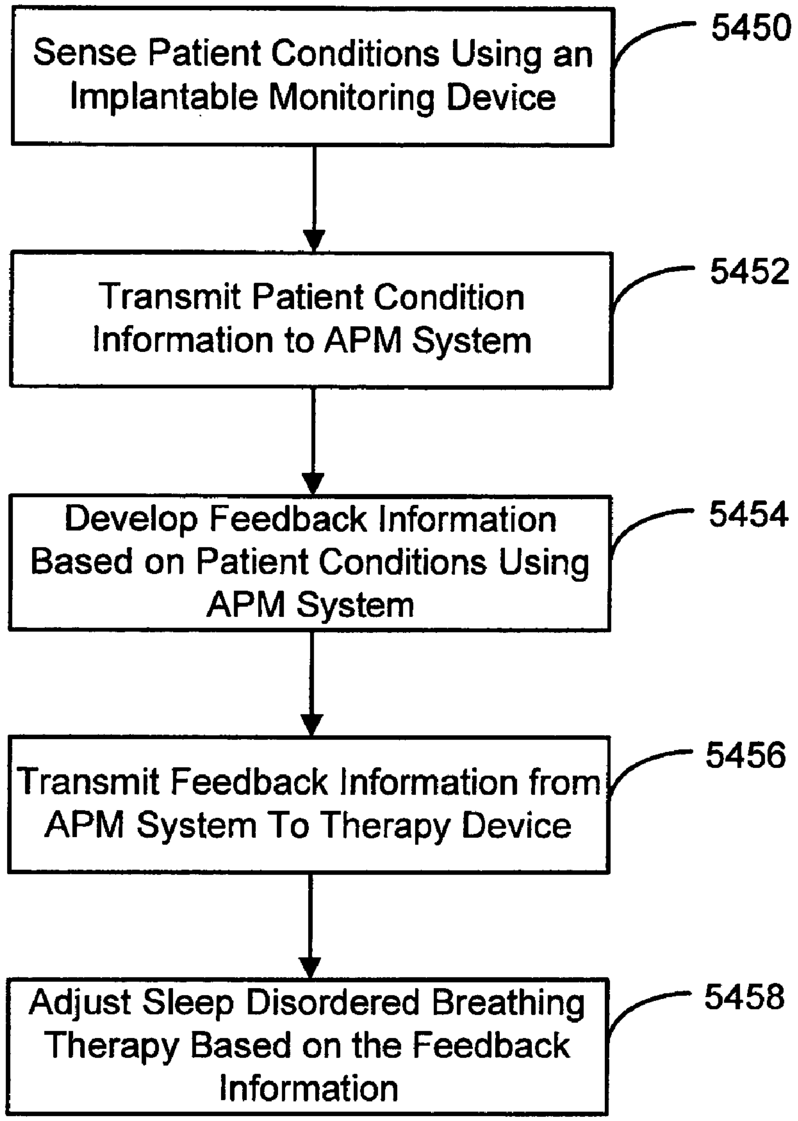

Another embodiment of the invention is illustrated in the flowchart of FIG. 54D. According to this method, one or more patient conditions are sensed 5450 using the implantable monitoring device. Information related to the patient conditions is transmitted 5452 to an advanced patient management (APM) system.

Feedback information based on the patient conditions is developed 5454 using the APM system. The feedback information is transmitted 5456 from the APM system to a therapy device delivering therapy for sleep disordered breathing. The sleep disordered breathing therapy is adjusted 5458 based on the feedback information.

Figure 54E:
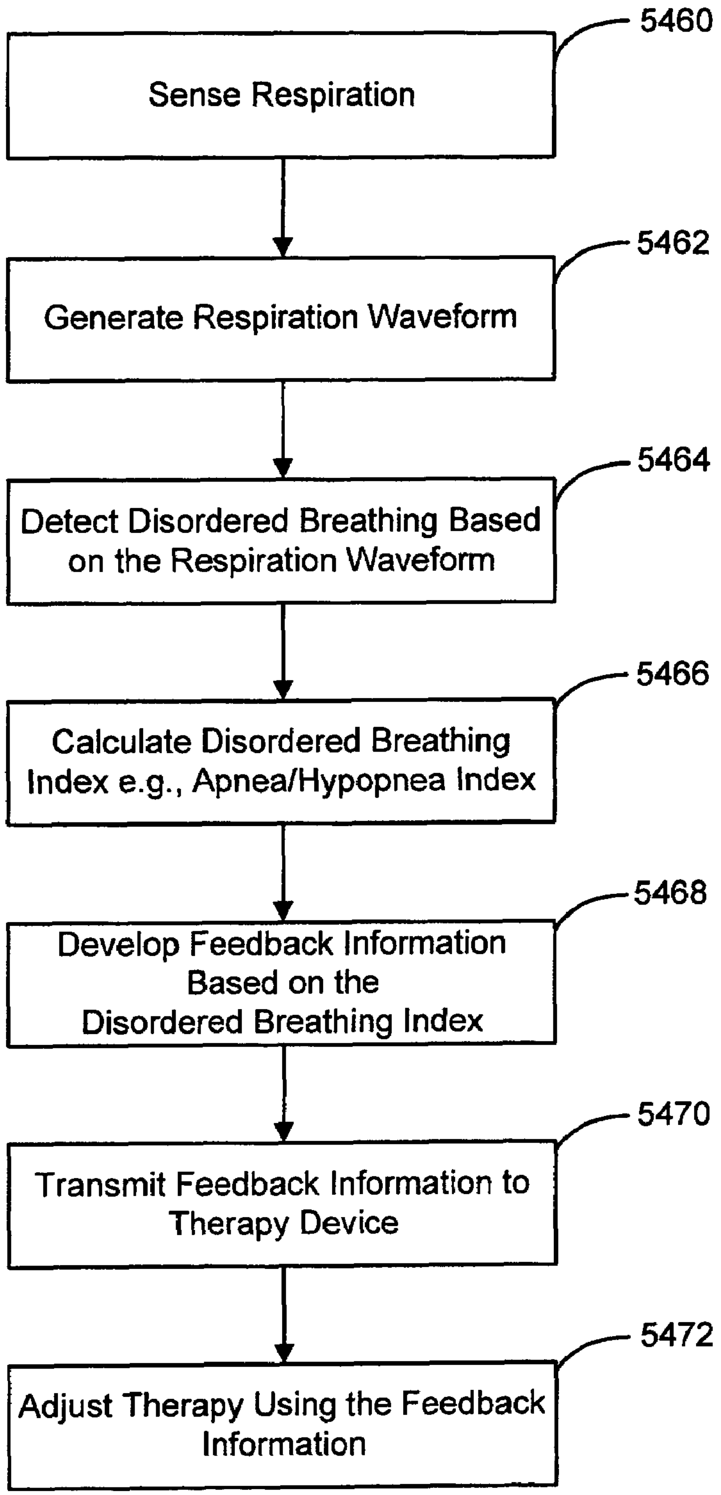

FIG. 54E is a flowchart illustrating a method for providing sleep disordered breathing therapy feedback information based on an effectiveness of the sleep disordered breathing therapy. The patient's respiration is sensed 5460 and a respiration waveform is generated 5462. The sensed respiration waveform is used to detect 5464 disordered breathing events.

An apnea/hypopnea index (AHI) is calculated 5466 based on the detected disordered breathing events. The AHI is used to assess the effectiveness 5468 of the sleep disordered breathing therapy. A lower AHI indicates more effective breathing treatment than a relatively higher AHI, for example. Feedback information is developed 5468 based on the disordered breathing index. The feedback information is transmitted 5470 to the therapy device. The therapy device uses the feedback information to adjust 5472 the sleep disordered breathing therapy.

Figure 54F:
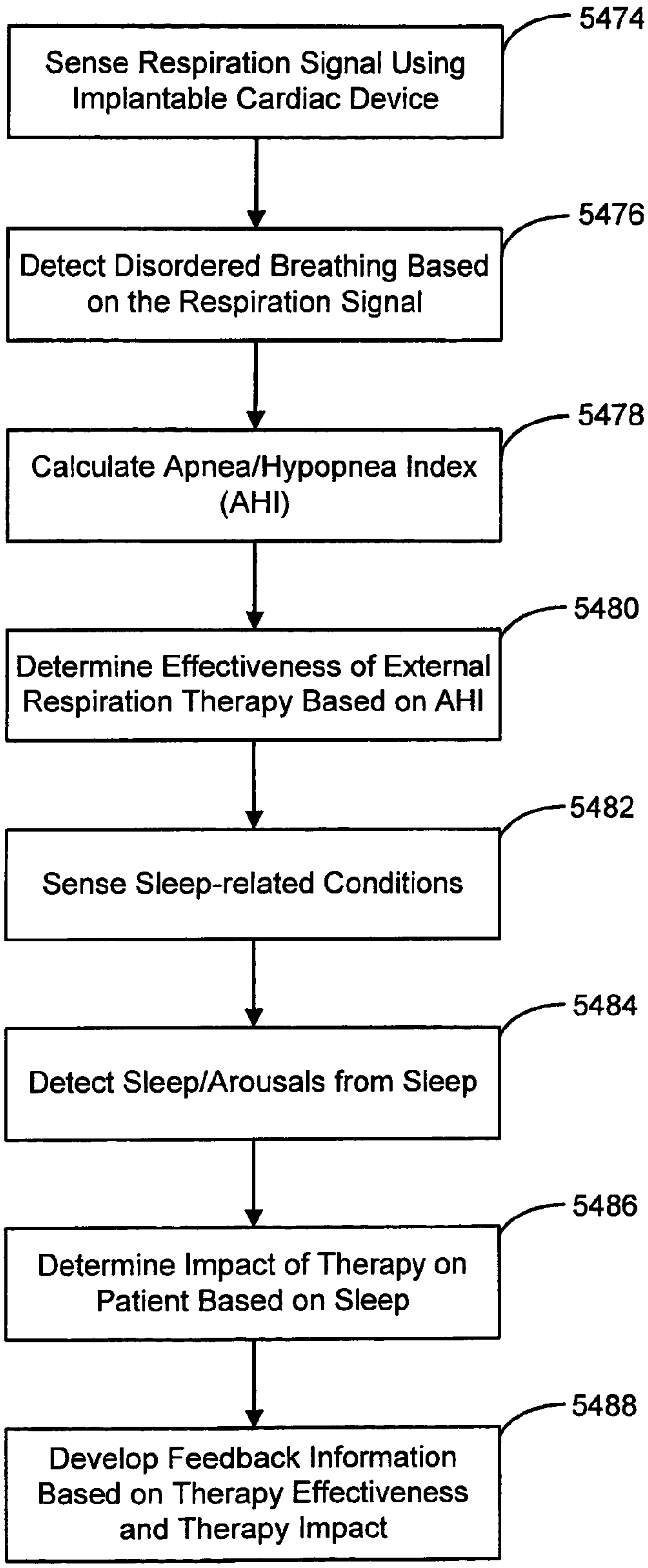

In accordance with one embodiment, feedback for the sleep breathing therapy may be based on therapy effectiveness and impact to the patient. The flowchart of FIG. 54F illustrates an example method that may involve the use of circuitry disposed within the housing of an implantable cardiac rhythm management (CRM) device to monitor breathing therapy delivered by an external breathing therapy device. In one example, therapy for sleep disordered breathing is delivered to the patient using a continuous positive airway pressure (CPAP) device. The effectiveness of the breathing therapy and the impact of the therapy on the patient are monitored by an implantable CRM device.

Sensors coupled to monitoring circuitry disposed within the cardiac device housing may sense one or more patient conditions related to therapy effectiveness. For example, a condition modulated by patient respiration may be sensed and a respiration waveform signal generated 5474. Monitoring circuitry disposed within the housing of the cardiac device may detect 5476 disordered breathing episodes based on the respiration signal. The monitoring circuitry may determine therapy effectiveness based on the severity, frequency and/or duration of sleep disordered breathing episodes experienced by the patient. In one implementation, the monitoring circuitry disposed within the CRM may calculate 5478 an apnea/hypopnea index (AHI) and/or a percent time in periodic breathing (% PB) indicative of the frequency of disordered breathing episodes. The effectiveness of the sleep disordered breathing therapy is determined based on the sleep disordered breathing index 5480. If the AHI and/or % PB are relatively low, the breathing therapy may be determined to be effective. If the AHI and/or % PB are relatively high, then the breathing therapy may be determined to be ineffective.

A CPAP device typically includes a respiratory mask, e.g., a nasal of facial mask, worn by the patient to facilitate delivery or air or other gas to the patient's airway. The respiratory mask may be inconvenient and/or uncomfortable for the patient to wear and may keep the patient awake. Further, delivery of positive airway pressure may inhibit sleep, or cause the patient to arouse frequently. Information about these side effects of the breathing therapy may be helpful in tailoring a therapy regimen for the patient. The CRM may monitor one or more conditions indicative of an impact of the CPAP therapy on the patient.

Impact of the CPAP therapy may be determined based on information related to sleep quality. Sensors coupled to the monitoring circuitry within the CRM are configured to sense 5482 one or more conditions related to sleep. The sleep related conditions are used to detect 5484 sleep and/or arousals from sleep. The monitoring circuitry within the CRM determines 5486 the impact of the CPAP therapy on the patient by monitoring the patient's sleep. For example, the monitoring circuitry may monitor the total time the patient spends sleeping, the number of arousals experienced by the patient in one night, the number of arousals correlated to sleep disordered breathing events, and/or the depth of the arousals. In various implementations the monitoring unit may calculate various indices characterizing sleep and/or one or more composite indices based on indices related to sleep and indices related to sleep disordered breathing. In one example, the monitoring unit calculates the number of arousals experienced by the patient per hour (A/h).

Feedback information is developed 5488 based on the therapy effectiveness and impact information. The feedback information may be transmitted to the therapy device and used to automatically adjust the therapy delivered to the patient. For example, if the AHI is high, the breathing therapy pressure may be adjusted upward to provide a more effective therapy. If the patient experiences an arousal rate greater than a threshold without experiencing sleep disordered breathing episodes, the therapy may be determined to be too aggressive. The breathing therapy pressure may be adjusted downward to provide a disordered breathing therapy that is more comfortable to the patient and allows the patient to sleep better.

Diagnosis and/or Therapy using Blood Chemistry/Expired Gas Parameter Analysis

Aspects of the invention that include diagnosis and/or therapy using blood chemistry/expired gas parameter analysis are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that include diagnosis and/or therapy using blood chemistry/expired gas parameter analysis are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention may incorporate medical gas therapy systems and methods, such as systems and methods for diagnosis and/or therapy using measurement of expired gases and/or blood gases. Embodiments may include systems and methods for detecting and/or diagnosing disorders, such as disordered breathing, a pulmonary disorder, and/or a cardiac disorder, and providing therapy based on one or more conditions or parameters influenced by such diseases/disorders, such as blood gas concentrations, expired gas concentrations, or blood acid-base balance (i.e., hydrogen ion concentration). Methods of providing disordered breathing therapy may involve determining one or more parameters influence by disordered breathing, which may include one or more of blood gas concentration, expired respiratory gas concentration, or blood hydrogen ion concentration, also known as pH. Respiratory and cardiac therapies may be adjusted based on the one or more detected parameters.

In certain embodiments, a disordered breathing therapy method may involve sensing at least one of an expired respiratory gas concentration, a blood gas concentration, or blood pH. Respiratory and cardiac therapies may be adjusted based on one or more of these parameters. In other embodiments, a medical system includes a detector configured to detect blood gas concentration, expire respiratory gas concentration, or hydrogen ion concentration. The medical system further includes a therapy delivery system. The therapy delivery system includes a respiratory therapy delivery device configured to deliver respiratory therapy to a patient and a cardiac therapy delivery device configured to deliver cardiac therapy to the patient. A therapy controller is coupled to the respiratory therapy delivery device and the cardiac therapy delivery device and is configured to adjust respiratory and cardiac therapies based on the detected blood gas concentration, expired gas concentration, and/or blood pH.

Systems and methods that employ diagnosis and/or therapy using blood chemistry/expired gas parameter analysis 130 (FIG. 1C) may be implemented as a stand-alone system or in combination with other individual medical systems, such as those described in FIGS. 1B-1D. Various embodiments involve a system for providing coordinated patient monitoring, diagnosis and/or therapy that utilizes diagnosis and/or therapy using blood chemistry/expired gas parameter analysis 130. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

The implantable and respiratory therapy devices 181, 184 may, for example, operate cooperatively based on detected blood gas concentration, expired gas concentration, and/or blood pH. For example, detection of detected blood gas concentration, expired gas concentration, and/or blood pH and/or deviation of same from pre-established thresholds may allow the implantable and respiratory therapy devices 181, 184 to operate cooperatively to adjust one or both of respiratory and cardiac therapies. Systems and methods directed to use of blood chemistry and/or expired gas parameter analysis for diagnosis and/or therapy may be implemented to include selected features, functions, and/or structures described in commonly owned, co-pending U.S. Publication No. 2005/0065572, which is hereby incorporated herein by reference.

Many patients suffering from obstructive sleep apnea (OSA) have intermittent oxygen desaturation associated with periods of apnea or hypopnea. Oxygen saturation levels below 90% are considered harmful. Usually, treatment is directed at correcting the apnea, which may in turn prevent hypoxemia. Unfortunately, many patients fail or are not candidates for nasal continuous positive airway pressure (CPAP) or surgical correction of their OSA. For these patients, oxygen administration for the correction of OSA-related nocturnal hypoxemia may reduce symptoms of OSA. Oxygen therapy has also been successfully used to treat central apneas as well, including Cheyne-Stokes respiration (CSR). Systems of the present invention may controls gas therapy using one or more patient-internal sensors, one or more patient-external sensors, and/or an implanted device.

Gas therapy, such as oxygen therapy, continuous positive airway pressure therapy, or other therapies provided to a patient through the pulmonary system, may mitigate a patient's suffering from a number of respiratory disorders. Some lung diseases, such as emphysema, sarcoidosis, and chronic obstructive pulmonary disorder, reduce lung function to the extent that supplemental oxygen is needed to continue normal bodily functions. For many patients with end stage lung disease, oxygen therapy allows the patients to get the oxygen they need, helps them be more active, and may also prevent heart failure.

Gas therapy devices may be used to provide a variety of respiration therapies, including, for example, providing vasodilating agents, continuous positive airway pressure (CPAP), bi-level positive airway pressure (bi-level PAP), proportional positive airway pressure (PPAP), auto-titrating positive airway pressure, ventilation, gas or oxygen therapies. All types of gas therapy and positive airway pressure devices are referred to generically herein as xPAP devices.

Expired gases or blood gases may be used to adjust cardiac rhythm management (CRM) and/or xPAP therapies to provide more effective treatment of disordered breathing, a pulmonary disorder, and/or a cardiac disorder. The blood gas sensors may be implemented using either a patient-internal sensor or a patient-external sensor. Expired gases may be sensed using a patient-external sensor positioned, for example, on the respiratory mask of the xPAP device. The use of external sensors avoids the stability, reliability, and power consumption problems associated with implanted sensors. The use of implanted sensors resolves compliance issues common to xPAP therapy. The gas concentration in the expired air collected at the very end of expiration (just before inhalation starts) is representative of the blood gas concentration. This provides a non-invasive way of measuring blood gas concentrations.

The blood hydrogen ion concentration (or pH) is related to the relative amount of carbon dioxide and various chemical buffering agents in the blood. The blood pH is therefore closely influenced by respiration. The blood pH is related to the internal respiratory control and is therefore an important indicator of respiratory disorders, including apnea, COPD and others. An example of a pH sensor suitable for implantation is described in U.S. Pat. No. 4,312,734, which is hereby incorporated herein by reference. An example of an oxygen sensor suitable for implantation is described in U.S. Pat. No. 4,390,405, which is hereby incorporated herein by reference.

Various diseases and disorders, e.g., sleep apnea, are associated with various levels of expired respiratory gases and/or blood gases. The detection of changes in expired gases, blood gases, and/or blood pH may be used in connection with diagnosis of a variety of diseases. Further, expired gas, blood gas concentrations, and/or pH may be used to detect and/or predict episodes of disordered breathing, a pulmonary disorder, and/or a cardiac disorder. Further, detection of expired gas, blood gas concentrations, and/or blood pH may be used to initiate, terminate, or modify respiratory and cardiac therapy.

Embodiments of the invention are directed to systems and methods that acquire and process blood chemistry information in an implantable or partially implantable device. Information acquired from blood gas or pH sensors, for example, may be used in connection with patient monitoring, diagnosis, and therapy. An implantable system may incorporate expired gas, blood gas, and/or pH detection for various purposes, including disease diagnosis and therapy control, among other functions. Systems may include one or more or expired gas, blood gas, and/or pH sensors, which may be implemented as one or more patient-internal and/or one or more patient-external sensors.

The following discussion, with reference to FIGS. 55 through 59, describes embodiments of the invention involving measurement of expired gases, blood gases or blood pH used for diagnosis and therapy. The processes and systems exemplified by these embodiments may be implemented alone or in combination with one or more processes and systems exemplified by other embodiments described herein (e.g., in FIGS. 1B-1D) to provide a coordinated approach to patient monitoring, diagnosis, and/or therapy.

In accordance with embodiments of the invention, a system controls gas therapy, such as oxygen therapy, using one or more patient-internal sensors, one or more patient-external sensors, and/or an implanted device. The gas therapy may be delivered to the patient, and measurement of exhaled gas concentration may be implemented using a respiratory mask, such as a CPAP mask, for example. The one or more sensors may include, for example, a gas saturation sensor or other implanted sensor for determining the patient's blood gas saturation. The patient's blood gas saturation may be determined externally, e.g., using pulse oximetry techniques, and/or external sensors positioned on a respiratory mask or nasal cannulae.

Figure 55A:
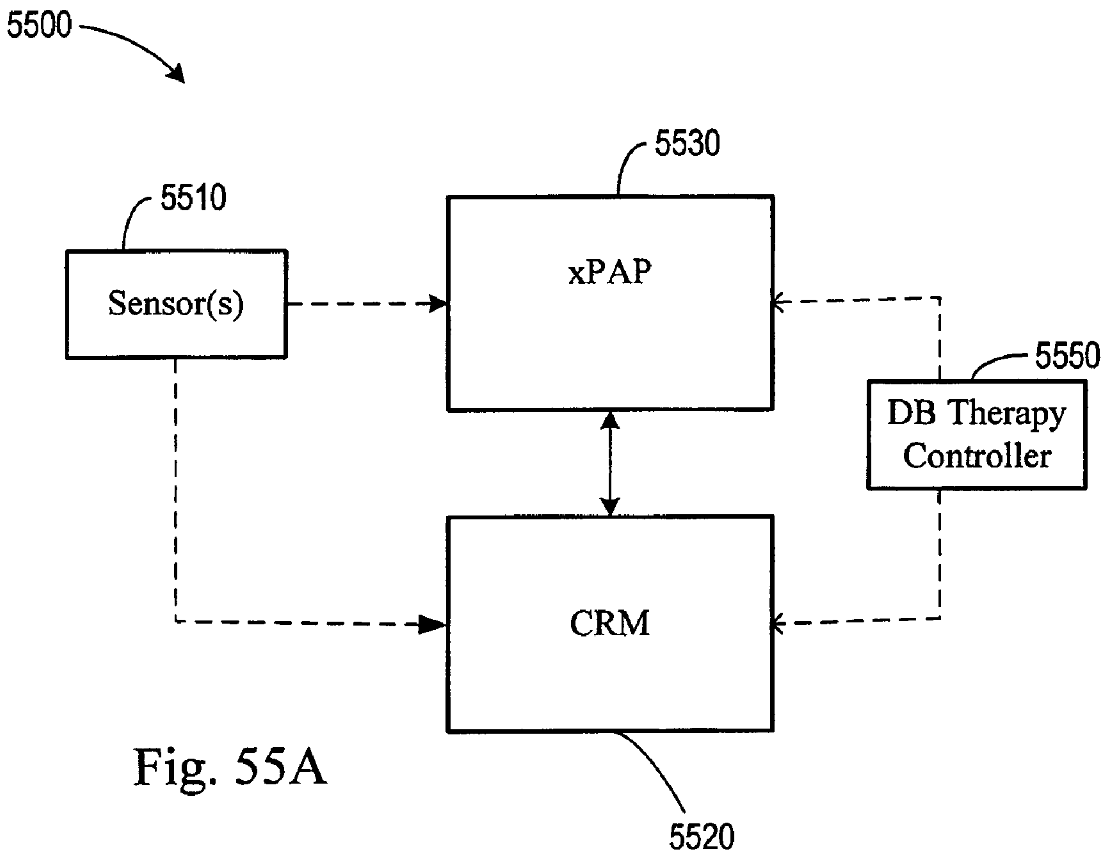
FIG. 55A is a block diagram of a system used to provide measurement of one or more parameters influenced by disordered breathing for diagnosis and therapy in accordance with embodiments of the invention.

As is illustrated in FIG. 55A, a system 5500 may be configured with one or more sensors 5510 that are configured to sense one or more parameters influence by disordered breathing. The sensors 5510 may be implemented as implantable sensors, patient-external sensors, or both implantable and patient-external sensors. A disordered breathing (DB) therapy controller 5550 may be configured for implantable or patient-external operation. For example, the DB therapy controller 5550 may be implemented as a controller of an xPAP device 5530 or a controller of a cardiac rhythm management device 5520. The DB therapy controller 5550 detects disordered breathing using sense information received from the sensors 5500, and adjusts therapies deliverable by the xPAP and CRM devices 5530, 5520 responsive to the sense information. Adjustment of xPAP and CRM therapies includes, for example, initiation, termination, or modification of such therapies.

Figure 55B:
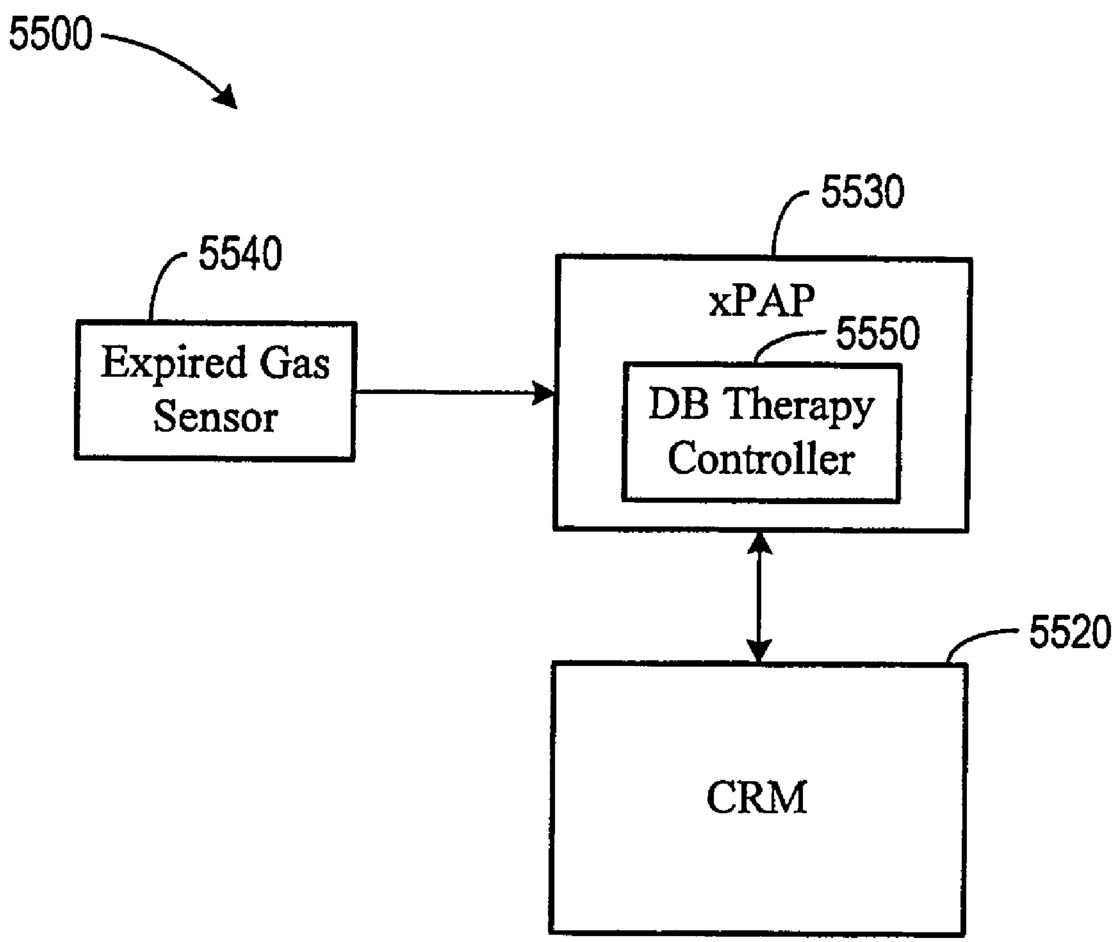
FIG. 55B is a block diagram of a system used to provide measurement of expired gases for diagnosis and therapy in accordance with embodiments of the invention.

In accordance with other embodiments, as illustrated in FIG. 55B, a system 5500 may be configured with a patient-external expired gas sensor 5540 used to modify cardiac pacing therapy and respiratory therapy for treating disordered breathing, a pulmonary disorder, and/or a cardiac disorder. The expired gas sensor 5540 may be positioned in an appropriate location on the mask of an xPAP device 5530. In the embodiment illustrated in FIG. 55B, the expired gas sensor 5540 is coupled to the xPAP device 5530. Expired gas concentration is measured at the end of expiration. A timing element (not shown) may be used to coordinate operations with the patient's respiration cycle to make the expired gas concentration measurement at the end of expiration.

The xPAP device 5530 includes a DB therapy controller 5550. The DB therapy controller 5550 detects expired gas, e.g., expired oxygen, and compares concentration of the expired gas to a predetermined threshold or range. When the gas concentration is beyond the threshold or range, the DB therapy controller 5550 may initiate, terminate, or modify a respiratory therapy provided by the xPAP device 5530. Further, the DB therapy controller 5550 may communicate with a CRM device 5520, e.g., through a wireless communication link or other communications mechanism, to initiate, terminate, or modify the electrical stimulation therapy provided by the CRM device 5520.

Figure 56:
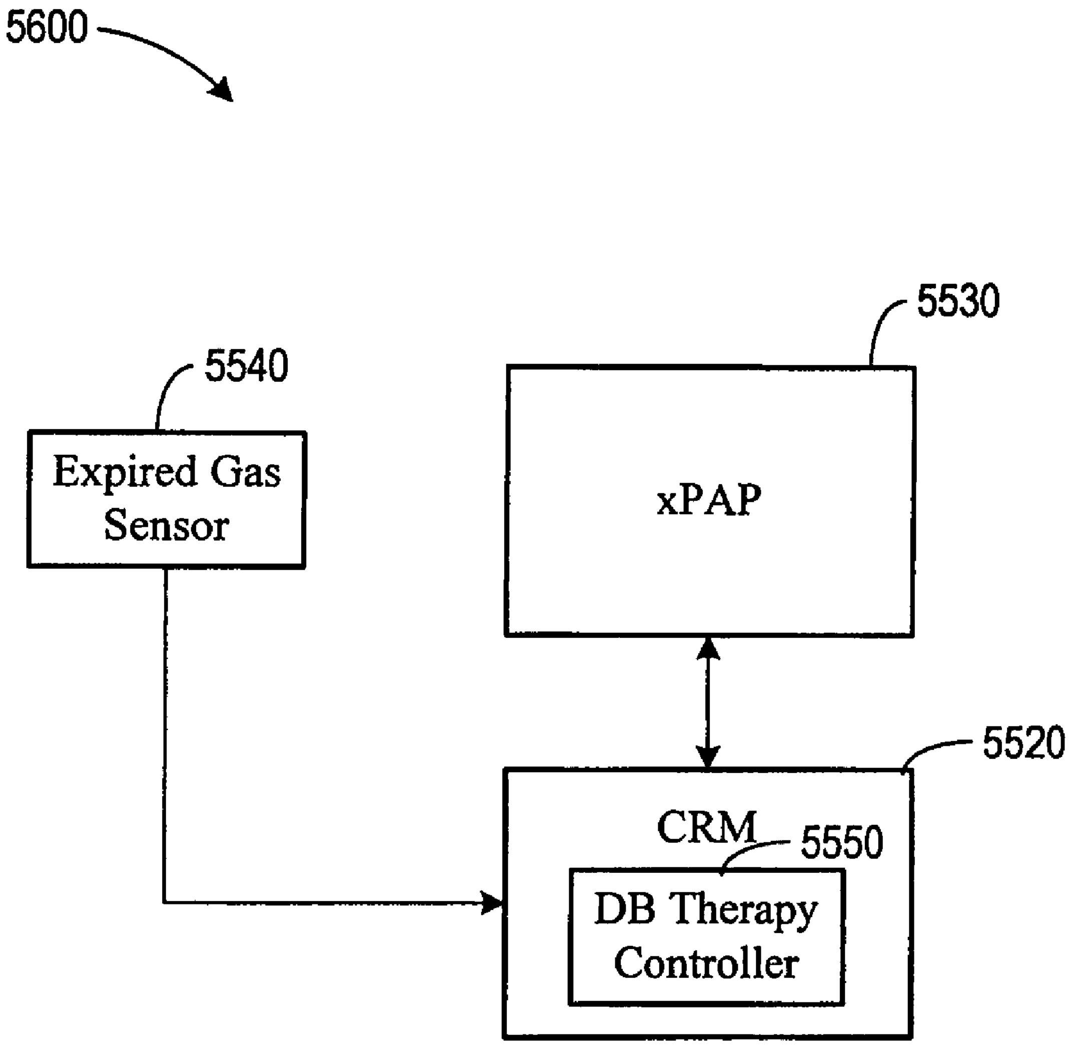
FIG. 56 is a block diagram illustrating a system for diagnosis and/or therapy using measurement of expired gases in accordance with embodiments of the invention.

In other embodiments, as illustrated in FIG. 56, a system 5600 includes the DB therapy controller 5550 located within the CRM device 5520. The external expired gas sensor 5540 may wirelessly transmit to the CRM device 5520 sensed signals associated with expired gas concentration. The DB therapy controller 5550 compares the concentration of the expired gas to a predetermined threshold or range. When the gas concentration is beyond the threshold or range, the DB therapy controller 5550 may initiate, terminate, or modify an electrical stimulation therapy provided by the CRM device 5520. Further, the DB therapy controller 5550 may communicate with the xPAP device 5530, e.g., through a wireless communication link or other communications mechanism, to initiate, terminate, or modify a respiratory therapy provided by the xPAP device 5530.

Figure 57:
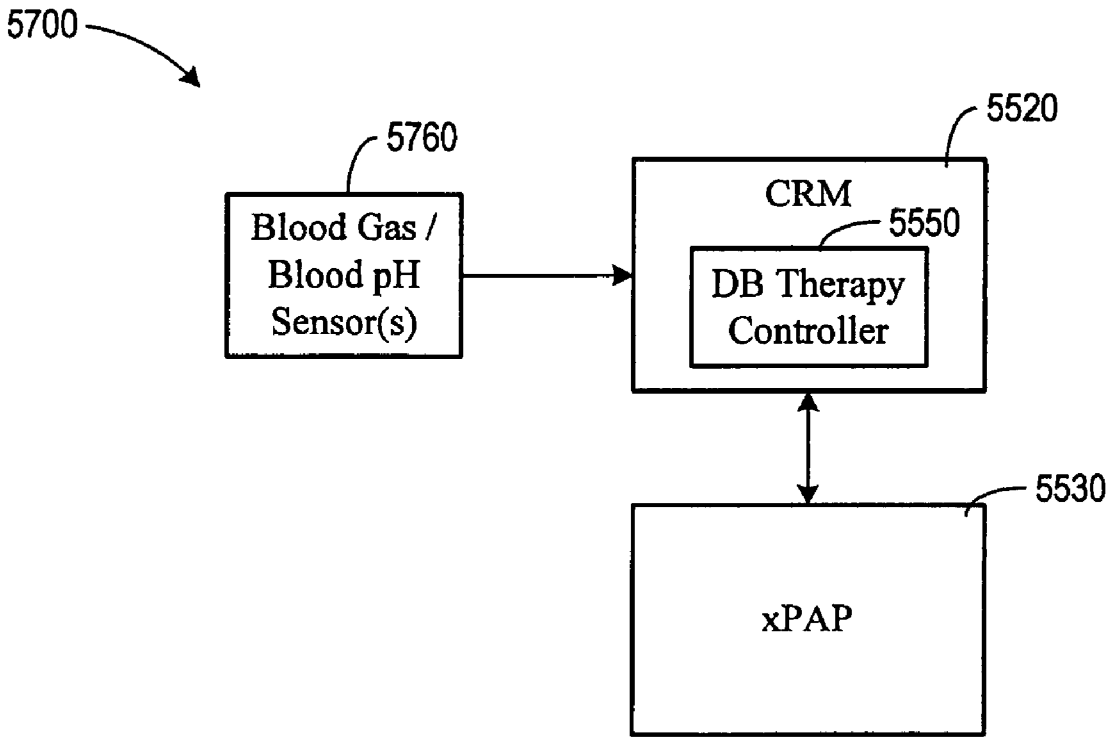
FIG. 57 is a block diagram illustrating a system for diagnosis and/or therapy using measurement of blood gases/blood pH in accordance with further embodiments of the invention.

In accordance with yet other embodiments, as illustrated in FIG. 57, a system 5700 includes an implanted blood sensor 5760 that provides information used to modify cardiac pacing therapy and respiratory therapy for disordered breathing, a pulmonary disorder, and/or a cardiac disorder. The implanted blood sensor 5760 may include one or both of a blood gas sensor or a blood pH sensor. For example, the blood sensor 5760 may be configured to sense one or more of blood oxygen concentration, blood carbon dioxide concentration, or blood pH.

The blood sensor 5760 may be positioned, for example, on an endocardiac lead implanted in a chamber of the patient's heart and coupled to the CRM device 5520. The CRM device 5520 in this example includes, or otherwise incorporates the functionality of, the DB therapy controller 5550. The DB therapy controller 5550 may detect blood gas concentration, e.g., blood oxygen and/or carbon dioxide concentration, and compare concentration of the blood gas to a predetermined threshold or range. When the blood gas concentration is beyond the threshold or range, the DB therapy controller 5550 may initiate, terminate, or modify the electrical stimulation therapy provided by the CRM device 5520. Further, the DB therapy controller 5550 may communicate with the xPAP device 5530, e.g., through a wireless communication link or other communications mechanism, to initiate, terminate, or modify the respiratory therapy provided by the xPAP device 5530. An equivalent to the above example could be implemented using a blood pH sensor or a combination of blood gas and blood pH sensors.

Figure 58:
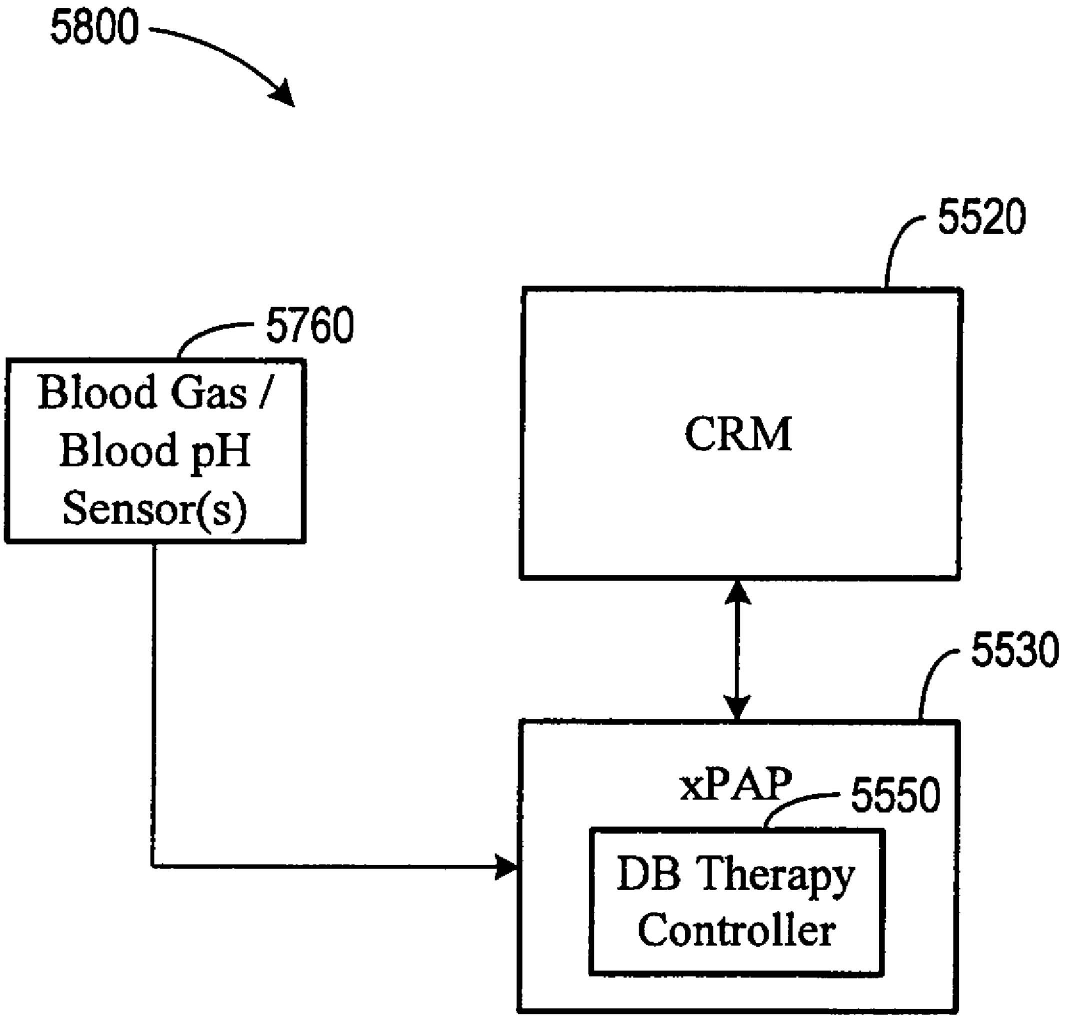
FIG. 58 is a block diagram illustrating a system for diagnosis and/or therapy using measurement of blood gases/blood pH in accordance with embodiments of the invention.

In further embodiments, as illustrated in FIG. 58, a system 5800 includes the DB therapy controller 5550 within the xPAP device 5530. The blood sensor 5760 may wirelessly transmit to the xPAP device 5530 sensed signals associated with blood gas concentration and/or blood pH. The DB therapy controller 5550 compares the concentration of the expired gas to a predetermined threshold or range. When the gas concentration is beyond the threshold or range, the DB therapy controller 5550 may initiate, terminate, or modify the respiratory therapy provided by the xPAP device 5530. Further, the DB therapy controller 5550 may communicate with the CRM device 5520, e.g., through a wireless communication link or other communications mechanism, to initiate, terminate, or modify the electrical stimulation therapy provided by the CRM device 5520. An equivalent to the above example could be implemented using a blood pH sensor or a combination of blood gas and blood pH sensors.

As is illustrated in the examples shown in FIGS. 55 through 58, many possible combinations of componentry and nesting or combinations of componentry are possible in accordance with the present invention. The specific configurations shown in FIGS. 55 through 58 are non-limiting examples of possible configurations of systems in accordance with the present invention.

Figure 59:
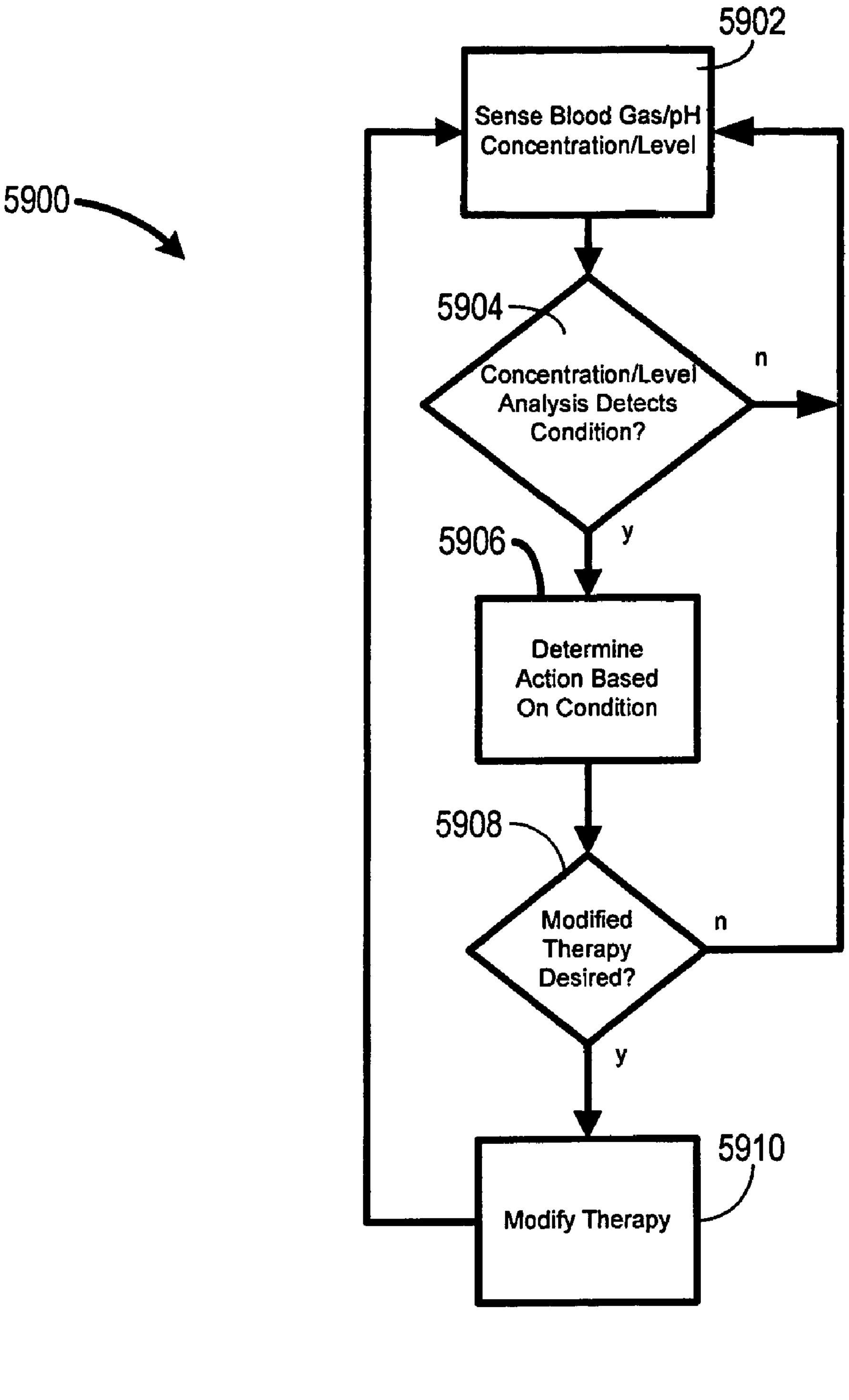
FIG. 59 is a flow chart illustrating a method of diagnosis and/or therapy in accordance with embodiments of the invention.

FIG. 59 is a flow chart illustrating a method 5900 of therapy control based on signals from a patient-internal device in accordance with embodiments of the invention. The method 5900 may be useful for controlling systems using combined gas and cardiac therapies, such as those illustrated with reference to FIGS. 55 through 58. For clarity of understanding, and not by way of limitation, the sensing of blood oxygen level and/or blood pH will be used as an example of one use of the method 5900. For example, an equivalent embodiment could be implemented using blood carbon dioxide level.

Block 5902 provides for the sensing of a blood chemistry parameter, such as blood gas concentration (e.g., blood oxygen level or blood carbon dioxide level) and/or blood pH. An analysis 5904 is made of the sensed blood gas concentration and/or blood pH. For example, a blood oxygen and/or pH level may be compared to a range of acceptable levels to detect whether the blood gas concentration/pH is within an acceptable range, or whether some disease/disorder is diagnosable. If blood oxygen/pH level is acceptable and no disease/disorder is diagnosed at analysis 5904, the blood gas/pH sensing continues at block 5902. Sensing may occur continuously, intermittently, by-request, periodically, or as otherwise desired.

If a disease/disorder is detected at analysis 5904, a determination 5906 is made, relative to the detected disease/disorder. For example, detecting a blood oxygen below a lower threshold may suggest that more oxygen is needed by the patient. A decision 5908 is made as to whether some modifications and/or therapies are desired to increase the blood oxygen level. For example, if a patient is receiving oxygen therapy and cardiac pacing, the oxygen level administered to the patient may be adjusted and the heart rate may be adjusted. In another embodiment, if the patient is sleeping and wearing a CPAP device, the air pressure may be increased and the heart rate may be increased. In a further embodiment, the patient may be administered a vasodilating agent, or have a level of vasodilating agent therapy modified along with adjustment of the heart rate. Combined therapies may also be performed, such as increasing gas pressure and adding a vasodilating agent, or other desired therapy combination.

If no therapy change is desired, the presence of the disease/disorder may be recorded and monitored, and/or an alert signal may be generated responsive to the detection of the disease/disorder, for example, before returning to the sense block 5902. If a therapy change is desired, the therapy is modified at a block 5910 before again returning to the blood sense block 5902. For example, if a patient is receiving oxygen therapy, the oxygen level administered to the patient is increased, and the method 5900 may be performed again after an appropriate time to determine if the change was effective, or whether other action is necessary.

Information about the patient's blood gas and/or pH levels may be used to enhance sleep monitoring and/or diagnosis of a variety of disorders. Detection of blood gas level and/or pH may be used to diagnose disorders as well as trigger the sleep-time therapy in a respiratory and cardiac device. Data acquired during sleep may assist in diagnosing various sleep-related disorders. The collected data may be stored, displayed, printed, or transmitted to a separate device.

Pulmonary Disease Assessment System

Aspects of the invention are directed to methods and systems configured to monitor, diagnose, and/or provide patient therapy using one or more individual medical procedures including assessment of pulmonary disease. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving pulmonary disease assessment are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 136 (FIG. 1D) for assessing a presence of a pulmonary disease. The pulmonary disease assessment system 136 may be implemented as a stand alone system or in combination with other individual medical systems, such as those described in FIGS. 1B-1D.

Embodiments of the invention are directed to methods and systems for assessing a presence of pulmonary disease. One embodiment of the invention involves a method for assessing a presence of a pulmonary disease other than a breathing rhythm disorder. The method includes sensing one or more conditions associated with the non-rhythm pulmonary disease using a respiratory therapy device. The presence of the non-rhythm pulmonary disease is assessed based on the one or more sensed conditions.

According to various aspects of the invention, sensing the one or more sensed conditions may include sensing one or more of respiratory pressure, respiratory flow, and exhaled gas concentration.

The presence of various types of non-rhythm pulmonary diseases may be assessed, including, for example, obstructive pulmonary diseases, restrictive pulmonary diseases, pulmonary vasculature disorders, pleural disorders, and/or other pulmonary diseases or disorders that are not breathing rhythm disorders.

According to another embodiment of the invention, a medical system for assessing a non-rhythm pulmonary disease presence includes a respiratory therapy device having a therapy unit and a sensor system. The therapy unit is configured to deliver respiration therapy to a patient. The sensor system is configured to sense one or more conditions associated with a pulmonary disease other than a breathing rhythm disorder. The system further includes a diagnosis unit coupled to the sensor system. The diagnosis unit is configured to assess a presence of the non-rhythm pulmonary disease based on the one or more sensed conditions.

Another embodiment of the invention involves a system for providing coordinated patient monitoring, diagnosis and/or therapy including non-rhythm pulmonary disease assessment. The coordinated system includes, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy further includes a pulmonary disease assessment system. The respiratory therapy device includes a sensor system configured to sense one or more conditions associated with a pulmonary disease other than a breathing rhythm disorder. The system further includes a diagnosis unit coupled to the sensor system and configured to assess a presence of the non-rhythm pulmonary disease based on the one or more sensed conditions, wherein the implantable device and the patient external respiratory therapy device operate cooperatively to implement the pulmonary disease assessment system. Systems and methods directed to assessing pulmonary disease may be implemented to include selected features, functions, and/or structures described in commonly owned, U.S. Pat. No. 7,575,553, which is hereby incorporated herein by reference.

Pulmonary disorders may be organized into broad categories encompassing disorders of breathing rhythm and non-rhythm pulmonary diseases and/or disorders. Breathing rhythm disorders include various syndromes characterized by patterns of disordered breathing that produce insufficient respiration, for example, sleep apnea, hypopnea, and Cheyne-Stokes Respiration (CSR), among others. Breathing rhythm disorders are not necessarily accompanied by alteration of pulmonary structures.

Non-rhythm pulmonary diseases or disorders typically involve physical changes to lung structures, such as loss of elasticity of the lung tissue, obstruction of airways with mucus, limitation of the expansion of the chest wall during inhalation, fibrous tissue within the lung, excessive pressure in the pulmonary arteries, and/or other characteristics. Pulmonary diseases or disorders that are not rhythm-related are referred to herein as non-rhythm pulmonary diseases and may include obstructive pulmonary diseases, restrictive pulmonary diseases, infectious and non-infectious pulmonary diseases, pulmonary vasculature disorders, and pleural cavity disorders, for example.

Embodiments of the invention are directed to methods and systems for assessing a presence of non-rhythm pulmonary diseases using a sensor system coupled to a respiratory therapy device. If the non-pulmonary disease is present based on the assessment, then a diagnosis of the non-pulmonary disease may be made. A non-rhythm pulmonary disease assessment system may be used to discriminate between types of non-rhythm pulmonary diseases, e.g., between obstructive pulmonary diseases and restrictive pulmonary diseases. The assessment system may additionally or alternatively be used to discriminate between non-rhythm pulmonary diseases of a particular type, e.g., between asthma and emphysema, both of which are pulmonary diseases of the obstructive type.

If the presence of a non-rhythm pulmonary disease is detected, then the progression of the disease may be monitored. Monitoring the progression of the non-rhythm pulmonary disease may involve, for example, evaluating one or more physiological changes or symptoms associated with the disease. Evaluating the physiological changes or symptoms may be accomplished by periodically sensing for conditions modulated by the symptoms or physiological changes and storing information about the sensed conditions. Monitoring disease progression may involve, for example, monitoring the severity of the disease, disease onset, changes during the course of the disease, regression, disease offset, and/or other aspects of the disease.

Embodiments of the invention utilize the sensor system of a patient-external respiratory therapy device to determine a presence of a non-rhythm pulmonary disease. The respiratory therapy device may comprise, for example, a gas therapy device, nebulizer, ventilator, positive airway pressure device, or other type of external respiration therapy device. In a preferred embodiment, the respiratory therapy device comprises a positive airway pressure device. Continuous positive airway pressure (CPAP) devices are frequently used to treat sleep apnea and/or other breathing rhythm disorders. A CPAP device may be used regularly during a patient's sleep time to prevent or treat sleep disordered breathing events. Use of a CPAP device for treatment of breathing rhythm disorders facilitates detection of non-rhythm pulmonary diseases. The CPAP device provides respiratory sensing functionality on a periodic basis that may be employed to sense conditions indicative of symptoms or physiological changes associated with non-rhythm pulmonary disease.

Figure 60A:
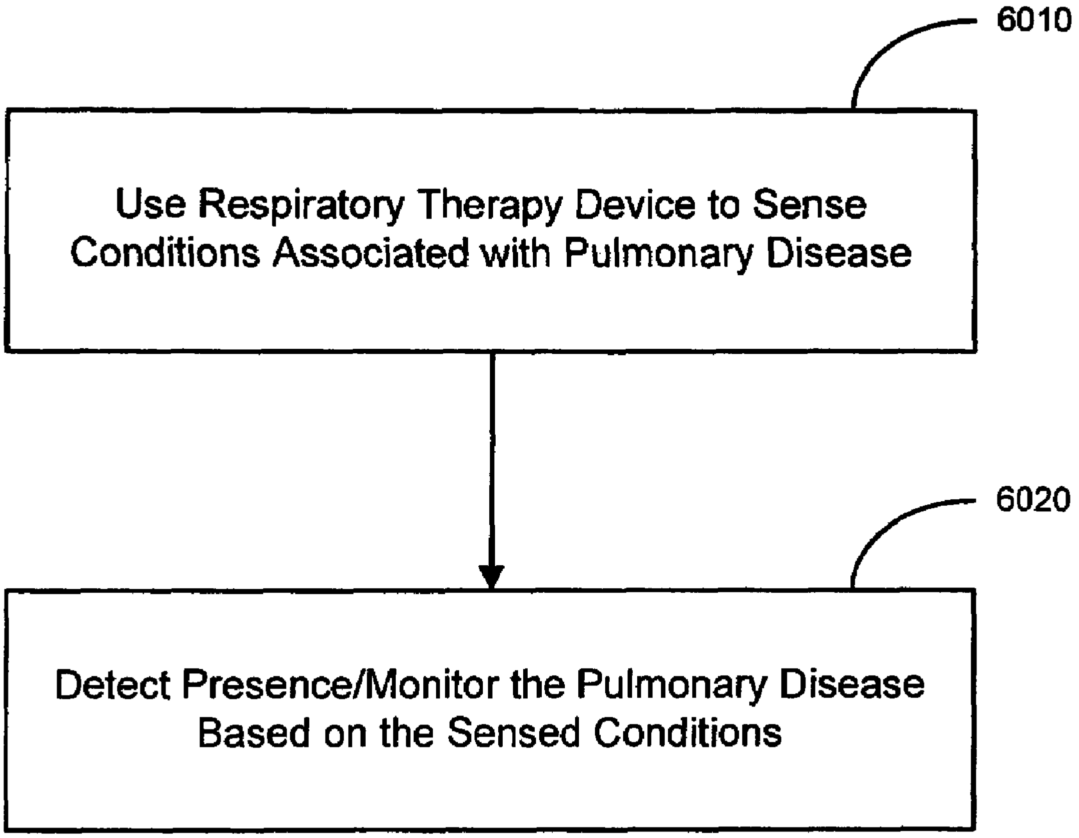
FIG. 60A is a flowchart of a method of diagnosing pulmonary diseases and disorders in accordance with embodiments of the invention.

FIG. 60 is a flowchart illustrating a method of assessing a presence of a non-rhythm related pulmonary disease in accordance with embodiments of the invention. The method involves using 6010 a respiratory therapy device to sense conditions associated with the non-rhythm related pulmonary disease and assessing 6020 a presence of the non-rhythm pulmonary disease based on the sensed conditions.

The respiratory therapy device may include one or more sensors used to sense physiological conditions related to non-rhythm pulmonary disease. The respiratory therapy device sensors may include, for example, one or more ventilatory pressure sensors, capable of sensing inspiratory pressure and/or expiratory pressure, one or more ventilatory flow sensors, capable of sensing inspiratory flow and/or expiratory flow, one or more ventilatory gas sensors, capable of sensing exhaled CO2 and/or exhaled O2, among other sensors.

One or more of the physiological conditions sensed by the sensors of the respiratory therapy device may be measured and compared to criteria associated with presence of a non-rhythm pulmonary disorder. In some implementations, the one or more physiological conditions may be trended over time and the trended measurements compared to trend criteria. In some implementations, the criteria depend on relationships between the various measurements acquired using the sensors of the respiratory therapy device.

The measurements collected using the respiratory therapy device sensors may be stored in memory, along with sets of criteria used for assessing the presence of various non-rhythm pulmonary disorders. In one implementation, the memory storing the criteria sets and a diagnostic processor are disposed within the housing of the respiratory therapy device controller, for example. The diagnostic processor compares the measured conditions to the criteria sets in memory to assess the presence of various non-rhythm pulmonary disorders.

In one implementation, the measurements acquired by the respiratory therapy device may be transmitted to a remote device, such as an advanced patient management system. Diagnostic circuitry within the advanced patient management system may compare the conditions measured by the respiratory therapy device to the criteria sets stored in the APM system to assess the presence of non-rhythm pulmonary disorders.

According to one aspect of the invention, pulmonary function testing may be employed to detect physiological changes associated with the presence of pulmonary disease. Pulmonary function tests performed in a clinical setting may be used to evaluate lung mechanics, gas exchange, pulmonary blood flow, and blood gases and pH. They are used to evaluate patients in the diagnosis of pulmonary disease, assessment of disease development, or evaluation of the risk of pulmonary complications from surgery.

Pulmonary performance may be evaluated based on data acquired by the respiratory therapy device during normal and forced inspiration and expiration. From such data, pulmonary parameters including tidal volume, minute ventilation, forced expiratory volume, forced vital capacity, among other parameters may be determined.

Pulmonary function testing is conventionally performed in a clinical setting and measures values indicative of the ability of the lungs to exchange oxygen and carbon dioxide. The total lung capacity (TLC) is divided into four volumes. The tidal volume ($V_T$) is the volume inhaled or exhaled in normal quiet breathing. The inspiratory reserve volume (IRV) is the maximum volume that can be inhaled following a normal quiet inhalation. The expiratory reserve volume (ERV) is the maximum volume that can be exhaled following a normal quiet exhalation. The residual volume (RV) is the volume remaining in the lungs following a maximal exhalation. The vital capacity (VC) is the maximum volume that can be exhaled following a maximal inhalation; $VC=IRV+V_T+ERV$. The inspiratory capacity (IC) is the maximum volume that can be inhaled following a normal quiet exhalation; $IC=IRV+V_T$. The functional residual capacity (FRC) is the volume remaining in the lungs following a normal quiet exhalation; FRC=ERV+RV.

The vital capacity and its components ($V_T$, IRV, ERV, IC) are typically measured using a spirometer, which is a device that measures the volumes of air inhaled and exhaled. The FRC is usually measured by the helium dilution method using a closed spirometry system. A known amount of helium is introduced into the system at the end of a normal quiet exhalation. When the helium equilibrates throughout the volume of the system, which is equal to the FRC plus the volume of the spirometer and tubing, the FRC is determined from the helium concentration. This test may underestimate the FRC of patients with emphysema. The FRC can be determined quickly and more accurately by body plethysmography. The residual volume and total lung capacity are determined from the FRC.

In the forced vital capacity (FVC) maneuver, the patient exhales as forcefully and rapidly as possible, beginning at maximal exhalation. Several parameters are determined from the spirogram. The FVC is the total volume of air exhaled during the maneuver; it is normally equal to the vital capacity. The forced expiratory volume (FEV) is the volume expired during a specified time period from the beginning of the test. The times used are 0.5, 1, 2, and 3 seconds; corresponding parameters are $FEV_{O.5}$, $FEV_{1.0}$, $FEV_{2.0}$, and $FEV_{3.0}$. The maximal expiratory flow rate (MEFR) is the slope of the line connecting the points where 200 ml and 1200 ml have been exhaled; it is also called $FEF_{200-1200}$ (forced expiratory flow). The maximal midexpiratory flow rate (MMFR, MMF) is the slope of the line connecting the points where 25 per cent and 75 per cent of the FVC have been exhaled; it is also called $FEF_{25-75\%}$.

The Maximal Voluntary Ventilation (MVV) is the maximal volume of air that can be breathed by the patient, expressed in liters per minute; it was formerly called maximal breathing capacity (MBC). The patient breathes as rapidly and deeply as possible for 12 to 15 seconds and the volume exhaled is determined by spirometry.

Various parameters related to pulmonary performance, some of which may be measured using sensors of a respiratory therapy device include, for example, tidal volume, minute ventilation, inspiratory reserve volume, forced expiratory volume (FEV), residual volume, and forced vital capacity (FVC), among other parameters. According to one embodiment, testing of some pulmonary function parameters may be performed using the ventilation pressure and ventilation flow sensors of a CPAP device. The pulmonary function testing may be used, for example, to discriminate between restrictive and obstructive pulmonary disorders. Methods and systems for acquiring and using pulmonary function testing information, aspects of which may be utilized in connection with embodiments of the invention, are described in commonly owned U.S. patent application Ser. No. 10/885,145, filed Jul. 6, 2004, which is incorporated herein by reference.

Because the results of pulmonary function tests vary with size and age, the normal values are calculated using prediction equations or nomograms, which give the normal value for a specific age, height, and sex. The prediction equations are derived using linear regression on the data from a population of normal subjects. The observed values are usually reported as a percentage of the predicted value. Abnormal test results may show either an obstructive or restrictive pattern. Sometimes, both patterns are present.

The results of pulmonary function testing, along with other measured physiological conditions, may be compared to initial or baseline results to detect changes in the patient's pulmonary status over time. The changes from baseline values may be used to discern a presence of disease processes. Further, over time, a database of information about relevant conditions and specific to the patient is established. The information may be used to develop sets of criteria specific to the patient and associated with the presence of a particular pulmonary disease processes. Thus, in some implementations, the system may learn to recognize the presence of disease based on the history of symptoms and/or physiological changes that occur in a particular patient.

Figures 60B, 60C, 60D:
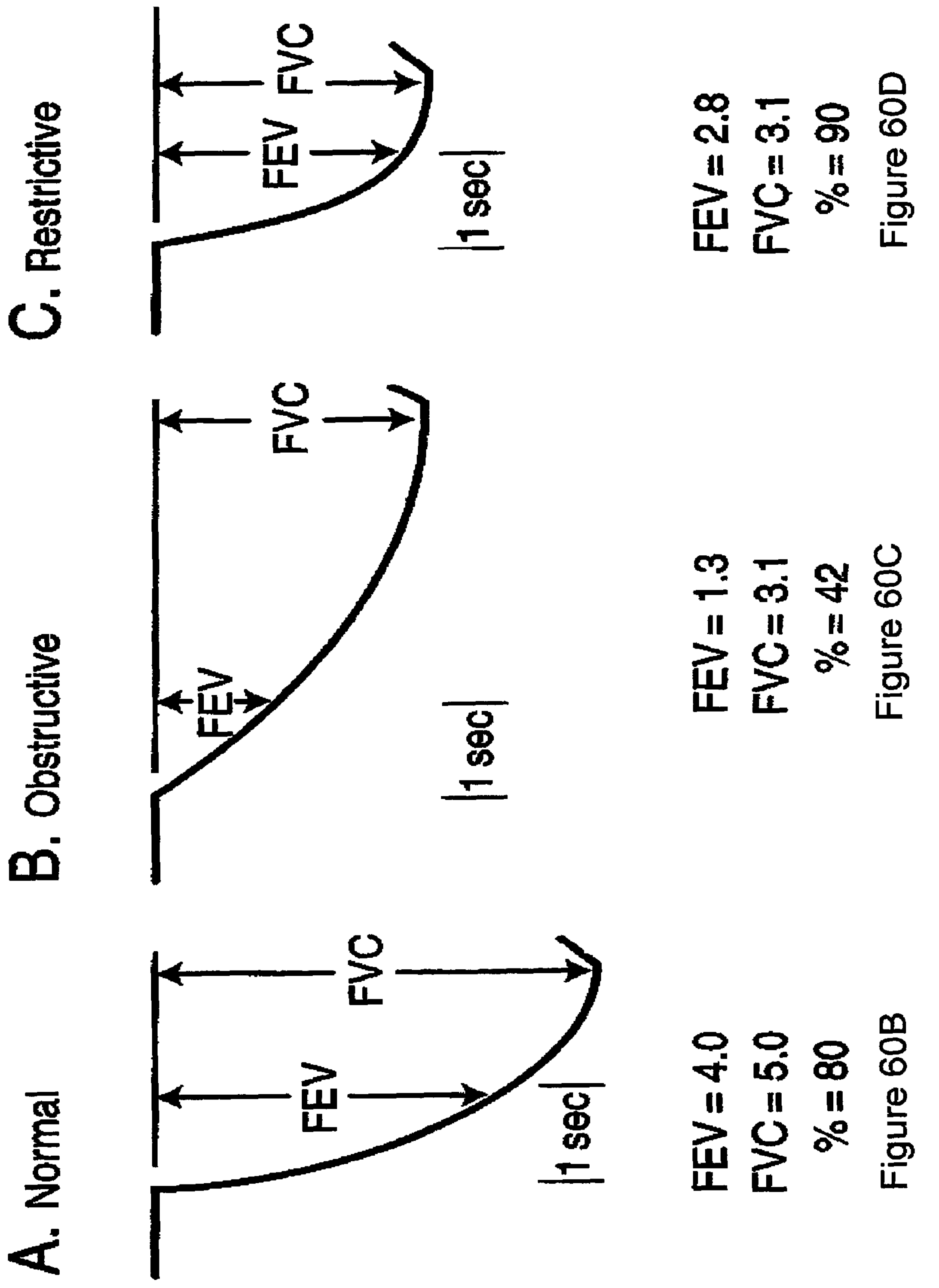
FIGS. 60B-60D are graphs of normal, obstructive and restrictive respiratory patterns, respectively, in accordance with embodiments of the invention.

FIG. 60B illustrates a normal respiratory pattern, having normal FEV and FVC. FIG. 60C illustrates an obstructive pattern. An obstructive pattern occurs when there is airway obstruction from any cause, as in asthma, bronchitis, emphysema, or advanced bronchiectasis; these conditions are grouped together in the nonspecific term chronic obstructive pulmonary disease (COPD). In this pattern, the residual volume is increased and the PV/TLC ratio is markedly increased. Owing to increased airway resistance, the flow rates are decreased. The FEV/FVC ratios, MMFR, and MEFR are all decreased; $FEV_{1.0}$/FVC is less than 75 percent.

FIG. 60D illustrates a restrictive pattern. A restrictive pattern occurs when there is a loss of lung tissue or when lung expansion is limited as a result of decreased compliance of the lung or thorax or of muscular weakness. The conditions in which this pattern can occur include pectus excavatum, myasthenia gravis, diffuse idiopathic interstitial fibrosis, and space occupying lesions (tumors, effusions). In this pattern, the vital capacity and FVC are less than 80 per cent of the predicted value, but the FEV/FVC ratios are normal. The TLC is decreased and the RV/TLC ratio is normal.

Embodiments of the invention utilize a patient-external respiratory therapy device to perform periodic pulmonary function testing. A CPAP or other external respiratory device may measure ventalitory pressure, ventilatory airflow, and/or ventalitory gas during periodic, e.g., nightly, therapy sessions. The ventalitory pressure and/or airflow measurements may be used to measure FVC and FEV during forced expiration. From these two parameters, FEV/FVC can be derived to differentiate obstructive versus restrictive respiratory patterns as shown in the FIGS. 60C and 60D. Other measurements that are possible using the respiratory device sensors include low forced expiratory flow (FEF), high functional residual capacity (FRC), total lung capacity (TLC), and high residual volume (RV).

In one embodiment, the patient may perform forced expirations while connected to the external respiratory device. During the forced expirations, circuitry in the external respiratory device may collect measurements, including FEV and FVC measurements.

In addition, the forced expiratory flow ($FEF_{25-75\%}$) may be measured. The middle half by volume of the total expiration is marked, and its duration is measured. The $FEF_{25-75\%}$ is the volume in liters divided by the time in seconds. In patients with obstructive diseases, the $FEF_{25-75\%}$ is generally greater than their expected values.

Circuitry incorporated in the CPAP device may be used to compare measured FVC, FEV and $FEF_{25-75\%}$ values derived from the pressure sensor and/or from the airflow sensor with predicted values from normal subjects in accordance with various embodiments. The comparison provides diagnostic information of lung mechanics. Data acquired by the CPAP device may be transmitted from the CPAP device to an advanced patient management (APM) system or other remote device.

Figure 61A:
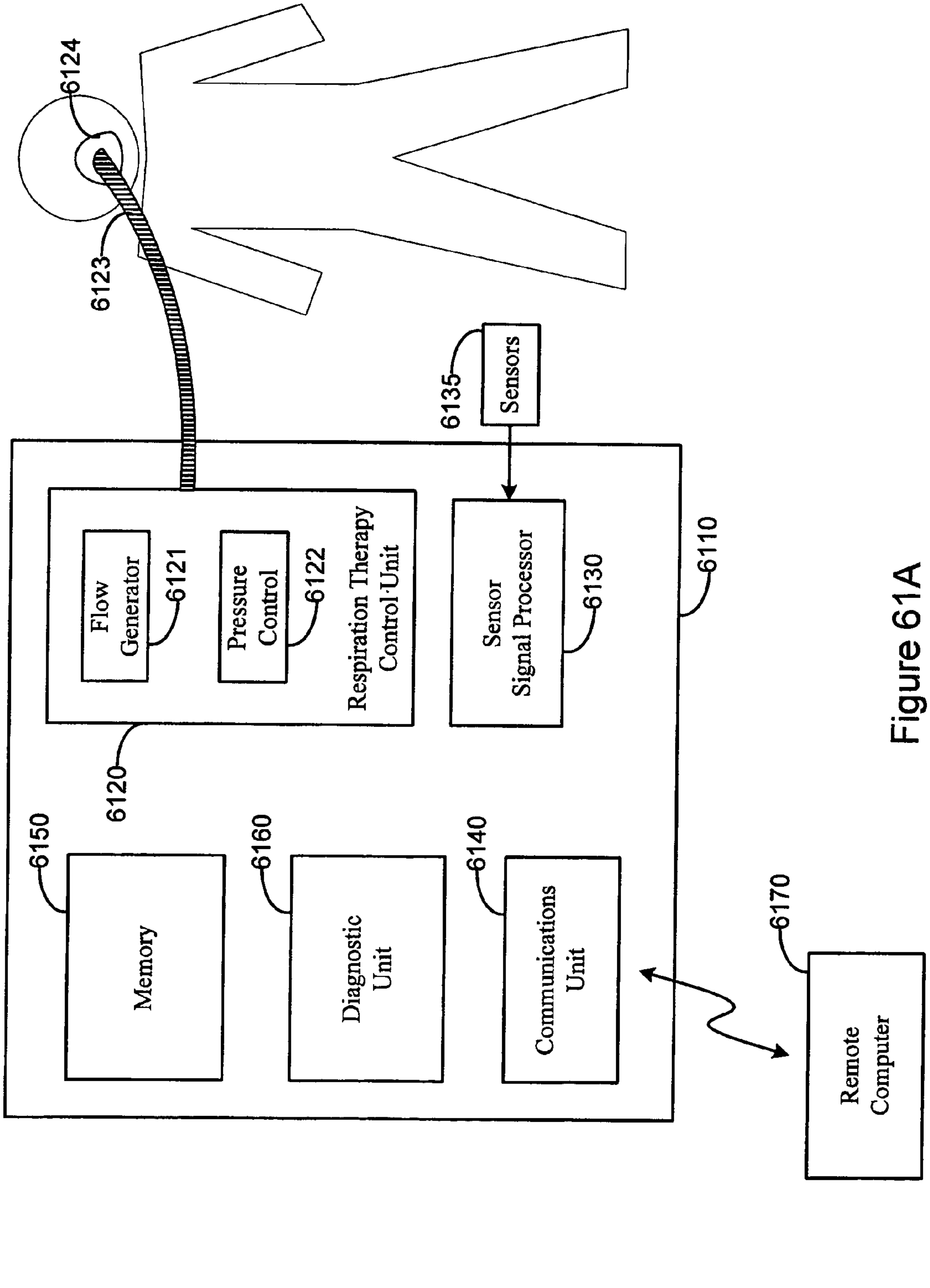
FIGS. 61A-61D are block diagrams of a pulmonary disease assessment system in accordance with embodiments of the invention.

FIGS. 61A-1D are block diagrams of systems that may be used for non-rhythm pulmonary disease assessment in accordance with embodiments of the invention. FIG. 61A illustrates an external respiratory therapy device 6110, e.g., a CPAP device, used to sense conditions associated with a non-rhythm pulmonary disease. The sensed conditions are evaluated by circuitry within the external respiratory therapy device 6110 to assess a presence of the non-rhythm pulmonary disease.

The respiratory therapy device 6110 is coupled to one or more sensors 6135 configured to sense one or more conditions modulated by physiological changes and/or symptoms of the non-rhythm pulmonary disease. The sensors of the respiratory device used to sense the conditions may include, for example, ventalitory airflow, ventilatory pressure, ventilatory gas, and/or other conditions modulated by symptoms of the non-rhythm pulmonary disease.

A representative set of symptoms and/or physiological changes associated with non-rhythm pulmonary diseases may involve dyspnea (e.g., non-specific dyspnea, orthopnea, exertional dyspnea, paroxysmal nocturnal dyspnea), abnormal concentrations of blood or respiratory gases (e.g., cyanosis, hypoxemia, hypercapnea, low pCO2, arterial acidosis, high alveolar—arterial $pO^2$ differential), pulmonary function dysfunction (e.g., low forced expiratory volume (FEV), forced vital capacity (FVC), FEV/FVC, low forced expiratory flow (FEF), high functional residual capacity (FRC), total lung capacity (TLC), high residual volume (RV), high lung compliance, slow exhalation, respiratory failure), other pulmonary conditions (e.g., ventilation-perfusion mismatch), and cardiovascular conditions (e.g., circulatory collapse).

Table 7 lists non-rhythm pulmonary disease symptoms or physiological changes, conditions indicative of the symptoms or physiological changes, and sensors of the respiratory therapy device that may be used to sense the conditions.

TABLE 7

| Symptom or Physiological Change | Condition | Sensor Used |
|---|---|---|
| Non-specific dyspnea | Exhaled % CO2 | CO2 sensor |
| Orthopnea | Exhaled % O2 | O2 sensor |
| Exertional dyspnea | Expiratory flow | Flowmeter |
| Paroxysmal nocturnal dyspnea | Inspiratory flow | Flowmeter |
| Cyanosis | Exhaled % O2 | O2 sensor |
| Hypoxemia | | |
| High alveolar-arterial pCO2 differential | | |
| Hypercapnea | Exhaled % CO2 | CO2 sensor |
| Low pCO2 | | |
| Arterial acidosis | | |
| Low FEV, FVC, FEV/FVC | Expiratory flow | Flowmeter |
| Low FEF | Inspiratory flow | Flowmeter |
| High FRC, TLC | Expiratory pressure | Pressure sensor |
| High RV | Inspiratory pressure | Pressure sensor |
| High lung compliance | | |
| Slow exhalation | | |
| Respiratory Failure | Exhaled % O2 | O2 sensor |
| Ventilation-perfusion mismatch | Exhaled % CO2 | CO2 sensor |
| Circulatory collapse | | |

The one or more sensors 6135 are coupled to sensor signal processor circuitry 6130 which may be configured to energize the sensors and to receive and condition signals generated by the sensors 6135. The sensor signal processor circuitry 6130 may comprise, for example, sensor driver circuitry, filters, sampling circuitry, and A/D converter circuitry. The sensor signals may be averaged, filtered, or otherwise processed by the signal processor circuitry 6130 prior to use by other components of the respiratory therapy device 6110.

The respiratory therapy device 6110, illustrated in FIG. 61A as a positive airway pressure (xPAP) device includes a respiration therapy control unit 6120. The respiration therapy control unit 6120 comprises a flow generator 6121 that pulls in air through a filter. The flow generator 6121 is controlled by the pressure control circuitry 6122 to deliver an appropriate air pressure to the patient. Air flows through tubing 6123 coupled to the xPAP device 6110 and is delivered to the patient's airway through a mask 6124. In one example, the mask 6124 may be a nasal mask covering only the patient's nose. In another example, the mask 6124 covers the patient's nose and mouth. Other air delivery systems are also possible.

Continuous positive airway pressure (CPAP) devices deliver a set air pressure to the patient. The pressure level for the individual patient may be determined during a titration study, for example. Such a study may take place in a sleep lab, and involves determination by a sleep physician or other professional of the optimum airway pressure for the patient. The CPAP device pressure control is set to the determined level. When the patient uses the CPAP device, a substantially constant airway pressure level is maintained by the device. The constant air pressure acts a pneumatic splint to keep soft tissue in the patient's throat from collapsing and obstructing the airway.

Autotitration PAP devices are similar to CPAP devices, however, the pressure controller for autotitration devices automatically determines the air pressure delivered to the patient. Instead of maintaining a constant pressure, the autotitration PAP device evaluates sensor signals and the changing needs of the patient to deliver a variable positive airway pressure. Autotitration PAP and CPAP are often used to treat sleep disordered breathing, for example.

Bi-level positive airway pressure (bi-PAP) devices provide two levels of positive airway pressure. A higher pressure is maintained while the patient inhales. The device switches to a lower pressure during expiration. Bi-PAP devices are used to treat a variety of respiratory dysfunctions, including chronic obstructive pulmonary disease (COPD), respiratory insufficiency, and ALS or Lou Gehrig's disease, among others.

The xPAP device may include a memory 6150 that stores criteria used in the assessment of pulmonary disease. The memory may additionally or alternatively store information related to measurements of the conditions sensed by the xPAP device.

In accordance with various embodiments of the invention, the xPAP device 6110 may include a diagnostic unit 6160 that evaluates patient conditions sensed by the sensors 6135 and assesses a presence of a non-rhythm pulmonary disease. For example, the diagnostic unit 6160 may compare the measured conditions to sets of criteria indicative of non-rhythm pulmonary diseases. If the measured conditions are consistent with a particular set of criteria, the diagnostic unit may indicate that the non-rhythm pulmonary disease associated with the particular criteria set is present.

The xPAP device 6110 may include a communications unit 6140 for communicating with one or more separate devices 6170, such as a device programmer or a cooperating patient-external or patient-internal monitoring, diagnostic and/or therapeutic device. Communication between cooperating devices allows the xPAP device 6110 to provide information to the cooperating device or devices or to control therapy delivered by the cooperating devices, for example. In one scenario, the xPAP device 6110 may transmit to a cooperating therapy device information about the presence of a non-rhythm pulmonary disease/disorder. The therapy device may adjust therapy delivered by the device based on the presence of the non-rhythm pulmonary disease/disorder. Additionally, or alternatively, the xPAP device 6110 may adjust the respiration therapy delivered to the patient based on the non-rhythm pulmonary disease assessment.

In one implementation, a system for assessment of non-rhythm pulmonary disorders may be used within the structure of an advanced patient management system. In this implementation, an advanced patient management system includes a remote computer system that allows a physician to remotely monitor cardiac, respiratory, and other patient functions. The advanced patient management system may have the capability of assessing the presence of various non-rhythm pulmonary diseases based on respiration measurements acquired by the xPAP device 6110 and transmitted to the APM system.

As previously discussed, the xPAP device 6110 may include a memory 6150 for storing data related to the non-rhythm pulmonary disease. For example, the xPAP device 6110 may initiate collection and storage of data hourly, nightly, weekly, or according to some other time schedule that corresponds to the patient's usage times of the respiratory therapy device. Typically an xPAP device is used nightly for treatment of sleep apnea and/or other breathing rhythm disorders. The xPAP device 6110 may collect data from the sensors 6135 during one or more periods of time that the device is used. The presence of the non-rhythm pulmonary disease may be assessed based on the collected data. Assessment of the presence of the non-rhythm pulmonary disease may involve assessment of the severity of the disease, disease onset, changes during the course of the disease, regression, disease offset, and/or other aspects of the disease.

Figure 61B:
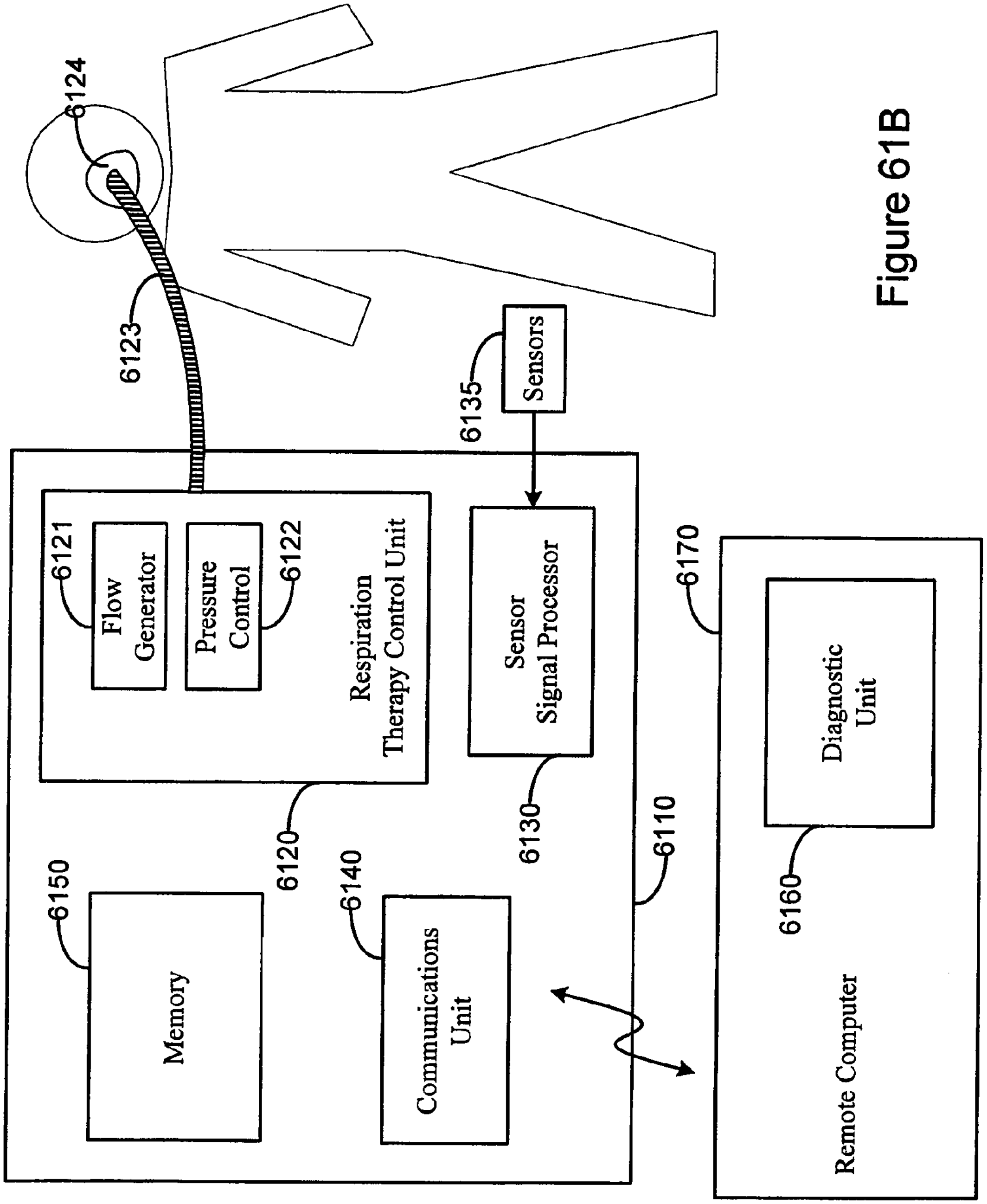

In one implementation, the diagnosis unit 6160 is a component of the respiratory therapy device 6110, as illustrated in FIG. 61A. In another implementation, the diagnosis unit 6160 may be configured as a component of a device 6170 separate from the respiratory therapy device 6110. The latter implementation is illustrated in the block diagram of FIG. 61B. In this implementation, the respiratory therapy device 6110 may transmit information about conditions sensed by the respiratory therapy device 6110 to the diagnosis unit 6160 of a remotely located device 6170. The diagnosis unit 6160 assesses the non-rhythm pulmonary disease presence based on the transmitted information.

The remote device 6170 may comprise a patient-external or patient-internal medical device. The remote device 6170 may be configured, for example, as a cardiac diagnostic and/or therapeutic device. In one configuration, for example, the remote device may comprise a cardiac rhythm management system, such as a pacemaker, defibrillator, and/or cardiac resynchronizer.

Figure 61C:
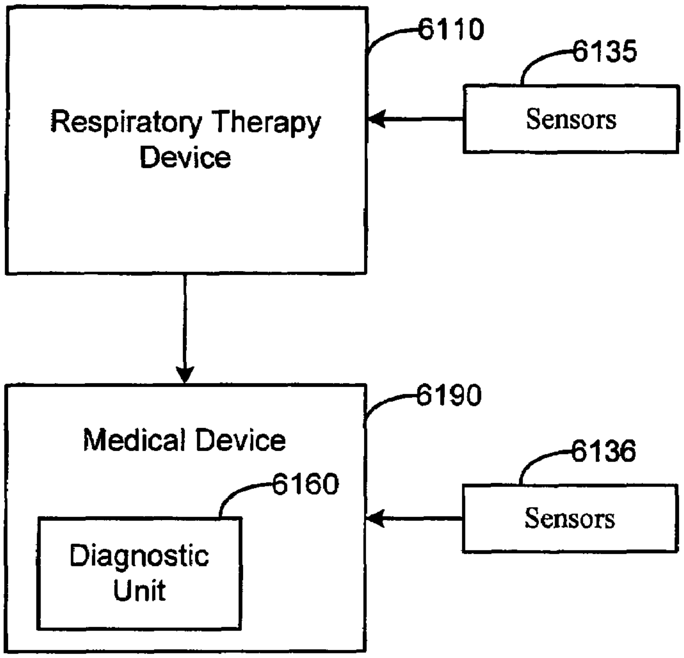
Figure 61D:
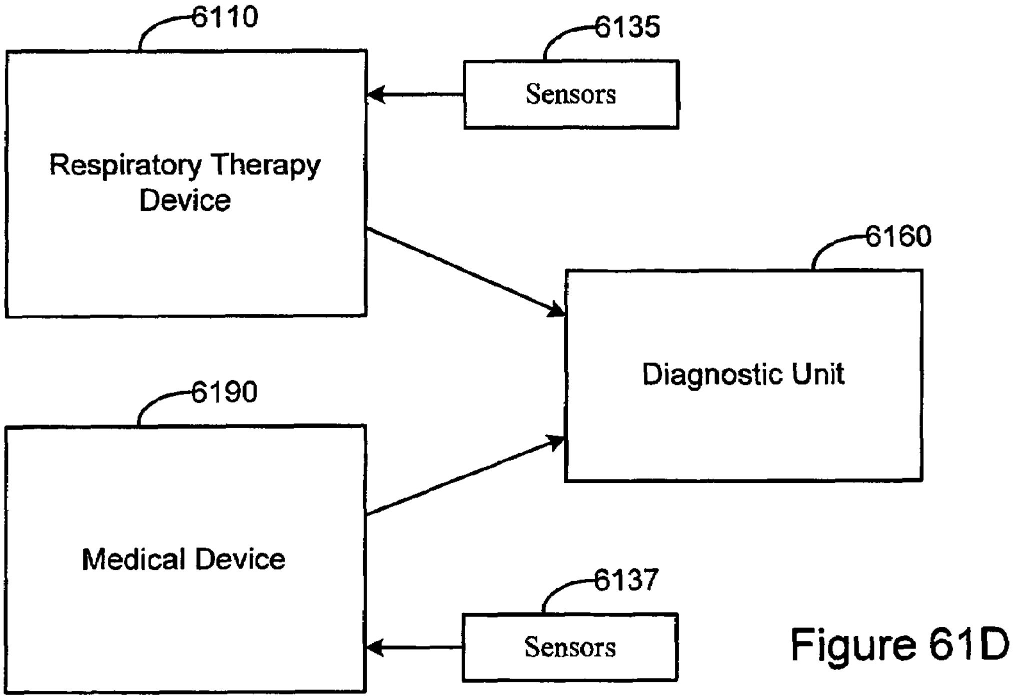

The block diagrams of FIGS. 61C and 61D illustrate other exemplary arrangements that may be used for pulmonary disease assessment in accordance with embodiments of the invention. The system illustrated in FIG. 61C includes a respiratory therapy device 6110 and a medical device 6190 remote from the respiratory therapy device 6110. In this example, both the respiratory therapy device 6110 and the medical device 6190 are equipped with sensors 6135, 6136 for sensing conditions associated with symptoms of one or more non-rhythm pulmonary diseases. For example, the respiratory therapy device 6110 and the additional medical device 6190 may each sense a subset of the conditions listed in Table 1. The respiratory therapy device 6110 may transmit its sensed condition information to the medical device 6190 over a wired or wireless communications link. The medical device 6190 includes a diagnostic unit 6160 configured to assess a presence of one or more non-rhythm pulmonary diseases. The diagnostic unit 6160 may assess the non-rhythm pulmonary diseases, for example, by comparing sensed conditions to one or more sets of criteria indicative of the non-rhythm pulmonary diseases as previously described.

The block diagram of FIG. 61D illustrates a further exemplary arrangement of a pulmonary disease assessment system. In this example, the system includes a respiratory therapy device 6110 and an additional medical device 6190, e.g., a therapeutic or monitoring device. The respiratory therapy device 6110 and the additional medical device 6190 communicate with a diagnostic unit 6160, such as a diagnostic unit of an APM system. The respiratory therapy device 6110 and the additional medical device 6190 are each equipped with sensors 6135, 6136 for sensing conditions associated with one or more non-rhythm pulmonary diseases. The respiratory therapy device 6110 and the medical device 6190 may transmit sensed condition information to the diagnostic unit 6160 through wireless or wired communication links. The pulmonary disease diagnostic unit 6160 is configured to use the information transmitted by the respiration therapy device 6110 and the medical device 6190 to assess the presence of one or more non-rhythm pulmonary diseases.

Figure 62A:
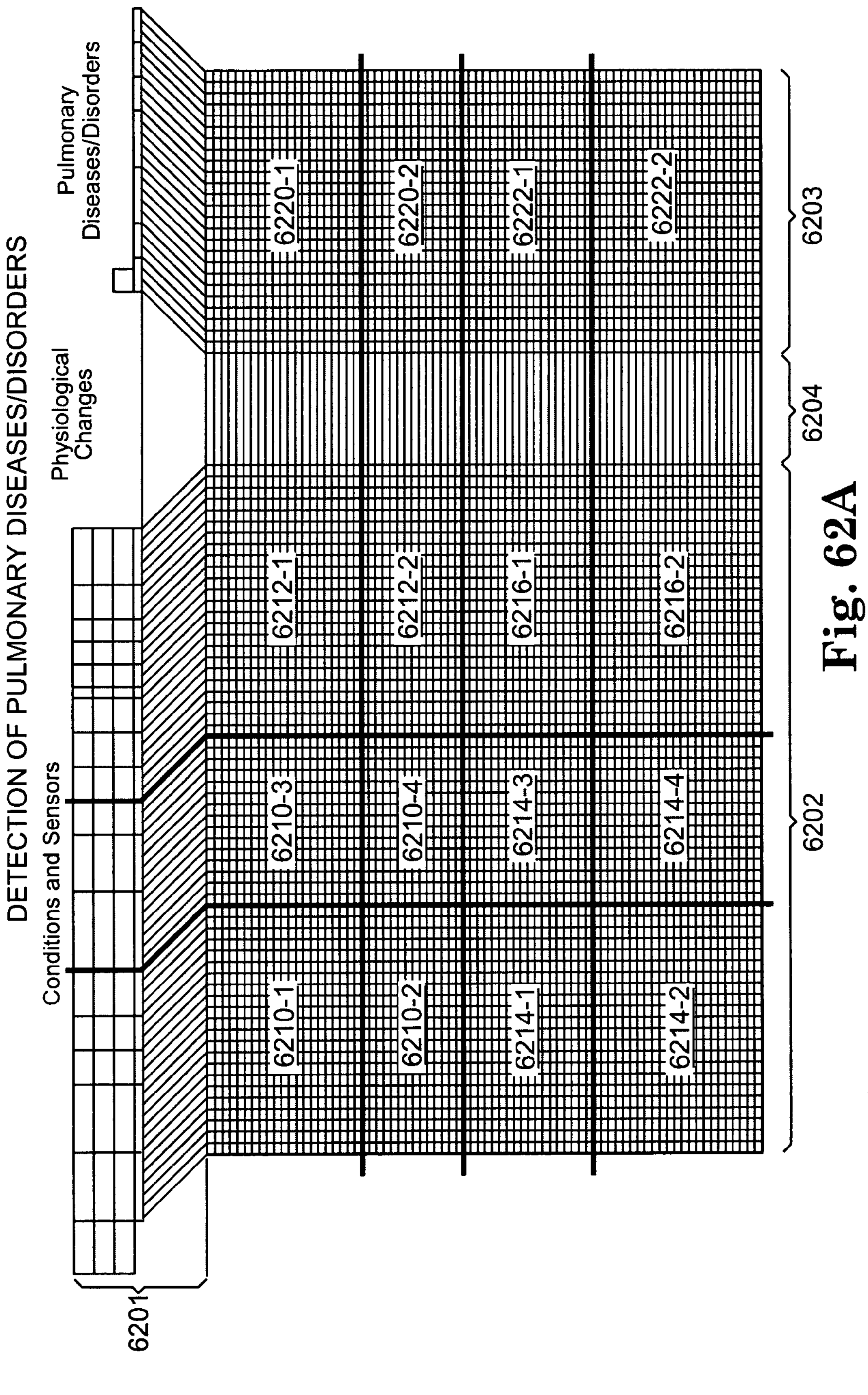
FIGS. 62A-62N are charts illustrating relationships between pulmonary or cardiac diseases, symptoms and/or physiological changes caused by the pulmonary diseases, and conditions used to detect the symptoms and/or physiological changes in accordance with embodiments of the invention.

Assessment of conditions indicative of non-rhythm pulmonary diseases/disorders may include assessing the patient's pulmonary function as previously described. The charts provided in FIGS. 62A-62G-2 illustrate conditions and sensors that may be used to determine physiological changes associated with various non-rhythm pulmonary diseases and disorders. The charts depicted in FIGS. 62A-62G-2 illustrate relationships between various physiological changes and/or disease symptoms associated with non-rhythm pulmonary diseases. FIG. 62A lists representative sets of non-rhythm pulmonary diseases that may be assessed in accordance with embodiments of the invention. The representative set of non-rhythm pulmonary diseases that may be assessed includes, for example, obstructive pulmonary diseases (e.g., chronic bronchitis, emphysema, asthma), restrictive pulmonary diseases (e.g., sarcoidosis, pulmonary fibrosis, pneumoconiosis), infections pulmonary diseases (e.g., bronchitis, pneumonia, bronchiolitis, tuberculosis, and bronchiectasis), pulmonary vasculature diseases (e.g., pulmonary hypertension, pulmonary edema, pulmonary embolism, atalectasis), and diseases of the pleural cavity (e.g., pleural effusion, pneumothorax, and hemothorax).

The non-rhythm pulmonary diseases listed in FIG. 62A are cross-referenced with the physiological changes and/or symptoms associated with the non-rhythm pulmonary disease. The physiological changes and/or symptoms are cross referenced with conditions indicative of the physiological changes and/or symptoms. Sensors used to sense the conditions indicative of the physiological changes or symptoms are provided in FIG. 62A. Sensors of the respiratory therapy device may include, for example, ventilation gas, ventilation flow and/or ventilation pressure sensors, or other sensors for example.

The left section 6202 of FIG. 62A illustrates various conditions that may be sensed using sensors of a respiratory therapy device (CPAP), a cardiac device (CRM), or an external non-CPAP, non-CRM device. The top section 6201 lists various conditions that may be sensed and information about sensors used to sense the conditions. The center section 6204 of FIG. 62A provides physiological changes and/or symptoms that may be evaluated using the conditions listed in the left section 6202. The right section 6203 of FIG. 62A provides pulmonary diseases/disorders. The presence of the pulmonary diseases/disorders of the right section 6203 may be assessed based on the physiological changes and/or symptoms of the center section 6204.

For legibility, the left and right sections 6202, 6203 of FIG. 62A are divided into sixteen portions, FIGS. 62B-1-62G-2. FIGS. 62B-1 to 62B-4 represent the upper left portions 6210-1 to 6210-4 of the left section 6202 of FIG. 62A. FIGS. 62C-1 to 62C-2 represent the upper right portions 6212-1 to 6212-2 of the left section 6202 of FIG. 62A. FIGS. 62D-1 to 62D-4 represent the lower left portions 6214-1 to 6214-4 of the left section 6202 of FIG. 62A. FIGS. 62E-1 to 62E-2 represent the lower right portions 6216-1 to 6216-2 of the left section 6202 of FIG. 62A. FIGS. 62F-1 to 62F-2 represent the upper portions 6220-1 to 6220-2 of the right section 6203 of FIG. 62A. FIGS. 62G-1 to 62G-2 represent the lower portions 6222-1 to 6222-2 of the right section 6203 of FIG. 62A. Relevant portions of the center section 6204 and the top section 6201 of FIG. 62A appear in each of the FIGS. 62B-1-62G-2 for convenience.

An example of how FIGS. 62A-62N may be used follows. Referring to FIGS. 62F-1 to 62G-1, the restrictive pulmonary disorder pneumoconiosis produces the physiological changes non-specific dyspnea (FIG. 62F-1) and cough (FIG. 62G-1). Non-specific dyspnea (FIG. 62F-1) and cough (FIG. 62G-1) are indicated by marks in the column denoted pneumoconiosis in FIGS. 62F-1 to 62G-1. Non-specific dyspnea may be detected based on one or more of the conditions listed in the row for non-specific dyspnea illustrated in FIGS. 62B-1, 62B-3, and 62C-1. The conditions include duration of symptoms, abnormal breathing/coughing, blood pO2, inspiratory flow, expiratory flow, exhaled % CO2 and exhaled % O2, illustrated in FIG. 62C-1. The conditions also include arterial/venous pO2, blood pCO2, blood pO2, exhalation time, inspiration time, minute ventilation, tidal volume, respiration rate, FIG. 62B-3, and/or respiration sounds illustrated in FIG. 62B-1.

The presence of a disorder/disease, such as those listed in FIGS. 62A-62G-2, may be assessed by based on physiological changes and/or symptoms associated with the disorder/disease. The physiological changes and/or symptoms may be detected using conditions sensed by a sensor system of a respiratory therapy alone or in combination with the sensor systems of other therapeutic or diagnostic medical devices. If the sensed conditions indicate that the physiological changes or symptoms of a disease or disorder are consistent with a threshold level, the presence of the disease or disorder may be determined.

In another example, assessment of disease presence may be based on relative changes in one or more conditions indicative of physiological changes or symptoms caused by the disease. For example, assessment of a presence of a disease or disorder may be accomplished by evaluating the changes in conditions indicative of physiological changes or symptoms caused by the disease. The changes in the one or more conditions may be compared to threshold criteria. If changes in the conditions indicative of physiological changes or symptoms caused by the disease are consistent with threshold levels, a presence of the disease or disorder may be determined.

In a further example, the threshold criteria may involve relationships between the conditions indicative of physiological changes or symptoms caused by the disease. The presence of a disease may be assessed by evaluating relationships between conditions indicative of physiological changes or symptoms caused by the disease. For example, assessment of a disease may involve the determination that levels or amounts of two or more conditions have a certain relationship with one another. If relationships between the conditions indicative of physiological changes or symptoms caused by the disease are consistent with threshold relationship criteria, the disease or disorder may be present.

In accordance with various embodiments of the invention, the presence of a non-rhythm pulmonary disease, such as those listed in FIGS. 62A-62G-2, may be assessed by evaluating conditions indicative of the non-rhythm pulmonary disease sensed using a respiration therapy device. In one example, the presence of a non-rhythm pulmonary disease may be assessed by comparing conditions indicative of physiological changes or symptoms caused by the disease to threshold criteria. If the conditions indicative of physiological changes or symptoms caused by the disease are consistent with threshold levels, the system may determine that the non-rhythm pulmonary disease or disorder is present.

In another example, assessment of disease presence may be based on relative changes in one or more conditions indicative of physiological changes or symptoms caused by the disease. For example, diagnosis of a non-rhythm pulmonary disease may be effected by evaluating the changes in conditions indicative of physiological changes or symptoms caused by the disease. The changes in the one or more conditions may be compared to threshold criteria. If changes in the conditions indicative of physiological changes or symptoms caused by the disease are consistent with threshold levels, the non-rhythm pulmonary disease or disorder may be present.

In a further example, the threshold criteria may involve relationships between the conditions indicative of physiological changes or symptoms caused by the disease. The presence of a non-rhythm pulmonary disease may be assessed by evaluating relationships between conditions indicative of physiological changes or symptoms caused by the disease. For example, assessment of a disease may involve the determination that levels or amounts of two or more conditions have a certain relationship with one another. If relationships between the conditions indicative of physiological changes or symptoms caused by the disease are consistent with threshold relationship criteria, the non-rhythm pulmonary disease or disorder may be present.

Figure 63A:
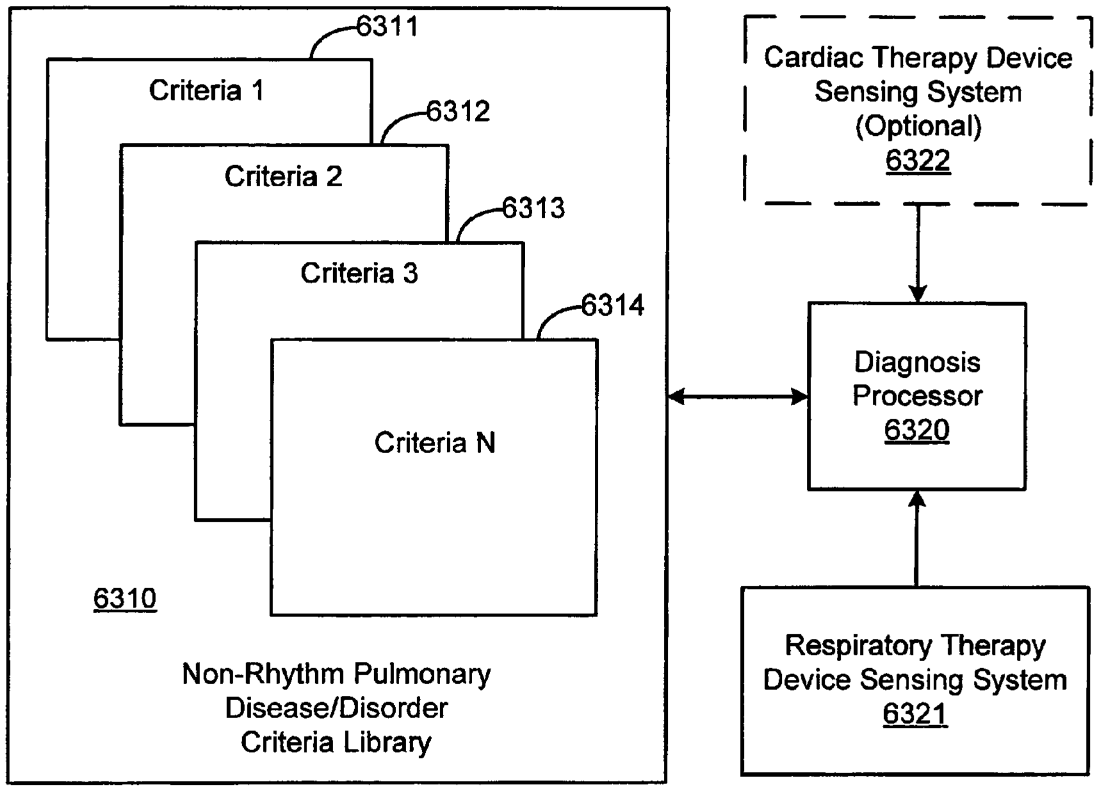
FIG. 63A is a block diagram of a system that may be used to assess a pulmonary disease in accordance with embodiments of the invention.

FIG. 63A illustrates a system for assessing a presence of a non-rhythm pulmonary disease/disorder in accordance with embodiments of the invention. The system includes a diagnosis processor 6320 that receives information from a sensing system of a respiratory device 6321. The sensing system 6321 measures one or more conditions associated with a non-rhythm pulmonary disease or disorder. In some embodiments, the diagnosis processor may also receive sensory information from another device 6322, such as a cardiac therapy device.

The diagnosis processor 6320 accesses a criteria library 6310. The criteria library 6310 stores sets of criteria 6311-6314 respectively associated with various non-pulmonary diseases/disorders. FIGS. 63B-63K illustrate criteria sets that may be used to assess a presence of non-rhythm pulmonary disease in accordance with embodiments of the invention. The exemplary criteria sets may be used to assess the presence of chronic bronchitis (FIG. 63B), emphysema (FIG. 63C), asthma (FIG. 63D), pulmonary fibrosis (FIG. 63E), pulmonary hypertension (FIG. 63F), pulmonary edema (FIG. 63G), pulmonary embolism (FIG. 63H), atelectasis (FIG. 63I), and hemothorax (FIG. 63J). The charts of FIGS. 63A-63J list physiological changes or symptoms associated with the non-rhythm pulmonary disease in the left hand column, conditions used to detect the particular physiological change or symptom in the middle column, and the respiration therapy device sensor used to sense the condition in the right hand column.

Using FIG. 63J as a representative example, the presence of atelectasis may be assessed based on the symptoms nonspecific dyspnea, hypoxemia, and/or hypercapnia. Non-specific dyspnea may be detected based on one or more of the following criteria: exhaled % CO2, exhaled % O2, expiratory flow, and/or inspiratory flow. The levels of one or more of these conditions may be compared to threshold levels for assessment of atelectasis. Other symptoms associated with atelectasis include hypoxemia, which may be determined based on comparison of the patient's exhaled % O2 to a threshold criterion, and hypercapnia, which may be determined based on comparison of the patient's exhaled % CO2 to a threshold criterion.

The criteria listed in FIGS. 63B-63J involve conditions that may be detected using sensors of a respiratory therapy device, such as a CPAP device. The non-rhythm pulmonary disease assessment system described herein may use one or more additional sensors and/or devices other than the respiratory therapy device to enhance disease assessment, such as those indicated in FIGS. 62A-62G-2. In one example, conditions detected using an external respiratory therapy device, e.g., CPAP device, may be used along with conditions detected using an implantable cardiac device, e.g., pacemaker or defibrillator to assess the presence of a non-rhythm pulmonary disease. In another example, conditions detected using an external respiratory therapy device, e.g., CPAP device, may be used along with conditions detected using an additional external device.

FIG. 63K illustrates an exemplary criteria set for assessing a presence of tuberculosis. Tuberculosis may be assessed based on conditions sensed using a respiratory therapy device in addition to conditions sensed using other devices. FIG. 63K lists physiological changes or symptoms associated with tuberculosis in the left hand column, conditions used to assess a presence of tuberculosis in the middle column, and the respiration therapy device sensor or other device sensor used to sense the condition in the right hand column.

Figure 64A:
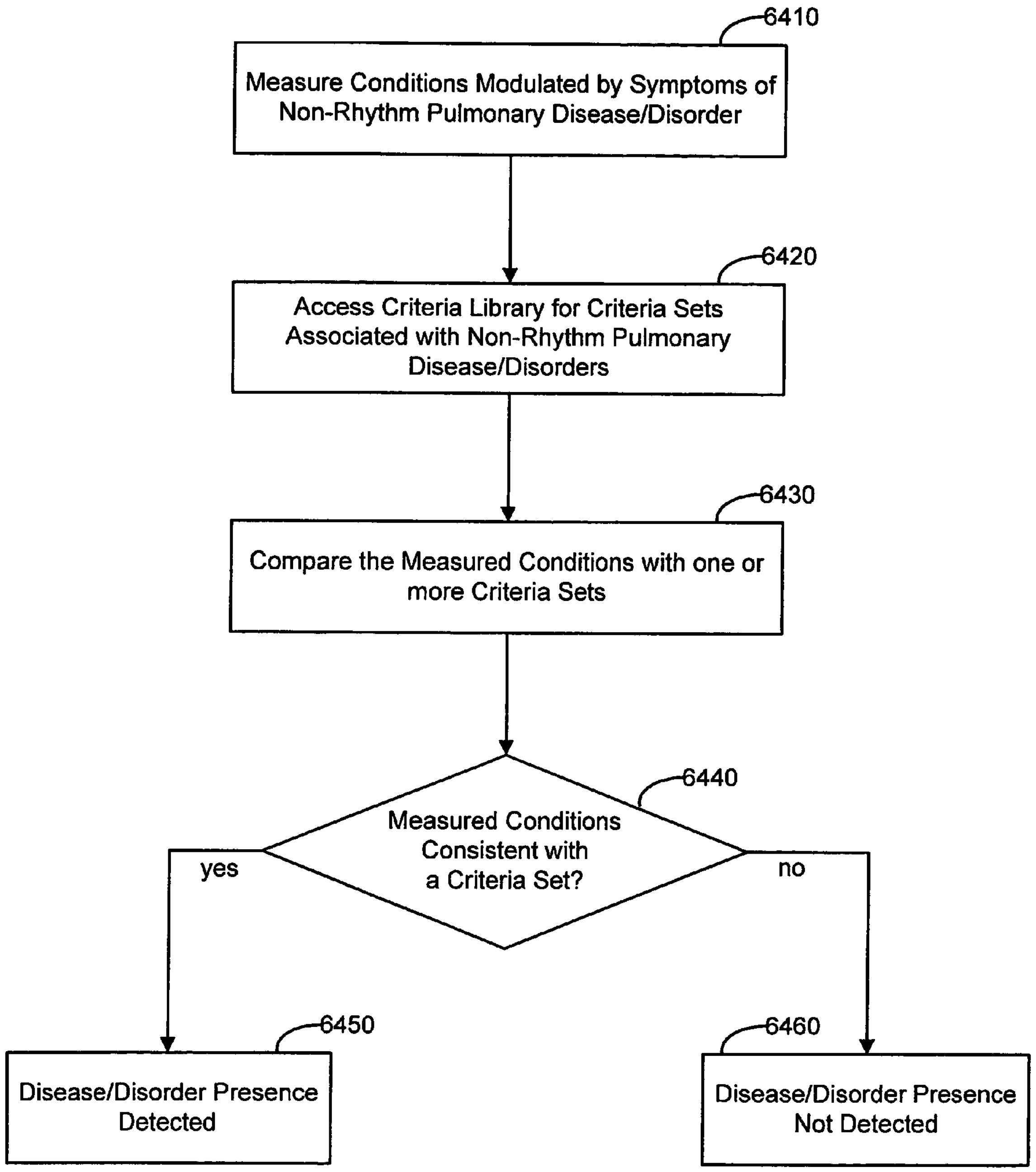
FIGS. 64A-64B are flowcharts illustrating methods of assessing a presence of a non-rhythm pulmonary disease in accordance with embodiments of the invention.

FIG. 64A is a flowchart illustrating a method for assessing a presence of a non-rhythm pulmonary disease/disorder in accordance with embodiments of the invention. The processes of FIG. 64A may be implemented using system components and criteria sets such as those illustrated in FIGS. 63A-63K.

One or more conditions modulated by symptoms of a non-rhythm pulmonary disease/disorder are measured 6410. The conditions may be sensed by a sensing system of a respiratory therapy device, and optionally, by a sensing system of another medical device, such as a cardiac rhythm management device. A diagnosis processor receives the measured conditions and accesses 6420 a criteria library. The diagnostic unit compares 6430 the measured conditions with the one or more criteria sets.

If the measured conditions are consistent 6440 with a particular criteria set, the presence of the non-rhythm pulmonary disease/disorder associated with the particular criteria set is detected 6450. If the If the measured conditions are not consistent 6440 with a particular criteria set, the presence of the non-rhythm pulmonary disease/disorder associated with the particular criteria set is not detected 6460.

According to some embodiments, the system may monitor the non-rhythm pulmonary disease/disorder. Monitoring the progression of the disease/disorder may include periodically measuring the conditions relevant to the disease/disorder and storing information relevant to the disease/disorder. The periodically measured conditions may be used to monitor the severity of the disease, disease onset, symptoms or physiological changes during the course of the disease, disease regression, disease offset, and/or other aspects of the disease.

Figure 64B:
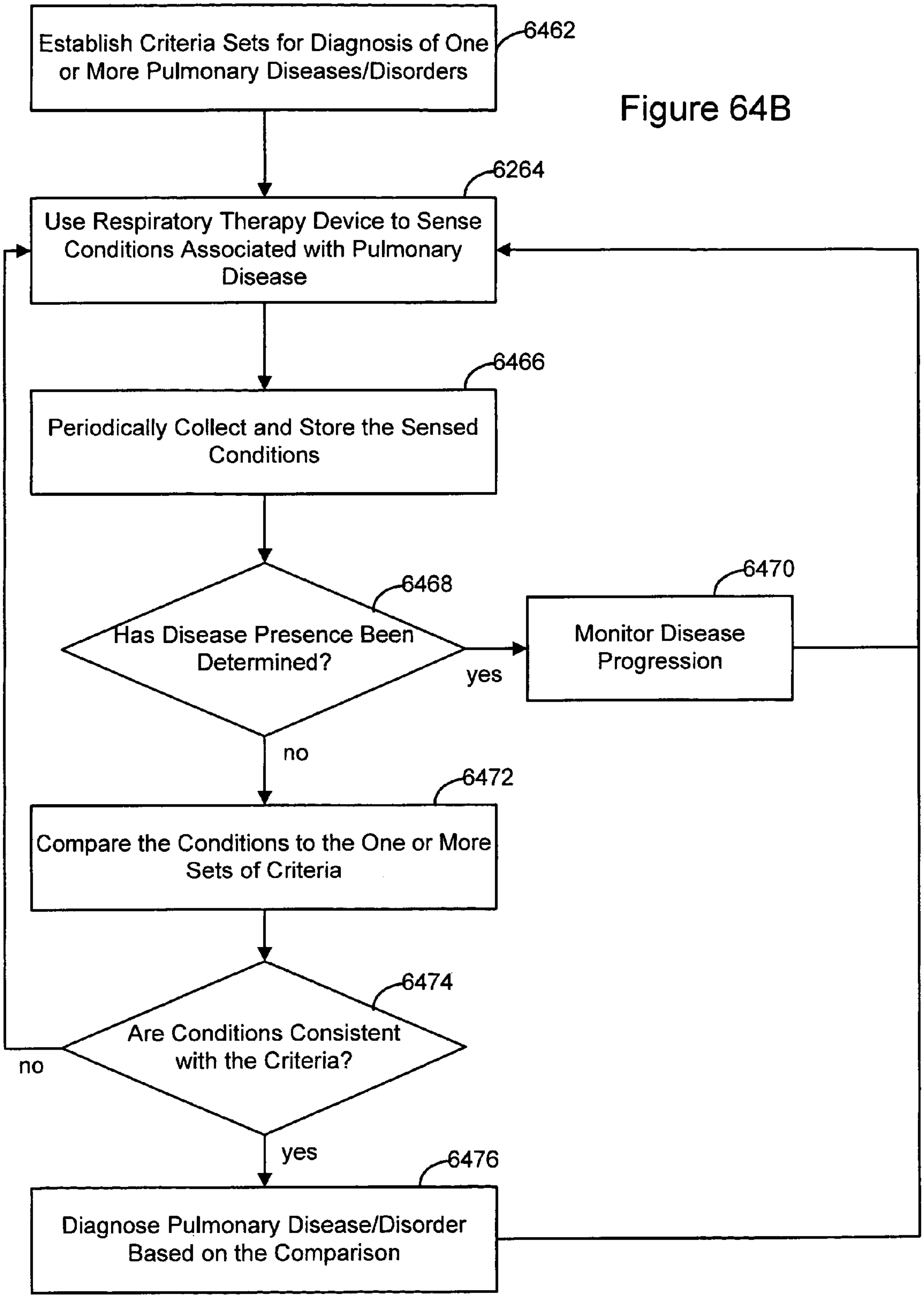

FIG. 64B is a flowchart illustrating a method of monitoring a presence of a non-rhythm pulmonary disease in accordance with embodiments of the invention. Criteria sets for assessment of the non-rhythm pulmonary diseases are established 6462. A respiratory therapy device such as a CPAP device is used 6464 to sense conditions modulated by disease symptoms. The sensor information may be gathered periodically 6466, e.g., nightly, and stored for evaluation. If a presence of the disease was previously determined 6468, then the progression of the disease may be monitored 6470 based on the conditions used to determine a presence of the disease, or other conditions.

If a presence of the disease was not previously determined 6468, then the levels of the sensed conditions are compared 6472 to a set of criteria associated with the disease. If levels of the conditions are consistent 6474 with the threshold levels, then the presence of the disease is determined 6476. If levels of the conditions are not consistent 6470 with the threshold levels, then the system continues 6464 to sense conditions modulated by disease symptoms.

Coordination of Respiratory and Cardiac Therapies for Disordered Breathing

Aspects of the invention are directed to methods and systems configured to provide coordinated respiratory and cardiac therapies for disordered breathing using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving disordered breathing therapy are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 138 (FIG. 1B) for coordinating disordered breathing therapy. The coordinated disordered breathing therapy system 138 may be implemented as a stand alone system or in combination with other individual medical systems, such as those described in FIGS. 1B-1D.

Various embodiments of present invention involve methods and systems for coordinating sleep disordered breathing therapies. In accordance with one embodiment, a method for treating disordered breathing includes controlling a patient-external respiratory therapy delivered to a patient and controlling a cardiac therapy delivered to the patient. The patient-external respiratory therapy and the cardiac therapy are coordinated to treat the disordered breathing.

In accordance with another embodiment of the invention, a medical system includes a respiratory therapy controller configured to control an external respiratory therapy delivered to a patient and a cardiac therapy controller configured to deliver a cardiac therapy to the patient. The system also includes a processor, coupled to the respiratory therapy controller and the cardiac therapy controller. The processor is configured to coordinate delivery of the external respiratory therapy and the cardiac therapy to treat disordered breathing.

Another embodiment of the invention involves a system for providing coordinated patient monitoring, diagnosis and/or therapy that utilizes coordination 138 of delivery of disordered breathing therapy. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy further includes a system 138 configured to coordinate delivery of disordered breathing therapy. The disordered breathing delivery coordination system 138 includes a respiratory therapy controller configured to control an external respiratory therapy delivered to a patient and a cardiac therapy controller configured to control a cardiac therapy delivered to the patient. The system further includes a processor coupled to the respiratory therapy controller and the cardiac therapy controller for coordinating delivery of the external respiratory therapy and the cardiac therapy in order to treat the disordered breathing. Systems and methods directed to coordinate use of respiratory and cardiac therapies for sleep disordered breathing may be implemented to include selected features, functions, and/or structures described in commonly owned, U.S. Pat. No. 7,591,265, which is hereby incorporated herein by reference.

Sleep disordered breathing may be more effectively monitored and/or treated using a coordinated approach. Various embodiments of the invention are implemented using medical systems employing two or more patient-external and/or patient-internal medical devices. The medical devices may communicate or otherwise operate in concert to provide coordinated disordered breathing therapy.

Embodiments of the invention are directed to methods and systems utilizing a plurality of therapies to treat sleep disordered breathing. The therapies include, at least, an external respiratory therapy and cardiac electrical stimulation therapy. Other therapies may also be cooperatively utilized.

Delivery of the plurality of therapies may be coordinated to achieve various therapeutic goals, e.g., to enhance overall therapy efficacy, to reduce impact to the patient, to avoid therapy interactions, among others. According to one example, coordination of therapies may involve shifting the therapy burden from one type of therapy to another type of therapy in response to events or conditions. In one implementation, shifting the burden from one type of therapy to another type of therapy may involve initiating or increasing a first type of disordered breathing therapy and terminating or decreasing a second type of disordered breathing therapy. Another example of coordinating therapy may involve using one type of therapy to treat one type of disordered breathing, and using another type of therapy to treat another type of disordered breathing.

Various types of therapies have been used to treat sleep disordered breathing. Positive airway pressure devices, e.g., continuous positive airway pressure (CPAP) devices are among the most frequently used mechanical respiration therapy devices employed for treating sleep disordered breathing. Sleep disordered breathing has also been treated using muscle and/or nerve stimulation therapy. For example, a treatment for obstructive sleep apnea involves electrical activation of the tongue muscles. The hypoglossal (HG) nerve innervates the protrusor and retractor tongue muscles. In one approach, an appropriately applied electrical stimulation to the hypoglossal nerve, for example, may prevent backward movement of the tongue, thus preventing the tongue from obstructing the airway.

Central sleep apnea may also be treated by phrenic nerve pacing, also referred to as diaphragmatic pacing. Phrenic nerve pacing uses an electrode implanted in the chest to stimulate the phrenic nerve. The phrenic nerve is generally known as the motor nerve of the diaphragm. It runs through the thorax, along the heart, and then to the diaphragm. Diaphragmatic pacing involves the use of electronic stimulation of the phrenic nerve to control the patient's diaphragm and induce a respiratory cycle. Pacing the phrenic nerve may be accomplished by surgically placing a nerve cuff on the phrenic nerve, and then delivering an electric stimulus. The electric stimulus of the phrenic nerve then causes the diaphragm to induce a respiratory cycle.

Recently, cardiac pacing therapy has been used as a therapy for disordered breathing. Cardiac pacing therapy may be implemented using an implanted electrical pulse generator coupled to endocardiac leads inserted into one or more heart chambers. Cardiac pacing for sleep disordered breathing treatment may include pacing one or more heart chambers, and may involve pacing at a rate above a lower rate limit during sleep and/or during episodes of disordered breathing, for example. Other forms of cardiac pacing such as cardiac resynchronization therapy, biventricular pacing can be delivered to the patient to treat disordered breathing.

Another cardiac therapy that can be adapted to mitigate disordered breathing involves non-excitatory stimulation therapy. In one example, non-excitatory cardiac stimulation therapy involves electrical stimulation of one or more heart chambers, e.g., the left and/or right ventricles, or other cardiac sites, at an energy level below a capture threshold. In another example, non-excitatory cardiac stimulation therapy involves cardiac electrical stimulation delivered to one or more heart chambers during absolute refractory periods of the cardiac tissue. The non-excitatory stimulation may improve cardiac contractility. The non-excitatory cardiac stimulation therapy may be used alone or in combination with cardiac pacing therapy to provide a comprehensive therapy regimen for patients with CHF and disordered breathing such as Cheyne-Stokes respiration.

Cardiac therapy has also been used to mitigate disordered breathing using methods that involve overdrive cardiac pacing of one or more atria or one or more ventricles.

Drug therapy may also be used to treat disordered breathing. Drugs may be delivered to the patient through one or more automatically controllable drug delivery devices, e.g., a drug pump, a controllable nebulizer, or an electrically activated drug patch, for example.

Figure 65:
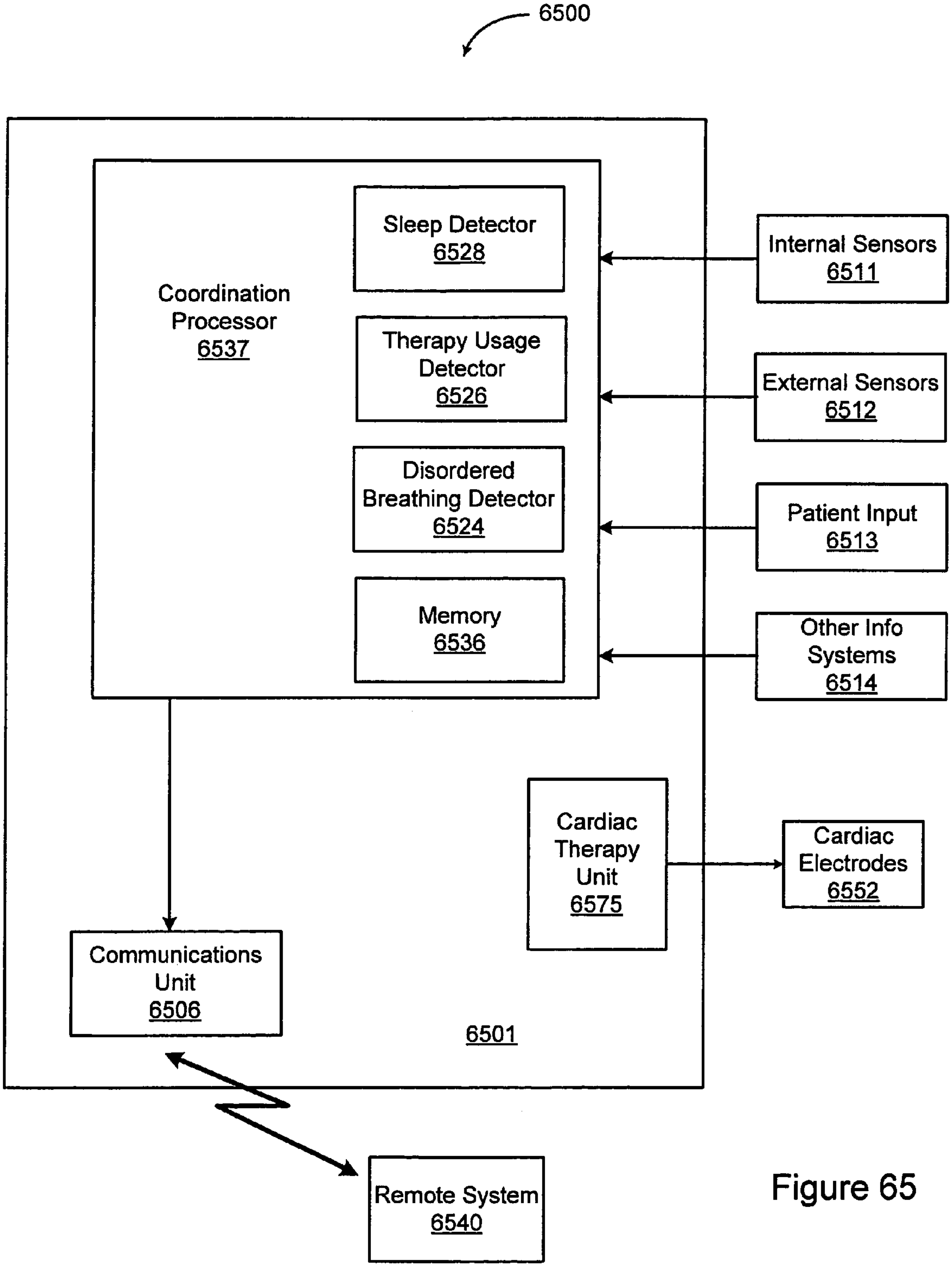
FIG. 65 is a block diagram of an implantable medical device including a cardiac therapy pulse generator that may be utilized in a system delivering coordinated disordered breathing therapy in accordance with embodiments of the invention.

The block diagram of FIG. 65 illustrates an example of system 6500 including a fully or partially implantable device 6501 that may be used to monitor patient conditions and to coordinate sleep disordered breathing therapy in accordance with embodiments of the invention. The medical device 6501 may be coupled to an array of data acquisition devices, including patient-internal sensors 6511, patient-external sensors 6512, patient input devices 6513, and/or other information systems 6514 as described in more detail above. Patient conditions monitored by the implantable device 6501 may include both physiological and non-physiological contextual conditions affecting the patient such as those listed in Table 1.

The implantable device 6501 of FIG. 65 includes a coordination processor 6537 for processing signals received from the sensors, 6511, 6512, patient input devices 6513, and/or other information system 6514. The coordination processor 6537 may include one or more a detection units 6524, 6526, 6528 that detect the occurrence of various physiological events. For example, the coordination processor 6537 may include one or more of a disordered breathing detector 6524, a sleep detector 6528, and/or a therapy usage detector 6526. Other event detection components may also be included. The coordination processor 6537 may be used to calculate various indices, e.g., AHI, % PB, and/or arousals per unit time, used for evaluating therapy efficacy, and/or therapy impact. The coordination processor 6537 may compare the patient's therapy usage to a prescribed therapy to determine therapy compliance. The coordination processor 6537 can develop control signals for implementing a coordinated therapy based on the monitored conditions, the detected events, and/or the calculated indices.

In one exemplary implementation, the disordered breathing detector 6524 may be coupled to a respiration sensor. The disordered breathing detector 6524 may use the respiration signal developed by the respiration sensor to detect disordered breathing events based on the inspiratory and expiratory phases of the patient's respiration cycles, for example. The sleep detector 6528 may analyze various inputs from the patient-internal sensors 6511, patient-external sensors 6512, patient input devices 6513, other information systems 6514 to detect sleep-related events, including, for example, sleep onset, sleep offset, sleep stages, and arousals from sleep.

The coordination processor 6537 may include a memory 6536 for storing information derived from signals produced by the patient-internal sensors 6511, patient-external sensors 6512, patient input devices 6513, and/or other information systems 6514. The memory 6536 may also store information about detected events, e.g., sleep and disordered breathing events, and/or information related to calculated indices characterizing various events such as sleep and/or disordered breathing events. The stored data may be used by coordination processor 6537 to develop a coordinated disordered breathing therapy. The stored data may be retrieved by another component of the medical device 6501 for later use, or may be transmitted to a separate device 6540 for storage, further processing, trending, analysis and/or display, for example. In one scenario, the stored data can be downloaded to a separate device periodically or on command. The stored data may be presented to the patient's health care professional on a real-time basis, or as a long-term, e.g., month long or year long, trend of daily measurements.

In the particular embodiment illustrated in FIG. 65, the medical device 6501 includes a cardiac therapy unit 6575. This example, the medical device 6501 comprises a cardiac therapy device 6575 configured as a cardiac pulse generator to deliver cardiac electrical stimulation therapy via electrical stimulation electrodes 6552.

The medical device 6501 may further include a communications unit 6506 that controls communications between the medical device 6501 and other devices or systems. For example, the communications unit 6506 may be used to provide wireless or wired communications links between the medical device 6501 and one or more of the patient-internal sensors 6511, patient-external sensors 6512, patient input devices 6513, and information systems 6514.

The communications unit 6506 may also facilitate communications between the medical device 6501 and a remote device 6540 such as another sleep disordered breathing therapy device, a programmer, and/or an APM system. The wireless connections coupling the medical device 6501 to various other devices and systems may utilize a variety of wireless protocols, including, for example, Bluetooth, IEEE 802.11, and/or a proprietary wireless protocol.

Detecting the onset, termination, duration, stages, and quality of sleep experienced by a patient may be employed in connection with constructing a coordinated disordered breathing therapy. Patients suffering from sleep apnea, or other types of sleep disordered breathing, may be treated for sleep disordered breathing only during periods of sleep. Coordinating disordered breathing therapy may involve determining if the patient is asleep and/or detecting various sleep-related processes, such as arousals from sleep and/or REM or non-REM sleep stages.

In addition, information associated with patient sleep may be used to assess an impact of breathing therapy on the patient. Therapy impact data may be used to develop information to coordinate and adjust the therapy. The implantable monitoring device 6501 may include a sleep detector 6528 for detecting when the patient is asleep and various stages and/or processes of sleep. Various methods of sleep detection implementable in an implanted device involve sensing one or more conditions indicative of sleep. The sleep-related conditions may be compared to one or more thresholds to determine if the patient is asleep.

The sleep-related conditions may be sensed or derived using patient-external or implantable sensors and analyzed by a sleep detector coupled to or incorporated in the implantable therapy coordination device. For example, sleep detection may be implemented in an implantable cardiac rhythm management system configured as a pacemaker/defibrillator and incorporating a coordination processor or an ITCS device.

Figure 66A:
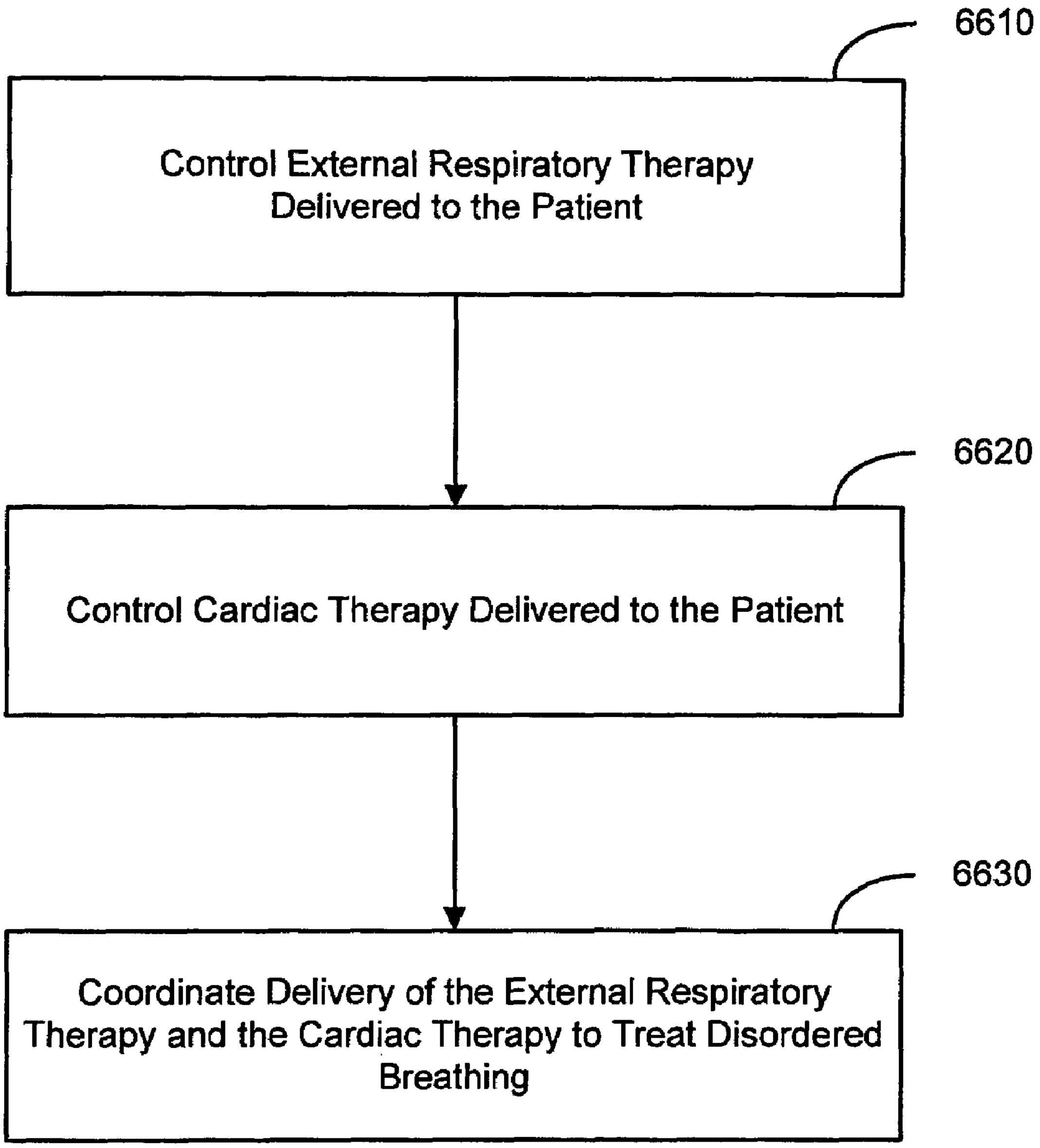
FIGS. 66A-66B are flowcharts illustrating methods that involve controlling and coordinating cardiac therapy and respiratory therapy in order to coordinate sleep disordered breathing therapy in accordance with embodiments of the invention.

As illustrated in the flowchart of FIG. 66A, embodiments of the invention are directed to an automated method for controlling disordered breathing therapy delivered to a patient. The method involves controlling 6610 delivery of an external respiratory therapy and controlling delivery 6620 of a cardiac therapy. The external respiratory therapy and the cardiac therapy are coordinated 6630 to treat disordered breathing.

In various implementations, one or more conditions affecting the patient and associated with disordered breathing and/or disordered breathing therapy may be sensed. The sensed conditions may be used, for example, to detect and/or predict disordered breathing episodes, determine a severity of disordered breathing, detect sleep, assess sleep quality, evaluate an efficacy of the therapy, evaluate an impact of the therapy on the patient, determine therapy interactions, determine patient usage of the therapies, among other factors. Coordination of the therapies may be performed based on the sensed conditions. The therapies may be adjusted to enhance therapy effectiveness, to reduce an impact of the therapy, to avoid or reduce therapy interactions, and/or to accomplish other therapeutic goals.

According to embodiments presented herein, a coordinating processor unit is used to generate control signals used for controlling disordered breathing therapies delivered to the patient. In one embodiment, the coordinating unit may transmit control signals directly to an external respiratory therapy device and a cardiac therapy device. The control signals may be used by the respective therapy devices to automatically adjust the therapy delivered to the patient. In another embodiment, both the coordinating unit and the therapy devices may be communicatively coupled to a separate medical device, such as a device programmer or patient management system. The coordinating unit may transmit control information indirectly to the therapy devices through a device programmer or patient management system.

In one embodiment of the invention, a sensor system may sense one or more conditions related to disordered breathing. Disordered breathing events may be detected based on the sensed conditions. Characteristics of the disordered breathing events such as severity, frequency, and/or duration, may be determined. Determination of the one or more characteristics of the sleep disordered breathing events may involve calculation of one or more indices characterizing the disordered breathing events. The indices may include, for example, an apnea/hypopnea index (AHI) and/or a percent time in periodic breathing (% PB), among other indices. The external respiratory therapy and the cardiac therapy maybe coordinated based on the characteristics of the disordered breathing events.

Figure 66B:
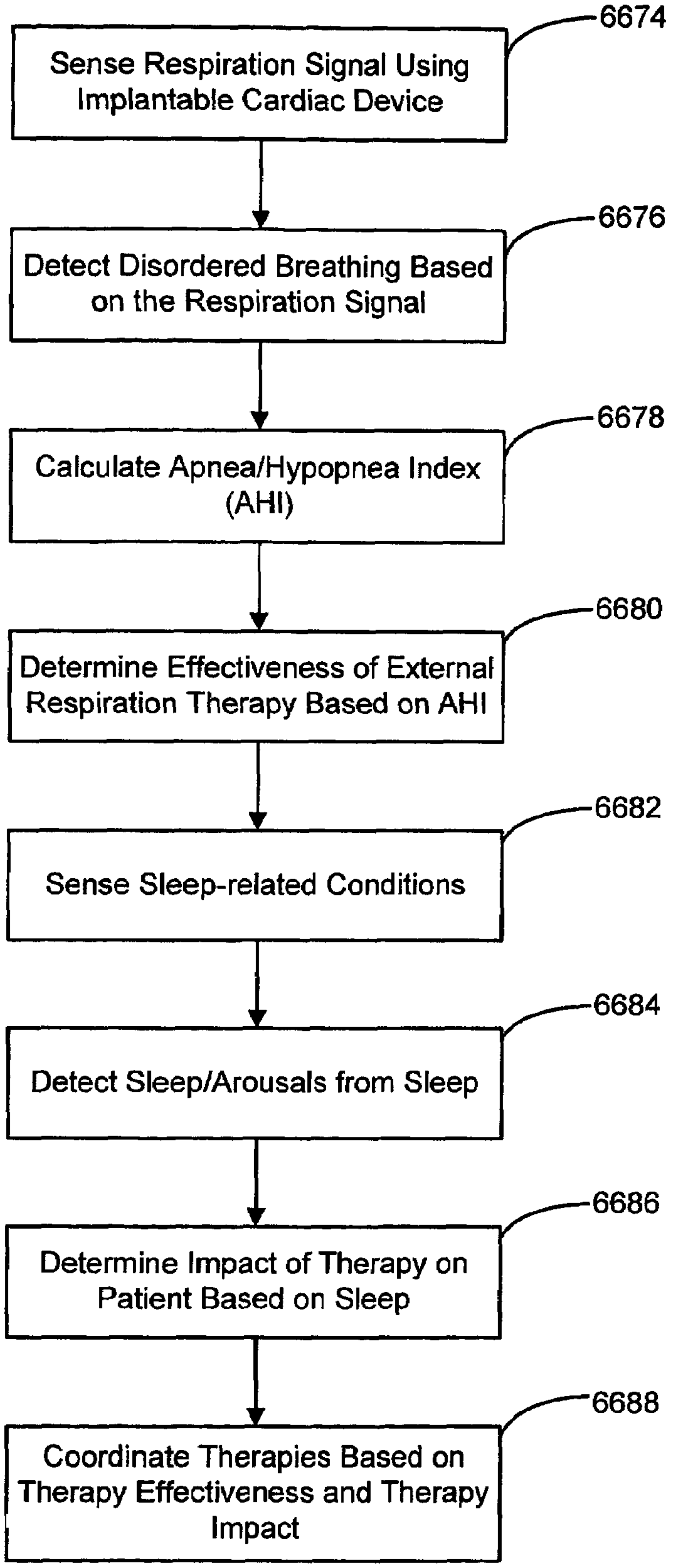

In accordance with an embodiment of the invention, illustrated in the flowchart of FIG. 66B, coordination of disordered breathing therapies, including an external respiratory therapy and a cardiac electrical stimulation therapy, may be implemented using circuitry disposed within the housing of an implantable cardiac rhythm management (CRM) device. The therapies delivered to the patient may be coordinated based on a variety of factors, including therapy effectiveness and/or impact of the therapy on the patient. In this embodiment, the external respiratory therapy is delivered by a continuous positive airway pressure (CPAP) device. The cardiac therapy comprises cardiac electrical stimulation therapy for treating disordered breathing delivered by the CRM device.

One or more sensors may be employed to sense conditions related to disordered breathing and/or disordered breathing therapy, including, for example, the effectiveness of the breathing therapy and/or the impact of the therapy on the patient. The sensors may be coupled to the CPAP device, the CRM device, or a first set of sensors may be coupled to the CPAP device and a second set coupled to the CRM device. The coordinating unit within the CRM device receives the signals from the sensors, determines therapy effectiveness and/or impact, and coordinates therapy delivered by the CPAP and CRM devices.

In one example, a condition modulated by patient respiration may be sensed 6674 and a respiration waveform signal generated. Circuitry disposed within the housing of the CRM device may detect 6676 disordered breathing episodes based on the respiration signal. The coordination unit may determine therapy effectiveness based on the severity, frequency and/or duration of sleep disordered breathing episodes experienced by the patient. In one implementation, coordination circuitry disposed within the CRM device may calculate 6678 an apnea/hypopnea index (AHI) indicative of the frequency of disordered breathing episodes. The effectiveness of the sleep disordered breathing therapy may be determined 6680 based on the sleep disordered breathing index. If the AHI is relatively low, the breathing therapy may be determined to be effective. If the AHI is relatively high, then the breathing therapy may be determined to be ineffective.

A CPAP device typically includes a respiratory mask, e.g., a nasal of facial mask, worn by the patient to facilitate delivery or air or other gas to the patient's airway. The respiratory mask may be inconvenient and/or uncomfortable for the patient to wear and may keep the patient awake. Further, delivery of positive airway pressure may inhibit sleep, or cause the patient to arouse frequently. Information about these side effects of the breathing therapy may be helpful in coordinating a therapy regimen for the patient.

Impact of the external breathing therapy and/or cardiac electrical stimulation therapy may be determined based on the patient's sleep quality. Sensors coupled to the coordination processor within the CRM device are configured to sense 6682 one or more conditions related to sleep. The sleep related conditions are used to detect 6684 sleep and/or arousals from sleep. The coordination processor within the CRM device determines 6686 the impact of the therapies on the patient by monitoring the patient's sleep. For example, the coordination processing may monitor the total time the patient spends sleeping, the number of arousals experienced by the patient in one night, the number of arousals correlated to sleep disordered breathing events, the number of arousals correlated to therapy delivery, and/or the depth of the arousals. In various implementations the coordination processor may calculate various indices characterizing sleep and/or one or more composite indices based on indices related to sleep and indices related to sleep disordered breathing. In one example, the monitoring unit calculates the number of arousals experienced by the patient per hour (A/h).

Therapy coordination may be accomplished 6688 based on the therapy effectiveness and impact information. Control signals may be transmitted from the coordinating processor unit to the therapy units of the CRM and CPAP devices. One or both of the therapies delivered by the CRM and CPAP devices may be adjusted to enhance therapy effectiveness and/or reduce side effects.

In various examples, coordinated disordered breathing therapy may involve adjusting the cardiac electrical stimulation therapy for disordered breathing, adjusting the neurostimulation therapy for disordered breathing and/or adjusting the external respiration therapy for disordered breathing. According to this scenario, a disordered breathing therapy coordination processor may distribute the burden of disordered breathing therapy between one or more therapy devices.

In one implementation, certain types of therapy may be used for predetermined periods of time. For example, a predetermined level of cardiac and/or nerve stimulation therapy may be used prior to the patient falling asleep. The therapy burden may be shifted to the external respiratory therapy device after sleep has been detected. In one implementation, the therapy burden may be distributed based on detected arousals. For example, if the delivery of one type of therapy causes the patient to arouse from sleep, the therapy burden may be shifted to other types of therapy to enhance the patient's sleep quality. Alternatively, rather than shifting to other types of therapy, therapy parameters of a particular therapy may be adjusted to provide more restful sleep. For example, an external respiratory therapy pressure may be adjusted downward to provide a disordered breathing therapy that is more comfortable to the patient and allows the patient to sleep better. In one implementation, the respiratory therapy pressure may be adjusted downward and the pacing rate may be adjusted upward to maintain effectiveness of the therapy while reducing an impact on the patient.

In another implementation, the therapy burden may be distributed based on therapy efficacy. In one scenario, the therapy controller may add therapies to the overall disordered breathing therapy regimen to improve therapy efficacy. For example, if the therapy coordination processor determines that disordered breathing is occurring despite the use of one type of therapy, additional one or more types of therapy may be added to the regimen in order to treat disordered breathing.

In one scenario, the disordered breathing therapy burden may be distributed based on device usage. For example, if the patient does not use the external respiratory therapy device, then the disordered breathing therapy coordination processor may signal a CRM device and/or an external respiratory therapy device to initiate or increase the level of therapy delivered by the CRM device, the external respiratory therapy device, and/or other therapy devices.

In one embodiment, the coordination processor may coordinate the disordered breathing therapy to enhance therapy efficacy while adjusting or avoiding a therapy impact. The coordination processor may acquire information related to the sensed conditions and may evaluate therapy efficacy and/or impact on the patient, i.e., side effects of the therapy, based on the sensed conditions. The coordination processor may modify the therapy delivered by one or more therapy devices to enhance therapy efficacy while reducing or avoiding side effects. The coordination processor may modify the therapy to reduce interactions between the disordered breathing therapy and other types of therapies delivered to the patient, e.g., neurostimulation for anti-hypertensive therapy and/or cardiac pacing for cardiac rhythm management. The coordination processor may modify the therapy to reduce interactions between different types of disordered breathing therapies, for example. The therapy controller may modify a therapy to increase the useable lifetime of an implantable device.

Pulmonary Disease Assessment with Drug Therapy Control

Aspects of the invention that include controlling a drug therapy for treating a non-rhythm pulmonary disease are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving pulmonary disease assessment and drug therapy are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 134 (FIG. 1B) for controlling drug therapy to treat non-rhythm pulmonary disease. The drug therapy control system 134 may be implemented as a stand alone system or in combination with other individual medical systems, such as those described in FIGS. 1B-1D.

Embodiments of the invention involve assessing a presence of a pulmonary disease or disorder that is not a breathing rhythm disorder and controlling the deliver of a drug therapy to treat the pulmonary disease. According to one embodiment, a method for controlling therapy for a non-rhythm related pulmonary disease includes sensing one or more conditions associated with the non-rhythm pulmonary disease using sensors of a patient-external respiratory therapy device. A presence of the non-rhythm pulmonary disease is assessed based on the one or more sensed conditions. A control signal for controlling a drug therapy to treat the non-rhythm pulmonary disease is generated based on the assessment of the non-rhythm pulmonary disease.

According to one aspect, sensing the one or more conditions associated with the non-rhythm pulmonary disease involves performing a pulmonary function test using the sensors of the respiratory therapy device. One or more pulmonary function conditions are determined based on the pulmonary function test.

According to another aspect, the method includes comprising delivering the drug therapy using the generated control signal. In one embodiment, the drug therapy may be delivered using the respiratory therapy device. In other embodiments, the drug therapy may be delivered using a therapy device other than the respiratory therapy device.

One or more additional conditions associated with the non-rhythm pulmonary disease may be sensed using an implantable device. The disease assessment may be based in part on the one or more additional conditions.

Another embodiment of the invention involves a medical system for controlling therapy to treat a non-breathing rhythm related pulmonary disease. The system includes an external respiratory therapy device. The external respiratory therapy device includes a therapy unit configured to deliver respiration therapy to a patient and a sensor system configured to sense one or more conditions associated with a non-rhythm pulmonary disease. A diagnosis unit is coupled to the sensor system and is configured to assess a presence of the non-rhythm pulmonary disease based on the one or more sensed conditions. A drug therapy controller is coupled to the diagnosis unit. The drug therapy controller is configured to control a drug therapy delivered to the patient to treat the non-rhythm pulmonary disease.

Another embodiment of the invention involves a system for providing coordinated patient monitoring, diagnosis and/or therapy that utilizes a system 134 for controlling a drug therapy to treat non-rhythm pulmonary disease. The coordinated system includes, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a system 134 configured to control drug therapy to treat non-rhythm pulmonary disease. The drug therapy control system 134 includes an external respiratory therapy device with a therapy unit configured to deliver respiration therapy to a patient and a sensor system configured to sense one or more conditions associated with a non-rhythm pulmonary disease. The system further includes a diagnosis unit coupled to the sensor system configured to assess a presence of the non-rhythm pulmonary disease based on one or more sensed conditions. A drug therapy controller is coupled to the diagnosis unit and is configured to control a drug therapy delivered to the patient to treat the non-rhythm pulmonary disease.

The implantable and respiratory therapy devices 181, 184 may operate cooperatively based on system 134 control of drug therapy delivered to a patient. For example, control of drug therapy to treat non-rhythm pulmonary disease may allow the implantable and respiratory therapy devices 181, 184 to operate cooperatively to provide therapies for treating conditions associated with non-rhythm pulmonary disease. Systems and methods directed to assessing pulmonary disease with drug therapy control may be implemented to include selected features, functions, and/or structures described in commonly owned, co-pending U.S. patent application entitled "Methods and Systems for Assessing Pulmonary Disease with Drug Therapy Control," filed Sep. 15, 2004, which is hereby incorporated herein by reference.

Pulmonary disorders may be organized into broad categories encompassing disorders of breathing rhythm and non-rhythm pulmonary diseases and/or disorders. Breathing rhythm disorders include various syndromes characterized by patterns of disordered breathing that produce insufficient respiration, for example, sleep apnea, hypopnea, and Cheyne-Stokes Respiration (CSR), among others. Breathing rhythm disorders are not necessarily accompanied by alteration of pulmonary structures.

Non-rhythm pulmonary diseases or disorders typically involve physical changes to lung structures, such as loss of elasticity of the lung tissue, obstruction of airways with mucus, limitation of the expansion of the chest wall during inhalation, fibrous tissue within the lung, excessive pressure in the pulmonary arteries, and/or other characteristics. Pulmonary diseases or disorders that are not rhythm-related are referred to herein as non-rhythm pulmonary diseases and may include various types, for example, obstructive pulmonary diseases, restrictive pulmonary diseases, infectious and non-infectious pulmonary diseases, pulmonary vasculature disorders, and pleural cavity disorders.

Embodiments of the invention are directed to controlling a drug therapy to treat a non-rhythm pulmonary disease. A presence of a non-rhythm pulmonary disease is determined using a sensor system coupled to a respiratory therapy device. If the non-pulmonary disease is present based on the assessment, then a drug therapy to treat the non-pulmonary disease may be delivered. In accordance with embodiments of the invention, a non-rhythm pulmonary disease assessment system may be used to discriminate between types of non-rhythm pulmonary diseases, e.g., between obstructive pulmonary diseases and restrictive pulmonary diseases. The non-rhythm pulmonary disease assessment system may discriminate between non-rhythm pulmonary diseases of a particular type, e.g., between asthma and emphysema, both of which are pulmonary diseases of the obstructive type. Discrimination between pulmonary diseases afflicting the patient facilitates delivery of an effective drug therapy, allowing the system to deliver an appropriate therapy for the particular pulmonary disease detected.

If the presence of a non-rhythm pulmonary disease is determined, then the progression of the disease may be monitored. Monitoring the progression of the non-rhythm pulmonary disease may involve, for example, periodically evaluating one or more physiological changes or symptoms associated with the disease. Evaluation of the one or more physiological changes or symptoms may be accomplished by sensing conditions associated with the symptoms or physiological changes. In a preferred embodiment, information about the sensed conditions is stored and may be trended or otherwise processed to facilitate disease detection.

Typically, a physiological sensor generates a signal modulated by a physiological parameter. In some cases, a physiological condition may be directly measured based on the sensor signal. For example, a blood pressure measurement may directly correlate to the signal generated by a calibrated blood pressure sensor. In other cases, a condition measurement may be derived from the sensor signal. For example, tidal volume is a respiratory system condition that may be derived based on the signal generated by a transthoracic impedance sensor. In another example, heart rate is a cardiac system condition that may be derived from a cardiac electrogram sensor.

Monitoring a disease may involve, for example, monitoring the severity and/or other characteristics of the disease over time. Monitoring the disease may involve detecting disease onset, monitoring progression and/or regression of the disease and detecting disease offset. Disease monitoring may involve monitoring one or more conditions associated with the physiological changes and/or symptoms of the disease.

In one implementation, the presence of the non-rhythm pulmonary disease is assessed based on one or more patient conditions indicative of symptoms or physiological changes associated with the disease. The one or more conditions are sensed using the sensing system of a patient-external respiratory therapy device. In a preferred embodiment, the respiratory therapy device comprises a positive airway pressure device.

Continuous positive airway pressure (CPAP) devices are frequently used to treat sleep apnea and/or other breathing rhythm disorders. A CPAP device may be used regularly during a patient's sleep time to alleviate symptoms of breathing rhythm related disorders. The sensors of the CPAP device, used nightly to treat disordered breathing disorders, may be employed to detect and/or assess non-rhythm pulmonary diseases. A drug therapy for the non-rhythm pulmonary disease may be controlled based on the assessment of the disease.

In another implementation, the presence of the non-rhythm pulmonary disease may be detected and/or assessed based on conditions sensed using sensors of a patient-external respiratory therapy device in combination with additional conditions sensed using sensors of an implantable device. The implantable device may comprise, for example, an implantable cardiac device, such as a pacemaker, defibrillator, cardioverter, cardiac monitor, and/or cardiac resynchronizer.

Figure 67:
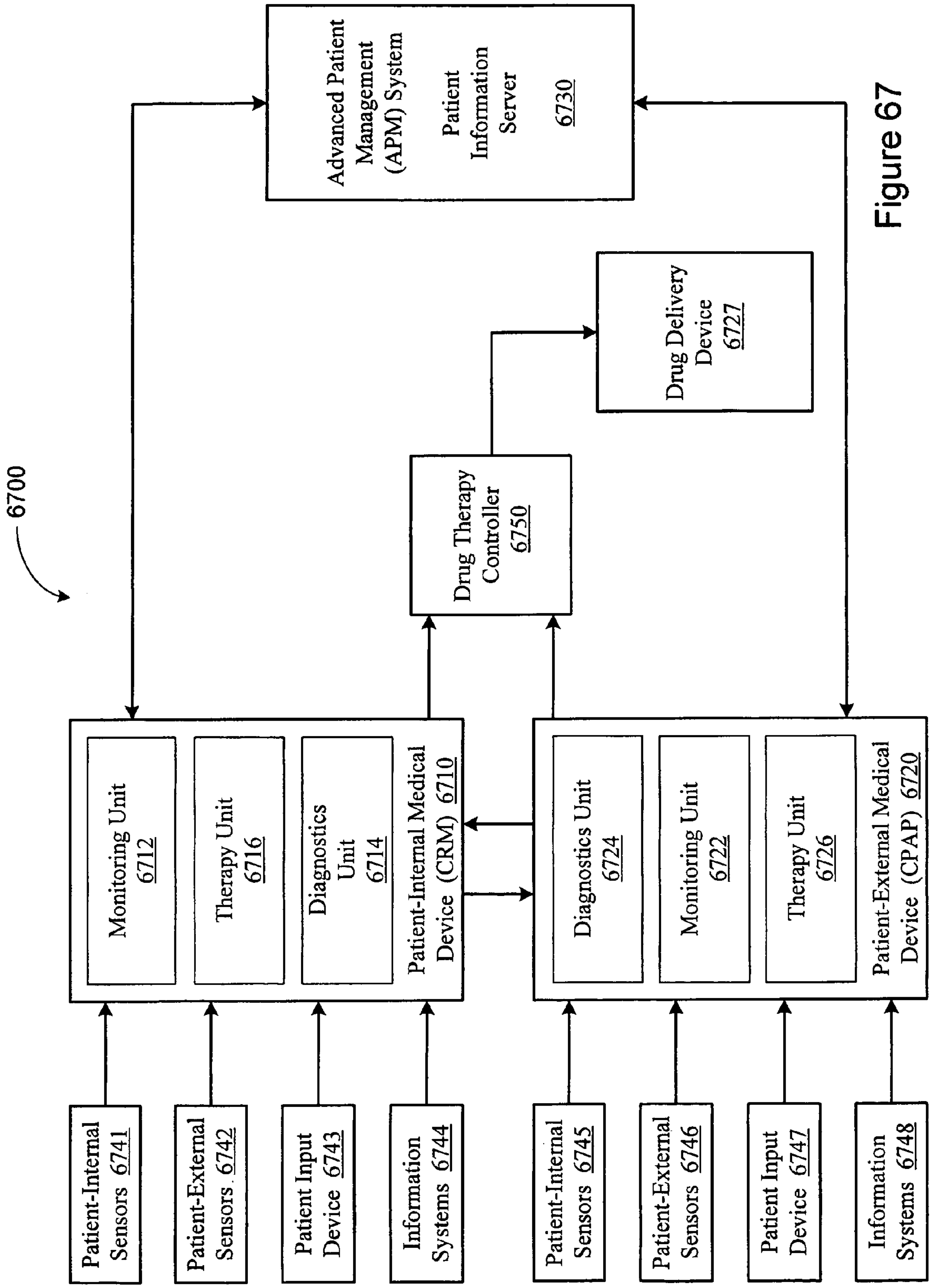
FIG. 67 is a block diagram of a medical system 100 that includes components useful in implementing detection and/or assessment of non-rhythm pulmonary diseases and controlling drug therapy in accordance with embodiments of the invention.

FIG. 67 is a block diagram of a medical system 6700 that includes components useful in implementing detection and/or assessment of non-rhythm pulmonary diseases and controlling drug therapy in accordance with embodiments of the invention. One or more of the components identified in FIG. 67 may be used for assessing pulmonary diseases and controlling delivery of drug therapy.

For example, the medical system 6700 may be implemented to include one or more of the features and/or processes described herein. A system for assessing pulmonary diseases and controlling delivery of drug therapy need not include all of the features and functions described, but may be implemented to include one or more selected features and functions that provide unique structures and/or functionality.

FIG. 67 illustrates a patient internal device 6710 and a patient external device 6720. Sensors and/or input devices 6741-748 coupled to the patient-internal device and the patient-external device may be used to sense patient conditions indicative of symptoms of a pulmonary disease. In addition to the sensing functions performed by the therapy devices 6710, 6720, the devices 6710, 6720 may respectively include therapy units 6716, 6726 providing therapy for disorders other than the detected pulmonary disease, e.g., cardiac therapy for cardiac rhythm disorders and/or CPAP therapy for breathing rhythm disorders. Either of the patient internal device 6710 and/or the patient external device 6720 may include a drug therapy control unit 6750 configured to generate control signals deliverable to a drug therapy device 6727. The drug therapy device provides drug therapy to treat one or more non-rhythm pulmonary diseases. In some embodiments, the components used to generate the drug therapy control signal or signals may be included in both the patient internal device and the patient external device. The patient internal device 6710 and/or the patient external device 6720 may generate control signals that initiate, modify, and/or terminate drug therapy for the non-rhythm pulmonary disease.

The patient-internal device 6710 is typically a fully or partially implantable device that includes circuitry for implantably performing one or more of monitoring 6712, diagnosis 6714, and/or therapy control/delivery functions 6716, 6750. The patient-external device 6720 includes circuitry for performing one or more of monitoring, diagnosis and/or therapy control/delivery functions patient-externally (i.e., not invasively implanted within the patient's body). The patient-external medical device 6720 may be positioned on the patient, near the patient, or in any location external to the patient. It is understood that a portion of a patient-external medical device 6720 may be positioned within an orifice of the body, such as the nasal cavity or mouth, yet can be considered external to the patient (e.g., mouth pieces/appliances, tubes/appliances for nostrils, or temperature sensors positioned in the ear canal).

Each of the patient-internal 6710 and patient-external 6720 devices may include a patient monitoring unit 6712, 6722. The patient-internal and patient-external devices 6710, 6720 may be coupled to one or more sensors 6741, 6742, 6745, 6746, patient input devices 6743, 6747 and/or other information acquisition devices 6744, 6748. The sensors 6741, 6742, 6745, 6746, patient input devices 6744, 6747, and/or other information acquisition devices 6744, 6748 may be employed to detect conditions relevant to the monitoring, diagnostic, and/or therapeutic functions of the patient-internal and patient-external medical devices 6710, 6720. The sensors 6741, 6742, 6745, 6746, patient input devices 6744, 6747, and/or other information acquisition devices 6744, 6748 may be used to detect conditions associated with pulmonary disease.

The medical devices 6710, 6720 may each be coupled to one or more patient-internal sensors 6741, 6745 that are fully or partially implantable within the patient. The medical devices 6710, 6720 may also be coupled to patient-external sensors 6742, 6746 positioned on, near, or in a remote location with respect to the patient. The patient-internal and patient-external sensors are used to sense conditions, such as physiological or environmental conditions.

The patient-internal sensors 6741 may be coupled to the patient-internal medical device 6710 through internal leads. In one example, an internal endocardial lead system is used to couple cardiac electrodes that sense cardiac electrical activity to an implantable pacemaker or other cardiac rhythm management device. In some applications, one or more patient-internal sensors 6741 may be equipped with transceiver circuitry to support wireless communications between the one or more patient-internal sensors 6741 and the patient-internal medical device 6710. Similarly, patient internal sensors 6745 may be coupled to a patient-external device 6720 through wireless communications links.

The patient-external sensors 6742, 6746 may be coupled to the patient-internal medical device 6710 and/or the patient-external medical device 6720 through leads or through wireless connections. Patient-external sensors 6742 preferably communicate with the patient-internal medical device 6710 wirelessly. Patient-external sensors 6746 may be coupled to the patient-external medical device 6720 through leads or through a wireless link.

The medical devices 6710, 6720 may be coupled to one or more patient-input devices 6743, 6747. The patient-input devices are used to allow the patient to manually transfer information to the medical devices 6710, 6720. The patient input devices 6743, 6747 may be particularly useful for inputting information concerning patient perceptions, such as how well the patient feels, and information such as patient smoking, drug use, or other activities that are not automatically sensed or detected by the medical devices 6710, 6720.

The medical devices 6710, 6720 may be connected to one or more information systems 6744, 6748, for example, a database that stores information useful in connection with the monitoring, diagnostic, or therapy functions of the medical devices 6710, 6720. For example, one or more of the medical devices 6710, 6720 may be coupled through a network to a information system server that provides information about environmental conditions affecting the patient, e.g., the pollution index for the patient's location.

The medical devices 6710, 6720 may incorporate therapy units 6716, 6726 for configured to control and deliver therapy to the patient. The therapy units 6716, 6726 may be implemented to provide therapy other than a drug therapy delivered to treat the pulmonary disease. For example, in one embodiment, the patient-internal device 6710 may comprise a cardiac rhythm management (CRM) system configured to deliver cardiac pacing therapy to the patient. The patient-external device 6720 may comprise a positive airway pressure (xPAP) device configured to deliver a respiratory therapy to treat a breathing rhythm disorder. One or both of the patient-internal device 6710 and the patient-external device 6720 may include components that control delivery of a drug therapy to treat the non-rhythm pulmonary disease.

The system 6700 further includes a diagnostics unit 6714 that is configured to detect and/or assess a presence of non-rhythm pulmonary disease. In some embodiments, the diagnostics unit 6714 may be fully incorporated into the patient-external device 6720. In other embodiments, the diagnostics unit 6714 may be fully incorporated into the patient-internal device 6710. In yet other embodiments, components of the diagnostics unit 6714 may be incorporated into both the patient-internal and patient-external devices 6710, 6720. In yet further embodiments, the diagnostics unit may be located remotely from both the patient-internal medical device 6710 and the patient-external medical device 6720. In one scenario, the diagnostics processor may be implemented as a component of an advanced patient management (APM) system 6730, for example.

The monitoring units 6712, 6722 of the patient-internal and patient external medical devices 6710, 6720 collect data based on conditions sensed or detected through the use of the sensors 6741, 6742, 6745, 6746, patient input devices 6743, 6746, and/or information systems 6744, 6748 coupled to the patient-internal and patient-external devices 6710, 6720. The collected data is transferred to a diagnostics unit 6714.

The diagnostics unit 6714 is configured to assess the presence of the non-rhythm pulmonary disease based on the sensed conditions. The diagnostics processor 6714 may also assess and/or monitor the progression, of the medical disease or disorder. Monitoring the progression of the disease may involve, for example, periodically evaluating one or more conditions indicative of physiological changes or symptoms of the disease. Monitoring disease progression may involve, for example, monitoring the severity of the disease, monitoring disease onset, progression, regression and offset, and/or monitoring other aspects of the disease.

A drug therapy controller 6750 may be configured as a component of the patient-internal device 6710, the patient external device 6720, a device remote from the patient-internal and patient external devices 6710, 6720, or as a stand alone unit. In some configurations, components of the drug therapy controller may be housed in both the patient-internal and patient external devices 6710, 6720. Components of the drug therapy controller and the drug therapy delivery unit may be disposed within a single housing.

The drug therapy controller 6750 generates a control signal for controlling drug therapy delivered to the patient based on the assessment of the non-rhythm pulmonary disease. The drug therapy controller 6750 may generate a control signal to initiate drug therapy if disease onset is detected or if one or more symptoms of the disease are determined to reach a threshold limit, for example. The control signal may indicate termination of the drug therapy if one or more symptoms of the disease subside. Further, during the course of the disease, the control signal may be adjusted based on the assessment of the presence of the non-rhythm pulmonary disease as indicated by sensed conditions indicative of disease symptoms.

The control signal generated by the drug therapy controller 6750 is received by the drug therapy unit 6727. The drug therapy unit 6727, which may comprise an implantable or patient-external device, provides a drug therapy to treat the non-rhythm pulmonary disease. Therapy delivered by the drug therapy unit 6727 is controlled by the control signal generated by the drug therapy controller 6750. In various embodiments, the drug therapy unit may be implemented as an implantable or patient-external drug pump, a gas therapy device, nebulizer, and/or an activatable drug patch.

In various embodiments, the patient-internal device 6710, the patient-external device 6720, drug controller 6750, drug delivery unit 6727, and/or other devices depicted in FIG. 67 may communicate through wireless links. For example, two or more devices, such as the patient-internal and patient-external devices 6710, 6720, may be coupled through a short-range radio link, such as Bluetooth or a proprietary wireless link. The wireless communications link may facilitate unidirectional or bi-directional communication between the patient-internal 6710 and patient-external 6720 medical devices. In one implementation, data and/or control signals may be transmitted between the patient-internal 6710 and patient-external 6720 medical devices to coordinate the functions of the medical devices 6710, 6720.

In an embodiment of the invention, the patient-internal and patient-external medical devices 6710, 6720 may be used within the structure of an advanced patient management system. Advanced patient management systems involve a system of medical devices that are accessible through various communications technologies. For example, patient data may be downloaded from one or more of the medical devices periodically or on command, and stored at a patient information server. The physician and/or the patient may communicate with the medical devices and the patient information server, for example, to acquire patient data or to initiate, terminate or modify therapy.

In the implementation illustrated in FIG. 67, the patient-internal device 6710 and the patient-external device 6720 may be coupled through a wireless or wired communications link to a patient information server that is part of an advanced patient management (APM) system 6730. The APM patient information server 6730 may be used to download and store data collected by the patient-internal and patient-external devices 6710, 6720.

The data stored on the APM patient information server 6730 may be accessible by the patient and the patient's physician through terminals, e.g., remote computers located in the patient's home or the physician's office. The APM patient information server 6730 may be used to communicate to one or more of the patient-internal and patient-external medical devices 6710, 6720 to effect remote control of the monitoring, diagnosis, and/or therapy functions of the medical devices 6710, 6720.

In one scenario, the patient's physician may access patient data transmitted from the medical devices 6710, 6720 to the APM patient information server 6730. After evaluation of the patient data, the patient's physician may communicate through one or more of the patient-internal or patient-external devices 6710, 6720 through the APM system 6730 to initiate, terminate, or modify the monitoring, diagnostic, and/or therapy functions of the patient-internal and/or patient-external medical systems 6710, 6720.

The patient-internal and patient-external medical devices 6710, 6720 may not communicate directly, but may communicate indirectly through the APM system 6730. In this embodiment, the APM system 6730 may operate as an intermediary between two or more of the medical devices 6710, 6720. For example, data and/or control information may be transferred from one of the medical devices 6710, 6720 to the APM system 6730. The APM system 6730 may transfer the data and/or control information to another of the medical devices 6710, 6720.

Figure 68A:
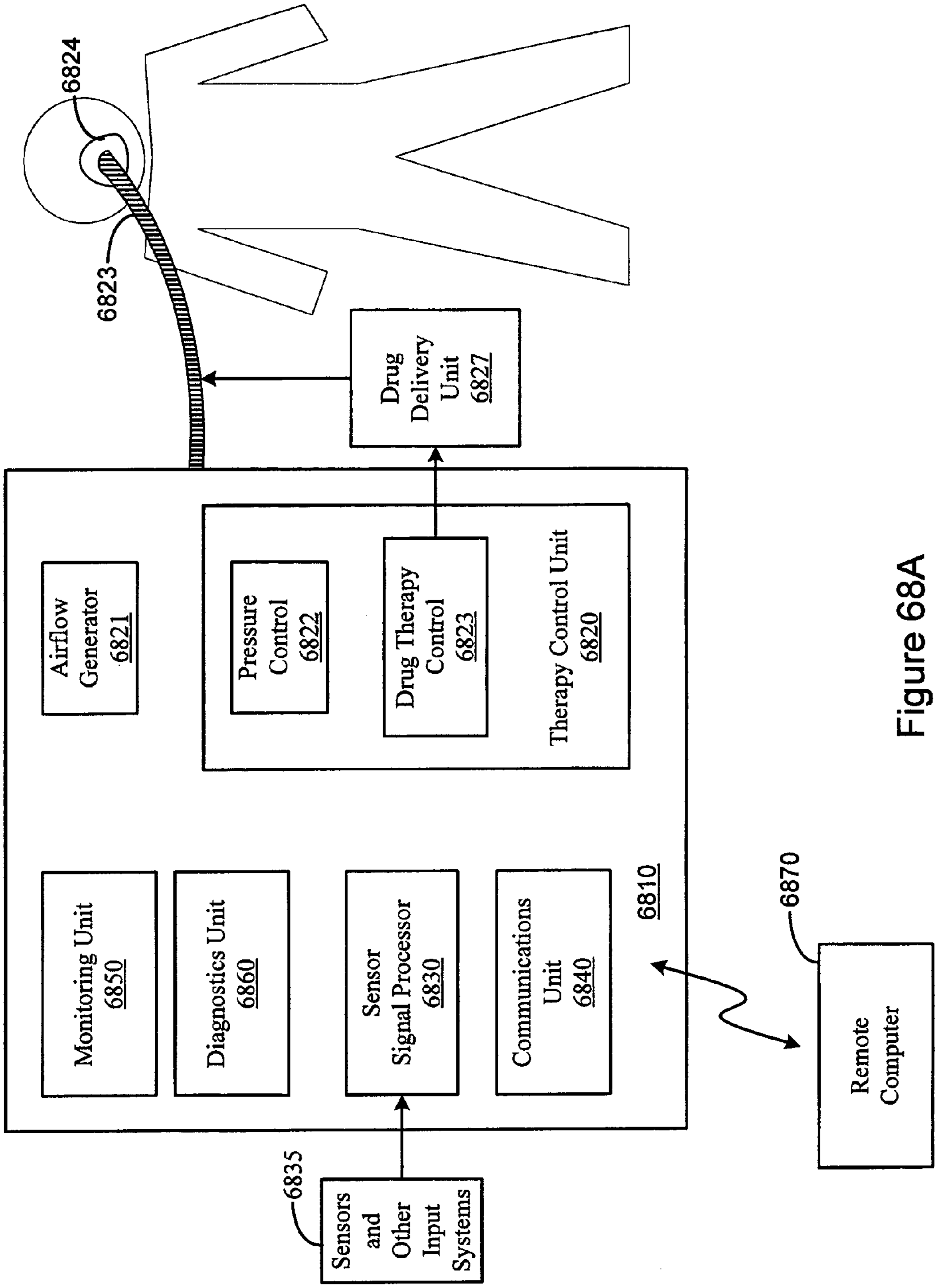

FIGS. 68A-68D are block diagrams of systems that may be used for non-rhythm pulmonary disease assessment with drug therapy control in accordance with embodiments of the invention. FIG. 68A illustrates an external respiratory therapy device 6810, e.g., a CPAP device, used to sense conditions associated with a non-rhythm pulmonary disease. The sensed conditions are evaluated by the external respiratory therapy device to assess a presence of the non-rhythm pulmonary disease.

The respiratory therapy device 6810 is coupled to one or more sensors or other input devices 6835 configured to sense or detect conditions indicative of physiological changes and/or symptoms associated with the non-rhythm pulmonary disease. A representative set of symptoms and/or physiological changes associated with non-rhythm pulmonary diseases may include, for example, dyspnea (e.g., non-specific dyspnea, orthopnea, exertional dyspnea, paroxysmal nocturnal dyspnea), abnormal concentrations of blood or respiratory gases (e.g., cyanosis, hypoxemia, hypercapnea, low pCO2, arterial acidosis, high alveolar-arterial pO2 differential), respiratory sounds (e.g., wheezing, crackles, rhonchi, fiction rub, attenuated breath sounds, snoring), pulmonary function dysfunction (e.g., low forced expiratory volume (FEV), forced vital capacity (FVC), FEV/FVC, low forced expiratory flow (FEF), high functional residual capacity (FRC), total lung capacity (TLC), high residual volume (RV), high lung compliance, slow exhalation, tachypnea, shallow breathing, high minute ventilation, respiratory failure, reduced diffusion capacity), other pulmonary conditions (e.g., hemoptysis, cough, pleuritic chest pain, local inflammation, excess mucous production, chest pain, respiratory infection, as indicated by a slightly elevated white blood count, pulmonary mucus, overinflated lungs, alveolar wall breakdown, mucosal pulmonary edema, ventilation-perfusion mismatch, subepithelial fibrosis (chronically), respiratory muscle fatigue, high small airway resistance, hoarseness), cardiovascular conditions (e.g., pulmonary hypertension, high pulmonary vascular resistance, tachycardia, circulatory collapse, pulsus paradoxicus, syncope, hypertension, S3 heart sounds, RV hypertrophy, systolic murmur), and general systemic conditions (e.g., fever, weight loss, weight gain, night sweats, peripheral edema, high hemoglobin, fatigue, joint pain, hypersomnolence.

The sensors and/or other input devices 6835 are coupled to signal processor circuitry 6830 which may be configured to energize the sensors, to receive and condition signals generated by the sensors, and/or to facilitate communication between the respiratory therapy device 6810 and the sensors 6835. The signal processor circuitry 6830 may comprise, for example, driver circuitry, filters, sampling circuitry, A/D converter circuitry. The sensor/input device signals may be averaged, filtered, or otherwise processed by the signal processor circuitry 6830 prior to use by other components of the respiratory therapy device 6810.

The respiratory therapy device 6810, illustrated in FIG. 68A as a positive airway pressure (xPAP) device includes a therapy control unit 6820. The therapy control unit 6820 comprises a flow generator 6821 that pulls in air through a filter. The flow generator 6821 is controlled by the pressure control circuitry 6822 to deliver an appropriate air pressure to the patient. Air flows through tubing 6823 coupled to the xPAP device 6810 and is delivered to the patient's airway through a mask 6824. In one example, the mask 6824 may be a nasal mask covering only the patient's nose. In another example, the mask 6824 covers the patient's nose and mouth. Other air delivery systems are also possible.

Continuous positive airway pressure (CPAP) devices deliver a set air pressure to the patient. The pressure level for the individual patient may be determined during a titration study, for example. Such a study may take place in a sleep lab, and involves determination by a sleep physician or other professional of the optimum airway pressure for the patient. The CPAP device pressure control is set to the determined level. When the patient uses the CPAP device, a substantially constant airway pressure level is maintained by the device. The constant air pressure acts a pneumatic splint to keep soft tissue in the patient's throat from collapsing and obstructing the airway.

Autotitration PAP devices are similar to CPAP devices, however, the pressure controller for autotitration devices automatically determines the air pressure delivered to the patient. Instead of maintaining a constant pressure, the autotitration PAP device evaluates sensor signals and the changing needs of the patient to deliver a variable positive airway pressure. Autotitration PAP and CPAP are often used to treat sleep disordered breathing, for example.

Bi-level positive airway pressure (bi-PAP) devices provide two levels of positive airway pressure. A higher pressure is maintained while the patient inhales. The device switches to a lower pressure during expiration. Bi-PAP devices are used to treat a variety of respiratory dysfunctions, including chronic obstructive pulmonary disease (COPD), respiratory insufficiency, and ALS or Lou Gehrig's disease, among others.

Some positive airway pressure devices may also be configured to provide both positive and negative pressure, such that negative pressure is selectively used (and de-activated) when necessary, such as when treating Cheyne-Stokes breathing, for example. The term xPAP will be used herein as a generic term for any such device, including devices using forms of positive airway pressure (and negative pressure when necessary), whether continuous or otherwise.

In accordance with various embodiments of the invention, the xPAP device 6810 may include a diagnostic unit 6810. The diagnostic unit 6810 evaluates patient conditions sensed or input directly by the sensors/input devices 6835 or derived from the sensor signals to assess a presence of a non-rhythm pulmonary disease.

In some embodiments, the therapy control unit 6820 of the respiratory therapy unit 6810 includes circuitry for drug therapy control 6823. The drug therapy controller 6823 generates a control signal to initiate, terminate, or modify drug therapy based on the assessment of the non-rhythm pulmonary disease. In one embodiment, the drug therapy comprises a gas that is delivered to the patient through the xPAP tubing 6823 and mask 6824. A gas therapy delivery unit is incorporated within the xPAP device 6810. The drug therapy controller 6823 generates a signal that controls and modulates the release of a gas by the gas therapy delivery unit 6827.

The xPAP device 6810 may include a communications unit 6840 for communicating with one or more separate devices 6870, such as a device programmer, APM system, and/or other patient-external or patient-internal monitoring, diagnostic and/or therapeutic devices. Communication between cooperating devices allows the xPAP device 6810 to provide or obtain information to/from the cooperating devices or to control therapy delivered by the cooperating devices, for example.

Figure 68B:
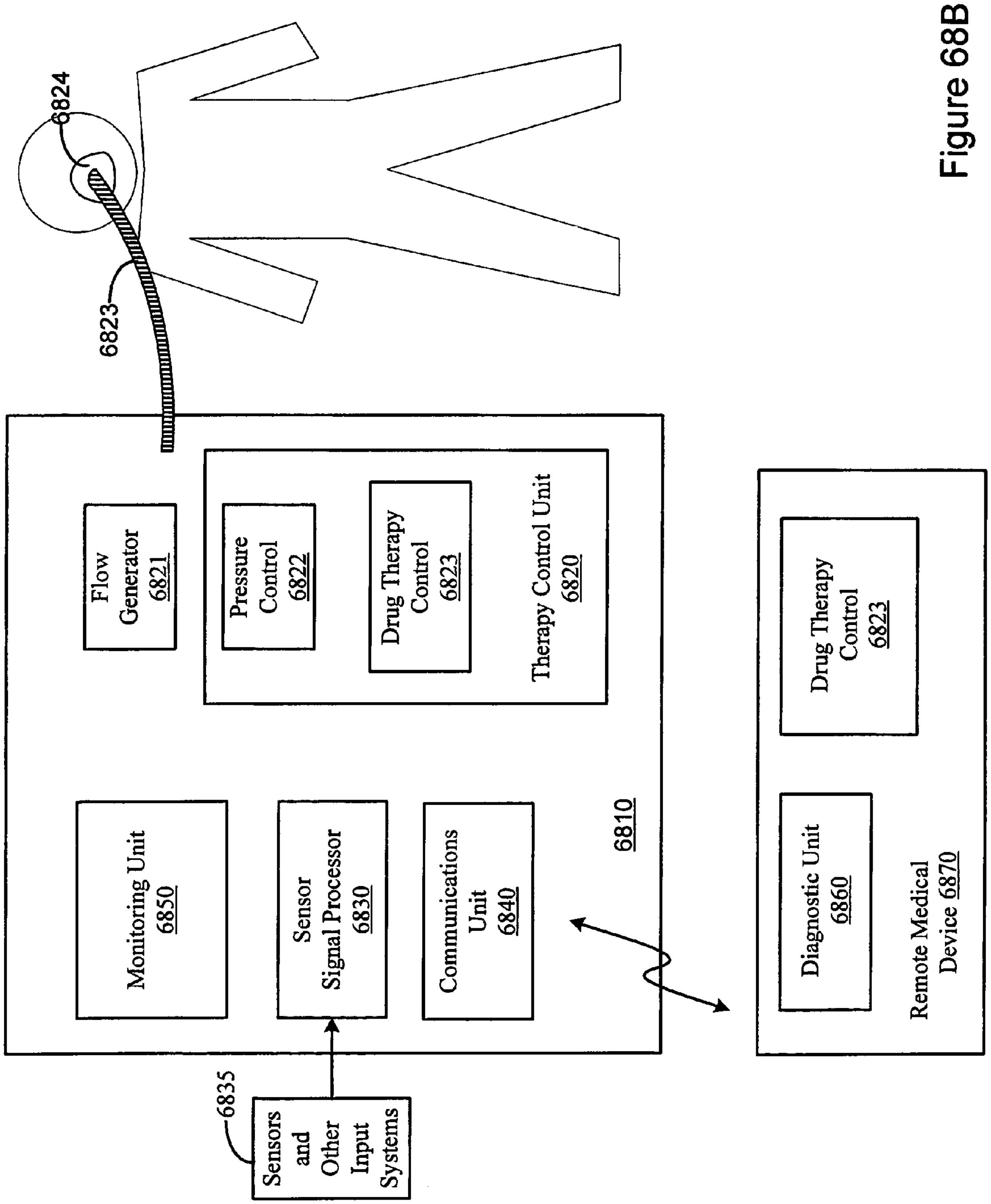

In one implementation, illustrated in FIG. 68B, one or both of the diagnostics unit and the drug therapy controller may be positioned remotely with respect to the patient-external respiratory therapy device 6810. The xPAP device 6810 may include a monitoring unit 6850 including a memory for storing data related to the non-rhythm pulmonary disease or other data. In one scenario, monitoring unit 6850 may sense the one or more patient conditions and may store data related to the sensed conditions. The monitoring unit may collect and store data hourly, nightly, weekly, randomly or according to a time schedule that corresponds to the patient's usage times of the respiratory therapy device 6810. Typically an xPAP device is used nightly for treatment of sleep apnea and/or other breathing rhythm disorders. The xPAP device 6810 may collect data from the sensors/input devices 6835 during one or more periods of time that the device is used. The presence of the non-rhythm pulmonary disease may be assessed based on the collected data. Assessment of the non-rhythm pulmonary disease may involve assessment of the onset, progression, regression and/or offset of the disease.

In the implementation illustrated in FIG. 68B, the respiratory therapy device 6810 may transmit information about conditions sensed by the respiratory therapy device 6810 to the diagnosis unit 6860 of a remotely located device 6870. The diagnosis unit 6860 assesses the non-rhythm pulmonary disease presence based on the transmitted information. The drug therapy controller develops a control signal for controlling drug therapy delivery. The remotely located device 6870 transmits the control signal to a drug delivery unit. In one embodiment, the drug delivery unit may be activated to release a gas, e.g., albuterol, into the airflow of the respiratory therapy device. In other embodiments, other types of drug delivery methodologies, such as a drug pump, an electrically activated drug patch, and/or other types of drug delivery devices may be employed.

The remote device 6870 may comprise a patient-external or patient-internal medical device. The remote device 6870 may be configured, for example, as a cardiac diagnostic and/or therapeutic device. In one configuration, for example, the remote device 6870 may comprise a cardiac rhythm management system, such as a pacemaker, defibrillator, or cardiac resynchronizer.

Figure 68C:
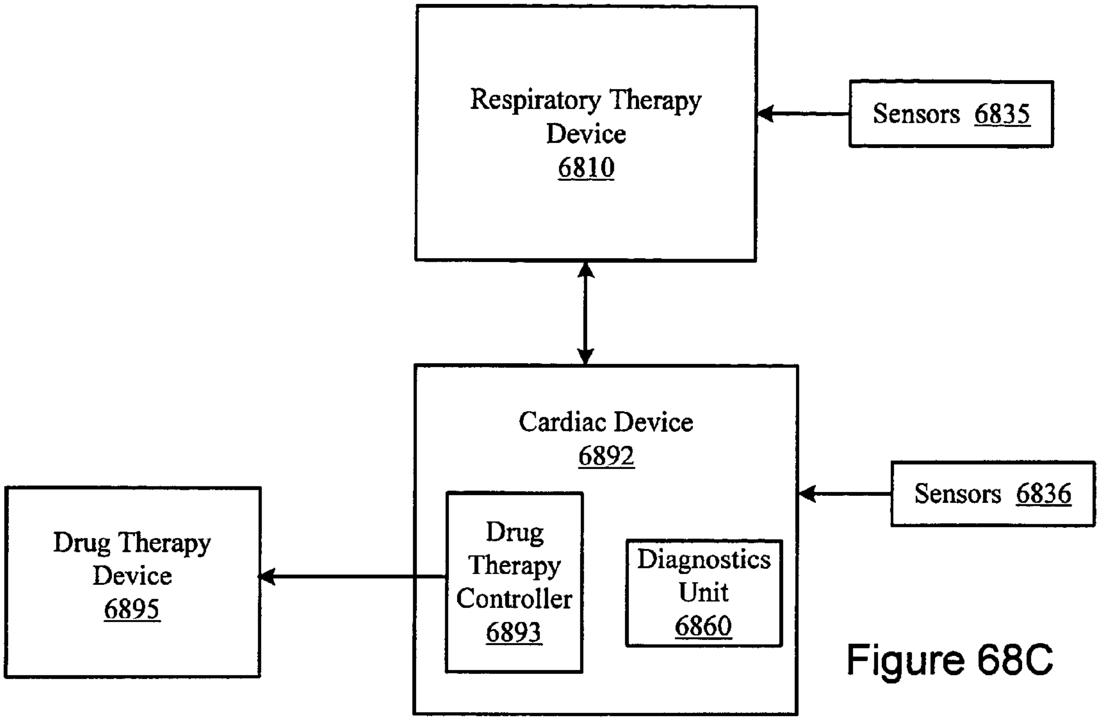
Figure 68D:
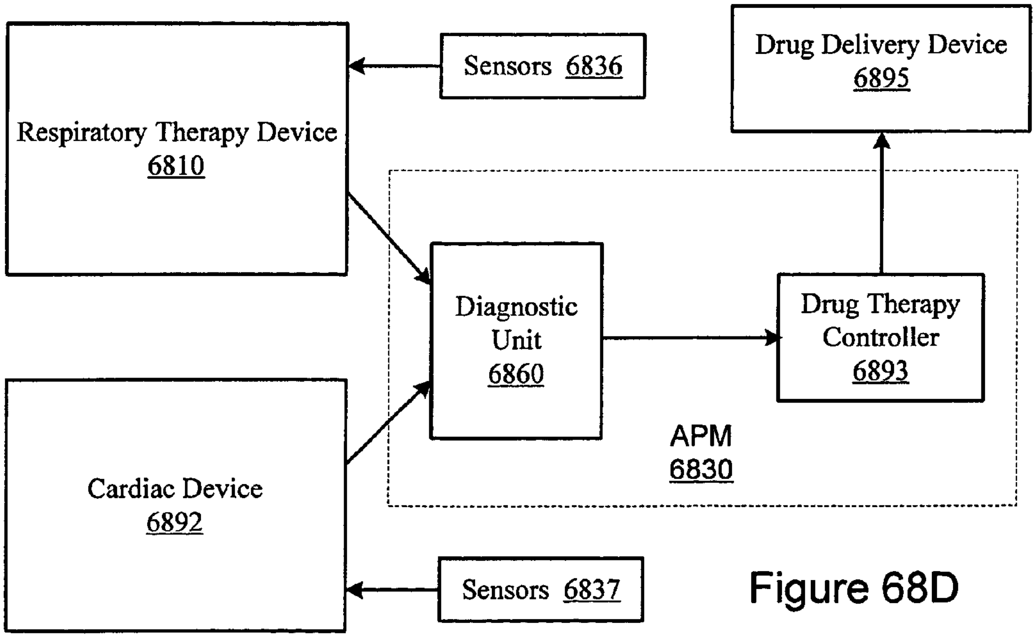

In some embodiments, as illustrated in FIGS. 68C and 68D, an external respiratory therapy device may be used in combination with an implantable device, such as an implantable cardiac rhythm management device, to detect and/or monitor a presence of a non-rhythm pulmonary disease. The system illustrated in FIG. 68C includes an external respiratory therapy device 6810 and a cardiac device 6892, such as an implantable pacemaker, defibrillator, cardioverter, cardiac resynchronizer or cardiac monitor. Both the respiratory therapy device 6810 and the cardiac device 6892 are equipped with sensors/input devices 6835, 6836 for sensing conditions associated with symptoms of one or more non-rhythm pulmonary diseases.

The respiratory therapy device 6810 may transmit its sensed condition information to the cardiac device 6892, e.g., over a wireless communications link. The cardiac device 6892 includes a diagnostic unit 6860 configured to assess a presence of one or more non-rhythm pulmonary diseases by evaluating the conditions sensed by the respiratory device and/or by evaluating additional conditions sensed by the cardiac device.

The diagnostic unit 6860 may assess the one or more non-rhythm pulmonary diseases, for example, by comparing sensed conditions to corresponding sets of criteria indicative of the non-rhythm pulmonary diseases. In this system depicted in FIG. 68C, the cardiac device 6892 includes a drug therapy controller 6893 that develops control signals to control a drug therapy delivered to the patient. The cardiac device 6892 transmits signals to the drug delivery device 6895 to initiate, modify or terminate drug therapy delivered to the patient based on the assessment of the pulmonary disease.

In an alternate implementation one or both of the diagnostics processor 6860 and the drug therapy controller 6893 may be disposed in the respiratory therapy device housing.

The block diagram of FIG. 68D illustrates another arrangement of a pulmonary disease assessment and drug therapy delivery system. In this example, the system includes a respiratory therapy device 6810 and a cardiac device 6892. The respiratory therapy device 6810 and the cardiac device 6892 communicate with a remote diagnostic unit 6860, such as may be incorporated in an APM system. The respiratory therapy device 6810 and the cardiac device 6892 are each equipped with sensors/input devices 6835, 6836 for sensing conditions associated with one or more non-rhythm pulmonary diseases. The respiratory therapy device 6810 and the cardiac device 6892 may transmit sensed condition information to the diagnostic unit 6860 through a wireless or wired communication links. The pulmonary disease diagnostic unit 6860 is configured to use the information transmitted by the respiration therapy device 6810 and the cardiac device 6892 to assess the presence of one or more non-rhythm pulmonary diseases.

A drug therapy controller 6893 uses the assessment of the non-rhythm pulmonary disease to develop signals from controlling the drug therapy delivered to the patient. In one configuration, the diagnostic unit 6860 and the drug therapy controller 6893 may be configured as components of an APM system 6830. A control signal developed by the drug therapy controller may be used to activate, modify, terminate or otherwise control therapy delivered by a drug therapy device 6895.

Assessment of conditions indicative of non-rhythm pulmonary diseases/disorders may include assessing the patient's pulmonary function as previously described. The charts provided in FIGS. 62A-62G-2 illustrate conditions and sensors that may be used to determine physiological changes associated with various non-rhythm pulmonary diseases and disorders. The charts depicted in FIGS. 62A-62G-2 illustrate relationships between various physiological changes and/or disease symptoms associated with non-rhythm pulmonary diseases. FIG. 62A lists representative sets of non-rhythm pulmonary diseases that may be assessed in accordance with embodiments of the invention. The representative set of non-rhythm pulmonary diseases that may be assessed includes, for example, obstructive pulmonary diseases (e.g., chronic bronchitis, emphysema, asthma), restrictive pulmonary diseases (e.g., sarcoidosis, pulmonary fibrosis, pneumoconiosis), infections pulmonary diseases (e.g., bronchitis, pneumonia, bronchiolitis, tuberculosis, and bronchiectasis), pulmonary vasculature diseases (e.g., pulmonary hypertension, pulmonary edema, pulmonary embolism, atalectasis), and diseases of the pleural cavity (e.g., pleural effusion, pneumothorax, and hemothorax).

The non-rhythm pulmonary diseases listed in FIG. 62A are cross-referenced with the physiological changes and/or symptoms associated with the non-rhythm pulmonary disease. The physiological changes and/or symptoms are cross referenced with conditions indicative of the physiological changes and/or symptoms. Sensors used to sense the conditions indicative of the physiological changes or symptoms are provided in FIG. 62A. Sensors of the respiratory therapy device may include, for example, ventilation gas, ventilation flow and/or ventilation pressure sensors, or other sensors for example.

Figure 69:
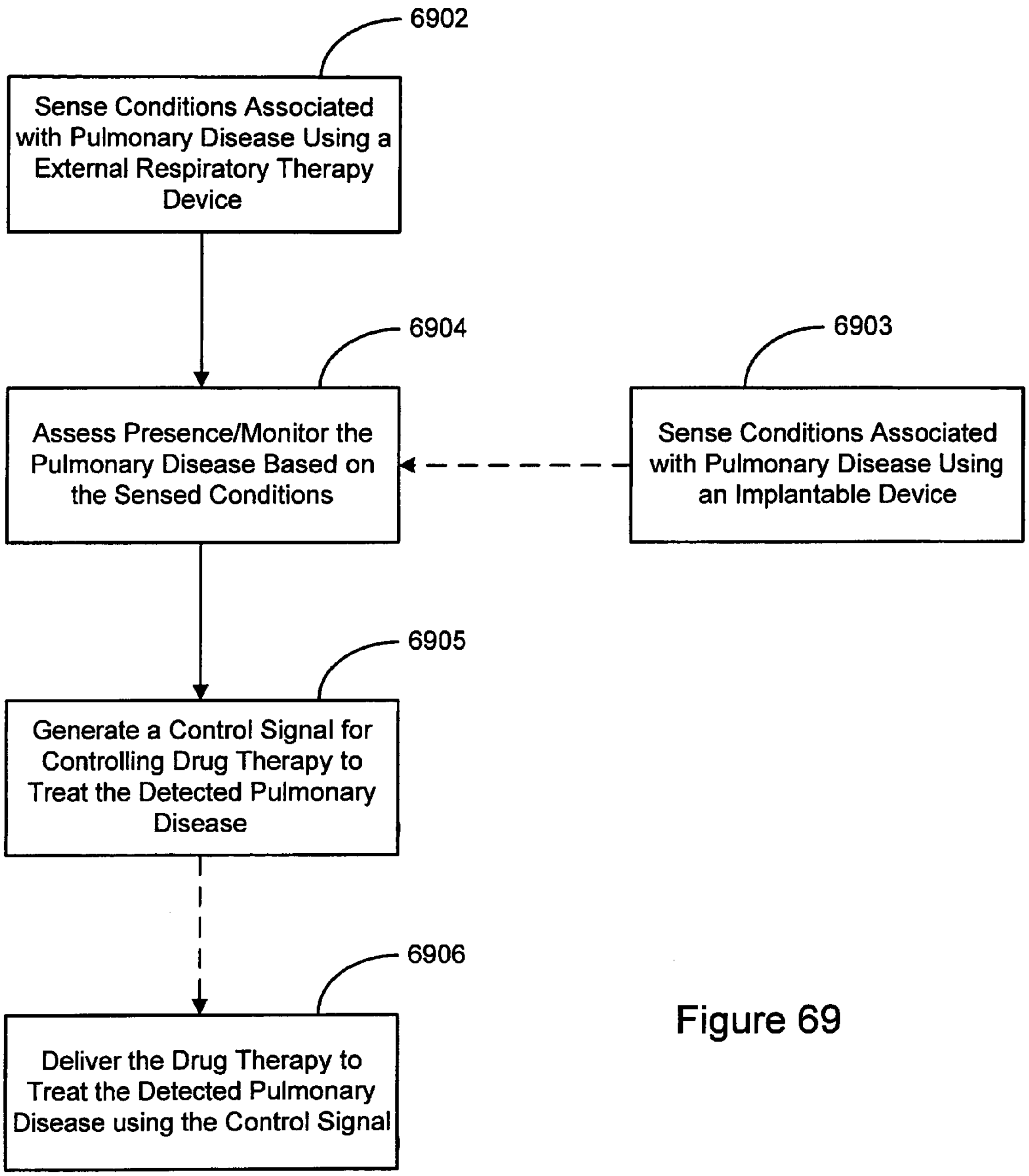
FIG. 69 is a flowchart illustrating a method of determining a presence of a non-rhythm pulmonary disease and delivering therapy in accordance with embodiments of the invention.

FIG. 69 is a flowchart illustrating various optional methods for controlling drug therapy in accordance with embodiments of the invention. In some embodiments, the system generates a control system for controlling the drug therapy. In other embodiments, the system includes a drug delivery unit that is controlled by the control signal.

One method involves using 6902 an external respiratory therapy device to sense conditions associated with the non-rhythm related pulmonary disease. A presence of the non-rhythm pulmonary disease is assessed 6904 based on the sensed conditions. A control signal for controlling drug therapy used to treat the detected pulmonary disease is generated 6905.

Optionally, the external respiratory therapy device may sense 6902 one set of conditions and an implantable device may be used to sense 6903 another set of conditions. The disease presence may be assessed based on the conditions sensed by the external respiratory therapy device and the conditions sensed by the implantable device. In one implementation, the external respiratory therapy device and the implantable device may be used cooperatively to sense conditions affecting the patient and to detect and/or assess a disease presence.

In some embodiments the system includes a drug delivery device. The drug delivery device delivers a drug therapy that is controlled by the control signal. The drug delivery device may be a component of the external respiratory therapy device, the implanted device, or a device separate from the external respiratory therapy device and the implanted device. The drug delivery device may comprise a drug pump, an activatable drug patch, and/or a gas therapy delivery device, for example.

In one scenario, the respiratory device is a CPAP device that has drug delivery functionality. Upon detection and/or assessment of a non-rhythm pulmonary disease, such as asthma, the CPAP device can activate a drug delivery unit to deliver a mist, e.g., an albuterol mist, into the air stream supplied by the CPAP device.

In another scenario, drug therapy may be accomplished using an implantable drug delivery device such as an implantable drug pump. In one implementation, the implantable drug delivery device is configured as a component of an implantable cardiac rhythm management (CRM) system. In another implementation, the implantable drug delivery device is separate from the CRM or other implantable device used for sensing.

Assessing the presence of pulmonary disease may be enhanced by the performance of pulmonary function tests. Pulmonary function testing evaluates lung mechanics, gas exchange, pulmonary blood flow, and blood gases and pH. These tests may be used to evaluate patients in the diagnosis of pulmonary disease and assessment of disease development. According to various aspects of the invention, pulmonary function testing may be implemented using the sensors of the respiratory therapy device, and/or using the sensors of the implantable device.

Various parameters related to pulmonary performance, some of which may be measured using sensors of a respiratory therapy device and/or sensors of an implantable device include, for example, tidal volume, minute ventilation, inspiratory reserve volume, forced expiratory volume, residual volume, and forced vital capacity, among other parameters. According to one embodiment, testing of some pulmonary function parameters may be performed using the ventilation pressure and ventilation flow sensors of a CPAP device or other patient-external respiratory therapy device. The pulmonary function testing may be used, for example, to assess a presence of restrictive and/or obstructive pulmonary disorders.

Pulmonary performance may be evaluated based on data acquired by the respiratory therapy device during normal and forced inspiration and expiration. From such data, pulmonary parameters including tidal volume, minute ventilation, forced expiratory volume, forced vital capacity, among other parameters may be determined.

Because the results of pulmonary function tests vary with size and age, the normal values are calculated using prediction equations or nomograms, which give the normal value for a specific age, height, and sex. The prediction equations are derived using linear regression on the data from a population of normal subjects. The observed values are usually reported as a percentage of the predicted value. Abnormal test results may show either an obstructive or restrictive pattern. Sometimes, both patterns are present.

Figure 70:
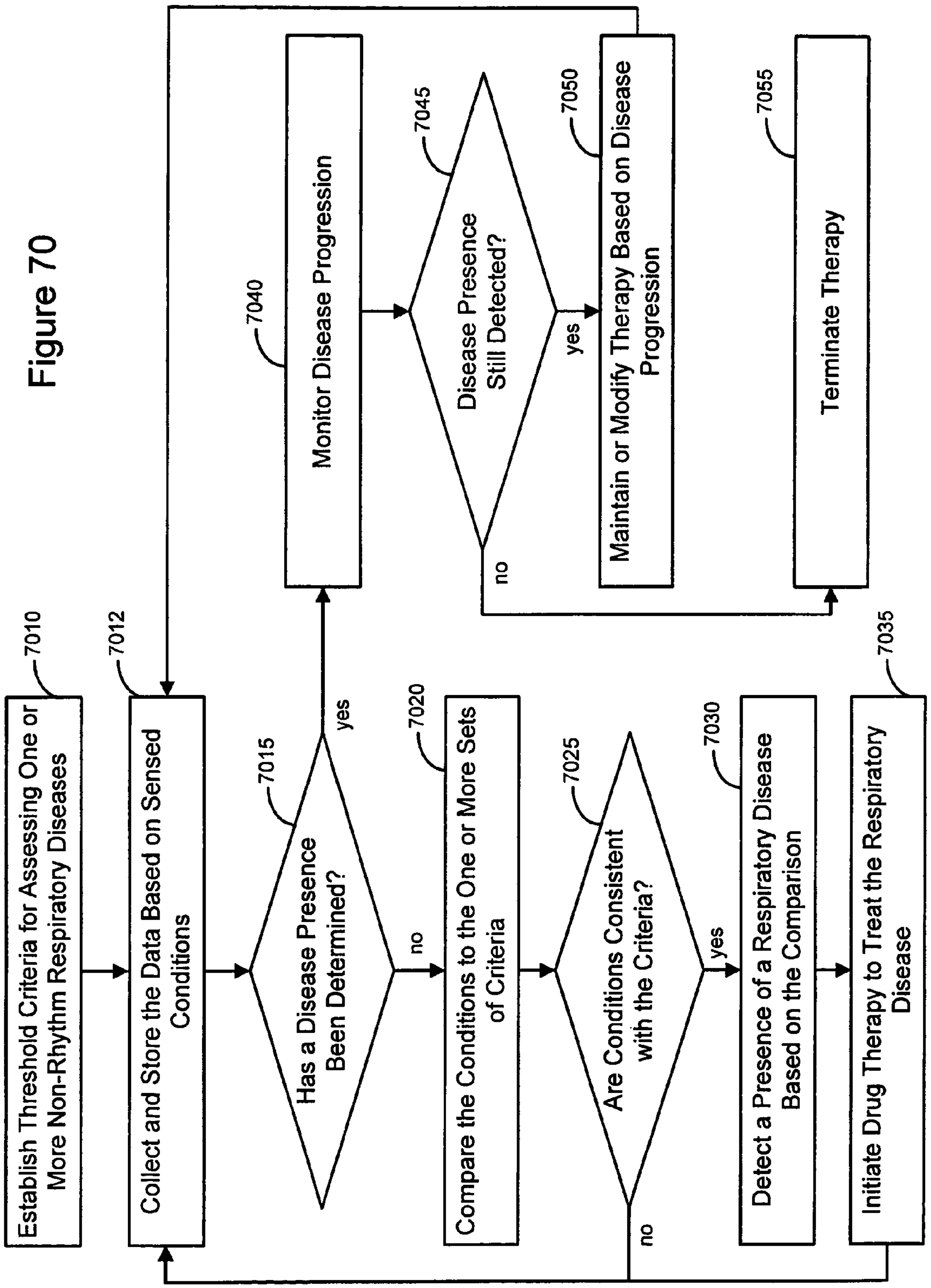
FIG. 70 is a flowchart illustrating a method of assessing a presence of a non-rhythm pulmonary disease and delivering drug therapy in accordance with embodiments of the invention.

FIG. 70 is a flowchart illustrating a method in accordance with embodiments of the invention. Criteria sets for assessment of the non-rhythm pulmonary diseases are established 7010. A respiratory therapy device such as a CPAP device is used to sense conditions modulated by disease symptoms. The sensor information may be collected 7012 periodically, e.g., nightly, and stored for evaluation. If a presence of the disease was not previously determined 7015, then the levels of the sensed conditions are compared 7020 to a set of criteria associated with the disease. If levels of the conditions are consistent 7025 with the threshold criteria levels, then a presence of the disease is determined 7030. Drug therapy is initiated 7035 to treat the respiratory disease.

If levels of the conditions are not consistent 7025 with the threshold criteria levels, then the system continues to sense conditions modulated by disease symptoms and collect 7012 and store data based on the sensed conditions.

If the presence of the disease was previously determined 7015, then the progression of the disease may be monitored 7040 based on the conditions and/or criteria used to determine a presence of the disease, or using other conditions and/or criteria. If the disease presence is still detected 7045 based on the conditions and criteria used for monitoring, then therapy is maintained or modified 7050 based on the disease progression. Disease progression may be determined, for example, by trending one or more conditions used for monitoring the disease presence over a period of time. Modifications to the drug therapy may be made based on the condition trends. If the disease presence is no longer detected 7045, then the drug therapy may be terminated.

Therapy Control Based on Cardiopulmonary Status

Aspects of the invention that include therapy control based on cardiopulmonary status are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving therapy control based on cardiopulmonary status are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 137 (FIG. 1B) for controlling patient therapy based on cardiopulmonary status. The patient therapy control system 137 may be implemented as a stand alone system or in combination with other individual medical systems, such as those described in FIGS. 1B-1D.

Various embodiments of present invention involve methods and systems for controlling therapy based on the cardiopulmonary status of the patient. One embodiment of the invention involves a method for controlling a therapy delivered to a patient based on cardiopulmonary status. One or more physiological conditions are sensed using an external respiratory therapy device. The patient's cardiopulmonary status is assessed based on the sensed physiological conditions. Therapy delivered to the patient is controlled based on the patient's cardiopulmonary status. At least one of assessing the patient's cardiopulmonary status and controlling the therapy is performed at least in part implantably.

According to various aspects of the invention, the physiological conditions are sensed using the sensors of a disordered breathing therapy device. The sensed physiological conditions may include, for example, sensing respiratory pressure, flow, and/or exhaled gas concentration.

In accordance with another aspect of the invention, the sensor system of an additional medical device, different from the respiratory therapy device may be used to sense additional physiological conditions used to assess cardiopulmonary status. In one implementation, the additional medical device comprises an implantable cardiac therapy device.

In accordance with another embodiment of the invention, a medical therapy control system controls therapy based on a patient's cardiopulmonary status. The control system includes an external respiratory device including a sensor system configured to sense one or more physiological conditions. A cardiopulmonary status processor is coupled to the sensor system. The cardiopulmonary status processor is configured to determine a cardiopulmonary status of a patient based on the sensed physiological conditions. A therapy controller is configured to control a therapy delivered to the patient based on the patient's cardiopulmonary status. At least one of the cardiopulmonary status processor and the therapy controller include an implantable component.

Another embodiment of the invention involves a system for providing coordinated patient monitoring, diagnosis and/or therapy that utilizes therapy control system 137. The coordinated system includes, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy includes a system 137 configured control patient therapy based on cardiopulmonary status The therapy control system 137 includes an external respiratory device having a sensor system configured to sense one or more physiological conditions. A cardiopulmonary status processor is coupled to the sensor system and is configured to determine a patient's cardiopulmonary status using sensed physiological conditions. The system further includes a therapy controller coupled to the cardiopulmonary status processor that is configured to control patient therapy using the patient's cardiopulmonary status. At least one of the cardiopulmonary status processor and the therapy controller are at least in part implantable The implantable and respiratory therapy devices 181, 184 may operate cooperatively based therapies delivered according to a patient's cardiopulmonary status. For example, control of patient therapy based on cardiopulmonary status may allow the implantable and respiratory therapy devices 181, 184 to operate cooperatively to provide external and implantable sensing capabilities and external and implantable therapy controlling capabilities. Systems and methods directed to therapy control based on cardiopulmonary status may be implemented to include selected features, functions, and/or structures described in commonly owned, U.S. Pat. No. 7,662,101, which is hereby incorporated herein by reference.

Figure 71A:
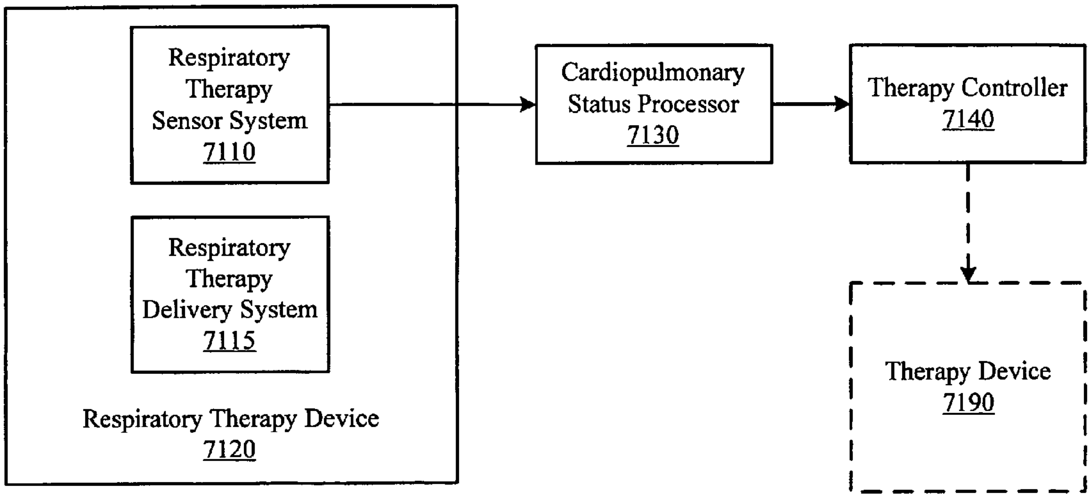
FIGS. 71A and 71B are block diagrams of medical systems that may be used to implement therapy control based on cardiopulmonary status assessment in accordance with embodiments of the invention.
Figure 71B:
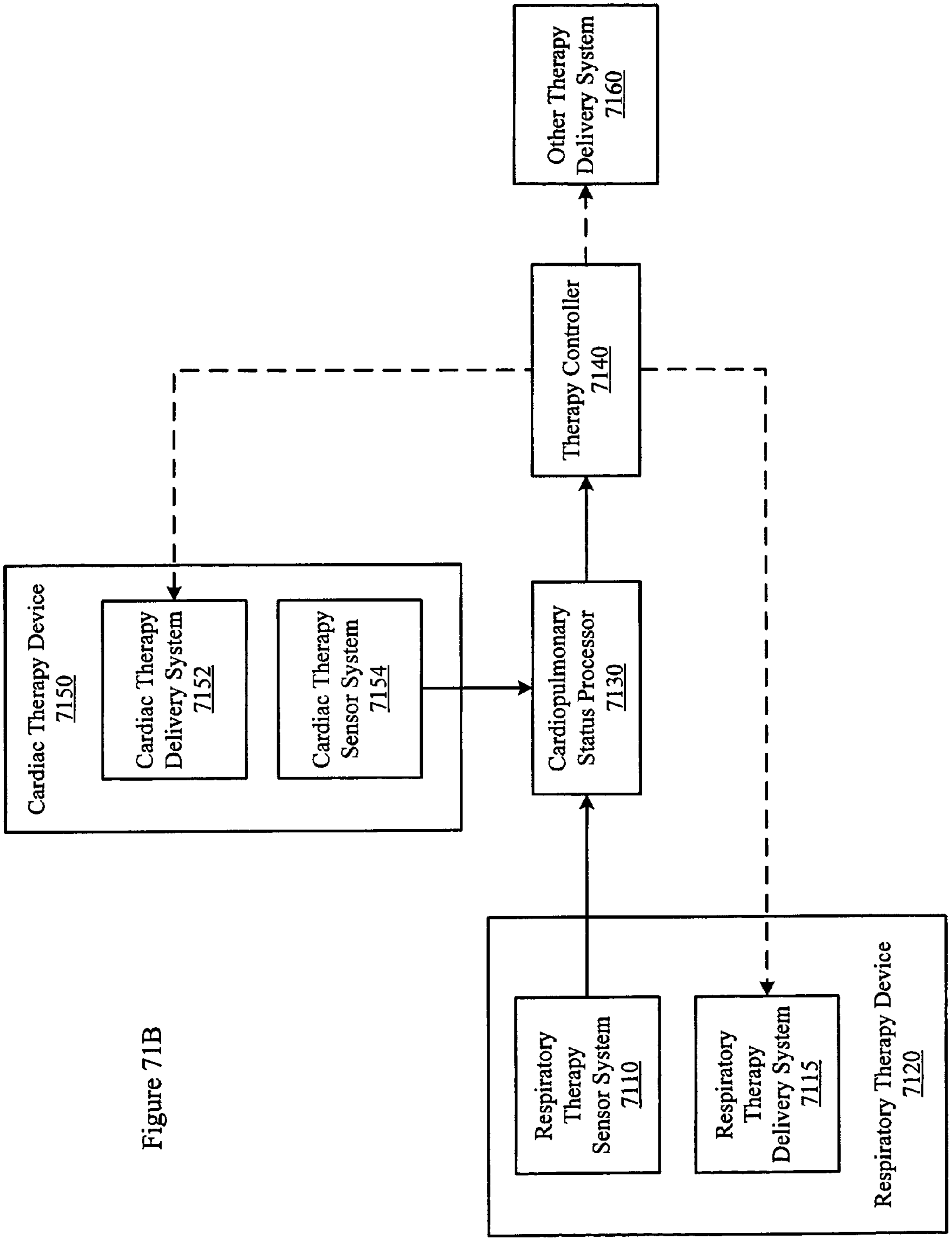

FIGS. 71A and 71B are block diagrams of medical systems that may be used to implement therapy control based on cardiopulmonary status assessment in accordance with embodiments of the invention. In these embodiments, the system utilizes a sensor system 7110 of a respiratory therapy device 7120 to sense one or more physiological conditions. For example, the sensor system 7110 may sense conditions associated with patient respiration, including breathing cycles, respiratory pressure, concentration of respiratory gases, respiratory airflow, and/or other physiological conditions. The respiratory therapy device 7110 includes a respiratory therapy delivery system 7115, such as a positive airway pressure delivery system in the case of a CPAP device, for example.

The system includes a cardiopulmonary status processor 7130 coupled to the respiratory therapy sensor system 7110. The cardiopulmonary status processor assesses the patient's cardiopulmonary status. Assessment of cardiopulmonary status may include evaluating the patient's pulmonary function as previously described. In some implementations, the cardiopulmonary status processor may work in cooperation with the respiratory therapy device, and/or other therapy or diagnostic devices to perform the pulmonary function testing required or desired. Cardiopulmonary status evaluation may comprise determining and/or assessing a presence of cardiac and/or pulmonary disease.

As illustrated in FIG. 71A, the system include a therapy controller 7140, that develops control signals that may be used to control one or more therapy devices 7160.

FIG. 71B illustrates another embodiment of the invention. The embodiment illustrated in FIG. 71B includes a cardiac therapy device 7150 including a cardiac therapy sensor system 7154 that is used in combination with the respiratory therapy sensor system 7110 to assess the patient's cardiopulmonary status. Signals from the cardiac therapy sensor system 7154 and the respiratory therapy system 7115 are utilized by the cardiopulmonary status processor 7130 to determine the cardiopulmonary status of the patient. Assessment of the patient's cardiopulmonary status may involve sensing a presence of a cardiac and/or pulmonary disease. The sensor systems 7110, 7154, of one or both of the respiratory therapy device 7120, the cardiac therapy device 7154, and/or other sensor systems (not shown), may be used for cardiopulmonary status assessment.

The sensor systems 7110, 7154, may be used in connection with performing pulmonary function testing as described above. Cardiopulmonary status assessment may comprise determining and/or assessing a presence of cardiac and/or pulmonary disease. According to one aspect of the invention, the cardiopulmonary status processor may assess a presence of a cardiac disease/disorder. The cardiac disease/disorder assessment may involve, for example, cardiac rhythm related disorders, arterial diseases, heart failure, and/or hypertension.

The cardiopulmonary status processor may be used to detect a presence of one or more rhythm-related and/or non-rhythm related pulmonary diseases/disorders. Rhythm-related breathing disorders involve disruption of the normal respiratory cycle. Although disordered breathing often occurs during sleep, the condition may also occur while the patient is awake. Disordered breathing may be detected by sensing and analyzing various conditions associated with disordered breathing. Table 1 above provides examples of how a representative subset of physiological and non-physiological, contextual conditions may be used in connection with disordered breathing detection.

Detection of apnea and severe apnea may utilize information related to the patient's sleep state. Because disordered breathing occurs more frequently during sleep, assessment of rhythm-related breathing disorders may involve determination of whether the patient is asleep. Other types of cardiopulmonary disorders may be modified by the patient's sleep state. The cardiopulmonary status processor may use sleep state information in connection with the assessment of the patient's cardiopulmonary status.

The cardiopulmonary status processor 7130 develops signals related to the patient's cardiopulmonary status. These signals are transmitted to a therapy controller 7140 that utilizes signals to control therapy delivered to the patient. The controlled therapy may comprise a respiratory therapy delivered to the patient by a respiratory therapy delivery system 7115, a cardiac therapy delivered to the patient by a cardiac therapy delivery system 7152, or a therapy delivered by another therapy system 7160, e.g., internal or external nerve or muscle stimulator and/or internal or external drug pump.

Figure 72:
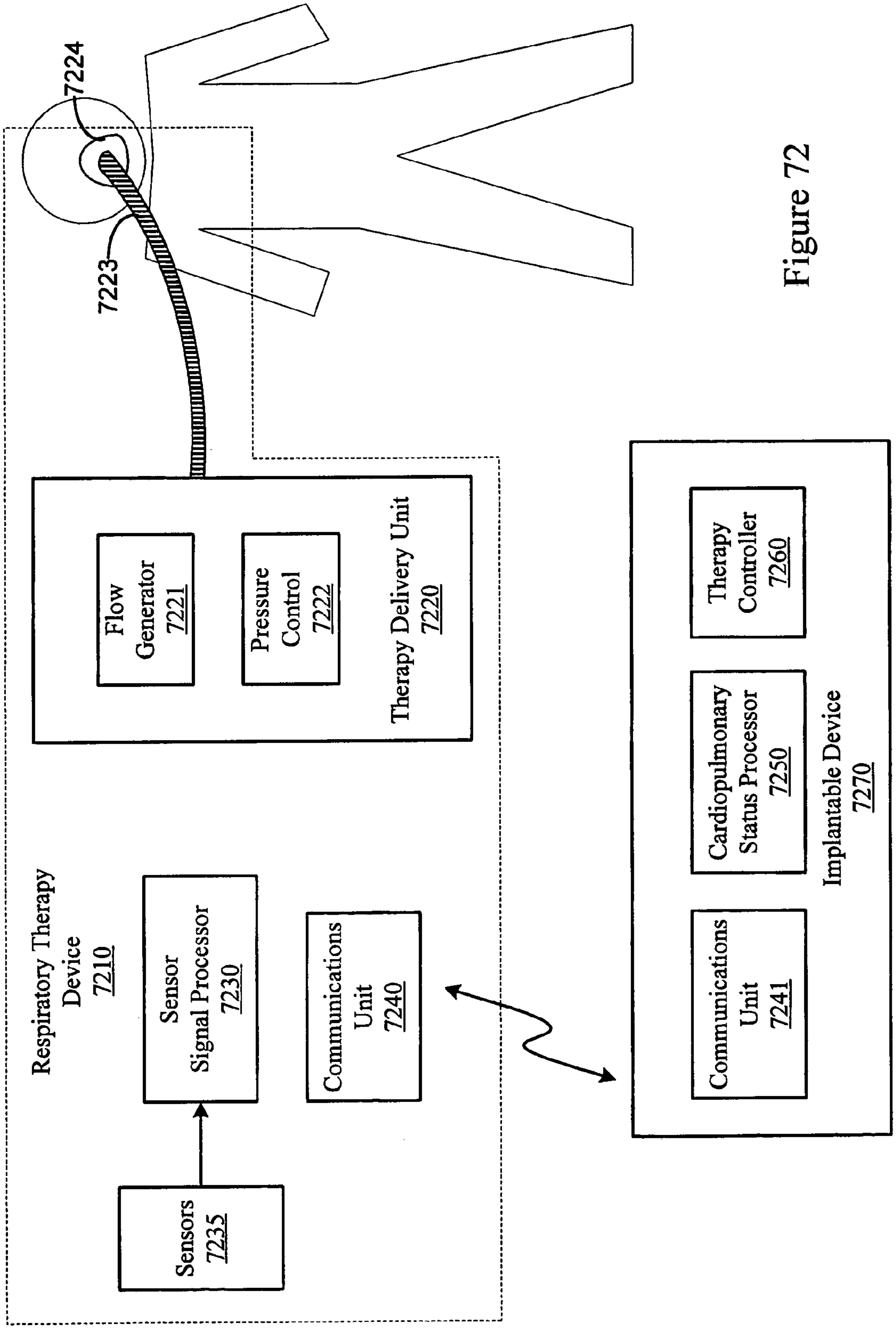
FIG. 72 illustrates a medical system including an external respiratory device and an implantable device that may be used to assess the patient's cardiopulmonary status and control the delivery of therapy in accordance with embodiments of the invention.

FIG. 72 illustrates a block diagram of a therapy system including a respiratory therapy device 7210, e.g., CPAP device or other respiratory therapy device, which may be used to provide external respiratory therapy for disordered breathing. The respiratory therapy device 7210 includes one or more sensors 7235, e.g., flow, pressure and/or exhaled gas concentration sensors used to sense respiratory conditions and/or other conditions useful in the assessment of the patient's cardiopulmonary status. Signals generated by the sensors 7235 are processed by signal processing circuitry 7230 within the respiratory therapy device 7210.

The respiratory therapy device 7210 may include a device that provides positive and negative airflow pressure to the patient. The breathing therapy delivery unit 7220 includes a flow generator 7221 that pulls in air through a filter. The flow generator 7221 is controlled by the pressure control circuitry 7222 to deliver an appropriate air pressure to the patient. Air flows through tubing 7223 and is delivered to the patient's airway through a mask 7224. In one example, the mask 7224 may be a nasal mask covering only the patient's nose. In another example, the mask 7224 covers the patient's nose and mouth.

The respiratory therapy device 7210 may include a communications unit 7240 for communicating with a compatible communications unit 7241 of one or more separate devices, such as an implantable device 7270. In one example, the respiratory therapy device 7210 sends information about sensed respiratory flow, pressure, and expired gas to the implantable device. The respiratory therapy device receives therapy control information controlling the therapy delivered by the respiratory therapy device 7210 from the implantable device 7270.

The implantable device 7270, which may comprise an implantable cardiac device, includes a cardiopulmonary status processor 7250 used to assess the cardiopulmonary status of the patient. The cardiopulmonary status processor 7250 uses the sensor information transferred to the implantable device 7270 from the respiratory therapy device 7210 to determine the status of the patient's cardiopulmonary system. Information from the respiratory therapy device sensors 7235 may be transferred from the respiratory therapy device 7210 to the implantable device 7270 through communications units 7240, 7241 of the respective devices 7210, 7270. In some embodiments, the cardiopulmonary assessment processor 7250 may use information acquired by the respiratory therapy device sensors 7235 in addition to other information received from other devices and/or sensors in performing the cardiopulmonary status assessment.

The implantable device 7270 may additionally or alternatively include a therapy controller 7260 that develops therapy control signals based on the patient's assessed cardiopulmonary status. Therapy control signals developed by the therapy controller 7260 may be transmitted to the respiratory therapy device 7210 through the communications units 7241, 7240. The therapy control signals are used to control the therapy delivered by the respiratory therapy device: For example, if the cardiopulmonary assessment processor 7250 detects a presence of a cardiopulmonary disease, the delivery of respiratory therapy to the patient may be controlled to treat the detected cardiopulmonary disease presence. In other examples, delivery of the respiratory therapy may be controlled to improve patient comfort based on the assessed cardiopulmonary status, or to meet other therapeutic goals.

The therapy controller 7260 may control the respiratory therapy by initiating, terminating or modifying the respiratory therapy. Controlling the respiratory therapy may involve initiating, terminating or modifying one or more therapy parameters. For example, the therapy controller 7260 may be used to modify gas pressure or gas flow delivered by the respiratory therapy device 7210. The therapy controller 7260 may initiate or terminate a gas flow or modify a gas concentration of the respiratory therapy, for example.

Additionally or alternatively, the therapy controller 7260 may develop control signals used to control therapy delivered by the implantable device 7270. The implantable device therapy may be controlled to treat a detected cardiopulmonary disease or disorder, to improve patient comfort, or for other purposes. In one embodiment, the implantable device comprises a cardiac therapy device that delivers cardiac electrical stimulation therapy to the patient. The therapy controller initiate or terminate the cardiac electrical stimulation therapy and/or control various parameters of the cardiac electrical stimulation, e.g., stimulation energy, stimulation timing. The cardiac electrical stimulation therapy may involve non-excitatory electrical stimulation involving sub-capture threshold stimulation or stimulation during a refractory period, for example. The therapy controller may modify one or more parameters of the non-excitatory electrical stimulation therapy.

The cardiac electrical stimulation may involve cardiac pacing therapy. The therapy controller may initiate or terminate the pacing therapy. The therapy controller may modify the cardiac pacing therapy by alter a pacing rate (e.g., change from a normal sleep rate to an overdrive pacing rate), pacing timing (e.g., modify the AV delay or other pacing timing parameter), pacing mode, (e.g., switch from DDD to VVI pacing or from a tracking mode to a non-tracking pacing mode) and/or pacing type (e.g., switch from dual chamber to biventricular pacing or from single chamber to dual chamber).

Figure 73:
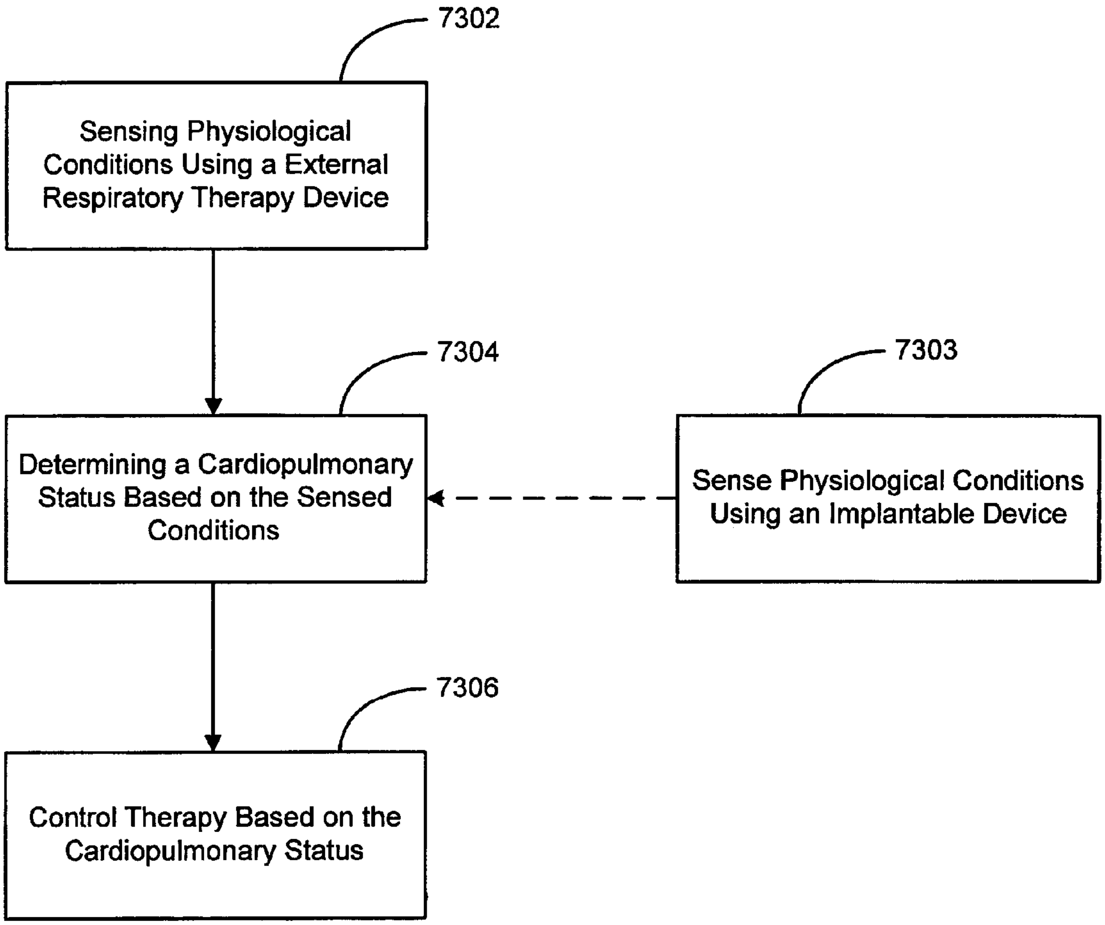
FIG. 73 is a flowchart illustrating a method of determining a presence of a non-rhythm pulmonary disease and delivering therapy in accordance with embodiments of the invention.

Embodiments of the invention involve methods of controlling a therapy delivered to the patient, as illustrated in the flowchart of FIG. 73. One or more physiological conditions are sensed 7302 using the sensing system of an external respiratory therapy device. In various implementations, the external respiratory therapy device may comprise, for example, a gas therapy device, nebulizer, ventilator, positive airway pressure device, or other type of respiration therapy device. The patient's cardiopulmonary status is assessed 7304 based on the sensed physiological conditions. Therapy delivered to the patient is controlled 7306 based on the patient's cardiopulmonary status. The therapy may be used to treat breathing rhythm disorders, non-rhythm related pulmonary diseases/disorders, cardiac disorders, and/or other diseases or disorders affecting the patient.

In one embodiment, an implantable device may be used to sense 7303 additional physiological conditions. The patient's cardiopulmonary status is assessed 7304 based on the physiological conditions sensed by the external respiratory device and the additional physiological conditions sensed by the implantable device. At least one of assessing the patient's cardiopulmonary status and controlling the therapy is performed at least in part implantably.

In one implementation, the presence of a cardiac and/or pulmonary disease or disorder is detected and therapy to treat the disease or disorder is delivered to the patient. The therapy may be modified to improve therapy effectiveness based on the assessment of the cardiac and/or pulmonary disease or disorder. In another embodiment of the invention, the patient's cardiopulmonary status is assessed and the therapy delivered to the patient is modified to enhance patient comfort or to achieve another result.

For example, the patient's cardiopulmonary status may be assessed based on sensed physiological conditions indicative of symptoms or physiological changes associated with a particular disease or disorder. A respiratory therapy device used to sense the physiological conditions may comprise, for example, a gas therapy device, nebulizer, ventilator, positive airway pressure device, or other type of respiration therapy device. In a preferred embodiment, the respiratory therapy device comprises a positive airway pressure device. Continuous positive airway pressure (CPAP) devices are frequently used to treat sleep apnea and/or other breathing rhythm disorders. A CPAP device may be used regularly during a patient's sleep time to prevent or treat sleep disordered breathing events. Use of a CPAP device for treatment of breathing rhythm disorders facilitates detection of rhythm-related and non-rhythm related pulmonary diseases. The CPAP device provides sensors available on a periodic basis, e.g., nightly, that may be used to sense conditions indicative of cardiopulmonary status.

In another implementation, assessment of the cardiopulmonary status of the patient is based on one or more physiological conditions sensed using a patient-external respiratory therapy device and on one or more additional physiological conditions sensed using a cardiac device. The cardiac device may comprise, for example, an implantable cardiac therapy device, such as a pacemaker, defibrillator, cardioverter, cardiac monitor, and/or cardiac resynchronizer.

In yet another implementation, assessment of the cardiopulmonary status of the patient is based on one or more physiological conditions sensed using a patient-external respiratory therapy device and one or more additional conditions sensed or detected using an additional patient-external device. The patient-external device may comprise, for example, a patient operated input device, a patient information database, or a network-connected server, for example.

According to one aspect of the invention, pulmonary function testing may be employed to detect physiological changes associated with the presence of cardiac and/or pulmonary disease. Pulmonary function tests may be used to evaluate lung mechanics, gas exchange, pulmonary blood flow, and blood gases and pH. They are used to evaluate patients in the diagnosis of pulmonary disease, assessment of disease development, or evaluation of the risk of pulmonary complications.

Various parameters related to pulmonary performance, some of which may be measured using sensors of a respiratory therapy device include, for example, tidal volume, minute ventilation, inspiratory reserve volume, forced expiratory volume, residual volume, and forced vital capacity, among other parameters. According to one embodiment, testing of some pulmonary function parameters may be performed using the ventilation pressure and ventilation flow sensors of a CPAP device or other patient-external respiratory therapy device. The pulmonary function testing may be used, for example, to assess a presence of restrictive and/or obstructive pulmonary disorders.

In some embodiments, pulmonary function testing may be performed using a cardiac rhythm management system (CRM) or other implantable device. In one implementation, the pulmonary function testing is performed using an implanted transthoracic impedance sensor. Transthoracic impedance sensing has been used in connection with rate-adaptive pacemakers to measure respiration cycles. An impedance sensor may be used to measure the variation in transthoracic impedance, which increases during the inspiratory and decreases during the expiratory phase of a respiration cycle. The sensor injects a sub-threshold stimulating current between the pacemaker case and an electrode on an intracardiac or subcutaneous lead, and measures the voltage across the case and another electrode on the same or another lead. Clinical investigations have shown that the impedance sensor can measure respiratory rate tidal volume, and minute ventilation accurately.

In accordance with various embodiments of the invention, a properly calibrated impedance sensor, implemented in cooperation with a pacemaker or other implantable device, may be used to measure FVC and FEV during forced expiration. From these two parameters, FEV/FVC can be derived to differentiate obstructive versus restrictive respiratory patterns as shown in the FIGS. 1C and 1D, respectively.

In addition, the forced expiratory flow ($FEF_{25-75\%}$) may be measured. The middle half by volume of the total expiration is marked, and its duration is measured. The $FEF_{25-75\%}$ is the volume in liters divided by the time in seconds. In patients with obstructive diseases, the $FEF_{25-75\%}$ is generally greater than their expected values.

The implantable device may be used to compare measured FVC, FEV and $FEF_{25-75\%}$ values derived from the implanted impedance sensor with predicted values from normal subjects in accordance with various embodiments. The comparison provides diagnostic information of lung mechanics.

Data acquired using the above-described techniques may be transmitted from the implantable device to an advanced patient management system or other remote device. Assessment of the patient's cardiopulmonary status or control of the therapy may be performed by the advanced patient management system.

Assessment of cardiopulmonary status may include assessing the patient's pulmonary function as previously described. In some implementations, the cardiopulmonary status processor may use sensed conditions acquired by the respiratory therapy device, and/or other therapy or diagnostic devices to assess patient's cardiopulmonary status. Cardiopulmonary status assessment may comprise evaluating a presence of cardiac and/or pulmonary disease. The charts provided in FIGS. 6A-6N illustrate conditions and sensors that may be used to determine physiological changes associated with various cardiac and/or pulmonary diseases and disorders.

The left section 6202 of FIG. 62A illustrates various conditions that may be sensed using sensors of a respiratory therapy device (CPAP), a cardiac device (CRM), or an external non-CPAP, non-CRM device. The top section 6201 lists various conditions that may be sensed and provides information about sensors used to sense the conditions. The center section 6204 of FIG. 62A provides physiological changes and/or symptoms that may be evaluated using the conditions listed in the left section 6202. The right section 603 of FIG. 6A provides pulmonary diseases/disorders. The presence of the pulmonary diseases/disorders of the right section 6203 may be assessed based on the physiological changes and/or symptoms of the center section 6204.

For legibility, the left and right sections 6202, 6203 of FIG. 62A are divided into sixteen portions, FIGS. 62B-1-62G-2. FIGS. 62B-1 to 62B-4 represent the upper left portions 6210-1 to 6210-4 of the left section 6202 of FIG. 62A. FIGS. 62C-1 to 62C-2 represent the upper right portions 6212-1 to 6212-2 of the left section 6202 of FIG. 62A. 62D-1 to 62D-4 represent the lower left portions 6214-1 to 6214-4 of the left section 6202 of FIG. 62A. FIGS. 62E-1 to 62E-4 represent the lower right portions 6216-1 to 6216-2 of the left section 6202 of FIG. 62A. FIGS. 62F-1 to 62F-2 represent the upper portions 6220-1 to 6220-2 of the right section 6203 of FIG. 62A. 62G-1 to 62G-2 represent the lower portions 6222-1 to 6222-2 of the right section 6203 of FIG. 62A. Relevant portions of the center section 6204 and the top section 6201 of FIG. 62A appear in each of the FIGS. 62B-1-62G-2 for convenience.

Figure 62H:
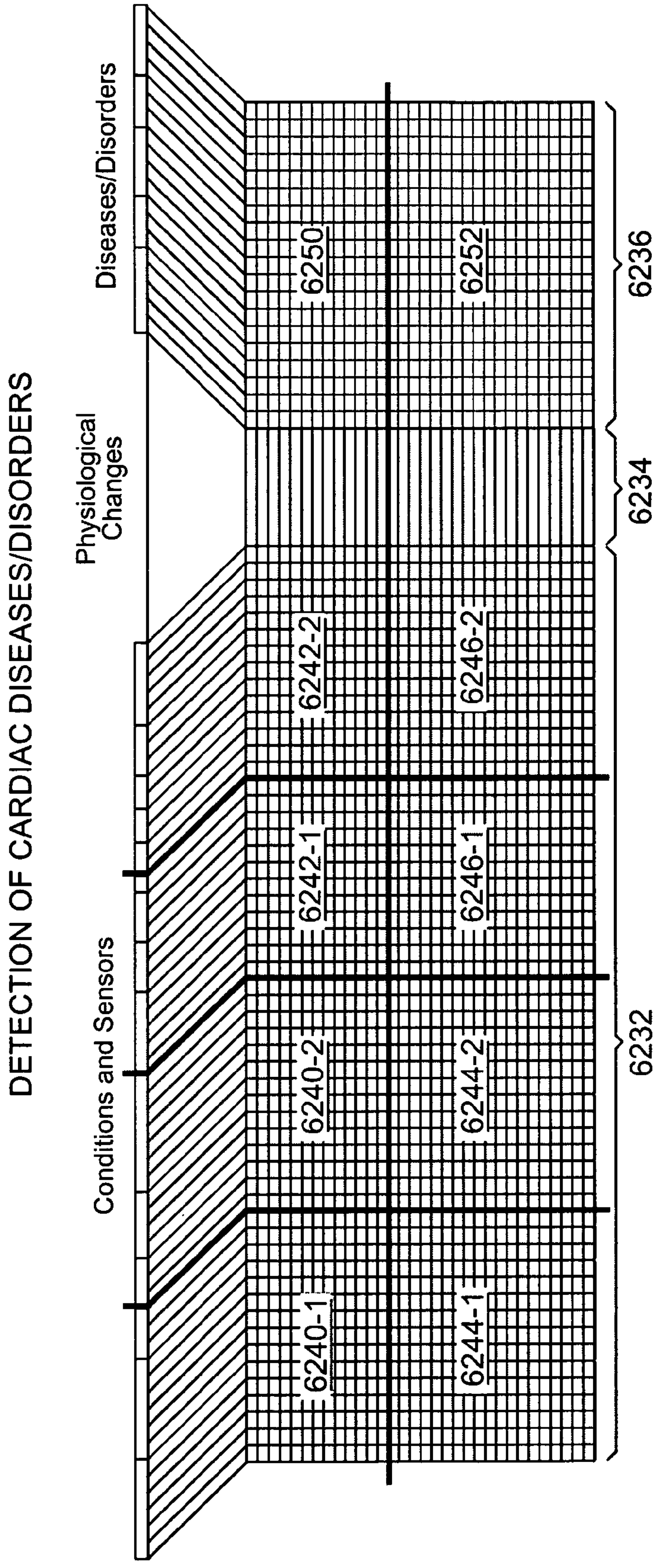

The charts provided in FIGS. 62H-62N illustrate conditions and sensors that may be used to determine physiological changes associated with various cardiac diseases and disorders. The left section 6232 of FIG. 62H illustrates various conditions that may be sensed using sensors of a respiratory therapy device (CPAP), a cardiac device (CRM), or an external non-CPAP, non-CRM device. The center section 6234 of FIG. 62H provides physiological changes and/or symptoms that may be evaluated using the conditions listed in the left section 6232. The right section 6236 of FIG. 62H lists cardiac diseases/disorders. The presence of the cardiac diseases/disorders of the right section 6236 may be assessed based on the physiological changes and/or symptoms of the center section 6234.

For legibility, the chart of FIG. 62H is divided into ten portions, FIGS. 62I-1-62N. FIGS. 62I-1 to 621-2 represent the upper left portions 6240-1 to 6240-2 of the left section 6232 of FIG. 62H. FIGS. 62J-1 to 62J-2 represent the upper right portions 6242-1 to 6242-2 of the left section 6232 of FIG. 62H. FIGS. 62K-1 to 62K-2 represent the lower left portions 6244-1 to 6244-2 of the left section 6232 of FIG. 62H. FIGS. 62L-1 to 62L-2 represent the lower right portions 6246-1 to 6246-2 of the left section 6232 of FIG. 62H. FIG. 62M represents the upper portion 6250 of the right section 6236 of FIG. 62H. FIG. 62N represents the lower portion 6252 of the right section 6236 of FIG. 62H. Relevant portions of the center section 6204 and the top section 6201 of FIG. 62H appear in each of the FIGS. 62I-1-62N for convenience.

An example of how FIGS. 62A-62N may be used follows. Referring to FIGS. 62F-1 to 62G-2, the restrictive pulmonary disorder pneumoconiosis produces the physiological changes non-specific dyspnea (FIG. 62F-1) and cough (FIG. 62G-1). Non-specific dyspnea (FIG. 62F-1) and cough (FIG. 62G-1) are indicated by X or D marks in the column denoted pneumoconiosis in FIGS. 62F-1 and 62G-1, respectively. An "X" mark indicates that the symptom or physiological change may be derived from the sensed condition. A "D" mark indicates that the symptom or physiological change may be directly determined from the sensed condition. Non-specific dyspnea may be detected based on one or more of the conditions listed in the row for non-specific dyspnea illustrated in FIGS. 62B-1, 62B-3, and 62C-1. The conditions include duration of symptoms, abnormal breathing/coughing, blood pO2, inspiratory flow, expiratory flow, exhaled % CO2 and exhaled % O2, illustrated in FIG. 62C-1. The conditions also include arterial/venous pO2, blood pCO2, blood pO2, exhalation time, inspiration time, minute ventilation, tidal volume, respiration rate, FIG. 62B-3, and/or respiration sounds illustrated in FIG. 62B-1.

Figure 74:
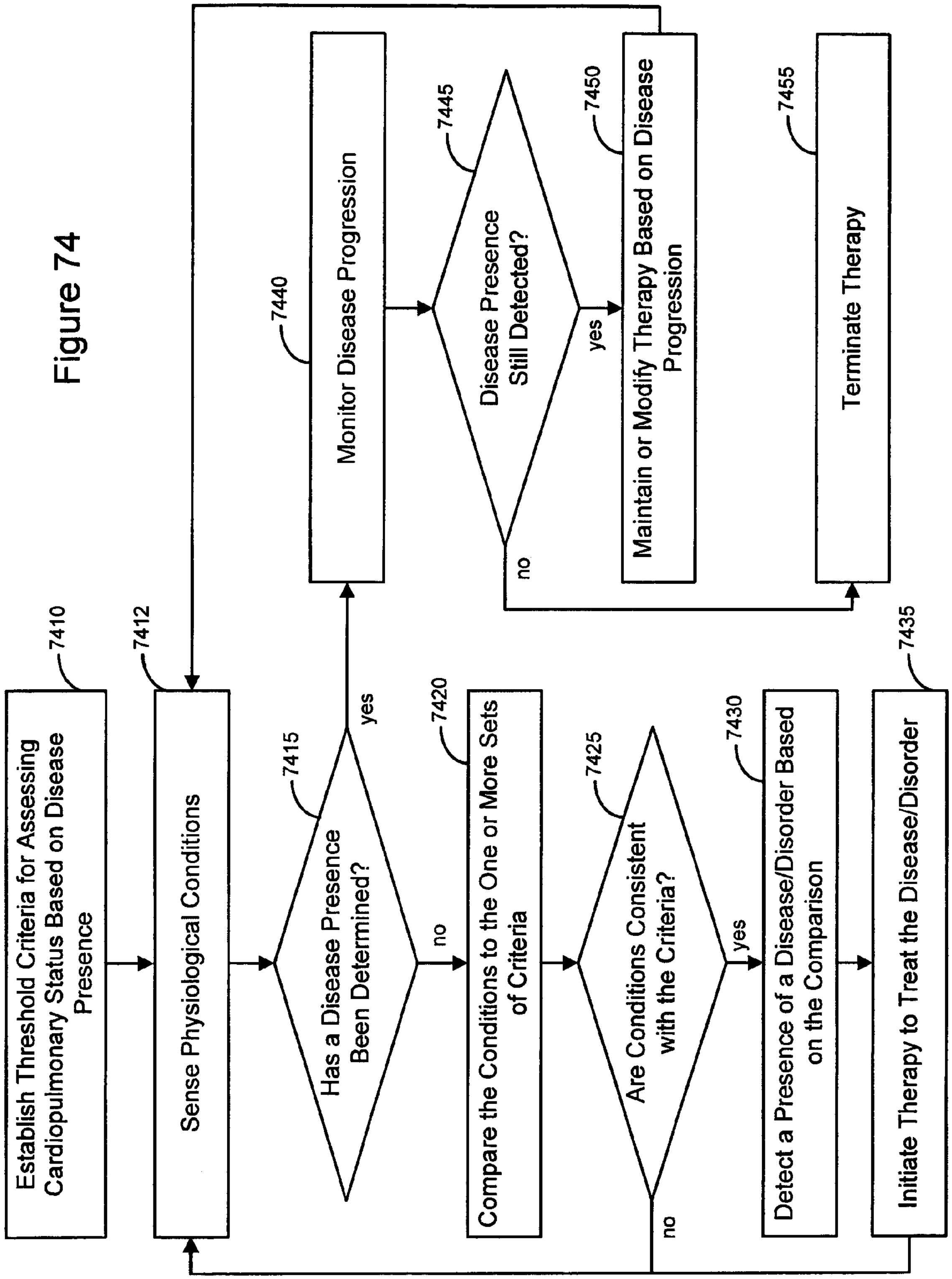
FIG. 74 is a flowchart illustrating a method of assessing a presence of a non-rhythm pulmonary disease and delivering drug therapy in accordance with embodiments of the invention.

FIG. 74 is a flowchart illustrating a method in accordance with embodiments of the invention. One or more threshold criteria sets for assessment of cardiopulmonary status based on the disease/disorder presence are established 7410. A respiratory therapy device such as a CPAP device may be used to sense 7412 conditions modulated by disease symptoms. The sensor information may be collected periodically, e.g., nightly, and stored for evaluation. If a presence of the disease has not been previously determined 7415, then the levels of the sensed conditions are compared 7420 to a set of criteria associated with the disease. If levels of the conditions are consistent 7425 with the threshold criteria levels, then a presence of the disease is determined 7430. Therapy may be modified based on the presence of the disease/disorder. In one implementation, therapy may be initiated 7435 to treat the disease.

If levels of the conditions are not consistent 7425 with the threshold criteria levels, then the system continues to sense conditions modulated by disease symptoms and collect 7412 data based on the sensed conditions.

If the presence of the disease was previously determined 7415, then the progression of the disease may be monitored 7440 based on the conditions and/or criteria used to determine a presence of the disease, or using other conditions and/or criteria. If the disease presence is still detected 7445 based on the conditions and criteria used for monitoring, then therapy may be maintained or modified 7450 based on the disease progression. Disease progression may be determined, for example, by trending one or more conditions used for monitoring the disease presence over a period of time. Modifications to the therapy may be made based on the condition trends.

Methods and Systems for Control of Gas Therapy

Aspects of the invention that include control of gas therapy are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that include control of gas therapy are directed methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve adapting gas therapy based on blood gas concentration. Methods may involve sensing concentration of a blood gas and adapting a gas therapy for a patient. Methods may further involve delivering the adapted gas therapy to the patient. At least one of sensing the blood gas concentration and adapting the gas therapy is performed at least in part implantably.

Other embodiments of methods involve both sensing the blood gas concentration and adapting the therapy being performed at least in part implantably. Adapting a therapy may involve comparing the sensed blood gas concentration to a threshold and modifying the therapy if the blood gas concentration is beyond the threshold. Modifying the therapy may involve increasing or decreasing a gas pressure of a positive airway pressure device. Adapting a therapy may involve comparing the sensed blood gas concentration to a predetermined range and modifying the therapy if the blood gas concentration is beyond the predetermined range.

Some embodiments may involve adapting oxygen therapy delivered to a patient, wherein adapting the therapy involves comparing a blood oxygen level to a predetermined range and modifying the therapy if the blood oxygen level is beyond a predetermined range, such as by increasing oxygen gas pressure in response to the blood oxygen level falling below a threshold. Alternatively, or additionally, adding or increasing a vasodilator or a bronchodilator in response to the blood oxygen level falling below a threshold may also be performed.

In other embodiments, a therapy system includes a sensor unit configured to sense blood gas concentration. A therapy controller is coupled to the sensor unit and is configured to adapt a gas therapy. The system further includes a gas therapy delivery unit coupled to the therapy controller and configured to deliver the adapted gas therapy to the patient. At least one of the sensor unit and the controller includes an implantable component.

Other embodiments include each of a sensor unit and a therapy controller having an implantable component. The sensor unit may be a component of an implantable cardiac therapy device or a component of a patient-external respiratory therapy device. The sensor unit may include a blood oxygen sensor and/or carbon dioxide sensor, and may be coupled to an implantable cardiac therapy device, directly or wirelessly. In further embodiments, the sensor unit is coupled to the controller through the gas therapy delivery unit, which may deliver a vasodilating or a bronchodilator agent.

According to additional embodiments, a sensor may be configured to detect disordered breathing, and, in response to detecting disordered breathing, gas therapy may be modified (e.g., initiated, modified, terminated) to suppress the disordered breathing. In addition, the type of disordered breathing may be discerned, such as discerning central apnea from obstructive apnea. If, for example, central apnea is detected, small amounts of carbon dioxide may be applied to the patient's air supply (e.g., via a positive airway pressure device) to mitigate the carbon dioxide instability that is leading to central apnea.

Embodiments of the invention may involve an individual system 135 (FIG. 1B) for sensing concentration of a blood gas and adapting a gas therapy for a patient. Sensing concentration of a blood gas and adapting a gas therapy for a patient may be implemented as a stand alone system or in combination with other individual medical systems, such as those described in FIGS. 1B-1D. For example, embodiments of the invention may involve a system for providing coordinated patient monitoring, diagnosis and/or therapy that utilizes sensing 135 concentration of a blood gas and adapting a gas therapy.

The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy. Systems and methods directed to gas therapy control may be implemented to include selected features, functions, and/or structures described in commonly owned, co-pending U.S. Publication No. 2005/0061323, which is hereby incorporated herein by reference.

Various embodiments of the present invention are implemented using medical systems employing one or a number of patient-external and/or patient-internal medical devices. Medical devices may communicate or otherwise operate in concert or in a stand-alone manner to provide more comprehensive patient monitoring, diagnosis, and therapy. For example, a system of the present invention may control gas therapy using one or more patient-internal sensors, one or more patient-external sensors, and/or an implanted device.

Gas therapy devices may be used to provide a variety of respiration therapies, including, for example, providing vasodilating or bronchodilator agents, continuous positive airway pressure (CPAP), bi-level positive airway pressure (bi-level PAP), proportional positive airway pressure (PPAP), auto-titrating positive airway pressure, ventilation, oxygen, carbon dioxide or other gas therapies. All types of gas therapy and positive airway pressure devices are referred to generically herein as xTherapy devices.

The following discussion, with reference to FIGS. 75 through 78, describes embodiments of the invention involving modulation of external gas therapy. The processes and systems exemplified by these embodiments may be implemented alone or in combination with one or more processes and systems exemplified by other embodiments described herein to provide a coordinated approach to patient monitoring, diagnosis, and/or therapy.

In accordance with embodiments of the invention, a system controls gas therapy, such as oxygen or carbon dioxide therapy, using one or more patient-internal sensors, one or more patient-external sensors and/or an implanted device. The gas therapy may be delivered to the patient, and measurement of exhaled gas concentration may be implemented using a respiratory mask, such as a CPAP mask, for example. The one or more sensors may include, for example, a gas saturation sensor or other implanted sensor for determining the patient's blood gas saturation. Other sensors, such as a disordered breathing detector (internal or external) may be used to determine the presence of disordered breathing, and then deliver gas therapy as needed to resolve or treat the disordered breathing. The patient's blood gas saturation may be determined externally, e.g., using pulse oximetry techniques, and/or external sensors positioned on a respiratory mask or nasal cannulae.

One illustrative approach involves sensing the patient's blood gas saturation and controlling the delivery of gas by a patient-external therapy device based on the blood gas saturation. At least one of sensing the blood gas saturation and controlling the delivery of gas is performed at least in part implantably. Another approach involves sensing the body's need for gas, as manifested, for example, as apnea, hypopnea, hypoxia, hypocapnia, or myocardial ischemia, and then providing appropriate gas therapy to remedy the physiological need. Sensing of the body's need for gas may be effected either internally or externally of the patient.

Figure 75:
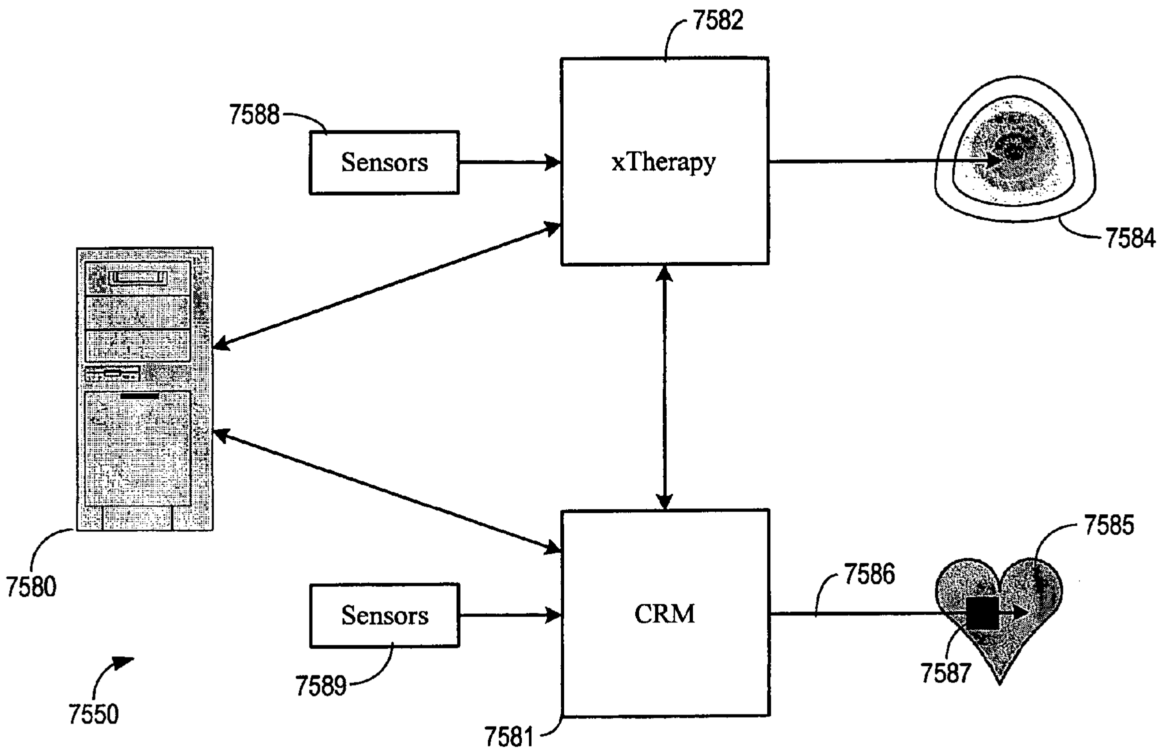
FIG. 75 is a block diagram of a system that provides and adjusts a gas therapy by cooperation between internal and external medical devices in accordance with embodiments of the present invention.

FIG. 75 illustrates a block diagram of a system 7550 for providing coordinated cardiac and respiratory therapy in accordance with embodiments of the invention. The system utilizes an xTherapy device 7582 to provide respiratory therapy to the patient. A controlled flow of air, oxygen, carbon dioxide or other gas is developed by the xTherapy device 7582 and delivered to the patient's airway through tubing and a mask 7584, such as a nasal mask.

The system 7550 provides electrical stimulation therapy using an implantable cardiac rhythm management (CRM) device 7581. The CRM device 7581 provides electrical stimulation to the heart 7585 through an implanted lead system 7586 with electrodes 7587 positioned in, on, or about the heart 7585 to electrically couple the heart 7585 to the CRM device 7581. The CRM device 7581 may be used to sense symptoms of a disease or disorder, such as hypoxemia and ischemia. The CRM device 7581 may also be used to improve cardiac output by atrial pacing, bi-ventricular pacing, atrial or ventricular overdrive pacing, pacing above a programmed pacing rate, and/or other therapies, which may, in turn, improve blood gas transport.

One or both of the xTherapy device 7582 and the CRM device 7581 have one or more sensors 7588, 7589 for sensing conditions associated with disordered breathing. For example, the CRM sensors 7589 may include, for example, cardiac signal electrodes, a minute ventilation (MV) sensor, and an accelerometer. The xTherapy device sensors 7588 may include a microphone and respiratory flow sensor.

The sensor signals are analyzed by the xTherapy device 7582, the CRM device 7581, or both devices 7582, 7581, to determine the presence and/or severity of a disorders such as ischemia, hypoxemia, pulmonary, and/or disordered breathing. The xTherapy and CRM devices 7582, 7581 may have bi-directional or uni-directional communication capability for communicating information about the disordered breathing to the other device 7581, 7582. In one scenario, the xTherapy 7582 and the CRM 7581 have the ability to communicate directly, e.g., through a wireless link. In another scenario, the xTherapy 7582 and the CRM 7581 do not have the ability to communicate directly, but communicate through an intermediate device 7580, such as a programmer or an information server 7580 used in connection with an advanced patient management system. The intermediary device 7580 may receive information from the xTherapy device 7582 and transmit the information to the CRM device 7581. Similarly, the intermediary device 7580 may receive information from the CRM device 7581 and transmit the information to the xTherapy device 7582.

In one example, either the CRM device 7581 or the xTherapy device 7582 may sense a set of patient conditions and transmit the patient conditions to the other device 7582, 7581. For example, the CRM device 7581 may sense a set of patient conditions using the sensors 7589 coupled to the CRM device 7581. The CRM device 7581 may then transmit the sensor information to the xTherapy device 7582. Each device 7581, 7582 may individually detect a disorder such as ischemia, hypoxemia, pulmonary, and/or disordered breathing and determine the severity of the disorder based on the sensor information. Each device 7581, 7582 may adjust the therapy provided by the device based on the detection and/or severity of the detected disorder.

In another example, the xTherapy device 7582 may sense a set of patient conditions and transmit the patient conditions to the CRM device 7581. The xTherapy device 7582 and the CRM device 7581 may individually modify their therapies based on the sensed conditions.

In yet another example the xTherapy device 7582 may sense a first set of patient conditions and transmit the first set of patient conditions to the CRM device 7581. The CRM device 7581 may detect a second set of patient conditions and transmit the second set of patient conditions to the xTherapy device 7582. The xTherapy and CRM devices 7582, 7581 may then individually modify their therapies based on the first and the second sets of conditions.

In another example, the detection and/or determination of the severity of a disorder, such as ischemia, hypoxemia, pulmonary, and/or disordered breathing, may be performed in one device and the information transmitted to the other device. For example, the CRM device 7581 may sense a first set of patient conditions from sensors 7589 coupled to the CRM device 7581 and receive a second set of patient conditions from the xTherapy device 7582. The CRM device 7581 may detect a disorder such as ischemia, hypoxemia, pulmonary, and/or disordered breathing and determine the severity of the disorder based on the first and the second set of conditions. The CRM device 7581 may transmit information about the detection/severity of a condition such as ischemia, hypoxemia, pulmonary, and/or disordered breathing to the xTherapy device 7582. The CRM device 7581 may modify its therapy based on the detection/severity of the disorder. The xTherapy device 7582 may also modify its therapy based on the detection/severity of the disorder. In an alternate embodiment, the detection and severity determination may be performed by the xTherapy device 7582 and transmitted to the CRM device 7581.

Therapy provided by the xTherapy device 7582 may include, for example, therapy delivery at a variable pressure, e.g., autotitration PAP, gas therapy, among others. Therapy provided by the CRM device 7581 may include, for example, cardiac resynchronization therapy, bi-ventricular pacing, atrial or ventricular overdrive pacing, and/or pacing above a programmed sleep rate.

The detection of a disorder such as ischemia, hypoxemia, pulmonary, and/or disordered breathing and determination of the severity of the disorder may be used to implement an adaptive therapy utilizing both the xTherapy device 7582 and the CRM device 7581. The adaptive therapy techniques described above may be used in connection with the xTherapy device 7582 alone or with the CRM and xTherapy devices 7581, 7582 together. Thus, the therapy provided by either or both devices 7581, 7582 may be initiated, terminated, or modified based on the effectiveness of the therapy, the impact of the therapy on the patient, or both effectiveness and impact.

Figure 76:
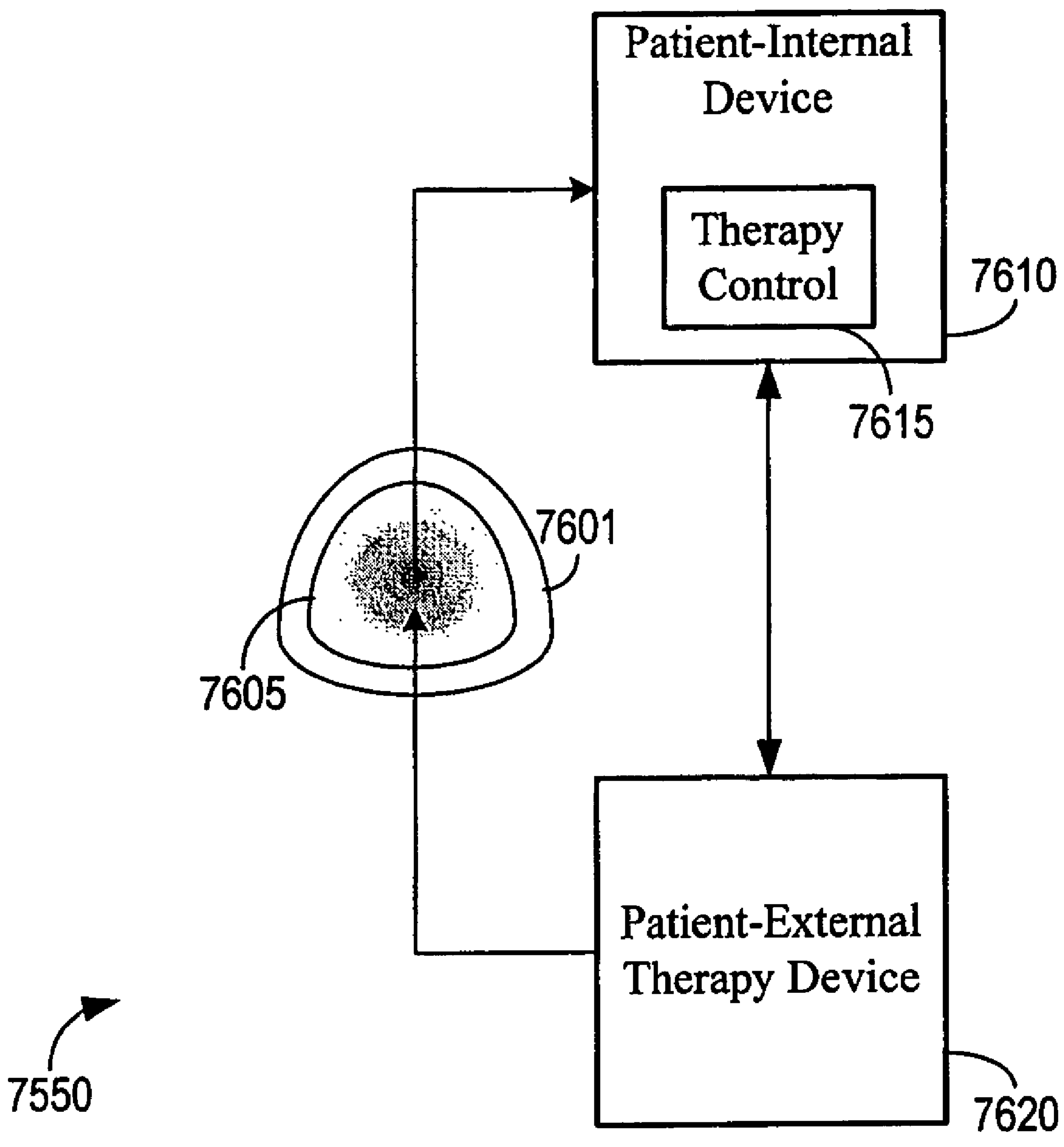
FIG. 76 is a block diagram illustrating a system for modulating a patient-external therapy device in combination with a patient-internal device incorporating therapy control in accordance with embodiments of the present invention.

FIG. 76 illustrates the use of one or more external sensors with the patient-internal device operating as the gas therapy control unit in accordance with embodiments of the invention. A patient-external therapy device 7620 provides gas therapy to a patient, for example, through a nasal or facial mask 7601. In this example, the therapy control unit 7615, located in a patient-internal device 7610, such as a CRM device, receives blood gas information from an external sensor 7605, such as, but not limited to, a sensor positioned on a respiratory mask. It is understood that other sensors may be used which are not positioned on a respiratory mask, such as a finger oximetry sensor. The sensor 7605 may communicate with the patient-internal device 7610 through, for example, a wireless communication link.

Alternatively, the sensor signals may be received by the patient-external therapy device 7620, e.g., CPAP device or other xTherapy device, and transmitted from the patient-external device 7620 to the patient-internal device 7610, for example. The therapy control unit 7615 compares the sensed gas saturation level to a predetermined threshold or range. When the gas saturation is beyond the threshold or range, the patient-internal device 7610 may transmit control signals to the patient-external therapy delivery device 7620 to initiate, terminate, or modify the gas therapy.

Figure 77A:
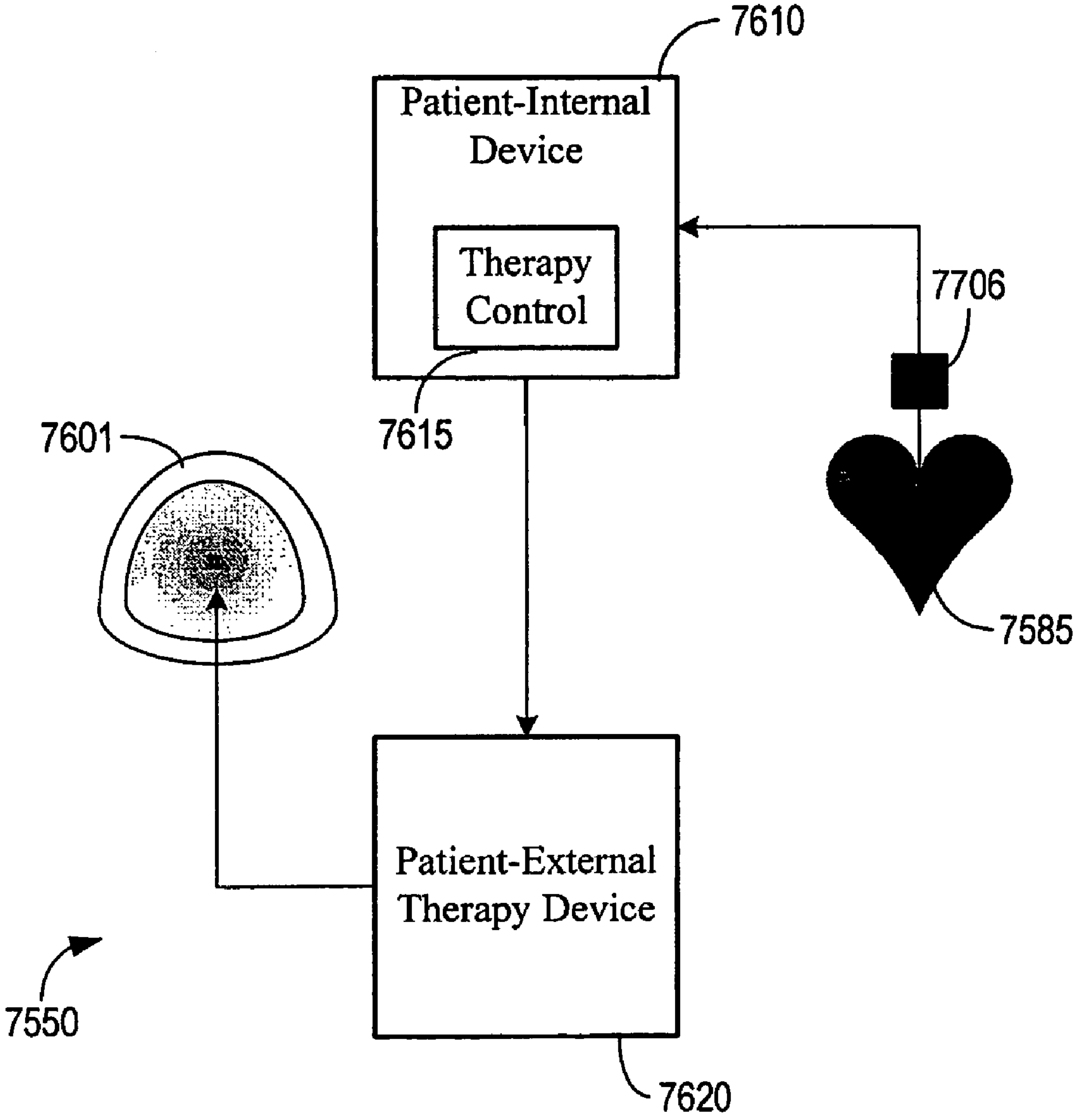
FIG. 77A is a block diagram illustrating a system for modulating a patient-external therapy device with a sensor in a respiratory mask in combination with a patient-internal device incorporating therapy control in accordance with embodiments of the present invention.

FIG. 77A illustrates another implementation of gas therapy control in accordance with an embodiment of the invention. In the example depicted in FIG. 77A, gas saturation is sensed using one or more patient-internal sensors 7706 positioned on an endocardial lead. In this implementation, the patient-internal sensors 7706 may include a gas saturation sensing lead used with an implantable CRM device. The gas sensing device need not be positioned on a lead, but may alternatively be located on the CRM device housing or header, or on a sensor lead independent from the pacing leads. The patient-internal device 7610 includes a gas therapy control unit 7615. In this example, the therapy control unit 7615 receives blood gas information from the blood gas sensor 7706. The therapy control unit 7615 compares the sensed gas saturation level to a predetermined threshold or range. When the gas saturation is beyond the threshold or range, the patient-internal device 7610 may transmit control signals to the patient-external therapy delivery device 7620 to initiate, terminate, or modify the gas therapy.

Figure 77B:
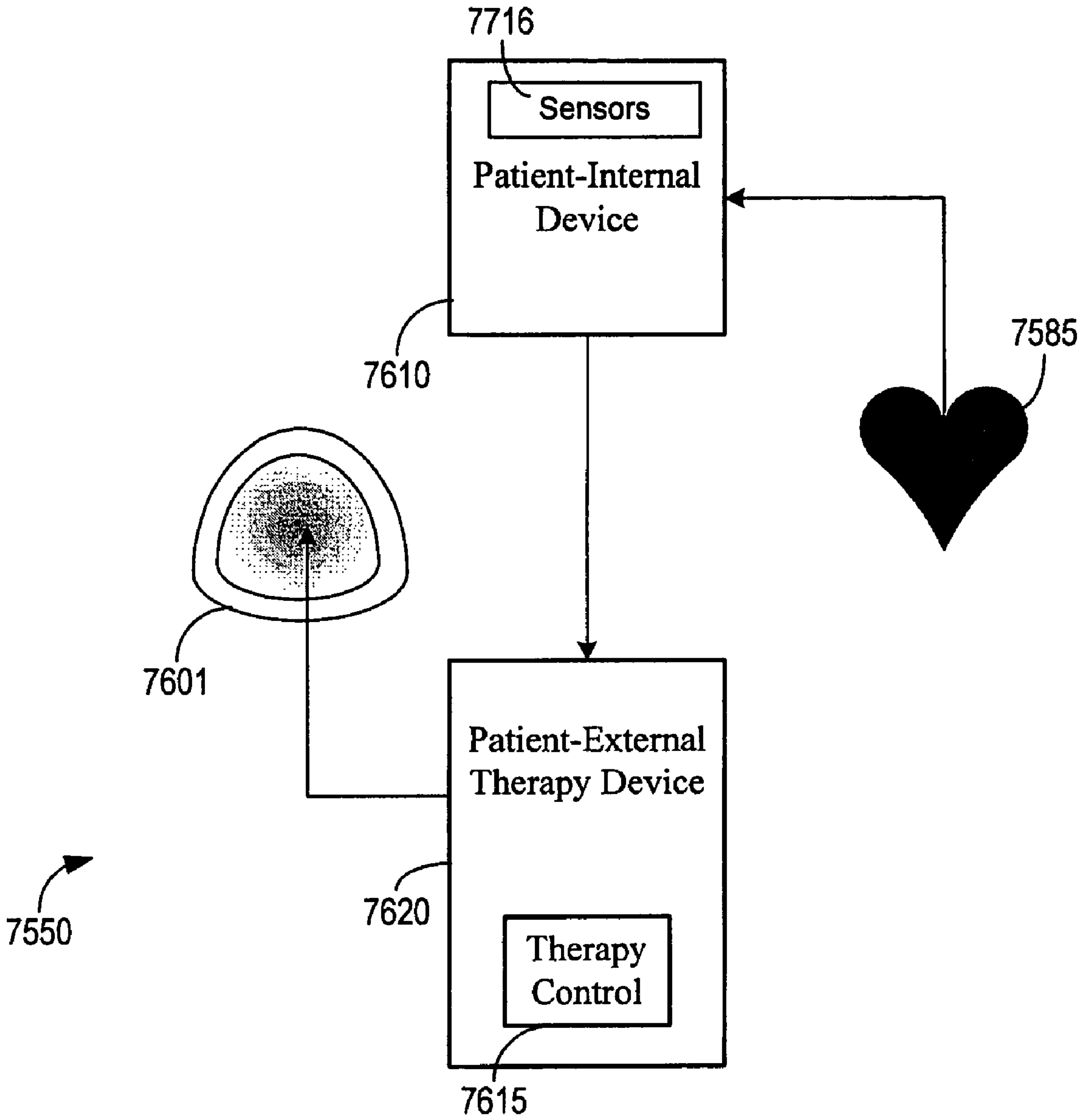
FIG. 77B is a block diagram illustrating a system for modulating a patient-external therapy device incorporating therapy control in combination with a patient-internal device configured to transmit information to the external device in accordance with embodiments of the present invention.

FIG. 77B illustrates another implementation of gas therapy control in accordance with an embodiment of the invention. In the example depicted in FIG. 77B, gas saturation is sensed using one or more patient-internal sensors 7706 positioned in or on the patient-internal device 7610, such as the can of a cardiac monitoring and/or stimulation device. In this implementation, the patient-internal sensors 7706 may include a gas saturation sensing lead used with an implantable CRM device. The patient-external device 7620 includes a gas therapy control unit 7615. In this example, the therapy control unit 7615 receives blood gas information from the blood gas sensor 7706 via, for example, wireless link. The therapy control unit 7615 compares the sensed gas saturation level to a predetermined threshold or range. When the gas saturation is beyond the threshold or range, the patient-external device 7620 may initiate, terminate, or modify the gas therapy.

Figure 78:
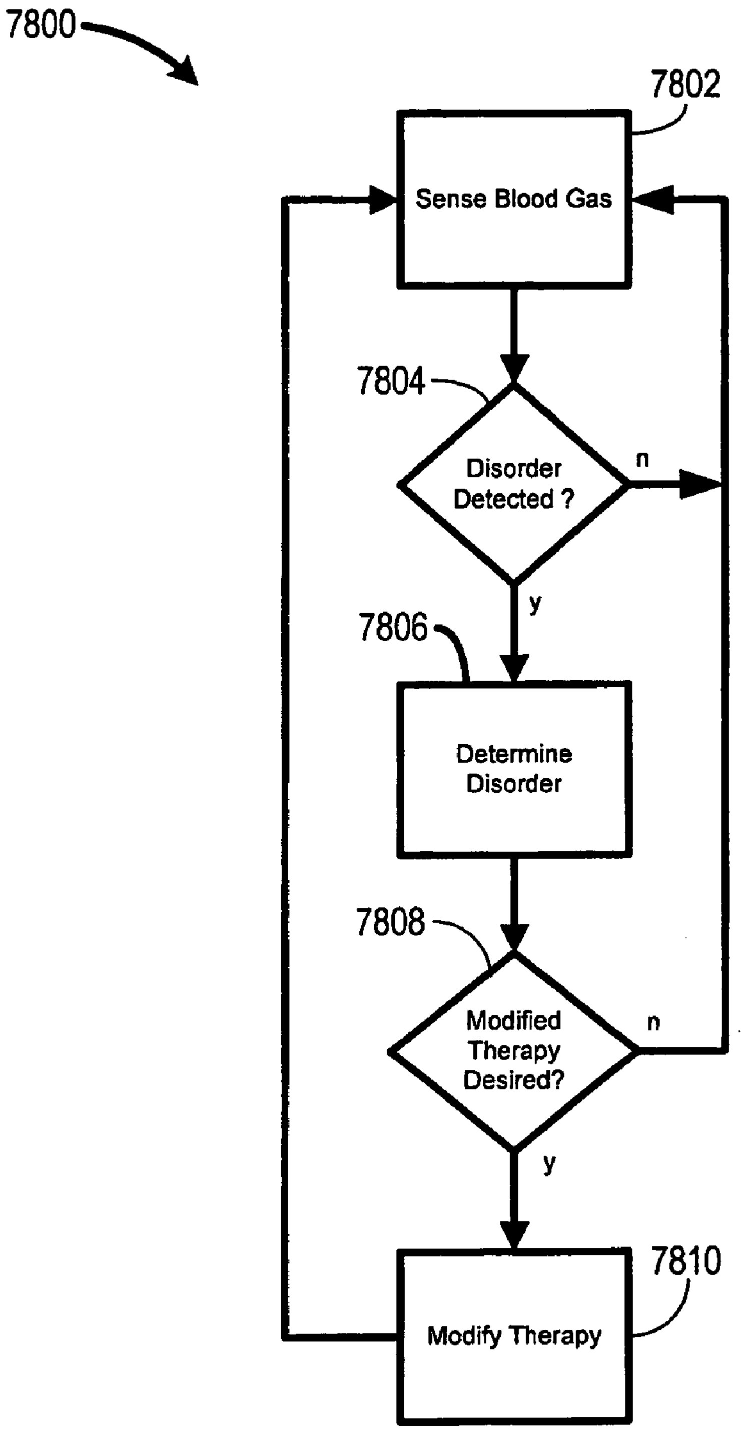
FIG. 78 is a flow chart illustrating a method of gas therapy control based on signals transmitted from a patient-internal device in accordance with embodiments of the present invention.

FIG. 78 is a flow chart illustrating a method 7800 of gas therapy control based on signals from a patient-internal device in accordance with embodiments of the present invention. The method 7800 may be useful for controlling any gas therapy system, such as those illustrated with reference to FIGS. 75 through 77. For clarity of understanding, and not by way of limitation, the sensing of blood oxygen level will be used as an example of one particular use of the method 7800.

Block 7802 provides for the sensing of blood gas, such as blood oxygen level. A disorder is detected 7804 using the sensed blood gas information. For example, a blood oxygen level may be compared to a range of acceptable blood oxygen levels to detect whether the blood gas is within an acceptable range, or whether some disorder is indicated. If no disorder is detected at block 7804, blood gas sensing continues at block 7802. Sensing may occur continuously, intermittently, by-request, periodically, or as otherwise desired or needed.

If a disorder is detected at detection block 7804, a determination of one or more possible actions and/or interventions is made at block 7806, relative to the detected disorder. For example, detecting a blood oxygen level below a lower threshold may suggest that more oxygen is needed by the patient. A decision is made at block 7808, based on the determination from block 7806, as to whether therapy initiation or therapy modification is desired to increase the patient's blood oxygen level. For example, if a patient is receiving oxygen therapy, the oxygen level administered to the patient may be increased. In another embodiment, if the patient is sleeping and wearing a CPAP device, the air pressure may be increased.

In a further embodiment, the patient may be administered a vasodilating or bronchodilator agent, or have a level of vasodilating or bronchodilator agent therapy modified. Combined therapies may also be performed, such as increasing gas pressure and adding a vasodilating or bronchodilator agent, increasing the heart rate of a patient using a pacemaker and increasing oxygen therapy, or other desired combined therapies.

If no therapy change is desired, the disorder may be recorded, monitored, or alerted, for example, before returning to the sense block 7802. If a therapy change is desired, the therapy is modified at block 7810 before again returning to the blood sense block 7802. For example, if a patient is receiving oxygen therapy, the oxygen level administered to the patient is increased, and the method 7800 may be performed again after an appropriate time to determine if the change was effective, or whether other action is necessary.

Synergistic Use of Medical Devices for Detecting Medical Disorders

Aspects of the invention that include synergistic use of medical devices for detecting medical disorders are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhanced patient monitoring, diagnosis and/or therapy.

Other aspects of the invention involving synergistic use of medical devices to detect disorders are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve a system providing synergistic use of medical devices for detecting medical disorders 126 (FIG. 1B). The medical disorder detection system may be implemented as a stand alone system or in combination with other individual medical systems, such as those described in FIGS. 1B-1D.

A system for assessing a disease presence includes a plurality of medical devices, each medical device comprising a sensing system configured to sense one or more physiological conditions. A selection processor is coupled to the plurality of medical devices. The selection processor is configured to select one or more medical devices to sense one or more physiological conditions. A diagnosis processor is coupled to the sensing systems of the plurality of medical devices. The diagnosis processor is configured to assess a presence of a medical disorder based on the one or more physiological conditions.

Another embodiment of the invention involves a system for providing coordinated patient monitoring, diagnosis and/or therapy that utilizes a disease assessment system 126. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy involves a disease assessment system. The implantable device and the respiratory therapy device work cooperatively to implement the disease assessment system and/or to perform a function involving the assessment of disease presence.

Embodiments of the invention are directed to synergistic use of medical devices for detecting the presence of a medical disease or disorder. Processes described herein involve automatically selecting one or more medical devices to sense one or more physiological conditions. A monitoring unit, which may be distributed among the selected medical devices, for example, collects data based on the one or more sensed conditions. A diagnostics unit detects a presence of a medical disorder based on the collected data and may assess the progression of the disorder. Systems and methods directed to synergistic use of medical devices for detecting medical disorders may be implemented to include selected features, functions, and/or structures described in commonly owned, co-pending US Patent Application entitled "Synergistic Use of Medical Devices for Detecting Medical Disorders," filed Sep. 13, 2004, which is hereby incorporated herein by reference.

FIG. 1A illustrates an implantable device 110 and a patient-external medical device 220. The medical devices 110, 120 may comprise circuitry for implementing synergistic use of medical devices for disease assessment.

In accordance with embodiments of the invention, the medical system 100 includes a selection processor and a diagnostics processor. The selection and diagnostics processors may be implemented as components of the patient-internal medical device 110, the patient-external medical device 120, or as a unit separate from the patient-internal medical device 110 and the patient-external medical device 120. The selection and diagnostics processors 114, 124 may be implemented as components of an advanced patient management (APM) system 170, for example.

The selection processor is configured to select one or more medical devices to sense patient conditions. The selection of the medical devices may be based, for example, on patient usage and/or on the proficiency or accuracy of the sensing system associated with a particular medical device. In one implementation, if the selection processor determines that the patient is not using the patient-external device, then the sensing function may be transferred to the patient-internal device.

Figure 79:
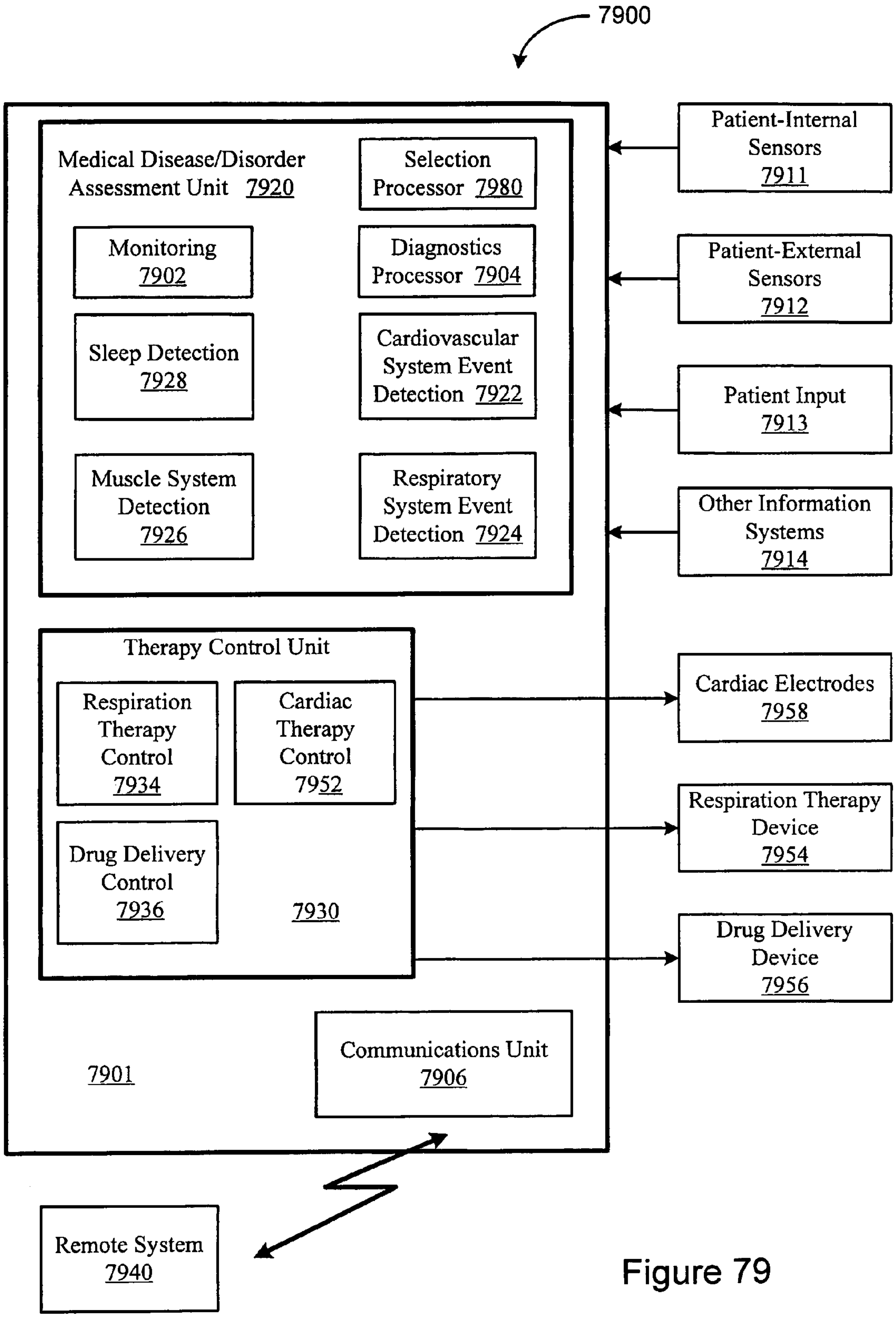
FIG. 79 is a block diagram of an implantable medical device that may be utilized in connection with a medical disease/disorder detection and/or monitoring system in accordance with embodiments of the invention.

The block diagram of FIG. 79 provides an example of a coordinated monitoring, diagnosis and/or therapeutic system 7900 in accordance with embodiments of the invention. The system 7900 employs a medical device 7901 that may be fully or partially implantable, or may be positioned on, near, or at a remote location external to the patient. The medical device 7901 may be coupled to an array of data acquisition devices, including patient-internal sensors 7911, patient-external sensors 7912, patient input devices 7913, and/or other information systems 7914 as described herein. The patient-internal sensors 7911, patient-external sensors 7912, patient input devices 7913, and/or other information systems 7914 are used to input a variety of conditions affecting the patient and useful for the monitoring, diagnostic, and/or therapeutic functions of the medical device 7901. One or more patient conditions may also be sensed using a remote system 7940.

The medical device 7901 of FIG. 79 includes a medical disease/disorder assessment unit 7920 that processes data collected from one or more of the patient-internal sensors 7911, patient-external sensors 7912, patient input devices 7913, information systems 7914, and/or data collected from the remote system 7940 to assess the presence of various medical diseases and/or disorders. The assessment unit 7920 may include detection circuitry for detecting the occurrence of various physiological events. For example, the assessment unit 7920 may include one or more of a cardiovascular system event/condition detector 7922, a respiratory event/condition detector 7924, a muscle system event/condition detector 7926 and/or a sleep stage detector 7928. Other event detection components may also be included in the assessment unit 7920. The event/condition detectors 7922, 7924, 7926, 7928 may be used to detect normal and/or abnormal physiological system events or conditions. For example, the cardiovascular system event/condition detector 7922 may used to detect abnormal or unusual events of the cardiovascular system such as ventricular tachycardia or fibrillation. The cardiovascular system event/condition detector 7922 may also be used to detect normal cardiac beats or other events or conditions associated with the usual functioning of the heart.

The respiratory system event detector 7924 may be used to detect events or conditions associated with various respiratory system disorders, such as a disordered breathing event or a pulmonary congestion condition. The respiratory system event/condition detector 7924 may also be used to detect the inspiratory and expiratory phases of normal respiration cycles, for example.

The muscle system event/condition detector 7926 may be used to detect normal or abnormal conditions, such as normal muscle atonia associated with REM sleep or abnormal muscle tone of the upper airway associated with obstructive sleep apnea events. The muscle system event/condition detector 7926 may also be used, for example, to detect the level of patient activity. Patient activity information may be useful, for example, in assessing the overall activity level of the patient, or determining if the patient is asleep.

The assessment unit 7920 may also include a sleep stage detector 7928. The sleep stage detector 7928 may analyze various inputs from the patient-internal sensors 7911, patient-external sensors 7912, patient input devices 7913, other information systems 7914 and/or events/conditions detected by the event/condition detectors 7922, 7924, 7926, to detect sleep-related events, including, for example, sleep onset, sleep offset, sleep stages, and arousals from sleep.

Components of the detection unit 7920 may cooperate with a monitoring unit 7902. The monitoring unit 7902 may incorporate a memory to store data derived from signals produced by the patient-internal sensors 7911, patient-external sensors 7912, patient input devices 7913, and/or other information systems 7914 and information derived from the event/condition detectors 7922, 7924, 7926, 7928. The stored data may be transmitted to another component of the medical device 7901 or to a separate device for storage, further processing, trending, analysis and/or display, for example. In one scenario, the stored data can be downloaded to a separate device periodically or on command. The stored data may be presented to the patient's health care professional on a real-time basis, or as a long-term, e.g., month long or year long, trend of daily measurements.

The assessment unit 7920 includes a selection processor 7980 for selecting one or more medical devices used for sensing various conditions used for the detection and/or assessment of the medical disease/disorder. Data collected from the one or more medical devices is evaluated in a diagnostics processor 7904. The diagnostics unit 7904 may evaluate events or conditions detected by the selected medical devices to provide diagnostic information related to various medical disorders or diseases affecting the patient. The diagnostics processor 7904 may detect a presence of a medical disease or disorder based on the data collected by the selected medical devices. The diagnostics processor 7904 may also assess the onset, progression, regression, and/or offset of the medical disease or disorder. Information related to the sensed conditions and/or disease or disorder diagnostics may be stored, analyzed, trended, transmitted to a separate device, printed and/or displayed, for example. In some implementations, the information may be transmitted to a device not used to sensed physiological conditions for medical disease diagnosis, for example. In some implementations, an alert may be activated based on detection or assessment of one or more medical diseases/disorders, for example a visual or audible alert.

The medical device 7901 may also include a therapy control unit 7930 that controls one or more types of therapy delivered to the patient. For example, the medical device may include a cardiac therapy control unit 7952 for controlling cardiac electrical stimulation delivered to the heart through one or more cardiac electrodes 7958. The therapy control unit 7930 may also include respiration therapy control unit 7934 that provides control signals to a respiratory therapy device 7954 and a drug control unit 7936 that provides control signals to a drug delivery device 7956. In one configuration, the medical device 7901 may control the therapy delivered by a separate therapy delivery device 7954, 7956 by communicating directly with the separate therapy delivery device 7954, 7956. In another configuration, the medical device 7901 may communicate with another medical device, e.g., APM system or programmer, to indirectly affect or control the therapy delivery device 7954, 7956.

The medical device 7901 may further include a communications unit 7906 that controls communications between the medical device 7901 and other devices or systems. For example, the communications unit 7906 may be used to provide wireless or wired communications links between the medical device 7901 and one or more of the patient-internal sensors 7911, patient-external sensors 7912, patient input devices 7913, and information systems 7914. The communications unit 7906 may also facilitate communication between the medical device 7901 and the therapy delivery devices 7954, 7956 through wireless or wired connections. The communications unit 7906 may also facilitate communications between the medical device 7901 and a remote device 7940 such as another medical device, a remote programmer and/or an APM system as described previously in connection with FIG. 1. The wireless connections coupling the medical device 7901 to various other devices and systems may utilize a variety of wireless protocols, including, for example, Bluetooth, IEEE 802.11, and/or a proprietary wireless protocol.

Embodiments of the invention are directed to the synergistic use of patient external and patient internal devices to detect a presence of and/or assess a variety of medical disorders, including cardiac disorders and/or pulmonary disorders. FIGS. 62A-62N list various cardiac and/or pulmonary diseases/disorders that may be detected using the approaches of the present invention.

As referenced in FIGS. 62A-2N, the term "condition," denotes an parameter that may be sensed and/or measured based on a signal generated by a sensor or other input device of the one or more medical devices. Typically, a physiological sensor generates a signal modulated by a physiological parameter. In some cases, a physiological condition may be directly measured based on the sensor signal. For example, a blood pressure measurement may directly correlate to the signal generated by a blood pressure sensor. In other cases, a condition may be derived from the sensor signal. For example, tidal volume is a respiratory system condition that may be derived from the signal generated by a transthoracic impedance sensor. In another example, heart rate is a cardiac system condition that may be derived from a cardiac electrogram sensor.

The terms "symptom" and "physiological change" refer to a manifestation of a medical disease or disorder. Symptoms and/or physiological changes may be detectable based on a sensed presence of one or more physiological conditions and/or measured values associated with the one or more sensed physiological conditions. The terms "disease" and/or "disorder" are used to refer to a medical dysfunction that is characterizable by a collection of symptoms or physiological changes.

The chart depicted in FIGS. 62A-2N illustrates relationships between various physiological changes and/or disease symptoms with medical disorders. The chart lists a representative set of medical disorders that may be evaluated in accordance with embodiments of the invention.

The presence of a disorder/disease, such as those listed in FIGS. 6A-6N, may be assessed by based on physiological changes and/or symptoms associated with the disorder/disease. The physiological changes and/or symptoms may be detected using conditions sensed by a sensor system of a respiratory therapy alone or in combination with the sensor systems of other therapeutic or diagnostic medical devices. If the sensed conditions indicate that the physiological changes or symptoms of a disease or disorder are consistent with a threshold level, the presence of the disease or disorder may be determined.

In another example, assessment of disease presence may be based on relative changes in one or more conditions indicative of physiological changes or symptoms caused by the disease. For example, assessment of a presence of a disease or disorder may be accomplished by evaluating the changes in conditions indicative of physiological changes or symptoms caused by the disease. The changes in the one or more conditions may be compared to threshold criteria. If changes in the conditions indicative of physiological changes or symptoms caused by the disease are consistent with threshold levels, a presence of the disease or disorder may be determined.

In a further example, the threshold criteria may involve relationships between the conditions indicative of physiological changes or symptoms caused by the disease. The presence of a disease may be assessed by evaluating relationships between conditions indicative of physiological changes or symptoms caused by the disease. For example, assessment of a disease may involve the determination that levels or amounts of two or more conditions have a certain relationship with one another. If relationships between the conditions indicative of physiological changes or symptoms caused by the disease are consistent with threshold relationship criteria, the disease or disorder may be present.

Figure 80:
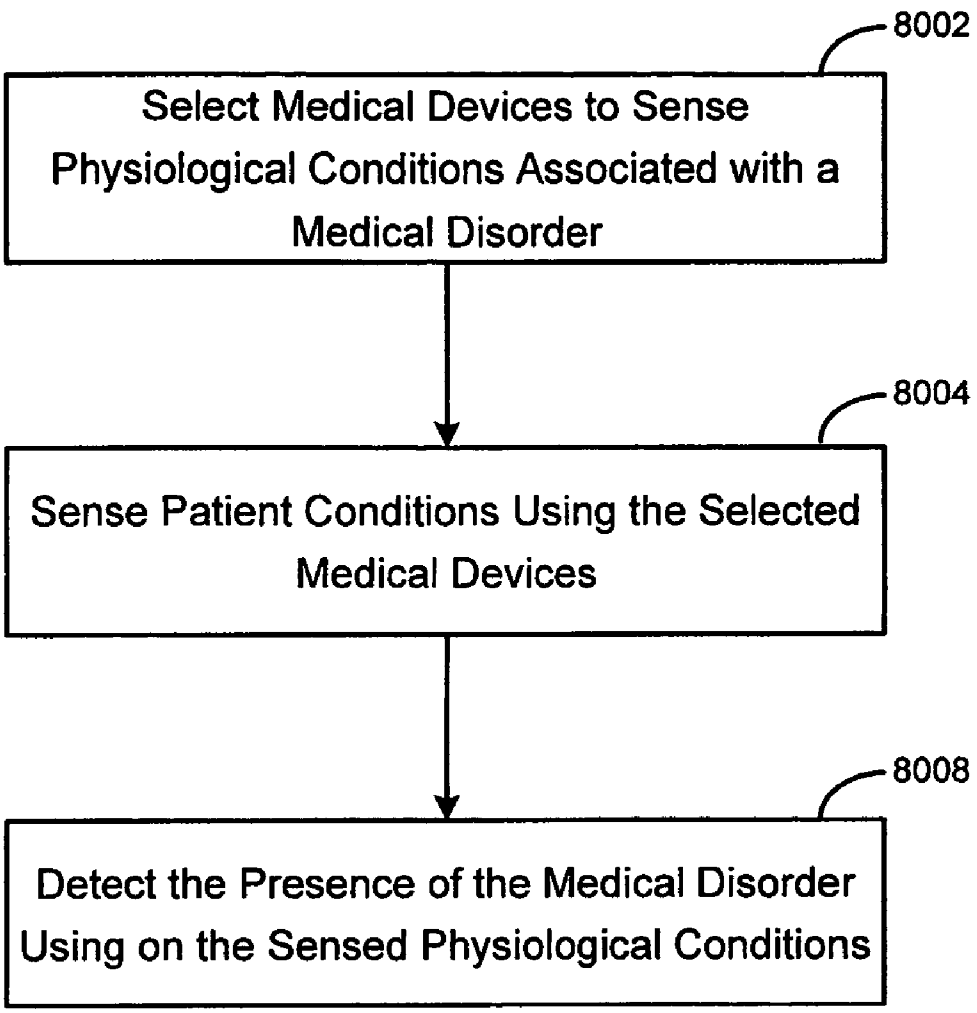
FIG. 80 is a flowchart of a method of detecting the presence of medical disorders in accordance with embodiments of the inventions.

FIG. 80 is a flowchart of a method of detecting the presence of medical disorders in accordance with embodiments of the inventions. The method involves selecting 8002 one or more medical devices to sense one or more patient conditions associated with symptoms of the medical disorder. The medical devices selected may comprise for example, one or more implantable devices, one or more patient-external devices, or a combination of implantable and patient-external devices. The medical devices selected may comprise any number of therapeutic and/or diagnostic devices, including, for example, various therapeutic or diagnostic devices, including cardiac devices (pacemakers, cardioverter/defibrillators, cardiac resynchronizers, cardiac monitors), muscle stimulators, neurostimulators, implantable or patient-external drug delivery devices (drug pumps, electrically activate drug patches), patient-external respiratory devices (respiratory monitors, nebulizers, oxygen or gas therapy devices, ventilators, respirators, respiratory therapy devices providing positive and/or negative airway pressure), and the like.

The selection of the medical devices may be based, for example, on patient usage and/or on the proficiency or accuracy of the sensing system associated with a particular medical device. The one or more patient conditions are sensed 8004 using the selected devices. Data may be collected based on the one or more sensed physiological conditions. The presence of a medical disorder is detected 8008 based on the one or more sensed physiological conditions. Data pertaining to the sensed physiological conditions may be collected and stored, for example, continuously, or periodically, or according to some other time basis.

In some embodiments of the invention, portions of the data collection may be initiated upon detection of a medical event. For example, data collection may be initiated upon detection of an arousal event, a respiratory event, such as a sleep apnea event, and/or a cardiac event, such as a cardiac arrhythmia event.

In an embodiment of the invention, data collection may occur periodically, e.g., daily or hourly. In some implementations, the data collection may occur continuously or according to a random schedule. In some scenarios, it may be desirable to collect data only when the patient is asleep or only when the patient is awake. The system may detect sleep events to implement nocturnal and/or diurnal data collection, for example. The system may select one set of medical devices for sensing conditions during the day and alter the selection to include a second set of medical devices for sensing conditions at night.

In one example, a patient may have an implanted cardiac pacemaker and may also use, on a periodic basis, e.g., nightly, an external respiratory therapy device, such as a CPAP device. One or more conditions, including respiration may be sensed each night using the cardiac pacemaker and the CPAP device. The airflow sensor of the CPAP device may be automatically selected to sense patient respiration due to the higher accuracy of the airflow measurement in the CPAP device compared to the cardiac pacemaker. However, on some nights the patient may not use the CPAP device. If the patient does not use the CPAP device during a particular period, then patient respiration may be sensed using a surrogate measure, such as the transthoracic impedance sensor of the cardiac pacemaker. The cardiac pacemaker may be automatically selected as the medical device used for sensing patient respiration.

The medical devices used for sensing may be selected based on the proficiency of the sensing system associated with a particular medical device. For example, respiration sounds may be detectable using the accelerometer of a CRM or a patient-external microphone. If patient movements or other interference degrades respiration sound detection acquired by the CRM accelerometer, then the system may select the microphone as the preferred method of sensing respiration sounds.

Assessment of disease presence may be based on relative changes in one or more conditions indicative of physiological changes or symptoms caused by the disease. For example, detection of a presence of a medical disorder may be accomplished by evaluating the changes in one or more conditions indicative of physiological changes or symptoms caused by the disease. The changes in the one or more conditions may be compared to threshold criteria. If changes in the conditions indicative of physiological changes or symptoms caused by the disease are consistent with threshold levels, the non-rhythm pulmonary disease or disorder may be present. For example, if the levels of one or more conditions increase or decrease by a threshold amount of change, then a determination that the medical disorder is present may be made.

The threshold criteria may involve relationships between the conditions indicative of physiological changes or symptoms caused by the disease or disorder. The presence of a medical disorder may be assessed by evaluating relationships between conditions indicative of physiological changes or symptoms caused by the disease. For example, detection of the presence of a medical disorder may involve the determination that levels or amounts of two or more conditions have a certain relationship with one another. If relationships between the conditions indicative of physiological changes or symptoms caused by the disease are consistent with threshold relationship criteria, the system may determine that a particular medical disorder is present.

If the presence of a medical disease/disorder is determined, then the progression of the disease may be monitored. Monitoring the progression of the disease or disorder may involve, for example, collecting data and periodically evaluating one or more physiological changes or symptoms of the disease. Evaluating the one or more physiological changes or symptoms may be accomplished by comparing patient conditions to thresholds or other quantifiable indices. Monitoring the medical disorder may involve, for example, monitoring the progression and/or regression of the medical disorder, determining a severity of the disease, detecting disease onset and offset, and/or monitoring other aspects and/or events associated with the disorder.

As illustrated in FIGS. 62H-62N, cardiac disorders may be organized into disorders of cardiac rhythm, such as bradycardia, ventricular tachyarrhythmia, ventricular fibrillation, paroxymal atrial tachyarrhythia/fibrillation and chronic atrial tachyarrhythmia/fibrillation). Heart failure may cause contractions of the ventricles to become uncoordinated. Non-rhythm cardiac disorders include coronary artery disease (acute myocardial infarction, ischemia), and hypertension, which may be associated with systolic or diastolic types.

According to one aspect of the invention, pulmonary function testing may be employed to detect physiological changes associated with the presence of cardiac and/or pulmonary disease. Pulmonary function tests may be used to evaluate lung mechanics, gas exchange, pulmonary blood flow, and blood gases and pH. They are used to evaluate patients in the diagnosis of pulmonary disease, assessment of disease development, or evaluation of the risk of pulmonary complications.

Data acquired using the above-described techniques may be transmitted from the implantable device to an advanced patient management system or other remote device. Assessment of the patient's cardiopulmonary status or control of the therapy may be performed by the advanced patient management system.

In accordance with various embodiments of the invention, the presence of a medical disease or disorder, such as those listed in FIGS. 62A-2N, may be assessed by evaluating sensed conditions indicative of the a medical disease or disorder. Sensing the conditions may be accomplished using a synergistic process involving selection of one or more medical devices based on various parameters, including, for example, usage of the medical device, quality of the available sensed signals and/or other factors.

In one implementation, the presence of medical disease or disorder may be assessed by comparing levels or values associated with conditions indicative of physiological changes or symptoms caused by the medical disease/disorder to threshold criteria. If the condition levels or values are determined to be beyond threshold criteria levels, the system may determine that the non-rhythm pulmonary disease or disorder is present. The system may use the comparison of condition levels or values to threshold criteria to detect a presence of the medical disease/disorder, the progression of the medical disease/disorder, the regression of the medical disease/disorder and/or the offset of the medical disease/disorder, for example.

The system may initially determine the threshold criteria for one or more medical diseases or disorders by establishing baseline conditions for an individual patient. The baseline conditions may be established using data collected from the patient over a period of time. Clinical data acquired from a number of patients may alternatively or additionally used for establishing the threshold criteria.

In one implementation, assessment of disease presence may be based on relative changes in one or more conditions indicative of physiological changes or symptoms caused by the disease. In this implementation, the threshold criteria may involve a rate of change. For example, diagnosis of a medical disease or disorder may be accomplished by evaluating the rate of change in conditions indicative of physiological changes or symptoms caused by the disease. The changes in the one or more conditions may be compared to threshold criteria involving rate of change. If changes in the conditions indicative of physiological changes or symptoms caused by the disease are consistent with threshold criteria, then the medical disease or disorder may be present.

In a further example, the threshold criteria may involve relationships between the conditions indicative of physiological changes or symptoms caused by the medical disease/disorder. The presence of a medical disease or disorder may be assessed by evaluating relationships between conditions indicative of physiological changes or symptoms caused by the disease. For example, assessment of a medical disease or disorder may involve the determination that levels or amounts of two or more conditions have a certain relationship with one another. If relationships between the conditions indicative of physiological changes or symptoms caused by the disease are consistent with threshold relationship criteria, the medical disease or disorder may be present.

The system may establish a number of thresholds used for monitoring the progress of the disease. Following detection of the presence of the medical disease or disorder, the system may track the progression, regression and/or offset of the disease by comparing the sensed conditions to the established thresholds.

Figure 81:
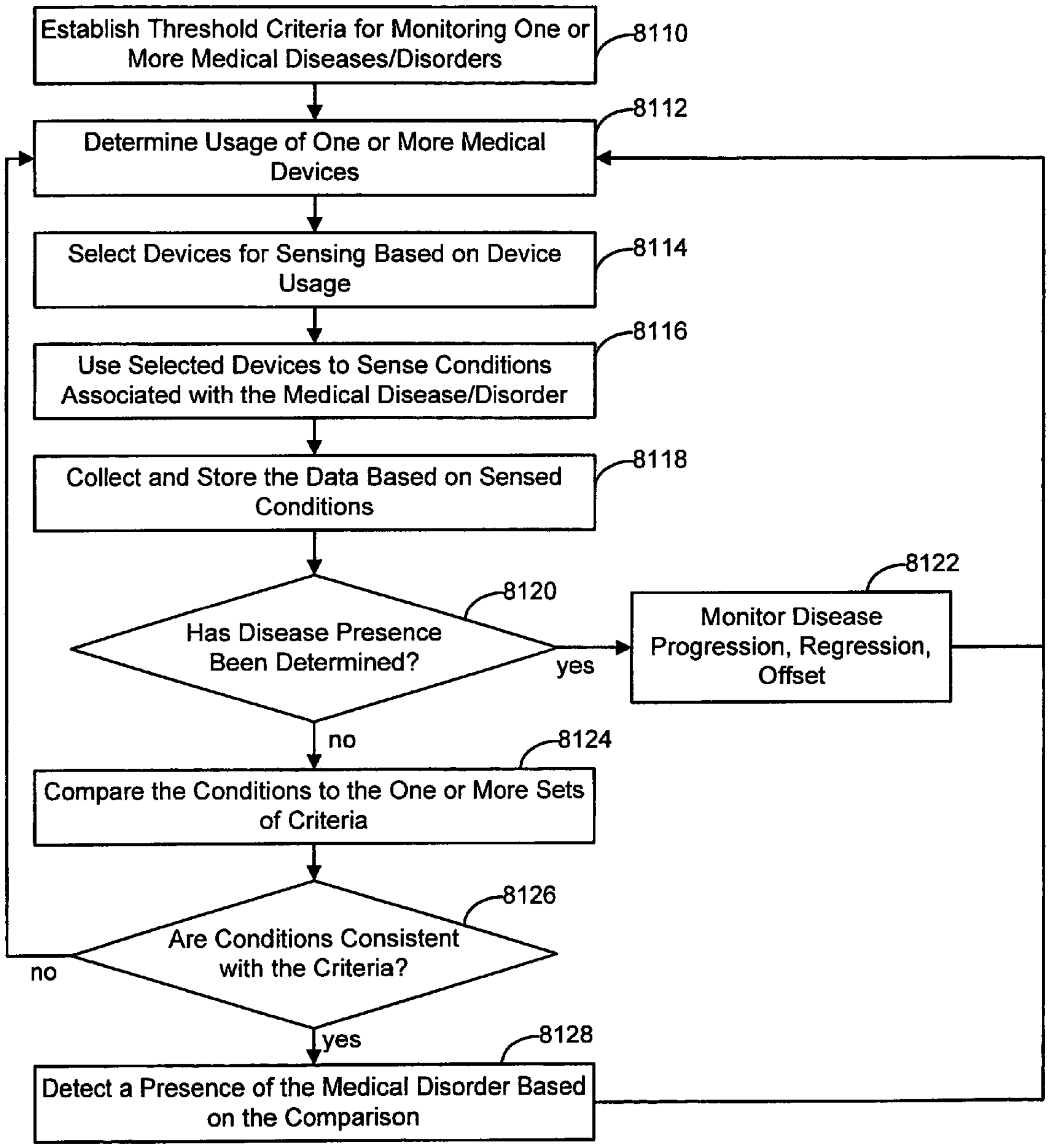
FIG. 81 is a flowchart illustrating a method of assessing a presence of a medical disease in accordance with embodiments of the invention.

FIG. 81 is a flowchart illustrating a method of assessing a presence of a medical disease in accordance with embodiments of the invention. Criteria sets for assessment of the non-rhythm pulmonary diseases are established 8110. The usage of one or more medical devices is determined 8112. Usage of a medical device may be implemented, for example, by determining a proximity of the patient to the medical device.

In one implementation, the proximity of the patient to an external breathing therapy device may be determined using a transmitter coupled to the external breathing therapy device and a receiver in the selection processor. If the patient is near the external breathing therapy device, the receiver receives a signal broadcast by the transmitter. The transmitter may be located on a bedside unit of the external breathing therapy device, or on the respiratory mask of the external breathing therapy device, for example.

Further, usage of an external device may be implemented in other ways, involving, for example, notification by the patient that the external device is in use, or by examining one or more sensed signals to determine if the sensed signals correspond to nominal signal values when the medical device is in use by the patient.

One or more medical devices are selected 8114 to sense one or more conditions associated with a medical disorder. The selected medical devices are used to sense 8116 the one or more conditions. The system may select the medical devices based on at least one of a sensing parameter of the medical devices. For example, the system may select the medical devices based on sensing characteristics including the type, quality, reliability, repeatability, efficiency, availability, accuracy, resolution, dynamic range, specificity, sensitivity or predictive value of the sensing or measurement provided by the medical device. In one implementation, a medical device may be selected based on patient usage. For example, if first and second medical devices are available to sense patient conditions, the first medical device may be selected to sense a first condition and a second medical device may be selected to sense a second condition. However, if only the first medical device is in use, then both conditions may be sensed using the first medical device.

In another implementation, medical device selection may depend on the sleep/wake cycle of the patient. A first medical device may be selected to monitor a physiological condition while the patient is awake, and a second medical device may be selected to monitor the physiological condition while the patient is asleep.

Data is collected 8118 based on the sensed information. In some implementations, data collection may be initiated based on the detection of a triggering event. For example, data collection may be initiated and/or terminated based on the detection of a respiratory system event, a cardiac event, a sleep event, and/or other types of events.

If a presence of the medical disorder was previously determined 8120, marking an onset of the medical disorder, then the progression, regression, and/or offset of the medical disorder is monitored 8122.

If the presence of the disease was not previously determined 8122, then the levels of the sensed conditions are compared 8124 to a set of criteria associated with the disease.

If levels of the conditions are consistent 8126 with the threshold levels, then a presence of the medical disorder is detected 8128.

The system may continue to collect data based on the sensed conditions to monitor the progression, regression and/or offset of the medical disorder. The system may modify the selection of the medical devices used to sense patient conditions before the disorder presence is detected and/or during the time that the system monitors the disorder. For example, the system may check nightly to determine the usage of a CPAP device. If the CPAP device is in use on a particular night, the CPAP device may be used to sense conditions associated with the medical disorder. However, on a different night, the patient may not use the CPAP. In this situation, the system may automatically shift the sensing function previously performed by the CPAP to another medical device.

Therapy Control Based on Physiologic Cycle

Aspects of the invention that include therapy control based on physiologic cycle are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention involving therapy control based on physiologic cycle are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention involve an individual system 140 (FIG. 1B) for controlling respiratory therapy based on a patient's cardiac cycle. The respiratory therapy control system 140 may be implemented as a stand alone system or in combination with other individual medical systems, such as those described in FIGS. 1B-1D.

Various embodiments of present invention involve methods and systems for matching intrathoracic pressure with cardiac cycle phase. One embodiment of the invention involves a method for delivering airway pressure to a patient. The method includes determining the cardiac cycle phase and controlling the airway pressure based on the cardiac cycle phase. Controlling the airway pressure is performed at least in part implantably.

In accordance with another embodiment of the invention, a therapy control system includes a detector system configured to determine cardiac cycle phase and control unit coupled to the detector system. The control unit is configured to control airway pressure based on the cardiac cycle phase. The control unit includes at least one implantable component.

In yet another embodiment of the invention, a method for controlling airway pressure comprises delivering cardiac pacing pulses to a patient and controlling airway pressure delivered to the patient based on the delivery of the cardiac pacing pulses.

A further embodiment of the invention involves a medical system is configured to control airway pressure delivered to a patient. The medical system includes a pulse generator configured to deliver cardiac pacing pulses to a patient's heart and control circuitry coupled to the pulse generator. The control unit configured to control airway pressure delivered to the patient based on the delivery of the cardiac pacing pulses.

Yet a further embodiment involves a method of delivering and external respiratory therapy to a patient. The external respiratory therapy is delivered to a patient to treat disordered breathing. The cardiac cycle phase of the patient is determined. The delivery of the external respiratory therapy is controlled based on the cardiac cycle phase.

In another embodiment of the invention, a medical system controls delivery of a patient-external respiratory therapy based on cardiac cycle phase. The medical system includes a respiratory therapy unit configured to deliver a patient-external respiratory therapy to a patient to treat disordered breathing. The system also includes detector circuitry configured to determine cardiac cycle phase. A control unit is coupled to the detector system and the respiratory therapy unit. The control unit is configured to control delivery of the respiratory therapy based on the cardiac cycle phase.

Various embodiments of present invention involve methods and systems for matching intrathoracic pressure with cardiac cycle phase. One embodiment of the invention involves a medical system configured to control cardiac pacing via a respiratory therapy device. The respiratory therapy device includes a sensor system and a therapy delivery unit. The system is configured to sense respiration cycles. The therapy delivery unit is configured to deliver an external respiratory therapy to the patient.

The system also includes a pulse generator configured to deliver cardiac pacing pulses to the patient. A controller is coupled to the sensing system and the pulse generator. The control unit configured to adjust a cardiac pacing rate based on the respiration cycles.

Another embodiment of the invention involves a method for controlling cardiac pacing therapy. Respiration cycles are sensed using one or more sensors of an external respiratory therapy device. The cardiac pacing is adjusted based on the respiration cycles.

Another embodiment of the invention involves a system for providing coordinated patient monitoring, diagnosis and/or therapy that utilizes the system 140 control of respiratory therapy based on cardiac cycle. The coordinated system includes, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

According to this embodiment, the system providing coordinated patient monitoring, diagnosis and/or therapy further includes a system 140 configured to control respiratory therapy based on cardiac cycle. The respiratory therapy control system 140 includes a detector system configured to determine cardiac cycle phase, and a control unit coupled to the detector system. The control unit is configured to control airway pressure based on the cardiac cycle phase and includes at least one implantable component.

Alternatively this embodiment can include a system for delivering respiratory therapy based on cardiac cycle using a system 140 that includes a pulse generator configured to deliver cardiac pacing pulses to a patient's heart; and a control unit coupled to the pulse generator. The control unit configured to control airway pressure delivered to the patient based on the delivery of the cardiac pacing pulses.

Another alternative embodiment can include a system for delivering respiratory therapy based on cardiac cycle using a system 140 that includes a respiratory therapy unit configured to deliver a patient-external respiratory therapy to a patient to treat disordered breathing, detector circuitry configured to determine cardiac cycle phase, and a control unit coupled to the detector system and the respiratory therapy unit. The control unit configured to control delivery of the respiratory therapy based on the cardiac cycle phase. Systems and methods directed to respiratory therapy control based on cardiac cycle may be implemented to include selected features, functions, and/or structures described in commonly owned, copending U.S. Publication No. 2005/0109339, which is hereby incorporated herein by reference.

Figure 82:
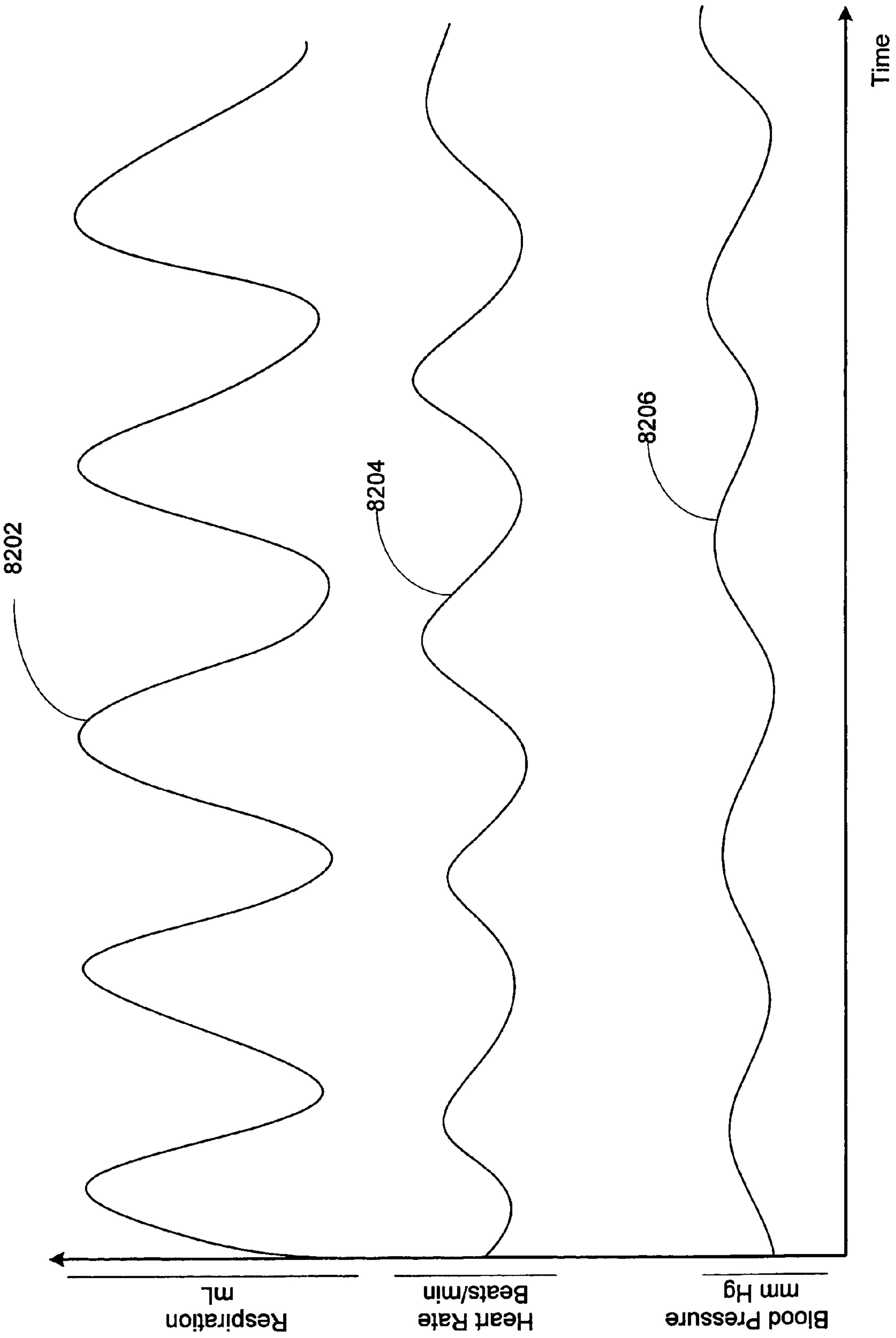
FIG. 82 is a graph illustrating the variation of heart rate and blood pressure with respiration cycles.

Under healthy conditions, heart rate and blood pressure vary with respiration. The heart rate varies in response to autonomic as well as other regulatory inputs to the sinoatrial node (SA). FIG. 82 is a graph comparing respiration 8202, blood pressure 8206, and heart rate 8204 in a healthy individual. Modulation of heart rate with respiration is known as respiratory sinus arrhythmia (RSA). The rate variations of RSA have been found to be important to survival. Individuals without RSA have higher rates of overall mortality than those with RSA.

Respiratory sinus arrhythmia has a role in increasing the efficiency of the cardiovascular system. In many patients with cardiovascular disease or heart failure, RSA is attenuated or absent. Studies have shown that RSA improves pulmonary gas exchange and circulatory efficiency. Mimicking RSA behavior using a cardiac pacemaker enhances cardiac function over fixed pacing.

Some patients suffer from multiple disorders affecting the cardiac and pulmonary systems. For example, patients suffering from congestive heart failure (CHF) may experience disordered breathing as well as a decrease in the pumping action of the heart. In some cases, patients receive therapy from multiple units to improve cardiac and respiratory functioning. For example, a patient may receive treatment for disordered breathing from a patient-external respiratory therapy unit and the patient may receive cardiac resynchronization pacing therapy from a patient-internal cardiac rhythm management (CRM) system.

Various aspects of the invention are directed to coordinated use of multiple therapy devices to increase cardiopulmonary functioning. Some embodiments of the invention utilize information acquired by sensors of a respiratory therapy device to control cardiac pacing based on the interactions of cardiac and pulmonary systems associated with RSA. The cardiac pacing rate may be modulated by respiration to mimic RSA. Systems and methods directed to cardiac pacing controllable by use of a respiration therapy device may be implemented to include selected features, functions, and/or structures described in commonly owned, U.S. Pat. No. 7,302,295, which is hereby incorporated herein by reference.

Other embodiments of the invention modulate intrathoracic pressure based on cardiac cycle phase. In these embodiments, although the cause/effect relationship of RSA is reversed, the cardiovascular system may benefit from similar efficiencies as RSA because intrathoracic pressure is matched to cardiac cycle.

Methods, devices, and systems in accordance with the present invention may incorporate one or more of the features, structures, methods, or combinations thereof described herein below. For example, a medical system may be implemented to include one or more of the features and/or processes described below. It is intended that such a method, device, or system need not include all of the features and functions described herein, but may be implemented to include one or more selected features and functions that provide unique structures and/or functionality.

Figure 83A:
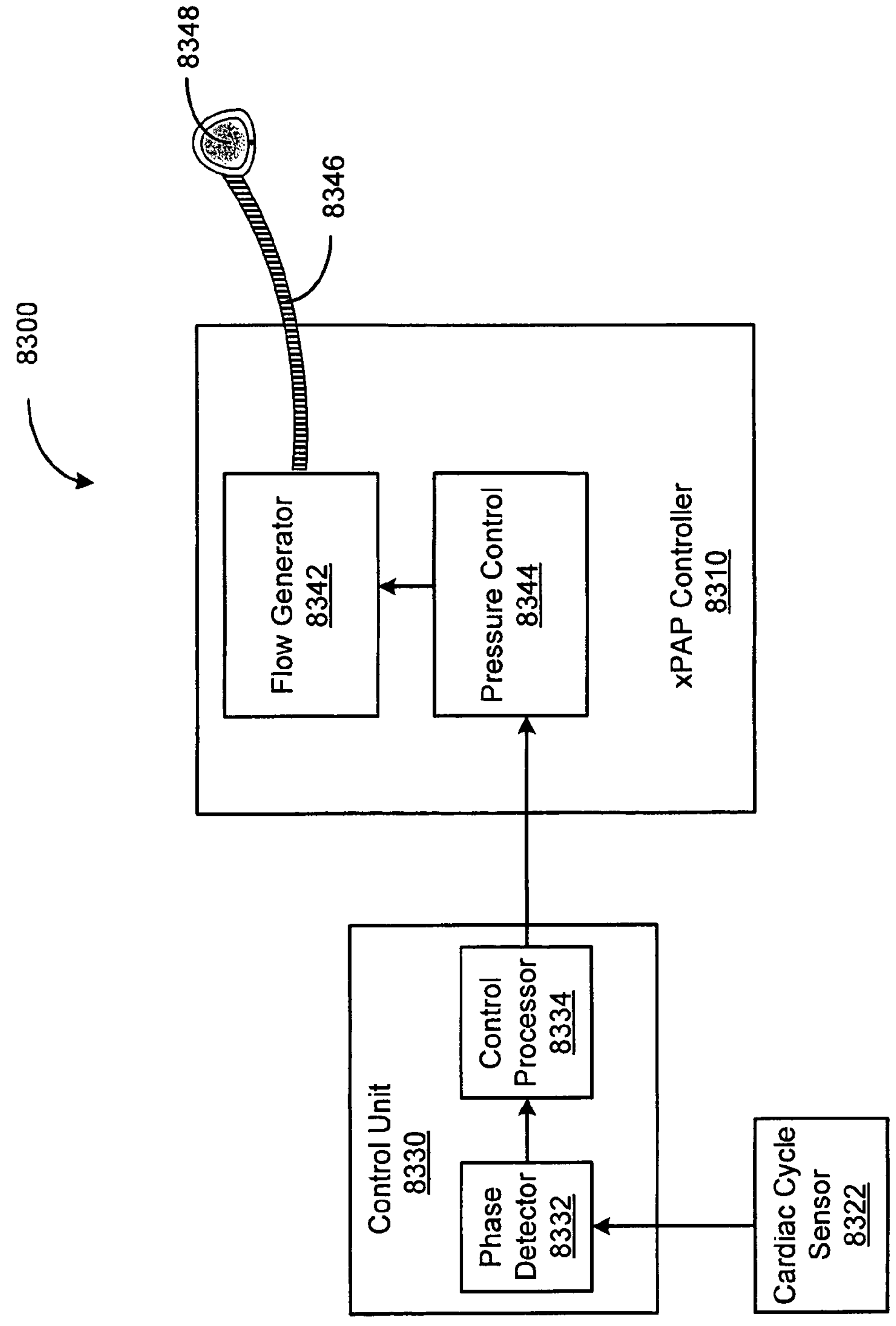
FIGS. 83A-83C are block diagrams illustrating systems that may be used to modulate intrathoracic pressure based on cardiac cycle phase in accordance with embodiments of the invention.
Figure 83B:
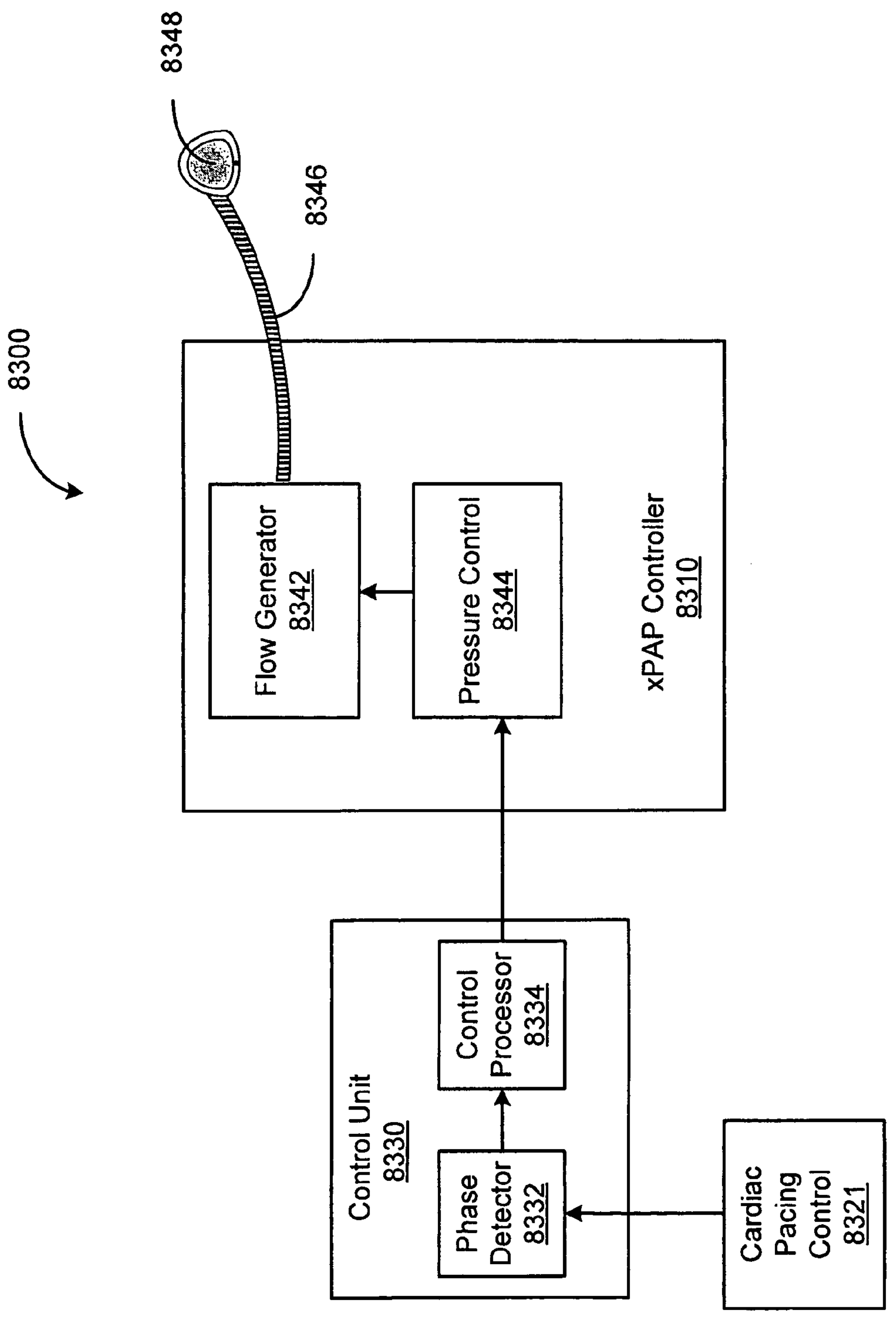
Figure 83C:
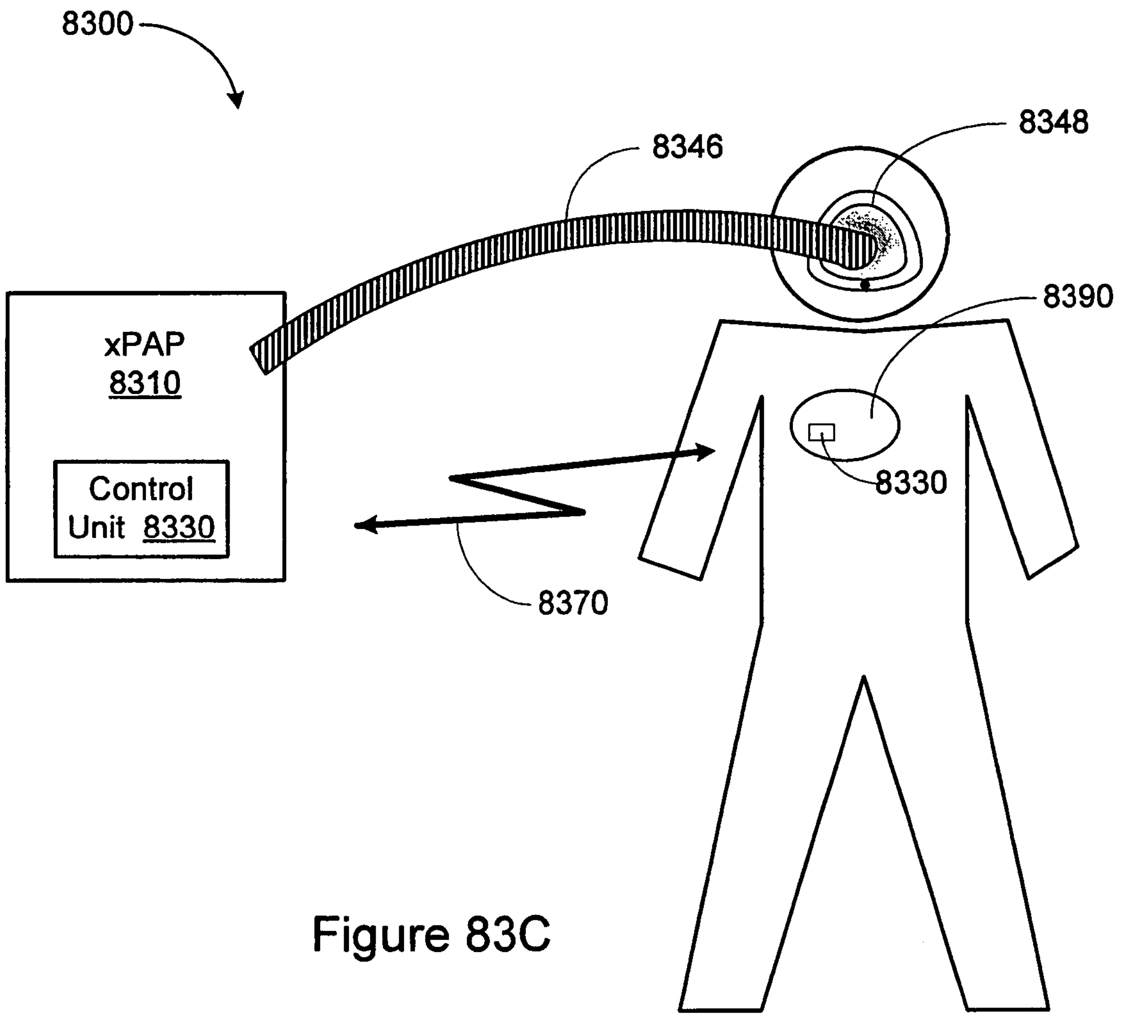

FIGS. 83A-83C are diagrams of systems employing a therapy controller that controls airway pressure delivered by the respiratory therapy device based on cardiac cycle phase. FIG. 83A is a block diagram illustrating a system 8300 that may be used to modulate intrathoracic pressure based on cardiac cycle phase in accordance with embodiments of the invention. In this example, intrathoracic pressure is modulated by a positive airway pressure therapy system 8300 comprising a positive airway pressure therapy controller unit 8330 and airway pressure delivery components 8348, 8346. Respiratory therapy devices, including positive airway pressure (xPAP) devices may be used to treat disordered breathing, heart failure and/or other pulmonary disorders.

Positive airway pressure therapy is particularly useful in the treatment of disordered breathing. Disordered breathing may be caused by an obstructed airway or by derangement of the signals controlling respiration from the brain. Disordered breathing typically occurs while the patient is asleep, and is associated with excessive daytime sleepiness, systemic hypertension, increased risk of stroke, angina and myocardial infarction. Disordered breathing is related to congestive heart failure and can be particularly serious for patients concurrently suffering from cardiovascular deficiencies. Treatment for disordered breathing and/or heart failure may involve the used of an xPAP therapy system. An xPAP therapy system develops a positive air pressure that is delivered to the patient's airway, keeping the patient's airway open and reducing the severity and/or number of occurrences of disordered breathing due to airway obstruction. Reducing the number of occurrences of disordered breathing lessens the strain on the heart, thus providing therapy for heart failure.

The positive airway pressure (xPAP) device 8310 of FIG. 83A, which is typically a bedside unit, delivers air or other gas through tubing 8346 to a facial or nasal mask 8348 worn by the patient. The airway pressure supplied by the xPAP device 8310 acts as a pneumatic splint keeping the patient's airway open and reducing the severity and/or number of occurrences of disordered breathing due to airway obstruction.

The xPAP device 8310 includes a flow generator 8342 that pulls in air through a filter. The flow generator 8342 is controlled by the pressure control circuitry 8344 to deliver an appropriate air pressure to the patient. Air flows through tubing 8346 coupled to the xPAP device 8310 and is delivered to the patient's airway through a mask 8348. In one example, the mask 8348 may be a nasal mask covering only the patient's nose. In another example, the mask 8348 covers the patient's nose and mouth.

The xPAP device 8310 may include a communications unit for communicating with one or more separate devices, including patient-external and/or patient-internal monitoring, diagnostic and/or therapeutic devices. In one example, the xPAP device 8310 may receive control signals for controlling delivery of the respiratory therapy from an implantable therapy or monitoring device. In another example, the xPAP device 8310 may receive control signals for controlling delivery of the respiratory therapy from a patient management server or other computing device.

In one configuration, the xPAP unit 8310 includes a control unit 8330 that further contains a cardiac cycle sensor 8322. The cardiac cycle sensor 8322 measures a physiological parameter associated with the patient's cardiac cycle and sends cardiac cycle information to a phase detector 8332. The phase detector 8332 detects cardiac cycle phase based on the monitored physiological parameter. In one implementation, the cardiac cycle information may be determined from cardiac electrical activity detected using implantable electrogram (EGM) sensors or patient-external electrocardiogram (ECG) sensors. In other implementations the cardiac cycle information may be detected, for example, based on various parameters that may be sensed by the cardiac cycle sensor 8322, including one or more of blood pressure, blood oxygen saturation, e.g., via pulse oximetry, thoracic motion, e.g., via thoracic electrical impedance, heart sounds, airway pressure modulation, and/or atrial tonometry.

Cardiac cycle phase may be determined by the timing of cardiac paces delivered to the patient. In one embodiment, illustrated in FIG. 83B, the phase detector determines cardiac cycle phase based on cardiac pacing information received from a pacemaker control unit 8321. Cardiac pacing information may be used to determine cardiac cycle phase alternatively or in addition to sensed physiological parameters acquired by sensors as described in connection with FIG. 83A.

FIG. 83C illustrates a medical system for controlling respiratory therapy in accordance with embodiments of the invention. The system includes an external respiratory therapy controller unit 8310 that delivers airway pressure through tubing 8346 and mask 8348. An implantable or patient-external cardiac cycle sensor is coupled a therapy controller 8330 disposed within a housing of an implantable cardiac device 8390. The implantable cardiac device 8390 may comprise, for example, a cardiac therapy device, cardiac rhythm management (CRM) system, pacemaker, defibrillator, bi-ventricular pacemaker, intrathoracic cardiac sensing and/or stimulation (ITCS) system, cardiac resynchronizer, cardiac monitor, or other implantable cardiac device.

In one example, cardiac electrodes may be positioned in, on or about the heart in appropriate locations to sense the cardiac electrical activity of one or more heart chambers and/or to deliver pacing pulses to the heart. The cardiac electrodes may be coupled to the implantable cardiac device 8390 through an intracardiac, intrathoracic, or subcutaneous lead system.

In one configuration, cardiac electrical activity is sensed by intracardiac EGM electrodes. Signals corresponding to the cardiac electrical activity are transmitted to a control unit 8330 disposed within the implantable housing of the cardiac therapy or monitoring device 8390. The control unit 8330 evaluates the cardiac electrical signals to determine cardiac cycle phase. Control signals for controlling the airway pressure therapy are developed by the control unit 8330 based on the sensed cardiac electrical activity. The control signals direct the respiratory therapy controller unit 8310 to modulate therapy based on cardiac cycle phase.

In another configuration, the implantable cardiac device 8390 comprises a cardiac rhythm management (CRM) system including a pacemaker that delivers cardiac pacing pulses to one or more heart chambers. The cardiac pacing pulses may be delivered to treat bradycardia, tachycardia and/or cardiac mechanical dysynchrony.

The pacing pulses produce contractions of the heart chambers that may be used to regulate and/or synchronize the heart contractions to enhance the pumping action of the heart. In this configuration, the cardiac cycle phase information may be determined from the timing of the cardiac paces. Cardiac pacing information, e.g., the timing of pacing pulses delivered to the heart chambers, may be provided to the therapy control unit 8330 by the pacemaker of the CRM system 8390. The cardiac pacing information is used by the therapy control unit 8330 to develop control signals for controlling the respiratory therapy based on cardiac phase.

Figure 84A:
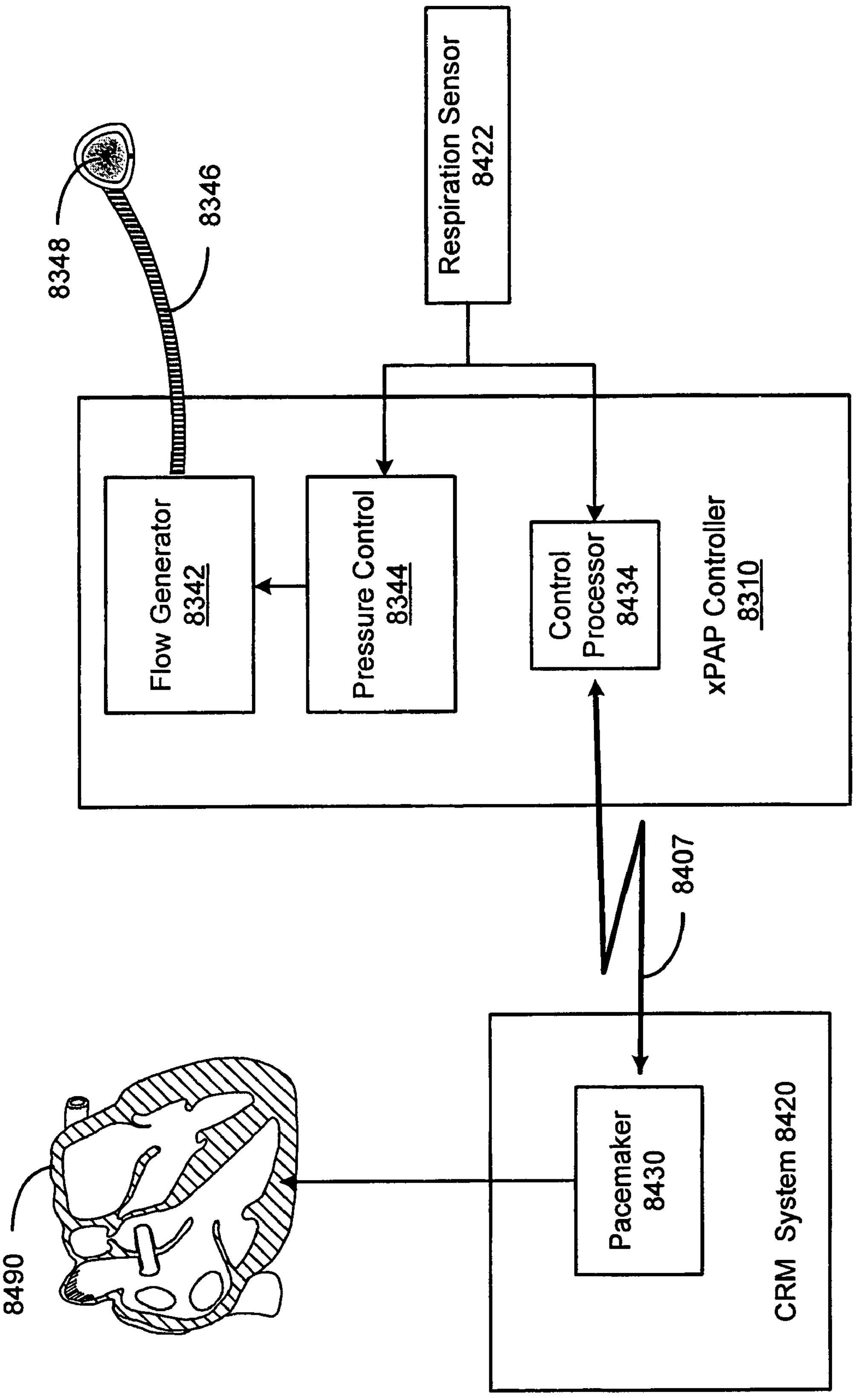
FIGS. 84A and 84B are block diagrams illustrating systems that may be used to modulate cardiac pacing based on respiration in accordance with embodiments of the invention.
Figure 84B:
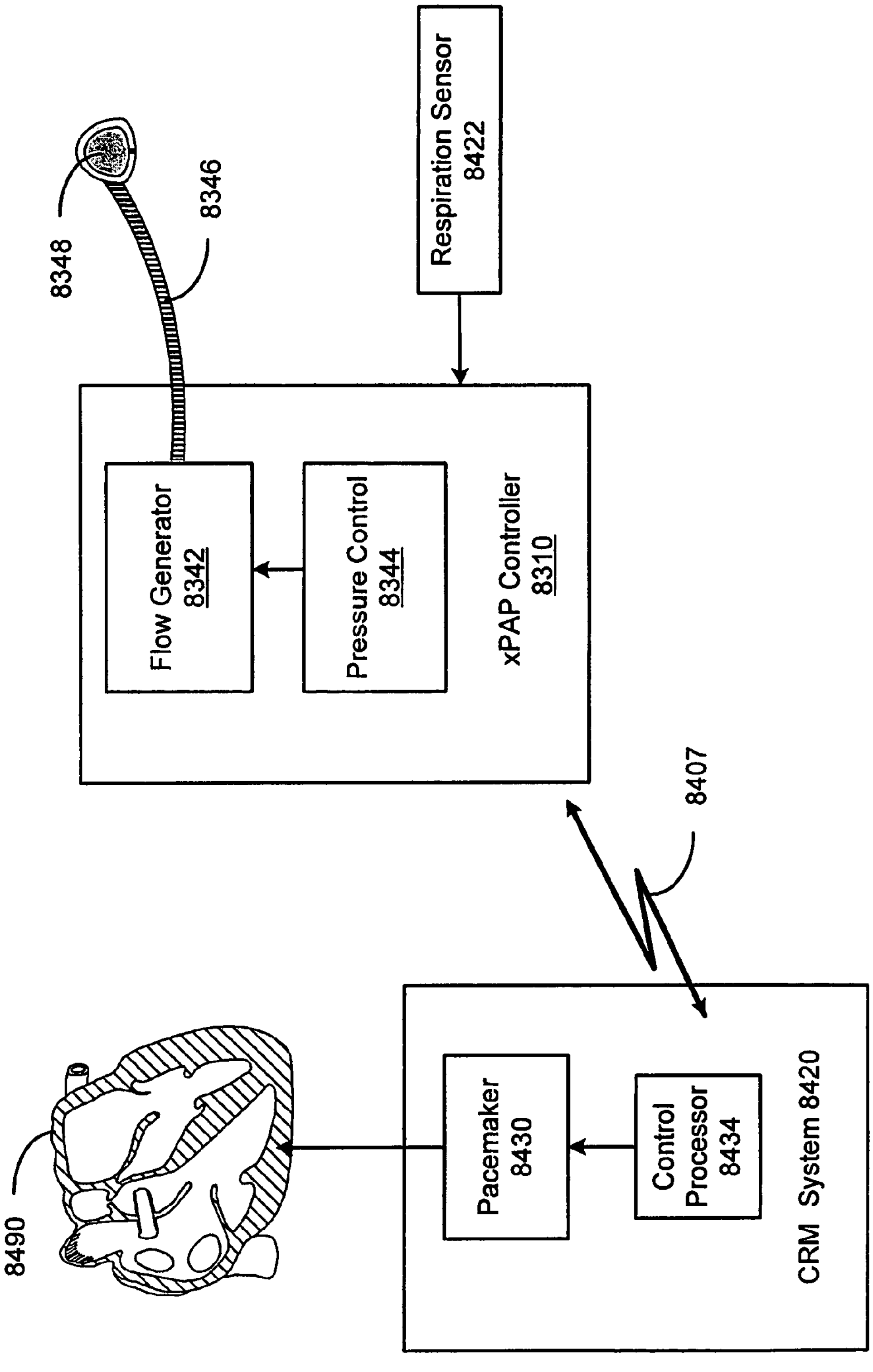

FIGS. 84A and 84B illustrate systems employing a therapy controller that develops a signal to control cardiac pacing based on respiration information acquired from sensors of a respiratory therapy system. In the block diagram of FIG. 84A, the control processor 8434 is implemented as a component of the xPAP controller unit 8310. The control processor 8434 receives respiration information from a sensor 8422 that senses a parameter modulated by respiration. In one example, the sensor 8422 may comprise an airflow sensor of the respiratory therapy device. In other examples, the sensor 8422 may comprise a motion sensor, such as a thoracic or abdominal motion sensor.

The control processor 8434 utilizes the respiration information to develop a signal for controlling cardiac pacing. The control information is transmitted to the cardiac pulse generator 8420 through a wireless communications link 8407. Cardiac pacing pulses, delivered to the heart via the pacemaker 8430 of the cardiac pulse generator 8420, are modulated with respiration based on the control signals provided by the control processor 8434.

FIG. 84B illustrates an embodiment wherein the control processor 8434 is disposed within the implantable housing of the cardiac pulse generator 8420. The control processor 8434 receives respiration information acquired by the respiration sensor 8422 of the respiratory therapy device. Respiration information is transmitted to the cardiac pulse generator 8420 through a wireless communications link 8407. The control processor develops a signal for controlling cardiac pacing based on the respiration information. Cardiac pacing pulses, delivered to the heart 8490 via the pacemaker 8430 of the cardiac pulse generator 8420, are modulated by respiration.

Figure 85A:
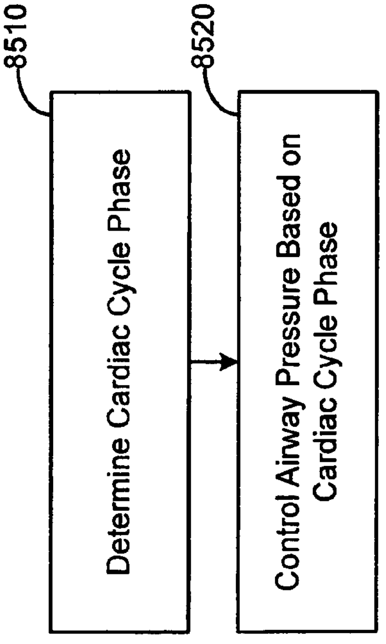
FIGS. 85A and 85B are flowcharts of methods of modulating airway pressure based on cardiac cycle phase in accordance with embodiments of the invention.
Figure 85B:
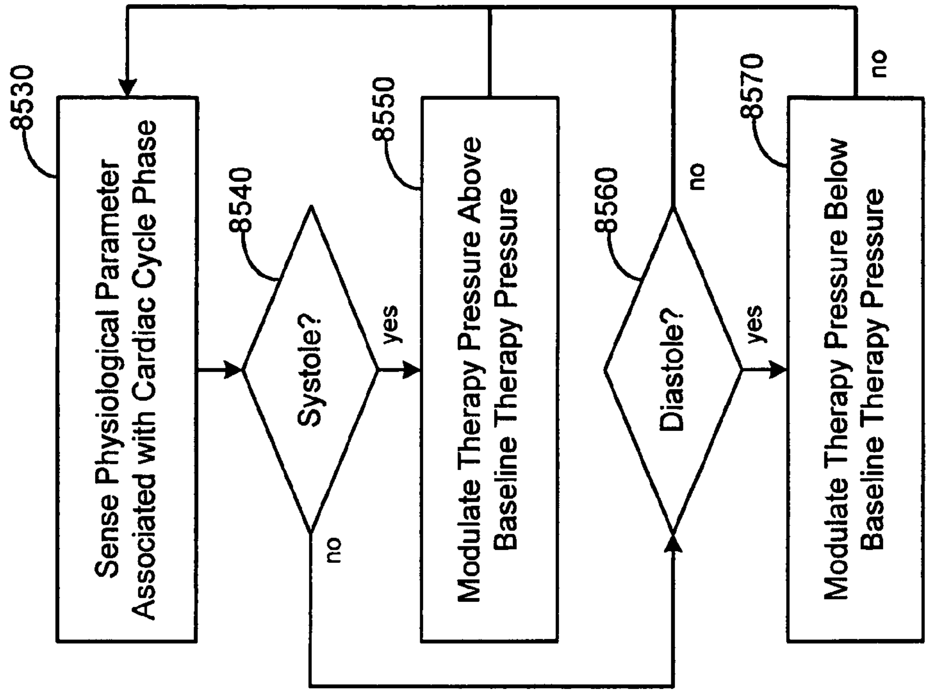

FIGS. 85A and 85B are flowcharts of methods that may be implemented by the systems depicted herein to adjust intrathoracic pressure based on cardiac cycle phase in accordance with embodiments of the invention. As illustrated in FIG. 85A, a method involves determining 8510 cardiac cycle phase by sensing a physiological parameter associated with a cardiac cycle. Control of airway pressure is based on 8520 the cardiac cycle phase. In one embodiment, the physiological parameter used to determine cardiac cycle comprises cardiac electrical activity which may be sensed using an EGM sensor. In other implementations, the cardiac cycle phase may be determined based on a cardiac stroke signal acquired via a transthoracic impedance sensor or a heart sound signal acquired via a microphone or an accelerometer.

The method depicted by the flowchart of FIG. 85B involves sensing 8530 a physiological parameter indicative of cardiac phase. During systole 8540, the therapy pressure is increased 8550, e.g., above a baseline pressure. During diastole 8560, the therapy pressure is decreased 8570.

Figure 85C:
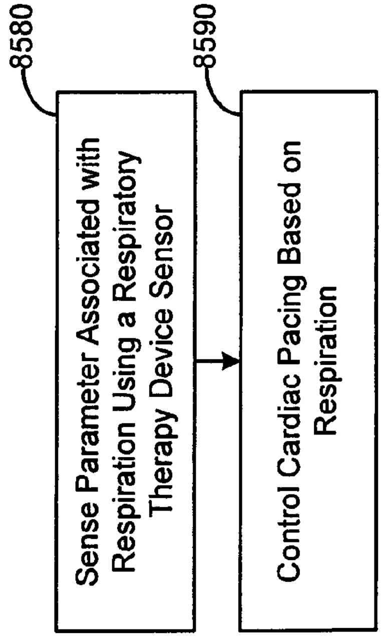
FIG. 85C is a flowchart of a method for controlling cardiac pacing based on respiration in accordance with embodiments of the invention.

FIG. 85C illustrates a method of controlling cardiac pacing in accordance with embodiments of the invention. A parameter associated with respiration is sensed 8580 using a sensor of a respiratory therapy device. For example, the respiratory therapy device may comprise a positive airway pressure device, gas therapy device, nebulizer, ventilator, or other device that delivers respiratory therapy to the patient and includes a sensing system configured to sense a parameter that is modulated by respiration. In one example, the respiratory therapy device may include or be coupled to a blood pressure sensor. In another example, the respiratory therapy device may include or be coupled to an air flow sensor.

According to some aspects of the invention, the therapy controller may control the cardiac device to adjust cardiac pacing based on respiration information acquired from sensors of the respiratory therapy system. The therapy controller may modulate cardiac pacing rate based on respiration cycle information acquired from the sensors of the respiratory therapy unit. Cardiac pacing is controlled based on the sensed parameter associated with respiration. For example, the cardiac pacing rate may be modulated above and below a base rate to mimic RSA. Modulating the cardiac pacing rate with respiration restores normal respiratory sinus arrhythmia in patients who have lost this functionality. Such therapy is particularly useful for patient's suffering from cardiopulmonary diseases such as congestive heart failure. In one embodiment a phase shift is imposed between the respiratory phase and the cardiac phase produced by the cardiac pacing to more closely mimic RSA. Methods and systems for controlling cardiac pacing rate based on respiration, aspects of which may be incorporated into embodiments of the invention described herein, are discussed in U.S. Pat. No. 5,964,788, which is incorporated herein by reference.

Figure 86:
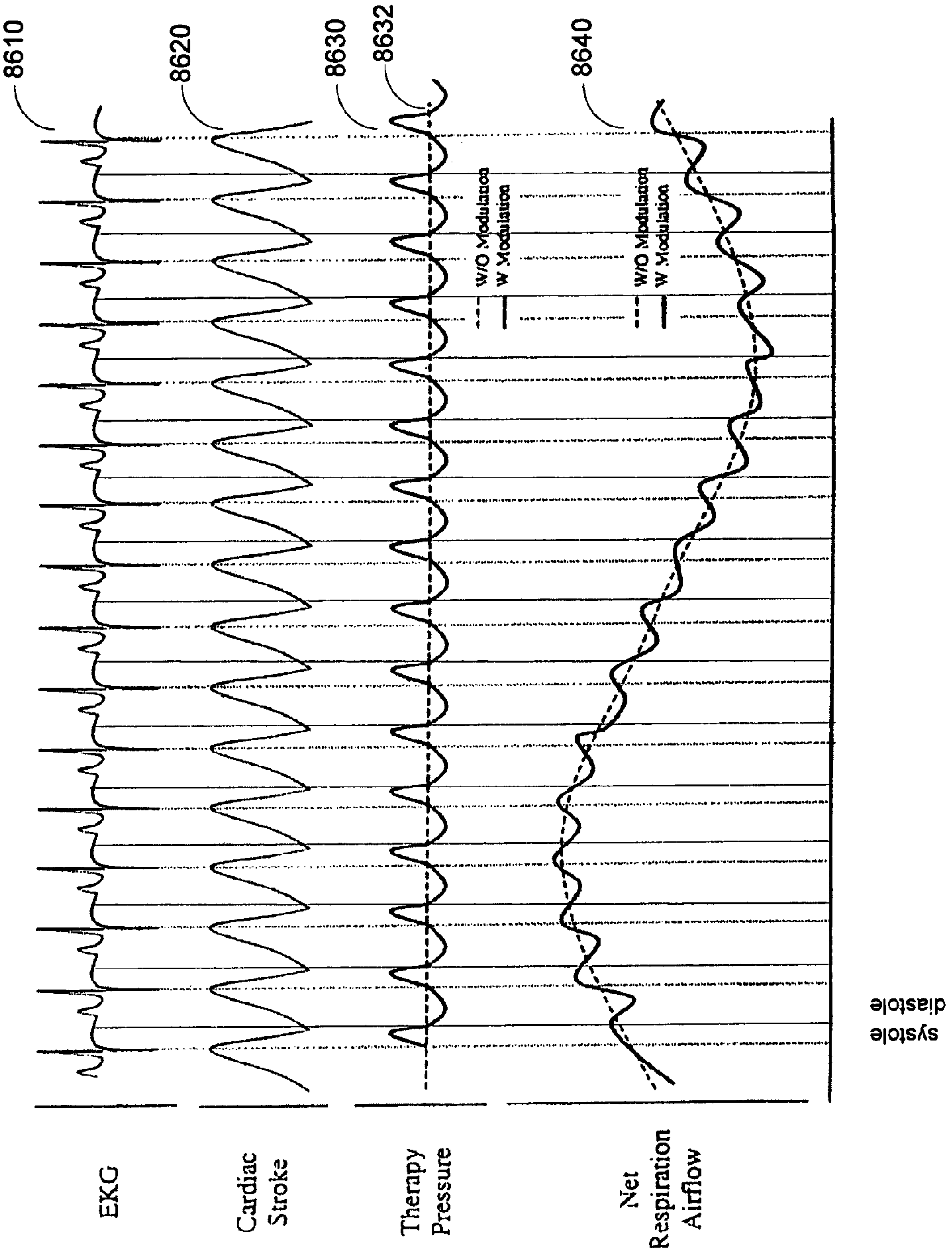
FIG. 86 illustrates modulation of therapy pressure during various cardiac cycles in accordance with embodiments of the invention.

FIG. 86 graphically illustrates modulation of respiratory therapy pressure based on cardiac phase in accordance with embodiments of the invention. FIG. 86 compares graphs of an ECG signal 8610, cardiac stroke signal from an implanted impedance sensor 8620, therapy pressure 8630, and net respiration flow 8640 (as measured into the patient). The net respiration flow 8640 illustrates the patient's respiration cycle modulated by the therapy pressure delivered to the patient. As shown in FIG. 86, the therapy pressure 8630 delivered by the respiratory therapy device is modulated by the phase of the cardiac cycle. The phase of the cardiac cycle may be determined based on the ECG signal 8610 and/or the cardiac impedance stroke signal 8620. Thus, the therapy pressure is increased above its otherwise static positive value 8632 during cardiac systole. The increased thoracic pressure reinforces the cardiac contraction and thus reduces cardiac afterload. During cardiac diastole, the respiratory therapy pressure is decreased from its otherwise static positive value 8632. Although reduced, the therapy pressure is still positive in this embodiment. However, in other embodiments the applied pressure may be zero or negative during cardiac diastole. The reduced ventilation pressure during cardiac diastole assists the heart in filling and thereby increases preload. The control unit may anticipate the cardiac cycle phase based on recent cardiac cycle history.

System and Method for Moderating a Therapy Delivered During Sleep using Physiologic Data Acquired During Non-Sleep Aspects of the invention that include moderating a therapy delivered during sleep using physiologic data acquired during non-sleep are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that include moderating a therapy delivered during sleep using physiologic data acquired during non-sleep are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

System and method embodiments provide for gathering patient related data during non-sleep periods and modulating a therapy delivered to the patient during sleep using the gathered data. According to one approach, data associated with a patient is gathered while the patient is awake. A therapy delivered to the patient during patient sleep is adjusted using the acquired data. The therapy includes one or both of a respiratory therapy and a therapy to treat a sleep-related disorder.

For example, the therapy delivered to the patient may include one or more of a respiratory therapy, such as a positive airway pressure (xPAP) therapy, a sleep disordered breathing therapy, a cardiac rhythm management therapy, such as a cardiac overdrive pacing therapy, a medication therapy, or a drug delivery therapy. The therapy delivered to the patient may be enhanced or optimized using the acquired data. For example, therapy adjustment and/or optimization may involve performing therapy titration using the acquired data.

A pathological disorder may also be detected using the acquired data. A rate of change in the pathological condition may be computed and evaluated. In one approach, a pathological condition may be detected using the acquired data, and a therapy delivered to the patient may be adjusted in response to the detected pathological condition.

The acquired data may include one or more of the following: respiratory data, breathing pattern data, breathing rate data, transthoracic impedance data, heart rate data, heart rate variability (HRV) data, PR interval data, cardiac arrhythmia data, patient activity data, cardiac sound data or pulmonary sound data, contextual data impacting the patient, glucose level data, autonomic nervous system activity data, medication use data, blood pressure data, blood oxygen level data, and/or symptom-based data. Contextual data may include environmental parameters, examples of which include temperature, humidity, pollution, barometric pressure, and body related parameters such as posture and location.

Embodiments of the invention involve an individual system 129 (FIG. 1B) for moderating a therapy delivered during sleep using physiologic data acquired during non-sleep. The system 129 for moderating a therapy delivered during sleep using physiologic data acquired during non-sleep may be implemented as a stand alone system or in combination with other individual medical systems, such as those described in FIGS. 1B-1D.

Embodiments of the invention involve a system for providing coordinated patient monitoring, diagnosis and/or therapy that utilizes moderation 129 of a therapy delivered during sleep using physiologic data acquired during non-sleep. The coordinated system may include, for example, an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy. Systems and methods directed to moderating a therapy delivered during sleep using physiologic data acquired during non-sleep may be implemented to include selected features, functions, and/or structures described in commonly owned, co-pending U.S. Publication No. 2005/0080461, which is hereby incorporated herein by reference.

Figure 87A:
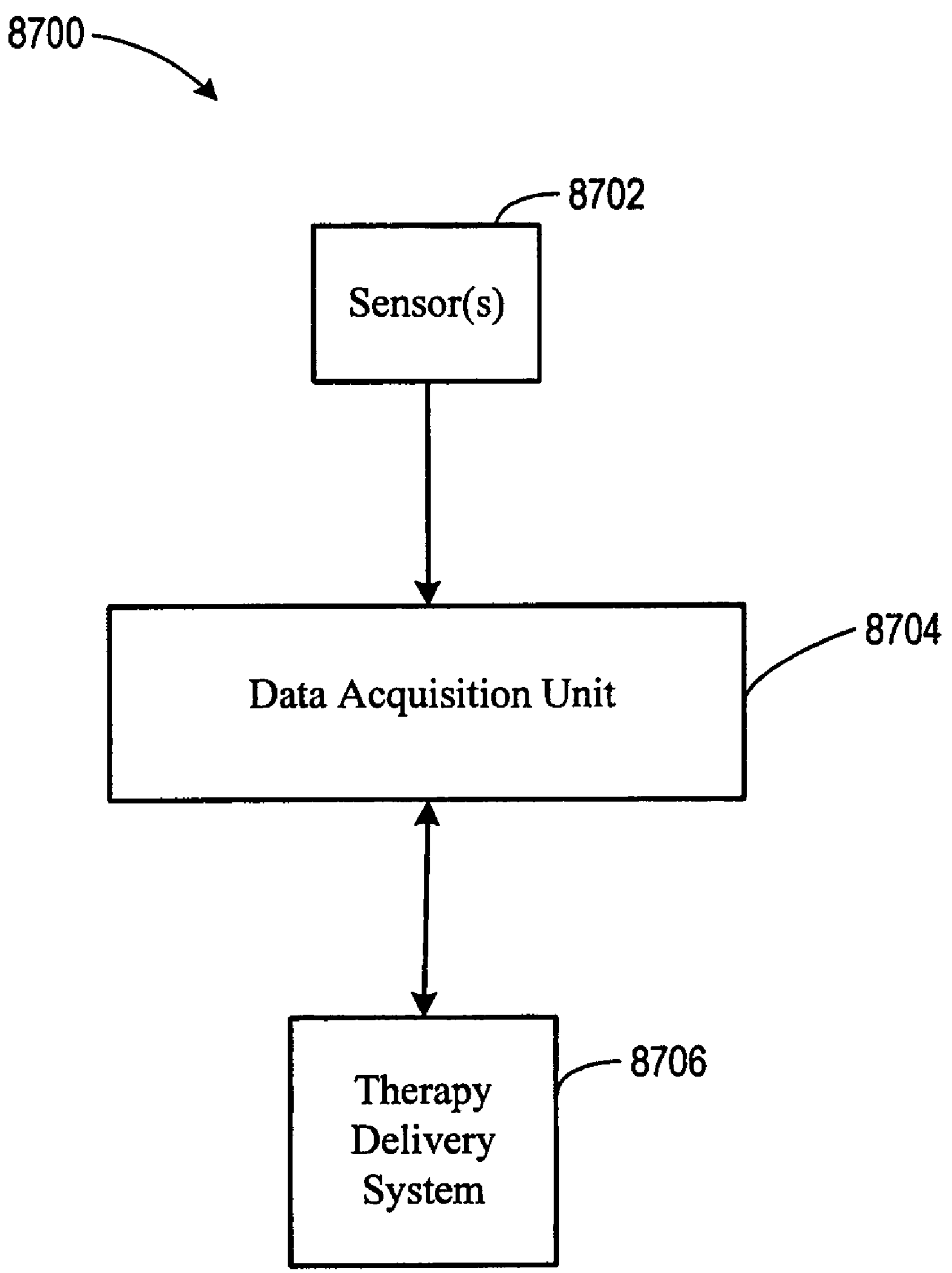
FIGS. 87A, 87B, and 87C are block diagrams of systems providing diurnal data collection to aid nocturnal therapy and diagnosis of sleep disorders in accordance with embodiments of the invention.
Figure 87B:
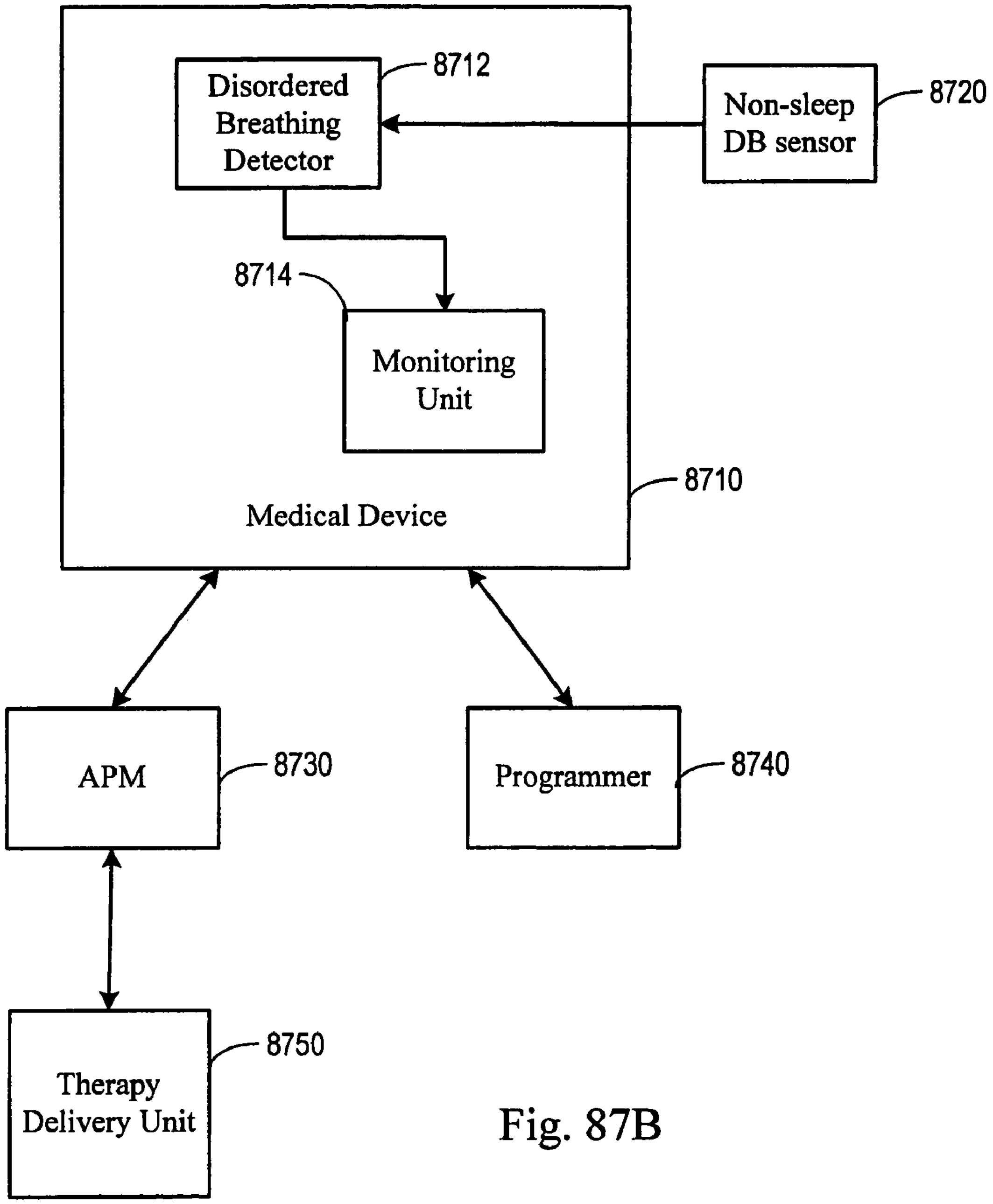
Figure 87C:
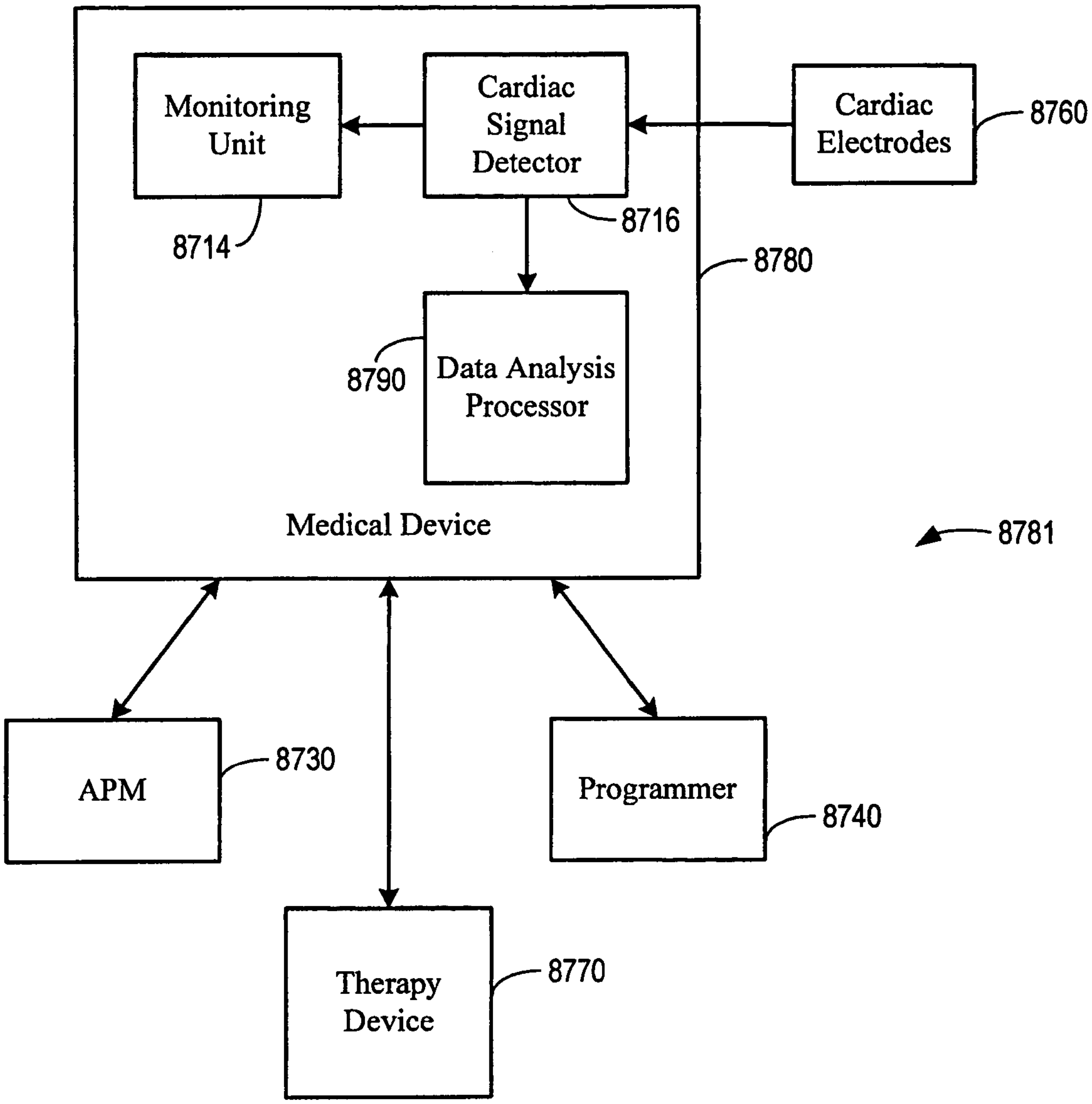

The following discussion, with reference to FIGS. 87A-87C, describes embodiments of the invention involving use of diurnal data to aid nocturnal therapy and diagnosis of sleep disorders. The processes and systems exemplified by these embodiments may be implemented alone or in combination with one or more processes and systems exemplified by other embodiments described herein to provide a coordinated approach to patient monitoring, diagnosis, and/or therapy.

In accordance with embodiments of the invention, many types of data acquired during non-sleep periods may be used to adjust or enhance therapy during periods of sleep. The data acquired during non-sleep may also be used to provide enhanced diagnostic capabilities for sleep-related disorders. The data acquired during non-sleep may be used, for example, to determine the existence of a condition that occurs during non-sleep periods and is caused, or results from, a sleep-related disorder. The data acquired during non-sleep may determine the extent of the condition, the rate of change of the condition, the amount of change of the condition relative to a baseline, and/or the effect of nocturnal therapy for the condition.

Examples of data acquired during non-sleep that may aid in nocturnal therapy and diagnosis include: transthoracic impedance or other arrangement to assess pathological breathing patterns or conditions such as Cheyne-Stokes breathing, periodic breathing, rapid breathing, respiratory rates, inspiration/expiration intervals, pulmonary function parameters, including for example, forced expiratory volume (FEV) and forced vital capacity (FVC); heart rates, postventricular (PV) intervals and cardiac arrhythmias; activity level; cardiac and pulmonary sounds, (e.g., S3, rates, coughs); environmental data, (e.g., air pollution, humidity); glucose levels; autonomic nervous system activity; medication use, particularly for patients whose use is aperiodic and patient determined (e.g., albuterol for asthma); blood pressure (e.g., average arterial, left atrial end diastolic); blood oxygen level; posture; and symptom-based data (e.g., dyspnea, daytime sleepiness, fatigue, restless leg syndrome (RLS) symptoms).

A variety of sleep-time therapy may be modulated using the data acquired during non-sleep. In one implementation, data acquired during non-sleep may be used to modulate respiration therapy for disordered breathing, e.g., xPAP therapy. In another implementation, data acquired during non-sleep may be used to adjust cardiac overdrive pacing for sleep disordered breathing. In yet another implementation, data acquired during non-sleep may be used to adjust medications used for sleep disorders, e.g., benzodiazepine, tricyclic antidepressants, and theophylline, among others. In another implementation, data acquired during non-sleep may be provided to the patient for behavior modification (e.g., excessive activity too close to sleep time).

Referring to FIG. 87A, a system 8700 in accordance with an embodiment of the present invention includes a data acquisition unit 8704 configured to acquire data associated with a patient while the patient is awake. The data acquisition unit 8704 is coupled to a therapy delivery system 8706 configured to adjust a therapy delivered to the patient, during patient sleep, using the acquired data. One or more sensor(s) 8702 are used to sense physiological signals useful to the data acquisition unit 8704.

As illustrated in FIG. 87B, a system, in accordance with an embodiment of the invention, includes one or more patient-internal and/or patient-external sensors 8720 for sensing non-sleep conditions related to disordered breathing. Signals from the one or more sensors 8720 may be acquired by a disordered breathing detector 8712 in a patient-internal or patient-external medical device 8710 and used to detect non-sleep episodes of disordered breathing. In one implementation, respiratory signals, sensed using the sensor 8720, such as a transthoracic impedance sensor, are detected during non-sleep periods.

The respiration signals may be stored in the memory of a monitoring unit 8714 within the medical device 8710. The respiration signals may be trended, displayed, and/or transmitted to another device, such as an advanced patient management (APM) system 8730 or a programmer 8740 periodically or on command.

The non-sleep respiration signals may be used to modify therapy for sleep disordered breathing. In one example, the APM system 8730 analyzes the non-sleep respiration signals to determine the presence and/or severity of non-sleep time periodic breathing. The APM system 8730 may use information about disordered breathing, such as the onset or extent of periodic and/or Cheyne-Stokes breathing during non-sleep periods, to determine the optimal sleep time xPAP therapy for Cheyne-Stokes breathing and/or central sleep apnea therapy. The APM system 8730 determines a modified therapy based on the non-sleep respiration signals.

In one example, when periodic and/or Cheyne-Stokes breathing increases or decreases, the pressure delivered by an xPAP therapy unit may be increased or decreased, respectively. In another example, non-sleep time breathing information may be used to modify the initial pressures for an auto-titrating PAP device. The APM system 8730 may transmit control signals to a therapy device 8750, e.g., a respiration therapy device such as an xPAP device, to modify therapy delivered to the patient during sleep.

Although the example provided in FIG. 87B contemplates the use of the APM system 8730 to analyze the non-sleep signals and modify the sleep time delivered therapy, the medical device 8710 may perform one or both of these functions.

In another embodiment of the invention, illustrated in FIG. 87C, cardiac information is used to adjust cardiac overdrive pacing prescribed for the treatment of sleep disordered breathing. In this embodiment, a cardiac signal detector unit 8716 within an implanted or external device 8780 detects cardiac signal information from cardiac electrodes 8760, e.g., implanted, subcutaneous, surface electrodes or combinations thereof, during non-sleep periods. The cardiac information may be saved in the memory of a monitoring unit 8712 within the medical device 8780. The cardiac information may be trended, displayed, or transmitted to another device, such as a programmer 8740 or an APM system 8730.

The non-sleep period cardiac information may be analyzed to determine an enhanced or optimum cardiac electrical stimulation therapy for sleep disordered breathing. In this example, the non-sleep cardiac information is analyzed in a data analysis unit 8790 within the medical device 8780. In another implementation, the cardiac information may be analyzed by the APM 8730 or other device.

In this example configuration, the medical device 8780 uses the cardiac information to adjust timing parameters in an implanted therapy device 8770, such as a CRM device. For example, the data analysis unit 8790 may determine an average intrinsic heart rate and/or an average PR interval during non-sleep periods. These values may be used to enhance the rate and AV delay used by the cardiac overdrive pacing therapy prescribed to treat sleep disordered breathing in subsequent sleep periods.

In one illustrative configuration, the functions of the medical device 8780, including the cardiac signal detector 8716, the monitoring unit 8712 and/or the data analysis unit 8790, and the implanted therapy device 8770 are located within an implantable CRM device 181. In this configuration, the data analysis unit 8790 receives cardiac signals from implanted cardiac electrodes during non-sleep times. The data analysis unit 8790 analyzes the cardiac signals to adjust therapy delivered by the CRM device 181 to treat sleep disordered breathing.

Figure 88:
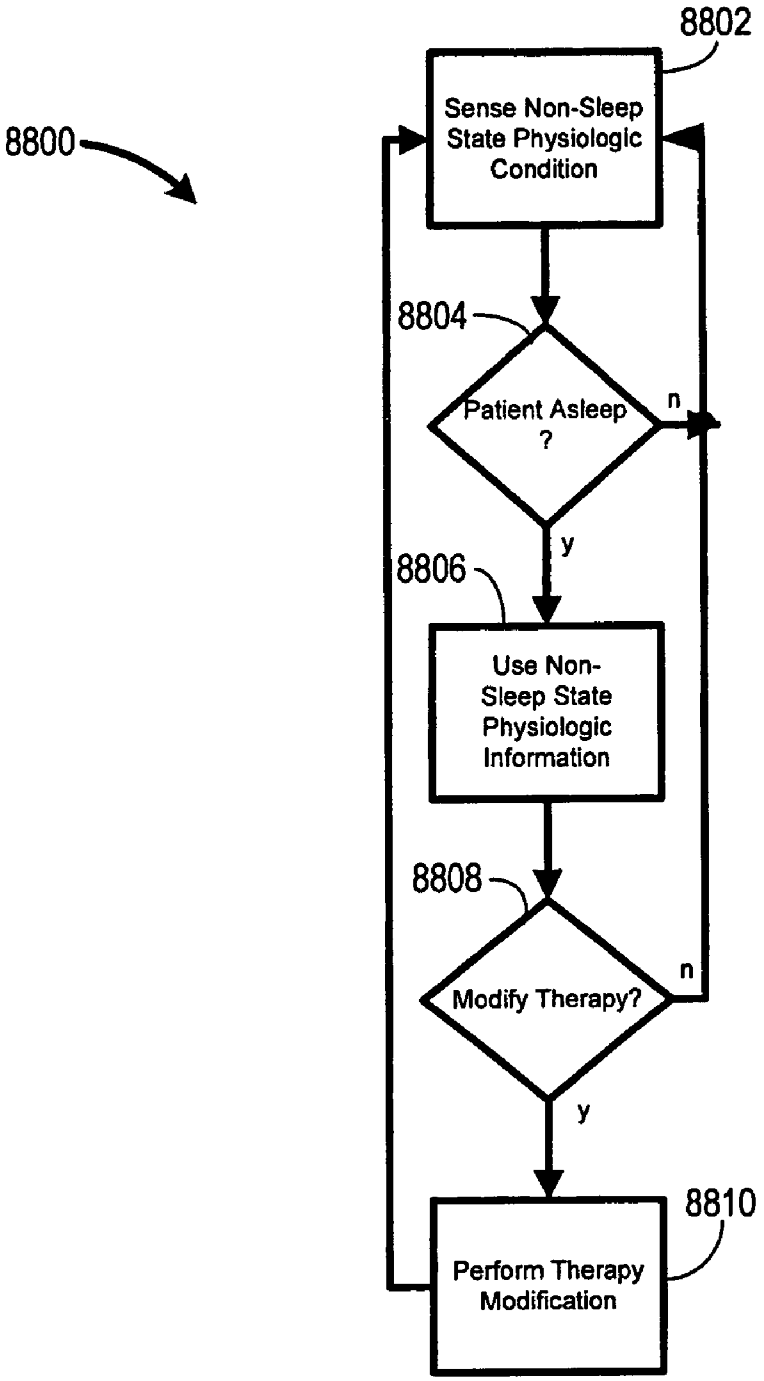
FIG. 88 is a flow chart illustrating of method of moderating sleep therapy using data acquired during non-sleep in accordance with embodiments of the present invention.

FIG. 88 illustrates a method 8800 of moderating sleep therapy using physiologic data acquired during non-sleep. A sensor (internal or external to the patient, such as an EEG sensor) is used at block 8802 to sense a patient's non-sleep state physiologic condition. The data, trends, or selected parameters may then be stored in memory of an implantable device and/or a patient-external device such as an APM device or server system.

A determination 8804 is made that the patient is asleep. If the patient is sleeping, the information stored during the non-sleep period is used at block 8806 to, for example, compare the current paced heart rate to the non-sleep intrinsic heart rate. A decision 8808 is then made to select continuation of the current therapy or to modify patient therapy based at least in part on physiologic data acquired during non-sleep. If treatment modification is desired, the modification is performed at block 8810 before re-starting the method 8800.

In certain embodiments, sounds, such as hearts sounds and pulmonary sounds, are used to aid in moderating sleep therapy using physiologic information acquired during non-sleep. Because heart sounds are time correlated with respect to the cardiac electrophysiological signals, the non-electrophysiologic signal may provide information about a patient's rhythm state even in the presence of electrical noise and/or electrocardiographic artifacts. A subcutaneous sensor, such as an accelerometer or acoustic transducer, may be used to detect heart sounds. It should also be noted that other sensor derived signals could replace heart sounds. For example, impedance, pulse pressure, blood volume/flow, or cardiac accelerations could be used.

Various types of acoustic sensors may be used to detect heart sounds. Examples of such acoustic sensors include diaphragm based acoustic sensors, MEMS-based acoustic sensors such as a MEMS-based acoustic transducer, fiber optic acoustic sensors, piezoelectric sensors, and accelerometer based acoustic sensors and arrays. These sensors may be used to detect audio frequency (and/or subsonic frequency) pressure waves associated with the heart sounds, and may also be used to detect other non-electrophysiologic cardiac related signals.

Figure 89:
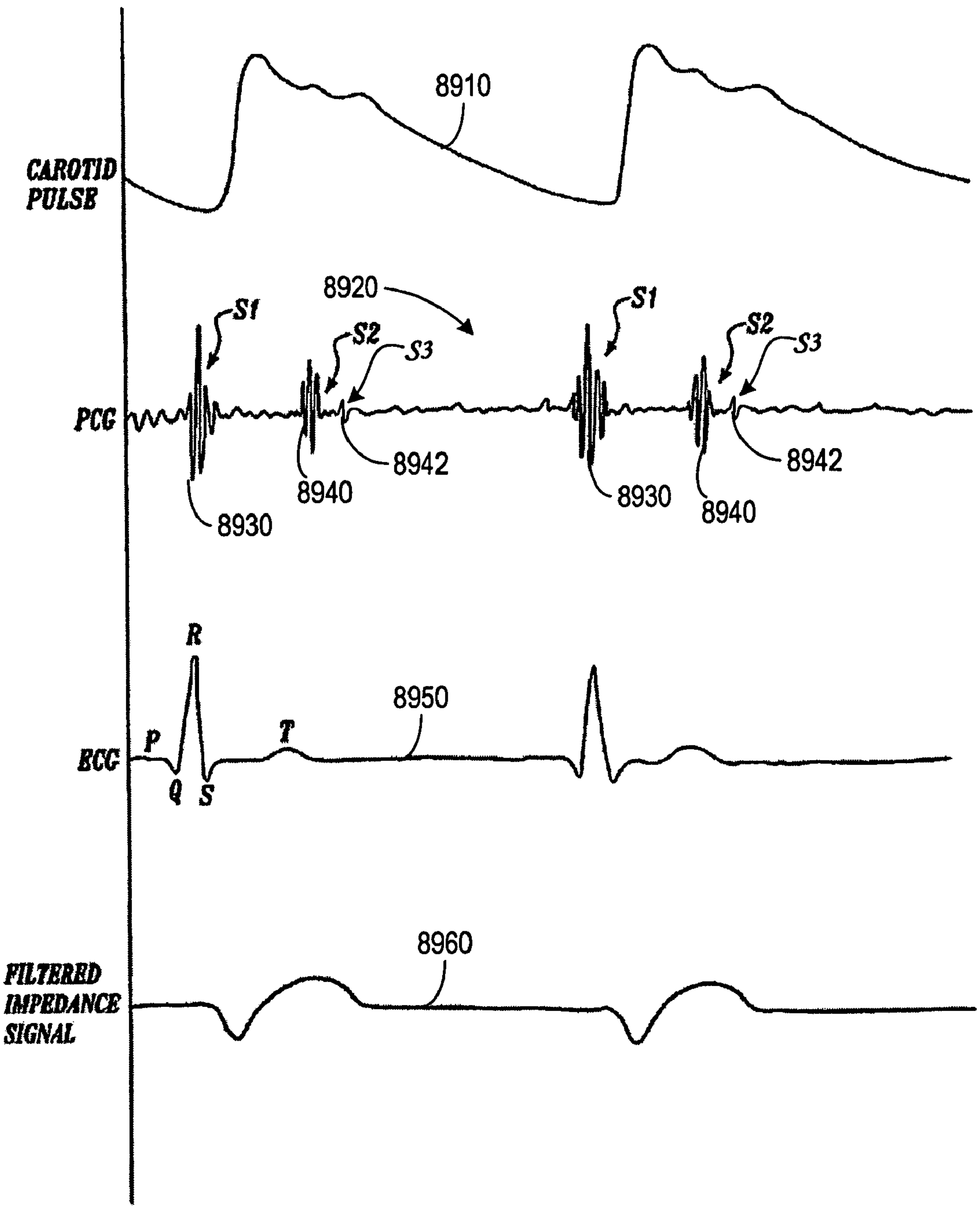
FIG. 89 is a pictorial diagram of a carotid pulse waveform, a phonocardiogram (PCG) waveform, an electrocardiogram (ECG) waveform, and a filtered transthoracic impedance signal for two consecutive heartbeats.

The presence of cardiac pulse, or heartbeat, in a patient is generally detected by palpating the patient's neck and sensing changes in the volume of the patient's carotid artery due to blood pumped from the patient's heart. A graph of a carotid pulse signal 8910, representative of the physical expansion and contraction of a patient's carotid artery during two consecutive pulses, or heartbeats, is shown at the top of FIG. 89. When the heart's ventricles contract during a heartbeat, a pressure wave is sent throughout the patient's peripheral circulation system. The carotid pulse signal 8910 shown in FIG. 89 rises with the ventricular ejection of blood at systole and peaks when the pressure wave from the heart reaches a maximum. The carotid pulse signal 8910 falls off again as the pressure subsides toward the end of each pulse.

The opening and closing of the patient's heart valves during a heartbeat causes high-frequency vibrations in the adjacent heart wall and blood vessels. These vibrations may be heard in the patient's body as heart sounds, and may be detected by sensors, as described earlier. A conventional phonocardiogram (PCG) transducer placed on a patient converts the acoustical energy of the heart sounds to electrical energy, resulting in a PCG waveform 8920 that may be recorded and displayed, as shown by the graph in the upper middle portion of FIG. 89.

As indicated by the PCG waveform 8920 shown in FIG. 89, a typical heartbeat produces two main heart sounds and may produce other sounds depending on pathology. A first heart sound 8930, denoted S1, is generated by vibration generally associated with the closure of the tricuspid and mitral valves at the beginning of systole. Typically, the heart sound 8930 is about 14 milliseconds long and contains frequencies up to approximately 500 Hz. A second heart sound 8940, denoted S2, is generally associated with vibrations resulting from the closure of the aortic and pulmonary valves at the end of systole. While the duration of the second heart sound 8940 is typically shorter than the first heart sound 8930, the spectral bandwidth of the second heart sound 8940 is typically larger than that of the first heart sound 8930. A third heart sound 8942, denoted S3, is also seen in the PCG waveform 8920.

The S3 heart sound 8942 is created when the ventricles relax and pressure from the filling blood rapidly distends the ventricle. When the stiff, non-compliant ventricular wall reaches its physical limits, it suddenly tenses, and the S3 sound is created. In children an S3 is common and normal. After age 40, it almost always indicates the failing heart in congestive heart failure. As stated earlier, an accelerometer or acoustic transducer may also detect pulmonary sounds, such as rales and/or coughs, to provide physiologic data.

An electrocardiogram (ECG) waveform 8950 describes the electrical activity of a patient's heart. The graph in the lower middle portion of FIG. 89 illustrates an example of the ECG waveform 8950 for two heartbeats and corresponds in time with the carotid pulse signal 8910 and PCG waveform 8920 also shown in FIG. 89. Referring to the first shown heartbeat, the portion of the ECG waveform 8950 representing depolarization of the atrial muscle fibers is referred to as the "P" wave. Depolarization of the ventricular muscle fibers is collectively represented by the "Q." "R," and "S" waves of the ECG waveform, referred to as the QRS complex. Finally, the portion of the waveform representing repolarization of the ventricular muscle fibers is known as the "T" wave. Between heartbeats, the ECG waveform 8950 returns to an isopotential level.

Fluctuations in a patient's transthoracic impedance signal 8960 also correlate with blood flow that occurs with each cardiac pulse wave as well as provide breathing information. The bottom graph of FIG. 89 illustrates an example of a filtered transthoracic impedance signal 8960 for a patient in which fluctuations in impedance correspond in time with the carotid pulse signal 8910, the PCG waveform 8920, and ECG waveform 8950, also shown in FIG. 89.

Automatic Activation of Medical Processes

Aspects of the invention that include automatic activation of medical processes are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that include automatic activation of medical processes are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention may involve automatic control of therapies or other medical processes based on sleep stage, such as is determined by brain activity. Automatic control may involve automatic activation, de-activation and/or modification of such therapies and processes. In various embodiments, a system includes a sensor system having one or more sensors configured to sense signals related to the brain activity of the patient. A brain activity analyzer detects various brain states, including, for example, sleep state/stage and/or brain seizures. The brain activity detector may also be configured to discriminate between sleep and wakefulness. A controller uses the brain state detection information to control a medical system configured to perform at least one respiratory or cardiac process.

Other embodiments include at least one of an EEG sensor and an EMG sensor configured for one or more of detecting brain state. One or more sensors may be positioned on a respiratory mask of a respiratory device, such as a positive airway pressure therapy device. Further embodiments include a cardiac rhythm management device, wherein the cardiac process may involve one or both of a cardiac therapy process and a breathing therapy process. The cardiac process may further involve a diagnostic process and/or a monitoring process.

According to other embodiments, a method involves sensing signals related to brain state and determining the brain state of a patient based on the sensed signals. At least one respiratory or cardiac medical process is activated, de-activated, modified or otherwise controlled based on the patient's brain state.

Further embodiments involve sensing the signals related to brain state using EEG signals and/or EMG signals. Sensing signals related to brain state may further involve sensing signals related to sleep stage. Sensing signals related to brain state may involve sensing seizure, and activating the medical process may involve activating, de-activating, modifying or otherwise controlling arrhythmia therapy based on seizure detection.

Embodiments of the invention involve an individual system 132 (FIG. 1B) for automatic activation of medical processes based on brain state. A system employing automatic activation of medical processes 132 may be implemented as a stand alone system or in combination with other individual medical systems, such as those described in FIGS. 1B-1D.

Other embodiments involve a system for providing coordinated patient monitoring, diagnosis and/or therapy that employ automatic activation of medical processes 132. A coordinated system may include, for example, one or both of an implantable cardiac device 181 and a patient-external respiratory therapy device 184. The system may further include an external processor 183 providing a coordination function. A communication channel couples the implantable device 181 and the respiratory therapy device 184. The implantable 181 and respiratory therapy devices 184 operate cooperatively via the communication channel to provide one or more of patient monitoring, diagnosis, and therapy.

Two or more of the implantable device 181, respiratory therapy device 184, and external processor 183 may operate cooperatively based on brain state for employing automatic activation of medical processes 132. For example, detection of brain state may allow two or more of the implantable device 181, respiratory therapy device 184, and external processor 183 to operate cooperatively to provide a therapy to treat a cardiac, respiratory, or other condition.

Figure 90A:
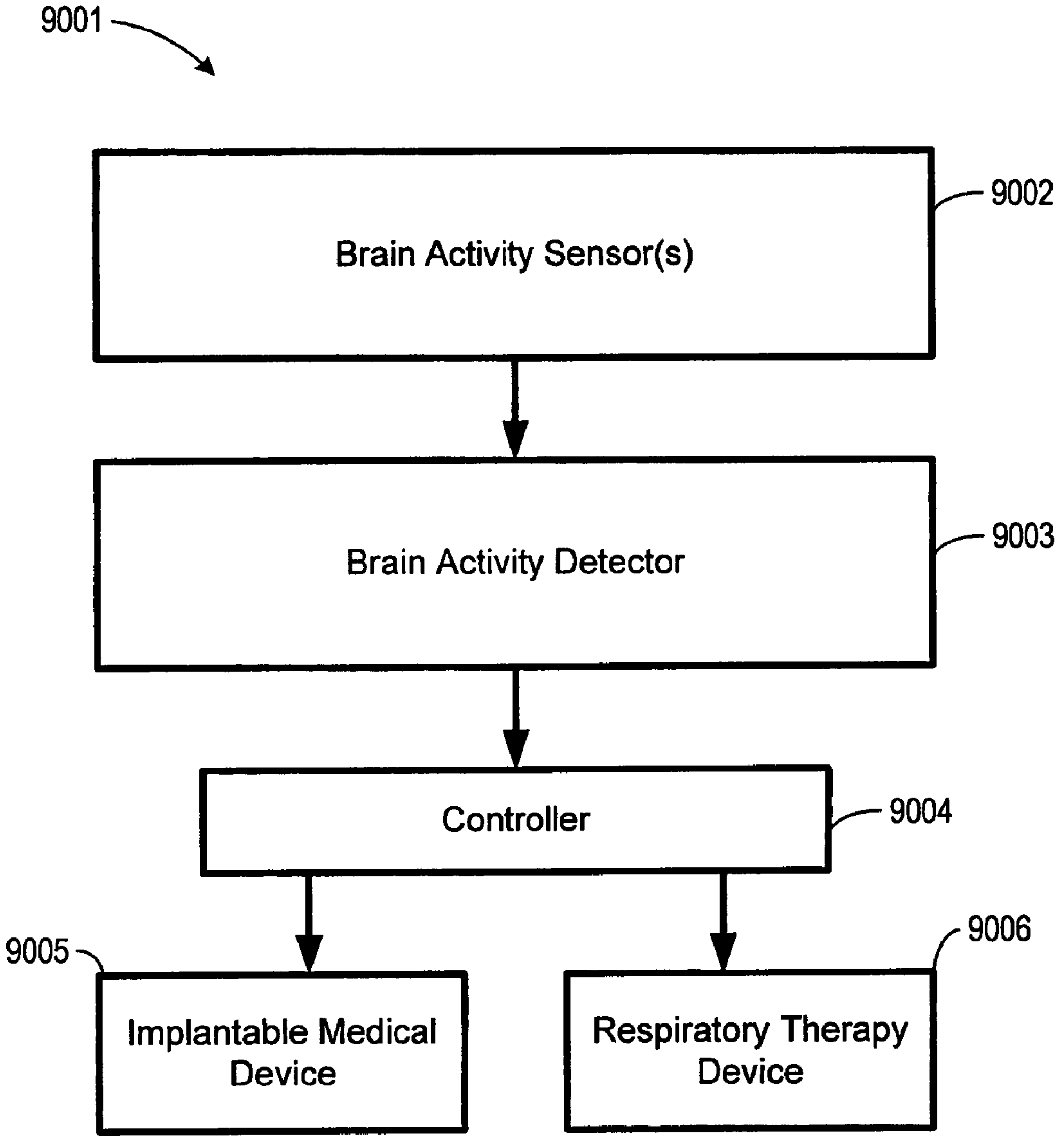
FIG. 90A is a flow chart illustrating a method of controlling a medical process using brain state information in accordance with embodiments of the invention.
Figure 90B:
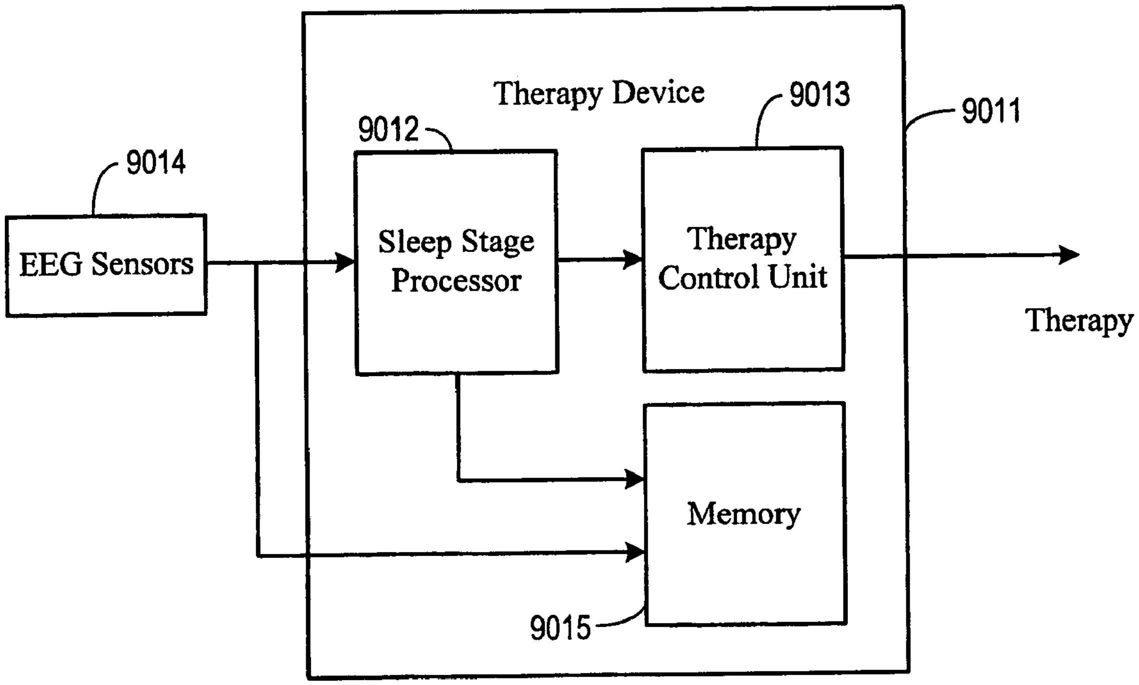
FIGS. 90B-90D are block diagrams of systems implementing control of medical processes using brain activity information in accordance with embodiments of the invention.
Figure 90C:
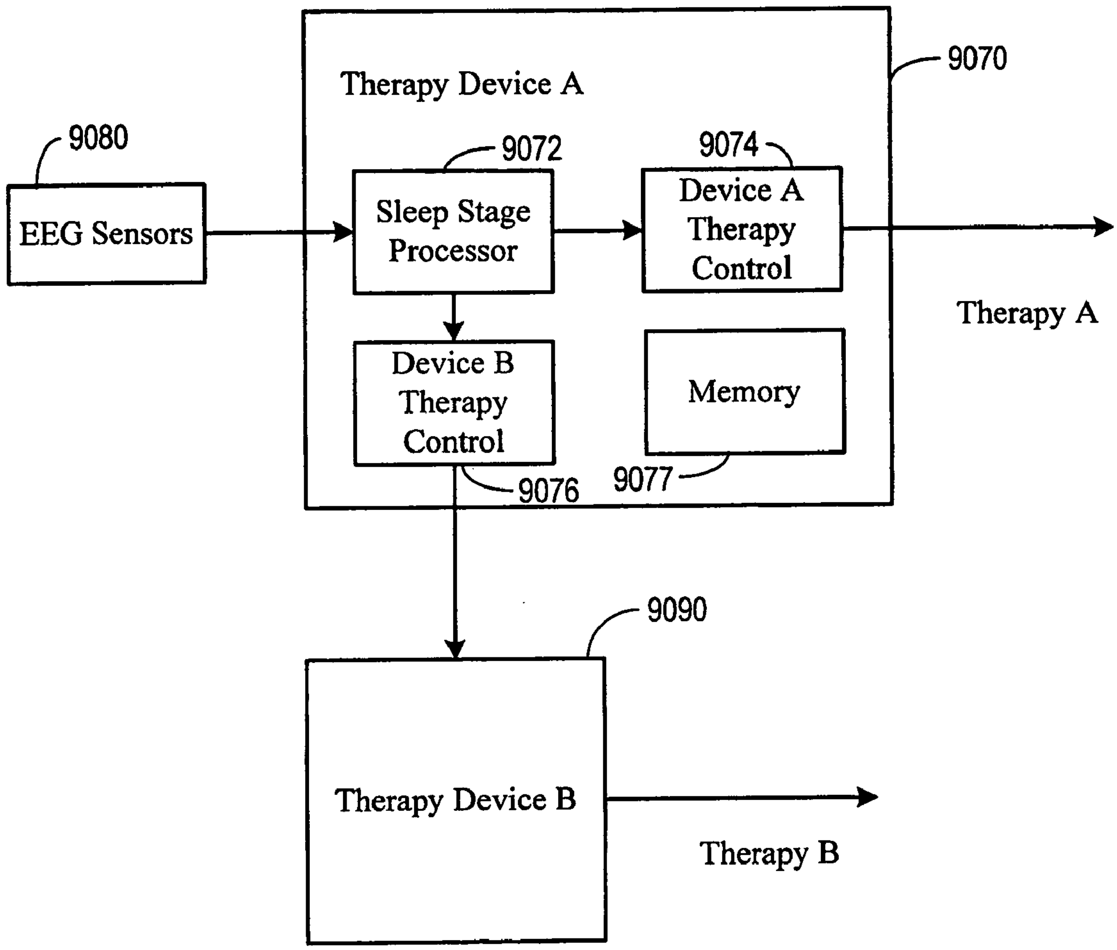
Figure 90D:
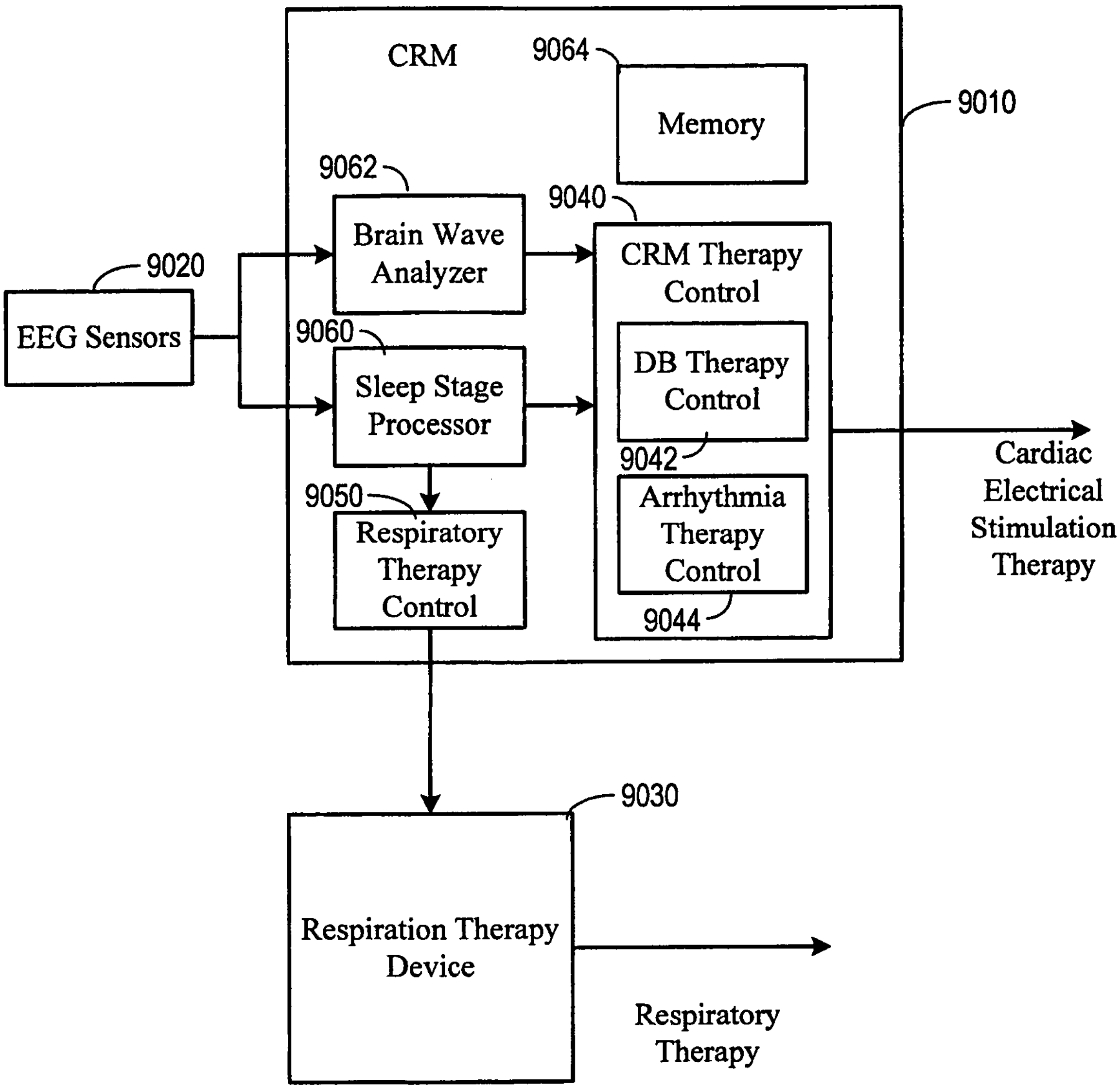
Figure 91:
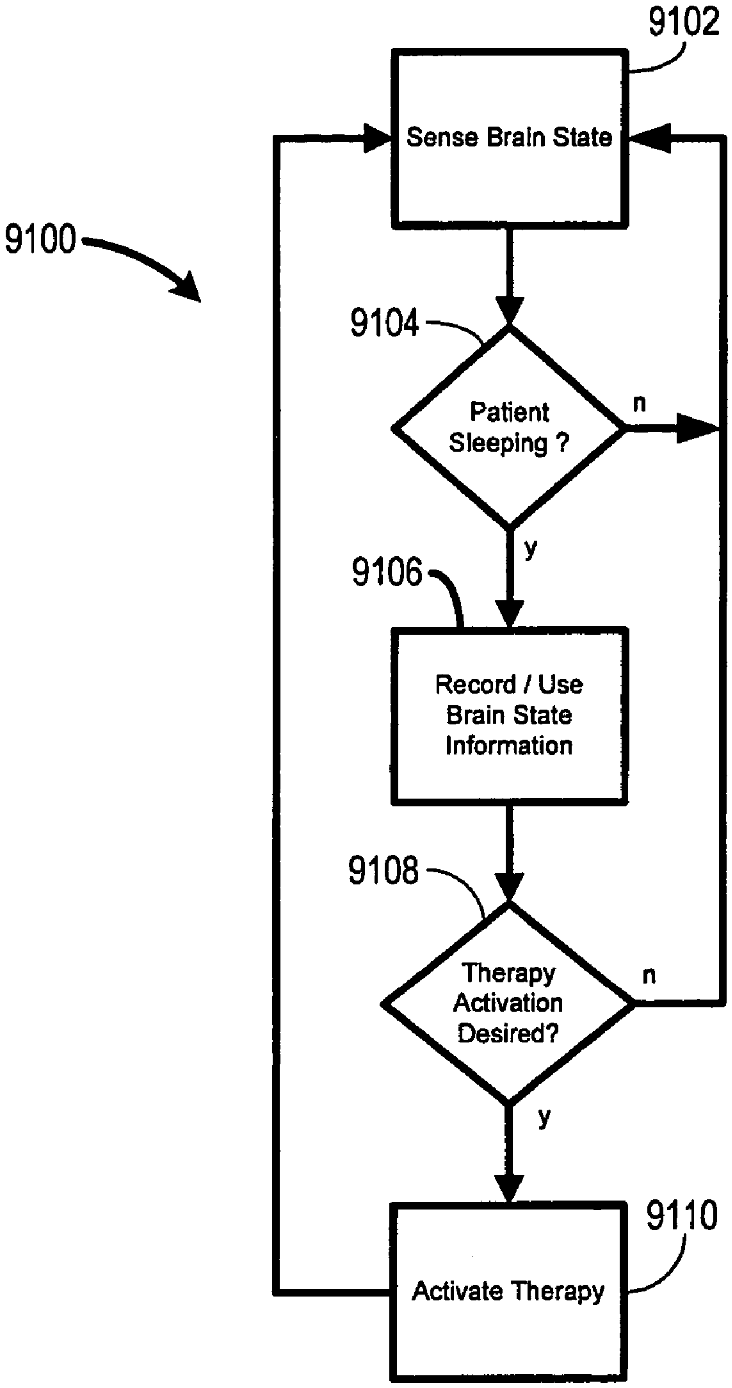
FIG. 91 is a flow chart illustrating a brain state algorithm based on signals from an EEG sensor in accordance with embodiments of the invention.

The following discussion, with reference to FIGS. 90A-91, describes embodiments of the invention involving automatic activation, de-activation, modification and/or control of therapy based on sleep stage. Sleep stage may be detected using various approaches, including, for example, by detecting brain activity, skeletal muscle movement, heart rate or other cardiac timing or intervals (e.g., PR interval), respiratory patterns, and/or other activity/signal that can be used as a surrogate measurement of sleep. The processes and systems exemplified by these embodiments may be implemented alone or in combination with one or more processes and systems exemplified by other embodiments described herein to provide a coordinated approach to patient monitoring, diagnosis, and/or therapy. Systems and methods directed to automatically activating medical processes may be implemented to include selected features, functions, and/or structures described in commonly owned, U.S. Pat. No. 7,668,591, which is hereby incorporated herein by reference.

Although disordered breathing may occur while the patient is awake, the disorder is much more prevalent while the patient is sleeping. In various embodiments of the invention, sleep stage information is used to enhance sleep disordered breathing therapy and/or diagnosis of a variety of sleep related disorders.

In accordance with various embodiments, sleep stage detection may be used to trigger therapy for disordered breathing. Using this approach, administration of disordered breathing therapy may be coordinated with a particular sleep stage. For example, disordered breathing episodes are typically more frequent during stage 1 or stage 2 sleep. The system may use sleep stage detection to deliver the therapy during these sleep stages. REM sleep and sleep stages 3 and 4 are the most restful sleep stages, therefore it is desirable to avoid interruption of sleep during these stages. The system may terminate or reduce the level of therapy during REM sleep and sleep stages 3 and 4 when avoidance of sleep interruptions are most desirable.

Sleep stage detection may be accomplished using a number of techniques, including, for example, a technique using muscle atonia sensors. Sleep stage detection may also be effected using patient-internal or patient-external sensors, including, for example EEG sensors and/or EMG sensors. In one configuration, the sensors, e.g., EEG and/or EMG sensors, used in combination with a respiratory therapy device, such as an xPAP device, may be positioned on the xPAP mask. Sleep stage detection may also be derived from heart rate, cardiac PR intervals (or other cardiac timing), tidal volume, respiratory rate, minute ventilation, body core temperature, or other physiological measurements that are affected by autonomic control.

Sleep stage information may also be valuable in the context of diagnosing various disorders, including sleep-related disorders. In accordance with one embodiment, sleep information, including sleep onset, offset, sleep stages, sleep efficiency, sleep latency, and the number and degree of arousals may be collected by the system for storage, display, or transmission to a remote device. The sleep-related information may be evaluated along with information about detected disordered breathing episodes to more fully understand how sleep disordered breathing affects a particular patient. The use of EEG sensors also allows detection of abnormal brain activity, including seizures. The EEG sensor information may be collected and used for a variety of diagnostic and therapeutic purposes.

FIG. 90A is a flow chart illustrating a system 9001 useful for activating, de-activating or modifying a medical process using brain state information in accordance with embodiments of the invention. The system 9001 involves sensing brain activity with a sensor 9002, either directly, such as by using an EEG sensor to measure brain-waves, or indirectly, such as by using an EMG sensor to measure muscular response to neurostimulation. An EMG sensor may be implemented, for example, using an electromyogram (EMG) electrode or force responsive sensor positioned on the housing of an implantable medical device. An EMG sensor may, for example, be positioned on the header of the implantable medical device. Alternatively, an EMG sensor (e.g., EMG electrode or strain gauge) may be positioned on a lead system or may be coupled to the housing through a catheter or lead system.

A brain activity detector 9003 receives information from the sensor 9002 and determines a brain state, which is used by a controller 9004. The controller 9004 may control one or both of an implantable medical device 9005 and a respiratory therapy unit 9006. The implantable medical device 9005 and/or the respiratory therapy unit 9006 provides therapy based on information about the sensed brain activity.

A system utilizing sleep stage sensors in connection with the control of diagnostic and/or therapeutic functions of a disordered breathing system in accordance with an embodiment of the invention is illustrated in FIG. 90B. In this embodiment, patient-internal or patient-external sensors 9014, for example EEG and/or EMG sensors, are coupled to a therapy device 9011. The therapy device 9011 includes a sleep stage processor 9012 that analyzes the sensor signals to detect the patient's sleep state, including sleep offset, onset, and stages of sleep.

The sleep stage processor 9012 is coupled to a therapy control unit 9013. The therapy control unit 9013 may control various types of therapy, including, for example, disordered breathing therapy, cardiac pacing therapy, respiratory therapy, electrical stimulation therapy, muscle stimulation therapy, nerve stimulation therapy, and/or pharmacological therapy, among other therapy types. The therapy control unit 9013 uses the sleep information to initiate, terminate or adjust therapy to the patient based on the patient's sleep stage.

The therapy device 9011 may further include a memory 9014 that receives and stores information from the sleep stage processor 9012, the sensors 9014 and/or other components. The information stored in the memory 9015 may be displayed and/or downloaded to a remote device, or used for a variety of diagnostic purposes.

Another embodiment of the invention is illustrated in FIG. 90C. In accordance with this embodiment, a first therapy device 9070 is used to control therapy delivery of a second therapy device 9090. The first therapy device 9070 includes a sleep stage processor 9072 coupled to sensors 9080, e.g., EEG and/or EMG sensors. The sleep stage processor receives signals from the sensors 9080 and analyzes the sensor signals to determine sleep onset, offset, and stages of sleep.

Sleep stage information is transferred from the sleep stage processor 9072 to a first therapy control unit 9074 and a second therapy control unit 9076. The therapy control units 9074, 9076 use the sleep stage information to initiate, terminate or modify the therapy delivered by the first and the second therapy devices 9070, 9090, respectively, based on the patient's sleep state.

The first therapy device 9070 may also include a memory 9077 that receives and stores information from the sleep stage processor 9072, the sensors 9080 and/or other components. The information stored in the memory 9077 may be displayed and/or downloaded to a remote device, or used for a variety of diagnostic purposes.

A further embodiment of the invention is illustrated in FIG. 90D. According to this embodiment, first and second therapy devices 9010, 9030 deliver first and second therapies to a patient. The first therapy device 9010 may be implemented as a CRM device, providing cardiac pacing and/or defibrillation therapies to treat various arrhythmias and/or to provide resynchronization therapy, for example. The CRM device 9010 may also deliver electrical stimulation therapy to the heart to treat disordered breathing.

The second therapy device 9030 may be implemented as respiratory therapy device, such as an xPAP device. The xPAP device 9030 delivers air or other gas therapy at a controlled pressure to the patient's airway.

EEG sensors 9020 are coupled to a sleep stage processor 9060 located in the CRM device 9010. Other sensors, such as EMG sensors, may also be included. Signals from the EEG and/or other sensors 9020 are analyzed by the sleep stage processor 9060 to determine various stages of sleep, including sleep onset, offset, sleep stage, the number and frequency of arousals, and the degree of arousal.

Information from the sleep stage processor 9060 is provided to the respiratory therapy controller 9050 located in the CRM device 9010. The respiratory therapy controller 9050 uses the sleep stage information to initiate, terminate, or modify the respiratory therapy based on the sleep stage.

Information from the sleep stage processor 9060 and a brain wave analyzer 9062 is provided to the CRM therapy controller 9040. The CRM therapy controller 140 includes a disordered breathing (DB) therapy control unit 9042 that uses the sleep stage information to initiate, terminate, or modify electrical stimulation DB therapy delivered by the CRM device 9010 based on the patient's sleep state.

The CRM therapy controller 9040 may further include an arrhythmia therapy control unit 9044. Information from the sleep stage processor 9060 and the brain wave analyzer 9062 may be used by the arrhythmia therapy control unit to 9044 initiate, terminate, or modify arrhythmia therapy delivered to the patient.

For example, the CRM therapy controller 9040 may decrease the cardiac pacing rate to a sleep rate upon sleep onset and raise the pacing rate at sleep offset. Further, the CRM therapy controller 9040 may adjust the pacing therapy delivered to the patient during proarrhythmic sleep periods, such as REM sleep or the during morning arousal. In one example, the arrhythmia therapy control unit 9044 may deliver atrial overdrive pacing during proarrhythmic sleep periods to prevent the occurrence of arrhythmia.

The EEG sensor signals may also be used by a brain wave analyzer 9062 to evaluate brain activity. The brain wave analyzer 9062 detects abnormal brain activity, such as seizures. Patients may have seizures during the night and not realize that the seizures have occurred. Some seizures are accompanied by cardiac rhythm disturbances. The brain wave analyzer 9062 may detect the occurrence of seizures and provide information about the seizures to the arrhythmia therapy control unit 9044. The arrhythmia therapy control unit 9044 may modify the CRM therapy to treat cardiac rhythm disturbances cause by, or associated with, seizures. The arrhythmia therapy control unit 9044 may also withhold therapy for rhythm disturbances that are associated with seizures.

The CRM device 9010 may include a memory 9064 for storing information from the sleep stage processor 9060, the brain wave analyzer 9062 and other components of the CRM device 9010. Stored information may be transferred to a display or other device.

Autonomic arousal responses, as detected using EEG sensors and EMG sensors, are indicative of brain state. Arousal may be detected from changes in the sympathetic or parasympathetic nervous system. These changes may be either short-term (i.e., changes associated with individual arousals) or long-term (i.e., aggregate effect of multiple arousals). A short-term effect of arousal includes, for example, the activation of sympathetic nerve activities. Sympathetic or parasympathetic changes, or the changes of autonomic balance, may be assessed, for example, by heart rate variability (HRV), which may be readily detected using a CRM device.

Arousal information may be also used by the sleep stage processor 9060 to augment disordered breathing detection. For example, arousal information may be used to confirm occurrences of disordered breathing. Arousal information may be used to distinguish between correctly and incorrectly identified disordered breathing occurrences indicated by the disordered breathing detector. Further, information from arousal detection may be used to separate disordered breathing episodes, e.g., apnea and/or hypopnea, followed by arousal versus those terminated without arousal. The disordered breathing events that are followed by arousal are considered to be the most disruptive, as these arousals interrupt the normal course of sleep and prevent the patient from receiving a full sleep cycle each night. Detecting these types of disordered breathing events may enhance the specificity of disordered breathing detection.

FIG. 91 illustrates a method 9100 for implantably sensing and detecting brain state. A brain state sense signal is sensed at a block 9102. Brain state may be sensed, for example, directly using EEG sensors, and/or indirectly using ECG sensors, EEG sensors, EMG sensors, transthoracic impedance sensors, or other sensors suitable for determining patient brain state. If the patient is sleeping, brain state may be detected using the brain state sense signal illustrated by determination block 9104.

The brain state detected at determination block 9104 provides various types of information recorded at block 9106. For example, date, time, sensor data, sense signal amplitudes and/or cycle lengths. This and other information may be useful for updating, developing, and/or determining an arousal index, an apnea/hypopnea index, a composite index and other parameters useful for patient diagnosis and treatment, such as the automatic activation, de-activation or modification of medical processes. This information may be useful for detecting abnormal brain activity, such as seizures. The information recorded at block 9106 may be useful, for example, to predict, verify, classify, and/or determine the severity of a disordered breathing episode and abnormal brain activity.

If intervention and/or treatment is desired at determination block 9108, the intervention and/or treatment may be performed at block 9110 before re-starting the method 9100. For example, the intervention at block 9110 may be the automatic activation of a medical process, modification of a patient's CRM stimulation, modification of a disordered breathing therapy, or other desirable action.

Implantable Device Employing Movement Sensing for Detecting Sleep-Related Disorders Aspects of the invention that include movement sensing for detecting sleep-related disorders are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that include movement sensing for detecting sleep-related disorders are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

Embodiments of the invention are directed to systems and methods for detecting sleep-related disorders involving sensing physiological signals including at least muscle movement signals. Sleep-related disorders are detected using the sensed physiological signals. The sleep-related disorders include at least an involuntary muscle movement disorder and sleep-disordered breathing. The physiological signals may include movement signals, such as electromyogram signals, at least some of which may be sensed from one or more intramuscular and/or skin/surface locations. The physiological signals may include transthoracic impedance signals, which may be sensed implantably.

Embodiments of methods of detecting sleep-related disorders may involve detecting one or more sleep stages using muscle movement signals. Methods may also involve delivering and/or controlling a therapy to treat one or more of the detected sleep-related disorders, such as a respiratory therapy, a cardiac pacing therapy, a nerve stimulation therapy, and/or a drug therapy.

Embodiments may involve detecting the sleep-related disorders patient-externally and/or patient-internally. Detecting the sleep-related disorders may involve detecting a first sleep-related disorder patient-internally and detecting a second sleep-related disorder patient-externally. Methods may further involve detecting one or more sleep stages using the muscle movement signals.

Sleep-disordered breathing may include sleep apnea, hypopnea, and/or Cheyne-Stokes respiration, and sleep-related disorders may include bruxism, periodic limb movement disorder, and/or restless leg syndrome. One or both of the physiological signals and information associated with the detected sleep-related disorders may be communicated to a patient-external processing system or an implantable medical device. Methods may further involve delivering and/or controlling a therapy to treat one or more of the detected sleep-related disorders, such as by delivering a respiratory therapy, a cardiac pacing therapy, a nerve stimulation therapy, and/or a drug therapy.

According to other embodiments, systems for detecting sleep-related disorders include one or more movement sensors, such as electromyogram (EMG) sensors, configured for sensing (internally and/or externally) movement of skeletal musculature and a sensor configured to sense a parameter associated with sleep-disordered breathing (SDB). A processor may be communicatively coupled to the movement sensors and the SDB sensor for detecting sleep-disordered breathing based on the sensed parameter and detecting an involuntary muscle movement disorder using signals produced by the movement sensors. The processor may be disposed in an implantable housing.

The processor may be disposed in a patient-external and/or patient-internal processing system. For example, the processor may be a networked processor, a component of a cardiac rhythm management system, a component of a respiratory therapy system, and/or a component of a positive airway pressure device.

The SDB sensor and/or sleep detector may include a transthoracic impedance sensor. The sleep detector may be communicatively coupled to the processor. Conditions detected by the processor include hypopnea, bruxism, involuntary muscle movement disorder, periodic limb movement disorder, and/or restless leg syndrome. A therapy delivery system may be configured to treat the sleep-disordered breathing and involuntary muscle movement disorder. A cardiac rhythm management system, a drug delivery device, a nerve stimulation device, and/or a positive airway pressure device may be configured to treat the sleep-related disorder.

Movement sensors may include one or more accelerometers, one or more electromyogram (EMG) sensors, or a combination of these sensors. The system may include a communications interface for communicating acquired movement data and/or detection information to a patient-external and/or patient-internal processing system. Control signals may also be communicated unidirectionally or bidirectionally between the system and a remote processing system.

Embodiments of the invention involve an individual system 127 (FIG. 1C) that provides movement sensing for detecting sleep-related disorders. The 127 may be implemented as a stand alone system or in combination with other individual medical systems, such as those described in FIGS. 1B-1D and in FIG. 92.

Other embodiments of the invention involve a system for providing coordinated patient monitoring, diagnosis and/or therapy that utilizes movement sensing for detecting sleep-related disorders 127. The coordinated system may include, for example, an implantable cardiac device 181, a patient-external respiratory therapy device 184, and/or other devices, such as a drug therapy device and/or a nerve stimulation therapy device. The system may further include an external processor 183 providing a coordination function. A communication channel couples the various devices. The devices (e.g., implantable device 181, respiratory therapy device 184, drug therapy device, nerve stimulation therapy device, and/or external processing device) operate cooperatively via the communication channel to provide one or more of patient monitoring, diagnosis, and therapy.

The devices may operate cooperatively based on sensed movement indicative of sleep-related disorders 127. For example, sensing movement indicative of sleep-related disorders 127 may allow the various implantable and/or external devices to operate cooperatively to provide an appropriate therapy to treat a detected sleep-related disorder.

A number of disorders, for example, sleep-disordered breathing and movement disorders such as PLMD, occur primarily while the patient is asleep. Information about the patient's sleep stage may be used to enhance sleep monitoring and/or diagnosis of a variety of disorders. In addition, it may be useful to provide a first therapy while the patient is awake and a second therapy while the patient is asleep. Detection of muscle movement, such as indicated by EMG, may be used to diagnose disorders as well as trigger the sleep-time therapy in a respiratory and/or cardiac device. Data acquired during sleep may assist in diagnosing various sleep-related disorders. The collected data may be stored, displayed, printed, or transmitted to a separate device.

Systems and methods may acquire and process electromyogram signals in an implantable or partially implantable device. Information acquired from electromyogram sensors may be used in connection with patient monitoring, diagnosis, and therapy. An implantable system may incorporate EMG and SDB detection for various purposes, including disease/disorder diagnosis, sleep detection, and therapy control, among other functions. The system may include one or more EMG sensors, which may be implemented as one or more patient-internal and/or one or more patient external EMG sensors. Systems and methods directed to movement sensing for detecting sleep-related disorders may be implemented to include selected features, functions, and/or structures described in commonly owned, co-pending U.S. Publication No. 2005/0113710, which is hereby incorporated herein by reference.

An electromyogram sensor detects the electrical activity of muscles during muscle activity. When muscles are active, they produce an electrical current that is proportional to the level of the muscle activity. The use of EMG sensing devices is helpful in the diagnosis of many pathological conditions.

Electromyogram sensing devices may facilitate diagnosis of many pathological conditions. These conditions include, for example, muscular dystrophy, inflammation of muscles, pinched nerves, peripheral nerve damage (damage to nerves in the arms and legs), amyotrophic lateral sclerosis (ALS, also known as Lou Gehrig disease), myasthenia gravis, disc herniation, sleep-disordered breathing, and movement disorders such as periodic limb movement, restless limb movement, and bruxism.

Embodiments are directed to systems and methods for screening and/or diagnosing and subsequently treating an involuntary limb movement condition, such as RLS or PLMD. PLMD, RLS, and/or other movement disorders such as bruxism, for example, may be diagnosed using a system that is fully or partially implantable. A partially or fully implantable device, such as a cardiac rhythm management system, may incorporate a movement detector. One or more movement sensors are coupled to the movement detector within the implantable device. The movement sensors may include any sensor or any combination of sensors capable of detecting motion and/or muscle activity associated with motion, such as accelerometers, electromyogram (EMG) sensors, and/or a combination of one or more accelerometers and one or more EMG sensors.

Signals from the movement sensors may be received and processed by the movement detector in the implantable device. The movement data may be stored in the implantable device or communicated to an external processing system, either of which may process the sensed movement information. Movement information may be processed, trended, displayed, etc. locally or remotely to detect presence of an involuntary limb movement condition.

Various therapies have been used to treat central and/or obstructive disordered breathing episodes, and may further be used to treat sleep-related muscle disorders. Obstructive sleep apnea has been associated with prolapse of the tongue and its surrounding structure into the pharynx, thus occluding the respiratory pathway. A commonly prescribed treatment for obstructive apnea is continuous positive airway pressure (CPAP). The application of continuous positive airway pressure keeps the patient's throat open, reducing or eliminating the obstruction causing apnea.

Figure 92:
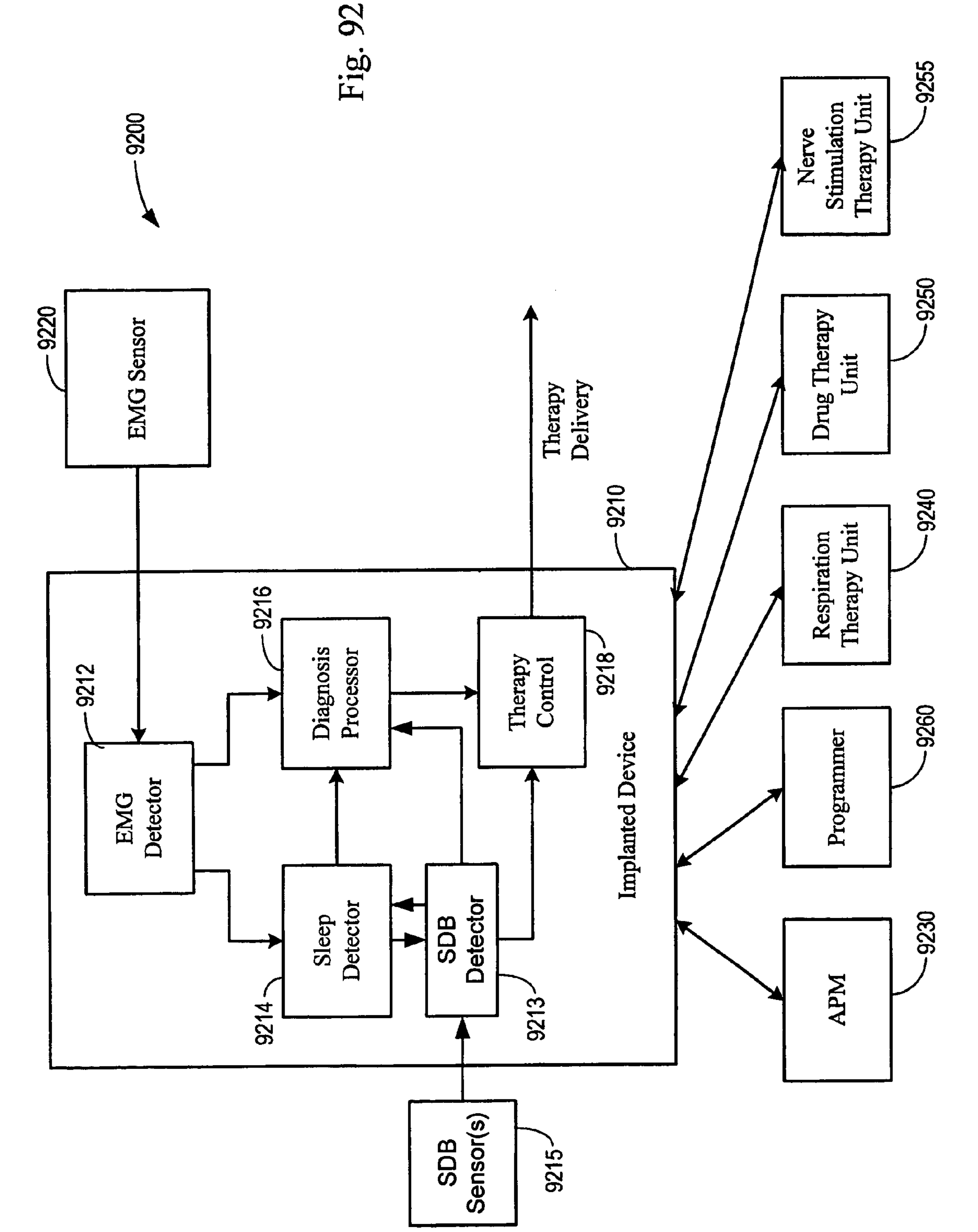
FIGS. 92-94 are block diagrams of systems implementing diagnosis of sleep-related disorders using EMG and sleep disordered breathing information in accordance with embodiments of the invention.

The following discussion, with reference to FIG. 92, describes embodiments of the invention involving disease/disorder diagnosis using an EMG detector and SDB detector in an implanted or partially implanted device. The processes and systems exemplified by these embodiments may be implemented alone or in combination with one or more processes and systems exemplified by other embodiments described herein to provide a coordinated approach to patient monitoring, diagnosis, and/or therapy. Information acquired from EMG detector and the SDB detector may be used in connection with patient monitoring, diagnosis, and therapy.

FIG. 92 illustrates an implantable system 9200 incorporating EMG and SDB detection that may be used for sleep-related disease/disorder diagnosis, sleep detection, and therapy control, among other functions. In accordance with various embodiments, the system 9200 includes one or more EMG sensors 9220, which may be implemented as one or more patient-internal and/or one or more patient external EMG sensors.

The EMG sensor or sensors 9220 may be positioned in or on the patient's body at one or more selected locations to sense electrical muscular activity at the one or more selected locations. The location of the EMG sensor or sensors 9220 depends on the specific application. For example, one or more EMG sensors 9220 may be positioned intramuscularly or on the surface of the skin above the muscle to detect the electrical activity of the muscle.

Intramuscular placement of EMG sensors involves inserting a needle electrode through the skin into the muscle whose electrical activity is to be measured. Because skeletal muscles are often large, several needle electrodes may need to be placed at various locations to obtain an accurate reading of muscle activity.

Signals from EMG sensor or sensors 9220 may be transmitted to an EMG detector 9212 of the implanted device 9210 through leads or using a wireless communications link. The EMG detector 9212 receives signals from the EMG sensor or sensors 9220 and processes the signals for use by a diagnosis processor 9216 and/or a sleep detector 9214, for example.

The sleep detector 9214 may use EMG information to determine various sleep stages, including REM sleep. The sleep detector 9214 may also provide information from the EMG detector 9212 to a sleep disordered breathing detector 9213, which may use the EMG sensors 9220 to detect sleep disordered breathing episodes, and/or may be coupled to one or more SDB sensors 9215. It is understood that other component connection/communication architectures are possible in addition to those shown in FIG. 92. In one implementation, one or more EMG sensors 9220 may be placed on the patient's face to facilitate the detection of REM sleep. For example, one or more surface EMG sensors 9220 may be placed on the patient's chin or jaw, e.g., on the mentalis muscle and/or submentalis muscle, to detect muscle atonia associated with rapid eye movement sleep.

In another implementation, one or more EMG sensors 9220 and/or SDB sensors 9215 may be placed on the housing, header, or lead of an implanted device 9210 positioned in the pectoral region of the patient. In one configuration, the EMG sensors 9220 may be used to detect atonia of the pectoral muscles during REM sleep. A sleep detector 9214 may use information from the EMG detector 9212 to facilitate the detection of sleep onset and offset, and to determine the various stages of sleep. Detection of sleep stages may be used, for example, in patient monitoring, diagnosis and/or therapy for various disorders, including sleep-disordered breathing.

The diagnosis processor 9216 may use EMG-related information and SDB detection to diagnose a variety of diseases or disorders such as those listed above. Disease/disorder diagnosis may be facilitated using information acquired from the EMG detector 9212 associated with the patient's muscle activity, limb movements, and respiratory motions, for example. The diagnosis processor 9216 may also use information about the patient's sleep stages to aid in diagnosis.

In various embodiments, the diagnosis processor 9216 may use EMG-related information and SDB detection to diagnose disorders and diseases involving muscle dysfunction, such as those caused by muscle inflammation and/or muscular dystrophy for example. The EMG information may be used to diagnose muscle weakness due to nerve disorders, including pinched nerves, peripheral nerve damage, amyotrophic lateral sclerosis (ALS), myasthenia gravis, and disc herniation, for example. The EMG- and SDB-related information may be used to diagnose a variety of movement disorders, such as periodic limb movement disorders and/or restless legs syndrome.

In other embodiments, the diagnosis processor may use information from the EMG detector 9212 to diagnose disordered breathing. For example, EMG sensor or sensors 9220 may be used to sense activity of the intercostal muscles produced by expansion of the chest during respiration. As previously described, the absence or presence of chest motion may be used to discriminate between central or obstructive apnea.

Alternatively, or additionally, an EMG sensor 9220 may be used to detect obstructive apnea based on the degree of patency of the upper airway. Obstructive apnea is caused by upper airway occlusion due to the collapse of soft tissue in the rear of the throat. One or more EMG sensors 9220 placed on the patient's chin or jaw may be used to detect muscle activity associated with tongue movement opening the upper airway.

A majority of disordered breathing episodes occur while the patient is sleeping. Sleep-related disorders such as sleep-disordered breathing may be more prevalent during particular sleep stages. Information about sleep stages, and about the frequency, number, and degree of arousals from sleep may be useful in the diagnosis of disordered breathing. Thus, a diagnosis of disordered breathing may be enhanced using sleep information from the sleep detector 9214.

In other embodiments, diagnosis of various movement disorders, such as periodic limb movement disorder (PLMD), restless leg syndrome (RLS), and bruxism (nighttime teeth grinding) may be facilitated using one or more EMG sensors 9220 coupled to an implantable device 9210. Periodic limb movement disorder and restless leg syndrome are disorders that involve undesirable movements of the limbs as described in more detail below.

One or more EMG sensors 9220 may be placed in or on the muscles of the limbs or other muscles to detect limb movements. For example, EMG sensors 9220 placed on or in the anterior tibialis muscles may be used to identify leg movements associated with PLMD and/or RLS. EMG sensors 9220 placed on the jaw may be used to identify tempomanidibular disorders such as nighttime teeth grinding or other involuntary jaw movements.

EMG-related information may be trended, stored, displayed, or transmitted from the implantable device 9210 to another device. In one embodiment, information from the EMG detector 9212, the sleep detector 9214, and/or the diagnosis processor 9216 is downloaded to a remote device, such as a programmer 9260 or advanced patient management system 9230 for further analysis by the remote device 9230, 9260 and/or the patient's physician.

Information from the EMG detector, 9212 the sleep detector 9214, the SDB detector 9213, and/or the diagnosis processor 9216 may optionally be used to adjust therapy provided to a patient. Therapy provided by the implanted device 9210 may be adjusted by the patient's physician or by a remote device, such as an APM 9230 device or programmer 9260. In one example, the patient's physician may send a command through the programmer 9260 or APM device 9230 to a therapy control unit 9218 in the implanted device 9210 to initiate, terminate, or modify therapy. In another example, the APM device 9230, 9260 may automatically command the implanted device 9210 to adjust therapy based on analysis performed in the remote device 9230, 9260. In another embodiment, the therapy control unit 9218 of the implanted device 9210 may use information from the EMG detector 9212, the sleep detector 9214, and/or the diagnosis processor 9216, to automatically adjust therapy provided to a patient.

The EMG-related information and SDB detection information acquired by the implantable device 9210 may be transferred to other therapy devices, such as drug delivery devices 9250, respiration therapy devices 9240, and/or nerve stimulation therapy devices 9255, such as devices that deliver a transcutaneous electric nerve stimulation therapy.

The EMG-related information acquired by the implantable device 9210 may be transferred to other therapy devices (internal or external), such as drug delivery devices 9250 and/or nerve stimulation therapy devices 9255. For example, transcutaneous electric nerve stimulation may improve symptoms in some RLS sufferers who also have PLMD. Electrical stimulation may be applied to an area of the legs or feet, usually before bedtime, for about 15 to 30 minutes. Transcutaneous electric nerve stimulation therapy has been found to be helpful in reducing nighttime leg jerking.

The transferred information may be used to adjust the therapy delivered by one or more of the therapy devices 9240, 9250, 9255, or used in further diagnosis and/or monitoring functions, for example. Examples of drugs useful with the drug therapy device 9250 include dopamine agents (muscle relaxers), benzodiazepines (sedatives), anti-convulsants (to reduce muscle activity), and opioids (narcotics to reduce motor activity).

Although the sleep detector 9214, the diagnosis processor 9216, and the therapy control unit 9218 are illustrated internal to the implantable device 9210, it is contemplated that any or all of these components may be patient-external in alternate embodiments, and may be incorporated into other components such as the APM 9230, for example. Similarly, the respiration therapy devices 9240, drug delivery devices 9250, and/or nerve stimulation therapy devices 9255 illustrated as patient-external in FIG. 92, may be included in the implantable device 9210 in alternate embodiments. Moreover, all or particular component(s) of these devices 9240, 9250, 9255 may be configured for patient-internal placement, patient-external placement, or both patient-internal and patient-external placement.

Figure 93:
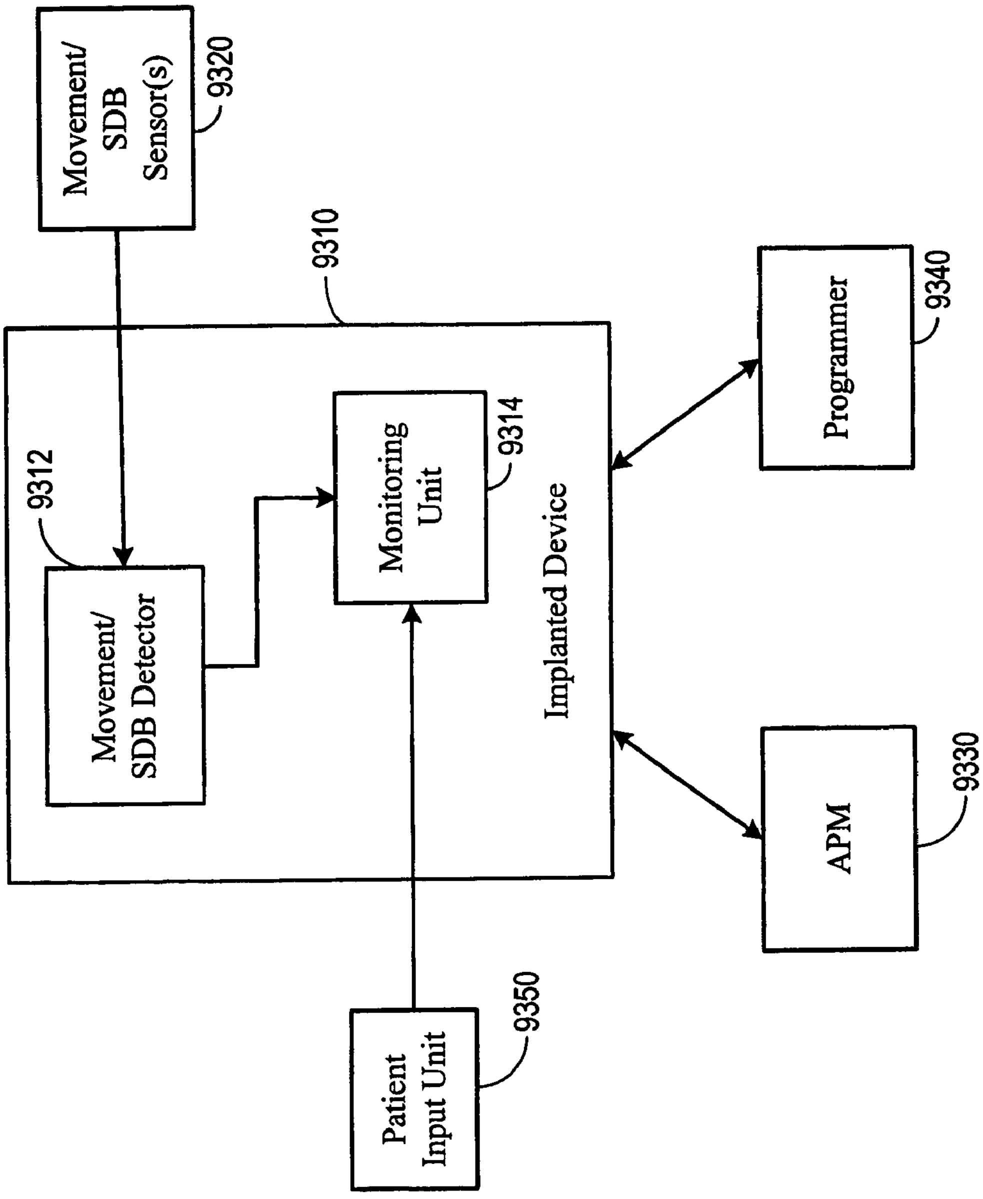
Figure 94:
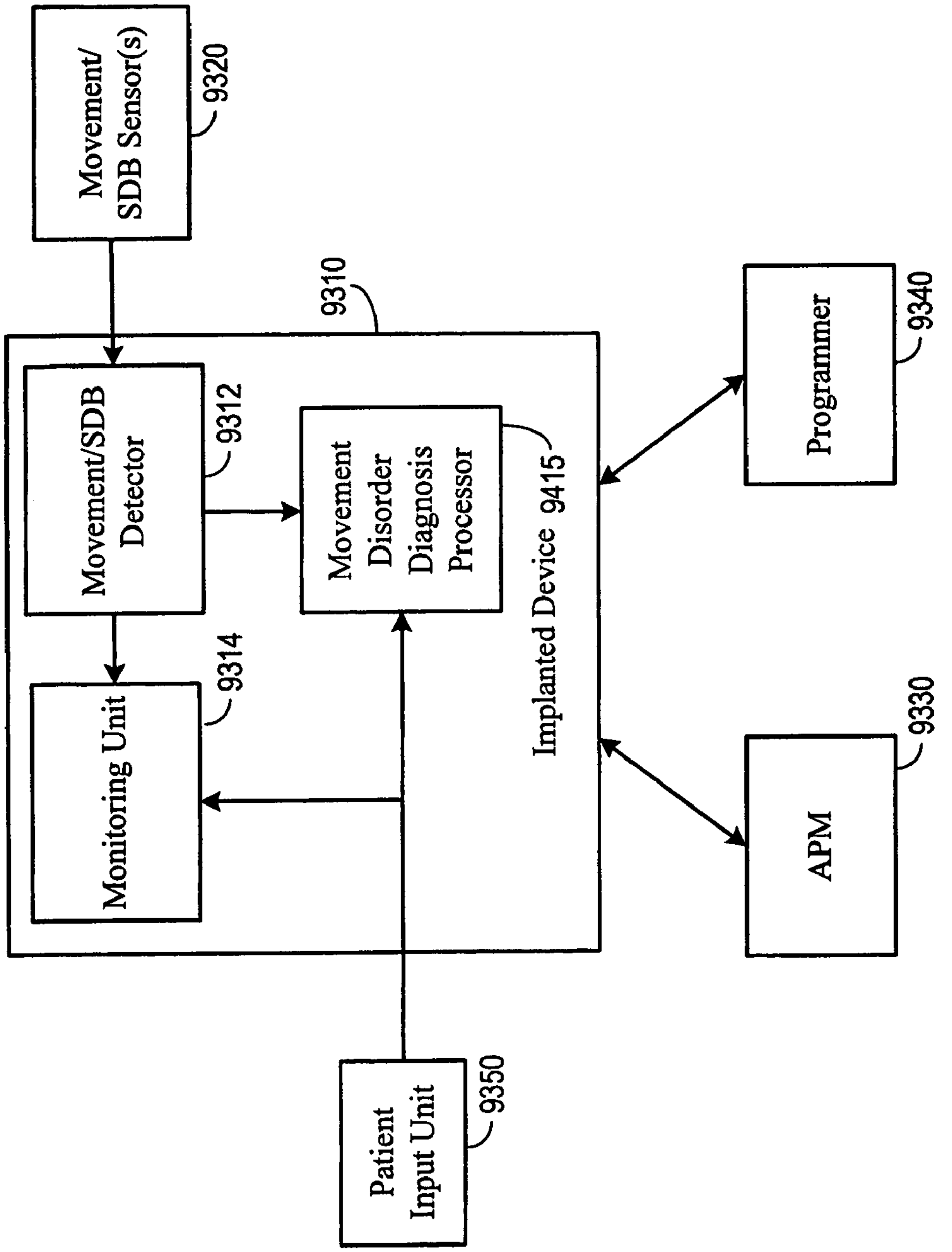
Figure 95:
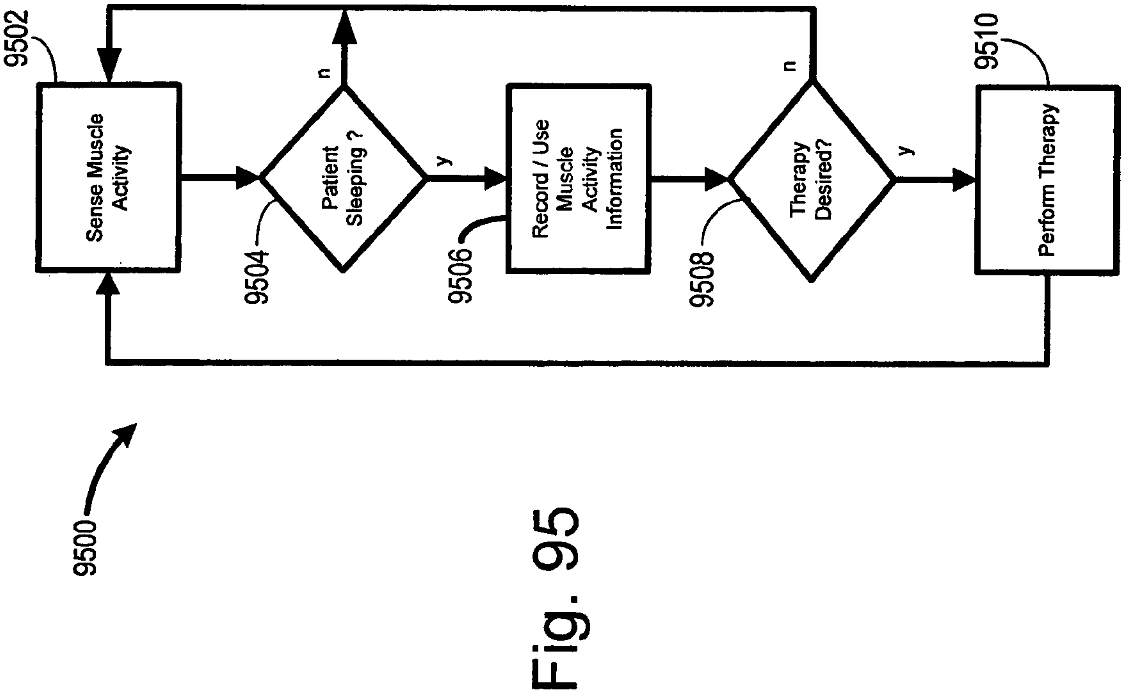
FIG. 95 is a flow chart illustrating an EMG based algorithm in accordance with embodiments of the invention.

The following discussion, with reference to FIGS. 93-95, describes embodiments involving detection of movement disorders. The processes and systems exemplified by these embodiments may be implemented alone or in combination with one or more processes and systems exemplified by other embodiments described herein to provide a coordinated approach to patient monitoring, diagnosis, and/or therapy.

In accordance with embodiments of the invention, PLMD, RLS, and/or other movement disorders such as bruxism, for example, may be diagnosed using a system that is fully or partially implantable. FIG. 93 illustrates an implantable medical device, e.g., a CRM that incorporates a movement/SDB detector 9312. One or more movement/SDB sensor(s) 9320 are coupled to the movement/SDB detector 9312 within an implantable device 9310. Although illustrated as a single block 9312 in FIG. 93 (and in FIG. 94) for simplicity, it is understood that the movement detector and SDB detector may be represented as separate blocks. Similarly, it is understood that the movement sensor(s) and SDB sensors(s) of block 9320 may be represented as separate blocks.

The movement/SDB sensor(s) 9320 may include any sensor or any combination of sensors capable of detecting motion and/or muscle activity associated with motion. For example, the patient's movements may be detected using one or more accelerometers, one or more EMG sensors, and/or a combination of one or more accelerometers and one or more EMG sensors.

In various embodiments, one or more movement sensors (e.g., accelerometers and/or EMG sensors) are coupled to the patient at appropriate locations to detect movements of the extremities, e.g., limb movements, or other movements. Signals from the movement/SDB sensor(s) 9320 are received and processed by a movement/SDB detector 9312 in the implantable device 9310. The movement/SDB detector 9312 may cooperate with a memory in a monitoring unit 9314 to store information about the detected movements. Movement information may be stored, trended, displayed, and/or transmitted to a separate device, such as an APM system 9330 or a programmer 9340 for further operations.

In other embodiments, as illustrated in FIG. 94, one or more movement/SDB sensor(s) 9320 are coupled to a movement/SDB detector 9312 within the implantable device 9310, as previously discussed. The implantable device 9310 also includes a movement disorder diagnosis processor 9415 that receives movement information from the movement/SDB detector 9312. The movement disorder diagnosis processor 9415 evaluates the movement information to determine if the movements are consistent with various movement disorders such as RLS and/or PLMD.

In one example, the movement/SDB sensor(s) 9320 may include one or more EMG sensors placed on or in the anterior tibialis. Typical EMG bursts due to PLMD movements may last between 0.5-5 seconds and may recur every 20-40 seconds, for example. The movement disorder diagnosis processor 9415 may make a diagnosis of PLMD if at least about 40 EMG bursts are detected within an 8-hour sleep period, for example. Sleep disruption caused by the PLMD movements may be determined by any or a combination of the sleep detection techniques described herein, including, for example, brain wave (EEG) sensing and/or a combination of respiration (MV) and activity sensing, among others. Movement disorder diagnosis may be downloaded to a programmer 9340, an APM system 9330, or other therapeutic or diagnostic device.

In accordance with another embodiment, RLS diagnosis may involve patient input regarding their symptoms. For example, as illustrated in FIGS. 93 and 94, a patient input device 9350 may be used to acquire information from the patient regarding the patient's perception of symptoms. The patient may be prompted to rate their symptoms on a scale of 0 to 4, or some other scale, for example with a lower number representing fewer RLS symptoms and higher number representing greater RLS symptoms, for example. The patient input may be acquired using the patient input device 9350 over a period of days, for example, about three days to about nine days to establish a diagnosis. Patient input through the patient input device 9350 may also be acquired after diagnosis and/or treatment, for example to assess status of the disorder or the efficacy of treatment.

For example, if the patient input is acquired over a period of six days, the maximum score is 24, i.e., a score of four for each or six days. In this scenario, a score greater than about 12 suggests a diagnosis of severe RLS. A score of about six to about twelve suggests a diagnosis of moderate RLS.

In the embodiment illustrated in FIG. 93, information about SDB and RLS symptoms may be acquired by the patient input device 9350 and transmitted to an APM device 9330, the programmer 9340, or other device for monitoring, display, storage, evaluation, and/or diagnosis. In the embodiment illustrated in FIG. 94, the information acquired by the patient input device 9350, along with the movement information, may be used by the movement disorder diagnosis processor 9415 in the implantable device 9310 to make a diagnosis of RLS.

Embodiments of the present invention are directed to methods and systems for diagnosis of SDB and movement disorders such as PLMD and RLS. RLS diagnosis may be complicated due to the symptom based nature of the RLS diagnosis. The use of patient input through a patient-input device provides a system for collection of symptom based information. Because PLMD and RLS are related disorders, the diagnosis of PLMD through movement detection techniques described herein may be used to enhance the RLS diagnosis.

Use of such methods and systems may reduce the need for in-clinic sleep studies typically used for movement disorder diagnosis. Further, daily measurements may be made over a number of days, which is not practical for in-clinic studies. Earlier and more frequent diagnosis of movement disorders may be enabled using the systems and methods of the invention.

FIG. 95 illustrates a method 9500 of implantably sensing and detecting movement useful for diagnosing sleep-related muscle disorders and sleep disordered breathing. A muscle activity signal is sensed at a block 9502. Muscle activity may be sensed, for example, using EMG sensors, accelerometers, or other sensors suitable for determining patient movement. A determination block 9504 is used to decide if the patient is sleeping. If determination 9504 concludes that the patient is not sleeping, the method 9500 loops back to the beginning.

If the patient is determined to be sleeping at block 9504, the muscle activity sensed at block 9502 provides information recorded at block 9506. For example, date, time, sensor data, sense signal amplitudes or other information may be useful for updating, developing, and/or determining an muscle disorder index, a diagnosis, a sleep-related muscle activity history, and other parameters useful for patient diagnosis and treatment. The information recorded at block 9506 may be useful, for example, to predict, verify, classify, and/or determine the existence of a sleep-related muscle disorder and sleep disordered breathing.

If intervention and/or treatment is desired at determination block 9508, the intervention and/or treatment may be performed at block 9510 before re-starting the method 9500. For example, the intervention at block 9510 may be the automatic activation of a medical process, modification of a disordered breathing therapy, notification to a patient-external device and/or a physician, or other desirable action.

System and Method for Detecting an Involuntary Muscle Movement Disorder

Aspects of the invention that include involuntary muscle movement disorder detection are directed to methods and systems configured to monitor, diagnose, and/or provide patient therapy using one or more individual medical procedures. Each of the circles 180 illustrated in FIGS. 1B-1D represents an individual medical procedure providing a specific monitoring, diagnosis or therapeutic function or set of functions. Each individual medical procedure may be implemented as a stand-alone system. Two or more of the individual medical procedures 180 may be used in combination to provide more comprehensive patient monitoring, diagnosis and/or therapy. One or more functions of two or more individual medical procedures 180 may be used in combination to enhance patient monitoring, diagnosis and/or therapy.

Other aspects of the invention that include involuntary muscle movement disorder detection are directed to methods and systems configured to monitor, diagnose, and/or provide therapy using coordinated medical procedures. Coordinated medical procedures may involve cooperative operation of two or more of the individual processes 180. Coordinated medical procedures may also involve cooperative operation of one or more functions of two or more of the individual processes 180.

Coordinated use of two or more medical procedures typically involves transfer of some form of information, such as data and/or control signals, that is used by, or influences the behavior of the medical procedures or devices implementing such medical procedures. The transfer of information may implicate one of the medical procedures, some of the medical procedures, or all of the medical procedures. The transfer of information may implicate other processes that interact with one or more medical procedures, such as processes implemented by a patient-external processing system. The transfer of information may be unidirectional or bi-directional with respect to medical procedures and/or other processes.

System and method embodiments provide for evaluating pathological conditions associated with an involuntary limb movement disorder. According various embodiments, evaluating a pathological condition involves sensing muscle movement signals, and implantably detecting presence of an involuntary muscle movement disorder using the muscle movement signals. Sensing the muscle movement signals may be preformed implantably and externally. Detecting presence of the involuntary muscle movement disorder may involve detecting a sleep-related involuntary muscle movement disorder and/or a non sleep-related involuntary muscle movement disorder using the sensed muscle movement signals.

Detecting presence of the involuntary muscle movement disorder may involve detecting a disease or pathological syndrome using the muscle movement signals. Detecting presence of the involuntary muscle movement disorder may involve detecting conditions associated with bruxism, periodic limb movement disorder, restless leg syndrome, muscular dystrophy, muscle inflammation, pinched nerves, peripheral nerve damage, amyotrophic lateral sclerosis, myasthenia gravis, and disc herniation, for example.

Sensing muscle movement signals may involve acquiring data from a sensor directly detecting physical movement, such as an accelerometer. Sensing muscle movement signals may involve acquiring data from a sensor detecting bio-electrical changes associated with movement, such as an electromyogram sensor. Sensing muscle movement signals may involve acquiring data from sensors detecting physical movement and bio-electrical changes.

Onset and offset of sleep may be detected, for purposes of discriminating between sleep-related and non sleep-related involuntary limb movement conditions, for example. Sensed muscle movement signals and/or information associated with the detected involuntary muscle movement disorder may be communicated to a patient-external processing system, such as a network, or to a patient-internal processing system.

A therapy based on one or both of the muscle movement signals and the detected involuntary muscle movement disorder may be delivered to the patient. For example, a drug therapy, nerve stimulation therapy, or other therapy may be delivered to treat the detected involuntary muscle movement disorder.

According other embodiments, systems for evaluating a pathological condition include a sensor configured to sense movement of skeletal musculature, a detector coupled to the sensor, and an implantable processor coupled to the detector. The processor is configured to determine presence of an involuntary muscle movement disorder, such as those discussed above.

In one configuration, one of the sensor and detector includes an implantable component. In another configuration, each of the sensor and detector includes an implantable component. The sensor may include one or both of electromyogram (EMG) sensors and an accelerometer. A sleep detector may be coupled to the processor, and the processor may detect a sleep-related involuntary muscle movement disorder and/or a non sleep-related involuntary muscle movement disorder.

Systems may include a communication interface coupled to the processor. The communication interface may be configured to effect connectivity between the processor and a patient-external processing system, such as an external network. Systems may also include a therapy delivery system configured to deliver a therapy to treat the involuntary muscle movement disorder, such as a drug therapy device, nerve stimulation therapy, or other therapy device.

Embodiments of the invention involve an individual system 141 (FIG. 1D) for detecting involuntary muscle movement disorder detection. The involuntary muscle movement disorder detection system 141 may be implemented as a stand alone system or in combination with other individual medical systems, such as those described in FIGS. 1B-1D and in FIG. 96.

Other embodiments of the invention involve a system for providing coordinated patient monitoring, diagnosis and/or therapy that utilizes involuntary muscle movement disorder detection 141. The coordinated system may include, for example, an implantable cardiac device 181, a patient-external respiratory therapy device 184, and/or other devices, such as a drug therapy device and/or a nerve stimulation therapy device. The system may further include an external processor 183 providing a coordination function. A communication channel couples the various devices. The devices (e.g., implantable device 181, respiratory therapy device 184, drug therapy device, nerve stimulation therapy device, and/or external processing device) operate cooperatively via the communication channel to provide one or more of patient monitoring, diagnosis, and therapy. The devices may operate cooperatively based on detection of an involuntary muscle movement disorder 141. For example, involuntary muscle movement disorder detection 141 may allow the various implantable and/or external devices to operate cooperatively to provide an appropriate therapy to treat the involuntary muscle movement disorder or other associated disorder. Systems and methods directed to detecting an involuntary muscle movement disorder may be implemented to include selected features, functions, and/or structures described in commonly owned, U.S. Pat. No. 7,616,988, which is hereby incorporated herein by reference.

Systems and methods provide for acquisition and processing of muscle movement signals in an implantable or partially implantable device. Information acquired from muscle movement sensors may be used in connection with patient monitoring, diagnosis, and therapy. An implantable system may incorporate muscle movement detection for various purposes, including disease diagnosis, sleep detection, and therapy control, among other functions. Systems may include one or more movement sensors, which may be implemented as one or more patient-internal and/or one or more patient external movement sensors. For example, systems may include one or more electromyogram (EMG) sensors, which may be implemented as one or more patient-internal and/or one or more patient external EMG sensors. Systems may alternatively, or additionally, include one or more accelerometers to detect muscle movement, and may further be used to detect patient sleep and non sleep.

An EMG sensor detects the electrical activity of muscles during muscle activity. When muscles are active, they produce an electrical current that is proportional to the level of the muscle activity. Electromyogram sensing devices of the present invention may facilitate diagnosis of many pathological conditions. These conditions include, for example, muscular dystrophy, inflammation of muscles, pinched nerves, peripheral nerve damage (damage to nerves in the arms and legs), amyotrophic lateral sclerosis (ALS, also known as Lou Gehrig disease), myasthenia gravis, disc herniation, and movement disorders such as periodic limb movement, restless limb movement, and bruxism.

Various embodiments are directed to systems and methods for screening and/or diagnosing an involuntary limb movement condition, such as Restless Leg Syndrome (RLS) or Periodic Limb Movement Disorder (PLMD). PLMD, RLS, and/or other movement disorders such as bruxism, for example, may be diagnosed using a system that is fully or partially implantable. A partially or fully implantable system, such as a cardiac rhythm management system, may incorporate a movement detector. One or more movement sensors are coupled to the movement detector within the implantable device. The movement sensors may include any sensor or any combination of sensors capable of detecting motion and/or muscle activity associated with motion, such as accelerometers, electromyogram (EMG) sensors, and/or a combination of one or more accelerometers and one or more EMG sensors.

Signals from the movement sensors may be received and processed by the movement detector in the implantable device. The movement data may be stored in the implantable device or communicated to an external processing system, either of which may process the sensed movement information. Movement information may be processed, trended, displayed, etc. locally or remotely to detect presence of an involuntary limb movement condition.

Embodiments of the present invention are directed to implementing components and/or functions of an electromyogram sensor in an implanted or partially implanted medical device. Information acquired from the electromyogram sensor(s) may be used in connection with patient monitoring, diagnosis, and therapy.

Figure 96:
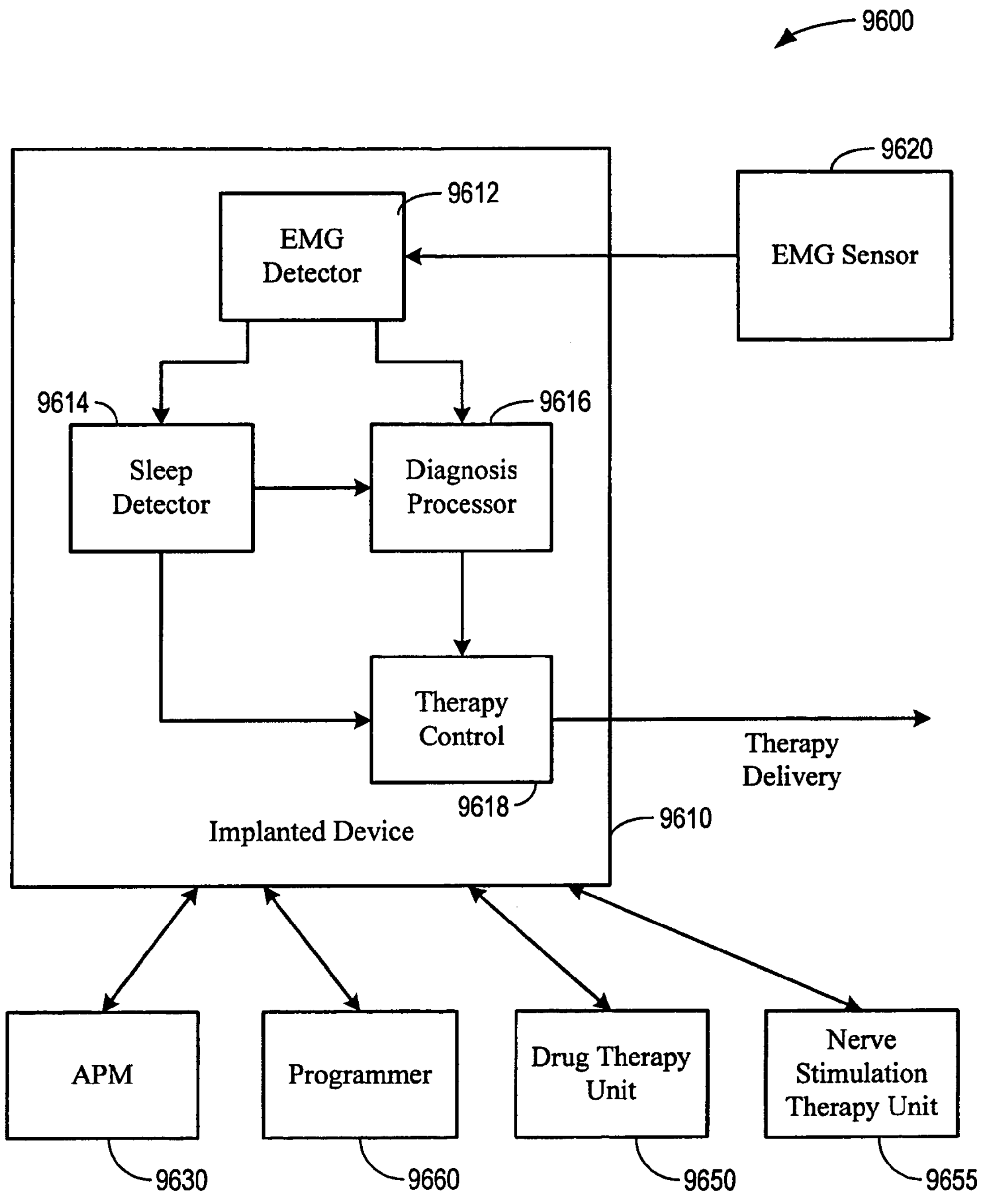
FIGS. 96 and 97A-97B are block diagrams of systems implementing diagnosis of medical conditions using muscle movement information in accordance with embodiments of the invention.

The following discussion, with reference to FIG. 96, describes embodiments of the invention involving disease diagnosis using an EMG in an implanted device. The processes and systems exemplified by these embodiments may be implemented alone or in combination with one or more processes and systems exemplified by other embodiments described or incorporated herein to provide a coordinated approach to patient monitoring, diagnosis, and/or therapy.

FIG. 96 illustrates an implantable system 9600 incorporating EMG detection that may be used for disease diagnosis, sleep detection, and therapy control, among other functions. In accordance with various embodiments, the system 9600 includes one or more EMG sensors 9620, which may be implemented as one or more patient-internal and/or one or more patient external EMG sensors.

The EMG sensor or sensors 9620 may be positioned in or on the patient's body at one or more selected locations to sense electrical muscular activity at the one or more selected locations. The location of the EMG sensor or sensors 9620 depends on the specific application. For example, one or more EMG sensors 9620 may be positioned intramuscularly or on the surface of the skin above the muscle to detect the electrical activity of the muscle.

Intramuscular placement of EMG sensors involves inserting a needle electrode through the skin into the muscle whose electrical activity is to be measured. Because skeletal muscles are often large, several needle electrodes may need to be placed at various locations to obtain an accurate reading of muscle activity.

Signals from EMG sensor or sensors 9620 may be transmitted to an EMG detector 9612 of the implanted device 9610 through leads or using a wireless communications link. The EMG detector 9612 receives signals from the EMG sensor or sensors 9620 and processes the signals for use by a diagnosis processor 9616 and/or a sleep detector 9614, for example.

A number of muscle-related disorders occur primarily while the patient is asleep. Information about the patient's sleep stage may be used to enhance sleep monitoring and/or diagnosis of a variety of disorders. In addition, it may be useful to provide a first therapy while the patient is awake and a second therapy while the patient is asleep. Detection of EMG signals may be used to diagnose disorders as well as trigger sleep-time therapy. Collected data may be stored, displayed, printed, or transmitted to a separate device.

By way of example, the sleep detector 9614 may use EMG information to determine various sleep stages, including REM sleep. In one implementation, one or more EMG sensors 9620 may be placed on the patient's face to facilitate the detection of REM sleep. For example, one or more surface EMG sensors 9620 may be placed on the patient's chin or jaw, e.g., on the mentalis muscle and/or submentalis muscle, to detect muscle atonia associated with rapid eye movement sleep.

In another implementation, one or more EMG sensors 9620 may be placed on the housing, header, or lead of an implanted device 9610 positioned in the pectoral region of the patient. In this configuration, the EMG sensors 9620 may be used to detect atonia of the pectoral muscles during REM sleep. A sleep detector 9614 may use information from the EMG detector 9612 to facilitate the detection of sleep onset and offset, and to determine the various stages of sleep. Detection of sleep stages may be used, for example, in patient monitoring, diagnosis and/or therapy for various disorders.

The diagnosis processor 9616 may use EMG-related information to diagnose a variety of diseases or disorders such as those listed above. Disease/disorder diagnosis may be facilitated using information acquired from the EMG detector 9612 associated with the patient's muscle activity, limb movements, and respiratory motions, for example. The diagnosis processor 9616 may also use information about the patient's sleep stages to aid in diagnosis.

In various embodiments, the diagnosis processor 9616 may use EMG information to diagnose muscle and/or nerve disorders, such as those caused by muscle inflammation and/or muscular dystrophy for example. The EMG information may be used to diagnose muscle weakness due to nerve disorders, including pinched nerves, peripheral nerve damage, amyotrophic lateral sclerosis (ALS), myasthenia gravis, and disc herniation, for example. The EMG information may be used to diagnose a variety of movement disorders, such as periodic limb movement disorders and/or restless legs syndrome.

In yet another embodiment, diagnosis of various movement disorders, such as PLMD, RLS, and bruxism (nighttime teeth grinding) may be facilitated using one or more EMG sensors 9620 coupled to an implantable device 9610. Periodic limb movement disorder and restless leg syndrome are disorders that involve undesirable movements of the limbs as described in more detail below.

One or more EMG sensors 9620 may be placed in or on the muscles of the limbs or other muscles to detect limb movements. For example, EMG sensors 9620 placed on or in the anterior tibialis muscles may be used to identify leg movements associated with PLMD and/or RLS. EMG sensors 9620 placed on the jaw may be used to identify tempomanidibular disorders such as nighttime teeth grinding or other involuntary jaw movements.

EMG-related information may be trended, stored, displayed, or transmitted from the implantable device 9610 to another device. In one embodiment, information from the EMG detector 9612, the sleep detector 9614, and/or the diagnosis processor 9616 is downloaded to a remote device, such as a programmer 9660 or an advanced patient management (APM) device 9630 for further analysis by the APM device 9630, programmer 9660 and/or the patient's physician.

Information from the EMG detector, 9612 the sleep detector 9614, and/or the diagnosis processor 9616 may optionally be used to adjust therapy provided to a patient. Therapy provided by the implanted device 9610 may be adjusted by the patient's physician or by a remote device, such as the APM device 130 or programmer 9660. In one example, the patient's physician may send a command through the programmer 9660 or APM device 9630 to a therapy control unit 9618 in the implanted device 9610 to initiate, terminate, or modify therapy.

In another example, the APM device 9630 and/or the programmer 9660 may automatically command the implanted device 9610 to adjust therapy based on analysis performed in the APM device 9630 and/or the programmer 9660. In another embodiment, the therapy control unit 9618 of the implanted device 9610 may use information from the EMG detector 9612, the sleep detector 9614, and/or the diagnosis processor 9616, to automatically adjust therapy provided to a patient.

The EMG-related information acquired by the implantable device 9610 may be transferred to other therapy devices (internal or external), such as drug delivery devices 9650 and/or nerve stimulation therapy devices 9655. For example, transcutaneous electric nerve stimulation may improve symptoms in some RLS sufferers who also have PLMD. Electrical stimulation may be applied to an area of the legs or feet, usually before bedtime, for about 15 to 30 minutes. Transcutaneous electric nerve stimulation therapy has been found to be helpful in reducing nighttime leg jerking.

The transferred information may be used to adjust the therapy delivered by the drug therapy device 9650, nerve stimulation therapy device 9655, and/or other therapy device, or used in further diagnosis and/or monitoring functions, for example. Examples of drugs useful with the drug therapy device 9650 include dopamine agents (muscle relaxers), benzodiazepines (sedatives), anti-convulsants (to reduce muscle activity), and opioids (narcotics to reduce motor activity).

Although the sleep detector 9614, the diagnosis processor 9616, and the therapy control unit 9618 are illustrated internal to the implantable device 9610, it is contemplated that any or all of these components may be patient-external in alternate embodiments, and may be incorporated into other components such as the APM 9630, for example. Similarly, the drug delivery devices 9650 and/or nerve stimulation devices 9655, illustrated patient-external in FIG. 96, may be included in the implantable device 9610 in alternate embodiments.

Figure 97A:
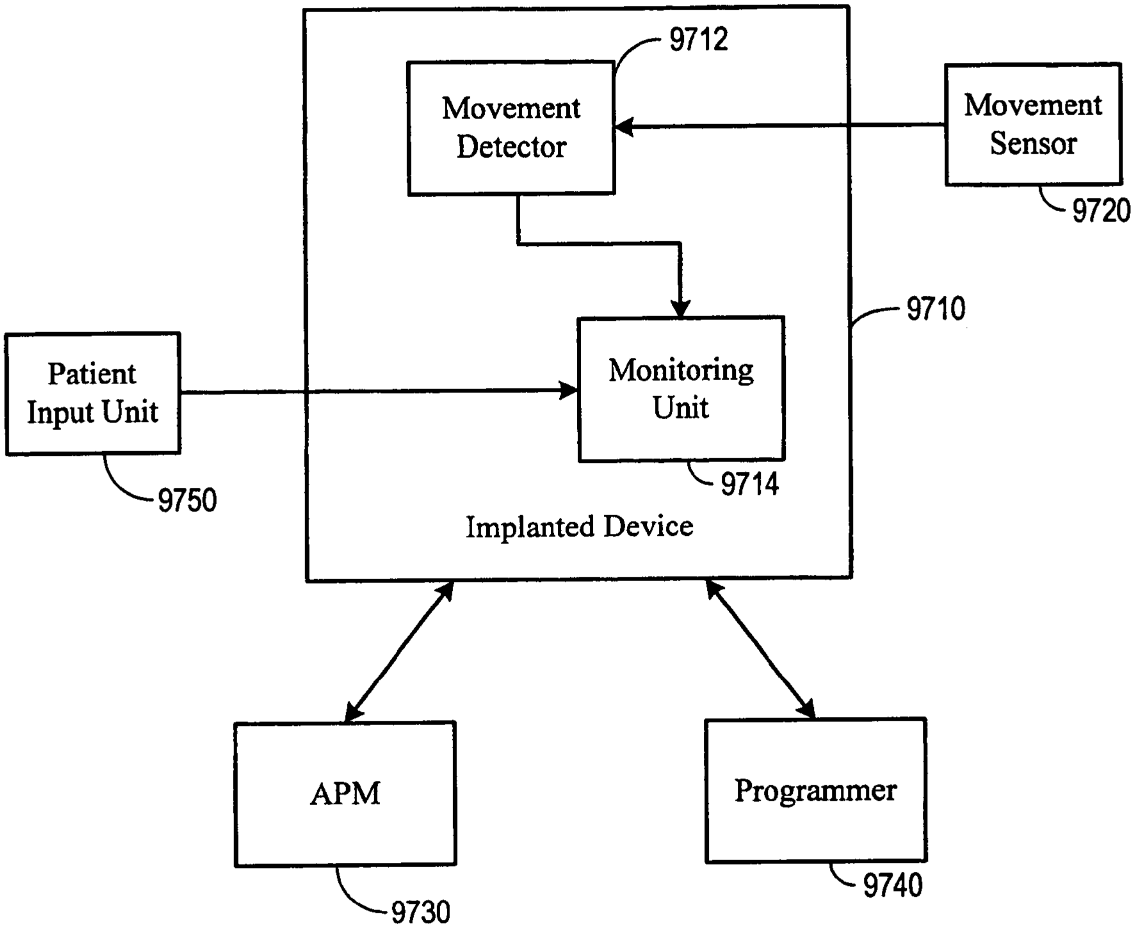
Figure 97B:
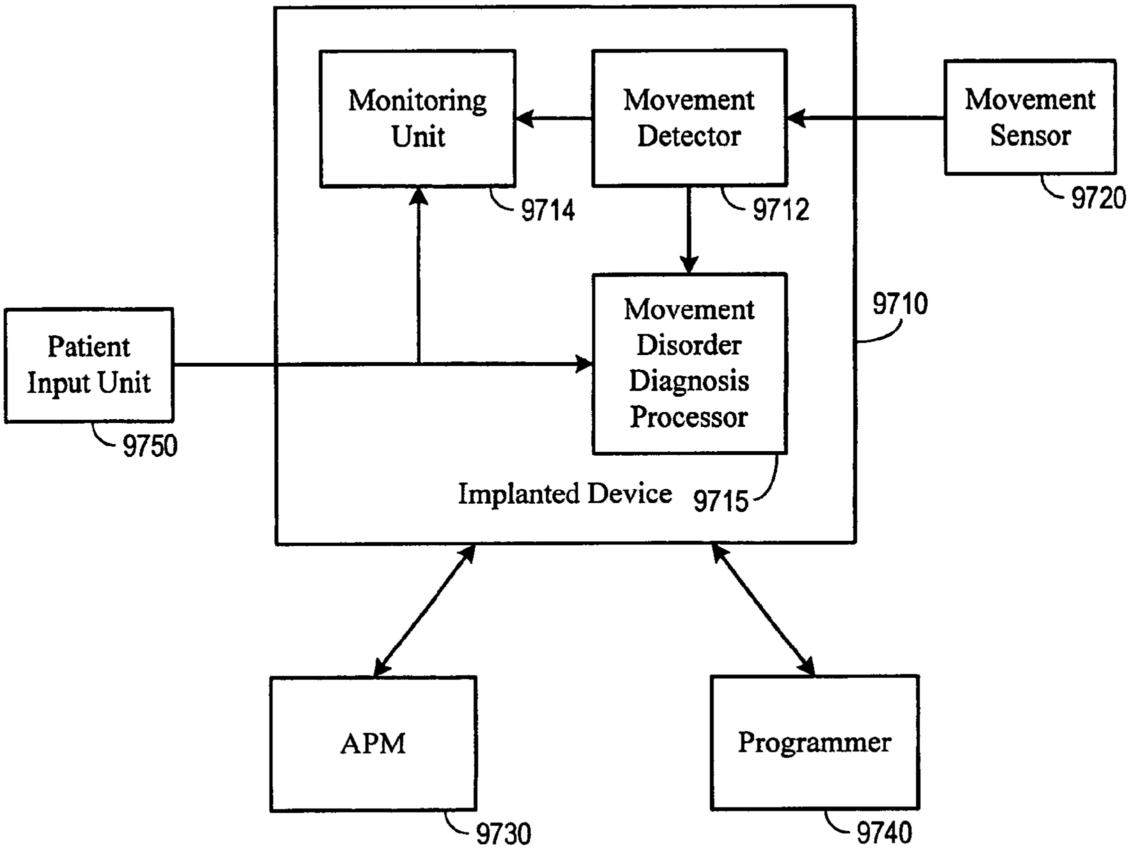

The following discussion, with reference to FIGS. 97A-97B, describes embodiments of the invention involving detection of movement disorders. The processes and systems exemplified by these embodiments may be implemented alone or in combination with one or more processes and systems exemplified by other embodiments described herein to provide a coordinated approach to patient monitoring, diagnosis, and/or therapy.

In accordance with embodiments of the invention, PLMD, RLS, and/or other movement disorders such as bruxism, for example, may be diagnosed using a system that is fully or partially implantable. FIG. 97A illustrates an implantable medical device, e.g., a CRM that incorporates a movement detector 9712. One or more movement sensors 9720 are coupled to the movement detector 9712 within an implantable device 9710.

The movement sensors 9720 may include any sensor or any combination of sensors capable of detecting motion and/or muscle activity associated with motion. For example, the patient's movements may be detected using one or more accelerometers, one or more EMG sensors, and/or a combination of one or more accelerometers and one or more EMG sensors.

In one embodiment, one or more movement sensors (e.g., accelerometers and/or EMG sensors) are coupled to the patient at appropriate locations to detect movements of the extremities, e.g., limb movements, or other movements. Signals from the movement sensors 9720 are received and processed by a movement detector 9712 in the implantable device 9710. The movement detector 9712 may cooperate with a memory in a monitoring unit 9714 to store information about the detected movements. Movement information may be stored, trended, displayed, and/or transmitted to a separate device, such as an APM system 9730 or a programmer 9740 for further operations.

In another embodiment, illustrated in FIG. 97B, one or more movement sensors 9720 are coupled to a movement detector 9712 within the implantable device 9710, as previously discussed. The implantable device 9710 also includes a movement disorder diagnosis processor 9715 that receives movement information from the movement detector 9712. The movement disorder diagnosis processor 9715 evaluates the movement information to determine if the movements are consistent with various movement disorders such as RLS and/or PLMD.

In one example, the movement sensors 9720 may include one of more EMG sensors placed on or in the anterior tibialis. Typical EMG bursts due to PLMD movements may last between 0.5-5 seconds and may recur every 20-40 seconds, for example. The movement disorder diagnosis processor 9715 may make a diagnosis of PLMD if at least about 40 EMG bursts are detected within an 8-hour sleep period, for example.

Sleep disruption caused by the PLMD movements may be determined by any or a combination of the sleep detection techniques described herein, including, for example, brain wave (EEG) sensing and/or a combination of respiration (e.g., minute ventilation) and activity sensing, among others. Alternately or additionally, detection of sleep disruption, such as by using a minute ventilation sensor, may be used to confirm PLMD. Movement disorder diagnosis may be downloaded to a programmer 9740, an APM system 9730, or other therapeutic or diagnostic device.

In accordance with another embodiment of the invention, RLS diagnosis may involve patient input regarding their symptoms. For example, as illustrated in FIGS. 97A and 97B, a patient input device 9750 may be used to acquire information from the patient regarding the patient's perception of symptoms. The patient may be prompted to rate their symptoms on a scale of 0 to 4, or some other scale, for example with a lower number representing fewer RLS symptoms and higher number representing greater RLS symptoms, for example. The patient input may be acquired using the patient input device 9750 over a period of days, for example, about three days to about nine days to establish a diagnosis. Patient input through the patient input device 9750 may also be acquired after diagnosis and/or treatment, for example to assess status of the disorder or the efficacy of treatment.

For example, if the patient input is acquired over a period of six days, the maximum score is 24, i.e., a score of four for each or six days. In this scenario, a score greater than about 12 suggests a diagnosis of severe RLS. A score of about six to about twelve suggests a diagnosis of moderate RLS.

In the embodiment illustrated in FIG. 97A, information about RLS symptoms may be acquired by the patient input device 9750 and transmitted to an APM device 9730, the programmer 9740, or other device for monitoring, display, storage, evaluation, and/or diagnosis. In the embodiment illustrated in FIG. 97B, the information acquired by the patient input device 9750, along with the movement information, may be used by the movement disorder diagnosis processor 9715 in the implantable device 9710 to make a diagnosis of RLS.

Embodiments of the present invention are directed to methods and systems for diagnosis of movement disorders such as PLMD and RLS. RLS diagnosis may be complicated due to the symptom based nature of the RLS diagnosis. The use of patient input through a patient-input device provides a system for collection of symptom based information. Because PLMD and RLS are related disorders, the diagnosis of PLMD through movement detection techniques described herein may be used to enhance the RLS diagnosis.

Use of the methods and systems of the invention may reduce the need for in-clinic sleep studies typically used for movement disorder diagnosis. Further, daily measurements may be made over a number of days which is not practical for in-clinic studies. Earlier and more frequent diagnosis of movement disorders may be enabled using the systems and methods of the invention.

FIGS. 98A-98D illustrate various configurations of an EMG sensor mechanically coupled to an implanted medical device 9820, such as an implantable pacemaker or implantable cardioverter/defibrillator in accordance with embodiments of the invention, which may be useful for diagnosing diseases such as sleep-related muscle disorders. The implantable medical device 9820 may include a housing 9822 enclosing the medical device circuitry and a header 9824 for coupling a lead system 9840 to the circuitry of the medical device 9820.

Figure 98A:
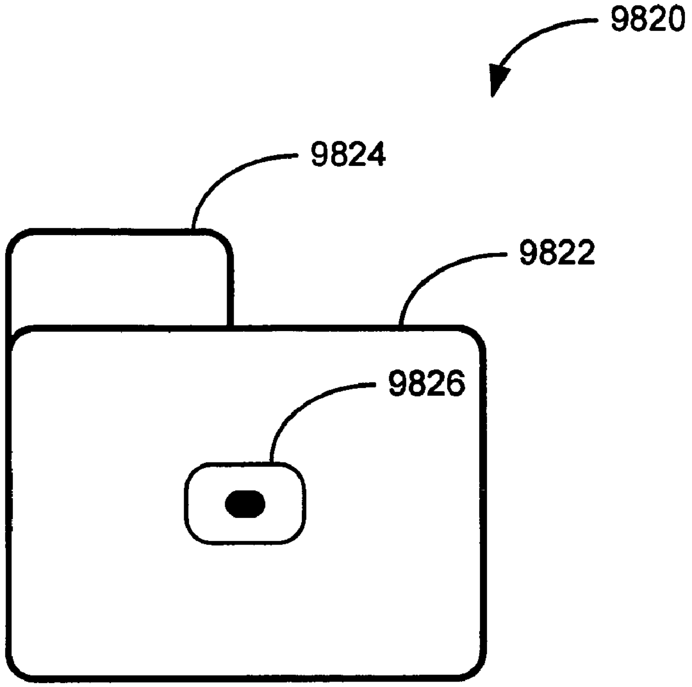
FIGS. 98A-98D are diagrams illustrating various configurations of sensors coupled to an implanted medical device in accordance with embodiments of the invention.
Figure 98B:
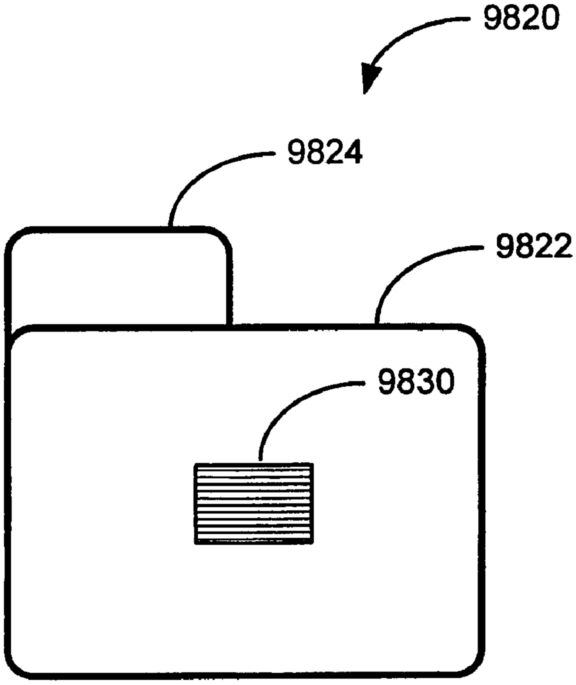
Figure 98C:
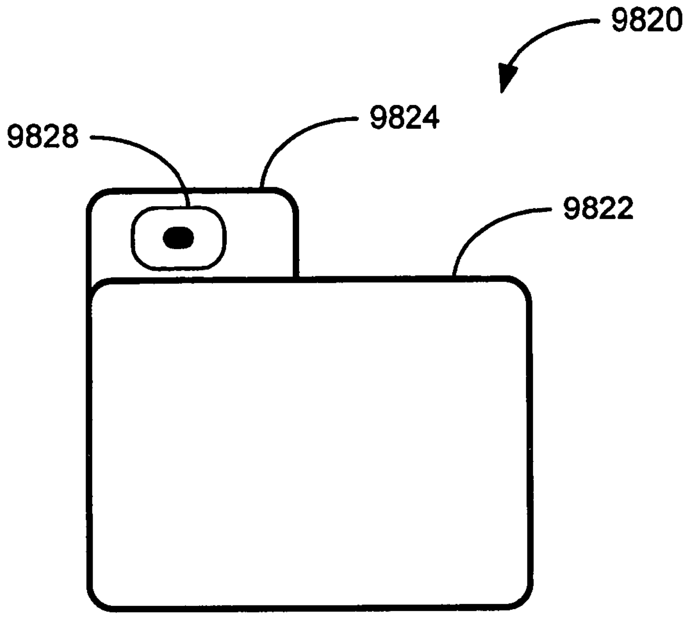
Figure 98D:
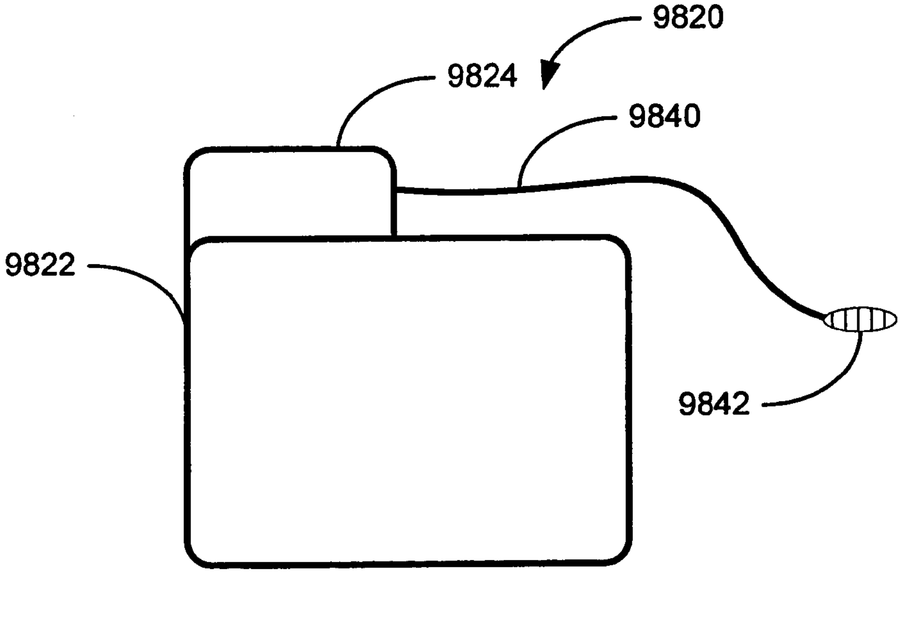

A movement sensor may be implemented, for example, to include an EMG sensor that employs one or more EMG electrodes 9826 or a force responsive sensor 9830 positioned on the housing 9822 of the medical device 9820 as illustrated in FIGS. 98C and 98D, respectively. FIG. 98C illustrates one or more EMG electrodes 9828 positioned on the header 9824 of the medical device 9820. Alternatively, a movement sensor 9842 (e.g., one that includes one or more EMG electrodes or a strain gauge) may be positioned on the lead system 9840 or may be coupled to the housing 9822 through a catheter or lead system 9840, such as by using the header 9824, as illustrated in FIG. 98D.

Figure 99:
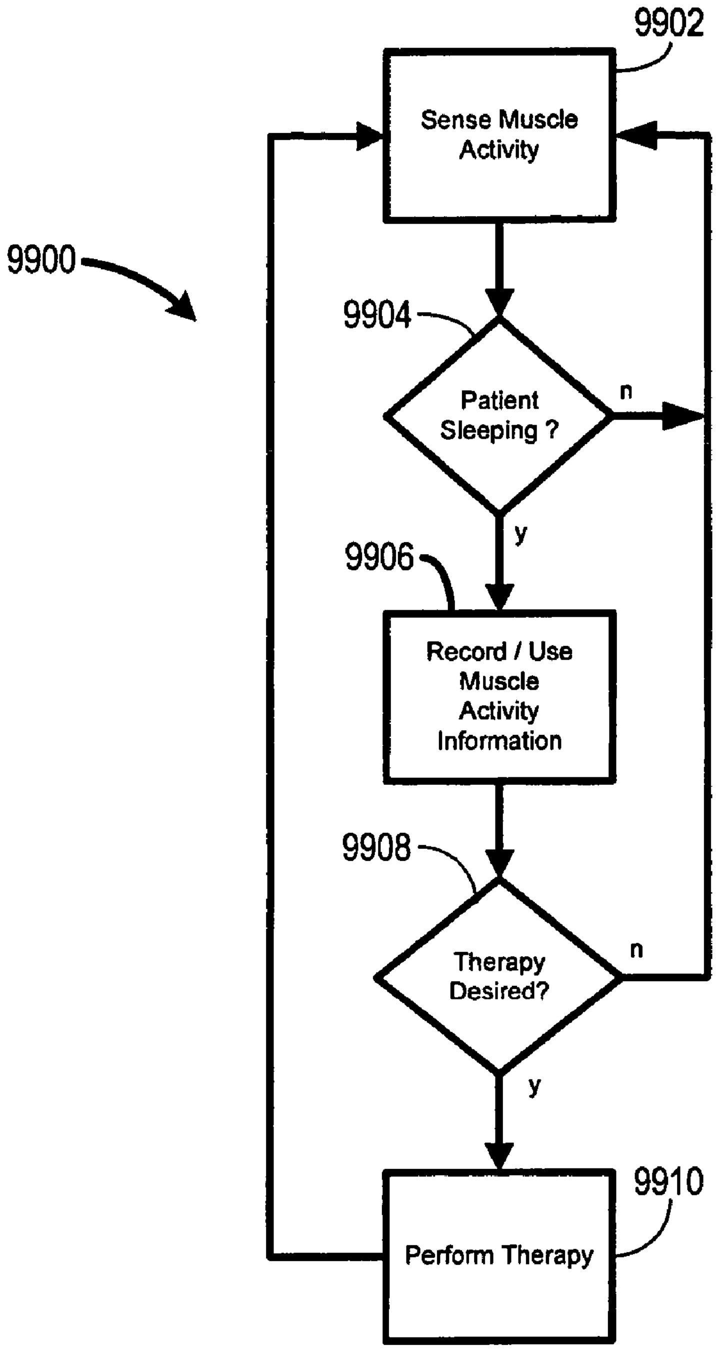
FIG. 99 is a flow chart illustrating an EMG based algorithm in accordance with embodiments of the invention.

FIG. 99 illustrates a method 9900 of implantably sensing and detecting movement used for diagnosis of sleep-related muscle disorders. A muscle activity signal is sensed at a block 9902. Muscle activity may be sensed, for example, using EMG sensors, accelerometers, or other sensors suitable for determining patient movement. A determination block 9904 is used to decide if the patient is sleeping. If determination 9904 decides the patient is not sleeping, the method 9900 loops back to the beginning.

If the patient is determined to be sleeping at block 9904, the muscle activity sensed at block 9902 provides information recorded at block 9906. For example, date, time, sensor data, sense signal amplitudes or other information may be useful for updating, developing, and/or determining an muscle disorder index, a diagnosis, a sleep-related muscle activity history, and other parameters useful for patient diagnosis and treatment. The information recorded at block 9906 may be useful, for example, to predict, verify, classify, and/or determine the existence of a sleep-related muscle disorder.

If intervention and/or treatment is desired at determination block 9908, the intervention and/or treatment may be performed at block 9910 before re-starting the method 9900. For example, the intervention at block 9910 may be the automatic activation of a medical process, modification of a patient's CRM stimulation, modification of a therapy, notification to a patient-external device and/or a physician, or other desirable action.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A system, comprising:

an implantable device configured to perform at least one cardiac-related function and including first sensors;

a patient-external respiratory therapy device and including second sensors;

a processing system external of the implantable and respiratory therapy devices; and a communication channel configured to facilitate communication between the processing system and at least one of the implantable device and the respiratory therapy device, the processing system communicatively coupled to the at least one of the implantable and respiratory therapy devices via the communication channel, the processing system configured to assess sensing characteristics of each of the first and second sensors and to select, based on the assessment of the sensing characteristics, between one and both of the implantable device and the patient-external respiratory therapy device to provide one or more of patient monitoring, diagnosis, and therapy, wherein the sensing characteristics include type, quality, reliability, repeatability, efficiency, availability, accuracy, resolution, dynamic range, specificity, sensitivity or predictive value.

2. The system of claim 1, wherein the communication channel is configured to facilitate communication between the implantable device and the respiratory therapy device.

3. The system of claim 1, wherein the communication channel is configured to facilitate communication between the processing system and one or both of the implantable and respiratory therapy devices and the processing system is configured to facilitate indirect communication between the implantable device and the patient-external device respiratory therapy device.

4. The system of claim 1, wherein the processing system is configured to manage patient-related information and is remotely located with respect to the implantable device and the patient-external device.

5. The system of claim 1, wherein the processing system is configured to coordinate one or more of initiation, modification, and termination of the therapy deliverable by one or both of the implantable and respiratory therapy devices based on interaction between the therapy and another therapy being delivered to the patient.

6. The system of claim 1, wherein the processing system is further configured to assess therapy characteristics of the implantable device and therapy characteristics of the patient-external respiratory device and to select between one and both of the implantable device and the patient-external respiratory therapy device to deliver therapy based on the assessment of the therapy characteristics.

7. The system of claim 6, wherein the one or more therapy characteristics comprises patient comfort and therapy effectiveness and the processing system is configured to coordinate therapy to decrease a level of therapy to increase patient comfort if the processing system determines that therapy effectiveness is sufficient.

8. The system of claim 1, wherein the one or more sensing characteristics comprises accuracy and the processing system is configured to assess accuracy of at least one of the first sensors and the second sensors and to select between one and both of the implantable device and the patient-external respiratory therapy device based on the assessment of accuracy.

9. The system of claim 1, wherein the one or more sensing characteristics comprises a type of sensor and the processing system is configured to assess sensing characteristics by determining the type of sensor of at least one of the first and second sensors and to select between one and both of the implantable device and the patient-external respiratory therapy device based on the type of sensor.

10. The system of claim 1, wherein the processing system is configured to implement one of the implantable device and the patient external respiratory therapy device to provide the patient monitoring and to implement another of the implantable device and the patient-external respiratory therapy device deliver the therapy, wherein the device selected to provide the patient monitoring is different from the device selected to provide the therapy.

11. The system of claim 1, wherein the processing system is configured to detect sleep and to select one or both of the implantable device and the patient-external respiratory therapy device based on the detection of sleep.

12. The system of claim 1, wherein the processing system is configured to determine a type of disordered breathing experienced by the patient and to select one or both of the implantable device and the patient external respiratory therapy device based on the type of disordered breathing.

13. The system of claim 1, wherein the processing system is configured to coordinate the therapy between one and both of the implantable device and the patient-external respiratory therapy device based on device lifetime.

14. The system of claim 1, wherein the processing system is configured to select between one and both of the implantable device and the patient-external respiratory therapy device based on patient use of the patient-external respiratory therapy device.

15. The system of claim 1, wherein the processing system is configured to select between one and both of the implantable device and the patient-external respiratory therapy device to deliver the therapy based on therapy effectiveness.

16. The system of claim 1, wherein the processing system is configured to select one or more sensors from the implantable device and to select one or more of sensors from the patient external respiratory therapy device.

17. The system of claim 1, wherein the processing system is configured to select both the implantable device and the patient-external respiratory device to deliver the therapy and the processing system is configured to coordinate the therapy between the implantable device and the patient-external respiratory device based on therapy characteristics of the implantable device and the patient-external respiratory device.

18. The system of claim 1, wherein both the implantable device and the patient-external respiratory therapy device are selected to provide the patient monitoring and the processing system is configured to coordinate the patient monitoring provided by the patient-external respiratory therapy device and the implantable device.

19. The system of claim 1, further comprising one or more additional devices including a patient input device, wherein coordination of the implantable device and the respiratory therapy device is based on information acquired from the patient input device.

* * * * *